US006321120B1

(12) United States Patent
Surbeck et al.

(10) Patent No.: US 6,321,120 B1
(45) Date of Patent: Nov. 20, 2001

(54) RF THERAPEUTIC CANCER APPARATUS AND METHOD

(75) Inventors: Margaret P. Surbeck, Atherton; Robert L. Devries, Palo Alto; Homer L. Surbeck, deceased, late of Atherton, all of CA (US), Margaret P. Surbeck, executrix

(73) Assignee: INDNJC, Inc., Los Angeles, CA (US)

( * ) Notice: Subject to any disclaimer, the term of this patent is extended or adjusted under 35 U.S.C. 154(b) by 0 days.

(21) Appl. No.: 09/141,691

(22) Filed: Aug. 28, 1998

Related U.S. Application Data

(63) Continuation of application No. PCT/US97/23845, filed on Dec. 29, 1997.

(51) Int. Cl.[7] .......... A61F 2/00

(52) U.S. Cl. .......... 607/101; 607/98; 606/45; 606/41

(58) Field of Search .......... 607/101, 96, 98, 607/99, 154, 155, 156; 606/70, 41, 45, 49, 48, 113

(56) References Cited

U.S. PATENT DOCUMENTS

| | | |
|---|---|---|
| Re. 32,057 | 12/1985 | LeVeen . |
| 1,445,951 | 2/1923 | Hoffman . |
| 1,647,512 | 11/1927 | Dunn . |
| 1,835,870 | 12/1931 | Henry . |
| 2,503,668 | 4/1950 | Hart . |
| 2,545,087 | 3/1951 | Hart . |
| 2,667,866 | 2/1954 | Hart . |
| 2,777,445 | 1/1957 | Hart . |
| 2,833,925 | 5/1958 | Lappe . |
| 3,055,372 | 9/1962 | Browner . |
| 3,181,535 | 5/1965 | Milinowski . |
| 3,299,892 | 1/1967 | Kendall et al. . |
| 3,513,851 | 5/1970 | Smith et al. . |
| 3,516,413 * | 6/1970 | McDonald et al. .......... 607/70 |
| 3,566,877 | 3/1971 | Smith et al. . |
| 3,609,566 | 9/1971 | Roschin . |

(List continued on next page.)

FOREIGN PATENT DOCUMENTS

136530 B1 6/1988 (EP) .

OTHER PUBLICATIONS

Thomas Colson, Introduction to Electronic Therapy, 1936 College of Electronic Medicine, San Francisco, California.

Thomas–Colson, Molecular Radiations, 1953 Electronic Medical Foundation, San Francisco, California.

Thomas Colson, Electronics Defined, published date unkown Electronic Medical Foundation, San Francisco, California.

William Hudgings, Dr. Abraham's Electron The Theory Delta Spectrum Research, Inola, Oklahoma.

T. Proctro Hall, Report on the Electronic Reactions of Abrams, read before the British Columbia Academy of Science, Apr. 27, 1923 Vancouver, B.C., Canada.

Fred J. Hart, Electronic Medical Digest, 1960 The Electronic Medical Foundation, San Francisco, California.

*Primary Examiner*—Linda C. M. Dvorak
*Assistant Examiner*—R. Kearney
(74) *Attorney, Agent, or Firm*—Hughes Hubbard & Reed LLP; Ronald Abramson; Peter A. Sullivan

(57) ABSTRACT

An apparatus and method for treating cancer and other illnesses in humans and animals are described. The treatment involves the low-power, pulsed application of radio frequency tuned with precision of at least one half part per million. Alternative embodiments are described for apparatus that generates the required RF signals and applies such signals therapeutically. Laboratory data is reported, showing the successful use of the disclosed apparatus and methods to suppress and eliminate cancerous tumors in mice.

5 Claims, 39 Drawing Sheets

U.S. PATENT DOCUMENTS

| | | | |
|---|---|---|---|
| 3,670,737 | | 6/1972 | Pearo . |
| 3,800,802 | | 4/1974 | Berry et al. . |
| 3,893,462 | | 7/1975 | Manning . |
| 3,952,751 | | 4/1976 | Yarger . |
| 4,197,851 | | 4/1980 | Fullus . |
| 4,315,503 | | 2/1982 | Ryaby et al. . |
| 4,454,883 | | 6/1984 | Fullus . |
| 4,671,286 | | 6/1987 | Renault . |
| 4,823,813 | | 4/1989 | Harrison . |
| 4,865,048 | * | 9/1989 | Eckerson ................................ 607/45 |
| 4,951,688 | | 8/1990 | Keren . |
| 5,099,756 | | 3/1992 | Franconi et al. . |
| 5,383,922 | * | 1/1995 | Zipes et al. .......................... 607/101 |
| 5,386,837 | | 2/1995 | Sterzer . |

* cited by examiner

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-470
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-473
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-496
TREATED MOUSE

*TOP GRAPH SHOWS TUMOR VOLUME IN cu inches vs TIME in DAYS*

*LOWER GRAPH SHOWS WEIGHT IN GRAMS & HEMATOCRIT % vs DAYS*

OUJ-506
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

TREATED MICE: SHOWING INDIVIDUAL WEIGHT CHANGES IN GRAMS

CONTROL MICE: SHOWING INDIVIDUAL WEIGHT CHANGES IN GRAMS

TREATED MICE: MAXIMUM SIZE OF EACH TUMOR

CONTROL MICE: MAXIMUM SIZE OF EACH TUMOR

OUJ-738
TREATED MOUSE

TOP GRAPH SHOWS TUMOR VOLUME in cu inches vs TIME in days

LOWER GRAPH SHOWS WEIGHT in grams & HEMATOCRIT % vs DAYS

Formula for Tumor Volume in cubic inches = 1/2 length X 1/2 width X height X 2.094
For more detailed information see OUJ-738-Data

RF THERAPEUTIC CANCER APPARATUS AND METHOD

CROSS REFERENCE TO RELATED APPLICATION

This application is a continuation of PCT Intentional Application Number PCT/US97/23845 designating the United States Dec. 12, 1997.

Dated: Aug. 28, 1998

This specification includes as Appendices A1–10, B1–10 and C, tables submitted on a compact disc, which tables are contained in the following files (the file names correspond to the Appendices referenced herein):

| Date Created | Bytes | File Name |
|---|---|---|
| 06/22/01 | 14,449 | A1.txt |
| 06/22/01 | 31,110 | A2.txt |
| 06/22/01 | 26,776 | A3.txt |
| 06/22/01 | 27,445 | A4.txt |
| 06/22/01 | 30,278 | A5.txt |
| 06/22/01 | 26,483 | A6.txt |
| 06/22/01 | 40,190 | A7.txt |
| 06/22/01 | 57,561 | A8.txt |
| 06/22/01 | 28,164 | A9.txt |
| 06/22/01 | 22,623 | A10.txt |
| 06/22/01 | 8,493 | B1.txt |
| 06/22/01 | 16,098 | B2.txt |
| 06/22/01 | 7,975 | B3.txt |
| 06/22/01 | 13,336 | B4.txt |
| 06/22/01 | 3,606 | B5.txt |
| 06/22/01 | 10,539 | B6.txt |
| 06/22/01 | 4,208 | B7.txt |
| 06/22/01 | 5,427 | B8.txt |
| 06/22/01 | 3,957 | B9.txt |
| 06/22/01 | 3,027 | B10.txt |
| 06/22/01 | 3,415 | C.txt |

The contents of each said files, in their entirety, are hereby incorporated by references in

FIELD OF INVENTION

This invention generally relates to apparatus and methods for treating cancer and other illness in humans and animals, and more particularly to a therapeutic apparatus and method based upon the administration of precisely regulated, low power, pulsed electromagnetic radiation (EMR).

BACKGROUND OF THE INVENTION

There is a considerable body of early literature regarding treatment of various illnesses with radio frequencies (RE) in the 43 MHz range. In U.S. Pat. No. 2,545,087, 1. J. Hart disclosed an apparatus for treating a subject with a sequence of radio frequencies in the 43 MHz. range, applied in a stepwise fashion. These frequencies were each modulated sinusoidally at 60 Hz., and further pulsed by a second slow sinusoidal oscillator operating at 90 cycles per minute (1.5 Hz.). The RF frequencies employed by Hart were specified to three decimal places.

The instruments available to Hart and the other researchers of his day were based on tube amplifiers, which resulted in oscillators with considerable drift that could not be precisely tuned. Hart's means for applying the RF energy to a subject most often consisted of a metal plate acting as an antenna. As a result of such oscillator drift and imprecision, and the inefficiency of the available output devices, Hart and his contemporaries were not able to conduct scientific tests with precisely controlled frequencies, or to discover optimal treatment modalities.

Modern electronic technologies make it relatively simple to construct more precise and stable instruments than Hart had at his disposal. As a consequence, it has become possible to study systematically the potential therapeutic value of EMR. The present inventors have undertaken such studies over the course of many years, and as a result have perfected apparatus and methods which have proved effective in treating cancerous tumors in laboratory mice. The inventors believe that the same methods can be effectively adapted for human treatment.

The present inventors have constructed apparatus designed to overcome the limitations of Hart's approach. They have further sought to establish the utility of their invention through a program of animal testing, and have in turn used the results of such testing to refine the apparatus and the methods for effectively using such apparatus. The resulting apparatus and methods, and the experimental results of applying such apparatus and methods to treat cancerous tumors in mice, will be described below.

SUMMARY OF THE INVENTION

It is generally the object of the present invention to utilize electromagnetic radiation to provide effective treatments for cancer and other illnesses.

It is a further object of this invention to achieve reliable and reproducible therapeutic results from EMR treatment methods by achieving precise control over the treatment frequency.

It is also an object of the present invention to provide an efficient means of transmitting EMR from the generating means to the subject.

It is another object of the present invention to provide an EMR treatment that may be applied at very low power levels that can cause no harm.

These and other objects are achieved in accordance with the present invention through the use of an apparatus involving an oscillator that outputs, at a power of less than one mw, an RF frequency in the 43 MHz range, regulated and stabilized to the fifth or sixth decimal place, which is in turn modulated with a 60 Hz. 50% duty cycle square wave, which is in turn gated, again on a 50% duty cycle, at a rate of 1.167 Hz. (70 pulses per minute).

The RF frequency is chosen for a particular subject based on the believed effectiveness of the frequency in treating the illness in question, as summarized herein.

The modulated RF signal output by the apparatus of the present invention is applied to a flat loop of wire approximately 60 cm. long, grounded at one end and wound in five flat, concentric spiralrectangular turns spaced about 3.175 mm. apart, the loop (herein referred to as a "treatment loop") being mounted on an insulating layer adhesively bonded to a metal plate.

In using this apparatus, the metal plate is placed loop down, on the subject's body near the area to be treated. RF power is applied to the loop at one precise treatment RF frequency for at least one hour at a time. During treatment, the treatment loop is shielded from direct light and moving air currents.

There are alternative embodiments of the invention that differ somewhat in their circuit and construction details. The first, referred to as the "Battery SCPO," is a battery-powered "Single Crystal Pulsed Oscillator" in a metal housing with an internal quartz crystal, and an integral, externally mounted treatment loop. Each Battery SCPO is limited to a single frequency. A variation is shown (the "Mouse SCPO")

in which an SCPO is powered by an external DC power module rather than batteries. An alternate embodiment, referred to as the "Generator Embodiment", derives its treatment signal from the modulated output of a Hewlett-Packard Model 8662A frequency generator, and supplies the signal to the treatment loop over a short coaxial cable. The frequency and power of the Generator Embodiment is easily adjusted with controls on the front panel of the 8662A frequency generator. Another alternative embodiment, also based on the HP 8662A Frequency Generator, modulates the RF signal entirely externally to the HP 8662A, and employs a specific type of coaxial cable to carry the signal from the modulator to the treatment loop. These alternative embodiments differ somewhat in their circuitry and construction details, as will be more fully described below.

In any of the alternative embodiments, treatment is non-restrictive and utilizes a low power believed to be completely safe for humans.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

FIGS. 9A1–9J4 show the treatment housings and treatment loops used for treating mice in the experiments described herein.

DETAILED DESCRIPTION OF THE PREFERRED EMBODIMENTS

1. DESIGN CONSIDERATIONS

Figure 1B:
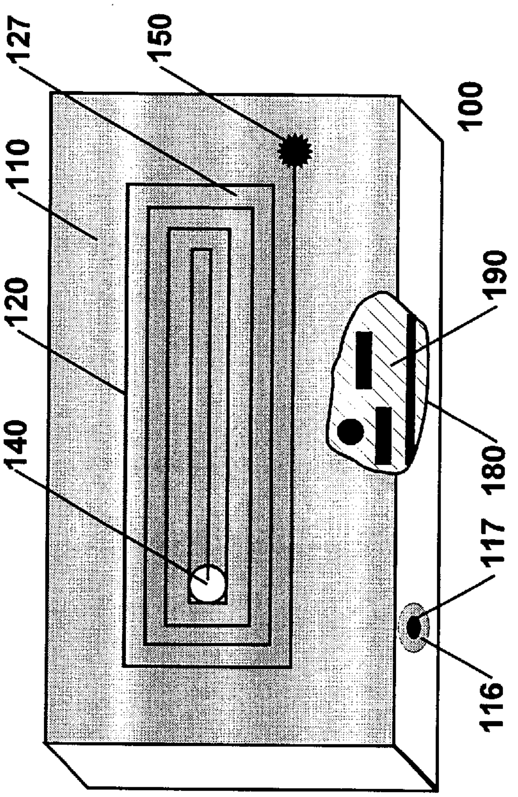
FIGS. 1A and 1B show top and bottom external views of the Battery SCPO.

According, to experiments conducted by the present inventors, treatment with EMR is most effective under the following conditions:

a) The treatment frequency is selected with a precision extending to the fifth or sixth decimal point, or,it least one half part per million.

b) The frequency is extremely stable over the course of the treatment.

c) The precise frequency chosen is held at that frequency and applied without variation for at least one hour.

d) RF power applied to the subject is held to less than one milliwatt (mW).

e) The EMR is applied through a coiled loop of wire, which, for treatments in the 43 MHz. Range, is approximately 60 cm. long.

The frequencies listed in Table 1 are believed to be effective for treating the indicated maladies:

TABLE 1

Treatment Frequencies

| Frequency | Malady |
|---|---|
| 43,322,480 | Sarcoma (generalized) |
| 43,322,492 | Sarcoma (intestines) |
| 43,322,485 | Sarcoma (breast) |
| 43,346,000 | Tuberculosis (general) |
| 43,346,090 | Tuberculosis (intestines) |
| 43,346,000 | Tuberculosis (breast) |
| 43,346,050 | Common cold |
| 43,353,800 | Carcinoma (general) |
| 43,353,800 | Carcinoma (intestines) |
| 43,353,850 | Carcinoma (breast) |
| 43,353,800 | Malignancy |
| 43,296,000 | Strep |
| 43,351,830 | Treats several diseases |
| 43,351,850 | Treats several diseases |
| 43,351,855 | Treats several diseases |
| 43,351,870 | Treats several diseases |
| 43,352,000 | Pneumonia |
| 43,245,000 | Staph |

The foregoing list includes all of the frequencies studied by the present inventors and found to be effective. The inventors believe that different frequencies, even close to the above-stated frequencies are not effective. They have found that the effectiveness of the treatment depends critically on the precise frequency chosen, to the precision indicated herein. They have also found that steady treatment frequencies are more effective than swept or varied frequencies.

This invention is not intended to be limited to the frequencies stated in the above table. The inventors believe that there may be other frequencies in the 43 MHz. range that the present inventors have not as yet studied, that may also be effective. Similarly, the present inventors believe that there may be effective treatment frequencies in completely different ranges, for example, at much higher frequencies. The most important factor, in the view of the present inventors, is a precisely chosen frequency steadily applied for at least an hour at a time.

2. CONSTRUCTION OF ALTERNATIVE TREATMENT DEVICES

For twenty years we have been working to obtain the correct frequencies with which to treat the mice and also the best possible instrument (method) with which to deliver the treatment to the mouse. Some of our experiments included using two plates (a hot and ground) rather than the treatment loop. All things considered, we feel the embodiments employing treatment loop electrodes have performed the best in our experiments on the mice.

Detailed descriptions of the alternate embodiments of the invention are set forth here to demonstrate that the principles taught in this invention are readily reducible to practice. It should be understood that these embodiments represent but a few of the possible configurations of the present invention, and that, utilizing the principles of the present invention as disclosed herein, analogous apparatus and methods may be readily devised for controlled therapeutic application of RF energy.

A. Battery SCPO

Figure 1A:
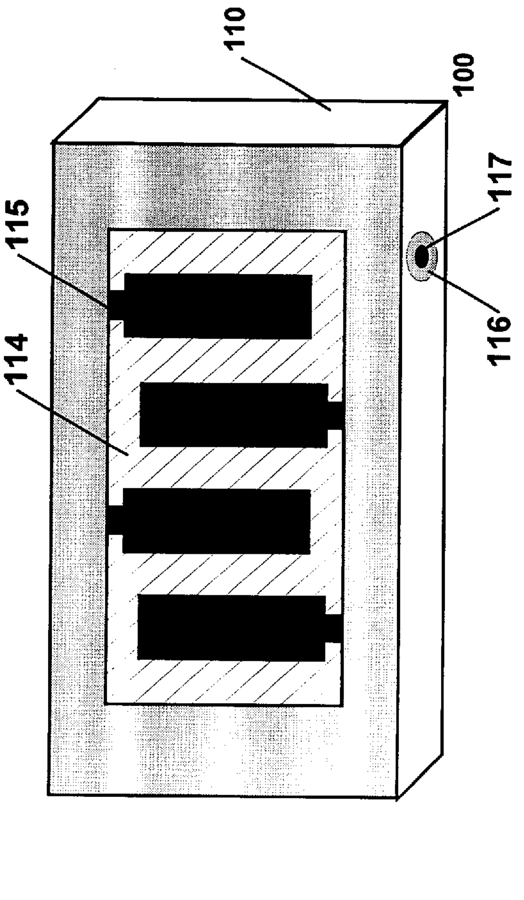

Top and bottom external views of the battery-operated embodiment of the treatment device are shown in FIGS. 1A and 1B. The device 100 is built in a small, self-contained rectangular metal package measuring about 7.37 cm. long, 5.46 cm. wide, and 1.78 cm. in thickness.

Housing 110 is preferably metal. It provides mechanical protection for the apparatus and serves as a electromagnetic shield. Housing 110 is soldered shut. In battery holder 114 (Caltronics BH-124) accessible from outside the package (and which may be recessed or attached to the exterior of housing 110), the housing accommodates four standard 1.5 volt "AA" alkaline batteries 115 of approximately 1.5 volts each, which provide the electrical power for the unit.

The underside of the device, shown in FIG. 1B, accommodates a surface mounted coil of wire 120 referred to as the "treatment loop." One end of treatment loop) 120 enters the bottom housing surface through a wire feed hole 140 in the bottom of housing 110. The other end of treatment loop is grounded at solder point 150 to the outside of housing 110. The treatment loop itself consists of five concentric, spiraled, rectangular turns of 20 AWG solid copper wire embedded in a 2 mm. (0.080 inch) thick sheet of high impact styrene 111 adhesively fastened to the bottom surface of housing 110. (Alternatively the treatment loop may be constructed on a printed circuit board.) The windings are spaced 3.175 mm. apart and the overall dimensions of the loop are 2.858×5.258 cm.

The treatment loop 120 has a broad radiating pattern off the coil. It is not a "focused" radiation but a spreading radiation. More signal is available from the front then off the back of treatment loop 120 (the back is shielded by a ground plane). Tests were run using a loop without the back shield but the results were not as good as with a back shield. The signal is strongest in the center since that is where the "hot" lead connects to treatment loop 120.

Figure 3:
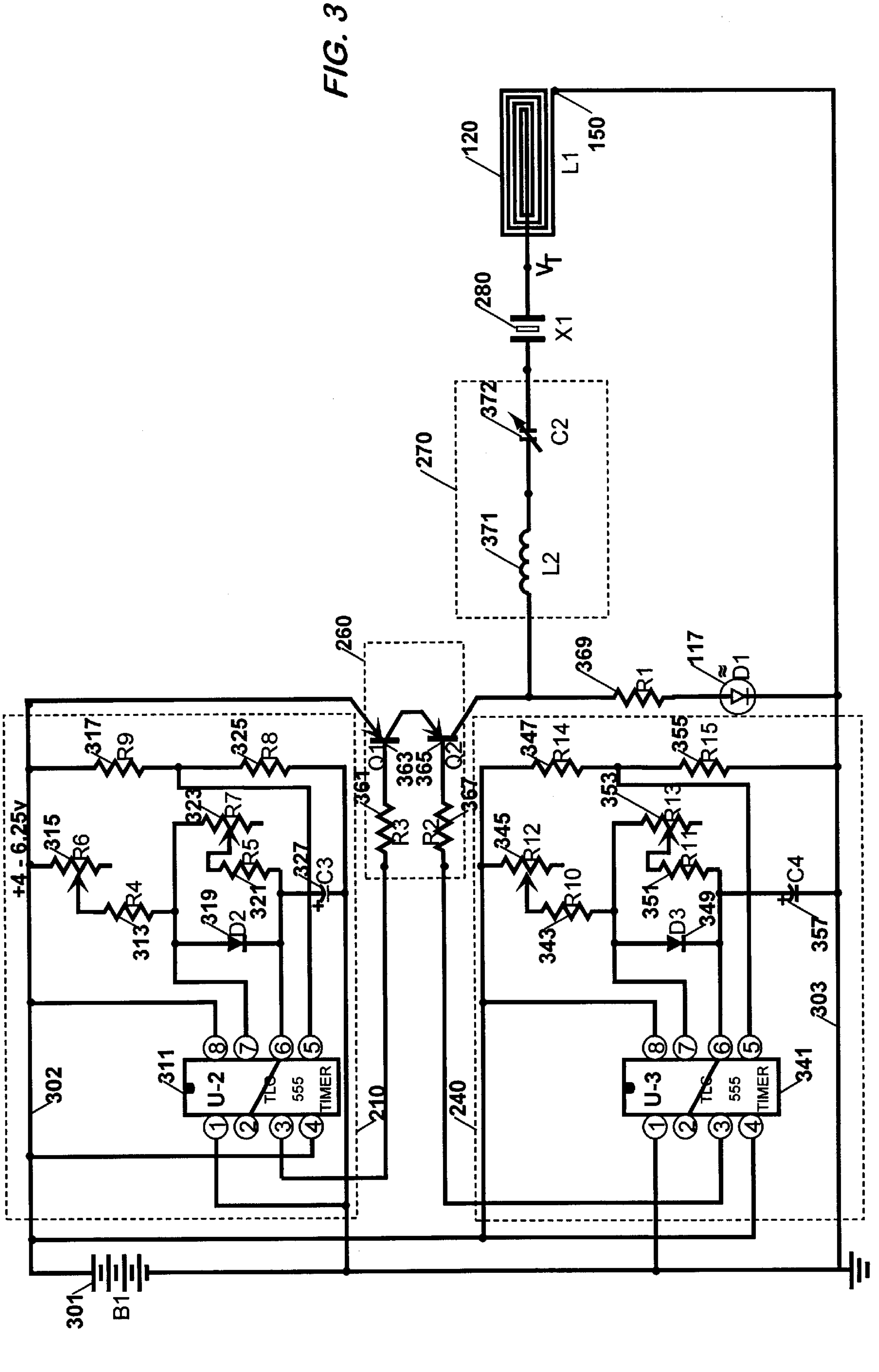
FIG. 3 is a schematic diagram of the Battery SCPO.
Figure 4A:
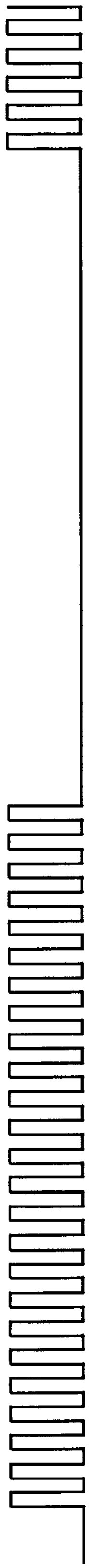
FIG. 4A shows the modulation waveform of the Battery SCPO.
Figure 4B:
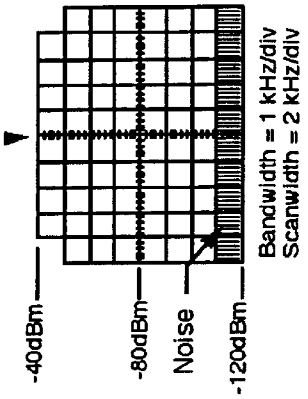
FIGS. 4B through 4F show spectrum analyses of the output of the Battery SCPO.
Figure 4C:
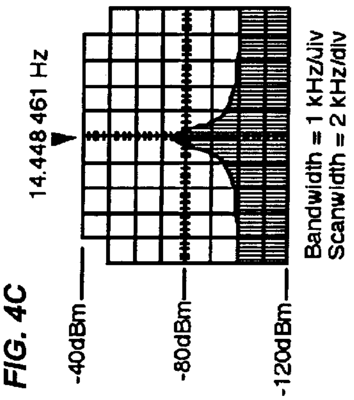
Figure 4D:
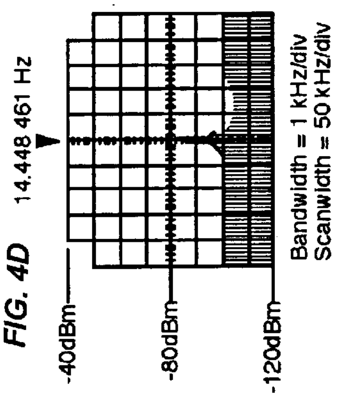
Figure 4E:
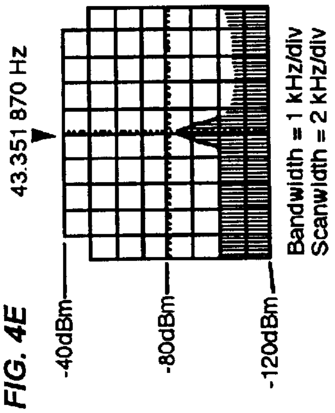
Figure 4F:
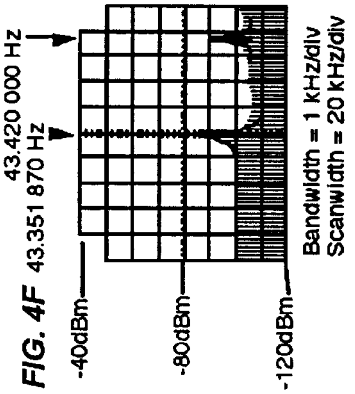

The circuitry that drives treatment loop 120 is contained on a printed circuit board 190 (shown in the cutaway 180 in FIG. 1B) within housing 110. The schematic for this circuit is shown in FIG. 3. The circuit comprises two timer circuits 210 and 240, which provide approximately a 60 Hz. approximately 50% duty cycle square wave, and an approximately 70 pulse per minute (1.167 Hz.) approximate 50% duty cycle square wave, respectively. These two square waves are combined in AND gate 260 in order to produce an approximately 60 Hz. square wave pulsed at approximately 1.167 Hz., each of the 60 Hz. Square wave and the 1.167 Hz. pulse having an approximate 50% duty cycle. The waveform output by AND gate 260 is shown in FIG. 4A.

The output of AND gate 260 is then directed through filter 270, and then to quartz crystal X1 280. Although many frequencies could be chosen from, the Battery SCPOs built to date have used a crystal cut for a third harmonic frequency of 43.351830±20 Hz., 43.351850±20 Hz., 43.351855±20 Hz. and 43.351870±20 Hz. (corresponding to base frequencies in the 14.450 MHz range). These frequencies have been found most effective for treating a broad range of maladies. The output of crystal 280 is directed to treatment loop 120.

Viewed in further detail, the schematic diagram in FIG. 3 shows the power for the circuit derived from the four cell battery 301. This power supply feeds positive rail 302 and ground rail 303.

The approximately 60 Hz. timing circuit 210 is based on a low power TLC 555 timer U2 311, set up as an astable multivibrator by connecting pins 2 (Trigger) and 6 (Threshold) together. Pin 1 is connected to ground 303. Pins 4 and 8 are connected to the positive supply rail 302. Pin 5 is connected to the midpoint of a voltage divider comprised of 1K resistor R9 317 (this, and all other fixed resistors referred to herein being 5%, ¼ Watt, unless otherwise specified) from the positive supply and 2.2 K resistor RB 325 to ground 302. Pin 6 is in addition connected to 1N914, 75 PIV, switching diode D2 319 forward biased from pin; to 0.22 uF (50 volt) electrolytic capacitor C3 327 to ground 303; to 47K resistor R5 321 to the wiper of 20K, 15 turn, ¾ watt adjustable resistor R7 323, once end of which is open and the other end of which is connected to pin 7. Pin 7 in addition is connected to 33K resistor R4 313 to the wiper of 20K, 15 turn, ¾ watt adjustable resistor R6 315, one end of which is open and the other end of which is connected to the positive supply rail 302. Pin 3 is the output.

The square wave frequency and duty cycle produced by 555K Timer U2 215 are adjusted by 20K. 15 turn, ¾ watt adjustable resistors R6 315 and R7 323 in accordance with the following formulas:

$$t1\ (\text{output high})=0.693\times(R4+R5+R6+R7)\times C3$$

$$t2\ (\text{output low})=0.693\times(R5+R7)\times C3$$

$$T\ (\text{total period})=t1+t2$$

$$f\ (\text{frequency})=1/T$$

$$D\ (\text{duty cycle})=(R5+R7)/(\ (R4+R6)+2\times(R5+R7))$$

(Units: R–Ohms; C–Farads; t, T–Seconds, f–Hz.)

The exact frequency and duty cycle of this square wave varies with the battery voltage and precise component values The 60 Hz. and 50% duty cycle figures required for successful operation of the preferred embodiment are believed to be plus or minus 10%, based on the condition of the batteries, exact component characteristics and environmental factors such as ambient and operating temperature.

The 1.167 Hz (70 pulse per minute) timing circuit 240 is similar to that of circuit 210. The approximately 1.167 Hz. timer circuit 240 is based on a low power TLC 555 timer U3 341, set up as an astable multivibrator by connecting pins 2 (Trigger) and 6 (Threshold) together. Pin 1 is connected to ground 303. Pins 4 and 8 are connected to the positive supply rail 302. Pin 5 is connected to the midpoint of a voltage divider comprised of 1K resistor R14 347 from the positive supply and 2.2 K resistor R15 355 to ground 303. Pin 6 is in addition connected to 1N914, 75 PIV, switching diode D3 349 forward biased from pin 7; to 10.0 uF (16 volt) electrolytic capacitor C4 357 to ground 303; to 47K resistor R11 351 to the wiper of 20K, 15 turn, ¾ watt adjustable resistor R13 353, one end of which is open and the other end of which is connected to pin 7. Pin 7 in addition is connected to 33K resistor R10 343 to tie wiper of 20K, 15 turn, ¾ watt adjustable resistor R12 345, one end of which is open and the other end of which is connected to the positive supply rail 302. Pin 3 is the output.

The output voltage of both TLC 555 timer circuits 210 and 240 is approximately 4 volts, which varies with battery supply voltage.

The approximately 1.667 Hz. signal is combined with the approximately 60 Hz. signal in AND gate 260 which consists of 330 Ohm input resistors R2 367 and R3 367, and MPS2907 PNP transistors Q1 280 and Q2 290. FIG. 4A shows the waveform output from AND gate 260.

From the output of the AND gate 260 is a 2.15K resistor R1 369 in series will 2 ma red light emitting diode (LED) D1 117 (Radio Shack 276-044 or equivalent) forward biased to ground 303. The LED is visible on the outside of housing 110, and is in the circuit merely to provide a visual indicator that the Battery SCPO is operating.

The remainder of the circuit consists of 8.2 mH inductor L2 371 (Miller 8230-18), 5.5–18 pF trimmer capacitor C2 372 (Sprague-Goodman GY A22000 or equivalent), quartz crystal X1 280 and treatment loop L1 120 to ground 303.

Crystal X1 280 is cut so as to have a base frequency in the 14.4 MHz. Range, and a third harmonic at one of the following frequencies: 43.351830±20 Hz., 43.351850±20 Hz., 43.351855±20 Hz and 43.351830±20 Hz. Quartz crystal 280 is obtained from International Crystal Manufactures, P.O. Box 26330, Oklahoma City, Okla. 73126, and selected with great care. Other sources for crystals that have been used include CTS Corporation, Knights Division, 400 East Reimann Ave., Sandwich Ill. 60548 (which is no longer in business) and NEL Frequency Controls, Inc. 357 Beloit Street, Blurlington Wis.

Crystals are ordered approximately 25–50 at a time for each frequency, and are then individually tested on a Saunders Crystal Test System so as to allow selection of crystals with the desired frequency characteristics. For one representative crystal, driven with a reference frequency near the expected series resonance frequency, with a drive level of 2060 Watts into 44 Ohms, with a 10 pF capacitative load, the results of this testing were as shown in Table 2.

TABLE 2

Exemplary Crystal Measurements

| Parameter | Description | Value |
|---|---|---|
| Fr(Hz.) | Series resonant frequency | 43,351,870 Hz. |
| Co(pF) | Shunt capacity | 4.0 pF |
| Rr(Ohms) | Motional Resistance | 18.2 Ohms |
| Q(k) | Quality factor | 161.0 K |
| C1(fF) | Motional capacity | 1.3 femtoFarads |
| L(mH) | Motional Inductance | 10.7 mH |
| Fl(Hz.) | Loaded resonant frequency | 43,353,820 Hz. |
| Ts(ppm/pF) | Trim sensitivity | 3.2 ppm/pF |
| PWR(uWatt) | Power level | 2740.0 uWatts |

No oven is used in this device. Instead, the unit is turned on for 10 minutes before use, and used in a room at an ambient temperature of approximately 72 degrees Fahrenheit.

The output portion of the Battery SCPO involves a series LC circuit, a series crystal, and the treatment loop, which is another inductor. The large Motional Inductance of the crystal, and its very small Motional Capacitance, dominate the output circuit. This is driven by the square wave train coming out of AND gate 260. The modulation waveform output from AND gate 260, measured at the collector of transistor Q2 365, as shown in FIG. 4A, has a rise time of 18 nS and fall time approximately 120 nS. To a reasonable approximation, each 60 Hz. cycle in the modulation waveform represents a 4 volt step input with the aforementioned rise and fall times, into a series LC circuit with low series resistance. The high frequency components of the steep rise and fall of this square wave stimulates a ringing of the crystal at its characteristic base frequency and harmonics.

The actual output of the Battery SCPO at the point of input to Treatment Loop 120 can be observed on an oscilloscope, and visibly contains RF frequencies. This was observed using an SCPO constructed with a 43.351870 Hz. Crystal. When the signal from the SCPO was input into a spectrum analyzer, a −75 dB peak is observed at the 14.448461 MHz. base crystal frequency, and a −85 dB peak is seen at the 43.351870 MHz. third harmonic frequency of the crystal. An additional, weaker RF signal is observed at 43.420000 MHz. These various spectrum analyzer scans are shown in FIGS. 4B through 4F.

In sum, rather than using a conventional crystal oscillator circuit, the battery SCPO uses a crystal series driven by audio range square wave input pulses, in order to generate low power, yet precisely tuned, pulsed RF energy.

The treatment device is used by applying it, treatment loop down, to the subject's body in the area desired to be treated. The unit is left in place for approximately one hour at a time.

As indicated above, battery SCPOs have been built with crystals tuned to 43.351830±20 Hz., 43.351850±20 Hz., 43.351855±20 Hz and 43.351870±20 Hz. These frequencies were chosen because are each believed to be useful for treating a plurality of illnesses, and because a multipurpose devise is advantageous by reason of the inconvenience of changing crystals. However, there is no reason this embodiment, would not be effective at any of the frequencies identified above as being therapeutically useful, as well as, with an appropriately tuned output element, if necessary, at any frequency found in the future to be therapeutically useful.

A parts list for the Battery SCPO is set forth in Table 3.

TABLE 3

Parts List for Battery SCPO

| Ref. No. | Description | Source |
|---|---|---|
| 110 | SCPO Housing | Fabricated- See text |
| 114 | Battery Holder | Caltronics BH-124 |
| 115 | "AA" Battery 4 ea | Wallgreens 1.5 V AA Ultra Alkaline or equiv. |
| 117 | D1 Indicator Light- 2 mA LED Diode | Radio Shack 276-044 or equiv. |
| 120 | Treatment Loop | Fabricated- See text |
| 127 | Backing for treatment loop | High Impact Styrene 0.080" thick |
| 280 | Quartz Crystal | ICM, CTS, or NEL- See text |
| 311 | U2 - TLC 555 Timer | Radio Shack 276-1723 or equiv. |
| 313 | R4 33K ± 5% ¼ Watt Carbon Resistor | Radio Shack 271-1341 or equiv. |
| 315 | R6 20K 15 Turn ¾ Watt Adj. Resistor | Radio Shack 271-340 or equiv. |
| 317 | R9 1.0 K ± 5% ¼ Watt Carbon Resistor | Radio Shack 271-1321 or equiv. |
| 319 | D2 1N914 Switching Diode 75 PIV | Radio Shack 276-1122 or equiv. |
| 321 | R5 47K ± 5% ¼ Watt Carbon Resistor | Radio Shack 271-1342 or equiv. |
| 323 | R7 20K 15 Turn ¾ Watt Adj. Resistor | Radio Shack 271-340 or equiv. |
| 325 | R8 2.2K ± 5% ¼ Watt Carbon Resistor | Radio Shack 271-1325 or equiv. |
| 327 | C3 0.22 uf Electrolytic Capacitor, 50 Volts | Radio Shack 272-1070 or equiv. |
| 341 | U3 - TLC 555 Timer | Radio Shack 276-1723 or equiv. |
| 343 | R10 33K ± 5% ¼ Watt Carbon Resistor | Radio Shack 271-1341 or equiv. |
| 345 | R12 20K 15 Turn ¾ Watt Adj. Resistor | Radio Shack 271-340 or equiv. |
| 347 | R14 1K ± 5% ¼ Watt Carbon Resistor | Radio Shack 271-1321 or equiv. |
| 349 | D3 1N914 Switching Diode 75 PIV | Radio Shack 276-1122 or equiv. |
| 351 | R11 47K ± 5% ¼ Watt Carbon Resistor | Radio Shack 271-1342 or equiv. |
| 353 | R13 20K 15 Turn ¾ Watt Adj. Resistor | Radio Shack 271-340 or equiv. |
| 355 | R15 2.2K ± 5% ¼ Watt Carbon Resistor | Radio Shack 271-1325 or equiv. |
| 357 | C4 1 Ouf Electrolytic Capacitor, 16 Volts | Radio Shack 272-1436 or equiv. |
| 361 | R2 330 Ohm ± 5% ¼ Watt Carbon Resistor | Radio Shack 271-1315 or equiv. |
| 363 | Q1 MPS2907 PNP Transistor | Radio Shack 276-2023 or equiv. |
| 365 | Q2 MPS2907 PNP Transistor | Radio Shack 276-2023 or equiv. |
| 367 | R3 330 Ohm ± 5% ¼ Watt Carbon Resistor | Radio Shack 271-1315 or equiv. |
| 369 | R1 2.2K ± 5% ¼ Watt Carbon Resistor | Radio Shack 271-1325 or equiv. |
| 371 | L2 8.2 uH Inductor | Miller 8230-18 |
| 372 | C2 5.5–18 pF Trimmer Capacitor | Sprague-Goodman GYA22000 or equiv. |

B. Generator Embodiment

Figure 5:
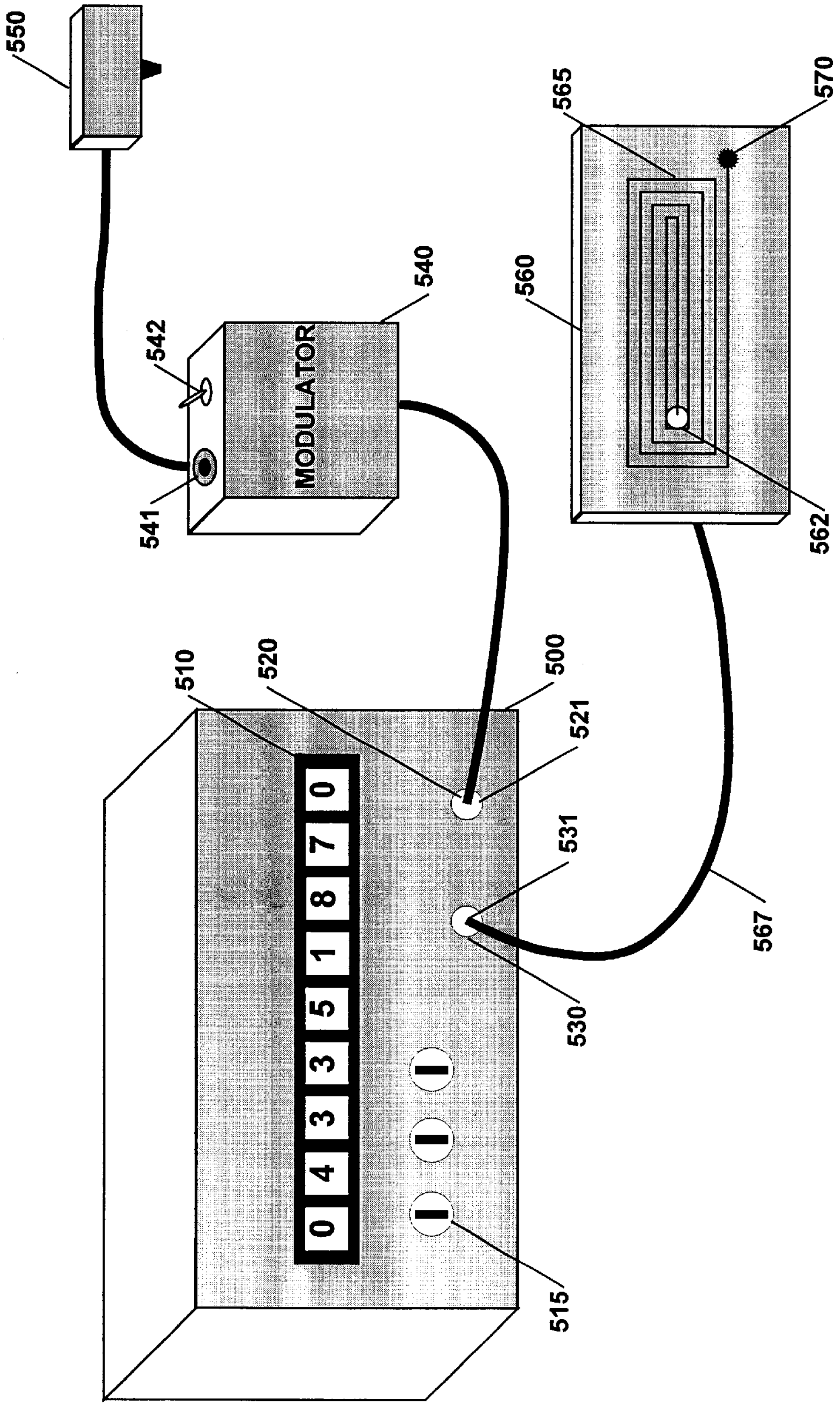
FIG. 5 is an external vies of the components of the Generator Embodiment.

The alternate embodiment of the treatment device is shown in FIG. 5. It employs a model 8662A frequency generator 500 manufactured by the Hewlett-Packard Company. Frequency generator 500 has a modulation input 520, to which is connected modulator unit 540, which provides an approximate 60 Hz square wave with an approximate 50% duty cycle, which is in turn gated with an approximately 1.167 (70 pulse per minute) square wave, also with an approximately 50% duty cycle.

The circuitry of modulator unit 540, which is more fully described below, is similar to that of the Battery SCPO, up to the point of AND gate.

Figure 6:
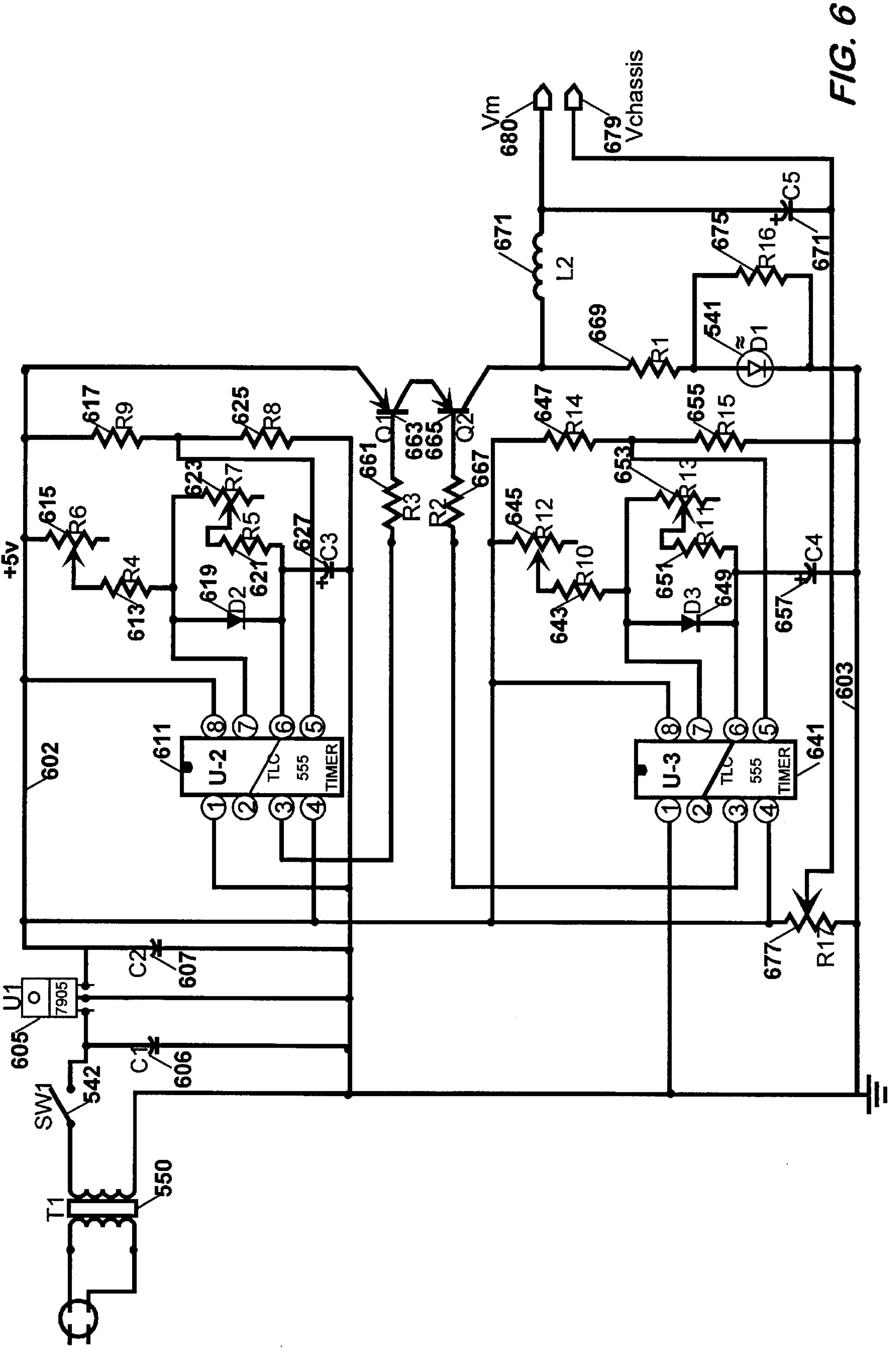
FIG. 6 is a schematics diagram of the modulator circuit for the Generator Embodiment.

As shown in FIG. 6, power is provided by a plug-in DC power module 550, Radio Shack Cat. No. 273-1455C or equivalent, which is rated at 9 volts D.C. at 0.3 amperes. The positive lead from the module is switched through power switch SW1 542, and then directed to a 7805 5 volt voltage regulator U1 605. The negative lead of the supply is attached to the unit's ground rail 603. Both the input and output of voltage regulator U1 605 is bypassed to ground by a 0.01 uF, 500 volt disc ceramic capacitor, C1 606 and C2 607. The output, a regulated 5 volts, is applied to positive supply rail 602.

The circuitry associated with the TLC 555 timers 611 and 641 is shown in FIG. 6, and is identical with the corresponding circuitry described above in the context of the Batter SCPO. The reference numerals "611" through "657" in FIG. 6 correspond to the identical elements "311" through "357" in FIG. 3.

The AND gate of the modulator for the Generator Embodiment is configured identically here as in the Battery SCPO. R2, R3, Q1 and Q2 (661, 663, 665, and 667) have the same values as in the SCPCO circuit (361, 363, 365 and 367).

The LED indicator circuit R1 669 and D1 541 differs from its counterpart in the Battery SCPO in that R1 669 is 330 Ohms rather than 2.151K . The resistor difference is for the purpose of obtaining the proper LED brightness in each circuit.

Adjustable resistor R17 677 provides a voltage divider between positive rail 602 and ground 603. The wiper of R17 677 provides a positively offset "ground" for purposes of output to the HP 8662A. The reason for this is that the HP 8662A expects an DC signal for purposes of modulation, so this adjustment is provided to offset the output around "zero volts" as referenced to the chassis of the HP 8662A.

The output of AND gate at the emitter of Q2 665 is connected to 8.2 uH inductor L2 671 (Miller 8230-18). The resultant signal is bypassed to ground by a relatively large electrolytic capacity or, 1.5 uF, rated at 35 volts C5 673, and then passed to the center lead of output BNC connector 521.

Figure 7A:
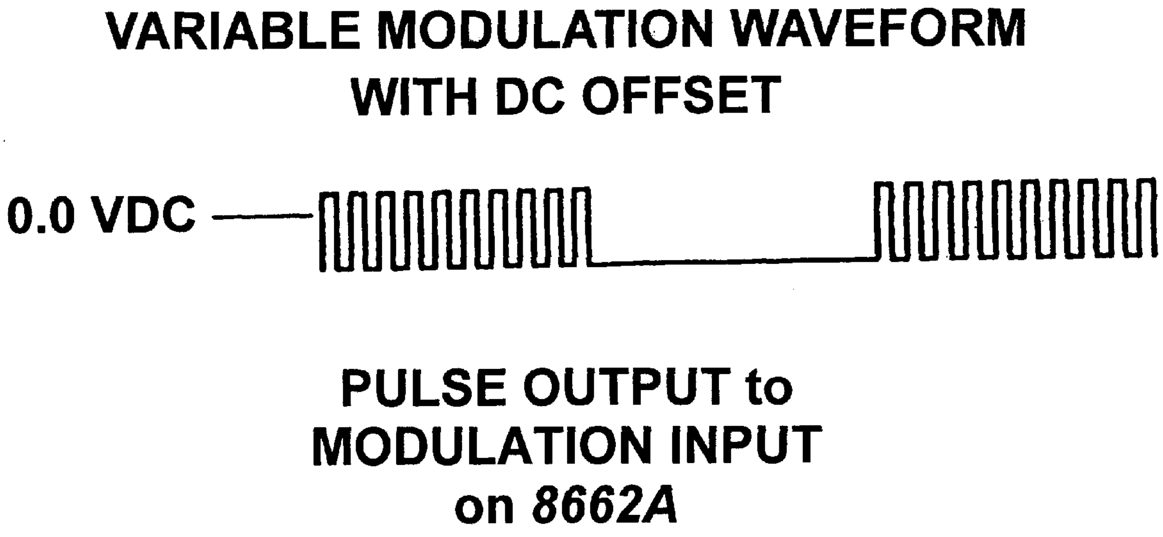
FIGS. 7A and 7B show respectively, the modulation waveform and a portion of the output waveform of the Generator Embodiment.
Figure 7B:
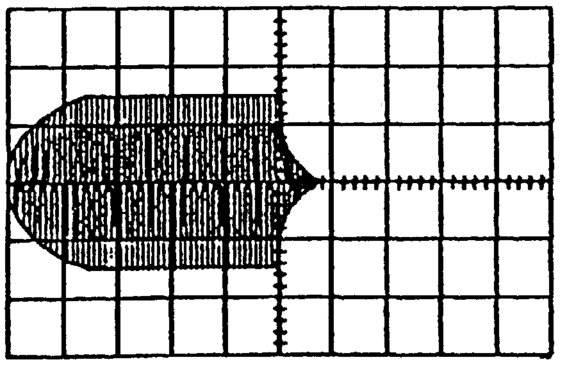

The approximate modulation waveform produced by modulator unit 540 is shown in FIG. 7A. The rounding of the rise and fall of the waveform is the result of capacitor C5 673. The modulated waveform of one of the 60 Hz. cycles output by the HP 8662A is shown in FIG. 7B (the RF component in figure is not drawn to scale). The output power of the frequency generator is less than 1 mw.

The output of frequency generator 500 is directed through a second BNC connector 531 connected to the panel of that instrument, and through a 50 Ohm, double-shielded coaxial cable 567 (RG 174 cable, Mouser #515-156-12 or equivalent). The coaxial cable is directed to a treatment loop 565 mounted on 2.0 mm. (0.080 inch) thick styrene sheet 566 which is laminated on stainless steel plate 560. The plate has dimensions of approximately 10.2 cm. by 6.35 cm. The treatment loop 565 is a 20 AWG solid copper wire approximately 60 cm. long, wound in a flat rectangular spiral comprising five turns, a turn-to-turn spacing of approximately 3.175 mm. and overall dimensions of 2.858×5.258 cm. The center of the loop is soldered to the center lead of coaxial cable 567. Shield 863 of coaxial cable 567 is soldered to the back of plate 560 at solder point 861. The outer end of treatment loop 565 is grounded by being soldered at solder point 570 to the loop side of plate 560. (Use A and B figures to show both sides of the plate.

The signal from the frequency generator based embodiment of the treatment device is stronger electromagnetically than that output by battery operated device 100. It is also characterized by having only a single pure RF component at the desired frequency in the 43 MHz range. The treatment loop of generator embodiment is applied to the subject in the same manner as in the case of the battery powered embodiment.

A parts list for the Generator Embodiment is set forth in Table 4.

TABLE 4

Parts List for Generator Embodiment

| Ref. No. | Description | Source |
|---|---|---|
| 500 | Hewlett-Packard 8662A Frequency Generator | Hewlett-Packard Company |
| 541 | D1 Indicator Light- 2 mA LED Diode | Radio Shack 276-044 or equiv. |
| 542 | SW1 Power Switch | Radio Shack 275-612 or equiv. |
| 550 | 9V DC Plug-In Power Supply Module | Radio Shack 273-1455C or equiv. |
| 560 | Treatment Loop holder | Fabricated- See text |
| 565 | Treatment Loop | Fabricated- See text |
| 567 | Coaxial Cable, 50 ohm, Shielded | RG174 cable Mouser #515-1156-12 |
| 605 | U1 7805 5 Volt Voltage Regulator 1C | Radio Shack 276-1770 or equiv. |
| 606 | 0.01 uF Disc Ceramic Capacitor, 500 Volt | Radio Shack 272-131 or equiv. |
| 607 | 0.01 uF Disc Ceramic Capacitor, 500 Volt | Radio Shack 272-131 or equiv. |
| 611 | U2 - TLC 555 Timer | Radio Shack 276-1723 or equiv. |
| 613 | R4 33K ± 5% ¼ Watt Carbon Resistor | Radio Shack 271-1341 or equiv. |
| 615 | R6 20K 15 Turn ¾ Watt Adj. Resistor | Radio Shack 271-340 or equiv. |
| 617 | R9 1.0 K ± 5% ¼ Watt Carbon Resistor | Radio Shack 271-1321 or equiv. |
| 619 | D2 1N914 Switching Diode 75 PIV | Radio Shack 276-1122 or equiv. |
| 621 | R5 47K ± 5% ¼ Watt Carbon Resistor | Radio Shack 271-1342 or equiv. |
| 623 | R7 20K 15 Turn ¾ Watt Adj. Resistor | Radio Shack 271-340 or equiv. |
| 625 | R8 2.2K ± 5% ¼ Watt Carbon Resistor | Radio Shack 271-1325 or equiv. |
| 627 | C3 0.22 uf Electrolytic Capacitor, 50 Volts | Radio Shack 272-1070 or equiv. |
| 641 | U3 - TLC 555 Timer | Radio Shack 276-1723 or equiv. |
| 643 | R10 33K ± 5% ¼ Watt Carbon Resistor | Radio Shack 271-1341 or equiv. |
| 645 | R12 20K 15 Turn ¾ Watt Adj. Resistor | Radio Shack 271-340 or equiv. |
| 647 | R14 1K ± 5% ¼ Watt Carbon Resistor | Radio Shack 271-1321 or equiv. |
| 649 | D3 1N914 Switching Diode 75 PIV | Radio Shack 276-1122 or equiv. |
| 651 | R11 47K ± 5% ¼ Watt Carbon Resistor | Radio Shack 271-1342 or equiv. |
| 653 | R13 20K 15 Turn ¾ Watt Adj. Resistor | Radio Shack 271-340 or equiv. |
| 655 | R15 2.2K ± 5% ¼ Watt Carbon Resistor | Radio Shack 271-1325 or equiv. |
| 657 | C4 1 Ouf Electrolytic Capacitor, 16 Volts | Radio Shack 272-1436 or equiv. |
| 661 | R2 330 Ohm ± 5% ¼ Watt Carbon Resistor | Radio Shack 271-1315 or equiv. |
| 663 | Q1 MPS2907 PNP Transistor | Radio Shack 276-2023 or equiv. |
| 665 | 02 MPS2907 PNP Transistor | Radio Shack 276-2023 or equiv. |
| 667 | R3 330 Ohm ± 5% ¼ Watt Carbon Resistor | Radio Shack 271-1315 or equiv. |
| 669 | R1 330 Ohm ± 5% ¼ Watt Carbon Resistor | Radio Shack 271-1315 or equiv. |
| 671 | L2 8.2 uH Inductor | Miller 8230-18 |
| 673 | C5 1.47 uF Electrolytic Capacitor, 35 Volts | Radio Shack 272-1433 & 1434 |
| 677 | R17 5K Adj. 15 Turn ¾ Watt Adj. Resistor | Radio Shack 271-340 or equiv. |

C. Alternative "Mouse SCPO" for Mouse Studies

Figure 2:
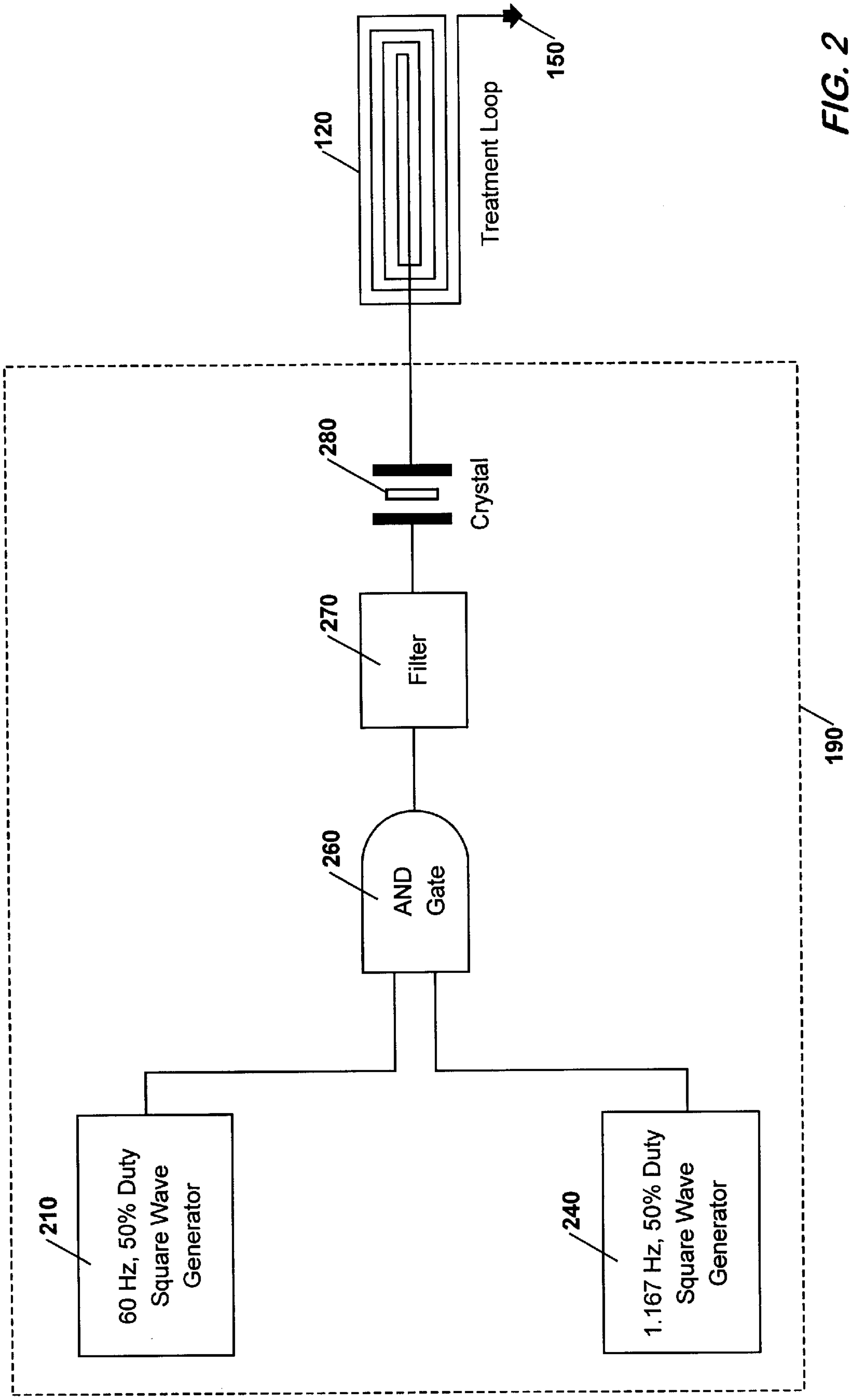
FIG. 2 is a block diagram of the major functional units of the Battery SCPO.

For purposes of the mouse studies described below, an alternative embodiment of the treatment device was developed, hereinafter referred to as the "Test Embodiment". The Mouse SCPO consisted of an apparatus similar to the battery SCPO described above, but without a battery compartment, and powered by an external AC power adapter. The power adapter used was the same Radio Shack adapter 550 used with the modulator for the Generator Embodiment. The power supply circuit in the Mouse SCPO was identical to that used in the modulator for the Generator Embodiment, comprising the 7805 regulator U1 605, and the two 0.01 uF bypass capacitors C1 606 and C2 607. In all other respects, the Mouse SCPO was as shown in FIGS. 1, 2 and 3, using the components listed in Table 4.

The feature lacked by the Mouse SCPO is the lack of restraint resulting from not being tethered by a wire. However, in the case of treating mice, this feature is irrelevant, since the mice must be immobilized for treatment in any event. On the other hand, the Test Embodiment had the advantage that it had no batteries to run low and to be checked and replaced.

D. Externally Pulsed Generator Embodiment

A further alternative embodiment of the treatment apparatus was developed, herein referred to as the "Externally Pulsed Generator." The Externally Pulsed Modulator embodiment is identical to the apparatus shown in FIG. 5, except that (1) the modulator does not attach to the Modulator Input of the HP 8662A, but rather attaches directly via a BNC connector to the Rf output of the HP8662A, (2) the modulator externally modulates the RF signal and does not utilize the internal modulation circuitry provided by the HP 8662A; and (3) the cable used to connect the modulator to the Treatment Loop is a specific type of coaxial cable, i.e., a Hewlett-Packard 10501A, 50 Ohm coaxial cable approximately 1.1 meters long.

The modulator in the Externally Pulsed Generator embodiment contains a series solid state RF switch and associated connectors, which is pulsed by a pulsing circuit identical to that shown in FIG. 6, except that potentiometer R17 677 and capacitor C5 671 have been removed and the ground is taken from the main power supply ground rail 1303 (corresponding to rail 603 in FIG. 6). (Since there is no need to interface with the modulator input of the 8662A, there is no need for the floating ground used in the output circuit of FIG. 6.)

Figure 36:
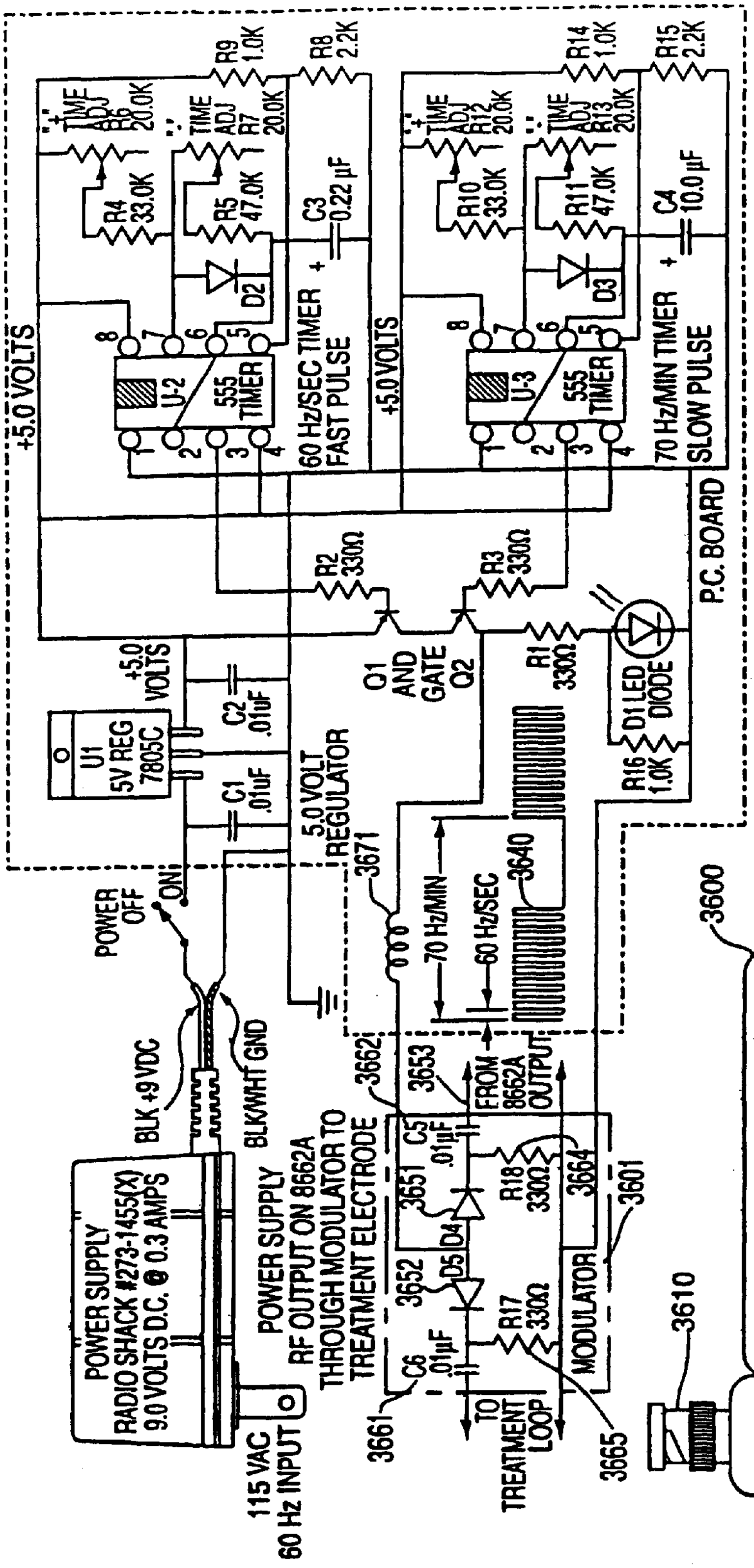
FIG. 36 is a schematic diagram for an external modulator that attaches to the radio frequency output of an HP 8662A Frequency Generator and FIG. 36A is a top view of the exterior of the device.
Figure 36A:
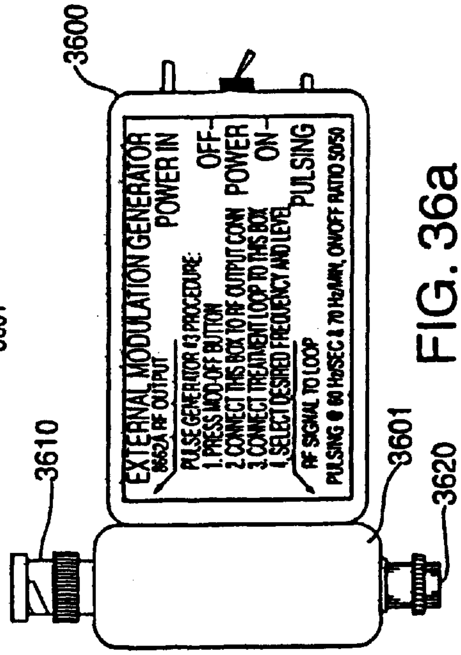

The schematic diagram in FIG. 36 shows the entire circuit of this external modulator. In FIG. 36A, which shows the exterior of the device, shielded box 3601 is attached to the end of modulator housing 3600. Male BNC connector 3610 attaches directly to the RF output of the 8662A. Female BNC connector 3620 attaches to the 10501 coax which in turn leads to the Treatment Loop. (Since this unit is a self-contained external modulator, it is necessary to turn off the modulation internal to the HP 8662A using the switch for that purpose on the control panel of the HP 8662A.)

In the RF switching circuit, the output of inductor L2 3671 is a 60 Hz/1.667 Hz. waveform 3640 (also as shown in FIG. 7A). This waveform shifts the bias on D4 3651 and D5 3652 so as to switch the RF applied to input 3653 in accordance with the pulses from L2 3671. In addition, inductor L2 3671 serves in this circuit as an RF choke keeping excessive RF from going back into the pulsing circuitry.

TABLE 4A

Additional Part for Externally Pulsed Generator Embodiment

| Ref. No. | Description | Source |
|---|---|---|
| 500 | C5 0.01 uf capacitor | Radio Shack 272-131 or equiv. |
| 541 | C6 0.01 uf capacitor | Radio Shack 272-131 or equiv. |
| 542 | R17 330 Ohm ± 5% ¼ Watt Carbon Resistor | Radio Shack 275-1315 or equiv. |
| 542 | R18 330 Ohm ± 5% ¼ Watt Carbon Resistor | Radio Shack 275-1315 or equiv. |
| 550 | D4 1N914 Switching Diode 75 PIV | Radio Shack 273-1122 or equiv. |
| 560 | Metal Box | Any suitable supplier |
| 565 | Male BNC connector | Any suitable supplier |
| 567 | Female BNC connector | Any suitable supplier |

3. EXPERIMENTAL PROCEDURE AND RESULTS

A controlled set of experiments were conducted during 1995 and 1996, to Jun. 25, 1996, to test the utility of the present invention wraith respect to the suppression and elimination of cancerous tumors, cysts, lesions, neoplasia. The experiments were performed upon mice, by the topical application of electromagnetic (EMR) radiation at specific frequencies and intensities on a regular schedule, using the apparatus of the present invention as adapted for applying EMR to mice. We also present some additional measuremnts taken in 1997 with respect to one mouse that was treated using the Externally Pulsed Generator Embodiment.

"Suppression and elimination" means that tumors, etc. that do develop are smaller in size, occur relatively infrequently and are likely, to disappear over time, as opposed to untreated tumors that are larger in size, occur more frequently and are unlikely to disappear before the death of the subject.

Use of JAX Mice as Experimental Subjects

The Jackson laboratory at Bar Harbor, Me, 04609 supplies mice for scientific research. These special mice are "JAX Mice," of a special inbred breed identified as C3HeOuJ. These mice are highly abnormal, in that they are inherently very susceptible to adenocarcinoma of the mammary gland, due to the contributing factors of inherited genes, excessive hormonal stimulation, and the mouse mammary tumor virus, which is passed to the young through the mother's milk The adenocarcinoma develop spontaneously in these mice, and the breed is characterized by a high incidence of mammary tumors by eight months of age. Our project has used "JAX Mice" type C3H HeOuJ throughout all of its research for treatment of mouse tumors, including all of the treated and control mice referred to herein.

The JAX C3H HeOuJ mice were selected in order to provide a sensitive animal model for testing anticancer treatments. The effectiveness of various treatments for such tumors is measured by determining improvements in lifespan or other physical characteristics, such as gross appearance, health status, and other related data, of groups that have received the treatment, as against untreated controls. This manner of testing using JAX mice is accepted as a valid animal model for determining the prospective utility of cancer treatments in humans.

In a memorandum dated Mar. 18,1997, The Jackson Laboratory notified users of C3H/HeOuJ that it had observed an alteration over time of the development and incidence of tumors in this strain. Our experiments were primarily conducted in a much earlier time frame than that concerned in this memorandum, and we do not believe any of our experimental results were affected thereby.

Summary of Experimental Procedures and Results

"Control" and "treated" selections of JAX mice (10 mice per group) were observed over the duration of their lives. Control mice were not exposed to the treatment procedure at all. The treated mice were exposed to EMR at the skin layer.

The treatment given was exposure to electromagnetic radiation applied to the skin of the mouse, with the radiation held at a given frequency throughout the treatment. The duration of treatment was usually one-half to one hour, and during the treatment, the treating electrode was shielded from undue light and moving air currents.

The data from our experiments, discussed in detail below, show that:

1. Treated mice live much longer than controls.
2. The life spans of treated mice compare favorably with life spins of normal (i.e., non-JAX) mice.
3. Treated mice have good health throughout their life.
4. Prior treatment has prevented abdominal tumor development.
5. When an abdominal tumor has been treated directly on the electrode it is caused to disappear.
6. By contrast:
   a) Tumors on control mice grow rapidly until death of the mouse,
   b) And as tumors grow, a control mouse gains weight, its hematocrit decreases and its health fails rapidly until death.

Treatment of the particular mice herein discussed was by exposure of the JAX mice to radiation from an electrode which was energized by a low power source that was preset to provide frequencies of 43.351830 MHz, 43.351850 MHz and 43.351870 MHz. In some cases, an HP-8662A Signal Generator preset to these frequencies was used, equipped with a modulator (in all but the 1997 data, an internally coupled modulator), to provide approximately 1.667 and 60 Hz., approximately 50% duty cycle square wave pulse trains as previously described. In other cases, the same pulsed treatment frequencies were obtained with the "Mouse SCPO" embodiment described above, which contained its own modulator circuit, driving an internal quartz crystal.

The frequencies selected, as listed in the preceding paragraph, were based on prior experiments conducted over a period of many years, during which a large number of mice were treated under varying conditions and with various treatments. The three frequencies specified in the preceding paragraph are believed by the inventors to be among the most effective frequencies for treating a range of maladies. When using the Mouse SCPO embodiment, the treatment frequency used 69% of the time (659 hours out of a total of 950) was 43351870 Hz. When using the HP 8662A signal generator for treatment, many (35) different frequencies were used.

Treatment Procedures

One of the treated mice (OUJ-479) received treatments before a tumor appeared and lived and died tumor free.

Treatment of the remaining mice started as soon as a tumor reached 0.07" in length, width, and height, corresponding to an ellipsoid having a volume of 0.0295 cubic cm. (0.00018 cubic inches). The treatments for all these ten mice were every day except Sunday. The treatment frequencies are limited to a few specific frequencies within a narrow range, and the intensities are normally set to 0 dBm into a 50 ohm load.

Due to variations among individual mice (as in other species, including humans), a treatment configuration that is effective for one subject doesn't always work for another. Frequencies of 43.351850 MHz and 43.351870 MHz were used for standard treatment on almost all of the mice These frequencies have demonstrated good results. Treating mice with 43.351850 MHz from a signal generator and/or pulsed crystal, appears to clear up their secondary infections, and treating with 43.351870 MHz seems to restore their general health. All of the treated mice appeared to be very lively and have a very healthy skin and hair appearance. Of the mice listed below, all hematocrit values have stayed in the healthy range of 38% to 46%, and their weight basically stayed the same since they began treatment.

Hematocrits for both the treated and the control mice were measured in accordance with the following procedure. The hematocrit was taken once a week. The mouse was placed under a heat lamp for a few minutes to cause the veins in the tail to dilate, thus making it easier to extract the blood for the sample. The amount of blood taken was about one-half of the standard 75 mm long capillary tube. The capillary tubes containing the blood are spun in a Micro-Hematocrit Centrifuge, at its "number three" marking. The capillary tubes are removed and placed in the Micro-hematocrit Tube Reader, which gives the percent of red blood cells found in the sample.

We have observed that tumors that have reached 0.07" in length, 0.07' in width, 0.07" in height are definitely a malignant growth, and benign or cystic lesions can be ruled out. Neoplasia measured under the agreed size are questionable. Almost all of the neoplasia encountered measured 0.07", 0.07", 0.07" and above.

The treatments employed a variety of treatment electrodes and housings, as shown in FIG. 9. The preferred housing was the "E" housing shown in FIG. 9A, and the preferred electrodes were the "I" electrode associated with the Mouse SCPO, FIG. 9J, and the "F" electrode used with the Hewlett-Packard signal generator, FIG. 9B.

Tumors treated directly on the treatment electrode slowly regressed until they were gone. Tumors that were not on, or only partially on, the electrode showed a decrease in growth rate, but the tumor would steadily grow and not regress back The electrode was re-designed so that any tumor could be treated. The tumor must be directly on the electrode to receive the maximum treatment needed for complete regression of growth. Mice with lesions on their abdomen had direct contact with the electrode, and all completely regressed back to zero. We've had similar success with some mice with lesions on the neck, left leg, right neck, right side, etc.

Since mammary tumors occur spontaneously in these mice, some mice were also treated before any tumors appeared in the hope of preventing the inevitable fate of the cancerous C3H strain, which have an almost 100% occurrence rate. At present one of the mice lived out its life span tumor free and died of old age.

Treated Mice

The following describes our experimental results with respect to each individual treated mouse. For each mouse, there is a corresponding drawing showing where on the mouse tumors appeared, and in which the tumors are identified by a "tumor number" T-X, as well as a drawing reference numeral; a graph showing tumor volume in cubic inches vs. time in days; a graph showing mouse weight in grams and hematocrit readings vs. time in days; and an Appendix setting forth all experimental measurements taken with respect to the mouse.

Figure 10A:
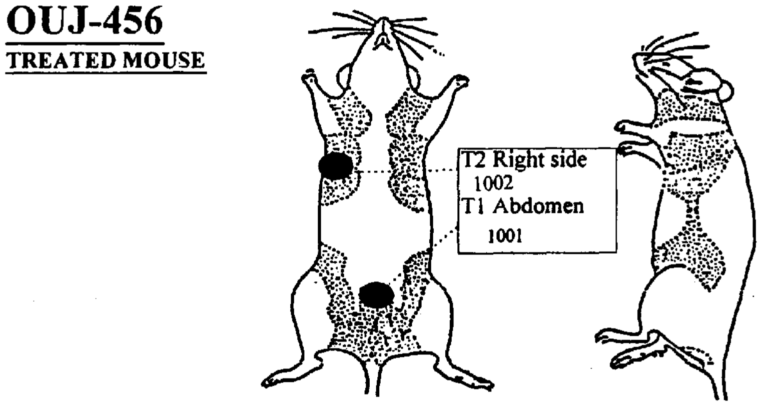
FIGS. 10 through 29 show, for each treated and control mouse involved in the inventors' experimental studies, A, the locations of the tumors (if any) that developed, B, plots (on a logarithmic scale) of the respective volumes of the various tumors as a function of time, and C, plots of the mouse's weight and hematocrit measurements as a function of time.
Figure 10B:
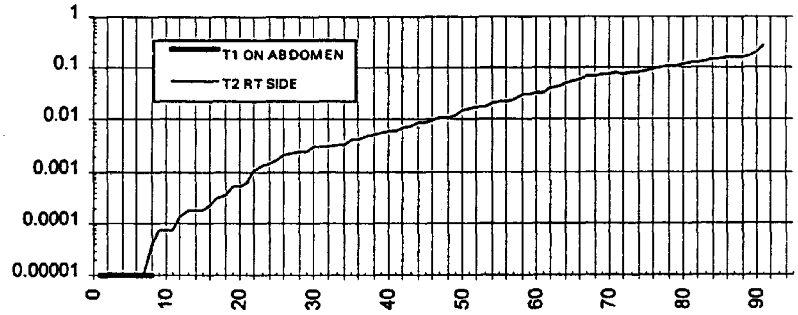
Figure 11A:
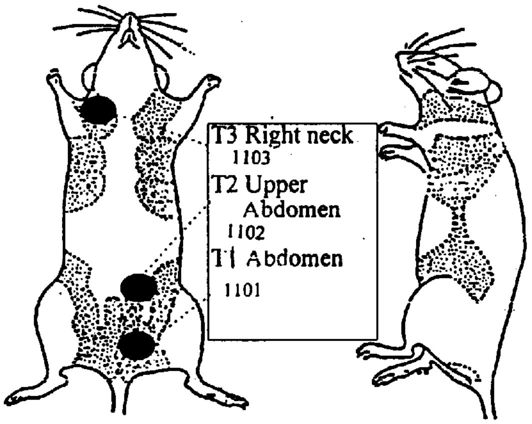
Figure 11B:
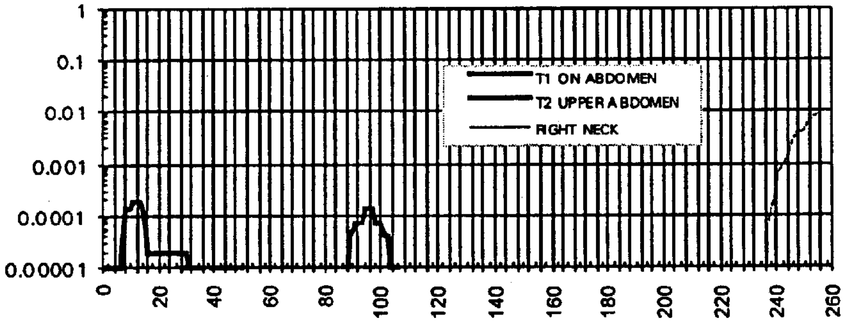

Each tumor growth graph (FIGs. 10B, 11B, etc.) shows the size of each tumor, in cubic inches, on the mouse in question as a logarithmic function of days after the appearance of the subject's first tumor. Tumor volume, in cubic inches, was calculated based on the assumption that the tumor was approximately an ellipsoid, and had a volume equal to ½ length×½ width×height×2.094.

Figure 10C:
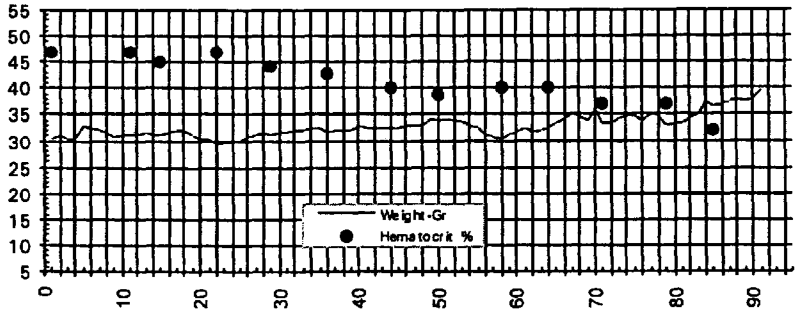
Figure 11C:
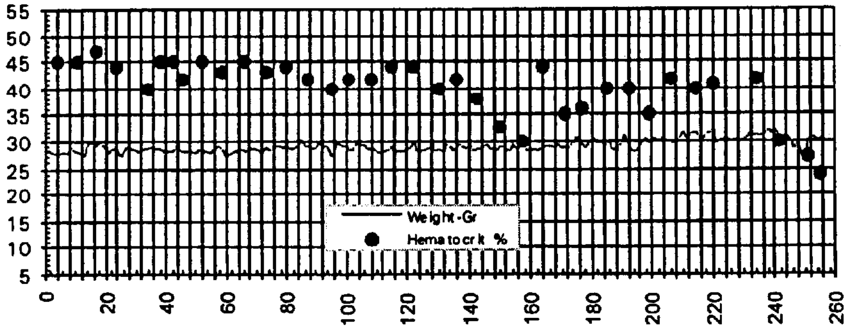

Each weight and hematocrit graph (FIGS. 10C, 11C, etc.) shows, in two separate plots, (a) the weight of the mouse, in grams, and (b) the subject's hematocrit values (percentage of red blood cells) as a linear function of days after the appearance of the subject's first tumor.

The detailed data collected with respect to each treated mouse is shown in tabular form in Appendices A-1, A-2, etc. attached hereto, and the data collected with respect to each control mouse is shown in tabular form in Appendices, B-1, B-2 , etc. attached hereto. The data with respect to one mouse tested in 1997 is shown in tabular form in Appendix C.

Example 1

Treated Mouse OUJ456

TABLE 5

| Treatment Summary for OUJ-456 | |
|---|---|
| Date of Birth: | 09/08/94 |
| Date Died: | 08/04/95 |
| Lived: | 310 days |
| Treated: | 91 days |
| Tumor measurements started: | 05/05/95 |
| Tumor measurements taken for: | 91 days |

This mouse lived 219 days before any tumor appeared. Notice (in FIG. 10B) that T-2 1002, which was hard to reach with our electrodes, grew, but at a slower rate than a typical control mouse. As will lie seen from this and the other examples herein, treated mice live three times longer than controls after a tumor appears.

Example 2

Treated Mouse OUJ470

TABLE 6

| Treatment Summary for OUJ-470 | |
|---|---|
| Date of Birth: | 03/03/94 |
| Date Died: | 07/30/95 |
| Lived: | 515 days |
| Treated: | 257 days |
| Tumor measurements started: | 11/16/94 |
| Tumor measurements taken for: | 257 days |

This mouse lived 258 days before any tumor appeared. Notice (in FIG. 11B) that T-1 1101 appeared and went away at two different times. T-2 1102 appeared for a short period. T-3 1103 appeared when this mouse was 496 days old. This is one of the longest-lived mice in our experiments.

Example 3

Treated Mouse OUJ471

TABLE 7

| Treatment Summary for OUJ-471 | |
|---|---|
| Date of Birth: | 03/03/94 |
| Date Died: | 07/20/95 |
| Lived: | 504 days |
| Treated: | 199 days |
| Tumor measurements started: | 01/02/94 |
| Tumor measurements taken for: | 199 days |

Figure 12A:
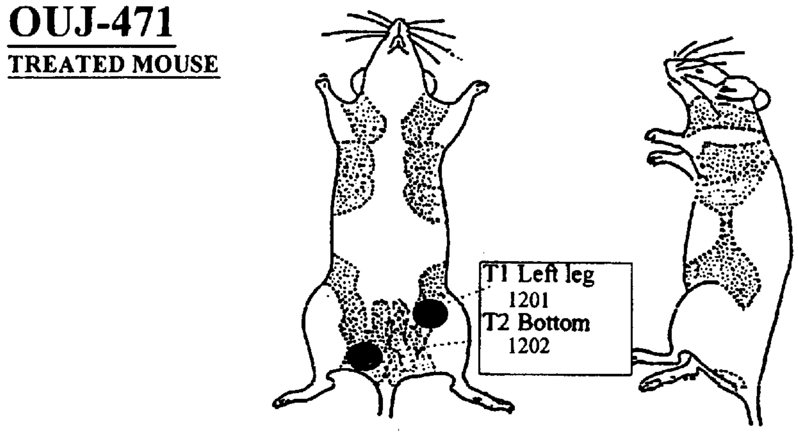
Figure 12B:
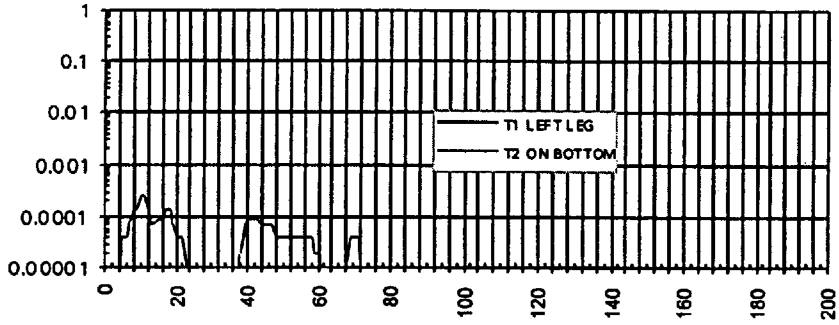
Figure 12C:
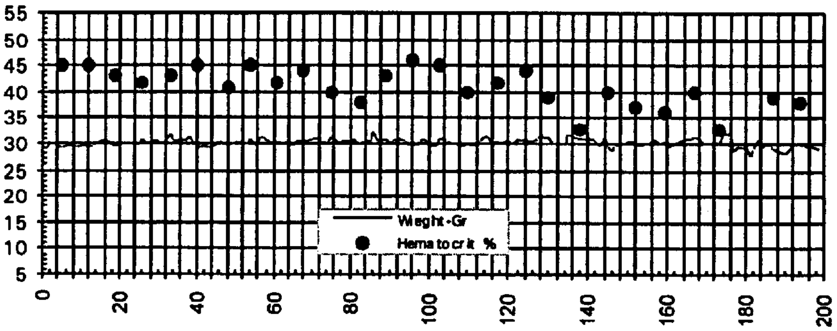

This mouse lived 305 days before any tumor appeared. Notice that T-1 1201 and T-2 1202 appeared for a short period. Notice (in FIG. 12C) the steady weight at 30 grams and constant high hematocrit percentage readings. This was also one of our longest-lived mice.

Example 4

Treated Mouse OUJ473

TABLE 8

| Treatment Summary for OUJ-473 | |
|---|---|
| Date of Birth: | 03/03/94 |
| Date Died: | 07/28/95 |
| Lived: | 514 days |
| Treated: | 211 days |
| Tumor measurements started: | 12/29/94 |
| Tumor measurements taken for: | 211 days |

Figure 13A:
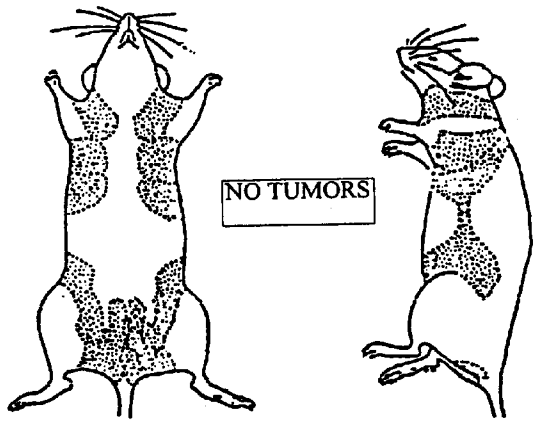
Figure 13B:
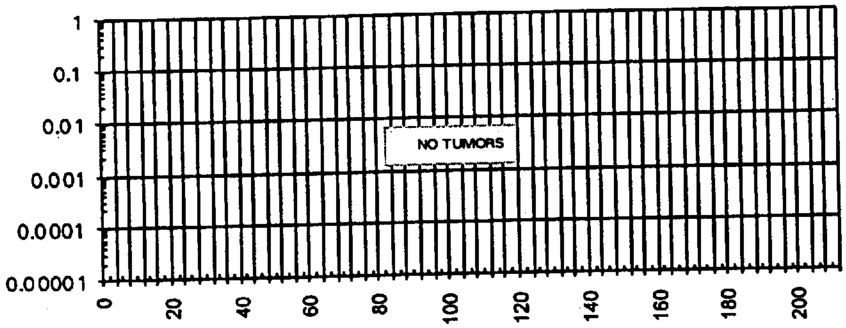
Figure 13C:
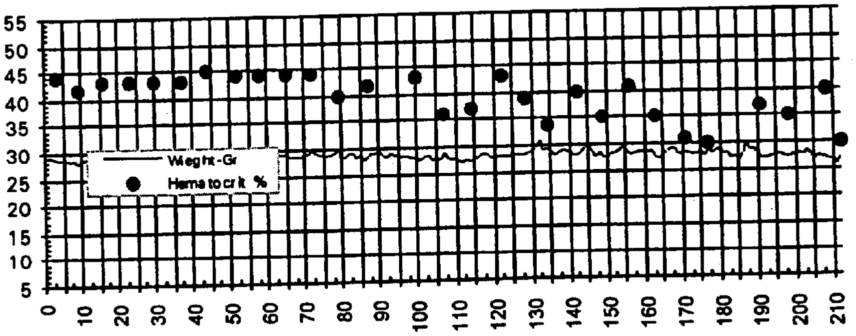

As an experiment, we treated this mouse before any tumors appeared. This mouse never developed any tumors (FIG. 13B). She lived 303 days before we started treatments. Notice (in FIG. 13C) the steady weight at 28 grams. This was also one of our longest-lived mice.

Example 5

Treated Mouse OUJ-475

TABLE 9

| Treatment Summary for OUJ-475 | |
|---|---|
| Date of Birth: | 03/03/94 |
| Date Died: | 07/28/95 |
| Lived: | 514 days |
| Treated: | 256 days |
| Tumor measurements started: | 11/14/94 |
| Tumor measurements taken for: | 256 days |

Figure 14A:
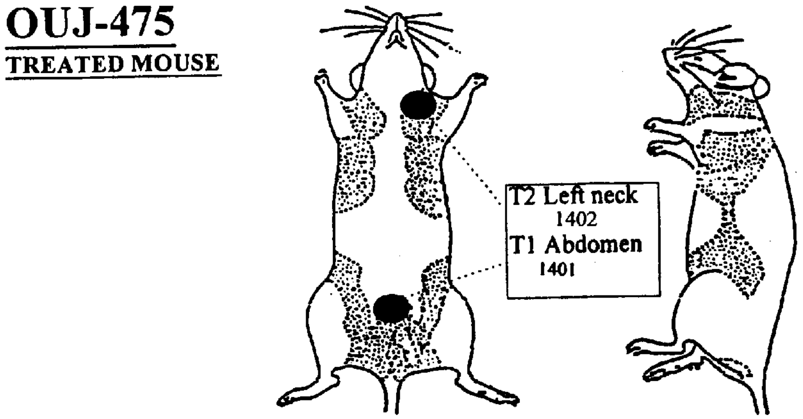
Figure 14B:
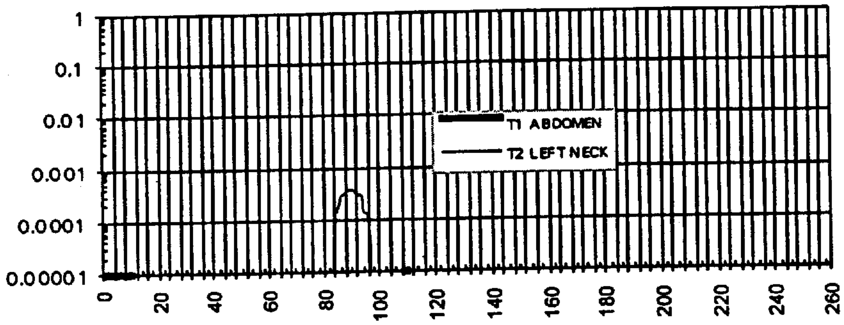
Figure 14C:
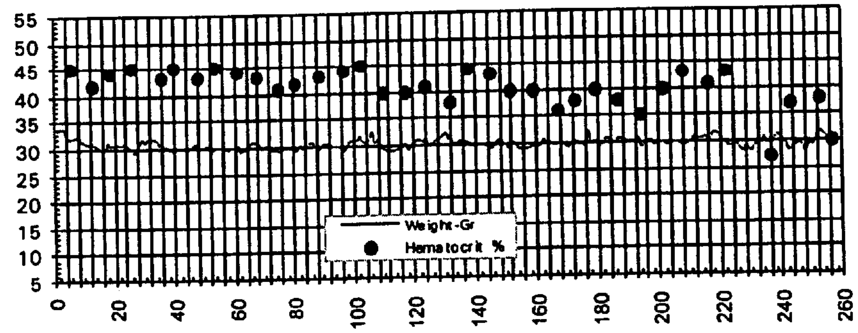

This mouse lived 258 days before any tumor appeared. Notice (FIG. 14B) that T-1 1401 and T-2 1402 appeared for a short period. Notice (FIG. 13C) the steady weight at 30 grams and quite-constant high hematocrit percentage readings. This was also one of our longest-lived mice.

Example 6

Treated Mouse OUJ496

TABLE 10

| Treatment Summary for OUJ-496 | |
|---|---|
| Date of Birth: | 12/21/94 |
| Date Died: | 01/05/96 |
| Lived: | 380 days |
| Treated: | 113 days |
| Tumor measurements started: | 09/15/95 |
| Tumor measurements taken for: | 113 days |

Figure 15A:
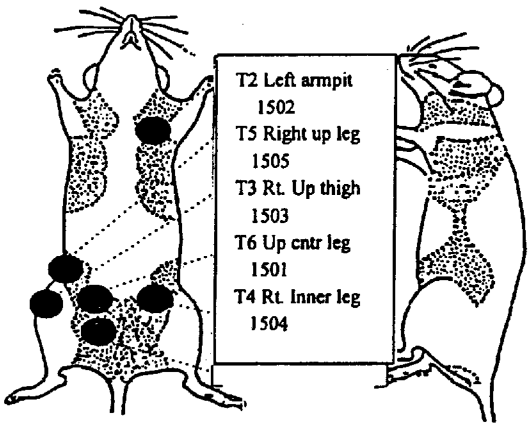
Figure 15B:
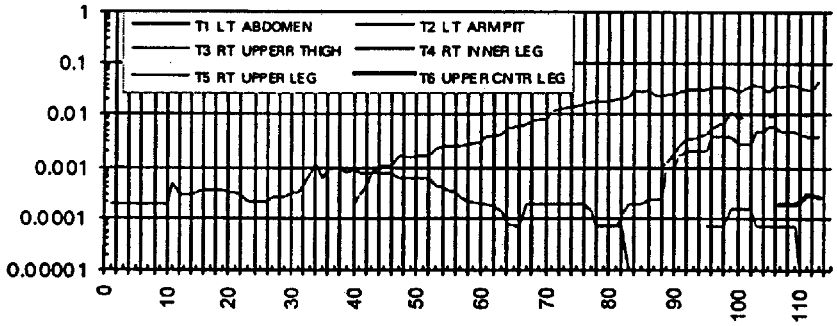
Figure 15C:
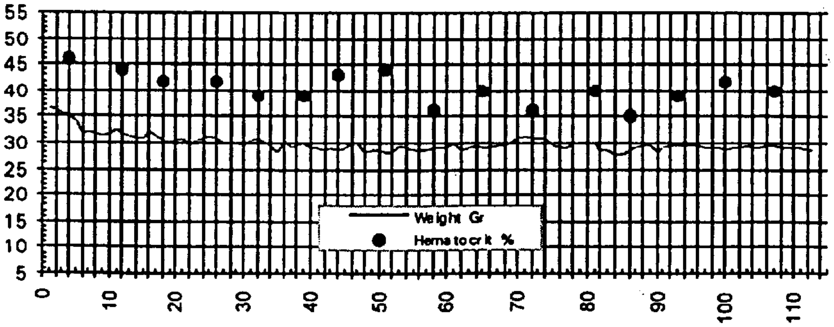

This mouse lived 267 days before any tumor appeared. Notice (FIG. 15B) that T-1 1501 and T-5 1505 appeared and left. Notice (FIG. 15C) the steady weight at 30 grams and high hematocrit percentage readings. Even with all these tumors, this mouse stayed healthy until the end and lived a long time.

Example 7

Treated Mouse OUJ-506

TABLE 11

| Treatment Summary for OUJ-506 | |
|---|---|
| Date of Birth: | 01/05/95 |
| Still living: | 06/25/96 |
| Lived: | 537 days |
| Treated (and/or took data): | 250 days |
| Tumor measurements started: | 10/19/95 |
| Tumor measurements taken for: | 250 days |

Figure 16A:
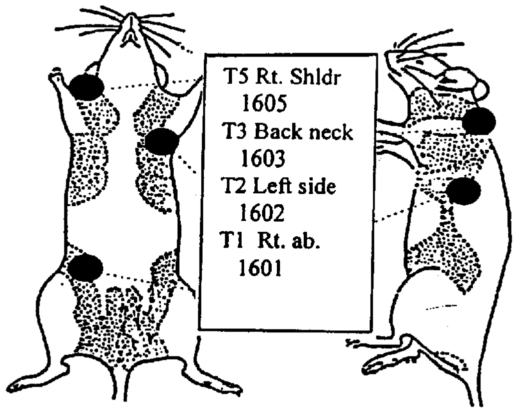
Figure 16B:
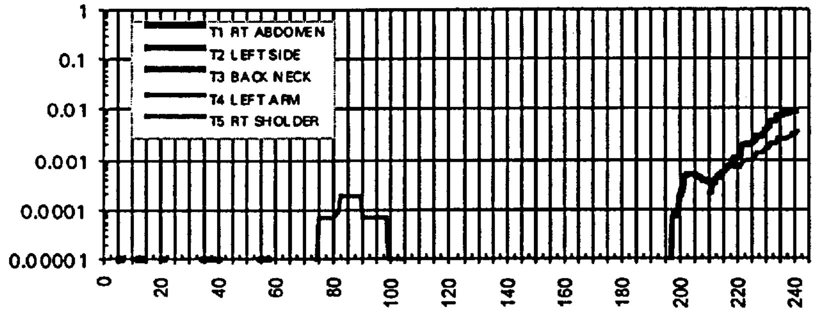
Figure 16C:
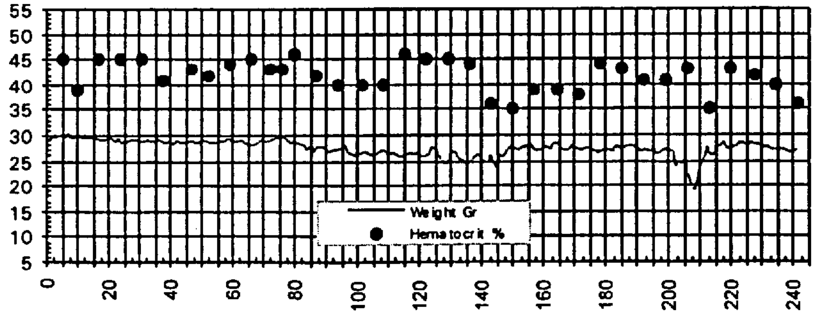

This mouse lived 287 days before any tumor appeared. Notice (FIG. 16B) that T1-1601, T-2 1602, and T-3 1603 appeared for a short period. After 170 days, T-2 1602 reappeared. Notice (FIG. 16C) the constant high hematocrit percentage readings. This was our longest-lived mouse, and it had a long healthy life.

Example 8

Treated Mouse OUJ-516

TABLE 12

| Treatment Summary for OUJ-516 | |
|---|---|
| Date of Birth: | 02/02/95 |
| Date Died: | 03/26/96 |
| Lived: | 418 days |
| Treated: | 240 days |
| Tumor measurements started: | 07/31/95 |
| Tumor measurements taken for: | 240 days |

Figure 17A:
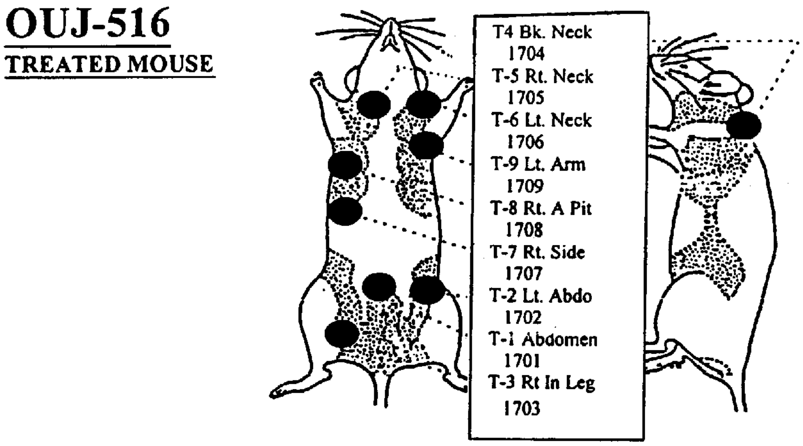
Figure 17B:
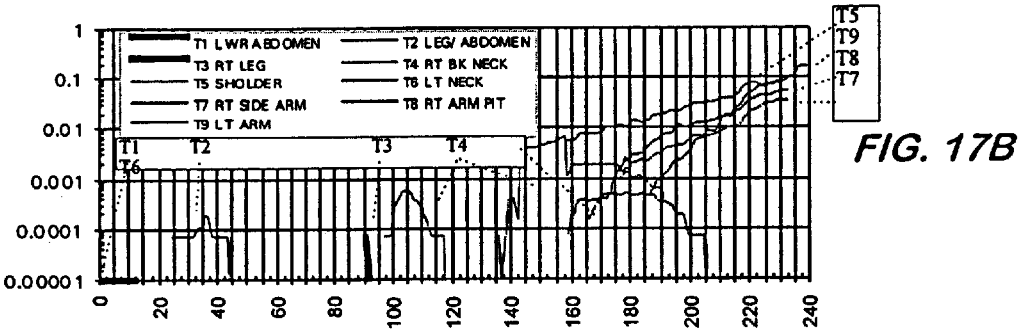
Figure 17C:

This mouse had a record number of tumors, many of which were not on the abdomen (FIG. 17A). After treatment all tumors disappeared except T5 1705, T7 1707, T8 1708, and T9 1709 (FIG. 17B). In spite of the large number of tumors, she lived 418 days.

Example 9

Treated Mouse OUJ-526

TABLE 13

| Treatment Summary for OUJ-526 | |
|---|---|
| Date of Birth: | 02/02/95 |
| Date Died: | 04/12/96 |
| Lived: | 435 days |
| Treated: | 168 days |
| Tumor measurements started: | 10/28/95 |
| Tumor measurements taken for: | 168 days |

Figure 18A:
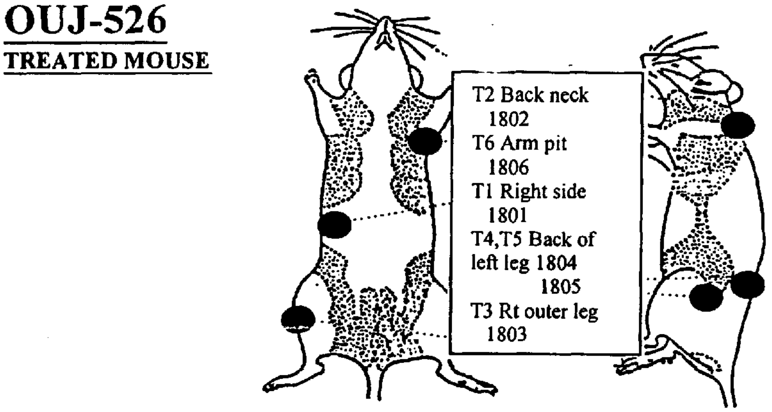
Figure 18B:
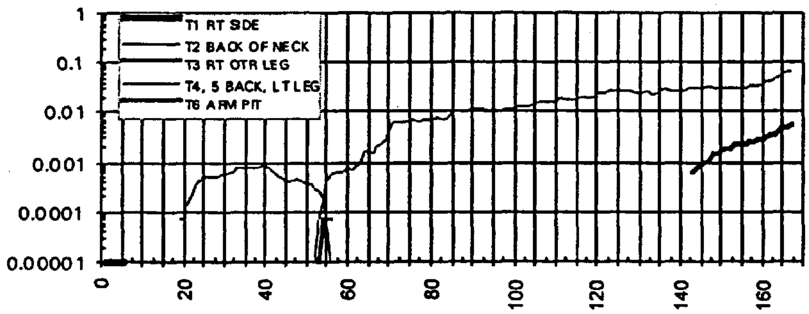
Figure 18C:
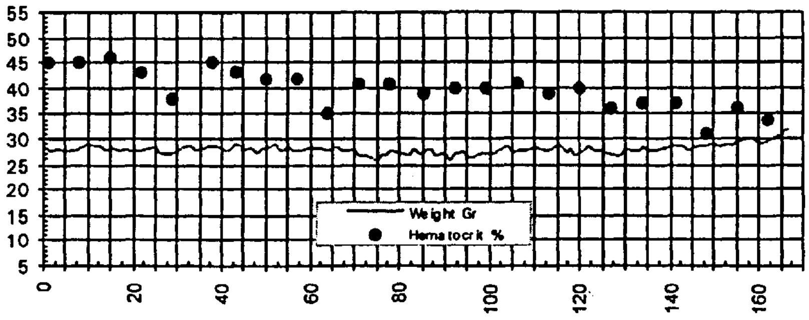

This mouse had three tumors which disappeared and never returned (FIG. 18B). She lived 267 days before any tumor appeared. T4 1804 and T5 1805 grew together as one tumor. Hematocrit percent (FIG. 18C) stayed quite high throughout her life.

Example 10

Treated Mouse OUJ-650

TABLE 14

| Treatment Summary for OUJ-650 | |
|---|---|
| Date of Birth: | 04/04/95 |
| Still living: | 06/25/96 |
| Lived: | 448 days |
| Treated: | 195 days |
| Tumor measurements started: | 12/13/95 |
| Tumor measurements taken for: | 195 days |

Figure 19A:
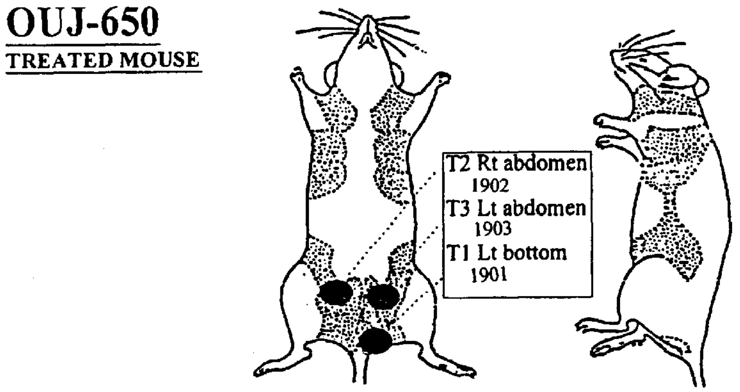
Figure 19B:
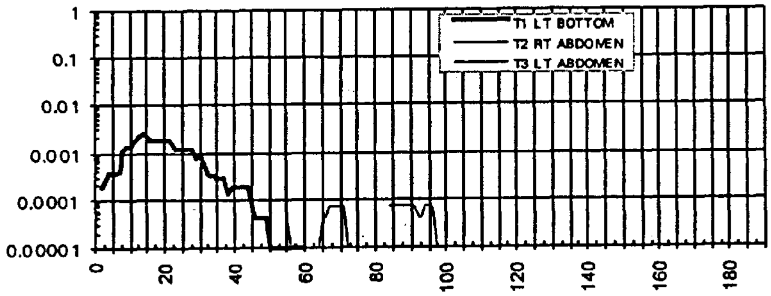
Figure 19C:
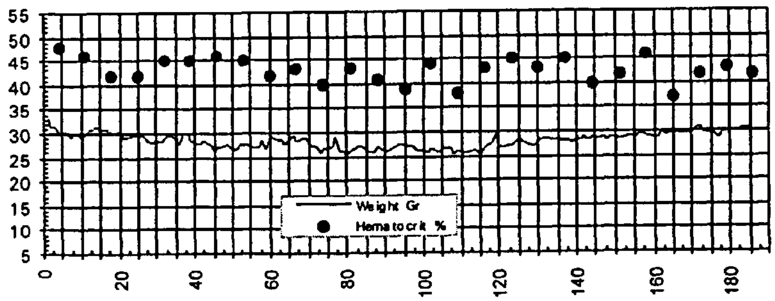

This mouse had three tumors, all of which disappeared and never re-appeared (FIG. 19B). Her hematocrit percent and remained high and her weight stayed constant throughout the measurement period (FIG. 19C).

Control Mice

The controls listed below all had spontaneous occurrences of multiple tumors that arose in various areas of the mammary gland region, and also had a very short survival time once the tumors appeared, usually around a two-month period.

None of the control mice in this study received EMR treatments or and other type of intervention methods. Daily weight and tumor measurements and observations were noted, as well as hematocrits to indicate the mouse s present health status at the time. These non-treated mice appeared to be in excellent health and appearance when the tumor remained small and didn't metastasize, but as the malignancy progressed and spread to other tissues, the effects on the mouse were readily seen.

The tumor measurements showed a rapid increase in tumor size that continuously, rose almost every day, accompanied with a steady) gain in weight, especially, with the arrival of news neoplasimis The hematrocrit steadily lowers with the increase in tumor measurements. Other side-effects were also observed in the controls, such as, the coat began to show a rougher appearance the back bone protruded out, they appeared to be malnourished, and the normal curiosity and physical activity, seen in healthy mice were absent The neoplasms' appearance also changed once the tumor reached a certain size, usually around 1.5 cm. in diameter and up. They usually would start to appear red and puffy, which would deepen in color showing areas of purple and black sores, which eventually ulcerated with severe bleeding. Some of the mice also appeared to get secondary infections once the tumor ulcerated, accompanied by the draining of clear fluid and WBC present in the wound. When the tumor reached a diameter of 1.8 cm., and the hematocrit value was 25% or lower, the mouse usually died within a couple of days.

As will be illustrated by the experimental data that follows, the characteristics of all control mice observed in the lab included the following: a rapid growth rate of tumors shown in the increasing size measurements and weight gain; metastasis; and continual decrease in hematocrit with the increasing tumor measurements. All the above symptoms affect the mouse's gross appearance, tumor appearance and shortened survival span once the tumors appear. This is reflected in the data that follows in the controls' rate of growth, and their decrease in hematocrit and length of survival period.

Example 11

Control Mouse A486

TABLE 15

| Summary for A-486 | |
|---|---|
| Date of Birth: | 04/04/95 |
| Date died: | 06/25/96 |
| Lived: | 448 days |
| Treated: | Not treated |
| Tumor measurements started: | 08/09/95 |
| Tumor measurements taken for: | 97 days |

Figure 20A:
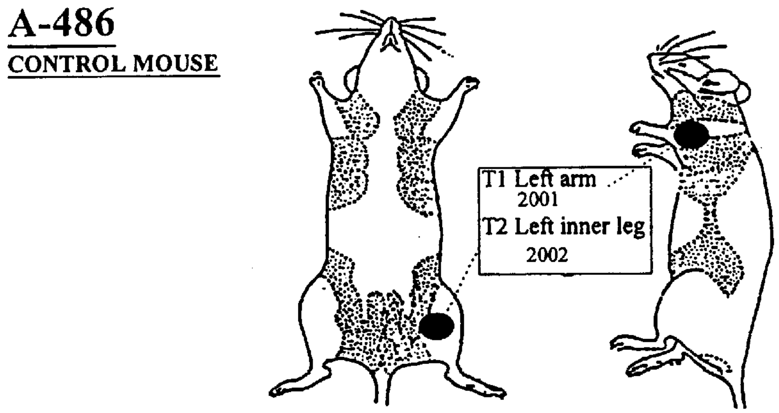
Figure 20B:
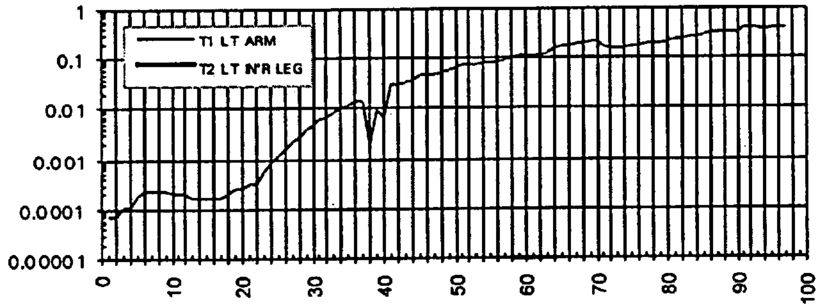
Figure 20C:
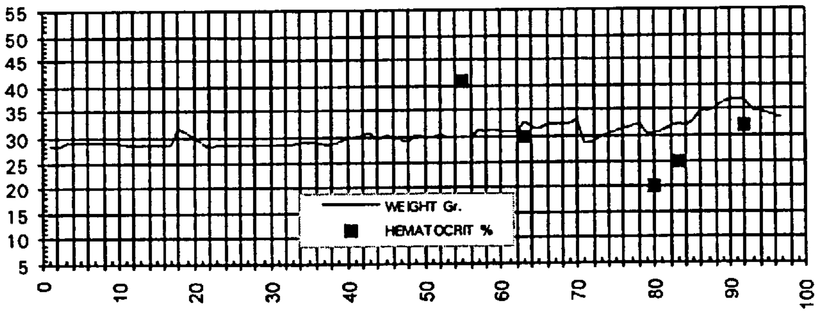

This mouse had one tumor which grew very rapidly to a large size (FIG. 20B). She had another tumor which appeared for 8 days. Her weight started to increase near the end, and the low hematocrit readings indicated a poor general health (FIG. 20C).

Example 12

Control Mouse A488

TABLE 16

| Summary for A-488 | |
|---|---|
| Date of Birth: | 11/28/94 |
| Date died: | 11/13/95 |
| Lived: | 350 days |
| Treated: | Not treated |
| Tumor measurements started: | 07/20/95 |
| Tumor measurements taken for: | 116 days |

Figure 21A:
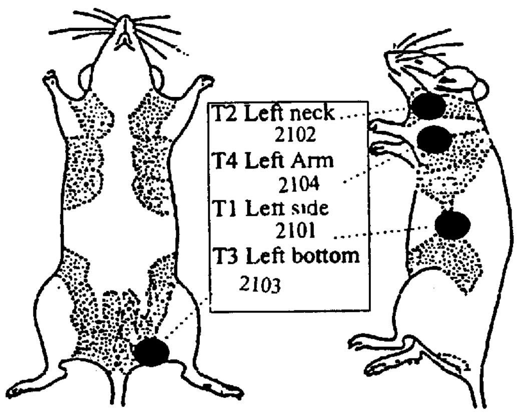
Figure 21B:
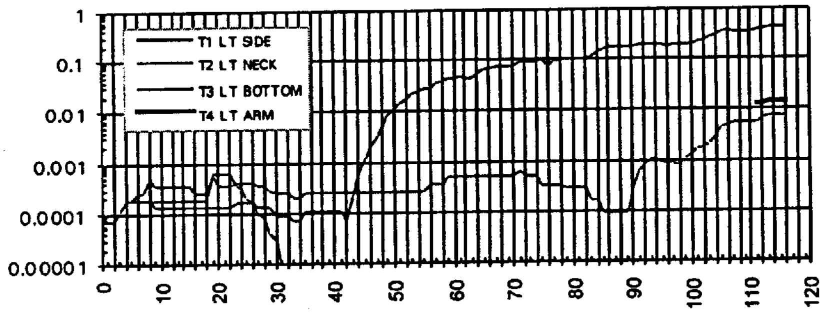
Figure 21C:
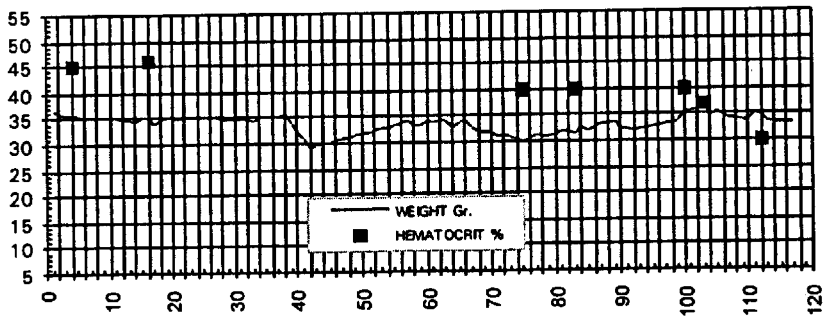

This mouse had one tumor (T1 2101) which didn't change much for forty days then grew rapidly (FIG. 21B) T-2 2102 came in and left after 32 days. T-3 2103 stayed constant in size for about 90 days, then grew rapidly.

Example 13

Control Mouse A490

TABLE 17

| Summary for A-490 | |
|---|---|
| Date of Birth: | 12/19/94 |
| Date died: | 11/29/95 |
| Lived: | 345 days |
| Treated: | Not treated |
| Tumor measurements started: | 10/11/95 |
| Tumor measurements taken for: | 50 days |

Figure 22A:
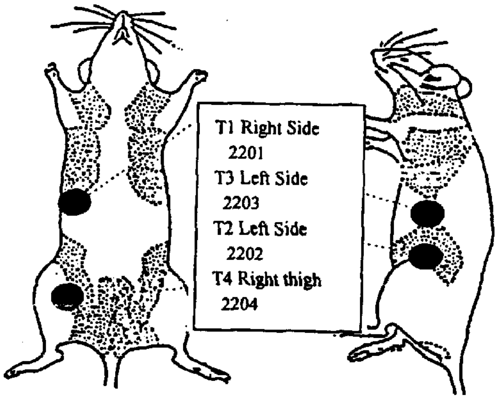
Figure 22B:
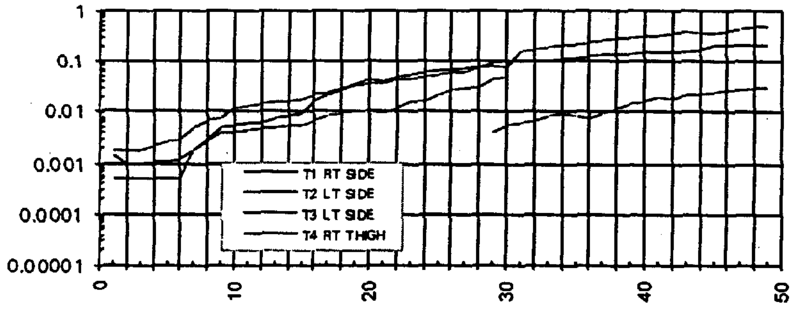
Figure 22C:
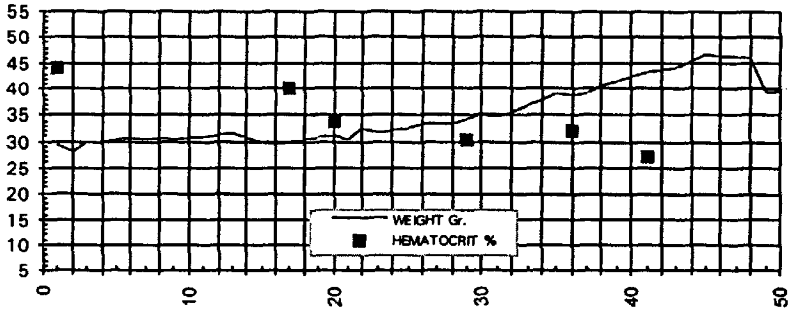

This mouse had four rapidly growing tumors and lived only fifty days after the first tumor appeared (FIG. 22B). After 20 days her weight increased and hematocrit reading steadily dropped (FIG. 22C).

Example 14

Control Mouse A-492

TABLE 18

| Summary for A-492 | |
|---|---|
| Date of Birth: | 12/19/94 |
| Date died: | 12/29/95 |
| Lived: | 375 days |
| Treated: | Not treated |
| Tumor measurements started: | 09/15/95 |
| Tumor measurements taken for: | 105 days |

Figure 23A:
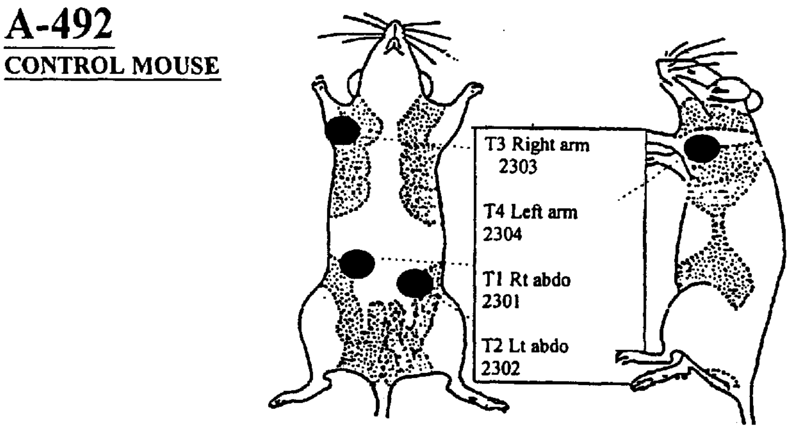
Figure 23B:
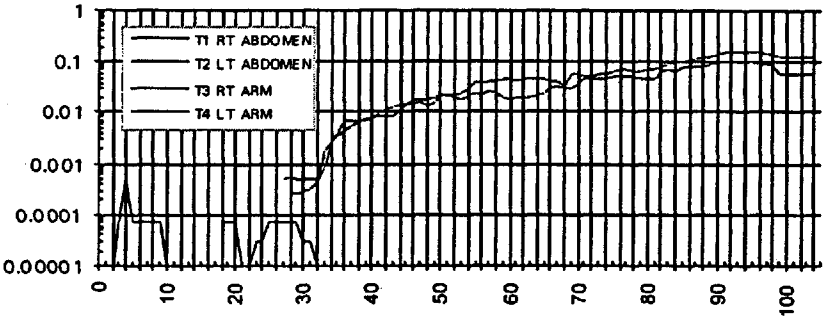
Figure 23C:
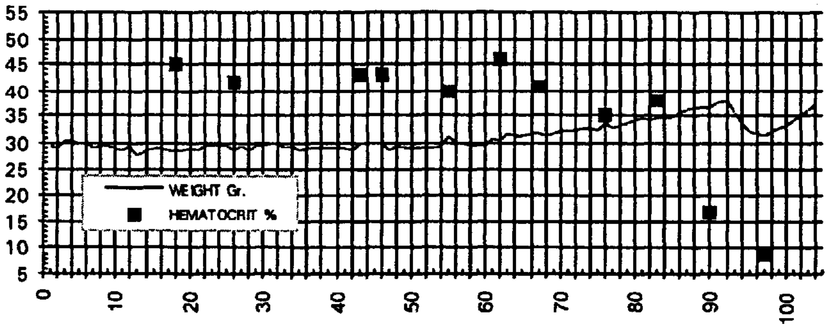

At 375 days, this is the longest lived control mouse. (Nine of our ten treated mice lived longer.) She had two tumors that left (FIG. 23B). But, after thirty, days, T3 2303 and T4 2304 appeared and started to grow very rapidly. Her hematocrits dropped rapidly after 70 days of measurements (FIG. 23C)

Example 15

Control Mouse A-500

TABLE 19

| Summary for A-500 | |
|---|---|
| Date of Birth: | 01/04/95 |
| Date died: | 10/11/95 |
| Lived: | 280 days |
| Treated: | Not treated |
| Tumor measurements started: | 09/15/95 |
| Tumor measurements taken for: | 26 days |

Figure 24A:
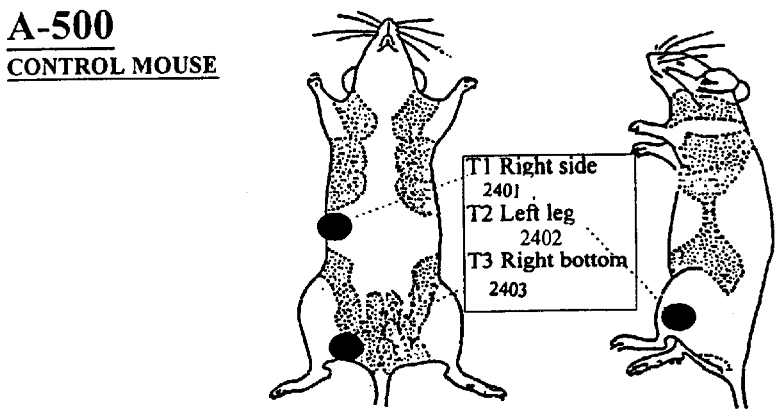
Figure 24B:
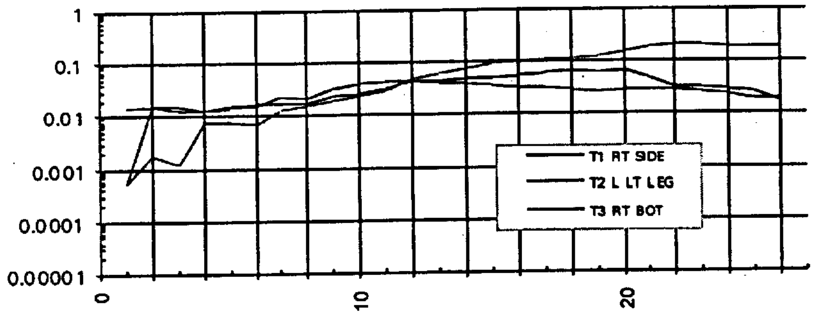
Figure 24C:
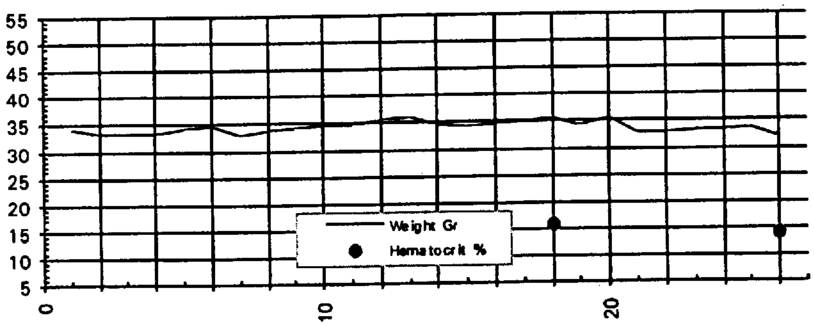

This mouse did not live very long and was observed only twenty-six days then she died. Tumors grew rapidly (FIG. 24B) and hematocrits were quite low (FIG. 24C).

Example 16

Control Mouse A-538

TABLE 20

| Summary for A-538 | |
|---|---|
| Date of Birth: | 03/24/95 |
| Date died: | 01/15/96 |
| Lived: | 297 days |
| Treated: | Not treated |
| Tumor measurements started: | 10/19/95 |
| Tumor measurements taken for: | 88 days |

Figure 25A:
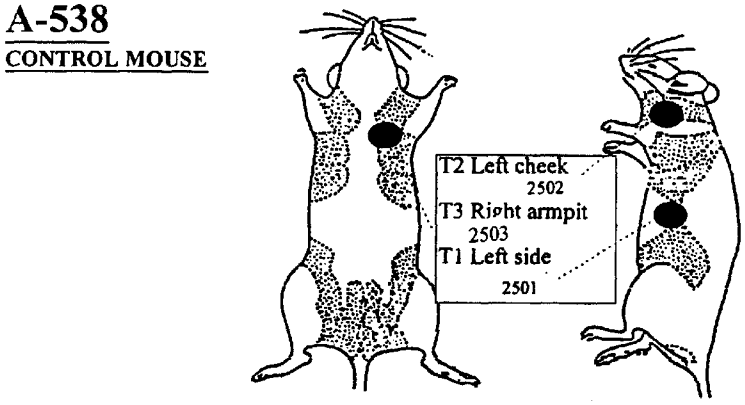
Figure 25B:
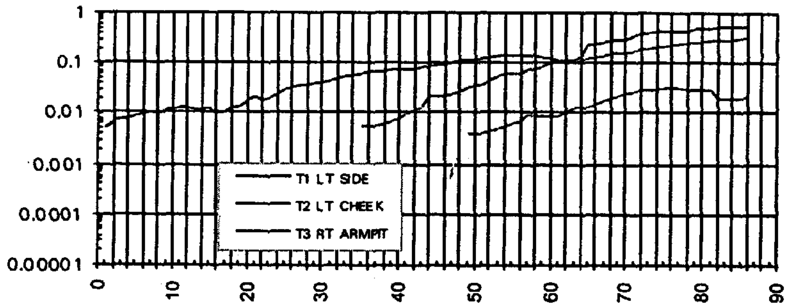
Figure 25C:
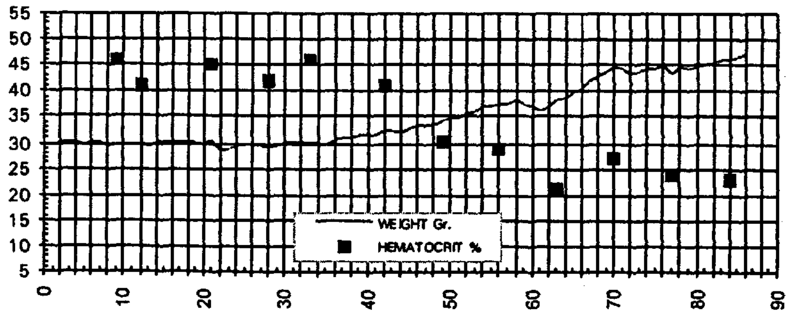

This mouse had three large tumors (FIG. 25B) and rapid weight increase and very low hematocrit percent readings (FIG. 25C). This mouse also did not live very long and was quite unhealthy.

Example 17

Control Mouse A-540

TABLE 21

| Summary for A-540 | |
|---|---|
| Date of Birth: | 03/25/95 |
| Date died: | 01/02/96 |
| Lived: | 283 days |
| Treated: | Not treated |
| Tumor measurements started: | 11/15/95 |
| Tumor measurements taken for: | 48 days |

Figure 26A:
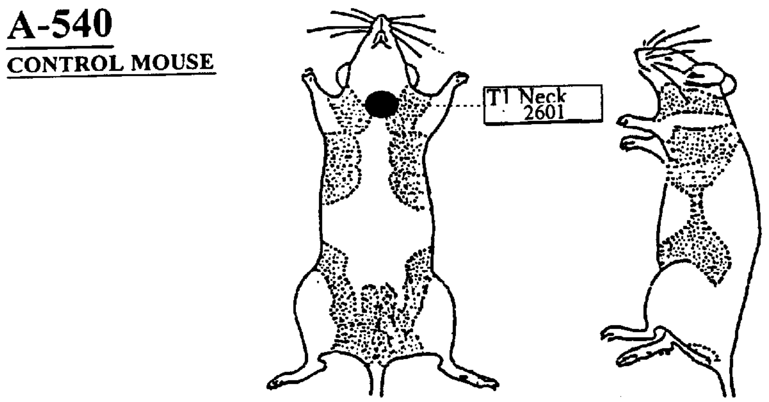
Figure 26B:
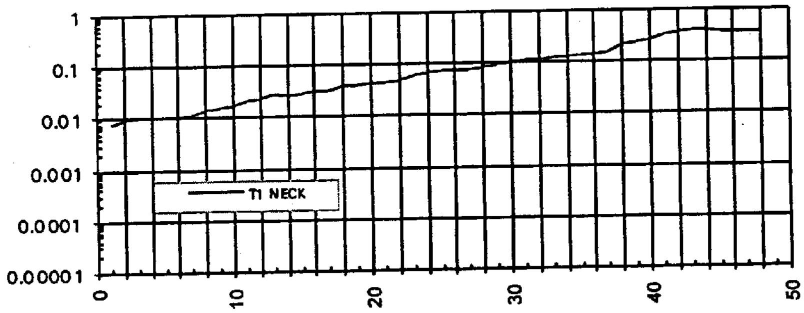
Figure 26C:
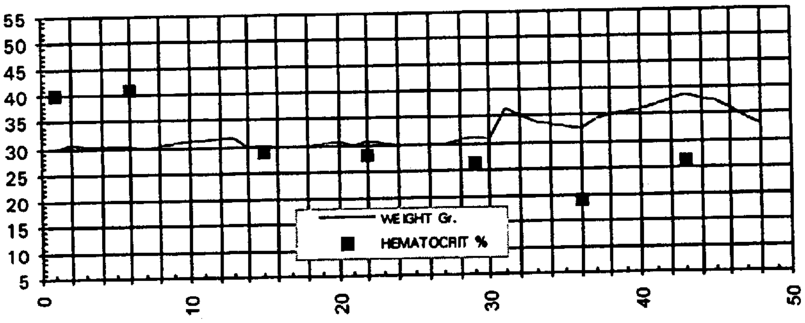

This mouse had one tumor that grew to a large size and grew fast (FIG. 26B). Low hematocrits caused this mouse to die in a short period (FIG. 26C).

Example 18

Control Mouse A-542

TABLE 22

| Summary for A-542 | |
|---|---|
| Date of Birth: | 03/25/95 |
| Date died: | 01/18/96 |
| Lived: | 299 days |
| Treated: | Not treated |
| Tumor measurements started: | 11/27/95 |
| Tumor measurements taken for: | 52 days |

Figure 27A:
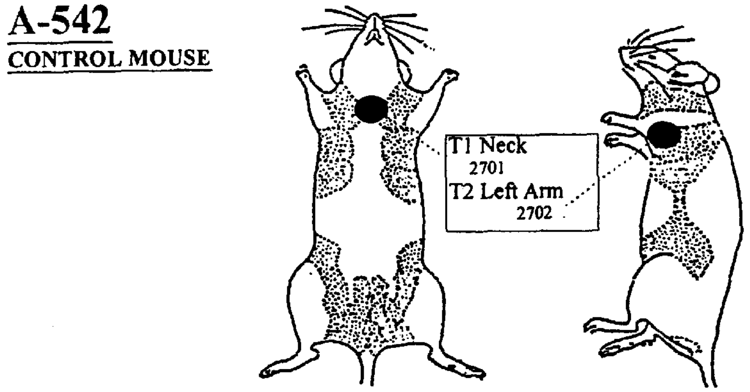
Figure 27B:
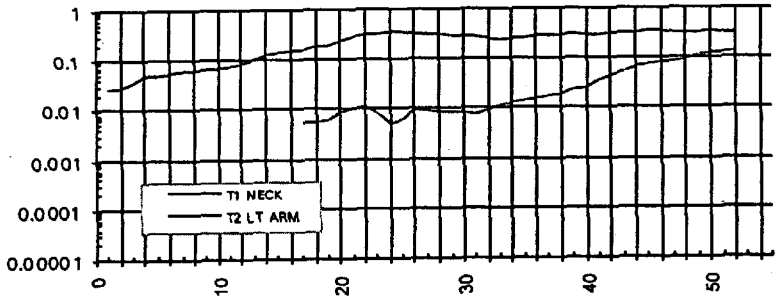
Figure 27C:
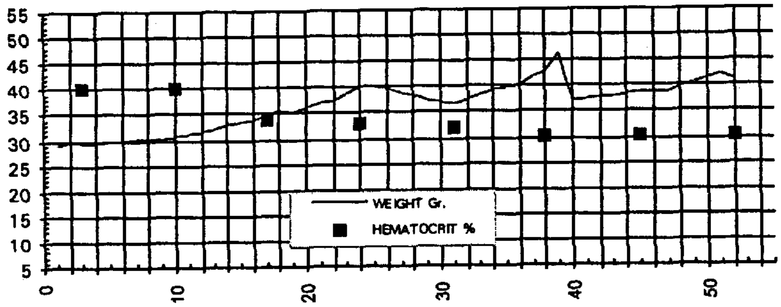

This mouse had two tumors that grew to a large size and grew fast (FIG. 27B). Weight continued to increase as the tumors grew (FIG. 27C). A tumor size of 0.1 to 0.5 cubic inches on a mouse this small is quite a burden for the mouse. They do not survive for long with tumors that size.

Example 19

Control Mouse A-592

TABLE 23

| Summary for A-592 | |
|---|---|
| Date of Birth: | 06/27/95 |
| Date died: | 02/14/96 |
| Lived: | 232 days |
| Treated: | Not treated |
| Tumor measurements started: | 01/19/96 |
| Tumor measurements taken for: | 26 days |

Figure 28A:
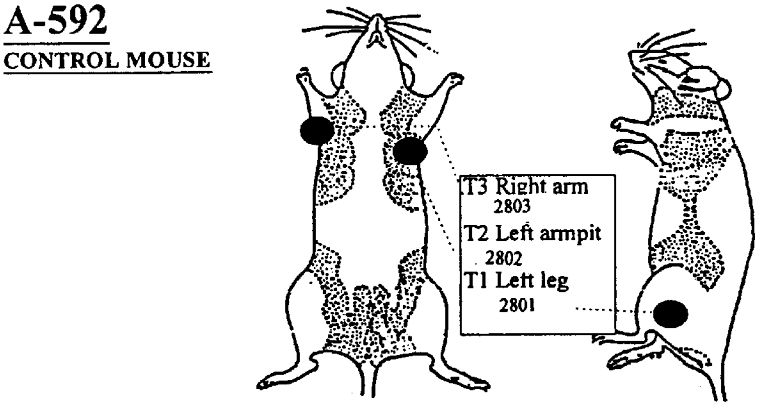
Figure 28B:
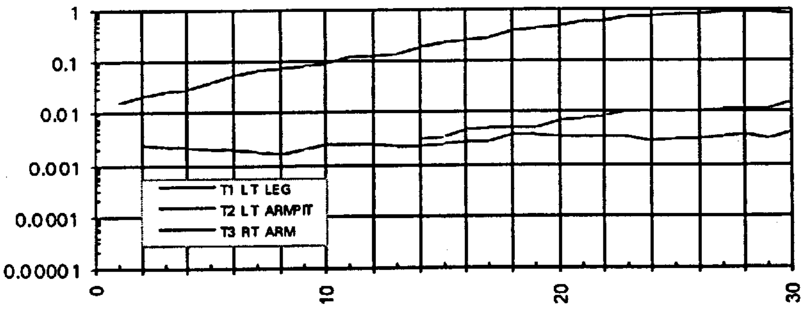
Figure 28C:
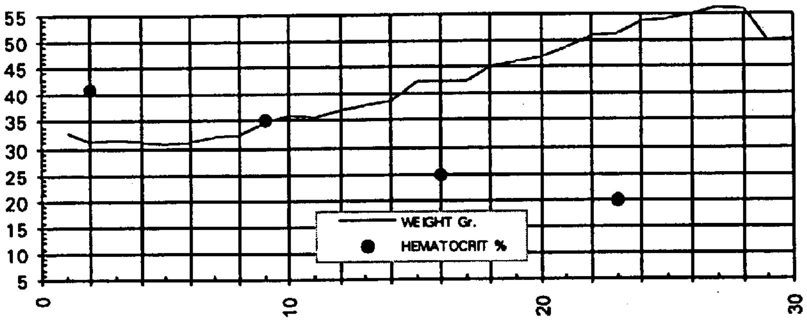

This mouse had one tumor that grew to a one cubic inch in size and grew fast (FIG. 28B). Rapid decline in hematocrits caused this mouse to die in a short period (FIG. 28C). Notice the rapid increase in weight: the mouse nearly doubled in weight in twenty days. This was a very short-lived mouse.

Example 20

Control Mouse A-594

TABLE 24

| Summary for A-594 | |
|---|---|
| Date of Birth: | 06/27/95 |
| Date died: | 02/15/96 |
| Lived: | 233 days |
| Treated: | Not treated |
| Tumor measurements started: | 01/12/96 |
| Tumor measurements taken for: | 34 days |

Figure 29A:
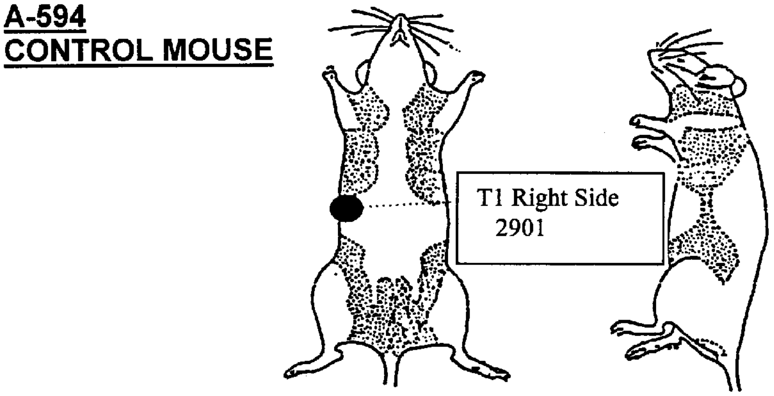
Figure 29B:
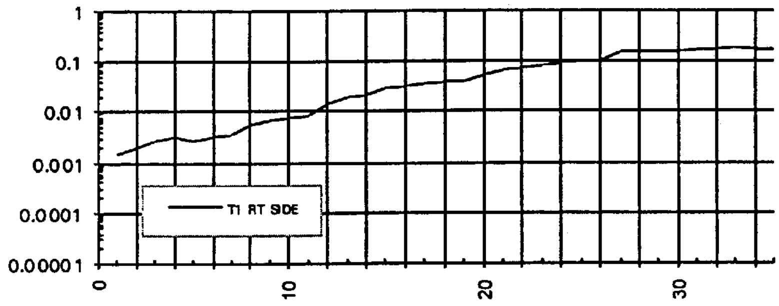
Figure 29C:
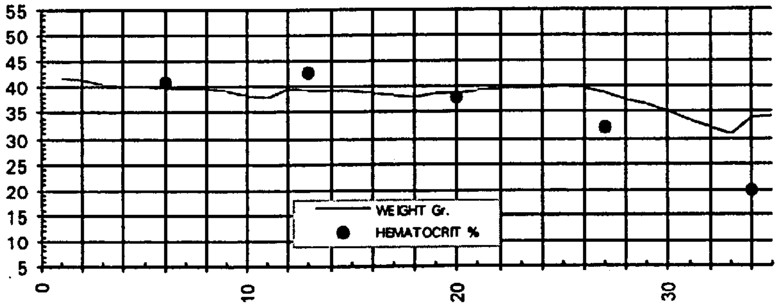

This mouse also had one tumor that grew to a large size and grew fast (FIG. 29B). Rapidly declining hematocrits caused this mouse to die in a short period (FIG. 29C). This is one of the shortest-lived control mice of the group.

Experimental Conclusions

Figure 30A:
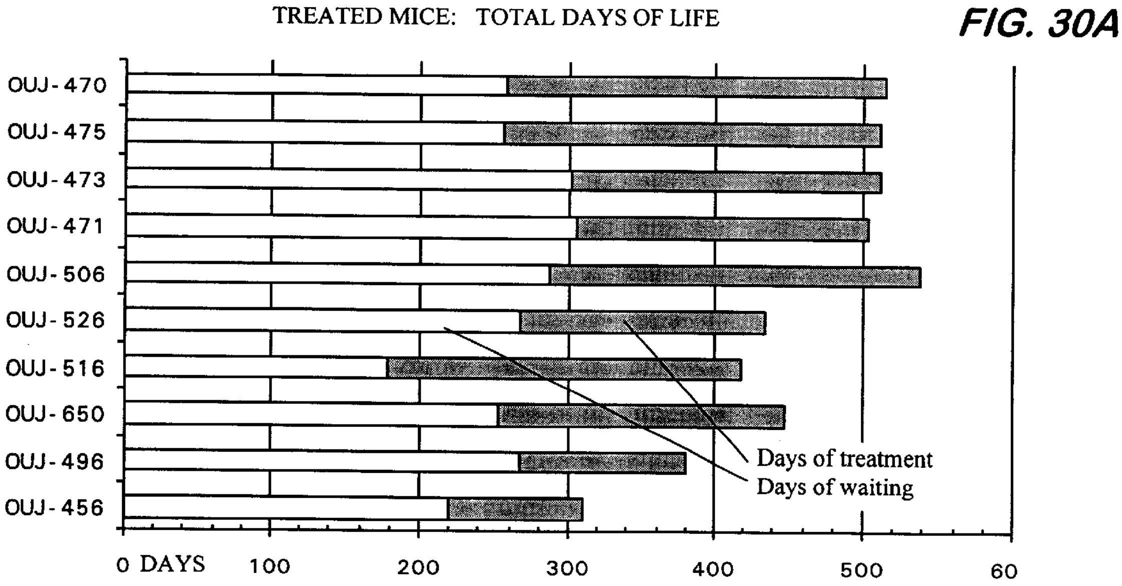
FIGS. 30A and B shows bar graphs of the life spans of the treated and control mice, respectively.
Figure 30B:
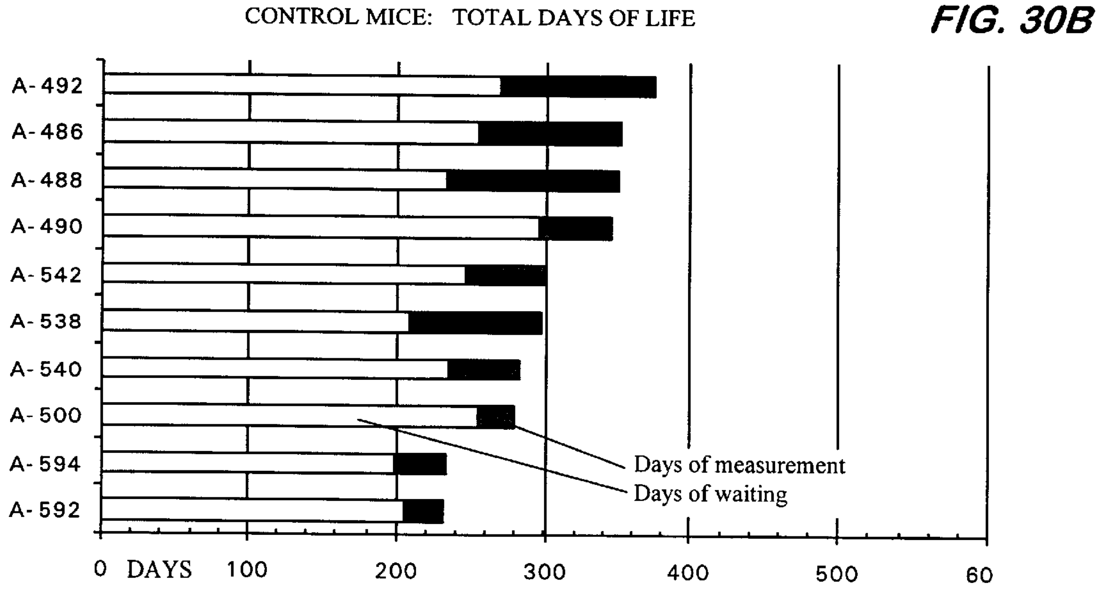

Our principal conclusion, based on the experiments described above, is that the cancer-prone JAX mice benefited considerably from the therapeutic apparatus and method of the present invention. The subsidiary experimental conclusions that support this assertion are as followers 1. Total Days of Life: Treated Mice Live 50% Longer The bar-graphs in FIG. 30 show that the treated mice lived approximately 50% longer on average than the controls. Each bar indicates: Days of Waiting 3001, Days of Treatment (or Measurement) 3002, 3003, and Total Days Of Life 3004.

The data underlying FIG. 30 (as well as FIGS. 31 and 32, discussed below) is presented below in tabular form.

TABLE 25

Days of Life, Measurement, and Number of Tumors

| SUBJECT | NON MEASURED DAYS | MEASURED DAYS | QTY OF TUMORS | TOTAL LIFE |
|---|---|---|---|---|
| OUJ-456 | 219 | 91 | 2 | 310 |
| OUJ-496 | 268 | 112 | 6 | 380 |
| OUJ-650 | 253 | 195 | 3 | 392 |
| OUJ-516 | 179 | 239 | 9 | 418 |
| OUJ-526 | 268 | 167 | 5 | 435 |
| OUJ-506 | 287 | 250 | 5 | 481 |
| OUJ-471 | 305 | 199 | 2 | 504 |
| OUJ-473 | 301 | 211 | 0 | 512 |
| OUJ-475 | 256 | 256 | 2 | 512 |
| OUJ-470 | 258 | 256 | 3 | 514 |
| Totals: | 2594 | 1976 | 37 | 4,458 |
| A-592 | 206 | 26 | 3 | 232 |
| A-594 | 199 | 34 | 1 | 233 |
| A-500 | 254 | 26 | 3 | 280 |
| A-540 | 235 | 48 | 1 | 283 |
| A-538 | 209 | 88 | 3 | 297 |
| A-542 | 247 | 52 | 2 | 299 |
| A-490 | 296 | 49 | 4 | 345 |
| A-488 | 234 | 116 | 4 | 350 |
| A-486 | 255 | 97 | 2 | 352 |
| A-492 | 270 | 105 | 4 | 375 |
| Totals: | 2405 | 641 | 27 | 3,046 |

Figure 31A:
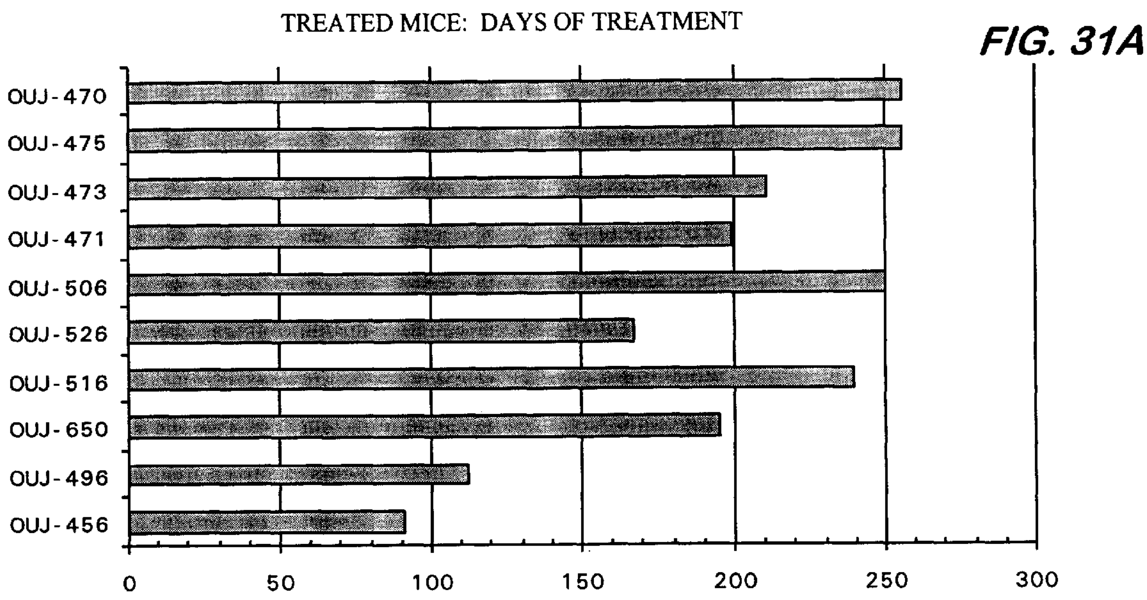
FIGS. 31A and B shows bar graphs of the life spans of the treated and control mice, respectively, after tumors were detected.
Figure 31B:
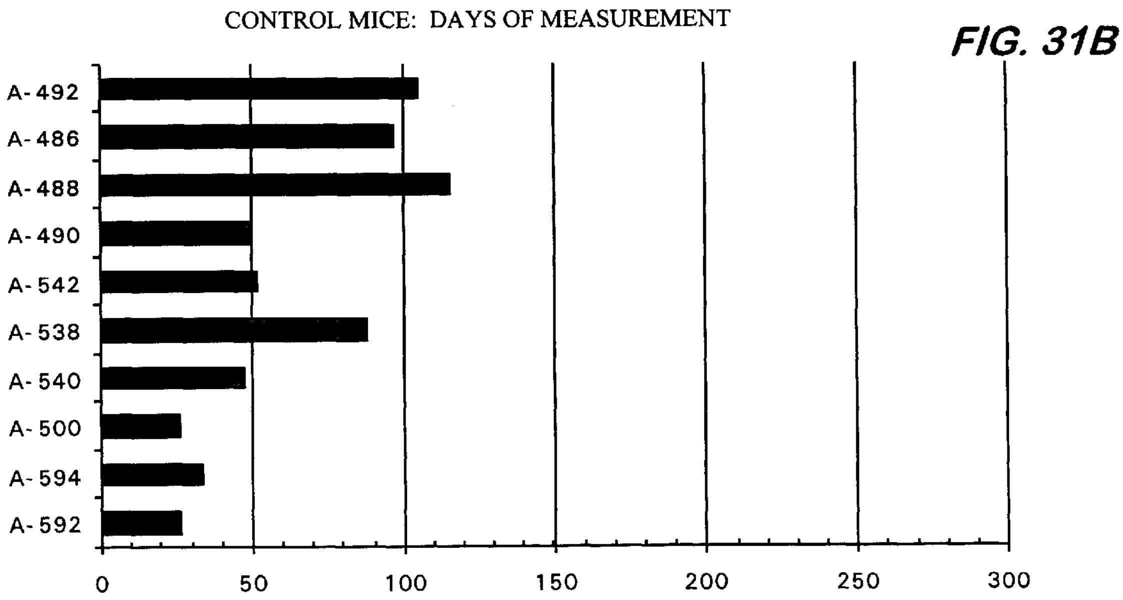

2. Starting Treatment After First Tumor Appears: Treated Mice Live More than 300% Longer FIG. 31 shows that after the first tumor appeared, the treated mice lived longer than the control mice. The bars in these graphs represent Days of Treatment for treated mice or Days of Measurement for control mice. The data underlying FIG. 31 is set forth in Table 25 above.

3. The Treated Mice Had More Tumors (by 37%), But Then Lived Longer

Figure 32A:
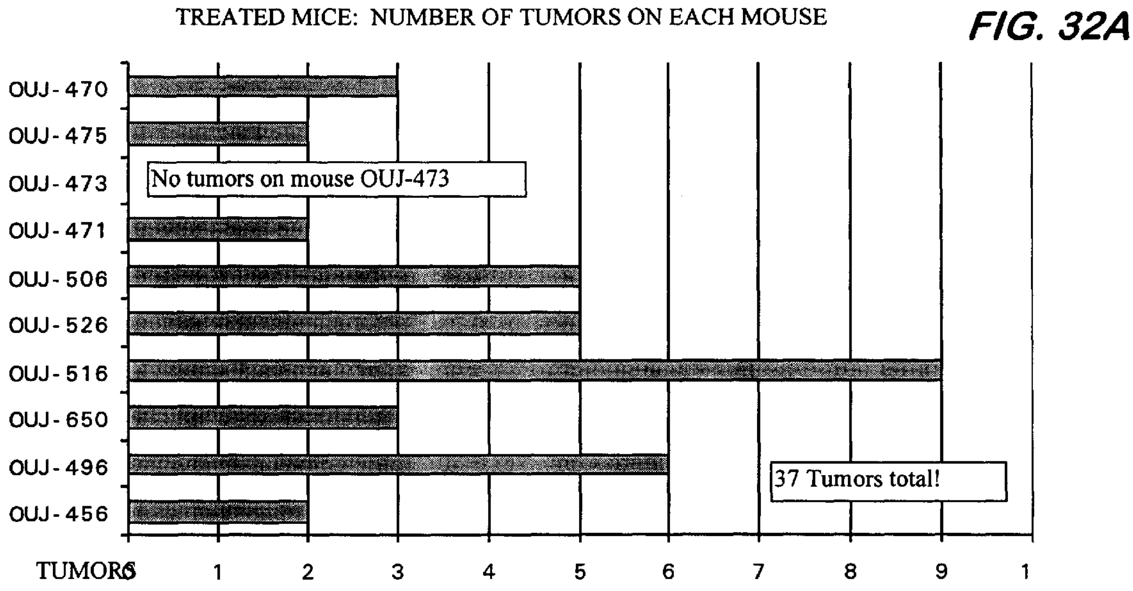
FIGS. 32A and B shows bar graphs of the number of tumors in the treated and control mice, respectively.
Figure 32B:
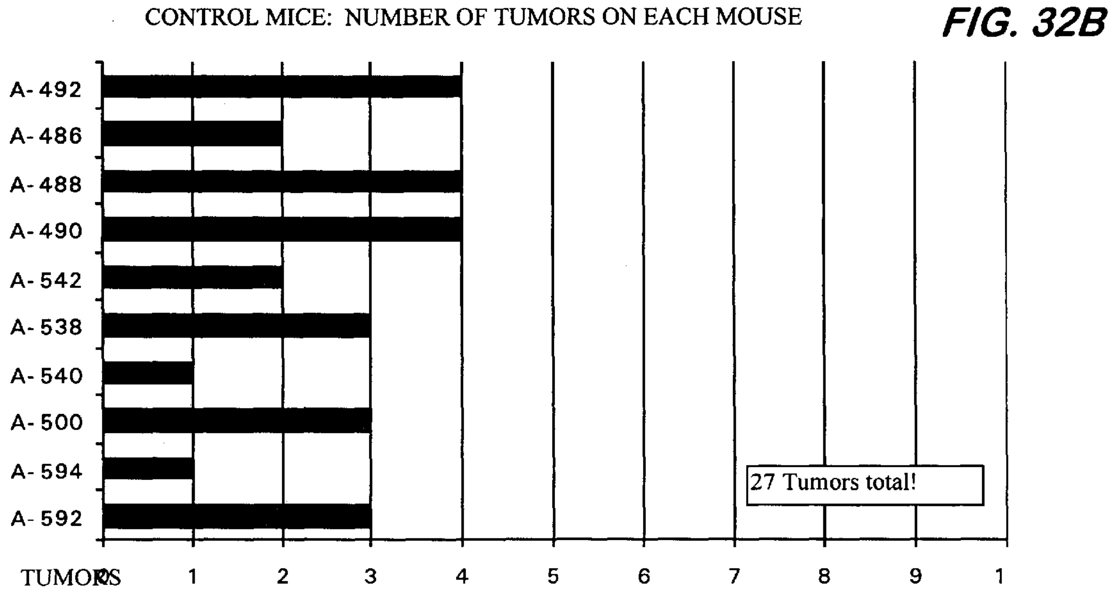

FIG. 32 shows the number of tumors that developed in each mouse. It must be noted that even though there were 37% more tumors in the treated mice, they lived longer than the controls. The data underlying FIG. 32 is set forth in Table 25 above.

4. Tumors that Appeared were Five Times More Likely to Disappear in the Treated Mice than in the Controls.

Figure 33A:
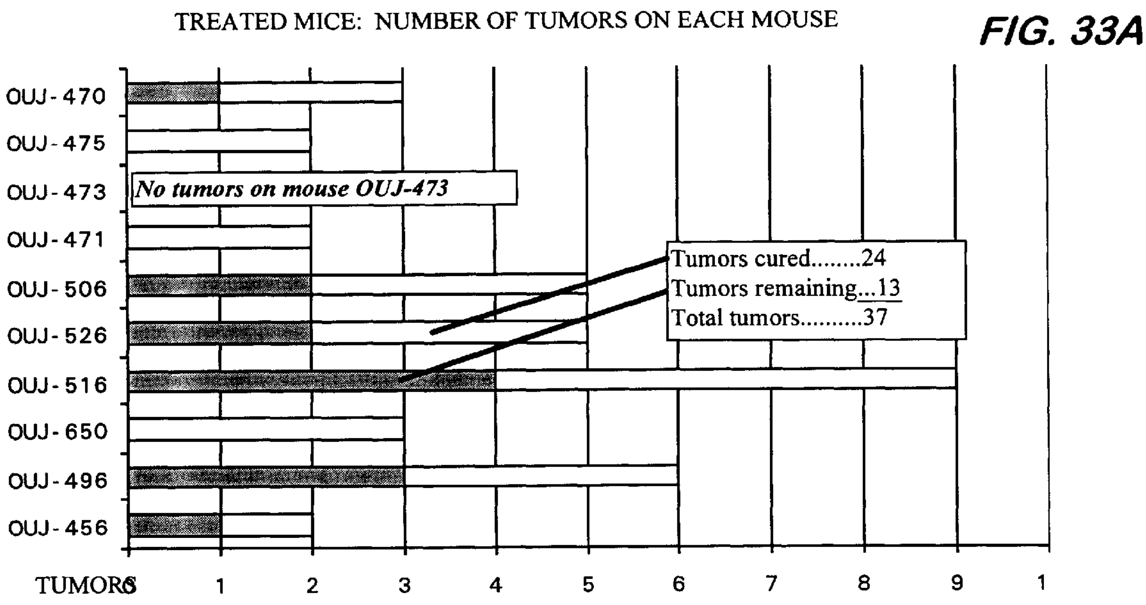
FIGS. 33A and B shows bar graphs of the outcome with respect to the tumors found in the treated and control mice, respectively.
Figure 33B:
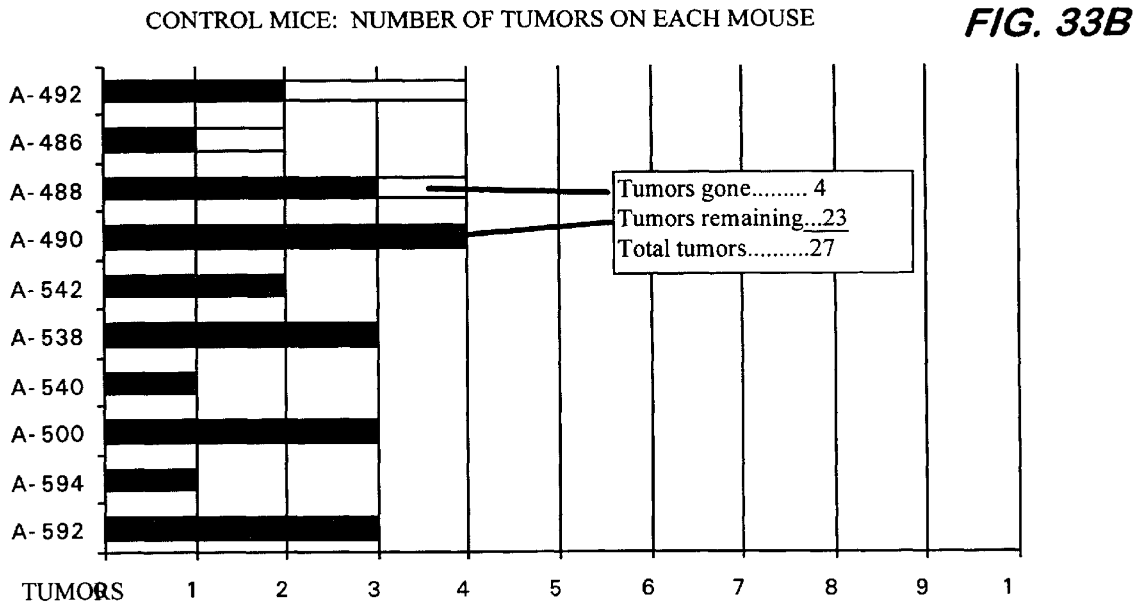

FIG. 33 shows the total number of tumors in each mouse, and those tumors that disappeared or were cured and the remaining tumors at the death of each mouse. (Note: OUJ-506 and OUJ-650 were still living as of Jun. 25, 1996, when this data was compiled.)

The data underlying FIG. 33 is set forth in Table 26 below.

TABLE 26

Tumors That Disappeared

| SUBJECT | MEAS-URED DAYS | REMAIN-ING TUMORS | CURED/ GONE TUMORS | TOTAL LIFE | NON MEASURED DAYS |
|---|---|---|---|---|---|
| OUJ-456 | 91 | 1 | 1 | 310 | 219 |
| OUJ-496 | 112 | 3 | 3 | 380 | 268 |
| OUJ-650 | 195 | 0 | 3 | 448 | 253 |
| OUJ-516 | 239 | 4 | 5 | 418 | 179 |
| OUJ-526 | 167 | 2 | 3 | 435 | 268 |
| OUJ-506 | 250 | 2 | 3 | 537 | 287 |
| OUJ-471 | 199 | 0 | 2 | 504 | 305 |
| OUJ-473 | 211 | 0 | 0 | 512 | 301 |
| OUJ-475 | 256 | 0 | 2 | 512 | 256 |
| OUJ-470 | 256 | 1 | 2 | 514 | 258 |
| Totals: | 1976 | 13 | 24 | 4,570 | 2594 |
| A-592 | 26 | 3 | 0 | 232 | 206 |
| A-594 | 34 | 1 | 0 | 233 | 199 |
| A-500 | 26 | 3 | 0 | 280 | 254 |
| A-540 | 48 | 1 | 0 | 283 | 235 |
| A-538 | 88 | 3 | 0 | 297 | 209 |
| A-542 | 52 | 2 | 0 | 299 | 247 |
| A-490 | 49 | 4 | 0 | 345 | 296 |
| A-488 | 116 | 3 | 1 | 350 | 234 |
| A-486 | 97 | 1 | 1 | 352 | 255 |
| A-492 | 105 | 2 | 2 | 375 | 270 |
| Totals: | 641 | 23 | 4 | 3,046 | 2405 |

Figure 34A:
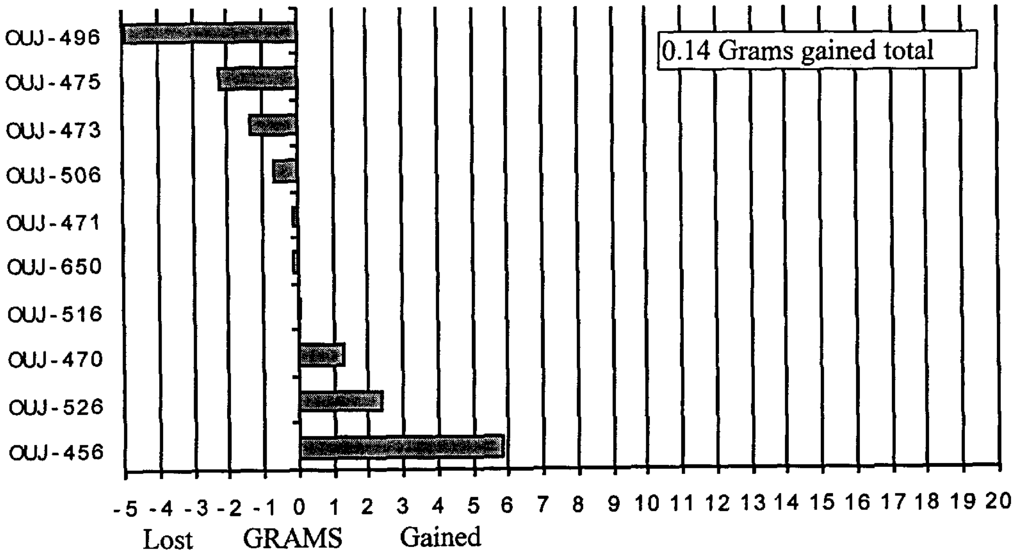
FIGS. 34A and B shows bar graphs of the weight changes observed in the treated and control mice, respectively.
Figure 34B:
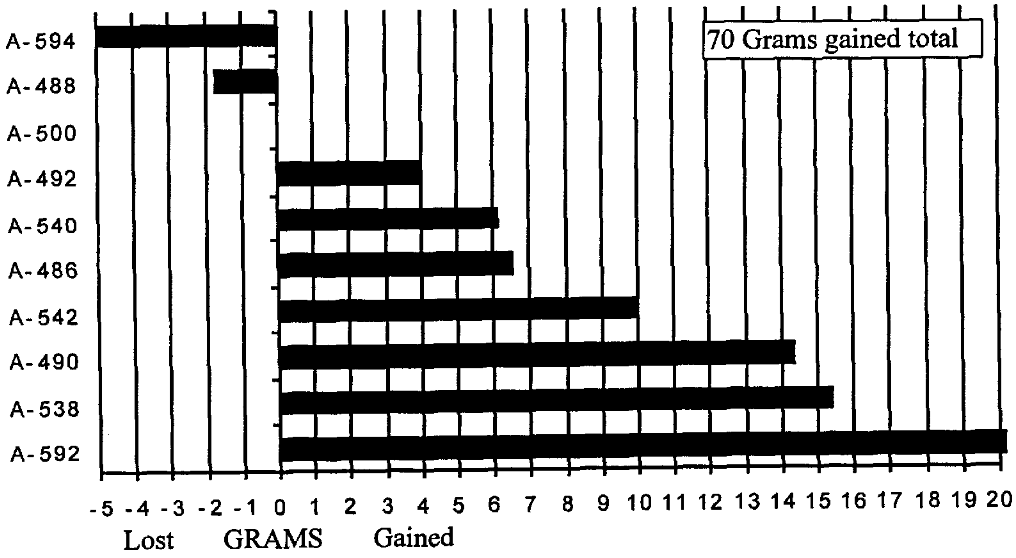

5. The Weight of the Treated Mice Remained Stable, Whereas the Control Mice Markedly Gained Weight FIG. 34 shows that the treated mice maintain their weight on average while the control mice gain considerable weight due to tumor growth. (Note: The weight change showing is the last 10day weight average minus the first 10 day weight average of each mouse.)

The data underlying FIG. 34 is set forth in Table 27 below.

TABLE 27

Comparative Weight Changes

| Treated Mouse | Weight Change | Control Mouse | Weight Change |
|---|---|---|---|
| OUJ-456 | 5.85 | A-592 | 20.31 |
| OUJ-526 | 2.37 | A-538 | 15.42 |
| OUJ-470 | 1.31 | A-490 | 14.32 |
| OUJ-471 | −0.15 | A-542 | 9.97 |
| OUJ-473 | −1.36 | A-486 | 6.54 |
| OUJ-475 | −2.22 | A-540 | 6.15 |
| OUJ-506 | −0.66 | A-492 | 3.98 |
| OUJ-650 | −0.15 | A-500 | 0.02 |
| OUJ-516 | 0.07 | A-488 | −1.73 |
| OUJ-496 | −4.92 | A-594 | −4.92 |
| Totals: | 0.14 | | 70.06 |

6. The Control Mice Had More Large Tumors

Figure 35A:
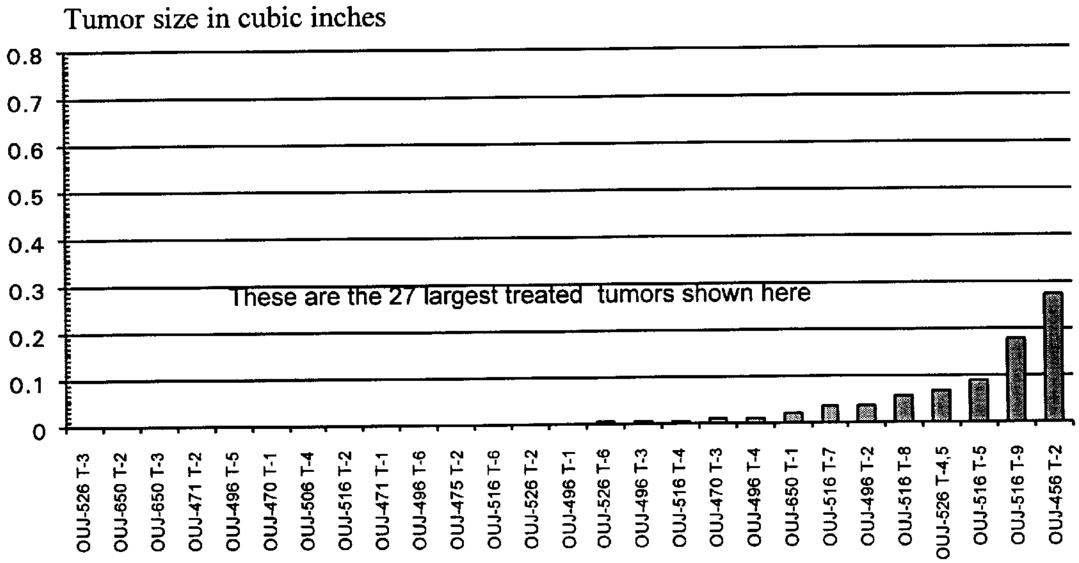
FIGS. 35A and B shows bar graphs of the maximum size of tumors observed in the treated and control mice, respectively.
Figure 35B:
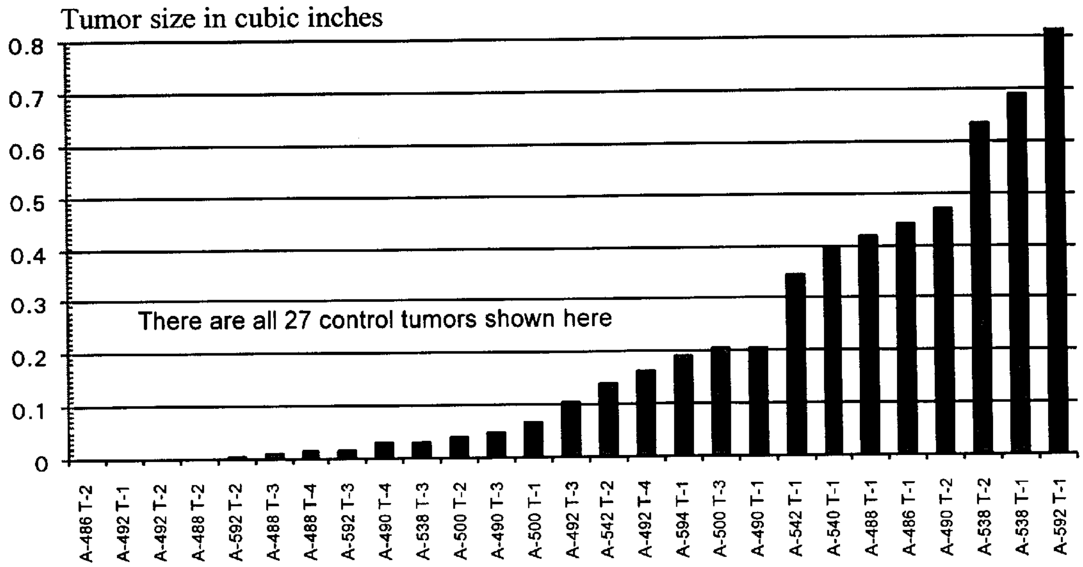

FIG. 35 shows the maximum sizes of each tumor on the twenty different mice. Some of these tumors disappeared. The vertical scale is tumor size in cubic inches. There were 37 treated and 27 control tumors but this graph show the 27 largest treated tumors and all 27 control tumors.

The data underlying FIG. 35 is set forth in Tables 28A and B below.

TABLE 28A

| Comparison of Maximum Tumor Size (in cubic inches) | | | | | | | | | |
|---|---|---|---|---|---|---|---|---|---|
| Treated Subject | Tumor 1 | Tumor 2 | Tumor 3 | Tumor 4 | Tumor 5 | Tumor 6 | Tumor 7 | Tumor 8 | Tumor 9 |
| OUJ-456 | 0.00001413 | 0.27320000 | | | | | | | |
| OUJ-470 | 0.00017960 | 0.00001413 | 0.00954900 | | | | | | |
| OUJ-471 | 0.00026180 | 0.00009161 | | | | | | | |
| OUJ-473 | | | | | | | | | |
| OUJ-475 | 0.00001413 | 0.00036650 | | | | | | | |
| OUJ-496 | 0.00117800 | 0.03799000 | 0.00633200 | 0.01099000 | 0.00015390 | 0.00029680 | | | |
| OUJ-506 | 0.00001413 | 0.01866000 | 0.00001413 | 0.00017960 | 0.01682000 | | | | |
| OUJ-516 | 0.00001413 | 0.00017960 | 0.00006544 | 0.00653300 | 0.08179000 | 0.00048370 | 0.03624000 | 0.05560000 | 0.17990000 |
| OUJ-526 | 0.00001413 | 0.00082920 | 0.00006544 | 0.06579000 | 0.00533600 | | | | |
| OUJ-650 | 0.00241900 | 0.00006544 | 0.00006544 | | | | | | |
| Total | 0.00410800 | 0.33140000 | 0.01609000 | 0.08349000 | 0.10410000 | 0.00078050 | 0.03624000 | 0.05560000 | 0.17990000 |
| Average | 0.00045650 | 0.03682000 | 0.00268200 | 0.02087000 | 0.02603000 | 0.00039030 | 0.03624000 | 0.05560000 | 0.17990000 |

TABLE 28B

| Comparison of Maximum Tumor Size (in cubic inches) | | | | |
|---|---|---|---|---|
| Control Subject | Tumor 1 | Tumor 2 | Tumor 3 | Tumor 4 |
| A-486 | 0.43920000 | 0.00001413 | | |
| A-488 | 0.41790000 | 0.00619300 | 0.00762200 | 0.01493000 |
| A-490 | 0.20800000 | 0.47080000 | 0.04913000 | 0.02954000 |
| A-492 | 0.00052350 | 0.00006544 | 0.10690000 | 0.16280000 |
| A-500 | 0.06478000 | 0.04252000 | 0.20560000 | |
| A-538 | 0.56350000 | 0.32310000 | 0.03216000 | |
| A-540 | 0.39520000 | | | |
| A-542 | 0.36820000 | 0.13700000 | | |
| A-592 | 0.81920000 | 0.00419200 | 0.01504000 | |
| A-594 | 0.19090000 | | | |
| Total | 3.46700000 | 0.98380000 | 0.41640000 | 0.20730000 |
| Average | 0.34670000 | 0.12300000 | 0.06940000 | 0.06910000 |

Test of Externally Pulsed Generator

Figure 8B:
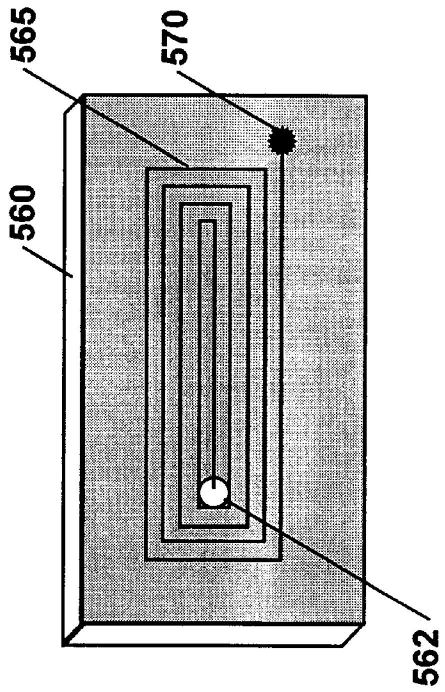
FIGS. 8A and 8B show front and back views of the treatment loop used in connection with the Generator Enmbodiment.
Figure 8A:
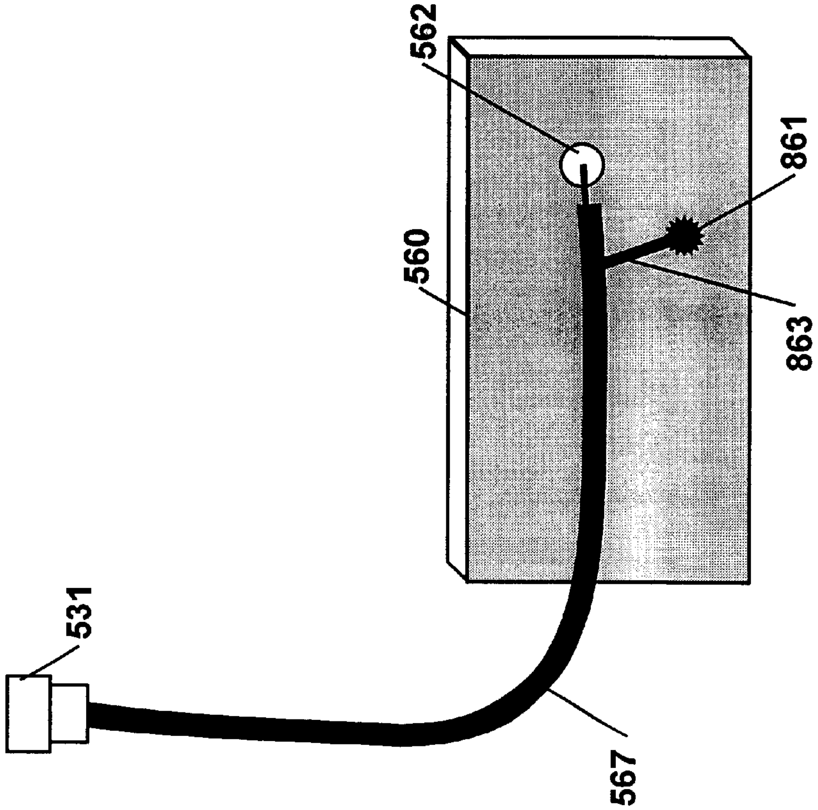
Figure 9A:
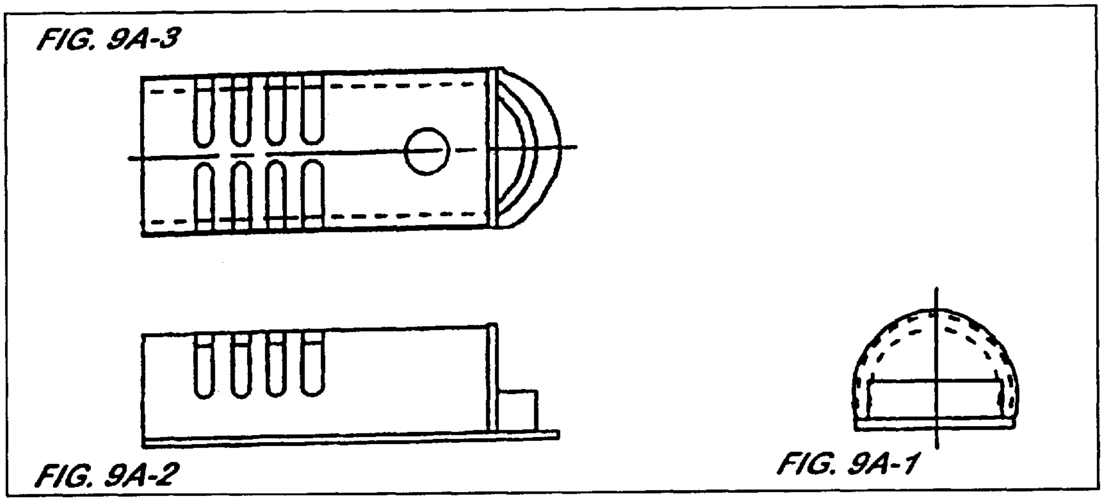
Figure 9B:
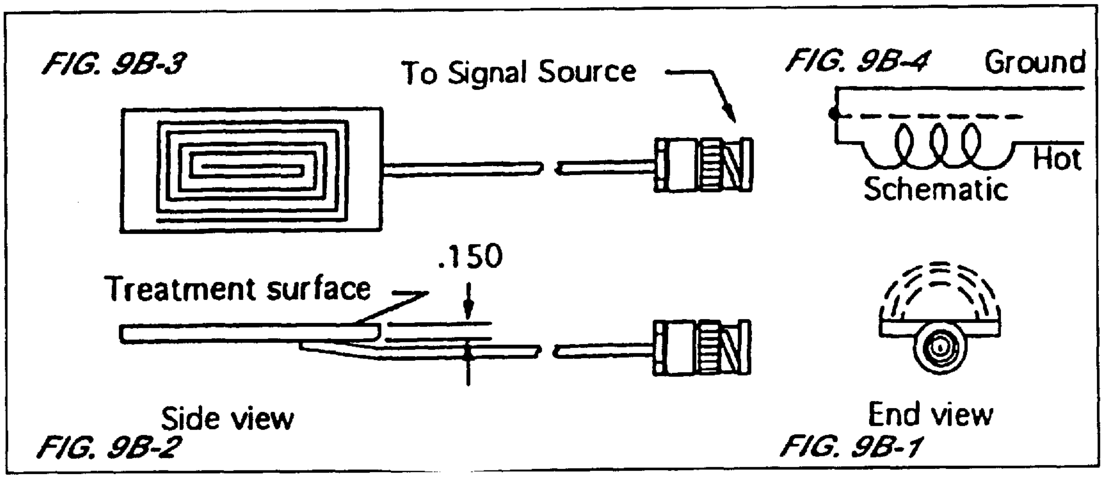
Figure 9C:
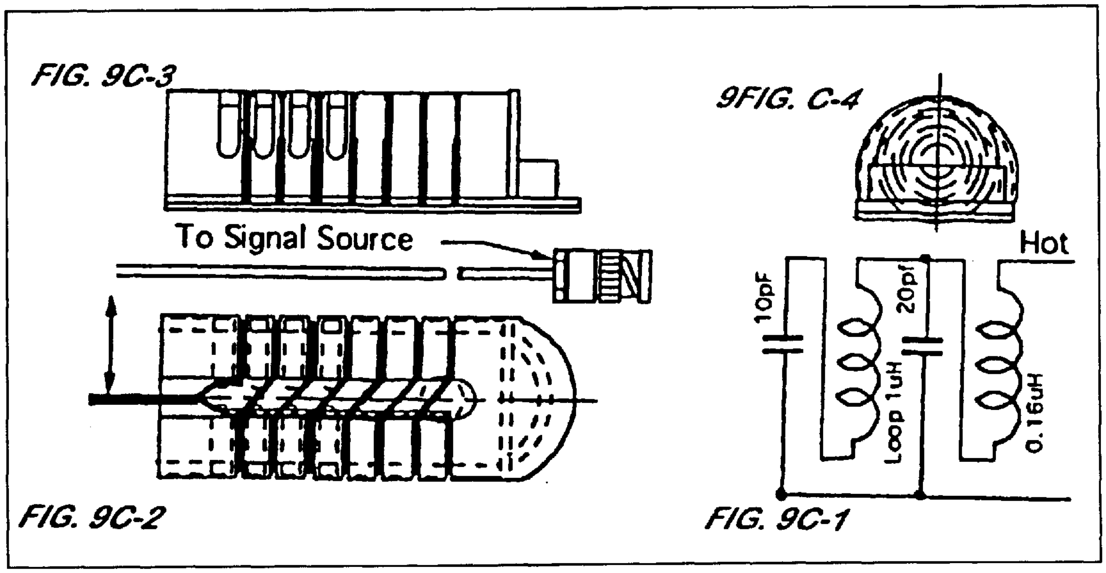
Figure 9D:
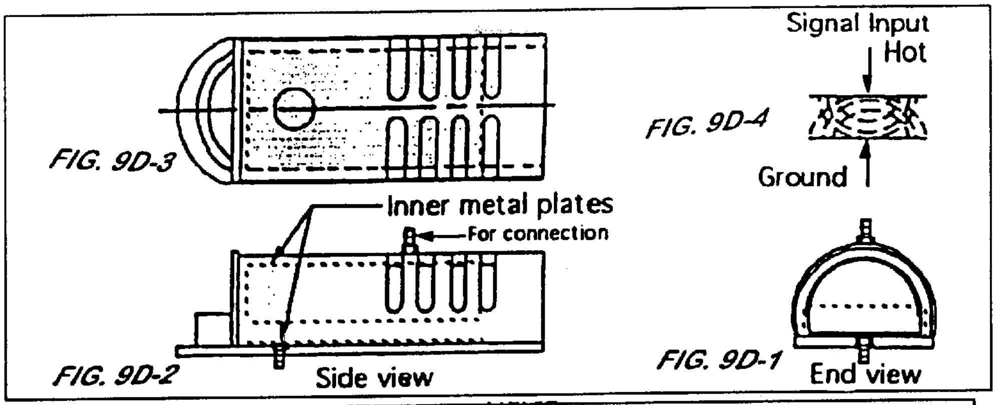
Figure 9E:
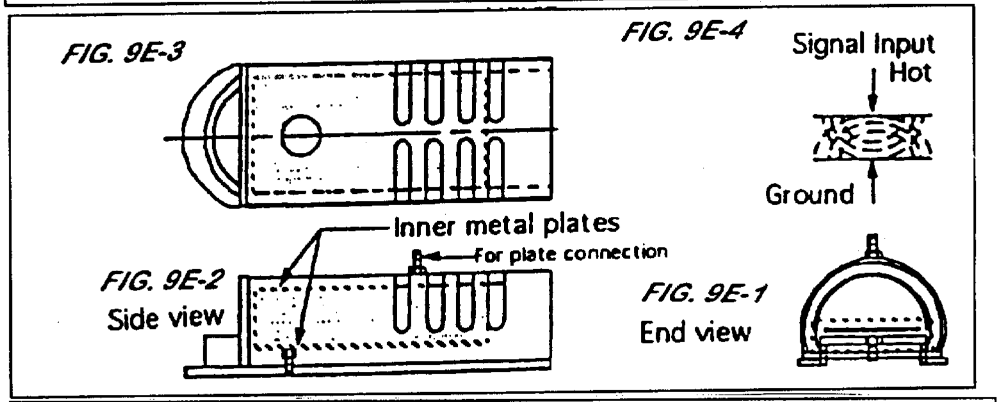
Figure 9F:
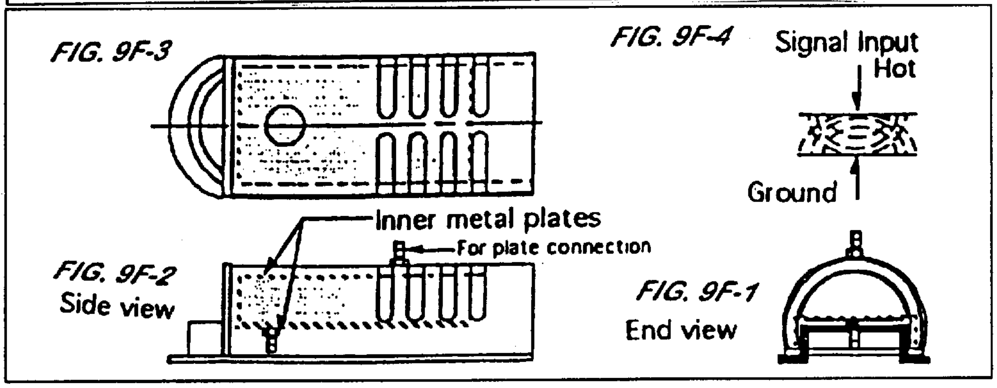
Figure 9G:
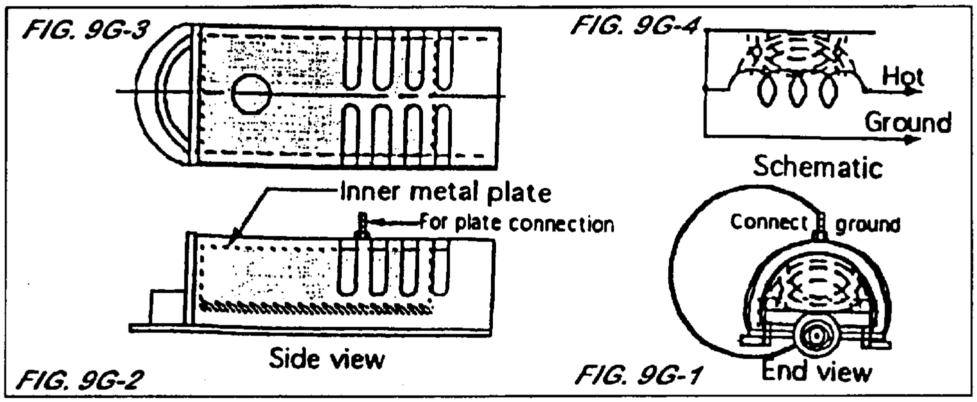
Figure 9H:
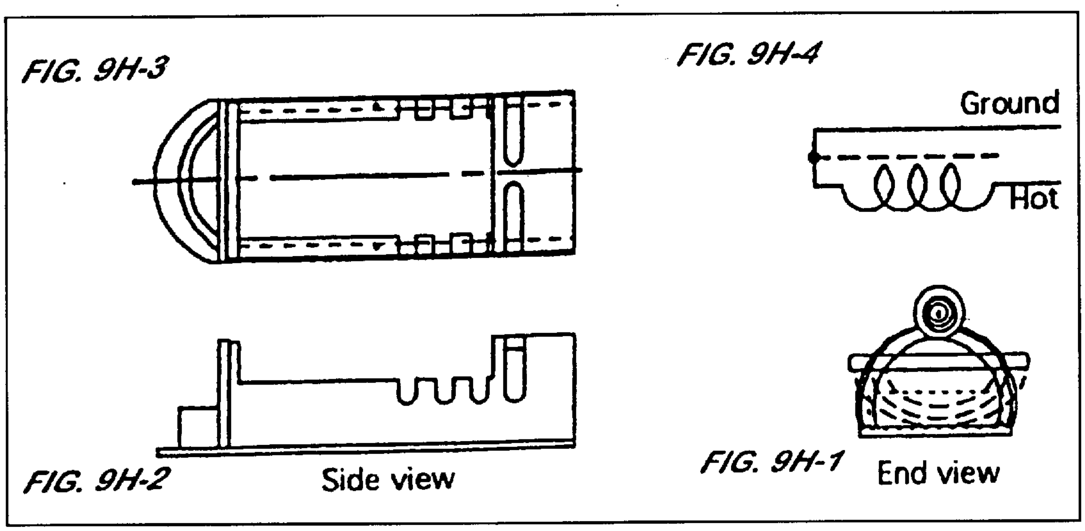
Figure 9I:
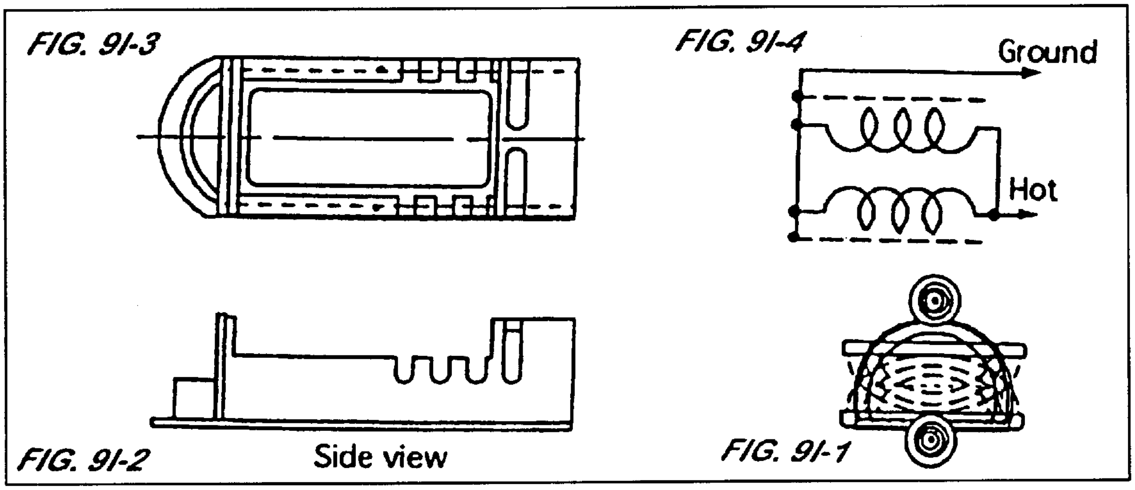
Figure 9J:
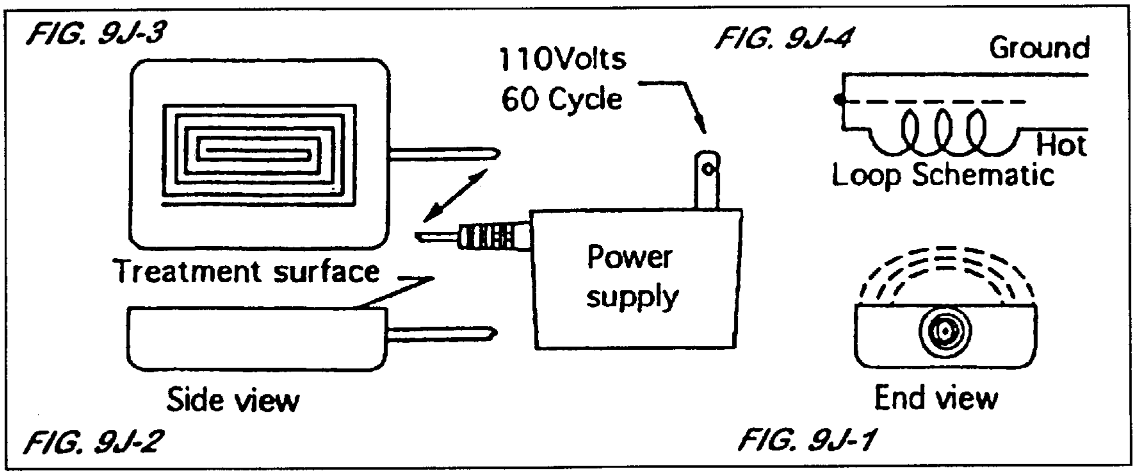

FIG. 37 shows the results of treating mouse OUJ-738 in 1997 with the Externally Pulsed Generator embodiment. Treatment was with the HIP 8662A frequency generator externally modulated with the modulator shown in FIG. 36, coupled to a treatment loop as shown in FIGS. 8A and 8B deployed in the "E" housing shown in FIG. 9A. The corresponding experimental data is shown in Appendix C.

Figure 37A:
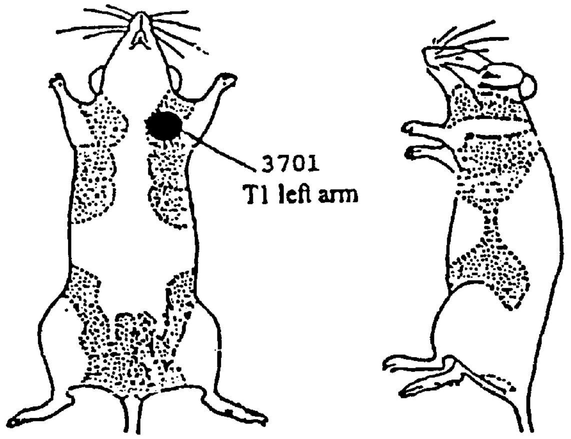
FIG. 37 shows, for a mouse treated with a Generator Embodiment pulsed externally by the modulator shown in FIG. 36, A, the location of the tumor that developed, B, plots (on a logarithmic scale) of tumor volume as a function of time, and C, plots of the mouse's weight and hematocrit measurements as a function of time.
Figure 37B:
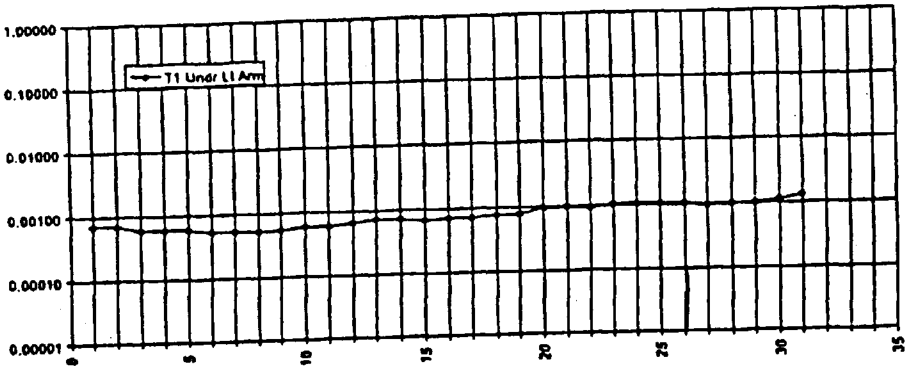
Figure 37C:
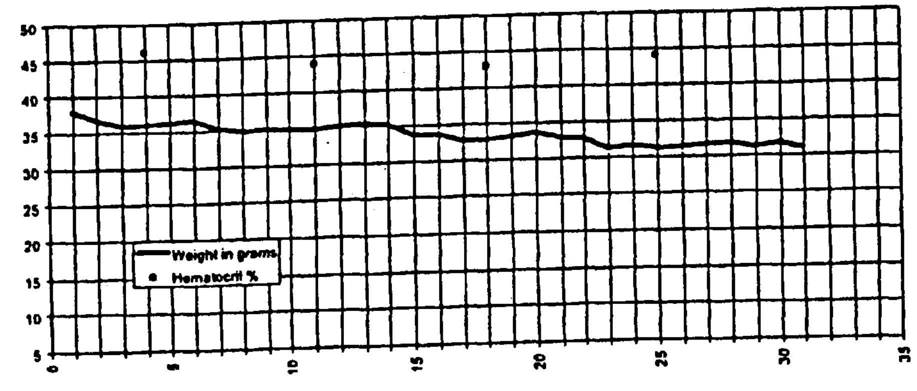

FIG. 37A shows that a single tumor T1 3701 developed on this mouse in the left arm position. This position is difficult to treat because it is out of the way and as a consequence it is difficult to position the treatment electrode close to the tumor. Nevertheless, the results with this mouse were extremely good for the period of testing. As shown in FIG. 37B, the tumor stayed small for the entire period, and as shown in FIG. 37C, the weight was stable and the hematocrits remained high. The data extends up to a few days prior to the filing of this application, and at the end of this period the mouse was alive and healthy.

In addition, data were compiled in 1997 with respect to tumors that disappeared after treatment with the generator embodiment. This data, which otherwise appears in the Figures. hereto, is as follows:

TABLE 29

| Disappearance of Tumors on Mice Treated with HP 8662A Frequency Generator Embodiment | | | | | | |
|---|---|---|---|---|---|---|
| Treated Mouse # | Tumor 1 | Tumor 2 | Tumor 3 | Tumor 4 | Tumor 5 | Tumor 6 |
| OUJ-650 | Yes | Yes | Yes | | | |
| OUJ-526 | Yes | Yes | Yes | | | |
| OUJ-516 | Yes | Yes | Yes | Yes | | Yes |
| OUJ-506 | Yes | Yes | Yes | Yes | | |
| OUJ-496 | Yes | | | | Yes | |
| OUJ-471 | Yes | Yes | | | | |
| OUJ-470 | Yes | Yes | | | | |
| OUJ-456 | Yes | | | | | |

It is apparent from the foregoing that a new treatment has been developed which has shown great effectiveness in treating cancer and other illnesses in laboratory mice and is believed to be a promising treatment for humans. While only presently preferred embodiments have been described in detail, it will be apparent to those skilled in the art that certain changes and modifications can be made without departing from the scope of the invention, as defined in the following claims.

APPENDICES A1 - A10

TREATED MOUSE DATA

Index (Pages numbered on back)

| Appendix | Subject | Pages |
|---|---|---|
| A1 | OUJ 456 | 48-49 |
| A2 | OUJ 470 | 50-55 |
| A3 | OUJ 471 | 56-59 |
| A4 | OUJ 473 | 60-63 |
| A5 | OUJ 475 | 64-69 |
| A6 | OUJ 496 | 70-71 |
| A7 | OUJ 506 | 72-75 |
| A8 | OUJ 516 | 76-83 |
| A9 | OUJ 526 | 84-91 |
| A10 | OUJ 650 | 92-93 |

OUJ-456- xls

*OUJ-456 Born 9/28/94 First tumor appeared on 05/05/95*

*Special Study...Treatment started when tumor appeared!*

| DAY | DATE | On Abdomen T-1 | | | Vol | On Rt Side T-2 | | | Vol | WEIGHT | HEMATO- | TREATMENT PARAMETERS | | | | | | | |
|---|---|---|---|---|---|---|---|---|---|---|---|---|---|---|---|---|---|---|---|
| | | Ln | Wd | Ht | T-1 | Ln | Wd | Ht | T-2 | Gr | CRIT-% | DEVICE | FREQ MHz | POWER | TIME | FREQ MHz | POWER | TIME | DEVICE |
| 1 | 5-May | 0 030 | 0 030 | 0 030 | 00001 | | | | 00000 | 30 30 | 47 | 8662A | 43 351 853 | 0 DBm | 2 0 Hr | | | | 1 Loop |
| 2 | 6-May | 0 030 | 0 030 | 0 030 | 00001 | | | | 00000 | 30 93 | | 8662A | 43 351 853 | 0 DBm | 2 0 Hr | | | | 1 Loop |
| 3 | 7-May | 0 030 | 0 030 | 0 030 | 00001 | | | | 00000 | 30 45 | | 8662A | 43 351 853 | 0 DBm | 2 0 Hr | | | | 1 Loop |
| 4 | 8-May | 0 030 | 0 030 | 0 030 | 00001 | | | | 00000 | 30 10 | | 8662A | 43 351 853 | 0 DBm | 2 0 Hr | | | | 1 Loop |
| 5 | 9-May | 0 030 | 0 030 | 0 030 | 00001 | | | | 00000 | 32 78 | | 8662A | 43 351 853 | 0 DBm | 2 0 Hr | | | | 1 Loop |
| 6 | 10-May | 0 030 | 0 030 | 0 030 | 00001 | 0 030 | 0 030 | 0 030 | 00001 | 32 33 | | 8662A | 43 351 853 | 0 DBm | 2 0 Hr | | | | 1 Loop |
| 7 | 11-May | 0 030 | 0 030 | 0 030 | 00001 | 0 030 | 0 030 | 0 030 | 00001 | 32 15 | | 8662A | 43 351 853 | 0 DBm | 2 0 Hr | | | | 1 Loop |
| 8 | 12-May | 0 030 | 0 030 | 0 030 | 00001 | 0 050 | 0 050 | 0 030 | 00004 | 31 73 | | 8662A | 43 351 853 | 0 DBm | 2 0 Hr | | | | 1 Loop |
| 9 | 13-May | | | | 00000 | 0 050 | 0 050 | 0 050 | 00007 | 30 79 | | 8662A | 43 351 853 | 0 DBm | 2 0 Hr | | | | 1 Loop |
| 10 | 14-May | | | | 00000 | 0 050 | 0 050 | 0 050 | 00007 | 30 96 | | 8662A | 43 351 830 | 0 DBm | 1 0 Hr | 43 351 870 | 0 DBm | 1 0 Hr | 1 Loop |
| 11 | 15-May | | | | 00000 | 0 050 | 0 050 | 0 050 | 00007 | 31 08 | 47 | 8662A | 43 351 830 | 0 DBm | 1 0 Hr | 43 351 870 | 0 DBm | 1 0 Hr | 1 Loop |
| 12 | 16-May | | | | 00000 | 0 070 | 0 070 | 0 050 | 00013 | 31 02 | | 8662A | 43 351 853 | 0 DBm | 1 0 Hr | 43 351 870 | 0 DBm | 1 0 Hr | 1 Loop |
| 13 | 17-May | | | | 00000 | 0 070 | 0 070 | 0 070 | 00018 | 31 39 | | 8662A | 43 351 830 | 0 DBm | 1 0 Hr | 43 351 870 | 0 DBm | 1 0 Hr | 1 Loop |
| 14 | 18-May | | | | 00000 | 0 070 | 0 070 | 0 070 | 00018 | 31 04 | | 8662A | 43 351 830 | 0 DBm | 1 0 Hr | 43 351 870 | 0 DBm | 1 0 Hr | 1 Loop |
| 15 | 19-May | | | | 00000 | 0 070 | 0 070 | 0 070 | 00018 | 31 25 | 45 | 8662A | 43 351 830 | 0 DBm | 1 0 Hr | 43 351 870 | 0 DBm | 1 0 Hr | 1 Loop |
| 16 | 20-May | | | | 00000 | 0 080 | 0 080 | 0 070 | 00023 | 31 60 | | 8662A | 43 251 830 | 0 DBm | 1 0 Hr | 43 351 870 | 0 DBm | 1 0 Hr | 1 Loop |
| 17 | 21-May | | | | 00000 | 0 090 | 0 090 | 0 070 | 00030 | 31 90 | | 8662A | 43 351 830 | 0 DBm | 1 0 Hr | 43 351 870 | 0 DBm | 1 0 Hr | 1 Loop |
| 18 | 22-May | | | | 00000 | 0 100 | 0 100 | 0 070 | 00037 | 32 14 | | 8662A | 43 351 830 | 0 DBm | 1 0 Hr | 43 351 870 | 0 DBm | 1 0 Hr | 1 Loop |
| 19 | 23-May | | | | 00000 | 0 120 | 0 120 | 0 070 | 00053 | 31 17 | | 8662A | 43 351 830 | 0 DBm | 1 0 Hr | 43 351 870 | 0 DBm | 1 0 Hr | Holder, Mod-1 |
| 20 | 24-May | | | | 00000 | 0 120 | 0 120 | 0 070 | 00053 | 30 24 | | 8662A | 43 351 830 | 0 DBm | 1 0 Hr | 43 351 870 | 0 DBm | 1 0 Hr | Holder, Mod-1 |
| 21 | 25-May | | | | 00000 | 0 120 | 0 120 | 0 080 | 00060 | 30 18 | | 8662A | 43 351 830 | 0 DBm | 1 0 Hr | 43 351 870 | 0 DBm | 1 0 Hr | Holder, Mod-1 |
| 22 | 26-May | | | | 00000 | 0 140 | 0 140 | 0 100 | 00103 | 29 37 | 47 | 8662A | 43 351 830 | 0 DBm | 1 0 Hr | 43 351 870 | 0 DBm | 1 0 Hr | Holder, Mod-1 |
| 23 | 27-May | | | | 00000 | 0 150 | 0 150 | 0 110 | 00130 | 29 42 | | 8662A | 43 351 830 | 0 DBm | 1 0 Hr | 43 351 870 | 0 DBm | 1 0 Hr | Holder, Mod-1 |
| 24 | 28-May | | | | 00000 | 0 160 | 0 160 | 0 110 | 00147 | 29 62 | | 8662A | 43 351 830 | 0 DBm | 1 0 Hr | 43 351 870 | 0 DBm | 1 0 Hr | Holder, Mod-1 |
| 25 | 29-May | | | | 00000 | 0 170 | 0 170 | 0 110 | 00165 | 29 78 | | 8662A | 43 351 830 | 0 DBm | 1 0 Hr | 43 351 870 | 0 DBm | 1 0 Hr | Holder, Mod-1 |
| 26 | 30-May | | | | 00000 | 0 180 | 0 180 | 0 120 | 00204 | 30 83 | | 8662A | 43 351 830 | 0 DBm | 1 0 Hr | 43 351 870 | 0 DBm | 1 0 Hr | Holder, Mod-2 |
| 27 | 31-May | | | | 00000 | 0 190 | 0 190 | 0 120 | 00227 | 31 34 | | 8662A | 43 251 830 | 0 DBm | 1 0 Hr | 43 351 870 | 0 DBm | 1 0 Hr | Holder, Mod-2 |
| 28 | 1-Jun | | | | 00000 | 0 200 | 0 200 | 0 120 | 00251 | 21 38 | | 8662A | 43 251 830 | 0 DBm | 1 0 Hr | 43 351 870 | 0 DBm | 1 0 Hr | Holder, Mod-2 |
| 29 | 2-Jun | | | | 00000 | 0 200 | 0 200 | 0 120 | 00251 | 31 07 | 44 | 8662A | 43 351 830 | 0 DBm | 1 0 Hr | 43 351 870 | 0 DBm | 1 0 Hr | Holder, Mod-2 |
| 30 | 3-Jun | | | | 00000 | 0 220 | 0 220 | 0 120 | 00304 | 31 37 | | 8662A | 43 351 830 | 0 DBm | 1 0 Hr | 43 351 870 | 0 DBm | 1 0 Hr | Holder, Mod-2 |
| 31 | 4-Jun | | | | 00000 | 0 220 | 0 220 | 0 120 | 00304 | 31 70 | | 8662A | 43 351 830 | 0 DBm | 1 0 Hr | 43 351 870 | 0 DBm | 1 0 Hr | Holder, Mod-2 |
| 32 | 5-Jun | | | | 00000 | 0 220 | 0 220 | 0 120 | 00304 | 32 09 | | 8662A | 43 351 830 | 0 DBm | 1 0 Hr | 43 351 870 | 0 DBm | 1 0 Hr | Holder, Mod-2 |
| 33 | 6-Jun | | | | 00000 | 0 220 | 0 230 | 0 120 | 00319 | 32 03 | | 8662A | 43 251 830 | 0 DBm | 1 0 Hr | 43 351 870 | 0 DBm | 1 0 Hr | Holder, Mod-2 |
| 34 | 7-Jun | | | | 00000 | 0 220 | 0 230 | 0 120 | 00318 | 32 27 | | 8662A | 43 351 830 | 0 DBm | 1 0 Hr | 43 351 870 | 0 DBm | 1 0 Hr | Holder, Mod-2 |
| 35 | 8-Jun | | | | 00000 | 0 220 | 0 250 | 0 140 | 00403 | 32 55 | | 8662A | 43 351 870 | 3 DBm | 1 0 Hr | 43 351 870 | 3 DBm | 1 0 Hr | Holder, Mod-2 |
| 36 | 9-Jun | | | | [illegible] | 0 230 | 0 250 | 0 140 | 00421 | 31 39 | 43 | 8662A | 43 351 870 | 3 DBm | 1 0 Hr | 43 351 870 | 3 DBm | 1 0 Hr | Holder, Mod-2 |
| 37 | 10-Jun | | | | 00000 | 0 250 | 0 250 | 0 140 | 00476 | 31 61 | | 8662A | 43 351 850 | 10 DBm | 1 0 Hr | 43 351 870 | 10 DBm | 1 0 Hr | Holder, Mod-2 |
| 38 | 11-Jun | | | | 00000 | 0 250 | 0 270 | 0 145 | 00512 | 31 95 | | 8662A | 43 351 850 | 10 DBm | 1 0 Hr | 43 351 870 | 10 DBm | 1 0 Hr | Holder, Mod-2 |
| 39 | 12-Jun | | | | 00000 | 0 250 | 0 280 | 0 150 | 00550 | 32 09 | | 8662A | 43 351 830 | 10 DBm | 1 0 Hr | 43 351 870 | 10 DBm | 1 0 Hr | Holder, Mod-2 |
| 40 | 13-Jun | | | | 00000 | 0 250 | 0 290 | 0 150 | 00607 | 32 91 | | 8662A | 43 251 830 | 10 DBm | 1 0 Hr | 43 351 870 | 10 DBm | 1 0 Hr | Holder, Mod-2 |
| 41 | 14-Jun | | | | 00000 | 0 250 | 0 290 | 0 160 | 00607 | 32 60 | | 8662A | 43 351 830 | 10 DBm | 1 0 Hr | 43 351 870 | 10 DBm | 1 0 Hr | Holder, Mod-2 |
| 42 | 15-Jun | | | | 00000 | 0 240 | 0 320 | 0 180 | 00724 | 32 33 | | 8662A | 43 351 850 | 10 DBm | 1 0 Hr | 43 351 870 | 10 DBm | 1 0 Hr | Holder, Mod-2 |
| 43 | 16-Jun | | | | 00000 | 0 240 | 0 340 | 0 180 | 00769 | 32 50 | | 8662A | 43 351 830 | 10 DBm | 1 0 Hr | 43 351 870 | 10 DBm | 1 0 Hr | Holder, Mod-2 |
| 44 | 17-Jun | | | | 00000 | 0 240 | 0 360 | 0 190 | 00859 | 32 59 | 40 | 8662A | 43 251 849 | 10 DBm | 1 0 Hr | 43 351 849 | 10 DBm | 1 0 Hr | Holder, Mod-2 |
| 45 | 18-Jun | | | | 00000 | 0 245 | 0 375 | 0 190 | 00914 | 32 65 | | 8662A | 43 251 849 | 10 DBm | 1 0 Hr | 43 251 870 | 10 DBm | 1 0 Hr | Holder, Mod-2 |
| 46 | 19-Jun | | | | 00000 | 0 250 | 0 390 | 0 190 | 00970 | 32 71 | | 8662A | 43 351 849 | 10 DBm | 1 0 Hr | 43 351 870 | 10 DBm | 1 0 Hr | Holder, Mod-2 |
| 47 | 20-Jun | | | | 00000 | 0 260 | 0 410 | 0 200 | 01115 | 32 97 | | 8662A | 43 351 850 | 10 DBm | 1 0 Hr | 43 351 870 | 10 DBm | 1 0 Hr | Holder, Mod-2 |
| 48 | 21-Jun | | | | 00000 | 0 260 | 0 410 | 0 200 | 01116 | 32 74 | | 8662A | 43 351 850 | 10 DBm | 1 0 Hr | 43 351 870 | 10 DBm | 1 0 Hr | Holder, Mod-2 |
| 49 | 22-Jun | | | | 00000 | 0 260 | 0 430 | 0 200 | 01171 | 34 39 | | 8662A | 43 351 850 | 10 DBm | 1 0 Hr | 43 351 850 | 10 DBm | 1 0 Hr | Holder, Mod-2 |
| 50 | 23-Jun | | | | 00000 | 0 290 | 0 460 | 0 220 | 01536 | 33 87 | 39 | 8662A | 43 351 830 | 10 DBm | 1 0 Hr | 43 351 870 | 10 DBm | 1 0 Hr | Holder, Mod-2 |
| 51 | 24-Jun | | | | 00000 | 0 300 | 0 480 | 0 220 | 01658 | 34 26 | | 8662A | 43 351 830 | 10 DBm | 1 0 Hr | 43 351 870 | 10 DBm | 1 0 Hr | Holder, Mod-2 |
| 52 | 25-Jun | | | | 00000 | 0 300 | 0 500 | 0 220 | 01728 | 34 02 | | 8662A | 43 351 830 | 10 DBm | 1 0 Hr | 43 351 870 | 10 DBm | 1 0 Hr | Holder, Mod-2 |
| 53 | 26-Jun | | | | 00000 | 0 300 | 0 520 | 0 220 | 01797 | 33 70 | | 8662A | 43 351 830 | 10 DBm | 1 0 Hr | 43 351 870 | 10 DBm | 1 0 Hr | Holder, Mod-2 |
| 54 | 27-Jun | | | | 00000 | 0 320 | 0 550 | 0 230 | 02119 | 33 08 | | 8662A | 43 351 830 | 10 DBm | 1 0 Hr | 43 351 870 | 10 DBm | 1 0 Hr | Loop-By Hand |

4/11/97 Page 1 OUJ-456- xls

OUJ-456-.xls

| | | | | | | | | | | | | | | | | | |
|---|---|---|---|---|---|---|---|---|---|---|---|---|---|---|---|---|---|
| 55 | 28-Jun | | 00000 | 0 320 | 0 530 | 0 240 | 02131 | 32 44 | | 8562A | 43 351 830 | 10 DBm | 1 0 Hr | 43 351 830 | 10 DBm | 1.0 Hr | Loop-By Hand |
| 56 | 29-Jun | | 00000 | 0 320 | 0 530 | 0 240 | 02131 | 31 32 | | 8562A | 42 351 830 | 10 DBm | 1 0 Hr | 43 351.830 | 10 DBm | 1 0 Hr | Loop-By Hand |
| 57 | 30-Jun | | 00000 | 0 340 | 0 540 | 0 240 | 02307 | 30 82 | | 8662A | 43 351 830 | 10 DBm | 1 0 Hr | 43 351 830 | 10 DBm | 1.0 Hr | Loop-By Hand |
| 58 | 1-Jul | | 00000 | 0 380 | 0 540 | 0 280 | 03008 | 30 28 | 40 | 8662A | 43 351 830 | 10 DBm | 1 0 Hr | 43 351,870 | 10 DBm | 1 0 Hr | Loop-By Hand |
| 59 | 2-Jul | | 00000 | 0 380 | 0 550 | 0 280 | 03054 | 31 04 | | 8662A | 43 351 830 | 10 DBm | 1 0 Hr | 43 351,870 | 10 DBm | 1 0 Hr | Loop-By Hand |
| 60 | 3-Jul | | 00000 | 0 380 | 0 560 | 0 280 | 03119 | 31 79 | | 8562A | 43 351 830 | 10 DBm | 1 0 Hr | 43 351,870 | 10 DBm | 1.0 Hr | Holder, Mod-2 |
| 61 | 4-Jul | | 00000 | 0 380 | 0 580 | 0 290 | 03345 | 32 34 | | 8562A | 43 351 830 | 10 DBm | 1 0 Hr | 43 351.870 | 10 DBm | 1 0 Hr | Holder, Mod-2 |
| 62 | 5-Jul | | 00000 | 0 410 | 0 610 | 0 320 | 04190 | 31 60 | | 8662A | 43 351.830 | 10 DBm | 1 0 Hr | 43.351.870 | 10 DBm | 1 0 Hr | Holder, Mod-2 |
| 63 | 6-Jul | | 00000 | 0 430 | 0 620 | 0 320 | 04456 | 31 85 | | 8562A | 43 351 830 | 10 DBm | 1 0 Hr | 43.351.870 | 10 DBm | 1 0 Hr | Holder, Mod-2 |
| 64 | 7-Jul | | 00000 | 0 440 | 0 640 | 0 340 | 05012 | 32 37 | 40 | 8662A | 43 351 830 | 10 DBm | 1 0 Hr | 43 351.870 | 10 DBm | 1 0 Hr | Holder Mod-2 |
| 65 | 8-Jul | | 00000 | 0 450 | 0 640 | 0 360 | 05428 | 33 18 | | 8562A | 43 351 830 | 10 DBm | 1 0 Hr | 43.351.870 | 10 DBm | 1 0 Hr | Holder Mod-2 |
| 66 | 9-Jul | | 00000 | 0 490 | 0 660 | 0 350 | 06095 | 34 07 | | 8662A | 43 351.830 | 10 DBm | 1 0 Hr | 43 351,870 | 10 DBm | 1 0 Hr | Holder Mod-2 |
| 67 | 10-Jul | | 00000 | 0 530 | 0 680 | 0 360 | 06792 | 34 96 | | 8562A | 43 351 830 | 10 DBm | 1 0 Hr | 43 351.850 | 10 DBm | 1 0 Hr | Holder, Mod-2 |
| 68 | 11-Jul | | 00000 | 0 530 | 0 680 | 0 360 | 06792 | 34 70 | | 8562A | 43 351 830 | 10 DBm | 1 0 Hr | 43 351 850 | 10 DBm | 1 0 Hr | Loop-By Hand |
| 69 | 12-Jul | | 00000 | 0 540 | 0 740 | 0 360 | 07531 | 32 68 | | 8662A | 43 351 830 | 10 DBm | 1 0 Hr | 43 351.870 | 10 DBm | 1 0 Hr | Holder, Mod-2 |
| 70 | 13-Jul | | 00000 | 0 540 | 0 740 | 0 360 | 07531 | 35 99 | | 8562A | 43 351 830 | 10 DBm | 1 0 Hr | 43 351.870 | 10 DBm | 1 0 Hr | Holder, Mod-2 |
| 71 | 14-Jul | | 00000 | 0 590 | 0 700 | 0 350 | 07783 | 33 42 | 37 | 8662A | 43.351.830 | 10 DBm | 1 0 Hr | 43 351.870 | 10 DBm | 1 0 Hr | Holder, Mod-2 |
| 72 | 15-Jul | | 00000 | 0 570 | 0 710 | 0 360 | 07627 | 33 32 | | 8562A | 43 351.830 | 10 DBm | 1 0 Hr | 43.351 870 | 10 DBm | 1 0 Hr | Holder, Mod-2 |
| 73 | 16-Jul | | 00000 | 0 570 | 0 710 | 0 375 | 07945 | 34 06 | | 8662A | 43 351 830 | 10 DBm | 1 0 Hr | 43.351.870 | 10 DBm | 1 0 Hr | Holder, Mod-2 |
| 74 | 17-Jul | | 00000 | 0 570 | 0 710 | 0 390 | 08263 | 34 80 | | 8662A | 43 351 830 | 10 DBm | 1 0 Hr | 43.351.870 | 10 DBm | 1 0 Hr | Holder, Mod-2 |
| 75 | 18-Jul | | 00000 | 0 580 | 0 720 | 0 410 | 08963 | 34 58 | | 8662A | 43 351.850 | 10 DBm | 1 0 Hr | 43.351 870 | 10 DBm | 1 0 Hr | Holder, Mod-2 |
| 76 | 19-Jul | | 00000 | 0 590 | 0 730 | 0 410 | 09244 | 34 01 | | 8662A | 43 351 830 | 10 DBm | 1 0 Hr | 43.351.870 | 10 DBm | 1 0 Hr | Holder, Mod-2 |
| 77 | 20-Jul | | 00000 | 0 600 | 0 730 | 0 430 | 09860 | 35 36 | | 8562A | 43 351 830 | 10 DBm | 1 0 Hr | 43.351.870 | 10 DBm | 1 0 Hr | Holder Mod-2 |
| 78 | 21-Jul | | 00000 | 0 630 | 0 760 | 0 450 | 11279 | 34 86 | | 8562A | 43 351 830 | 10 DBm | 1 0 Hr | 43.351.850 | 10 DBm | 1 0 Hr | Holder, Mod-2 |
| 79 | 22-Jul | | 00000 | 0 650 | 0 770 | 0 430 | 11267 | 33 05 | 37 | 8562A | 43 351 830 | 10 DBm | 1 0 Hr | 43 351 850 | 10 DBm | 1 0 Hr | Holder Mod-2 |
| 80 | 23-Jul | | 00000 | 0 675 | 0 780 | 0 435 | 11990 | 33 21 | | 8662A | 43 351 830 | 10 DBm | 1 0 Hr | 43 351 850 | 10 DBm | 1 0 Hr | Holder, Mod-2 |
| 81 | 24-Jul | | 00000 | 0 680 | 0 790 | 0 440 | 12374 | 33 36 | | 8562A | 43 351 830 | 10 DBm | 1 0 Hr | 43 351 870 | 10 DBm | 1 0 Hr | Holder, Mod-2 |
| 82 | 25-Jul | | 00000 | 0 700 | 0 795 | 0 450 | 13110 | 34 35 | | 8562A | 43 351 830 | 10 DBm | 1 0 Hr | 43.351.870 | 10 DBm | 1 0 Hr | Holder, Mod-2 |
| 83 | 26-Jul | | 00000 | 0 720 | 0 800 | 0 460 | 13871 | 35 33 | | 8562A | 43 351 830 | 10 DBm | 1 0 Hr | 43 351.870 | 10 DBm | 1 0 Hr | Holder Mod-2 |
| 84 | 27-Jul | | 00000 | 0 750 | 0 800 | 0 460 | 14449 | 37 65 | | 8652A | 43 351 830 | 10 DBm | 1 0 Hr | 43 351.870 | 10 DBm | 1 0 Hr | Holder, Mod-1 |
| 85 | 28-Jul | | 00000 | 0 770 | 0 800 | 0 460 | 14834 | 35 47 | 32 | 8562A | 43 351 830 | 10 DBm | 1 0 Hr | 43 351.870 | 10 DBm | 1 0 Hr | Holder Mod-1 |
| 86 | 29-Jul | | 00000 | 0 800 | 0 810 | 0 480 | 16283 | 37 12 | | 8562A | 43 351 830 | 10 DBm | 1 0 Hr | 43 351.870 | 10 DBm | 1 0 Hr | Holder Mod-1 |
| 87 | 30-Jul | | 00000 | 0 800 | 0 810 | 0 480 | 15283 | 37 44 | | 8562A | 43 351 830 | 10 DBm | 1 0 Hr | 43 351 870 | 10 DBm | 1 0 Hr | Holder, Mod-1 |
| 88 | 31-Jul | | 00000 | 0 800 | 0 810 | 0 480 | 16283 | 37 76 | | 8562A | 43 351 830 | 10 DBm | 1 0 Hr | 43 351.870 | 10 DBm | 1 0 Hr | Holder, Mod-1 |
| 89 | 1-Aug | | 00000 | 0 810 | 0 830 | 0 510 | 17949 | 37 22 | | 8562A | 43 351 830 | 10 DBm | 1 0 Hr | 43.351 870 | 10 DBm | 1 0 Hr | Holder, Mod-1 |
| 90 | 2-Aug | | 00000 | 0 870 | 0 850 | 0 530 | 20518 | 37 98 | | 8562A | 43 351 830 | 10 DBm | 1 0 Hr | 43 351 870 | 10 DBm | 1 0 Hr | Box 6 Electrod |
| 91 | 3-Aug | | 00000 | 0 920 | 0 930 | 0 610 | 27322 | 39 74 | | 8652A | 43 351 830 | 10 DBm | 1 0 Hr | 43.351 870 | 10 DBm | 1 0 Hr | Box 6 Electrod |
| 92 | 4-Aug | Died 8 4 93 | #VALUE! | | Died 8-4-93 | | #VALUE! | | | | | | | | | | |

4/11/97 Page 2 OUJ-456-.xls

OUJ-470-.xls

*OUJ-470 Born 3/3/94 First tumor appeared on 11/18/94*
*Conventional SCPO Treatment. Treated at first appearance of tumor T1, located on abdomen.*

| DAY | DATE | T1 ON ABDOMEN | | | Vol | T2 UPPER ABDOMEN | | | Vol | WEIGHT | HEMATO- | TREATMENT PARAMETERS | | | | | |
|---|---|---|---|---|---|---|---|---|---|---|---|---|---|---|---|---|---|
| | | Ln | Wd | Ht | T-1 | Ln | Wd | Ht | T-2 | Gr | CRIT-% | DEVICE | FREQ MHz | TIME | DEVICE | FREQ MHz | TIME |
| 1 | 16-Nov | 0.030 | 0.030 | 0.030 | 00001 | | | | 00000 | 28.79 | | SCPO#1 | 43,351,830 | .5 Hr | SCPO#3 | 43,351,870 | .5 Hr |
| 2 | 17-Nov | 0.030 | 0.030 | 0.030 | 00001 | | | | 00000 | 28.07 | | SCPO#1 | 43,351,830 | .5 Hr | SCPO#3 | 43,351,870 | .5 Hr |
| 3 | 18-Nov | 0.030 | 0.030 | 0.030 | 00001 | | | | 00000 | 27.66 | | SCPO#1 | 43,351,830 | .5 Hr | SCPO#3 | 43,351,870 | .5 Hr |
| 4 | 19-Nov | 0.030 | 0.030 | 0.030 | 00001 | | | | 00000 | 27.70 | 45 | SCPO#1 | 43,351,830 | .5 Hr | SCPO#3 | 43,351,870 | .5 Hr |
| 5 | 20-Nov | 0.030 | 0.030 | 0.030 | 00001 | | | | 00000 | 27.86 | | SCPO#1 | 43,351,830 | .5 Hr | SCPO#3 | 43,351,870 | .5 Hr |
| 6 | 21-Nov | 0.030 | 0.030 | 0.030 | 00001 | | | | 00000 | 28.02 | | SCPO#1 | 43,351,830 | .5 Hr | SCPO#3 | 43,351,870 | .5 Hr |
| 7 | 22-Nov | 0.050 | 0.050 | 0.030 | 00004 | | | | 00000 | 27.84 | | SCPO#1 | 43,351,830 | 1 Hr | SCPO#3 | 43,351,870 | 1 Hr |
| 8 | 23-Nov | 0.070 | 0.070 | 0.050 | 00013 | | | | 00000 | 29.04 | | SCPO#1 | 43,351,830 | 1 Hr | SCPO#3 | 43,351,870 | 1 Hr |
| 9 | 24-Nov | 0.070 | 0.070 | 0.050 | 00013 | | | | 00000 | 28.61 | | SCPO#1 | 43,351,830 | 1 Hr | SCPO#3 | 43,351,870 | 1 Hr |
| 10 | 25-Nov | 0.070 | 0.070 | 0.050 | 00013 | | | | 00000 | 28.17 | | SCPO#1 | 43,351,830 | 1 Hr | SCPO#3 | 43,351,870 | 1 Hr |
| 11 | 26-Nov | 0.070 | 0.070 | 0.070 | 00018 | | | | 00000 | 28.03 | 45 | SCPO#1 | 43,351,830 | 1 Hr | SCPO#3 | 43,351,870 | 1 Hr |
| 12 | 27-Nov | 0.070 | 0.070 | 0.070 | 00018 | | | | 00000 | 27.61 | | SCPO#1 | 43,351,830 | 1 Hr | SCPO#3 | 43,351,870 | 1 Hr |
| 13 | 28-Nov | 0.070 | 0.070 | 0.070 | 00018 | | | | 00000 | 27.20 | | SCPO#1 | 43,351,830 | 1 Hr | SCPO#3 | 43,351,870 | 1 Hr |
| 14 | 29-Nov | 0.050 | 0.070 | 0.070 | 00013 | | | | 00000 | 28.91 | | SCPO#1 | 43,351,830 | 1 Hr | SCPO#3 | 43,351,870 | 1 Hr |
| 15 | 30-Nov | 0.050 | 0.050 | 0.050 | 00007 | | | | 00000 | 30.22 | | SCPO#1 | 43,351,830 | 1 Hr | SCPO#3 | 43,351,870 | 1 Hr |
| 16 | 1-Dec | 0.050 | 0.030 | 0.030 | 00002 | | | | 00000 | 29.70 | | SCPO#1 | 43,351,830 | 1 Hr | SCPO#3 | 43,351,870 | 1 Hr |
| 17 | 2-Dec | 0.050 | 0.030 | 0.030 | 00002 | | | | 00000 | 28.97 | 47 | SCPO#1 | 43,351,830 | 1 Hr | SCPO#3 | 43,351,870 | 1 Hr |
| 18 | 3-Dec | 0.050 | 0.030 | 0.030 | 00002 | | | | 00000 | 29.92 | | SCPO#1 | 43,351,830 | 1 Hr | SCPO#3 | 43,351,870 | 1 Hr |
| 19 | 4-Dec | 0.050 | 0.030 | 0.030 | 00002 | | | | 00000 | 29.41 | | SCPO#1 | 43,351,830 | 1 Hr | SCPO#3 | 43,351,870 | 1 Hr |
| 20 | 5-Dec | 0.050 | 0.030 | 0.030 | 00002 | | | | 00000 | 28.77 | | SCPO#1 | 43,351,830 | 1 Hr | SCPO#3 | 43,351,870 | 1 Hr |
| 21 | 6-Dec | 0.050 | 0.030 | 0.030 | 00002 | | | | 00000 | 27.80 | | SCPO#1 | 43,351,830 | 1 Hr | SCPO#3 | 43,351,870 | 1 Hr |
| 22 | 7-Dec | 0.050 | 0.030 | 0.030 | 00002 | | | | 00000 | 28.52 | | SCPO#1 | 43,351,830 | 1 Hr | SCPO#3 | 43,351,870 | 1 Hr |
| 23 | 8-Dec | 0.050 | 0.030 | 0.030 | 00002 | | | | 00000 | 28.62 | | SCPO#1 | 43,351,830 | 1 Hr | SCPO#3 | 43,351,870 | 1 Hr |
| 24 | 9-Dec | 0.050 | 0.030 | 0.030 | 00002 | | | | 00000 | 28.49 | 44 | SCPO#1 | 43,351,830 | 1 Hr | SCPO#3 | 43,351,870 | 1 Hr |
| 25 | 10-Dec | 0.050 | 0.030 | 0.030 | 00002 | | | | 00000 | 27.23 | | SCPO#1 | 43,351,830 | 1 Hr | SCPO#3 | 43,351,870 | 1 Hr |
| 26 | 11-Dec | 0.050 | 0.030 | 0.030 | 00002 | | | | 00000 | 28.11 | | SCPO#1 | 43,351,830 | 1 Hr | SCPO#3 | 43,351,870 | 1 Hr |
| 27 | 12-Dec | 0.050 | 0.030 | 0.030 | 00002 | | | | 00000 | 29.01 | | SCPO#1 | 43,351,830 | 1 Hr | SCPO#3 | 43,351,870 | 1 Hr |
| 28 | 13-Dec | 0.050 | 0.030 | 0.030 | 00002 | 0.030 | 0.030 | 0.030 | 00001 | 28.77 | | SCPO#1 | 43,351,830 | 1 Hr | SCPO#3 | 43,351,870 | 1 Hr |
| 29 | 14-Dec | 0.050 | 0.030 | 0.030 | 00002 | 0.030 | 0.030 | 0.030 | 00001 | 28.78 | | SCPO#1 | 43,351,830 | 1 Hr | SCPO#3 | 43,351,870 | 1 Hr |
| 30 | 15-Dec | 0.050 | 0.030 | 0.030 | 00002 | 0.030 | 0.030 | 0.030 | 00001 | 27.88 | | SCPO#1 | 43,351,830 | 1 Hr | SCPO#3 | 43,351,870 | 1 Hr |
| 31 | 16-Dec | 0.030 | 0.030 | 0.030 | 00001 | 0.030 | 0.030 | 0.030 | 00001 | 28.05 | | SCPO#1 | 43,351,830 | 1 Hr | SCPO#3 | 43,351,870 | 1 Hr |
| 32 | 17-Dec | 0.030 | 0.030 | 0.030 | 00001 | 0.030 | 0.030 | 0.030 | 00001 | 28.31 | | SCPO#1 | 43,351,830 | 1 Hr | SCPO#3 | 43,351,870 | 1 Hr |
| 33 | 18-Dec | 0.030 | 0.030 | 0.030 | 00001 | 0.030 | 0.030 | 0.030 | 00001 | 28.55 | | SCPO#1 | 43,351,830 | 1 Hr | SCPO#3 | 43,351,870 | 1 Hr |
| 34 | 19-Dec | 0.030 | 0.030 | 0.030 | 00001 | 0.030 | 0.030 | 0.030 | 00001 | 28.75 | 40 | SCPO#1 | 43,351,830 | 1 Hr | SCPO#3 | 43,351,870 | 1 Hr |
| 35 | 20-Dec | 0.030 | 0.030 | 0.030 | 00001 | 0.030 | 0.030 | 0.030 | 00001 | 28.84 | | SCPO#1 | 43,351,830 | 1 Hr | SCPO#3 | 43,351,870 | 1 Hr |
| 36 | 21-Dec | | | | 00000 | 0.030 | 0.030 | 0.030 | 00001 | 28.65 | | SCPO#1 | 43,351,830 | 1 Hr | SCPO#3 | 43,351,870 | 1 Hr |
| 37 | 22-Dec | | | | 00000 | 0.000 | 0.000 | 0.000 | 00000 | 28.79 | | SCPO#1 | 43,351,830 | 1 Hr | SCPO#3 | 43,351,870 | 1 Hr |
| 38 | 23-Dec | | | | 00000 | 0.000 | 0.000 | 0.000 | 00000 | 28.72 | 45 | SCPO#1 | 43,351,830 | 1 Hr | SCPO#3 | 43,351,870 | 1 Hr |
| 39 | 24-Dec | | | | 00000 | 0.030 | 0.030 | 0.030 | 00001 | 28.08 | | SCPO#1 | 43,351,830 | 1 Hr | SCPO#3 | 43,351,870 | 1 Hr |
| 40 | 25-Dec | | | | 00000 | 0.030 | 0.030 | 0.030 | 00001 | 28.19 | | SCPO#1 | 43,351,830 | 1 Hr | SCPO#3 | 43,351,870 | 1 Hr |
| 41 | 26-Dec | | | | 00000 | 0.030 | 0.030 | 0.030 | 00001 | 28.33 | | SCPO#1 | 43,351,830 | 1 Hr | SCPO#3 | 43,351,870 | 1 Hr |
| 42 | 27-Dec | | | | 00000 | 0.030 | 0.030 | 0.030 | 00001 | 28.30 | 45 | SCPO#1 | 43,351,830 | 1 Hr | SCPO#3 | 43,351,870 | 1 Hr |
| 43 | 28-Dec | | | | 00000 | 0.030 | 0.030 | 0.030 | 00001 | 28.61 | | SCPO#1 | 43,251,830 | 1 Hr | SCPO#3 | 43,351,870 | 1 Hr |
| 44 | 29-Dec | | | | 00000 | 0.030 | 0.030 | 0.030 | 00001 | 29.95 | | SCPO#1 | 43,351,830 | 1 Hr | SCPO#3 | 43,351,870 | 1 Hr |
| 45 | 30-Dec | | | | 00000 | 0.030 | 0.030 | 0.030 | 00001 | 28.08 | | SCPO#1 | 43,351,830 | 1 Hr | SCPO#3 | 43,351,870 | 1 Hr |
| 46 | 31-Dec | | | | 00000 | 0.030 | 0.030 | 0.030 | 00001 | 27.92 | 42 | SCPO#1 | 43,351,830 | 1 Hr | SCPO#3 | 43,351,870 | 1 Hr |
| 47 | 1-Jan | | | | 00000 | 0.030 | 0.030 | 0.030 | 00001 | 28.10 | | SCPO#1 | 43,351,830 | 1 Hr | SCPO#3 | 43,351,870 | 1 Hr |

09141951 . 082898

OUJ-470-.xls

| | | | | | | | | | | | | | | | | |
|---|---|---|---|---|---|---|---|---|---|---|---|---|---|---|---|---|
| 48 | 2-Jan | | | | 00000 | 0 030 | 0 030 | 0 030 | .00001 | 28 25 | | SCPO#1 | 43,351,830 | 1 Hr | SCPO#3 | 43,351,870 | 1 Hr |
| 49 | 3-Jan | | | | 00000 | 0 030 | 0 030 | 0 030 | .00001 | 28 34 | | SCPO#1 | 43,351,830 | 1 Hr | SCPO#3 | 43,351,870 | 1 Hr |
| 50 | 4-Jan | | | | 00000 | 0 030 | 0 030 | 0 030 | .00001 | 27 78 | | SCPO#1 | 43,351,830 | 1 Hr | SCPO#3 | 43,351,870 | 1 Hr |
| 51 | 5-Jan | | | | 00000 | | | | 00000 | 28 56 | | SCPO#1 | 43,351,830 | 1 Hr | SCPO#3 | 43,351,870 | 1 Hr |
| 52 | 6-Jan | | | | 00000 | | | | 00000 | 28 26 | 45 | SCPO#1 | 43,351,830 | 1 Hr | SCPO#3 | 43,351,870 | 1 Hr |
| 53 | 7-Jan | | | | 00000 | | | | 00000 | 28 16 | | SCPO#1 | 43,351,830 | 1 Hr | SCPO#3 | 43,351,870 | 1 Hr |
| 54 | 8-Jan | | | | 00000 | | | | 00000 | 27 98 | | SCPO#1 | 43,351,830 | 1 Hr | SCPO#3 | 43,351,870 | 1 Hr |
| 55 | 9-Jan | | | | 00000 | | | | 00000 | 27 82 | | SCPO#1 | 43,351,830 | 1 Hr | SCPO#3 | 43,351,870 | 1 Hr |
| 56 | 10-Jan | | | | 00000 | | | | 00000 | 28 50 | | SCPO#1 | 43,351,830 | 1 Hr | SCPO#3 | 43,351,870 | 1 Hr |
| 57 | 11-Jan | | | | 00000 | | | | .00000 | 28 96 | | SCPO#1 | 43,351,830 | 1 Hr | SCPO#3 | 43,351,870 | 1 Hr |
| 58 | 12-Jan | | | | 00000 | | | | 00000 | 28 91 | | SCPO#1 | 43,351,830 | 1 Hr | SCPO#3 | 43,351,870 | 1 Hr |
| 59 | 13-Jan | | | | 00000 | | | | 00000 | 28 35 | 43 | SCPO#1 | 43,351,830 | 1 Hr | SCPO#3 | 43,351,870 | 1 Hr |
| 60 | 14-Jan | | | | 00000 | | | | .00000 | 27 28 | | SCPO#1 | 43,351,830 | 1 Hr | SCPO#3 | 43,351,870 | 1 Hr |
| 61 | 15-Jan | | | | 00000 | | | | .00000 | 27 58 | | SCPO#1 | 43,351,830 | 1 Hr | SCPO#3 | 43,351,870 | 1 Hr |
| 62 | 16-Jan | | | | 00000 | | | | .00000 | 27.82 | | SCPO#1 | 43,351,830 | 1 Hr | SCPO#3 | 43,351,870 | 1 Hr |
| 63 | 17-Jan | | | | 00000 | | | | .00000 | 28 05 | | SCPO#1 | 43,351,830 | 1 Hr | SCPO#3 | 43,351,870 | 1 Hr |
| 64 | 18-Jan | | | | 00000 | | | | 00000 | 28 07 | | SCPO#1 | 43,351,830 | 1 Hr | SCPO#3 | 43,351,870 | 1 Hr |
| 65 | 19-Jan | | | | 00000 | | | | 00000 | 28 38 | | SCPO#1 | 43,351,830 | 1 Hr | SCPO#3 | 43,351,870 | 1 Hr |
| 66 | 20-Jan | | | | 00000 | | | | .00000 | 28 32 | 45 | SCPO#1 | 43,351,830 | 1 Hr | SCPO#3 | 43,351,870 | 1 Hr |
| 67 | 21-Jan | | | | 00000 | | | | .00000 | 28 26 | | SCPO#1 | 43,351,830 | 1 Hr | SCPO#3 | 43,351,870 | 1 Hr |
| 68 | 22-Jan | | | | 00000 | | | | 00000 | 28 36 | | SCPO#1 | 43,351,830 | 1 Hr | SCPO#3 | 43,351,870 | 1 Hr |
| 69 | 23-Jan | | | | 00000 | | | | 00000 | 28 46 | | SCPO#1 | 43,351,830 | 1 Hr | SCPO#3 | 43,351,870 | 1 Hr |
| 70 | 24-Jan | | | | 00000 | | | | 00000 | 28 62 | | SCPO#1 | 43,351,830 | 1 Hr | SCPO#3 | 43,351,870 | 1 Hr |
| 71 | 25-Jan | | | | 00000 | | | | 00000 | 28 03 | | SCPO#1 | 43,351,830 | 1 Hr | SCPO#3 | 43,351,870 | 1 Hr |
| 72 | 26-Jan | | | | 00000 | | | | 00000 | 27 70 | | SCPO#1 | 43,351,830 | 1 Hr | SCPO#3 | 43,351,870 | 1 Hr |
| 73 | 27-Jan | | | | 00000 | | | | 00000 | 29 19 | 43 | SCPO#1 | 43,351,830 | 1 Hr | SCPO#3 | 43,351,870 | 1 Hr |
| 74 | 28-Jan | | | | 00000 | | | | 00000 | 28 01 | | SCPO#1 | 43,351,830 | 1 Hr | SCPO#3 | 43,351,870 | 1 Hr |
| 75 | 29-Jan | | | | 00000 | | | | 00000 | 28 55 | | SCPO#1 | 43,351,830 | 1 Hr | SCPO#3 | 43,351,870 | 1 Hr |
| 76 | 30-Jan | | | | 00000 | | | | .00000 | 29 19 | | SCPO#1 | 43,351,830 | 1 Hr | SCPO#3 | 43,351,870 | 1 Hr |
| 77 | 31-Jan | | | | 00000 | | | | 00000 | 28 90 | | SCPO#1 | 43,351,830 | 1 Hr | SCPO#3 | 43,351,870 | 1 Hr |
| 78 | 1-Feb | | | | 00000 | | | | 00000 | 28 95 | | SCPO#1 | 43,351,830 | 1 Hr | SCPO#3 | 43,351,870 | 1 Hr |
| 79 | 2-Feb | | | | 00000 | | | | 00000 | 28 58 | | SCPO#1 | 43,351,830 | 1 Hr | SCPO#3 | 43,351,870 | 1 Hr |
| 80 | 3-Feb | | | | 00000 | | | | 00000 | 29 76 | 44 | SCPO#1 | 43,351,830 | 1 Hr | SCPO#3 | 43,351,870 | 1 Hr |
| 81 | 4-Feb | | | | 00000 | | | | 00000 | 28 54 | | SCPO#1 | 43,351,830 | 1 Hr | SCPO#3 | 43,351,870 | 1 Hr |
| 82 | 5-Feb | | | | 00000 | | | | 00000 | 28 75 | | SCPO#1 | 43,351,830 | 1 Hr | SCPO#3 | 43,351,870 | 1 Hr |
| 83 | 6-Feb | | | | 00000 | | | | 00000 | 29 09 | | SCPO#1 | 43,351,830 | 1 Hr | SCPO#3 | 43,351,870 | 1 Hr |
| 84 | 7-Feb | | | | 00000 | | | | 00000 | 29 00 | | SCPO#1 | 43,351,830 | 1 Hr | SCPO#3 | 43,351,870 | 1 Hr |
| 85 | 8-Feb | | | | 00000 | | | | 00000 | 30 31 | | SCPO#1 | 43,351,830 | 1 Hr | SCPO#3 | 43,351,870 | 1 Hr |
| 86 | 9-Feb | | | | 00000 | | | | 00000 | 28 96 | | SCPO#1 | 43,351,830 | 1 Hr | SCPO#3 | 43,351,870 | 1 Hr |
| 87 | 10-Feb | | | | 00000 | | | | 00000 | 28 95 | 42 | SCPO#1 | 43,351,830 | 1 Hr | SCPO#3 | 43,351,870 | 1 Hr |
| 88 | 11-Feb | 0 030 | 0 030 | 0 030 | 00001 | | | | 00000 | 28 85 | | SCPO#1 | 43,351,830 | 1 Hr | SCPO#3 | 43,351,870 | 1 Hr |
| 89 | 12-Feb | 0 050 | 0 050 | 0 030 | 00004 | | | | 00000 | 28 66 | | SCPO#1 | 43,351,830 | 1 Hr | SCPO#3 | 43,351,870 | 1 Hr |
| 90 | 13-Feb | 0 050 | 0 050 | 0 040 | 00005 | | | | 00000 | 28 48 | | SCPO#1 | 43,351,830 | 1 Hr | SCPO#1 | 43,351,830 | 1 Hr |
| 91 | 14-Feb | 0 050 | 0 050 | 0 050 | 00007 | | | | 00000 | 30 18 | | SCPO#1 | 43,351,830 | 1 Hr | SCPO#1 | 43,351,830 | 1 Hr |
| 92 | 15-Feb | 0 050 | 0 050 | 0 050 | 00007 | | | | 00000 | 28 86 | | SCPO#1 | 43,351,830 | 1 Hr | SCPO#3 | 43,351,870 | 1 Hr |
| 93 | 16-Feb | 0 050 | 0 050 | 0 050 | 00007 | | | | 00000 | 28 83 | | SCPO#3 | 43,351,870 | 1 Hr | SCPO#3 | 43,351,870 | 1 Hr |
| 94 | 17-Feb | 0 070 | 0 070 | 0 050 | 00013 | | | | 00000 | 28 92 | | SCPO#3 | 43,351,870 | 1 Hr | SCPO#3 | 43,351,870 | 1 Hr |
| 95 | 18-Feb | 0 070 | 0 070 | 0 050 | 00013 | | | | 00000 | 27 31 | 40 | SCPO#3 | 43,351,870 | 1 Hr | SCPO#3 | 43,351,870 | 1 Hr |
| 96 | 19-Feb | 0 070 | 0 070 | 0 050 | 00013 | | | | 00000 | 28 00 | | SCPO#3 | 43,351,870 | 1 Hr | SCPO#3 | 43,351,870 | 1 Hr |
| 97 | 20-Feb | 0 070 | 0 070 | 0 050 | 00013 | | | | 00000 | 29 65 | | SCPO#3 | 43,351,870 | 1 Hr | SCPO#3 | 43,351,870 | 1 Hr |
| 98 | 21-Feb | 0 050 | 0 050 | 0 050 | 00007 | | | | 00000 | 29 45 | | SCPO#3 | 43,351,870 | 1 Hr | SCPO#3 | 43,351,870 | 1 Hr |

4/11/97 Page 2 OUJ-470-.xls 09141691.082898

OUJ-470-.xls

| | | | | | | | | | | | | | | |
|---|---|---|---|---|---|---|---|---|---|---|---|---|---|---|
| 99 | 22-Feb | 0.050 | 0.050 | 0.050 | 00007 | 00000 | 29.08 | | SCPO#3 | 43,351,870 | 1 Hr | SCPO#3 | 43,351,870 | 1 Hr |
| 100 | 23-Feb | 0.050 | 0.050 | 0.050 | 00007 | 00000 | 29.15 | | SCPO#3 | 43,351,870 | 1 Hr | SCPO#3 | 43,351,870 | 1 Hr |
| 101 | 24-Feb | 0.050 | 0.050 | 0.030 | 00004 | 00000 | 26.48 | 42 | SCPO#3 | 43,351,870 | 1 Hr | SCPO#3 | 43,351,870 | 1 Hr |
| 102 | 25-Feb | 0.050 | 0.050 | 0.030 | 00004 | 00000 | 28.34 | | SCPO#3 | 43,351,870 | 1 Hr | SCPO#3 | 43,351,870 | 1 Hr |
| 103 | 26-Feb | 0.030 | 0.030 | 0.030 | 00001 | 00000 | 29.25 | | SCPO#3 | 43,351,870 | 1 Hr | SCPO#3 | 43,351,870 | 1 Hr |
| 104 | 27-Feb | 0.030 | 0.030 | 0.030 | 00001 | 00000 | 30.21 | | SCPO#3 | 43,351,870 | 1 Hr | SCPO#3 | 43,351,870 | 1 Hr |
| 105 | 28-Feb | 0.030 | 0.030 | 0.030 | 00001 | 00000 | 28.97 | | SCPO#3 | 43,351,870 | 1 Hr | SCPO#3 | 43,351,870 | 1 Hr |
| 106 | 1-Mar | 0.030 | 0.030 | 0.030 | 00001 | 00000 | 29.49 | | SCPO#3 | 43,351,870 | 1 Hr | SCPO#3 | 43,351,870 | 1 Hr |
| 107 | 2-Mar | | | | 00000 | 00000 | 28.58 | | SCPO#3 | 43,351,870 | 1 Hr | SCPO#3 | 43,351,870 | 1 Hr |
| 108 | 3-Mar | | | | 00000 | 00000 | 28.75 | 42 | SCPO#3 | 43,351,870 | 1 Hr | SCPO#3 | 43,351,870 | 1 Hr |
| 109 | 4-Mar | | | | 00000 | 00000 | 28.42 | | SCPO#3 | 43,351,870 | 1 Hr | SCPO#3 | 43,351,870 | 1 Hr |
| 110 | 5-Mar | | | | 00000 | 00000 | 27.90 | | SCPO#3 | 43,351,870 | 1 Hr | SCPO#3 | 43,351,870 | 1 Hr |
| 111 | 6-Mar | | | | 00000 | 00000 | 27.51 | | SCPO#3 | 43,351,870 | 1 Hr | SCPO#3 | 43,351,870 | 1 Hr |
| 112 | 7-Mar | | | | 00000 | 00000 | 28.04 | | SCPO#3 | 43,351,870 | 1 Hr | SCPO#3 | 43,351,870 | 1 Hr |
| 113 | 8-Mar | | | | 00000 | 00000 | 28.18 | | SCPO#3 | 43,351,870 | 1 Hr | SCPO#3 | 43,351,870 | 1 Hr |
| 114 | 9-Mar | | | | 00000 | 00000 | 28.78 | | SCPO#3 | 43,351,870 | 1 Hr | SCPO#3 | 43,351,870 | 1 Hr |
| 115 | 10-Mar | | | | 00000 | 00000 | 29.27 | 44 | SCPO#3 | 43,351,870 | 1 Hr | SCPO#3 | 43,351,870 | 1 Hr |
| 116 | 11-Mar | | | | 00000 | 00000 | 28.06 | | SCPO#3 | 43,351,870 | 1 Hr | SCPO#3 | 43,351,870 | 1 Hr |
| 117 | 12-Mar | | | | 00000 | 00000 | 28.14 | | SCPO#3 | 43,351,870 | 1 Hr | SCPO#3 | 43,351,870 | 1 Hr |
| 118 | 13-Mar | | | | 00000 | 00000 | 28.22 | | SCPO#3 | 43,351,870 | 1 Hr | SCPO#3 | 43,351,870 | 1 Hr |
| 119 | 14-Mar | | | | 00000 | 00000 | 28.10 | | SCPO#3 | 43,351,870 | 1 Hr | SCPO#3 | 43,351,870 | 1 Hr |
| 120 | 15-Mar | | | | 00000 | 00000 | 26.46 | | SCPO#3 | 43,351,870 | 1 Hr | SCPO#3 | 43,351,870 | 1 Hr |
| 121 | 16-Mar | | | | 00000 | 00000 | 28.77 | | SCPO#3 | 43,351,870 | 1 Hr | SCPO#3 | 43,351,870 | 1 Hr |
| 122 | 17-Mar | | | | 00000 | 00000 | 30.11 | 44 | SCPO#3 | 43,351,870 | 1 Hr | SCPO#3 | 43,351,870 | 1 Hr |
| 123 | 18-Mar | | | | 00000 | 00000 | 28.25 | | SCPO#6 | 43,351,850 | 1 Hr | SCPO#3 | 43,351,870 | 1 Hr |
| 124 | 19-Mar | | | | 00000 | 00000 | 28.20 | | SCPO#6 | 43,351,850 | 1 Hr | SCPO#3 | 43,351,870 | 1 Hr |
| 125 | 20-Mar | | | | 00000 | 00000 | 28.15 | | SCPO#6 | 43,351,850 | 1 Hr | SCPO#3 | 43,351,870 | 1 Hr |
| 126 | 21-Mar | | | | 00000 | 00000 | 26.39 | | SCPO#5 | 43,351,850 | 1 Hr | SCPO#3 | 43,351,870 | 1 Hr |
| 127 | 22-Mar | | | | 00000 | 00000 | 28.78 | | SCPO#3 | 43,351,870 | 1 Hr | SCPO#3 | 43,351,870 | 1 Hr |
| 128 | 23-Mar | | | | 00000 | 00000 | 31.00 | | SCPO#3 | 43,351,870 | 1 Hr | SCPO#3 | 43,351,870 | 1 Hr |
| 129 | 24-Mar | | | | 00000 | 00000 | 28.06 | | SCPO#3 | 43,351,870 | 1 Hr | SCPO#3 | 43,351,870 | 1 Hr |
| 130 | 25-Mar | | | | 00000 | 00000 | 28.40 | 40 | SCPO#3 | 43,351,870 | 1 Hr | SCPO#3 | 43,351,870 | 1 Hr |
| 131 | 25-Mar | | | | 00000 | 00000 | 28.28 | | SCPO#3 | 43,351,870 | 1 Hr | SCPO#3 | 43,351,870 | 1 Hr |
| 132 | 27-Mar | | | | 00000 | 00000 | 28.13 | | SCPO#3 | 43,351,870 | 1 Hr | SCPO#3 | 43,351,870 | 1 Hr |
| 133 | 28-Mar | | | | 00000 | 00000 | 29.30 | | SCPO#3 | 43,351,870 | 1 Hr | SCPO#3 | 43,351,870 | 1 Hr |
| 134 | 29-Mar | | | | 00000 | 00000 | 29.15 | | SCPO#3 | 43,351,870 | 1 Hr | SCPO#3 | 43,351,870 | 1 Hr |
| 135 | 30-Mar | | | | 00000 | 00000 | 28.14 | | SCPO#3 | 43,351,870 | 1 Hr | SCPO#3 | 43,351,870 | 1 Hr |
| 136 | 31-Mar | | | | 00000 | 00000 | 28.91 | 42 | SCPO#3 | 43,351,870 | 1 Hr | SCPO#3 | 43,351,870 | 1 Hr |
| 137 | 1-Apr | | | | 00000 | 00000 | 29.49 | | SCPO#3 | 43,351,870 | 1 Hr | SCPO#3 | 43,351,870 | 1 Hr |
| 138 | 2-Apr | | | | 00000 | 00000 | 28.99 | | SCPO#3 | 43,351,870 | 1 Hr | SCPO#3 | 43,351,870 | 1 Hr |
| 139 | 3-Apr | | | | 00000 | 00000 | 28.53 | | SCPO#3 | 43,351,870 | 1 Hr | SCPO#3 | 43,351,870 | 1 Hr |
| 140 | 4-Apr | | | | 00000 | 00000 | 29.55 | | SCPO#3 | 43,351,870 | 1 Hr | SCPO#3 | 43,351,870 | 1 Hr |
| 141 | 5-Apr | | | | 00000 | 00000 | 28.79 | | SCPO#3 | 43,351,870 | 1 Hr | SCPO#3 | 43,351,870 | 1 Hr |
| 142 | 6-Apr | | | | 00000 | 00000 | 28.32 | | SCPO#3 | 43,351,870 | 1 Hr | SCPO#3 | 43,351,870 | 1 Hr |
| 143 | 7-Apr | | | | 00000 | 00000 | 28.71 | 38 | SCPO#3 | 43,351,870 | 1 Hr | SCPO#3 | 43,351,870 | 1 Hr |
| 144 | 8-Apr | | | | 00000 | 00000 | 28.36 | | SCPO#3 | 43,351,870 | 1 Hr | SCPO#3 | 43,351,870 | 1 Hr |
| 145 | 9-Apr | | | | 00000 | 00000 | 29.05 | | SCPO#3 | 43,351,870 | 1 Hr | SCPO#3 | 43,351,870 | 1 Hr |
| 146 | 10-Apr | | | | 00000 | 00000 | 29.74 | | SCPO#1 | 43,351,830 | 1 Hr | SCPO#3 | 43,351,870 | 1 Hr |
| 147 | 11-Apr | | | | 00000 | 00000 | 28.78 | | SCPO#1 | 43,351,830 | 1 Hr | SCPO#3 | 43,351,870 | 1 Hr |
| 148 | 12-Apr | | | | 00000 | 00000 | 28.54 | | SCPO#1 | 43,351,830 | 1 Hr | SCPO#3 | 43,351,870 | 1 Hr |
| 149 | 13-Apr | | | | 00000 | 00000 | 28.22 | | SCPO#1 | 43,351,830 | 1 Hr | SCPO#3 | 43,351,870 | 1 Hr |

OUJ-470-.xls

| | | | | | | | | | | |
|---|---|---|---|---|---|---|---|---|---|---|
| 150 | 14-Apr | 00000 | 00000 | 28.86 | SCPO#1 | 43,351,830 | 1 Hr | SCPO#3 | 43,351,870 | 1 Hr |
| 151 | 15-Apr | 00000 | 00000 | 28.92 | SCPO#1 | 43,351,830 | 1 Hr | SCPO#3 | 43,351,870 | 1 Hr |
| 152 | 16-Apr | 00000 | 00000 | 28.45 | SCPO#1 | 43,351,830 | 1 Hr | SCPO#3 | 43,351,870 | 1 Hr |
| 153 | 17-Apr | 00000 | 00000 | 28.00 | SCPO#1 | 43,351,830 | 1 Hr | SCPO#3 | 43,351,870 | 1 Hr |
| 154 | 18-Apr | 00000 | 00000 | 29.63 | SCPO#1 | 43,351,830 | 1 Hr | SCPO#3 | 43,351,870 | 1 Hr |
| 155 | 19-Apr | 00000 | 00000 | 28.78 | SCPO#1 | 43,351,830 | 1 Hr | SCPO#3 | 43,351,870 | 1 Hr |
| 156 | 20-Apr | 00000 | 00000 | 28.42 | SCPO#1 | 43,351,830 | 1 Hr | SCPO#3 | 43,351,870 | 1 Hr |
| 157 | 21-Apr | 00000 | 00000 | 29.12 | SCPO#1 | 43,351,830 | 1 Hr | SCPO#3 | 43,351,870 | 1 Hr |
| 158 | 22-Apr | 00000 | 00000 | 28.35 | SCPO#1 | 43,351,830 | 1 Hr | SCPO#3 | 43,351,870 | 1 Hr |
| 159 | 23-Apr | 00000 | 00000 | 28.18 | SCPO#1 | 43,351,830 | 1 Hr | SCPO#3 | 43,351,870 | 1 Hr |
| 160 | 24-Apr | 00000 | 00000 | 28.04 | SCPO#1 | 43,351,830 | 1 Hr | SCPO#3 | 43,351,870 | 1 Hr |
| 161 | 25-Apr | 00000 | 00000 | 28.36 | SCPO#1 | 43,351,830 | 1 Hr | SCPO#3 | 43,351,870 | 1 Hr |
| 162 | 26-Apr | 00000 | 00000 | 28.29 | SCPO#1 | 43,351,830 | 1 Hr | SCPO#3 | 43,351,870 | 1 Hr |
| 163 | 27-Apr | 00000 | 00000 | 28.42 | SCPO#1 | 43,351,830 | 1 Hr | SCPO#3 | 43,351,870 | 1 Hr |
| 164 | 28-Apr | 00000 | 00000 | 28.47 | SCPO#1 | 43,351,830 | 1 Hr | SCPO#3 | 43,351,870 | 1 Hr |
| 165 | 29-Apr | 00000 | 00000 | 29.18 | SCPO#1 | 43,351,830 | 1 Hr | SCPO#3 | 43,351,870 | 1 Hr |
| 166 | 30-Apr | 00000 | 00000 | 29.22 | SCPO#1 | 43,351,830 | 1 Hr | SCPO#3 | 43,351,870 | 1 Hr |
| 167 | 1-May | 00000 | 00000 | 29.25 | SCPO#1 | 43,351,830 | 1 Hr | SCPO#3 | 43,351,870 | 1 Hr |
| 168 | 2-May | 00000 | 00000 | 28.37 | SCPO#1 | 43,351,830 | 1 Hr | SCPO#3 | 43,351,870 | 1 Hr |
| 169 | 3-May | 00000 | 00000 | 29.72 | SCPO#1 | 43,351,830 | 1 Hr | SCPO#3 | 43,351,870 | 1 Hr |
| 170 | 4-May | 00000 | 00000 | 28.78 | SCPO#1 | 43,351,830 | 1 Hr | SCPO#3 | 43,351,870 | 1 Hr |
| 171 | 5-May | 00000 | 00000 | 29.28 | SCPO#1 | 43,351,830 | 1 Hr | SCPO#3 | 43,351,870 | 1 Hr |
| 172 | 6-May | 00000 | 00000 | 28.65 | SCPO#1 | 43,351,830 | 1 Hr | SCPO#3 | 43,351,870 | 1 Hr |
| 173 | 7-May | 00000 | 00000 | 29.02 | SCPO#1 | 43,351,830 | 1 Hr | SCPO#3 | 43,351,870 | 1 Hr |
| 174 | 8-May | 00000 | 00000 | 29.30 | SCPO#1 | 43,351,830 | 1 Hr | SCPO#3 | 43,351,870 | 1 Hr |
| 175 | 9-May | 00000 | 00000 | 31.02 | SCPO#1 | 43,351,830 | 1 Hr | SCPO#3 | 43,351,870 | 1 Hr |
| 176 | 10-May | 00000 | 00000 | 29.54 | SCPO#1 | 43,351,830 | 1 Hr | SCPO#3 | 43,351,870 | 1 Hr |
| 177 | 11-May | 00000 | 00000 | 29.44 | SCPO#1 | 43,351,830 | 1 Hr | SCPO#3 | 43,351,870 | 1 Hr |
| 178 | 12-May | 00000 | 00000 | 28.71 | SCPO#1 | 43,351,830 | 1 Hr | SCPO#3 | 43,351,870 | 1 Hr |
| 179 | 13-May | 00000 | 00000 | 29.95 | SCPO#1 | 43,351,830 | 1 Hr | SCPO#3 | 43,351,870 | 1 Hr |
| 180 | 14-May | 00000 | 00000 | 30.25 | SCPO#1 | 43,351,830 | 1 Hr | SCPO#3 | 43,351,870 | 1 Hr |
| 181 | 15-May | 00000 | 00000 | 30.45 | SCPO#1 | 43,351,830 | 1 Hr | SCPO#3 | 43,351,870 | 1 Hr |
| 182 | 16-May | 00000 | 00000 | 29.50 | SCPO#1 | 43,351,830 | 1 Hr | SCPO#3 | 43,351,870 | 1 Hr |
| 183 | 17-May | 00000 | 00000 | 29.85 | SCPO#1 | 43,351,830 | 1 Hr | SCPO#3 | 43,351,870 | 1 Hr |
| 184 | 18-May | 00000 | 00000 | 28.89 | SCPO#1 | 43,351,830 | 1 Hr | SCPO#3 | 43,351,870 | 1 Hr |
| 185 | 19-May | 00000 | 00000 | 29.49 | SCPO#1 | 43,351,830 | 1 Hr | SCPO#3 | 43,351,870 | 1 Hr |
| 186 | 20-May | 00000 | 00000 | 29.85 | SCPO#1 | 43,351,830 | 1 Hr | SCPO#3 | 43,351,870 | 1 Hr |
| 187 | 21-May | 00000 | 00000 | 28.65 | SCPO#1 | 43,351,830 | 1 Hr | SCPO#3 | 43,351,870 | 1 Hr |
| 188 | 22-May | 00000 | 00000 | 28.33 | SCPO#1 | 43,351,830 | 1 Hr | SCPO#3 | 43,351,870 | 1 Hr |
| 189 | 23-May | 00000 | 00000 | 29.16 | SCPO#1 | 43,351,830 | 1 Hr | SCPO#3 | 43,351,870 | 1 Hr |
| 190 | 24-May | 00000 | 00000 | 29.71 | SCPO#1 | 43,351,830 | 1 Hr | SCPO#3 | 43,351,870 | 1 Hr |
| 191 | 25-May | 00000 | 00000 | 31.30 | SCPO#1 | 43,351,830 | 1 Hr | SCPO#3 | 43,351,870 | 1 Hr |
| 192 | 26-May | 00000 | 00000 | 29.09 | SCPO#1 | 43,351,830 | 1 Hr | SCPO#3 | 43,351,870 | 1 Hr |
| 193 | 27-May | 00000 | 00000 | 28.22 | SCPO#1 | 43,351,830 | 1 Hr | SCPO#3 | 43,351,870 | 1 Hr |
| 194 | 28-May | 00000 | 00000 | 28.18 | SCPO#1 | 43,351,830 | 1 Hr | SCPO#3 | 43,351,870 | 1 Hr |
| 195 | 29-May | 00000 | 00000 | 28.14 | SCPO#1 | 43,351,830 | 1 Hr | SCPO#3 | 43,351,870 | 1 Hr |
| 196 | 30-May | 00000 | 00000 | 29.17 | SCPO#1 | 43,351,830 | 1 Hr | SCPO#3 | 43,351,870 | 1 Hr |
| 197 | 31-May | 00000 | 00000 | 30.44 | SCPO#1 | 43,351,830 | 1 Hr | SCPO#3 | 43,351,870 | 1 Hr |
| 198 | 1-Jun | 00000 | 00000 | 30.69 | SCPO#1 | 43,351,830 | 1 Hr | SCPO#3 | 43,351,870 | 1 Hr |
| 199 | 2-Jun | 00000 | 00000 | 29.74 | SCPO#1 | 43,351,830 | 1 Hr | SCPO#3 | 43,351,870 | 1 Hr |
| 200 | 3-Jun | 00000 | 00000 | 30.41 | SCPO#1 | 43,351,830 | 1 Hr | SCPO#3 | 43,351,870 | 1 Hr |

09141691 . 082898

OUJ-470-.xls

| | | | | | | | | | | | | | | |
|---|---|---|---|---|---|---|---|---|---|---|---|---|---|---|
| 201 | 4-Jun | 00000 | | | | 00000 | 30 32 | | SCPO#1 | 43 351 830 | 1 Hr | SCPO#3 | 43,351,870 | 1 Hr |
| 202 | 5-Jun | 00000 | | | | 00000 | 30 22 | | SCPO#1 | 43 351 830 | 1 Hr | SCPO#3 | 43,351,870 | 1 Hr |
| 203 | 6-Jun | 00000 | | | | 00000 | 30 44 | | SCPO#6 | 43 351 850 | 1 Hr | SCPO#3 | 43,351,870 | 1 Hr |
| 204 | 7-Jun | 00000 | | | | 00000 | 30 41 | | SCPO#6 | 43 351 850 | 1 Hr | SCPO#3 | 43,351,870 | 1 Hr |
| 205 | 8-Jun | 00000 | | | | 00000 | 29.97 | | SCPO#6 | 43,351,850 | 1 Hr | SCPO#3 | 43,351,870 | 1 Hr |
| 206 | 9-Jun | 00000 | | | | 00000 | 29 83 | 42 | SCPO#6 | 43 351 850 | 1 Hr | SCPO#3 | 43,351,870 | 1 Hr |
| 207 | 10-Jun | 00000 | | | | 00000 | 29 69 | | SCPO#6 | 43 351 850 | 1 Hr | SCPO#3 | 43,351,870 | 1 Hr |
| 208 | 11-Jun | 00000 | | | | 00000 | 29 90 | | SCPO#6 | 43,351,850 | 1 Hr | SCPO#3 | 43,351,870 | 1 Hr |
| 209 | 12-Jun | 00000 | | | | 00000 | 30 31 | | SCPO#6 | 43 351 850 | 1 Hr | SCPO#3 | 43 351,870 | 1 Hr |
| 210 | 13-Jun | 00000 | | | | 00000 | 31 86 | | SCPO#6 | 43,351,850 | 1 Hr | SCPO#3 | 43 351,870 | 1 Hr |
| 211 | 14-Jun | 00000 | | | | 00000 | 30 47 | | SCPO#6 | 43,351,850 | 1 Hr | SCPO#3 | 43,351,870 | 1 Hr |
| 212 | 15-Jun | 00000 | | | | 00000 | 31 06 | | SCPO#6 | 43,351,850 | 1 Hr | SCPO#3 | 43,351,870 | 1 Hr |
| 213 | 16-Jun | 00000 | | | | 00000 | 31 19 | | SCPO#6 | 43,351,850 | 1 Hr | SCPO#3 | 43,351,870 | 1 Hr |
| 214 | 17-Jun | 00000 | | | | 00000 | 31 94 | 40 | SCPO#6 | 43,351,850 | 1 Hr | SCPO#3 | 43,351,870 | 1 Hr |
| 215 | 18-Jun | 00000 | | | | 00000 | 31 00 | | SCPO#6 | 43,351,850 | 1 Hr | SCPO#3 | 43,351,870 | 1 Hr |
| 216 | 19-Jun | 00000 | | | | 00000 | 30 34 | | SCPO#6 | 43,351,850 | 1 Hr | SCPO#3 | 43,351,870 | 1 Hr |
| 217 | 20-Jun | 00000 | | | | 00000 | 30 54 | | SCPO#6 | 43,351,850 | 1 Hr | SCPO#3 | 43,351,870 | 1 Hr |
| 218 | 21-Jun | 00000 | | | | 00000 | 31 40 | | SCPO#6 | 43,351,850 | 1 Hr | SCPO#3 | 43,351,870 | 1 Hr |
| 219 | 22-Jun | 00000 | | | | 00000 | 31 89 | | SCPO#5 | 43,351,850 | 1 Hr | SCPO#3 | 43,351,870 | 1 Hr |
| 220 | 23-Jun | 00000 | | | | 00000 | 32 33 | 41 | SCPO#6 | 43 351 850 | 1 Hr | SCPO#3 | 43,351,870 | 1 Hr |
| 221 | 24-Jun | 00000 | | | | 00000 | 29 58 | | SCPO#6 | 43,351,850 | 1 Hr | SCPO#3 | 43,351,870 | 1 Hr |
| 222 | 25-Jun | 00000 | | | | 00000 | 29 95 | | SCPO#6 | 43 351 850 | 1 Hr | SCPO#3 | 43,351,870 | 1 Hr |
| 223 | 26-Jun | 00000 | | | | 00000 | 30 47 | | SCPO#6 | 43 351 850 | 1 Hr | SCPO#3 | 43,351,870 | 1 Hr |
| 224 | 27-Jun | 00000 | | | | 00000 | 30 49 | | SCPO#6 | 43 351 850 | 1 Hr | SCPO#3 | 43,351,870 | 1 Hr |
| 225 | 28-Jun | 00000 | | | | 00000 | 30 63 | | SCPO#6 | 43 351 850 | 1 Hr | SCPO#3 | 43,351,870 | 1 Hr |
| 226 | 29-Jun | 00000 | | | | 00000 | 29 84 | | SCPO#6 | 43 351 850 | 1 Hr | SCPO#3 | 43,351,870 | 1 Hr |
| 227 | 30-Jun | 00000 | | | | 00000 | 30 35 | | SCPO#6 | 43,351,850 | 1 Hr | SCPO#3 | 43,351,870 | 1 Hr |
| 228 | 1-Jul | 00000 | | | | 00000 | 29 91 | | SCPO#6 | 43 351 850 | 1 Hr | SCPO#3 | 43,351 870 | 1 Hr |
| 229 | 2-Jul | 00000 | | | | 00000 | 30 20 | | SCPO#6 | 43 351 850 | 1 Hr | SCPO#3 | 43,351,870 | 1 Hr |
| 230 | 3-Jul | 00000 | | | | 00000 | 30 48 | | SCPO#6 | 43,351,850 | 1 Hr | SCPO#3 | 43,351,870 | 1 Hr |
| 231 | 4-Jul | 00000 | | | | 00000 | 30,42 | | SCPO#6 | 43 351 850 | 1 Hr | SCPO#3 | 43,351,870 | 1 Hr |
| 232 | 5-Jul | 00000 | | | | 00000 | 31 78 | | SCPO#6 | 43,351,850 | 1 Hr | SCPO#3 | 43,351,870 | 1 Hr |
| 233 | 6-Jul | 00000 | | | | 00000 | 30.77 | | SCPO#6 | 43 351,850 | 1 Hr | SCPO#3 | 43,351,870 | 1 Hr |
| 234 | 7-Jul | 00000 | | | | 00000 | 31 49 | 42 | SCPO#6 | 43 351 850 | 1 Hr | SCPO#3 | 43 351 870 | 1 Hr |
| 235 | 8-Jul | 00000 | T-3 RT NECK | | | #VALUE! | 30 87 | | SCPO#1 | 43 351 830 | 1 Hr | SCPO#1 | 43,351,830 | 1 Hr |
| 236 | 9-Jul | 00000 | 0 030 | 0 030 | 0 030 | 00001 | 31 34 | | SCPO#1 | 43,351,830 | 1 Hr | SCPO#1 | 43 351,830 | 1 Hr |
| 237 | 10-Jul | 00000 | 0 050 | 0 050 | 0 050 | 00007 | 31 81 | | SCPO#1 | 43,351,830 | 1 Hr | SCPO#1 | 43 351,830 | 1 Hr |
| 238 | 11-Jul | 00000 | 0 070 | 0 070 | 0 050 | 00013 | 32 32 | | SCPO#1 | 43 351 830 | 1 Hr | SCPO#3 | 43,351 870 | 1 Hr |
| 239 | 12-Jul | 00000 | 0 070 | 0 070 | 0 070 | 00018 | 31 18 | | SCPO#1 | 43 351 830 | 1 Hr | SCPO#6 | 43,351 850 | 1 Hr |
| 240 | 13-Jul | 00000 | 0 100 | 0 100 | 0 070 | 00037 | 32 32 | | SCPO#1 | 43 351 830 | 1 Hr | SCPO#6 | 43,351,850 | 1 Hr |
| 241 | 14-Jul | 00000 | 0 120 | 0 120 | 0 090 | 00058 | 31 54 | 30 | SCPO#1 | 43 351 830 | 1 Hr | SCPO#6 | 43 351 850 | 1 Hr |
| 242 | 15-Jul | 00000 | 0 120 | 0 150 | 0 100 | 00054 | 30 75 | | SCPO#1 | 43 351 830 | 1 Hr | SCPO#6 | 43,351,850 | 1 Hr |
| 243 | 16-Jul | 00000 | 0 135 | 0 165 | 0 100 | 00117 | 31 15 | | 8662A | | 2hr | | Homer's Elect | |
| 244 | 17-Jul | 00000 | 0 150 | 0 180 | 0 100 | 00141 | 31 55 | | 8662A | | 2hr | | Homer's Elect | |
| 245 | 18-Jul | 00000 | 0 180 | 0 210 | 0 100 | 00198 | 29 83 | | 8662A | | 2hr | | Homer's Elect | |
| 246 | 19-Jul | 00000 | 0 200 | 0 230 | 0 120 | 00289 | 25 79 | | 8662A | | 2hr | | Homer's Elect | |
| 247 | 20-Jul | 00000 | 0 220 | 0 250 | 0 120 | 00345 | 29 07 | | 8662A | | 2hr | | Homer's Elect | |
| 248 | 21-Jul | 00000 | 0 240 | 0 250 | 0 120 | 00377 | 29 41 | | 8662A | | 2hr | | Homer's Elect | |
| 249 | 22-Jul | 00000 | 0 260 | 0 250 | 0 120 | 00408 | 26 25 | | 8662A | | 2hr | | Homer's Elect | |
| 250 | 23-Jul | 00000 | 0 270 | 0 265 | 0 130 | 00487 | 28 05 | | 8662A | | 2hr | | Homer's Elect | |
| 251 | 24-Jul | 00000 | 0 280 | 0 280 | 0 140 | 00575 | 29 84 | 27 | 8662A | | 2hr | | Homer's Elect | |

4/11/97 Page 5 OUJ-470-.xls

OUJ-470-.xls

| | | | | | | | | | | | | |
|---|---|---|---|---|---|---|---|---|---|---|---|---|
| 252 | 25-Jul | | 00000 | 0 300 | 0 280 | 0 150 | 00560 | 30 33 | | 8662A | 2hr | Homer's Elect |
| 253 | 26-Jul | | 00000 | 0 320 | 0 280 | 0 160 | 00750 | 30 81 | | 8662A | 2hr | Homer's Elect |
| 254 | 27-Jul | | 00000 | 0 350 | 0 280 | 0 160 | 00821 | 30 19 | | 8662A | 2hr | Homer's Elect |
| 255 | 28-Jul | | 00000 | 0 350 | 0 280 | 0 160 | 00821 | 30 65 | 24 | 8662A | 2hr | Homer's Elect |
| 256 | 29-Jul | | 00000 | 0 370 | 0 290 | 0 170 | 00955 | 30 26 | | 8662A | 2hr | Homer's Elect |
| 257 | 30-Jul | *Died 7/30/95* | | | *Died 7/30/95* | | | | | | | |

*OUJ-471 Born 3/3/94 First tumor appeared on 1/5/95*

*Special Study...Treatment started before tumor appeared*

| DAY | DATE | SIDE OF LT LEG T-1 Ln | Wd | Ht | Vol T-1 | T-2 Ln | Wd | Ht | Vol T-2 | WEIGHT Gr | HEMATO-CRIT-% | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|
| 1 | 2-Jan | | | | 00000 | | | | 00000 | 28 98 | | 8562A | 43 351 830 | 0 DBm | 5 Hr | | | | 1 Loop |
| 2 | 3-Jan | | | | 00000 | | | | 00000 | 30 03 | | 8562A | 43 351 830 | 0 DBm | 5 Hr | | | | 1 Loop |
| 3 | 4-Jan | | | | 00000 | | | | 00000 | 29 95 | | 8562A | 43 351 830 | 0 DBm | 5 Hr | | | | 1 Loop |
| 4 | 5-Jan | 0 030 | 0 030 | 0 030 | 00001 | | | | 00000 | 29 34 | | 8562A | 43 351 830 | 0 DBm | 5 Hr | | | | 1 Loop |
| 5 | 6-Jan | 0 050 | 0 050 | 0 030 | 00004 | | | | 00000 | 29 15 | 45 | 8562A | 43 351 830 | 0 DBm | 5 Hr | | | | 1 Loop |
| 6 | 7-Jan | 0 050 | 0 050 | 0 030 | 00004 | | | | 00000 | 29 65 | | 8562A | 43 351 830 | 0 DBm | 5 Hr | | | | 1 Loop |
| 7 | 8-Jan | 0 060 | 0 060 | 0 040 | 00008 | | | | 00000 | 29 57 | | 8562A | 43 351 830 | 0 DBm | 5 Hr | | | | 1 Loop |
| 8 | 9-Jan | 0 070 | 0 070 | 0 050 | 00013 | | | | 00000 | 29 49 | | 8562A | 43 351 830 | -10DBm | 1 Hr | 43 351 870 | -10DBm | 1 Hr | 2 Loops |
| 9 | 10-Jan | 0 070 | 0 070 | 0 050 | 00013 | | | | 00000 | 29 21 | | 8562A | 43 351 830 | 10DBm | 1 Hr | 43 351 870 | -10DBm | 1 Hr | 2 Loops |
| 10 | 11-Jan | 0 100 | 0 100 | 0 050 | 00026 | | | | 00000 | 29 41 | | 8562A | 43 351 830 | -10DBm | 1 Hr | 43 351 870 | -10DBm | 1 Hr | 2 Loops |
| 11 | 12-Jan | 0 100 | 0 100 | 0 050 | 00026 | | | | 00000 | 29 47 | | 8562A | 43 351 830 | -10DBm | 1 Hr | 43 351 870 | -10DBm | 1 Hr | 2 Loops |
| 12 | 13-Jan | 0 070 | 0 070 | 0 050 | 00013 | | | | 00000 | 29 28 | 45 | 8562A | 43 351 830 | -10DBm | 1 Hr | 43 351 870 | -10DBm | 1 Hr | 2 Loops |
| 13 | 14-Jan | 0 050 | 0 050 | 0 050 | 00007 | | | | 00000 | 29 47 | | 8562A | 43 351 830 | -10DBm | 1 Hr | 43 351 870 | -10DBm | 1 Hr | 2 Loops |
| 14 | 15-Jan | 0 060 | 0 050 | 0 050 | 00008 | | | | 00000 | 29 84 | | 8562A | 43 351 830 | -10DBm | 1 Hr | 43 351 870 | -10DBm | 1 Hr | 2 Loops |
| 15 | 16-Jan | 0 070 | 0 050 | 0 050 | 00009 | | | | 00000 | 30 25 | | 8562A | 43 351 830 | -10DBm | 1 Hr | 43 351 870 | -10DBm | 1 Hr | 2 Loops |
| 15 | 17-Jan | 0 070 | 0 050 | 0 050 | 00009 | | | | 00000 | 30 26 | | 8562A | 43 351 830 | -10DBm | 1 Hr | 43 351 870 | -10DBm | 1 Hr | 2 Loops |
| 17 | 18-Jan | 0 070 | 0 070 | 0 050 | 00013 | | | | 00000 | 30 43 | | 8562A | 43 351 830 | -10DBm | 1 Hr | 43 351 870 | -10DBm | 1 Hr | 2 Loops |
| 18 | 19-Jan | 0 070 | 0 070 | 0 050 | 00013 | | | | 00000 | 29 34 | | 8562A | 43 351 830 | -10DBm | 1 Hr | 43 351 870 | -10DBm | 1 Hr | 2 Loops |
| 19 | 20-Jan | 0 050 | 0 050 | 0 050 | 00007 | | | | 00000 | 29 47 | 43 | 8562A | 43 351 830 | -10DBm | 1 Hr | 43 351 870 | -10DBm | 1 Hr | 2 Loops |
| 20 | 21-Jan | 0 050 | 0 050 | 0 030 | 00004 | | | | 00000 | 29 46 | | 8562A | 43 351 830 | -10DBm | 1 Hr | 43 351 870 | -10DBm | 1 Hr | 2 Loops |
| 21 | 22-Jan | 0 050 | 0 050 | 0 030 | 00004 | | | | 00000 | 29 80 | | 8562A | 43 351 830 | -10DBm | 1 Hr | 43 351 870 | -10DBm | 1 Hr | 2 Loops |
| 22 | 23-Jan | 0 050 | 0 050 | 0 030 | 00004 | | | | 00000 | 30 12 | | 8562A | 43 351 830 | -10DBm | 1 Hr | 43 351 870 | -10DBm | 1 Hr | 2 Loops |
| 23 | 24-Jan | 0 030 | 0 030 | 0 030 | 00001 | | | | 00000 | 30 21 | | 8562A | 43 351 830 | -10DBm | 1 Hr | 43 351 870 | -10DBm | 1 Hr | 2 Loops |
| 24 | 25-Jan | 0 030 | 0 030 | 0 030 | 00001 | | | | 00000 | 29 50 | | 8562A | 43 351 830 | -10DBm | 1 Hr | 43 351 870 | -10DBm | 1 Hr | 2 Loops |
| 25 | 26-Jan | | | | 00000 | | | | 00000 | 29 79 | | 8562A | 43 351 830 | -10DBm | 1 Hr | 43 351 870 | -10DBm | 1 Hr | 2 Loops |
| 26 | 27-Jan | | | | 00000 | | | | 00000 | 30 71 | 42 | 8562A | 43 351 830 | -10DBm | 1 Hr | 43 351 870 | -10DBm | 1 Hr | 2 Loops |
| 27 | 28-Jan | | | | 00000 | | | | 00000 | 30 06 | | 8562A | 43 351 830 | -10DBm | 1 Hr | 43 351 870 | -10DBm | 1 Hr | 2 Loops |
| 28 | 29-Jan | | | | 00000 | | | | 00000 | 30 31 | | 8562A | 43 351 830 | -10DBm | 1 Hr | 43 351 870 | -10DBm | 1 Hr | 2 Loops |
| 29 | 30-Jan | | | | 00000 | | | | 00000 | 30 61 | | 8562A | 43 351 830 | -10DBm | 1 Hr | 43 351 870 | -10DBm | 1 Hr | 2 Loops |
| 30 | 31-Jan | | | | 00000 | 0 030 | 0 030 | 0 030 | 00001 | 30 64 | | 8562A | 43 351 830 | -10DBm | 1 Hr | 43 351 870 | -10DBm | 1 Hr | 2 Loops |
| 31 | 1-Feb | | | | 00000 | 0 030 | 0 030 | 0 030 | 00001 | 30 16 | | 8562A | 43 351 830 | -10DBm | 1 Hr | 43 351 870 | -10DBm | 1 Hr | 2 Loops |
| 32 | 2-Feb | | | | 00000 | 0 030 | 0 030 | 0 030 | 00001 | 30 44 | | 8562A | 43 351 830 | -10DBm | 1 Hr | 43 351 870 | -10DBm | 1 Hr | 2 Loops |
| 33 | 3-Feb | | | | 00000 | 0 030 | 0 030 | 0 030 | 00001 | 31 91 | 42 | 8562A | 43 351 830 | -10DBm | 1 Hr | 43 351 870 | -10DBm | 1 Hr | 2 Loops |
| 34 | 4-Feb | | | | 00000 | 0 030 | 0 030 | 0 030 | 00001 | 30 35 | | 8562A | 43 351 830 | -10DBm | 1 Hr | 43 351 870 | -10DBm | 1 Hr | 2 Loops |
| 35 | 5-Feb | | | | 00000 | 0 030 | 0 030 | 0 030 | 00001 | 30 66 | | 8562A | 43 351 830 | -10DBm | 1 Hr | 43 351 870 | -10DBm | 1 Hr | 2 Loops |
| 36 | 6-Feb | | | | 00000 | 0 030 | 0 030 | 0 030 | 00001 | 30 96 | | 8562A | 43 351 830 | -10DBm | 1 Hr | 43 351 870 | -10DBm | 1 Hr | 2 Loops |
| 37 | 7-Feb | | | | 00000 | 0 030 | 0 030 | 0 030 | 00001 | 30 57 | | 8562A | 43 351 830 | -10DBm | 1 Hr | 43 351 870 | -10DBm | 1 Hr | 2 Loops |
| 38 | 8-Feb | | | | 00000 | 0 030 | 0 030 | 0 050 | 00002 | 31 29 | | 8562A | 43 351 830 | -10DBm | 1 Hr | 43 351 870 | -10DBm | 1 Hr | 2 Loops |
| 39 | 9-Feb | | | | 00000 | 0 050 | 0 050 | 0 050 | 00007 | 30 55 | | 8562A | 43 351 830 | -10DBm | 1 Hr | 43 351 870 | -10DBm | 1 Hr | 1 Loops |
| 40 | 10-Feb | | | | 00000 | 0 070 | 0 050 | 0 050 | 00009 | 29 39 | 45 | 8562A | 43 351 830 | -10DBm | 1 Hr | 43 351 870 | -10DBm | 1 Hr | 1 Loops |
| 41 | 11-Feb | | | | 00000 | 0 070 | 0 050 | 0 050 | 00009 | 29 06 | | 8562A | 43 351 830 | -10DBm | 1 Hr | 43 351 870 | -10DBm | 1 Hr | 1 Loops |
| 42 | 12-Feb | | | | 00000 | 0 070 | 0 050 | 0 050 | 00009 | 29 58 | | 8562A | 43 351 830 | -10DBm | 1 Hr | 43 351 870 | -10DBm | 1 Hr | 1 Loops |
| 43 | 13-Feb | | | | 00000 | 0 070 | 0 050 | 0 050 | 00009 | 29 29 | | 8562A | 43 351 830 | -10DBm | 1 Hr | 43 351 870 | -10DBm | 1 Hr | 1 Loops |
| 44 | 14-Feb | | | | 00000 | 0 050 | 0 050 | 0 050 | 00007 | 29 47 | | 8562A | 43 351 830 | -10DBm | 1 Hr | 43 351 870 | -10DBm | 1 Hr | 1 Loops |
| 45 | 15-Feb | | | | 00000 | 0 050 | 0 050 | 0 050 | 00007 | 29 30 | | 8562A | 43 351 830 | -10DBm | 1 Hr | 43 351 870 | -10DBm | 1 Hr | 1 Loops |
| 46 | 16-Feb | | | | 00000 | 0 050 | 0 050 | 0 050 | 00007 | 30 60 | | 8562A | 43 351 830 | -10DBm | 1 Hr | 43 351 870 | -10DBm | 1 Hr | 1 Loops |
| 47 | 17-Feb | | | | 00000 | 0 050 | 0 050 | 0 050 | 00007 | 29 95 | | 8562A | 43 351 830 | -10DBm | 1 Hr | 43 351 870 | -10DBm | 1 Hr | 1 Loops |
| 48 | 18-Feb | | | | 00000 | 0 050 | 0 050 | 0 030 | 00004 | 29 63 | 41 | 8562A | 43 351 830 | -10DBm | 1 Hr | 43 351 870 | -10DBm | 1 Hr | 1 Loops |
| 49 | 19-Feb | | | | 00000 | 0 050 | 0 050 | 0 030 | 00004 | 29 93 | | 8562A | 43 351 830 | -10DBm | 1 Hr | 43 351 870 | -10DBm | 1 Hr | 1 Loops |
| 50 | 20-Feb | | | | 00000 | 0 050 | 0 050 | 0 030 | 00004 | 30 21 | | 8562A | 43 351 830 | -10DBm | 1 Hr | 43 351 870 | -10DBm | 1 Hr | 1 Loops |
| 51 | 21-Feb | | | | 00000 | 0 050 | 0 050 | 0 030 | 00004 | 30 47 | | 8562A | 43 351 830 | -10DBm | 1 Hr | 43 351 870 | -10DBm | 1 Hr | 1 Loops |
| 52 | 22-Feb | | | | 00000 | 0 050 | 0 050 | 0 030 | 00004 | 30 16 | | 8562A | 43 351 830 | -10DBm | 1 Hr | 43 351 870 | -10DBm | 1 Hr | 1 Loops |
| 53 | 23-Feb | | | | 00000 | 0 050 | 0 050 | 0 030 | 00004 | 30 20 | | 8562A | 43 351 830 | -10DBm | 1 Hr | 43 351 870 | -10DBm | 1 Hr | 1 Loops |
| 54 | 24-Feb | | | | 00000 | 0 050 | 0 050 | 0 030 | 00004 | 31 15 | 45 | 8562A | 43 351 830 | -10DBm | 1 Hr | 43 351 870 | -10DBm | 1 Hr | 1 Loops |

OUJ-471- xls

| | | | | | | | | | | | | | | | | |
|---|---|---|---|---|---|---|---|---|---|---|---|---|---|---|---|---|
| 55 | 25-Feb | 00000 | 0 050 | 0 050 | 0 030 | 00004 | 29 56 | | 8662A | 43 351 830 | -10DBm | 1 Hr | 43 351 870 | -10DBm | 1 Hr | 1 Loops |
| 56 | 26-Feb | 00000 | 0 050 | 0 050 | 0 030 | 00004 | 30 50 | | 8662A | 43 351 830 | -10DBm | 1 Hr | 43 351 870 | -10DBm | 1 Hr | 1 Loops |
| 57 | 27-Feb | 00000 | 0 050 | 0 050 | 0 030 | 00004 | 31 50 | | 8662A | 43 351 830 | -10DBm | 1 Hr | 43 351 870 | -10DBm | 1 Hr | 1 Loops |
| 58 | 28-Feb | 00000 | 0 050 | 0 050 | 0 030 | 00004 | 30 39 | | 8662A | 43 351 830 | -10DBm | 1 Hr | 43 351 870 | -10DBm | 1 Hr | 1 Loops |
| 59 | 1-Mar | 00000 | 0 050 | 0 030 | 0 030 | 00002 | 30 61 | | 8662A | 43 351 830 | -10DBm | 1 Hr | 43 351 870 | -10DBm | 1 Hr | 1 Loops |
| 60 | 2-Mar | 00000 | 0 050 | 0 030 | 0 030 | 00002 | 30 07 | | 8662A | 43 351 830 | -10DBm | 1 Hr | 43 351 870 | -10DBm | 1 Hr | 1 Loops |
| 61 | 3-Mar | 00000 | 0 030 | 0 030 | 0 030 | 00001 | 30 42 | 42 | 8662A | 43 351 830 | -10DBm | 1 Hr | 43 351 870 | -10DBm | 1 Hr | 1 Loops |
| 62 | 4-Mar | 00000 | 0 030 | 0 030 | 0 030 | 00001 | 30 11 | | 8662A | 43 351 830 | -10DBm | 1 Hr | 43 351 870 | -10DBm | 1 Hr | 1 Loops |
| 63 | 5-Mar | 00000 | 0 030 | 0 030 | 0 030 | 00001 | 30 22 | | 8662A | 43 351 830 | -10DBm | 1 Hr | 43 351 870 | -10DBm | 1 Hr | 1 Loops |
| 64 | 6-Mar | 00000 | 0 030 | 0 030 | 0 030 | 00001 | 30 33 | | 8662A | 43 351 830 | -10DBm | 1 Hr | 43 351 870 | -10DBm | 1 Hr | 1 Loops |
| 65 | 7-Mar | 00000 | 0 030 | 0 030 | 0 030 | 00001 | 29 55 | | 8662A | 43 351 830 | -10DBm | 1 Hr | 43 351 870 | -10DBm | 1 Hr | 1 Loops |
| 66 | 8-Mar | 00000 | 0 030 | 0 030 | 0 030 | 00001 | 30 55 | | 8662A | 43 351 850 | -10DBm | 1 Hr | 43 351 870 | -10DBm | 1 Hr | 1 Loops |
| 67 | 9-Mar | 00000 | 0 030 | 0 030 | 0 030 | 00001 | 30 54 | | 8662A | 43 351 850 | 0DBm | 1 Hr | 43 351 870 | 0DBm | 1 Hr | 1 Loops |
| 68 | 10-Mar | 00000 | 0 030 | 0 030 | 0 030 | 00001 | 30 69 | 44 | 8662A | 43 351 850 | 0DBm | 1 Hr | 43 351 870 | 0DBm | 1 Hr | 1 Loops |
| 69 | 11-Mar | 00000 | 0 050 | 0 050 | 0 030 | 00004 | 30 60 | | 8662A | 43 351 830 | -10DBm | 1 Hr | 43 351 870 | -10DBm | 1 Hr | 1 Loops |
| 70 | 12-Mar | 00000 | 0 050 | 0 050 | 0 030 | 00004 | 30 80 | | 8662A | 43 351 830 | -10DBm | 1 Hr | 43 351 870 | -10DBm | 1 Hr | 1 Loops |
| 71 | 13-Mar | 00000 | 0 050 | 0 050 | 0 030 | 00004 | 31 00 | | 8662A | 43 351 830 | -10DBm | 1 Hr | 43 351 870 | -10DBm | 1 Hr | 1 Loops |
| 72 | 14-Mar | 00000 | 0 030 | 0 030 | 0 030 | 00001 | 30 96 | | 8662A | 43 351 830 | -10DBm | 1 Hr | 43 351 870 | -10DBm | 1 Hr | 1 Loops |
| 73 | 15-Mar | 00000 | 0 030 | 0 030 | 0 030 | 00001 | 30 69 | | 8662A | 43 351 830 | -10DBm | 1 Hr | 43 351 870 | -10DBm | 1 Hr | 1 Loops |
| 74 | 16-Mar | 00000 | | | | 00000 | 29 90 | | 8662A | 43 351 830 | -10DBm | 1 Hr | 43 351 870 | -10DBm | 1 Hr | 1 Loops |
| 75 | 17-Mar | 00000 | | | | 00000 | 31 50 | 40 | 8662A | 43 351 830 | -10DBm | 1 Hr | 43 351 870 | -10DBm | 1 Hr | 1 Loops |
| 76 | 18-Mar | 00000 | | | | 00000 | 30 85 | | 8662A | 43 351 830 | -10DBm | 1 Hr | 43 351 870 | -10DBm | 1 Hr | 1 Loops |
| 77 | 19-Mar | 00000 | | | | 00000 | 30 12 | | 8662A | 43 351 830 | -10DBm | 1 Hr | 43 351 870 | -10DBm | 1 Hr | 1 Loops |
| 78 | 20-Mar | 00000 | | | | 00000 | 30 41 | | 8662A | 43 351 830 | -10DBm | 1 Hr | 43 351 870 | -10DBm | 1 Hr | 1 Loops |
| 79 | 21-Mar | 00000 | | | | 00000 | 30 61 | | 8662A | 43 351 830 | -10DBm | 1 Hr | 43 351 870 | -10DBm | 1 Hr | 1 Loops |
| 80 | 22-Mar | 00000 | | | | 00000 | 30 26 | | 8662A | 43 351 830 | -10DBm | 1 Hr | 43 351 870 | -10DBm | 1 Hr | 1 Loops |
| 81 | 23-Mar | 00000 | | | | 00000 | 30 83 | | 8662A | 43 351 830 | -10DBm | 1 Hr | 43 351 870 | -10DBm | 1 Hr | 1 Loops |
| 82 | 24-Mar | 00000 | | | | 00000 | 29 81 | | 8662A | 43 351 830 | -10DBm | 1 Hr | 43 351 870 | -10DBm | 1 Hr | 1 Loops |
| 83 | 25-Mar | 00000 | | | | 00000 | 30 23 | 38 | 8662A | 43 351 850 | -10DBm | 1 Hr | 43 351 870 | -10DBm | 1 Hr | 1 Loops |
| 84 | 26-Mar | 00000 | | | | 00000 | 30 43 | | 8662A | 43 351 850 | -10DBm | 1 Hr | 43 351 870 | -10DBm | 1 Hr | 1 Loops |
| 85 | 27-Mar | 00000 | | | | 00000 | 30 62 | | 8662A | 43 351 850 | -10DBm | 1 Hr | 43 351 870 | -10DBm | 1 Hr | 1 Loops |
| 86 | 28-Mar | 00000 | | | | 00000 | 32 36 | | 8662A | 43 351 850 | -10DBm | 1 Hr | 43 351 870 | -10DBm | 1 Hr | 1 Loops |
| 87 | 29-Mar | 00000 | | | | 00000 | 30 69 | | 8662A | 43 351 850 | -10DBm | 1 Hr | 43 351 870 | -10DBm | 1 Hr | 1 Loops |
| 88 | 30-Mar | 00000 | | | | 00000 | 30 36 | | 8662A | 43 351 850 | -10DBm | 1 Hr | 43 351 870 | -10DBm | 1 Hr | 1 Loops |
| 89 | 31-Mar | 00000 | | | | 00000 | 30 57 | 43 | 8662A | 43 351 850 | -10DBm | 1 Hr | 43 351 870 | -10DBm | 1 Hr | 1 Loops |
| 90 | 1-Apr | 00000 | | | | 00000 | 30 22 | | 8662A | 43 351 850 | -10DBm | 1 Hr | 43 351 870 | -10DBm | 1 Hr | 1 Loops |
| 91 | 2-Apr | 00000 | | | | 00000 | 30 52 | | 8662A | 43 351 850 | -10DBm | 1 Hr | 43 351 870 | -10DBm | 1 Hr | 1 Loops |
| 92 | 3-Apr | 00000 | | | | 00000 | 30 83 | | 8662A | 43 351 850 | -10DBm | 1 Hr | 43 351 870 | -10DBm | 1 Hr | 1 Loops |
| 93 | 4-Apr | 00000 | | | | 00000 | 30 80 | | 8662A | 43 351 850 | -10DBm | 1 Hr | 43 351 870 | -10DBm | 1 Hr | 1 Loops |
| 94 | 5-Apr | 00000 | | | | 00000 | 30 60 | | 8662A | 43 351 850 | -10DBm | 1 Hr | 43 351 870 | -10DBm | 1 Hr | 1 Loops |
| 95 | 6-Apr | 00000 | | | | 00000 | 29 72 | | 8662A | 43 351 850 | -10DBm | 1 Hr | 43 351 870 | -10DBm | 1 Hr | 1 Loops |
| 96 | 7-Apr | 00000 | | | | 00000 | 29 89 | 46 | 8662A | 43 351 850 | -10DBm | 1 Hr | 43 351 870 | -10DBm | 1 Hr | 1 Loops |
| 97 | 8-Apr | 00000 | | | | 00000 | 29 75 | | 8662A | 43 351 850 | -10DBm | 1 Hr | 43 351 870 | -10DBm | 1 Hr | 1 Loops |
| 98 | 9-Apr | 00000 | | | | 00000 | 30 30 | | 8662A | 43 351 850 | -10DBm | 1 Hr | 43 351 870 | -10DBm | 1 Hr | 1 Loops |
| 99 | 10-Apr | 00000 | | | | 00000 | 30 92 | | 8662A | 43 351 850 | -10DBm | 1 Hr | 43 351 870 | -10DBm | 1 Hr | 1 Loops |
| 100 | 11-Apr | 00000 | | | | 00000 | 29 67 | | 8662A | 43 351 850 | -10DBm | 1 Hr | 43 351 870 | -10DBm | 1 Hr | 1 Loops |
| 101 | 12-Apr | 00000 | | | | 00000 | 29 63 | | 8662A | 43 351 850 | -10DBm | 1 Hr | 43 351 870 | -10DBm | 1 Hr | 1 Loops |
| 102 | 13-Apr | 00000 | | | | 00000 | 29 65 | | 8662A | 43 351 830 | -10DBm | 1 Hr | 43 351 870 | -10DBm | 1 Hr | 1 Loops |
| 103 | 14-Apr | 00000 | | | | 00000 | 31 17 | 45 | 8662A | 43 351 830 | -10DBm | 1 Hr | 43 351 870 | -10DBm | 1 Hr | 1 Loops |
| 104 | 15-Apr | 00000 | | | | 00000 | 30 78 | | 8662A | 43 351 830 | -10DBm | 1 Hr | 43 351 870 | -10DBm | 1 Hr | 1 Loops |
| 105 | 16-Apr | 00000 | | | | 00000 | 30 45 | | 8662A | 43 351 830 | -10DBm | 1 Hr | 43 351 870 | -10DBm | 1 Hr | 1 Loops |
| 106 | 17-Apr | 00000 | | | | 00000 | 30 13 | | 8662A | 43 351 850 | -10DBm | 1 Hr | 43 351 870 | -10DBm | 1 Hr | 1 Loops |
| 107 | 18-Apr | 00000 | | | | 00000 | 30 10 | | 8662A | 43 351 850 | -10DBm | 1 Hr | 43 351 870 | -10DBm | 1 Hr | 1 Loops |
| 108 | 19-Apr | 00000 | | | | 00000 | 29 60 | | 8662A | 43 351 850 | -10DBm | 1 Hr | 43 351 870 | -10DBm | 1 Hr | 1 Loops |
| 109 | 20-Apr | 00000 | | | | 00000 | 29 71 | | 8662A | 43 351 850 | -10DBm | 1 Hr | 43 351 870 | -10DBm | 1 Hr | 1 Loops |
| 110 | 21-Apr | 00000 | | | | 00000 | 29 91 | 40 | 8662A | 43 351 850 | -10DBm | 1 Hr | 43 351 870 | -10DBm | 1 Hr | 1 Loops |
| 111 | 22-Apr | 00000 | | | | 00000 | 29 58 | | 8662A | 43 351 850 | -10DBm | 1 Hr | 43 351 870 | -10DBm | 1 Hr | 1 Loops |
| 112 | 23-Apr | 00000 | | | | 00000 | 30 10 | | 8662A | 43 351 850 | -10DBm | 1 Hr | 43 351 870 | -10DBm | 1 Hr | 1 Loops |

4/11/97 Page 2 OUJ-471- xls

OUJ-471-.xls

| | | | | | | | | | | | | | |
|---|---|---|---|---|---|---|---|---|---|---|---|---|---|
| 113 | 24-Apr | 00000 | 00000 | 30 50 | | 8562A | 43 351 850 | -10DBm | 1 Hr | 43 351 870 | -10DBm | 1 Hr | 1 Loops |
| 114 | 25-Apr | 00000 | 00000 | 31 27 | | 8562A | 43 351 830 | -10DBm | 1 Hr | 43 351 870 | -10DBm | 1 Hr | 1 Loops |
| 115 | 26-Apr | 00000 | 00000 | 31 18 | | 8562A | 43 351 830 | -10DBm | 1 Hr | 43 351 870 | -10DBm | 1 Hr | 1 Loops |
| 116 | 27-Apr | 00000 | 00000 | 30 17 | | 8562A | 43 351 830 | -10DBm | 1 Hr | 43 351 870 | -10DBm | 1 Hr | 1 Loops |
| 117 | 28-Apr | 00000 | 00000 | 30 40 | 42 | 8562A | 43 351 830 | -10DBm | 1 Hr | 43 351 870 | -10DBm | 1 Hr | 1 Loops |
| 118 | 29-Apr | 00000 | 00000 | 29 91 | | 8562A | 43 351 830 | -10DBm | 1 Hr | 43 351 870 | -10DBm | 1 Hr | 1 Loops |
| 119 | 30-Apr | 00000 | 00000 | 30 25 | | 8562A | 43 351 830 | -10DBm | 1 Hr | 43 351 870 | -10DBm | 1 Hr | 1 Loops |
| 120 | 1-May | 00000 | 00000 | 30 43 | | 8562A | 43 351 830 | -10DBm | 1 Hr | 43 351 870 | -10DBm | 1 Hr | 1 Loops |
| 121 | 2-May | 00000 | 00000 | 30 03 | | 8562A | 43 351 830 | -10DBm | 1 Hr | 43 351 870 | -10DBm | 1 Hr | 1 Loops |
| 122 | 3-May | 00000 | 00000 | 30 92 | | 8562A | 43 351 830 | -10DBm | 1 Hr | 43 351 870 | -10DBm | 1 Hr | 1 Loops |
| 123 | 4-May | 00000 | 00000 | 30 62 | | 8562A | 43 351 830 | -10DBm | 1 Hr | 43 351 870 | -10DBm | 1 Hr | 1 Loops |
| 124 | 5-May | 00000 | 00000 | 30 95 | 44 | 8562A | 43 351 830 | -10DBm | 1 Hr | 43 351 870 | -10DBm | 1 Hr | 1 Loops |
| 125 | 6-May | 00000 | 00000 | 30 34 | | 8562A | 43 351 830 | -10DBm | 1 Hr | 43 351 870 | -10DBm | 1 Hr | 1 Loops |
| 126 | 7-May | 00000 | 00000 | 30 64 | | 8562A | 43 351 830 | -10DBm | 1 Hr | 43 351 870 | -10DBm | 1 Hr | 1 Loops |
| 127 | 8-May | 00000 | 00000 | 30 92 | | 8562A | 43 351 830 | -10DBm | 1 Hr | 43 351 870 | -10DBm | 1 Hr | 1 Loops |
| 128 | 9-May | 00000 | 00000 | 32 04 | | 8562A | 43 351 830 | -10DBm | 1 Hr | 43 351 870 | -10DBm | 1 Hr | 1 Loops |
| 129 | 10-May | 00000 | 00000 | 30 92 | | 8562A | 43 351 830 | -10DBm | 1 Hr | 43 351 870 | -10DBm | 1 Hr | 1 Loops |
| 130 | 11-May | 00000 | 00000 | 31 21 | 39 | 8562A | 43 351 830 | -10DBm | 1 Hr | 43 351 870 | -10DBm | 1 Hr | 1 Loops |
| 131 | 12-May | 00000 | 00000 | 30 20 | | 8562A | 43 351 830 | -10DBm | 1 Hr | 43 351 870 | -10DBm | 1 Hr | 1 Loops |
| 132 | 13-May | 00000 | 00000 | 30 02 | | 8562A | 43 351 830 | -10DBm | 1 Hr | 43 351 870 | -10DBm | 1 Hr | 1 Loops |
| 133 | 14-May | 00000 | 00000 | 30 01 | | 8562A | 43 351 830 | -10DBm | 1 Hr | 43 351 870 | -10DBm | 1 Hr | 1 Loops |
| 134 | 15-May | 00000 | 00000 | 30 00 | | 8562A | 43 351 830 | -10DBm | 1 Hr | 43 351 870 | -10DBm | 1 Hr | 1 Loops |
| 135 | 16-May | 00000 | 00000 | 32 05 | | 8562A | 43 351 830 | -10DBm | 1 Hr | 43 351 870 | -10DBm | 1 Hr | 1 Loops |
| 136 | 17-May | 00000 | 00000 | 31 31 | | 8562A | 43 351 830 | -10DBm | 1 Hr | 43 351 870 | -10DBm | 1 Hr | 1 Loops |
| 137 | 18-May | 00000 | 00000 | 30 99 | | 8562A | 43 351 830 | -10DBm | 1 Hr | 43 351 870 | -10DBm | 1 Hr | 1 Loops |
| 138 | 19-May | 00000 | 00000 | 30 71 | 33 | 8562A | 43 351 830 | -10DBm | 1 Hr | 43 351 870 | -10DBm | 1 Hr | 1 Loops |
| 139 | 20-May | 00000 | 00000 | 30 75 | | 8562A | 43 351 830 | -10DBm | 1 Hr | 43 351 870 | -10DBm | 1 Hr | 1 Loops |
| 140 | 21-May | 00000 | 00000 | 30 79 | | 8562A | 43 351 830 | -10DBm | 1 Hr | 43 351 870 | -10DBm | 1 Hr | 1 Loops |
| 141 | 22-May | 00000 | 00000 | 30 82 | | 8562A | 43 351 830 | -10DBm | 1 Hr | 43 351 870 | -10DBm | 1 Hr | 1 Loops |
| 142 | 23-May | 00000 | 00000 | 30 64 | | 8562A | 43 351 830 | -10DBm | 1 Hr | 43 351 870 | -10DBm | 1 Hr | 1 Loops |
| 143 | 24-May | 00000 | 00000 | 29 65 | | 8562A | 43 351 830 | -10DBm | 1 Hr | 43 351 870 | -10DBm | 1 Hr | 1 Loops |
| 144 | 25-May | 00000 | 00000 | 31 46 | | 8562A | 43 351 830 | -10DBm | 1 Hr | 43 351 870 | -10DBm | 1 Hr | 1 Loops |
| 145 | 26-May | 00000 | 00000 | 29 44 | 40 | 8562A | 43 351 830 | -10DBm | 1 Hr | 43 351 870 | -10DBm | 1 Hr | 1 Loops |
| 146 | 27-May | 00000 | 00000 | 28 78 | | 8562A | 43 351 830 | -10DBm | 1 Hr | 43 351 870 | -10DBm | 1 Hr | 1 Loops |
| 147 | 28-May | 00000 | 00000 | 29 40 | | 8562A | 43 351 830 | -10DBm | 1 Hr | 43 351 870 | -10DBm | 1 Hr | 1 Loops |
| 148 | 29-May | 00000 | 00000 | 30 07 | | 8562A | 43 351 830 | -10DBm | 1 Hr | 43 351 870 | -10DBm | 1 Hr | 1 Loops |
| 149 | 30-May | 00000 | 00000 | 30 01 | | 8562A | 43 351 830 | -10DBm | 1 Hr | 43 351 870 | -10DBm | 1 Hr | 1 Loops |
| 150 | 31-May | 00000 | 00000 | 30 67 | | 8562A | 43 351 830 | -10DBm | 1 Hr | 43 351 870 | -10DBm | 1 Hr | 1 Loops |
| 151 | 1-Jun | 00000 | 00000 | 30 63 | | 8562A | 43 351 830 | -10DBm | 1 Hr | 43 351 870 | -10DBm | 1 Hr | 1 Loops |
| 152 | 2-Jun | 00000 | 00000 | 30 04 | 37 | 8562A | 43 351 830 | -10DBm | 1 Hr | 43 351 870 | -10DBm | 1 Hr | 1 Loops |
| 153 | 3-Jun | 00000 | 00000 | 29 70 | | 8562A | 43 351 830 | -10DBm | 1 Hr | 43 351 870 | -10DBm | 1 Hr | 1 Loops |
| 154 | 4-Jun | 00000 | 00000 | 29 85 | | 8562A | 43 351 830 | -10DBm | 1 Hr | 43 351 870 | -10DBm | 1 Hr | 1 Loops |
| 155 | 5-Jun | 00000 | 00000 | 30 01 | | 8562A | 43 351 830 | -10DBm | 1 Hr | 43 351 870 | -10DBm | 1 Hr | 1 Loops |
| 156 | 6-Jun | 00000 | 00000 | 30 52 | | 8562A | 43 351 830 | -10DBm | 1 Hr | 43 351 870 | -10DBm | 1 Hr | 1 Loops |
| 157 | 7-Jun | 00000 | 00000 | 30 71 | | 8562A | 43 351 830 | -10DBm | 1 Hr | 43 351 870 | -10DBm | 1 Hr | 1 Loops |
| 158 | 8-Jun | 00000 | 00000 | 30 01 | | 8562A | 43 351 830 | -10DBm | 1 Hr | 43 351 870 | -10DBm | 1 Hr | 1 Loops |
| 159 | 9-Jun | 00000 | 00000 | 30 67 | 35 | 8562A | 43 351 830 | -10DBm | 1 Hr | 43 351 870 | -10DBm | 1 Hr | 1 Loops |
| 160 | 10-Jun | 00000 | 00000 | 29 53 | | 8562A | 43 351 830 | -10DBm | 1 Hr | 43 351 870 | -10DBm | 1 Hr | 1 Loops |
| 161 | 11-Jun | 00000 | 00000 | 29 70 | | 8562A | 43 351 830 | -10DBm | 1 Hr | 43 351 870 | -10DBm | 1 Hr | 1 Loops |
| 162 | 12-Jun | 00000 | 00000 | 29 84 | | 8562A | 43 351 830 | -10DBm | 1 Hr | 43 351 870 | -10DBm | 1 Hr | 1 Loops |
| 163 | 13-Jun | 00000 | 00000 | 30 41 | | 8562A | 43 351 830 | -10DBm | 1 Hr | 43 351 870 | -10DBm | 1 Hr | 1 Loops |
| 164 | 14-Jun | 00000 | 00000 | 30 78 | | 8562A | 43 351 830 | -10DBm | 1 Hr | 43 351 870 | -10DBm | 1 Hr | 1 Loops |
| 165 | 15-Jun | 00000 | 00000 | 30 76 | | 8562A | 43 351 830 | -10DBm | 1 Hr | 43 351 870 | -10DBm | 1 Hr | 1 Loops |
| 166 | 16-Jun | 00000 | 00000 | 31 16 | | 8562A | 43 351 830 | -10DBm | 1 Hr | 43 351 870 | -10DBm | 1 Hr | 1 Loops |
| 167 | 17-Jun | 00000 | 00000 | 31 41 | 40 | 8562A | 43 351 830 | -10DBm | 1 Hr | 43 351 870 | -10DBm | 1 Hr | 1 Loops |
| 168 | 18-Jun | 00000 | 00000 | 30 77 | | 8562A | 43 351 830 | -10DBm | 1 Hr | 43 351 870 | -10DBm | 1 Hr | 1 Loops |
| 169 | 19-Jun | 00000 | 00000 | 30 17 | | 8562A | 43 351 830 | -10DBm | 1 Hr | 43 351 870 | -10DBm | 1 Hr | 1 Loops |
| 170 | 20-Jun | 00000 | 00000 | 30 15 | | 8562A | 43 351 830 | -10DBm | 1 Hr | 43 351 870 | -10DBm | 1 Hr | 1 Loops |

4/11/97 Page 3 OUJ-471-.xls 09141691.082898

OUJ-471-.xls

| | | | | | | | | | | | | | | | |
|---|---|---|---|---|---|---|---|---|---|---|---|---|---|---|---|
| 171 | 21-Jun | | 00000 | | 00000 | 29.96 | | 8662A | 43 351.830 | -10DBm | 1 Hr | 43 351.870 | -10DBm | 1 Hr | 1 Loops |
| 172 | 22-Jun | | 00000 | | 00000 | 30.38 | | 8662A | 43 351.830 | -10DBm | 1 Hr | 43 351.870 | -10DBm | 1 Hr | 1 Loops |
| 173 | 23-Jun | | 00000 | | 00000 | 30.14 | 33 | 8662A | 43 351.830 | -10DBm | 1 Hr | 43 351.870 | -10DBm | 1 Hr | 1 Loops |
| 174 | 24-Jun | | 00000 | | 00000 | 31.66 | | 8662A | 43 351.830 | -10DBm | 1 Hr | 43 351.870 | -10DBm | 1 Hr | 1 Loops |
| 175 | 25-Jun | | 00000 | | 00000 | 31.76 | | 8662A | 43 351.830 | -10DBm | 1 Hr | 43 351.870 | -10DBm | 1 Hr | 1 Loops |
| 176 | 26-Jun | | 00000 | | 00000 | 31.91 | | 8662A | 43 351.830 | -10DBm | 1 Hr | 43 351.870 | -10DBm | 1 Hr | 1 Loops |
| 177 | 27-Jun | | 00000 | | 00000 | 28.70 | | 8662A | 43 351.830 | -10DBm | 1 Hr | 43 351.870 | -10DBm | 1 Hr | 1 Loops |
| 178 | 28-Jun | | 00000 | | 00000 | 29.69 | | 8662A | 43 351.830 | -10DBm | 1 Hr | 43 351.870 | -10DBm | 1 Hr | 1 Loops |
| 179 | 29-Jun | | 00000 | | 00000 | 29.04 | | 8662A | 43 351.830 | -10DBm | 1 Hr | 43 351.870 | -10DBm | 1 Hr | 1 Loops |
| 180 | 30-Jun | | 00000 | | 00000 | 29.57 | | 8662A | 43 351.830 | -10DBm | 1 Hr | 43 351.870 | -10DBm | 1 Hr | 1 Loops |
| 181 | 1-Jul | | 00000 | | 00000 | 27.72 | | 8662A | 43 351.830 | -10DBm | 1 Hr | 43 351.870 | -10DBm | 1 Hr | 1 Loops |
| 182 | 2-Jul | | 00000 | | 00000 | 29.24 | | 8662A | 43 351.830 | -10DBm | 1 Hr | 43 351.870 | -10DBm | 1 Hr | 1 Loops |
| 183 | 3-Jul | | 00000 | | 00000 | 30.76 | | 8662A | 43 351.830 | -10DBm | 1 Hr | 43 351.870 | -10DBm | 1 Hr | 1 Loops |
| 184 | 4-Jul | | 00000 | | 00000 | 29.14 | | 8662A | 43 351.830 | -10DBm | 1 Hr | 43 351.870 | -10DBm | 1 Hr | 1 Loops |
| 185 | 5-Jul | | 00000 | | 00000 | 29.91 | | 8662A | 43 351.830 | -10DBm | 1 Hr | 43 351.870 | -10DBm | 1 Hr | 1 Loops |
| 186 | 6-Jul | | 00000 | | 00000 | 29.69 | | 8662A | 43 351.830 | -10DBm | 1 Hr | 43 351.870 | -10DBm | 1 Hr | 1 Loops |
| 187 | 7-Jul | | 00000 | | 00000 | 29.29 | 39 | 8662A | 43 351.830 | -10DBm | 1 Hr | 43 351.870 | -10DBm | 1 Hr | 1 Loops |
| 188 | 8-Jul | | 00000 | | 00000 | 28.66 | | 8662A | 43 351.830 | -10DBm | 1 Hr | 43 351.870 | -10DBm | 1 Hr | 1 Loops |
| 189 | 9-Jul | | 00000 | | 00000 | 28.40 | | 8662A | 43 351.830 | -10DBm | 1 Hr | 43 351.870 | -10DBm | 1 Hr | 1 Loops |
| 190 | 10-Jul | | 00000 | | 00000 | 28.13 | | 8662A | 43 351.830 | -10DBm | 1 Hr | 43 351.870 | -10DBm | 1 Hr | 1 Loops |
| 191 | 11-Jul | | 00000 | | 00000 | 29.13 | | 8662A | 43 351.830 | -10DBm | 1 Hr | 43 351.870 | -10DBm | 1 Hr | 1 Loops |
| 192 | 12-Jul | | 00000 | | 00000 | 29.80 | | 8662A | 43 351.830 | -10DBm | 1 Hr | 43 351.870 | -10DBm | 1 Hr | 1 Loops |
| 193 | 13-Jul | | 00000 | | 00000 | 29.84 | | 8662A | 43 351.830 | -10DBm | 1 Hr | 43 351.870 | -10DBm | 1 Hr | 1 Loops |
| 194 | 14-Jul | | 00000 | | 00000 | 29.81 | 38 | 8662A | 43 351.830 | -10DBm | 1 Hr | 43 351.870 | -10DBm | 1 Hr | 1 Loops |
| 195 | 15-Jul | | 00000 | | 00000 | 29.55 | | 8662A | 43 351.830 | -10DBm | 1 Hr | 43 351.870 | -10DBm | 1 Hr | 1 Loops |
| 196 | 16-Jul | | 00000 | | 00000 | 29.58 | | 8662A | 43 351.830 | -10DBm | 1 Hr | 43 351.870 | -10DBm | 1 Hr | 1 Loops |
| 197 | 17-Jul | | 00000 | | 00000 | 29.60 | | 8662A | 43 351.830 | -10DBm | 1 Hr | 43 351.870 | -10DBm | 1 Hr | 1 Loops |
| 198 | 18-Jul | | 00000 | | 00000 | 28.93 | | 8662A | 43 351.830 | -10DBm | 1 Hr | 43 351.870 | -10DBm | 1 Hr | 1 Loops |
| 199 | 19-Jul | | 00000 | | 00000 | 28.95 | | 8662A | 43 351.830 | -10DBm | 1 Hr | 43 351.870 | -10DBm | 1 Hr | 1 Loops |
| 200 | 20-Jul | *Died 7/20/95* | #VALUE! | *Died 7/20/95* | #VALUE! | | | 8662A | 43 351.830 | -10DBm | 1 Hr | 43 351.870 | -10DBm | 1 Hr | 1 Loops |

4/11/97 Page 4 OUJ-471-.xls

OUJ-473-.xls

*OUJ-473 Born 3/1/94 THIS MOUSE NEVER DEVELOPED A TUMOR*

*Special Study...Treatment started before any tumors appeared*

| DAY | DATE | T-1 | | | Vol | T-2 | | | Vol | WEIGHT | HEMATO- | | | | TREATMENT PARAMETERS | | | | | |
|---|---|---|---|---|---|---|---|---|---|---|---|---|---|---|---|---|---|---|---|---|
| | | Ln | Wd | Ht | T-1 | Ln | Wd | Ht | T-2 | Gr | CRIT-% | DEVICE | FREQ MHz | POWER | TIME | DEVICE | FREQ MHz | POWER | TIME | DEVICE |
| 1 | 29-Dec | | | | 00000 | | | | 00000 | 29.07 | | 8662A | 43.351.830 | 0 DBm | 1 Hr | 8662A | 43.351.870 | 0 DBm | 1 Hr | 1 LOOP |
| 2 | 30-Dec | | | | 00000 | | | | 00000 | 28.90 | | 8662A | 43.351.830 | 0 DBm | 1 Hr | 8662A | 43.351.870 | 0 DBm | 1 Hr | 1 LOOP |
| 3 | 31-Dec | | | | 00000 | | | | 00000 | 28.54 | 44 | 8662A | 43.351.830 | 0 DBm | 1 Hr | 8662A | 43.351.870 | 0 DBm | 1 Hr | 1 LOOP |
| 4 | 1-Jan | | | | 00000 | | | | 00000 | 28.56 | | 8662A | 43.351.830 | 0 DBm | 1 Hr | 8662A | 43.351.870 | 0 DBm | 1 Hr | 1 LOOP |
| 5 | 2-Jan | | | | 00000 | | | | 00000 | 28.58 | | 8662A | 43.351.830 | 0 DBm | 1 Hr | 8662A | 43.351.870 | 0 DBm | 1 Hr | 1 LOOP |
| 6 | 3-Jan | | | | 00000 | | | | 00000 | 28.53 | | 8662A | 43.351.830 | 0 DBm | 1 Hr | 8662A | 43.351.870 | 0 DBm | 1 Hr | 1 LOOP |
| 7 | 4-Jan | | | | 00000 | | | | 00000 | 28.31 | | 8662A | 43.351.830 | 0 DBm | 1 Hr | 8662A | 43.351.870 | 0 DBm | 1 Hr | 1 LOOP |
| 8 | 5-Jan | | | | 00000 | | | | 00000 | 28.37 | | 8662A | 43.351.830 | 0 DBm | 1 Hr | 8662A | 43.351.870 | 0 DBm | 1 Hr | 1 LOOP |
| 9 | 6-Jan | | | | 00000 | | | | 00000 | 27.72 | 42 | 8662A | 43.351.830 | 0 DBm | 1 Hr | 8662A | 43.351.870 | 0 DBm | 1 Hr | 1 LOOP |
| 10 | 7-Jan | | | | 00000 | | | | 00000 | 28.51 | | 8662A | 43.351.830 | 0 DBm | 1 Hr | 8662A | 43.351.870 | 0 DBm | 1 Hr | 1 LOOP |
| 11 | 8-Jan | | | | 00000 | | | | 00000 | 28.78 | | 8662A | 43.351.830 | 0 DBm | 1 Hr | 8662A | 43.351.870 | 0 DBm | 1 Hr | 1 LOOP |
| 12 | 9-Jan | | | | 00000 | | | | 00000 | 29.10 | | 8662A | 43.351.830 | 0 DBm | 1 Hr | 8662A | 43.351.870 | 0 DBm | 1 Hr | 1 LOOP |
| 13 | 10-Jan | | | | 00000 | | | | 00000 | 29.47 | | 8662A | 43.351.830 | 0 DBm | 1 Hr | 8662A | 43.351.870 | 0 DBm | 1 Hr | 1 LOOP |
| 14 | 11-Jan | | | | 00000 | | | | 00000 | 28.74 | | 8662A | 43.351.830 | 0 DBm | 1 Hr | 8662A | 43.351.870 | 0 DBm | 1 Hr | 1 LOOP |
| 15 | 12-Jan | | | | 00000 | | | | 00000 | 28.58 | | 8662A | 43.351.830 | 0 DBm | 1 Hr | 8662A | 43.351.870 | 0 DBm | 1 Hr | 1 LOOP |
| 16 | 13-Jan | | | | 00000 | | | | 00000 | 29.12 | 43 | 8662A | 43.351.830 | 0 DBm | 1 Hr | 8662A | 43.351.870 | 0 DBm | 1 Hr | 1 LOOP |
| 17 | 14-Jan | | | | 00000 | | | | 00000 | 30.02 | | 8662A | 43.351.830 | 0 DBm | 1 Hr | 8662A | 43.351.870 | 0 DBm | 1 Hr | 1 LOOP |
| 18 | 15-Jan | | | | 00000 | | | | 00000 | 30.03 | | 8662A | 43.351.830 | 0 DBm | 1 Hr | 8662A | 43.351.870 | 0 DBm | 1 Hr | 1 LOOP |
| 19 | 16-Jan | | | | 00000 | | | | 00000 | 30.04 | | 8662A | 43.351.830 | 0 DBm | 1 Hr | 8662A | 43.351.870 | 0 DBm | 1 Hr | 1 LOOP |
| 20 | 17-Jan | | | | 00000 | | | | 00000 | 29.92 | | 8662A | 43.351.830 | 0 DBm | 1 Hr | 8662A | 43.351.870 | 0 DBm | 1 Hr | 1 LOOP |
| 21 | 18-Jan | | | | 00000 | | | | 00000 | 29.16 | | 8662A | 43.351.830 | 0 DBm | 1 Hr | 8662A | 43.351.870 | 0 DBm | 1 Hr | 1 LOOP |
| 22 | 19-Jan | | | | 00000 | | | | 00000 | 28.54 | | 8662A | 43.351.830 | 0 DBm | 1 Hr | 8662A | 43.351.870 | 0 DBm | 1 Hr | 1 LOOP |
| 23 | 20-Jan | | | | 00000 | | | | 00000 | 28.40 | 43 | 8662A | 43.351.830 | 0 DBm | 1 Hr | 8662A | 43.351.870 | 0 DBm | 1 Hr | 1 LOOP |
| 24 | 21-Jan | | | | 00000 | | | | 00000 | 28.71 | | 8662A | 43.351.830 | 0 DBm | 1 Hr | 8662A | 43.351.870 | 0 DBm | 1 Hr | 1 LOOP |
| 25 | 22-Jan | | | | 00000 | | | | 00000 | 28.62 | | 8662A | 43.351.830 | 0 DBm | 1 Hr | 8662A | 43.351.870 | 0 DBm | 1 Hr | 1 LOOP |
| 26 | 23-Jan | | | | 00000 | | | | 00000 | 28.53 | | 8662A | 43.351.830 | 0 DBm | 1 Hr | 8662A | 43.351.870 | 0 DBm | 1 Hr | 1 LOOP |
| 27 | 24-Jan | | | | 00000 | | | | 00000 | 28.80 | | 8662A | 43.351.830 | 0 DBm | 1 Hr | 8662A | 43.351.870 | 0 DBm | 1 Hr | 1 LOOP |
| 28 | 25-Jan | | | | 00000 | | | | 00000 | 28.88 | | 8662A | 43.351.830 | 0 DBm | 1 Hr | 8662A | 43.351.870 | 0 DBm | 1 Hr | 1 LOOP |
| 29 | 26-Jan | | | | 00000 | | | | 00000 | 28.34 | | 8662A | 43.351.830 | 0 DBm | 1 Hr | 8662A | 43.351.870 | 0 DBm | 1 Hr | 1 LOOP |
| 30 | 27-Jan | | | | 00000 | | | | 00000 | 28.60 | 43 | 8662A | 43.351.830 | 0 DBm | 1 Hr | 8662A | 43.351.870 | 0 DBm | 1 Hr | 1 LOOP |
| 31 | 28-Jan | | | | 00000 | | | | 00000 | 28.73 | | 8662A | 43.351.830 | 0 DBm | 1 Hr | 8662A | 43.351.870 | 0 DBm | 1 Hr | 1 LOOP |
| 32 | 29-Jan | | | | 00000 | | | | 00000 | 29.00 | | 8662A | 43.351.830 | 0 DBm | 1 Hr | 8662A | 43.351.870 | 0 DBm | 1 Hr | 1 LOOP |
| 33 | 30-Jan | | | | 00000 | | | | 00000 | 29.33 | | 8662A | 43.351.830 | 0 DBm | 1 Hr | 8662A | 43.351.870 | 0 DBm | 1 Hr | 1 LOOP |
| 34 | 31-Jan | | | | 00000 | | | | 00000 | 29.18 | | 8662A | 43.351.830 | 0 DBm | 1 Hr | 8662A | 43.351.870 | 0 DBm | 1 Hr | 1 LOOP |
| 35 | 1-Feb | | | | 00000 | | | | 00000 | 29.11 | | 8662A | 43.351.830 | 0 DBm | 1 Hr | 8662A | 43.351.870 | 0 DBm | 1 Hr | 1 LOOP |
| 36 | 2-Feb | | | | 00000 | | | | 00000 | 28.83 | | 8662A | 43.351.830 | 0 DBm | 1 Hr | 8662A | 43.351.870 | 0 DBm | 1 Hr | 1 LOOP |
| 37 | 3-Feb | | | | 00000 | | | | 00000 | 29.44 | 43 | 8662A | 43.351.830 | 0 DBm | 1 Hr | 8662A | 43.351.870 | 0 DBm | 1 Hr | 1 LOOP |
| 38 | 4-Feb | | | | 00000 | | | | 00000 | 29.58 | | 8662A | 43.351.830 | 0 DBm | 1 Hr | 8662A | 43.351.870 | 0 DBm | 1 Hr | 1 LOOP |
| 39 | 5-Feb | | | | 00000 | | | | 00000 | 29.54 | | 8662A | 43.351.830 | 0 DBm | 1 Hr | 8662A | 43.351.870 | 0 DBm | 1 Hr | 1 LOOP |
| 40 | 6-Feb | | | | 00000 | | | | 00000 | 29.57 | | 8662A | 43.351.830 | 0 DBm | 1 Hr | 8662A | 43.351.870 | 0 DBm | 1 Hr | 1 LOOP |
| 41 | 7-Feb | | | | 00000 | | | | 00000 | 28.82 | | 8662A | 43.351.830 | 0 DBm | 1 Hr | 8662A | 43.351.870 | 0 DBm | 1 Hr | 1 LOOP |
| 42 | 8-Feb | | | | 00000 | | | | 00000 | 28.90 | | 8662A | 43.351.830 | 0 DBm | 1 Hr | 8662A | 43.351.870 | 0 DBm | 1 Hr | 1 LOOP |
| 43 | 9-Feb | | | | 00000 | | | | 00000 | 28.50 | | 8662A | 43.351.830 | 0 DBm | 1 Hr | 8662A | 43.351.870 | 0 DBm | 1 Hr | 1 LOOP |
| 44 | 10-Feb | | | | 00000 | | | | 00000 | 27.96 | 45 | 8662A | 43.351.830 | 0 DBm | 1 Hr | 8662A | 43.351.870 | 0 DBm | 1 Hr | 1 LOOP |
| 45 | 11-Feb | | | | 00000 | | | | 00000 | 29.44 | | 8662A | 43.351.830 | 0 DBm | 1 Hr | 8662A | 43.351.870 | 0 DBm | 1 Hr | 1 LOOP |
| 46 | 12-Feb | | | | 00000 | | | | 00000 | 29.55 | | 8662A | 43.351.830 | 0 DBm | 1 Hr | 8662A | 43.351.870 | 0 DBm | 1 Hr | 1 LOOP |
| 47 | 13-Feb | | | | 00000 | | | | 00000 | 29.68 | | 8662A | 43.351.830 | 0 DBm | 1 Hr | 8662A | 43.351.870 | 0 DBm | 1 Hr | 1 LOOP |
| 48 | 14-Feb | | | | 00000 | | | | 00000 | 29.63 | | 8662A | 43.351.830 | 0 DBm | 1 Hr | 8662A | 43.351.870 | 0 DBm | 1 Hr | 1 LOOP |
| 49 | 15-Feb | | | | 00000 | | | | 00000 | 28.72 | | 8662A | 43.351.830 | 0 DBm | 1 Hr | 8662A | 43.351.870 | 0 DBm | 1 Hr | 1 LOOP |
| 50 | 16-Feb | | | | 00000 | | | | 00000 | 28.46 | | 8662A | 43.351.830 | 0 DBm | 1 Hr | 8662A | 43.351.870 | 0 DBm | 1 Hr | 1 LOOP |
| 51 | 17-Feb | | | | 00000 | | | | 00000 | 28.57 | | 8662A | 43.351.830 | 0 DBm | 1 Hr | 8662A | 43.351.870 | 0 DBm | 1 Hr | 1 LOOP |
| 52 | 18-Feb | | | | 00000 | | | | 00000 | 27.91 | 44 | 8662A | 43.351.830 | 0 DBm | 1 Hr | 8662A | 43.351.870 | 0 DBm | 1 Hr | 1 LOOP |
| 53 | 19-Feb | | | | 00000 | | | | 00000 | 28.30 | | 8662A | 43.351.830 | 0 DBm | 1 Hr | 8662A | 43.351.870 | 0 DBm | 1 Hr | 1 LOOP |
| 54 | 20-Feb | | | | 00000 | | | | 00000 | 28.57 | | 8662A | 43.351.830 | 0 DBm | 1 Hr | 8662A | 43.351.870 | 0 DBm | 1 Hr | 1 LOOP |
| 55 | 21-Feb | | | | 00000 | | | | 00000 | 28.33 | | 8662A | 43.351.830 | 0 DBm | 1 Hr | 8662A | 43.351.870 | 0 DBm | 1 Hr | 1 LOOP |
| 56 | 22-Feb | | | | 00000 | | | | 00000 | 28.57 | | 8662A | 43.351.830 | 0 DBm | 1 Hr | 8662A | 43.351.870 | 0 DBm | 1 Hr | 1 LOOP |
| 57 | 23-Feb | | | | 00000 | | | | 00000 | 28.61 | | 8662A | 43.351.830 | 0 DBm | 1 Hr | 8662A | 43.351.870 | 0 DBm | 1 Hr | 1 LOOP |

4/11/97 Page 1 OUJ-473-.xls 09141691.080298

OUJ-473- xls

| | | | | | | | | | | | | | | |
|---|---|---|---|---|---|---|---|---|---|---|---|---|---|---|
| 58 | 24-Feb | 00000 | 00000 | 29 05 | 44 | 8662A | 43 351 830 | 0 DBm | 1 Hr | 8662A | 43 351 870 | 0 DBm | 1 Hr | 1 LOOP |
| 59 | 25-Feb | 00000 | 00000 | 28 17 | | 8662A | 43 351 830 | 0 DBm | 1 Hr | 8662A | 43 351 870 | 0 DBm | 1 Hr | 1 LOOP |
| 60 | 26-Feb | 00000 | 00000 | 28 82 | | 8662A | 43 351 830 | 0 DBm | 1 Hr | 8662A | 43 351 870 | 0 DBm | 1 Hr | 1 LOOP |
| 61 | 27-Feb | 00000 | 00000 | 29 47 | | 8662A | 43 351 830 | 0 DBm | 1 Hr | 8662A | 43 351 870 | 0 DBm | 1 Hr | 1 LOOP |
| 62 | 28-Feb | 00000 | 00000 | 28 10 | | 8662A | 43 351 830 | 0 DBm | 1 Hr | 8662A | 43 351 870 | 0 DBm | 1 Hr | 1 LOOP |
| 63 | 1-Mar | 00000 | 00000 | 29 04 | | 8662A | 43 351 830 | 0 DBm | 1 Hr | 8662A | 43 351 870 | 0 DBm | 1 Hr | 1 LOOP |
| 64 | 2-Mar | 00000 | 00000 | 29 01 | | 8662A | 43 351 850 | 0 DBm | 1 Hr | 8662A | 43 351 850 | 0 DBm | 1 Hr | 1 LOOP |
| 65 | 3-Mar | 00000 | 00000 | 29 03 | 44 | 8662A | 43 351 830 | 0 DBm | 1 Hr | 8662A | 43 351 870 | 0 DBm | 1 Hr | 1 LOOP |
| 66 | 4-Mar | 00000 | 00000 | 28 77 | | 8662A | 43 351 830 | 0 DBm | 1 Hr | 8662A | 43 351 870 | 0 DBm | 1 Hr | 1 LOOP |
| 67 | 5-Mar | 00000 | 00000 | 28 80 | | 8662A | 43 351 830 | 0 DBm | 1 Hr | 8662A | 43 351 870 | 0 DBm | 1 Hr | 1 LOOP |
| 68 | 6-Mar | 00000 | 00000 | 28 82 | | 8662A | 43 351 830 | 0 DBm | 1 Hr | 8662A | 43 351 870 | 0 DBm | 1 Hr | 1 LOOP |
| 69 | 7-Mar | 00000 | 00000 | 28 61 | | 8662A | 43 351 830 | 0 DBm | 1 Hr | 8662A | 43 351 870 | 0 DBm | 1 Hr | 1 LOOP |
| 70 | 8-Mar | 00000 | 00000 | 29 06 | | 8662A | 43 351 830 | 0 DBm | 1 Hr | 8662A | 43 351 870 | 0 DBm | 1 Hr | 1 LOOP |
| 71 | 9-Mar | 00000 | 00000 | 29 22 | | 8662A | 43 351 830 | 0 DBm | 1 Hr | 8662A | 43 351 870 | 0 DBm | 1 Hr | 1 LOOP |
| 72 | 10-Mar | 00000 | 00000 | 30 10 | 44 | 8662A | 43 351 830 | 0 DBm | 1 Hr | 8662A | 43 351 870 | 0 DBm | 1 Hr | 1 LOOP |
| 73 | 11-Mar | 00000 | 00000 | 29 14 | | 8662A | 43 351 830 | 0 DBm | 1 Hr | 8662A | 43 351 870 | 0 DBm | 1 Hr | 1 LOOP |
| 74 | 12-Mar | 00000 | 00000 | 28 96 | | 8662A | 43 351 830 | 0 DBm | 1 Hr | 8662A | 43 351 870 | 0 DBm | 1 Hr | 1 LOOP |
| 75 | 13-Mar | 00000 | 00000 | 28 75 | | 8662A | 43 351 830 | 0 DBm | 1 Hr | 8662A | 43 351 870 | 0 DBm | 1 Hr | 1 LOOP |
| 76 | 14-Mar | 00000 | 00000 | 28 66 | | 8662A | 43 351 830 | 0 DBm | 1 Hr | 8662A | 43 351 870 | 0 DBm | 1 Hr | 1 LOOP |
| 77 | 15-Mar | 00000 | 00000 | 28 95 | | 8662A | 43 351 830 | 0 DBm | 1 Hr | 8662A | 43 351 870 | 0 DBm | 1 Hr | 1 LOOP |
| 78 | 16-Mar | 00000 | 00000 | 29 08 | | 8662A | 43 351 830 | 0 DBm | 1 Hr | 8662A | 43 351 870 | 0 DBm | 1 Hr | 1 LOOP |
| 79 | 17-Mar | 00000 | 00000 | 29 79 | 40 | 8662A | 43 351 830 | 0 DBm | 1 Hr | 8662A | 43 351 870 | 0 DBm | 1 Hr | 1 LOOP |
| 80 | 18-Mar | 00000 | 00000 | 27 89 | | 8662A | 43 351 830 | 0 DBm | 1 Hr | 8662A | 43 351 870 | 0 DBm | 1 Hr | 1 LOOP |
| 81 | 19-Mar | 00000 | 00000 | 28 50 | | 8662A | 43 351 830 | 0 DBm | 1 Hr | 8662A | 43 351 870 | 0 DBm | 1 Hr | 1 LOOP |
| 82 | 20-Mar | 00000 | 00000 | 29 18 | | 8662A | 43 351 830 | 0 DBm | 1 Hr | 8662A | 43 351 870 | 0 DBm | 1 Hr | 1 LOOP |
| 83 | 21-Mar | 00000 | 00000 | 28 92 | | 8662A | 43 351 830 | 0 DBm | 1 Hr | 8662A | 43 351 870 | 0 DBm | 1 Hr | 1 LOOP |
| 84 | 22-Mar | 00000 | 00000 | 28 32 | | 8662A | 43 351 830 | 0 DBm | 1 Hr | 8662A | 43 351 870 | 0 DBm | 1 Hr | 1 LOOP |
| 85 | 23-Mar | 00000 | 00000 | 29 21 | | 8662A | 43 351 830 | 0 DBm | 1 Hr | 8662A | 43 351 870 | 0 DBm | 1 Hr | 1 LOOP |
| 86 | 24-Mar | 00000 | 00000 | 27 78 | | 8662A | 43 351 830 | 0 DBm | 1 Hr | 8662A | 43 351 870 | 0 DBm | 1 Hr | 1 LOOP |
| 87 | 25-Mar | 00000 | 00000 | 28 81 | 42 | 8662A | 43 351 830 | 0 DBm | 1 Hr | 8662A | 43 351 870 | 0 DBm | 1 Hr | 1 LOOP |
| 88 | 26-Mar | 00000 | 00000 | 28 85 | | 8662A | 43 351 830 | 0 DBm | 1 Hr | 8662A | 43 351 870 | 0 DBm | 1 Hr | 1 LOOP |
| 89 | 27-Mar | 00000 | 00000 | 28 92 | | 8662A | 43 351 830 | 0 DBm | 1 Hr | 8662A | 43 351 870 | 0 DBm | 1 Hr | 1 LOOP |
| 90 | 28-Mar | 00000 | 00000 | 29 41 | | 8662A | 43 351 830 | 0 DBm | 1 Hr | 8662A | 43 351 870 | 0 DBm | 1 Hr | 1 LOOP |
| 91 | 29-Mar | 00000 | 00000 | 28 46 | | 8662A | 43 351 830 | 0 DBm | 1 Hr | 8662A | 43 351 870 | 0 DBm | 1 Hr | 1 LOOP |
| 92 | 30-Mar | 00000 | 00000 | 28 26 | | 8662A | 43 351 830 | 0 DBm | 1 Hr | 8662A | 43 351 870 | 0 DBm | 1 Hr | 1 LOOP |
| 93 | 31-Mar | 00000 | 00000 | 28 94 | | 8662A | 43 351 850 | 0 DBm | 1 Hr | 8662A | 43 351 870 | 0 DBm | 1 Hr | 1 LOOP |
| 94 | 1-Apr | 00000 | 00000 | 28 74 | | 8662A | 43 351 850 | 0 DBm | 1 Hr | 8662A | 43 351 870 | 0 DBm | 1 Hr | 1 LOOP |
| 95 | 2-Apr | 00000 | 00000 | 28 51 | | 8662A | 43 351 850 | 0 DBm | 1 Hr | 8662A | 43 351 870 | 0 DBm | 1 Hr | 1 LOOP |
| 96 | 3-Apr | 00000 | 00000 | 28 30 | | 8662A | 43 351 850 | 0 DBm | 1 Hr | 8662A | 43 351 870 | 0 DBm | 1 Hr | 1 LOOP |
| 97 | 4-Apr | 00000 | 00000 | 28 78 | | 8662A | 43 351 850 | 0 DBm | 1 Hr | 8662A | 43 351 870 | 0 DBm | 1 Hr | 1 LOOP |
| 98 | 5-Apr | 00000 | 00000 | 28 13 | | 8662A | 43 351 850 | 0 DBm | 1 Hr | 8662A | 43 351 870 | 0 DBm | 1 Hr | 1 LOOP |
| 99 | 6-Apr | 00000 | 00000 | 25 04 | | 8662A | 43 351 850 | 0 DBm | 1 Hr | 8662A | 43 351 870 | 0 DBm | 1 Hr | 1 LOOP |
| 100 | 7-Apr | 00000 | 00000 | 27 85 | 42 | 8662A | 43 351 850 | 0 DBm | 1 Hr | 8662A | 43 351 870 | 0 DBm | 1 Hr | 1 LOOP |
| 101 | 8-Apr | 00000 | 00000 | 27 47 | | 8662A | 43 351 850 | 0 DBm | 1 Hr | 8662A | 43 351 870 | 0 DBm | 1 Hr | 1 LOOP |
| 102 | 9-Apr | 00000 | 00000 | 28 02 | | 8662A | 43 351 850 | 0 DBm | 1 Hr | 8662A | 43 351 870 | 0 DBm | 1 Hr | 1 LOOP |
| 103 | 10-Apr | 00000 | 00000 | 28 55 | | 8662A | 43 351 850 | 0 DBm | 1 Hr | 8662A | 43 351 870 | 0 DBm | 1 Hr | 1 LOOP |
| 104 | 11-Apr | 00000 | 00000 | 27 86 | | 8662A | 43 351 850 | 0 DBm | 1 Hr | 8662A | 43 351 870 | 0 DBm | 1 Hr | 1 LOOP |
| 105 | 12-Apr | 00000 | 00000 | 27 46 | | 8662A | 43 351 850 | 0 DBm | 1 Hr | 8662A | 43 351 870 | 0 DBm | 1 Hr | 1 LOOP |
| 106 | 13-Apr | 00000 | 00000 | 27 70 | | 8662A | 43 351 850 | 0 DBm | 1 Hr | 8662A | 43 351 870 | 0 DBm | 1 Hr | 1 LOOP |
| 107 | 14-Apr | 00000 | 00000 | 29 11 | 35 | 8662A | 43 351 850 | 0 DBm | 1 Hr | 8662A | 43 351 870 | 0 DBm | 1 Hr | 1 LOOP |
| 108 | 15-Apr | 00000 | 00000 | 27 81 | | 8662A | 43 351 850 | 0 DBm | 1 Hr | 8662A | 43 351 870 | 0 DBm | 1 Hr | 1 LOOP |
| 109 | 16-Apr | 00000 | 00000 | 27 69 | | 8662A | 43 351 850 | 0 DBm | 1 Hr | 8662A | 43 351 870 | 0 DBm | 1 Hr | 1 LOOP |
| 110 | 17-Apr | 00000 | 00000 | 27 64 | | 8662A | 43 351 850 | 0 DBm | 1 Hr | 8662A | 43 351 870 | 0 DBm | 1 Hr | 1 LOOP |
| 111 | 18-Apr | 00000 | 00000 | 27 25 | | 8662A | 43 351 850 | 0 DBm | 1 Hr | 8662A | 43 351 870 | 0 DBm | 1 Hr | 1 LOOP |
| 112 | 19-Apr | 00000 | 00000 | 27 05 | | 8662A | 43 351 850 | 0 DBm | 1 Hr | 8662A | 43 351 870 | 0 DBm | 1 Hr | 1 LOOP |
| 113 | 20-Apr | 00000 | 00000 | 27 81 | | 8662A | 43 351 850 | 0 DBm | 1 Hr | 8662A | 43 351 870 | 0 DBm | 1 Hr | 1 LOOP |
| 114 | 21-Apr | 00000 | 00000 | 27 37 | 37 | 8662A | 43 351 850 | 0 DBm | 1 Hr | 8662A | 43 351 870 | 0 DBm | 1 Hr | 1 LOOP |
| 115 | 22-Apr | 00000 | 00000 | 27 50 | | 8662A | 43 351 850 | 0 DBm | 1 Hr | 8662A | 43 351 870 | 0 DBm | 1 Hr | 1 LOOP |
| 116 | 23-Apr | 00000 | 00000 | 28 11 | | 8662A | 43 351 850 | 0 DBm | 1 Hr | 8662A | 43 351 870 | 0 DBm | 1 Hr | 1 LOOP |
| 117 | 24-Apr | 00000 | 00000 | 28 62 | | 8662A | 43 351 850 | 0 DBm | 1 Hr | 8662A | 43 351 870 | 0 DBm | 1 Hr | 1 LOOP |
| 118 | 25-Apr | 00000 | 00000 | 28 55 | | 8662A | 43 351 850 | 0 DBm | 1 Hr | 8662A | 43 351 870 | 0 DBm | 1 Hr | 1 LOOP |

4/11/97 Page 2 OUJ-473- xls 09141691.082898

OUJ-473-.xls

| | | | | | | | | | | | | | | |
|---|---|---|---|---|---|---|---|---|---|---|---|---|---|---|
| 119 | 26-Apr | 00000 | 00000 | 28 31 | | 8662A | 43 351 850 | 0 DBm | 1 Hr | 8662A | 43 351 870 | 0 DBm | 1 Hr | 1 LOOP |
| 120 | 27-Apr | 00000 | 00000 | 27 79 | | 8662A | 43 351 850 | 0 DBm | 1 Hr | 8662A | 43 351 870 | 0 DBm | 1 Hr | 1 LOOP |
| 121 | 28-Apr | 00000 | 00000 | 27 97 | | 8662A | 43 351 850 | 0 DBm | 1 Hr | 8662A | 43 351 870 | 0 DBm | 1 Hr | 1 LOOP |
| 122 | 29-Apr | 00000 | 00000 | 27 92 | 43 | 8662A | 43 351 850 | 0 DBm | 1 Hr | 8662A | 43 351 870 | 0 DBm | 1 Hr | 1 LOOP |
| 123 | 30-Apr | 00000 | 00000 | 28 00 | | 8662A | 43 351 850 | 0 DBm | 1 Hr | 8662A | 43 351 870 | 0 DBm | 1 Hr | 1 LOOP |
| 124 | 1-May | 00000 | 00000 | 28 07 | | 8662A | 43 351 850 | 0 DBm | 1 Hr | 8662A | 43 351 870 | 0 DBm | 1 Hr | 1 LOOP |
| 125 | 2-May | 00000 | 00000 | 27 96 | | 8662A | 43 351 850 | 0 DBm | 1 Hr | 8662A | 43 351 870 | 0 DBm | 1 Hr | 1 LOOP |
| 126 | 3-May | 00000 | 00000 | 28 66 | | 8662A | 43 351 850 | 0 DBm | 1 Hr | 8662A | 43 351 870 | 0 DBm | 1 Hr | 1 LOOP |
| 127 | 4-May | 00000 | 00000 | 28 29 | | 8662A | 43 351 850 | 0 DBm | 1 Hr | 8662A | 43 351 870 | 0 DBm | 1 Hr | 1 LOOP |
| 128 | 5-May | 00000 | 00000 | 28 38 | 39 | 8662A | 43 351 850 | 0 DBm | 1 Hr | 8662A | 43 351 870 | 0 DBm | 1 Hr | 1 LOOP |
| 129 | 6-May | 00000 | 00000 | 28 74 | | 8662A | 43 351 850 | 0 DBm | 1 Hr | 8662A | 43 351 870 | 0 DBm | 1 Hr | 1 LOOP |
| 130 | 7-May | 00000 | 00000 | 29 15 | | 8662A | 43 351 850 | 0 DBm | 1 Hr | 8662A | 43 351 870 | 0 DBm | 1 Hr | 1 LOOP |
| 131 | 8-May | 00000 | 00000 | 29 64 | | 8662A | 43 351 850 | 0 DBm | 1 Hr | 8662A | 43 351 870 | 0 DBm | 1 Hr | 1 LOOP |
| 132 | 9-May | 00000 | 00000 | 30 99 | | 8662A | 43 351 850 | 0 DBm | 1 Hr | 8662A | 43 351 870 | 0 DBm | 1 Hr | 1 LOOP |
| 133 | 10-May | 00000 | 00000 | 29 13 | | 8662A | 43 351 850 | 0 DBm | 1 Hr | 8662A | 43 351 870 | 0 DBm | 1 Hr | 1 LOOP |
| 134 | 11-May | 00000 | 00000 | 29 73 | 34 | 8662A | 43 351 850 | 0 DBm | 1 Hr | 8662A | 43 351 870 | 0 DBm | 1 Hr | 1 LOOP |
| 135 | 12-May | 00000 | 00000 | 29 07 | | 8662A | 43 351 850 | 0 DBm | 1 Hr | 8662A | 43 351 870 | 0 DBm | 1 Hr | 1 LOOP |
| 136 | 13-May | 00000 | 00000 | 28 17 | | 8662A | 43 351 850 | 0 DBm | 1 Hr | 8662A | 43 351 870 | 0 DBm | 1 Hr | 1 LOOP |
| 137 | 14-May | 00000 | 00000 | 28 67 | | 8662A | 43 351 850 | 0 DBm | 1 Hr | 8662A | 43 351 870 | 0 DBm | 1 Hr | 1 LOOP |
| 138 | 15-May | 00000 | 00000 | 29 18 | | 8662A | 43 351 850 | 0 DBm | 1 Hr | 8662A | 43 351 870 | 0 DBm | 1 Hr | 1 LOOP |
| 139 | 16-May | 00000 | 00000 | 29 11 | | 8662A | 43 351 850 | 0 DBm | 1 Hr | 8662A | 43 351 870 | 0 DBm | 1 Hr | 1 LOOP |
| 140 | 17-May | 00000 | 00000 | 28 64 | | 8662A | 43 351 850 | 0 DBm | 1 Hr | 8662A | 43 351 870 | 0 DBm | 1 Hr | 1 LOOP |
| 141 | 18-May | 00000 | 00000 | 28 24 | | 8662A | 43 351 850 | 0 DBm | 1 Hr | 8662A | 43 351 870 | 0 DBm | 1 Hr | 1 LOOP |
| 142 | 19-May | 00000 | 00000 | 28 19 | 40 | 8662A | 43 351 850 | 0 DBm | 1 Hr | 8662A | 43 351 870 | 0 DBm | 1 Hr | 1 LOOP |
| 143 | 20-May | 00000 | 00000 | 28 70 | | 8662A | 43 351 850 | 0 DBm | 1 Hr | 8662A | 43 351 870 | 0 DBm | 1 Hr | 1 LOOP |
| 144 | 21-May | 00000 | 00000 | 29 35 | | 8662A | 43 351 850 | 0 DBm | 1 Hr | 8662A | 43 351 870 | 0 DBm | 1 Hr | 1 LOOP |
| 145 | 22-May | 00000 | 00000 | 29 92 | | 8662A | 43 351 850 | 0 DBm | 1 Hr | 8662A | 43 351 870 | 0 DBm | 1 Hr | 1 LOOP |
| 146 | 23-May | 00000 | 00000 | 28 49 | | 8662A | 43 351 850 | 0 DBm | 1 Hr | 8662A | 43 351 870 | 0 DBm | 1 Hr | 1 LOOP |
| 147 | 24-May | 00000 | 00000 | 27 55 | | 8662A | 43 351 850 | 0 DBm | 1 Hr | 8662A | 43 351 870 | 0 DBm | 1 Hr | 1 LOOP |
| 148 | 25-May | 00000 | 00000 | 28 57 | | 8662A | 43 351 850 | 0 DBm | 1 Hr | 8662A | 43 351 870 | 0 DBm | 1 Hr | 1 LOOP |
| 149 | 26-May | 00000 | 00000 | 27 86 | 35 | 8662A | 43 351 850 | 0 DBm | 1 Hr | 8662A | 43 351 870 | 0 DBm | 1 Hr | 1 LOOP |
| 150 | 27-May | 00000 | 00000 | 27 54 | | 8662A | 43 351 850 | 0 DBm | 1 Hr | 8662A | 43 351 870 | 0 DBm | 1 Hr | 1 LOOP |
| 151 | 28-May | 00000 | 00000 | 28 05 | | 8662A | 43 351 850 | 0 DBm | 1 Hr | 8662A | 43 351 870 | 0 DBm | 1 Hr | 1 LOOP |
| 152 | 29-May | 00000 | 00000 | 28 62 | | 8662A | 43 351 850 | 0 DBm | 1 Hr | 8662A | 43 351 870 | 0 DBm | 1 Hr | 1 LOOP |
| 153 | 30-May | 00000 | 00000 | 28 58 | | 8662A | 43 351 850 | 0 DBm | 1 Hr | 8662A | 43 351 870 | 0 DBm | 1 Hr | 1 LOOP |
| 154 | 31-May | 00000 | 00000 | 29 67 | | 8662A | 43 351 850 | 0 DBm | 1 Hr | 8662A | 43 351 870 | 0 DBm | 1 Hr | 1 LOOP |
| 155 | 1-Jun | 00000 | 00000 | 29 51 | | 8662A | 43 351 850 | 0 DBm | 1 Hr | 8662A | 43 351 870 | 0 DBm | 1 Hr | 1 LOOP |
| 156 | 2-Jun | 00000 | 00000 | 28 15 | 41 | 8662A | 43 351 850 | 0 DBm | 1 Hr | 8662A | 43 351 870 | 0 DBm | 1 Hr | 1 LOOP |
| 157 | 3-Jun | 00000 | 00000 | 27 92 | | 8662A | 43 351 850 | 0 DBm | 1 Hr | 8662A | 43 351 870 | 0 DBm | 1 Hr | 1 LOOP |
| 158 | 4-Jun | 00000 | 00000 | 28 25 | | 8662A | 43 351 850 | 0 DBm | 1 Hr | 8662A | 43 351 870 | 0 DBm | 1 Hr | 1 LOOP |
| 159 | 5-Jun | 00000 | 00000 | 28 72 | | 8662A | 43 351 850 | 0 DBm | 1 Hr | 8662A | 43 351 870 | 0 DBm | 1 Hr | 1 LOOP |
| 160 | 6-Jun | 00000 | 00000 | 28 77 | | 8662A | 43 351 850 | 0 DBm | 1 Hr | 8662A | 43 351 870 | 0 DBm | 1 Hr | 1 LOOP |
| 161 | 7-Jun | 00000 | 00000 | 28 49 | | 8662A | 43 351 850 | 0 DBm | 1 Hr | 8662A | 43 351 870 | 0 DBm | 1 Hr | 1 LOOP |
| 162 | 8-Jun | 00000 | 00000 | 28 60 | | 8662A | 43 351 850 | 0 DBm | 1 Hr | 8662A | 43 351 870 | 0 DBm | 1 Hr | 1 LOOP |
| 163 | 9-Jun | 00000 | 00000 | 27 59 | 35 | 8662A | 43 351 850 | 0 DBm | 1 Hr | 8662A | 43 351 870 | 0 DBm | 1 Hr | 1 LOOP |
| 164 | 10-Jun | 00000 | 00000 | 27 26 | | 8662A | 43 351 850 | 0 DBm | 1 Hr | 8662A | 43 351 870 | 0 DBm | 1 Hr | 1 LOOP |
| 165 | 11-Jun | 00000 | 00000 | 27 95 | | 8662A | 43 351 850 | 0 DBm | 1 Hr | 8662A | 43 351 870 | 0 DBm | 1 Hr | 1 LOOP |
| 166 | 12-Jun | 00000 | 00000 | 28 65 | | 8662A | 43 351 850 | 0 DBm | 1 Hr | 8662A | 43 351 870 | 0 DBm | 1 Hr | 1 LOOP |
| 167 | 13-Jun | 00000 | 00000 | 29 02 | | 8662A | 43 351 850 | 0 DBm | 1 Hr | 8662A | 43 351 870 | 0 DBm | 1 Hr | 1 LOOP |
| 168 | 14-Jun | 00000 | 00000 | 29 04 | | 8662A | 43 351 850 | 0 DBm | 1 Hr | 8662A | 43 351 870 | 0 DBm | 1 Hr | 1 LOOP |
| 169 | 15-Jun | 00000 | 00000 | 28 21 | | 8662A | 43 351 850 | 0 DBm | 1 Hr | 8662A | 43 351 870 | 0 DBm | 1 Hr | 1 LOOP |
| 170 | 16-Jun | 00000 | 00000 | 28 34 | | 8662A | 43 351 850 | 0 DBm | 1 Hr | 8662A | 43 351 870 | 0 DBm | 1 Hr | 1 LOOP |
| 171 | 17-Jun | 00000 | 00000 | 28 39 | 31 | 8662A | 43 351 850 | 0 DBm | 1 Hr | 8662A | 43 351 870 | 0 DBm | 1 Hr | 1 LOOP |
| 172 | 18-Jun | 00000 | 00000 | 28 22 | | 8662A | 43 351 850 | 0 DBm | 1 Hr | 8662A | 43 351 870 | 0 DBm | 1 Hr | 1 LOOP |
| 173 | 19-Jun | 00000 | 00000 | 28 07 | | 8662A | 43 351 850 | 0 DBm | 1 Hr | 8662A | 43 351 870 | 0 DBm | 1 Hr | 1 LOOP |
| 174 | 20-Jun | 00000 | 00000 | 28 04 | | 8662A | 43 351 850 | 0 DBm | 1 Hr | 8662A | 43 351 870 | 0 DBm | 1 Hr | 1 LOOP |
| 175 | 21-Jun | 00000 | 00000 | 28 67 | | 8662A | 43 351 850 | 0 DBm | 1 Hr | 8662A | 43 351 870 | 0 DBm | 1 Hr | 1 LOOP |
| 176 | 22-Jun | 00000 | 00000 | 27 85 | | 8662A | 43 351 850 | 0 DBm | 1 Hr | 8662A | 43 351 870 | 0 DBm | 1 Hr | 1 LOOP |
| 177 | 23-Jun | 00000 | 00000 | 28 87 | 30 | 8662A | 43 351 850 | 0 DBm | 1 Hr | 8662A | 43 351 870 | 0 DBm | 1 Hr | 1 LOOP |
| 178 | 24-Jun | 00000 | 00000 | 28 34 | | 8662A | 43 351 850 | 0 DBm | 1 Hr | 8662A | 43 351 870 | 0 DBm | 1 Hr | 1 LOOP |
| 179 | 25-Jun | 00000 | 00000 | 28 75 | | 8662A | 43 351 850 | 0 DBm | 1 Hr | 8662A | 43 351 870 | 0 DBm | 1 Hr | 1 LOOP |

| | | | | | | | | | | | | | | | | | | |
|---|---|---|---|---|---|---|---|---|---|---|---|---|---|---|---|---|---|---|
| 180 | 26-Jun | | 00000 | | | | 00000 | 29 06 | | 8562A | 43 351 850 | 0 DBm | 1 Hr | 8562A | 43 351 870 | 0 DBm | 1 Hr | 1 LOOP |
| 181 | 27-Jun | | 00000 | | | | 00000 | 28 14 | | 8562A | 43 351 850 | 0 DBm | 1 Hr | 8562A | 43 351 870 | 0 DBm | 1 Hr | 1 LOOP |
| 182 | 28-Jun | | 00000 | | | | 00000 | 28 09 | | 8562A | 43 351 850 | 0 DBm | 1 Hr | 8562A | 43 351 870 | 0 DBm | 1 Hr | 1 LOOP |
| 183 | 29-Jun | | 00000 | | | | 00000 | 27 27 | | 8562A | 43 351 850 | 0 DBm | 1 Hr | 8562A | 43 351 870 | 0 DBm | 1 Hr | 1 LOOP |
| 184 | 30-Jun | | 00000 | | | | 00000 | 27 58 | | 8562A | 43 351 850 | 0 DBm | 1 Hr | 8562A | 43 351 870 | 0 DBm | 1 Hr | 1 LOOP |
| 185 | 1-Jul | | 00000 | | | | 00000 | 26 70 | | 8562A | 43 351 850 | 0 DBm | 1 Hr | 8562A | 43 351 870 | 0 DBm | 1 Hr | 1 LOOP |
| 186 | 2-Jul | | 00000 | | | | 00000 | 28 24 | | 8562A | 43 351 850 | 0 DBm | 1 Hr | 8562A | 43 351 870 | 0 DBm | 1 Hr | 1 LOOP |
| 187 | 3-Jul | | 00000 | | | | 00000 | 29 77 | | 8562A | 43 351 850 | 0 DBm | 1 Hr | 8562A | 43 351 870 | 0 DBm | 1 Hr | 1 LOOP |
| 188 | 4-Jul | | 00000 | | | | 00000 | 28 79 | | 8562A | 43 351 850 | 0 DBm | 1 Hr | 8562A | 43 351 870 | 0 DBm | 1 Hr | 1 LOOP |
| 189 | 5-Jul | | 00000 | | | | 00000 | 28 96 | | 8562A | 43 351 850 | 0 DBm | 1 Hr | 8562A | 43 351 870 | 0 DBm | 1 Hr | 1 LOOP |
| 190 | 6-Jul | | 00000 | | | | 00000 | 27 97 | | 8562A | 43 351 850 | 0 DBm | 1 Hr | 8562A | 43 351 870 | 0 DBm | 1 Hr | 1 LOOP |
| 191 | 7-Jul | | 00000 | | | | 00000 | 27 28 | 37 | 8562A | 43 351 850 | 0 DBm | 1 Hr | 8562A | 43 351 870 | 0 DBm | 1 Hr | 1 LOOP |
| 192 | 8-Jul | | 00000 | | | | 00000 | 27 10 | | 8562A | 43 351 850 | 0 DBm | 1 Hr | 8562A | 43 351 870 | 0 DBm | 1 Hr | 1 LOOP |
| 193 | 9-Jul | | 00000 | | | | 00000 | 27 30 | | 8562A | 43 351 850 | 0 DBm | 1 Hr | 8562A | 43 351 870 | 0 DBm | 1 Hr | 1 LOOP |
| 194 | 10-Jul | | 00000 | | | | 00000 | 27 50 | | 8562A | 43 351 850 | 0 DBm | 1 Hr | 8562A | 43 351 870 | 0 DBm | 1 Hr | 1 LOOP |
| 195 | 11-Jul | | 00000 | | | | 00000 | 28 05 | | 8562A | 43 351 850 | 0 DBm | 1 Hr | 8562A | 43 351 870 | 0 DBm | 1 Hr | 1 LOOP |
| 196 | 12-Jul | | 00000 | | | | 00000 | 27 58 | | 8562A | 43 351 850 | 0 DBm | 1 Hr | 8562A | 43 351 870 | 0 DBm | 1 Hr | 1 LOOP |
| 197 | 13-Jul | | 00000 | | | | 00000 | 27 74 | | 8562A | 43 351 850 | 0 DBm | 1 Hr | 8562A | 43 351 870 | 0 DBm | 1 Hr | 1 LOOP |
| 198 | 14-Jul | | 00000 | | | | 00000 | 27 20 | 35 | 8562A | 43 351 850 | 0 DBm | 1 Hr | 8562A | 43 351 870 | 0 DBm | 1 Hr | 1 LOOP |
| 199 | 15-Jul | | 00000 | | | | 00000 | 27 46 | | 8562A | 43 351 850 | 0 DBm | 1 Hr | 8562A | 43 351 870 | 0 DBm | 1 Hr | 1 LOOP |
| 200 | 16-Jul | | 00000 | | | | 00000 | 27 82 | | 8562A | 43 351 850 | 0 DBm | 1 Hr | 8562A | 43 351 870 | 0 DBm | 1 Hr | 1 LOOP |
| 201 | 17-Jul | | 00000 | | | | 00000 | 28 18 | | 8562A | 43 351 850 | 0 DBm | 1 Hr | 8562A | 43 351 870 | 0 DBm | 1 Hr | 1 LOOP |
| 202 | 18-Jul | | 00000 | | | | 00000 | 27 61 | | 8562A | 43 351 850 | 0 DBm | 1 Hr | 8562A | 43 351 870 | 0 DBm | 1 Hr | 1 LOOP |
| 203 | 19-Jul | | 00000 | | | | 00000 | 28 62 | | 8562A | 43 351 850 | 0 DBm | 1 Hr | 8562A | 43 351 870 | 0 DBm | 1 Hr | 1 LOOP |
| 204 | 20-Jul | | 00000 | | | | 00000 | 27 42 | | 8562A | 43 351 850 | 0 DBm | 1 Hr | 8562A | 43 351 870 | 0 DBm | 1 Hr | 1 LOOP |
| 205 | 21-Jul | | 00000 | | | | 00000 | 26 57 | | 8562A | 43 351 850 | 0 DBm | 1 Hr | 8562A | 43 351 870 | 0 DBm | 1 Hr | 1 LOOP |
| 206 | 22-Jul | | 00000 | | | | 00000 | 27 70 | | 8562A | 43 351 850 | 0 DBm | 1 Hr | 8562A | 43 351 870 | 0 DBm | 1 Hr | 1 LOOP |
| 207 | 23-Jul | | 00000 | | | | 00000 | 27 39 | | 8562A | 43 351 850 | 0 DBm | 1 Hr | 8562A | 43 351 870 | 0 DBm | 1 Hr | 1 LOOP |
| 208 | 24-Jul | | 00000 | | | | 00000 | 27 07 | 40 | 8562A | 43 351 850 | 0 DBm | 1 Hr | 8562A | 43 351 870 | 0 DBm | 1 Hr | 1 LOOP |
| 209 | 25-Jul | | 00000 | | | | 00000 | 26 88 | | 8562A | 43 351 850 | 0 DBm | 1 Hr | 8562A | 43 351 870 | 0 DBm | 1 Hr | 1 LOOP |
| 210 | 26-Jul | | 00000 | 0 030 | 0 030 | 0 030 | 00001 | 26 68 | | 8562A | 43 351 850 | 0 DBm | 1 Hr | 8562A | 43 351 870 | 0 DBm | 1 Hr | 1 LOOP |
| 211 | 27-Jul | | 00000 | 0 030 | 0 030 | 0 030 | 00001 | 25 90 | | 8562A | 43 351 850 | 0 DBm | 1 Hr | 8562A | 43 351 870 | 0 DBm | 1 Hr | 1 LOOP |
| 212 | 28-Jul | *Died 7/28/95* | #VALUE | | *Died 7/28/95* | | #VALUE | 27 28 | 30 | 8562A | 43 351 850 | 0 DBm | 1 Hr | 8562A | 43 351 870 | 0 DBm | 1 Hr | 1 LOOP |

*OUJ-475 Born 3/1/94 First tumor appeared on 11/14/94*
*Conventional SCPO Treatment. Treated at first appearance of tumor located on abdomen.*

| DAY | DATE | T1 On Abdomen | | | Vol | T-2 | | | Vol | WEIGHT | HEMATO- | TREATMENT PARAMETERS | | | | | |
|---|---|---|---|---|---|---|---|---|---|---|---|---|---|---|---|---|---|
| | | Ln | Wd | Ht | T-1 | Ln | Wd | Ht | T-2 | Gr | CRIT-% | DEVICE | FREQ MHz | TIME | DEVICE | FREQ MHz | TIME |
| 1 | 11/14/94 | 0.030 | 0.030 | 0.030 | 00001 | | | | 00000 | 33.16 | | SCPO#1 | 43,351,830 | .5 Hr | SCPO#3 | 43,351,870 | .5 Hr |
| 2 | 11/15/94 | 0.030 | 0.030 | 0.030 | 00001 | | | | 00000 | 33.85 | | SCPO#1 | 43,351,830 | .5 Hr | SCPO#3 | 43,351,870 | .5 Hr |
| 3 | 11/16/94 | 0.030 | 0.030 | 0.030 | 00001 | | | | 00000 | 33.57 | | SCPO#1 | 43,351,830 | .5 Hr | SCPO#3 | 43,351,870 | .5 Hr |
| 4 | 11/17/94 | 0.030 | 0.030 | 0.030 | 00001 | | | | 00000 | 32.58 | | SCPO#1 | 43,351,830 | .5 Hr | SCPO#3 | 43,351,870 | .5 Hr |
| 5 | 11/18/94 | 0.030 | 0.030 | 0.030 | 00001 | | | | 00000 | 31.85 | | SCPO#1 | 43,351,830 | .5 Hr | SCPO#3 | 43,351,870 | .5 Hr |
| 6 | 11/19/94 | 0.030 | 0.030 | 0.030 | 00001 | | | | 00000 | 32.12 | 45 | SCPO#1 | 43,351,830 | .5 Hr | SCPO#3 | 43,351,870 | .5 Hr |
| 7 | 11/20/94 | 0.030 | 0.030 | 0.030 | 00001 | | | | 00000 | 32.26 | | SCPO#1 | 43,351,830 | .5 Hr | SCPO#3 | 43,351,870 | .5 Hr |
| 8 | 11/21/94 | 0.030 | 0.030 | 0.030 | 00001 | | | | 00000 | 32.39 | | SCPO#1 | 43,351,830 | .5 Hr | SCPO#3 | 43,351,870 | .5 Hr |
| 9 | 11/22/94 | 0.030 | 0.030 | 0.030 | 00001 | | | | 00000 | 31.55 | | SCPO#1 | 43,351,830 | 1 Hr | SCPO#3 | 43,351,870 | 1 Hr |
| 10 | 11/23/94 | 0.030 | 0.030 | 0.030 | 00001 | | | | 00000 | 31.27 | | SCPO#1 | 43,351,830 | 1 Hr | SCPO#3 | 43,351,870 | 1 Hr |
| 11 | 11/24/94 | 0.030 | 0.030 | 0.030 | 00001 | | | | 00000 | 31.00 | | SCPO#1 | 43,351,830 | 1 Hr | SCPO#3 | 43,351,870 | 1 Hr |
| 12 | 11/25/94 | | | | 00000 | | | | 00000 | 30.71 | | SCPO#1 | 43,351,830 | 1 Hr | SCPO#3 | 43,351,870 | 1 Hr |
| 13 | 11/26/94 | | | | 00000 | | | | 00000 | 30.93 | 42 | SCPO#1 | 43,351,830 | 1 Hr | SCPO#3 | 43,351,870 | 1 Hr |
| 14 | 11/27/94 | | | | 00000 | | | | 00000 | 30.62 | | SCPO#1 | 43,351,830 | 1 Hr | SCPO#3 | 43,351,870 | 1 Hr |
| 15 | 11/28/94 | | | | 00000 | | | | 00000 | 30.31 | | SCPO#1 | 43,351,830 | 1 Hr | SCPO#3 | 43,351,870 | 1 Hr |
| 16 | 11/29/94 | | | | 00000 | | | | 00000 | 29.38 | | SCPO#1 | 43,351,830 | 1 Hr | SCPO#3 | 43,351,870 | 1 Hr |
| 17 | 11/30/94 | | | | 00000 | | | | 00000 | 29.93 | | SCPO#1 | 43,351,830 | 1 Hr | SCPO#3 | 43,351,870 | 1 Hr |
| 18 | 12/1/94 | | | | 00000 | | | | 00000 | 31.21 | | SCPO#1 | 43,351,830 | 1 Hr | SCPO#3 | 43,351,870 | 1 Hr |
| 19 | 12/2/94 | | | | 00000 | | | | 00000 | 30.53 | 44 | SCPO#1 | 43,351,830 | 1 Hr | SCPO#3 | 43,351,870 | 1 Hr |
| 20 | 12/3/94 | | | | 00000 | | | | 00000 | 30.75 | | SCPO#1 | 43,351,830 | 1 Hr | SCPO#3 | 43,351,870 | 1 Hr |
| 21 | 12/4/94 | | | | 00000 | | | | 00000 | 30.71 | | SCPO#1 | 43,351,830 | 1 Hr | SCPO#3 | 43,351,870 | 1 Hr |
| 22 | 12/5/94 | | | | 00000 | | | | 00000 | 30.67 | | SCPO#1 | 43,351,830 | 1 Hr | SCPO#3 | 43,351,870 | 1 Hr |
| 23 | 12/6/94 | | | | 00000 | | | | 00000 | 30.79 | | SCPO#1 | 43,351,830 | 1 Hr | SCPO#3 | 43,351,870 | 1 Hr |
| 24 | 12/7/94 | | | | 00000 | | | | 00000 | 31.04 | | SCPO#1 | 43,351,830 | 1 Hr | SCPO#3 | 43,351,870 | 1 Hr |
| 25 | 12/8/94 | | | | 00000 | | | | 00000 | 30.21 | | SCPO#1 | 43,351,830 | 1 Hr | SCPO#3 | 43,351,870 | 1 Hr |
| 26 | 12/9/94 | | | | 00000 | | | | 00000 | 29.71 | 45 | SCPO#1 | 43,351,830 | 1 Hr | SCPO#3 | 43,351,870 | 1 Hr |
| 27 | 12/10/94 | | | | 00000 | | | | 00000 | 29.14 | | SCPO#1 | 43,351,830 | 1 Hr | SCPO#3 | 43,351,870 | 1 Hr |
| 28 | 12/11/94 | | | | 00000 | | | | 00000 | 30.40 | | SCPO#1 | 43,351,830 | 1 Hr | SCPO#3 | 43,351,870 | 1 Hr |
| 29 | 12/12/94 | | | | 00000 | | | | 00000 | 31.72 | | SCPO#1 | 43,351,830 | 1 Hr | SCPO#3 | 43,351,870 | 1 Hr |
| 30 | 12/13/94 | | | | 00000 | | | | 00000 | 31.13 | | SCPO#1 | 43,351,830 | 1 Hr | SCPO#3 | 43,351,870 | 1 Hr |
| 31 | 12/14/94 | | | | 00000 | | | | 00000 | 31.73 | | SCPO#1 | 43,351,830 | 1 Hr | SCPO#3 | 43,351,870 | 1 Hr |
| 32 | 12/15/94 | | | | 00000 | | | | 00000 | 31.40 | | SCPO#1 | 43,351,830 | 1 Hr | SCPO#3 | 43,351,870 | 1 Hr |
| 33 | 12/16/94 | | | | 00000 | | | | 00000 | 31.93 | | SCPO#1 | 43,351,830 | 1 Hr | SCPO#3 | 43,351,870 | 1 Hr |
| 34 | 12/17/94 | | | | 00000 | | | | 00000 | 31.30 | | SCPO#1 | 43,351,830 | 1 Hr | SCPO#3 | 43,351,870 | 1 Hr |
| 35 | 12/18/94 | | | | 00000 | | | | 00000 | 30.60 | | SCPO#1 | 43,351,830 | 1 Hr | SCPO#3 | 43,351,870 | 1 Hr |
| 36 | 12/19/94 | | | | 00000 | | | | 00000 | 29.92 | 43 | SCPO#1 | 43,351,830 | 1 Hr | SCPO#3 | 43,351,870 | 1 Hr |
| 37 | 12/20/94 | | | | 00000 | | | | 00000 | 30.25 | | SCPO#1 | 43,351,830 | 1 Hr | SCPO#3 | 43,351,870 | 1 Hr |
| 38 | 12/21/94 | | | | 00000 | | | | 00000 | 30.16 | | SCPO#1 | 43,351,830 | 1 Hr | SCPO#3 | 43,351,870 | 1 Hr |
| 39 | 12/22/94 | | | | 00000 | | | | 00000 | 29.76 | | SCPO#1 | 43,351,830 | 1 Hr | SCPO#3 | 43,351,870 | 1 Hr |
| 40 | 12/23/94 | | | | 00000 | | | | 00000 | 29.45 | 45 | SCPO#1 | 43,351,830 | 1 Hr | SCPO#3 | 43,351,870 | 1 Hr |
| 41 | 12/24/94 | | | | 00000 | | | | 00000 | 30.03 | | SCPO#1 | 43,351,830 | 1 Hr | SCPO#3 | 43,351,870 | 1 Hr |
| 42 | 12/25/94 | | | | 00000 | | | | 00000 | 30.09 | | SCPO#1 | 43,351,830 | 1 Hr | SCPO#3 | 43,351,870 | 1 Hr |
| 43 | 12/26/94 | | | | 00000 | | | | 00000 | 30.14 | | SCPO#1 | 43,351,830 | 1 Hr | SCPO#3 | 43,351,870 | 1 Hr |
| 44 | 12/27/94 | | | | 00000 | | | | 00000 | 29.48 | | SCPO#1 | 43,351,830 | 1 Hr | SCPO#3 | 43,351,870 | 1 Hr |
| 45 | 12/28/94 | | | | 00000 | | | | 00000 | 30.00 | | SCPO#1 | 43,351,830 | 1 Hr | SCPO#3 | 43,351,870 | 1 Hr |
| 46 | 12/29/94 | | | | 00000 | | | | 00000 | 30.08 | | SCPO#1 | 43,351,830 | 1 Hr | SCPO#3 | 43,351,870 | 1 Hr |
| 47 | 12/30/94 | | | | 00000 | | | | 00000 | 30.71 | | SCPO#1 | 43,351,830 | 1 Hr | SCPO#3 | 43,351,870 | 1 Hr |

09141691.082898

| | | | | | | | | | | | | | | |
|---|---|---|---|---|---|---|---|---|---|---|---|---|---|---|
| 48 | 12/31/94 | 00000 | | | | 00000 | 30.35 | 43 | SCPO#1 | 43,351,830 | 1 Hr | SCPO#3 | 43,351,870 | 1 Hr |
| 49 | 1/1/95 | 00000 | | | | 00000 | 30.12 | | SCPO#1 | 43,351,830 | 1 Hr | SCPO#3 | 43,351,870 | 1 Hr |
| 50 | 1/2/95 | 00000 | | | | 00000 | 29.89 | | SCPO#1 | 43,351,830 | 1 Hr | SCPO#3 | 43,351,870 | 1 Hr |
| 51 | 1/3/95 | 00000 | | | | 00000 | 30.46 | | SCPO#1 | 43,351,830 | 1 Hr | SCPO#3 | 43,351,870 | 1 Hr |
| 52 | 1/4/95 | 00000 | | | | 00000 | 30.58 | | SCPO#1 | 43,351,830 | 1 Hr | SCPO#3 | 43,351,870 | 1 Hr |
| 53 | 1/5/95 | 00000 | | | | 00000 | 29.73 | | SCPO#1 | 43,351,830 | 1 Hr | SCPO#3 | 43,351,870 | 1 Hr |
| 54 | 1/6/95 | 00000 | | | | 00000 | 29.78 | 45 | SCPO#1 | 43,351,830 | 1 Hr | SCPO#3 | 43,351,870 | 1 Hr |
| 55 | 1/7/95 | 00000 | | | | 00000 | 29.84 | | SCPO#1 | 43,351,830 | 1 Hr | SCPO#3 | 43,351,870 | 1 Hr |
| 56 | 1/8/95 | 00000 | | | | 00000 | 30.01 | | SCPO#1 | 43,351,830 | 1 Hr | SCPO#3 | 43,351,870 | 1 Hr |
| 57 | 1/9/95 | 00000 | | | | 00000 | 30.19 | | SCPO#1 | 43,351,830 | 1 Hr | SCPO#3 | 43,351,870 | 1 Hr |
| 58 | 1/10/95 | 00000 | | | | 00000 | 29.66 | | SCPO#1 | 43,351,830 | 1 Hr | SCPO#3 | 43,351,870 | 1 Hr |
| 59 | 1/11/95 | 00000 | | | | 00000 | 30.07 | | SCPO#1 | 43,351,830 | 1 Hr | SCPO#3 | 43,351,870 | 1 Hr |
| 60 | 1/12/95 | 00000 | | | | 00000 | 30.06 | | SCPO#1 | 43,351,830 | 1 Hr | SCPO#3 | 43,351,870 | 1 Hr |
| 61 | 1/13/95 | 00000 | | | | 00000 | 30.41 | 44 | SCPO#1 | 43,351,830 | 1 Hr | SCPO#3 | 43,351,870 | 1 Hr |
| 62 | 1/14/95 | 00000 | | | | 00000 | 28.93 | | ***All treatment stopped 1/14/95 for now...*** | | | | | |
| 63 | 1/15/95 | 00000 | | | | 00000 | 29.31 | | | - | | | - | |
| 64 | 1/16/95 | 00000 | | | | 00000 | 29.70 | | | - | | | - | |
| 65 | 1/17/95 | 00000 | | | | 00000 | 30.82 | | | - | | | - | |
| 66 | 1/18/95 | 00000 | | | | 00000 | 30.78 | | | - | | | - | |
| 67 | 1/19/95 | 00000 | | | | 00000 | 31.17 | | | - | | | - | |
| 68 | 1/20/95 | 00000 | | | | 00000 | 31.14 | 43 | | - | | | - | |
| 69 | 1/21/95 | 00000 | | | | 00000 | 29.55 | | | - | | | - | |
| 70 | 1/22/95 | 00000 | | | | 00000 | 30.06 | | | - | | | - | |
| 71 | 1/23/95 | 00000 | | | | 00000 | 30.68 | | | - | | | - | |
| 72 | 1/24/95 | 00000 | | | | 00000 | 29.67 | | | - | | | - | |
| 73 | 1/25/95 | 00000 | | | | 00000 | 29.54 | | | - | | | - | |
| 74 | 1/26/95 | 00000 | | | | 00000 | 29.31 | | | - | | | - | |
| 75 | 1/27/95 | 00000 | | | | 00000 | 28.94 | 41 | | - | | | - | |
| 76 | 1/28/95 | 00000 | | | | 00000 | 29.40 | | | - | | | - | |
| 77 | 1/29/95 | 00000 | | | | 00000 | 29.65 | | | - | | | - | |
| 78 | 1/30/95 | 00000 | | | | 00000 | 29.97 | | | - | | | - | |
| 79 | 1/31/95 | 00000 | | | | 00000 | 29.31 | | SCPO#1 | 43,351,830 | 1 Hr | SCPO#1 | 43,351,830 | 1 Hr |
| 80 | 2/1/95 | 00000 | | | | 00000 | 29.77 | | SCPO#3 | 43,351,870 | 1 Hr | SCPO#3 | 43,351,870 | 1 Hr |
| 81 | 2/2/95 | 00000 | | | | 00000 | 29.27 | 42 | SCPO#3 | 43,351,870 | 1 Hr | SCPO#3 | 43,351,870 | 1 Hr |
| 82 | 2/3/95 | 00000 | 0.030 | 0.030 | 0.030 | 00001 | 30.55 | | SCPO#1 | 43,351,830 | 1 Hr | SCPO#3 | 43,351,870 | 1 Hr |
| 83 | 2/4/95 | 00000 | 0.030 | 0.030 | 0.030 | 00001 | 29.51 | | SCPO#1 | 43,351,830 | 1 Hr | SCPO#3 | 43,351,870 | 1 Hr |
| 84 | 2/5/95 | 00000 | 0.050 | 0.050 | 0.040 | 00005 | 29.82 | | SCPO#1 | 43,351,830 | 1 Hr | SCPO#3 | 43,351,870 | 1 Hr |
| 85 | 2/6/95 | 00000 | 0.070 | 0.070 | 0.050 | 00013 | 30.34 | | SCPO#1 | 43,351,830 | 1 Hr | SCPO#3 | 43,351,870 | 1 Hr |
| 86 | 2/7/95 | 00000 | 0.090 | 0.090 | 0.070 | 00030 | 30.90 | | SCPO#1 | 43,351,830 | 1 Hr | SCPO#3 | 43,351,870 | 1 Hr |
| 87 | 2/8/95 | 00000 | 0.090 | 0.090 | 0.070 | 00030 | 30.02 | | SCPO#1 | 43,351,830 | 1 Hr | SCPO#3 | 43,351,870 | 1 Hr |
| 88 | 2/9/95 | 00000 | 0.100 | 0.100 | 0.070 | 00037 | 29.38 | | SCPO#1 | 43,351,830 | 1 Hr | SCPO#3 | 43,351,870 | 1 Hr |
| 89 | 2/10/95 | 00000 | 0.100 | 0.100 | 0.070 | 00037 | 29.68 | 43 | SCPO#1 | 43,351,830 | 1 Hr | SCPO#3 | 43,351,870 | 1 Hr |
| 90 | 2/11/95 | 00000 | 0.100 | 0.100 | 0.070 | 00037 | 30.38 | | SCPO#1 | 43,351,830 | 1 Hr | SCPO#3 | 43,351,870 | 1 Hr |
| 91 | 2/12/95 | 00000 | 0.100 | 0.100 | 0.070 | 00037 | 30.35 | | SCPO#1 | 43,351,830 | 1 Hr | SCPO#3 | 43,351,870 | 1 Hr |
| 92 | 2/13/95 | 00000 | 0.090 | 0.090 | 0.070 | 00030 | 30.32 | | SCPO#1 | 43,351,830 | 1 Hr | SCPO#3 | 43,351,870 | 1 Hr |
| 93 | 2/14/95 | 00000 | 0.090 | 0.090 | 0.070 | 00030 | 29.84 | | SCPO#1 | 43,351,830 | 1 Hr | SCPO#3 | 43,351,870 | 1 Hr |
| 94 | 2/15/95 | 00000 | 0.070 | 0.070 | 0.050 | 00013 | 29.87 | | SCPO#1 | 43,351,830 | 1 Hr | SCPO#3 | 43,351,870 | 1 Hr |
| 95 | 2/16/95 | 00000 | 0.070 | 0.070 | 0.050 | 00013 | 29.85 | | SCPO#1 | 43,351,830 | 1 Hr | SCPO#3 | 43,351,870 | 1 Hr |
| 96 | 2/17/95 | 00000 | 0.050 | 0.050 | 0.050 | 00007 | 29.74 | | SCPO#1 | 43,351,830 | 1 Hr | SCPO#3 | 43,351,870 | 1 Hr |
| 97 | 2/18/95 | 00000 | 0.030 | 0.030 | 0.030 | 00001 | 28.92 | 44 | SCPO#1 | 43,351,830 | 1 Hr | SCPO#3 | 43,351,870 | 1 Hr |
| 98 | 2/19/95 | 00000 | 0.030 | 0.030 | 0.030 | 00001 | 29.83 | | SCPO#1 | 43,351,830 | 1 Hr | SCPO#3 | 43,351,870 | 1 Hr |

OUJ-475-.xls

| | | | | | | | | | | | | | | |
|---|---|---|---|---|---|---|---|---|---|---|---|---|---|---|
| 99 | 2/20/95 | 00000 | 0.030 | 0.030 | 0.030 | 00001 | 30.73 | | SCPO#1 | 43,351,830 | 1 Hr | SCPO#3 | 43,351,870 | 1 Hr |
| 100 | 2/21/95 | 00000 | | | | 00000 | 30.84 | | SCPO#1 | 43,351,830 | 1 Hr | SCPO#3 | 43,351,870 | 1 Hr |
| 101 | 2/22/95 | 00000 | | | | 00000 | 30.74 | | SCPO#1 | 43,351,830 | 1 Hr | SCPO#3 | 43,351,870 | 1 Hr |
| 102 | 2/23/95 | 00000 | | | | 00000 | 31.66 | | SCPO#1 | 43,351,830 | 1 Hr | SCPO#3 | 43,351,870 | 1 Hr |
| 103 | 2/24/95 | 00000 | | | | 00000 | 30.90 | 45 | SCPO#1 | 43,351,830 | 1 Hr | SCPO#3 | 43,351,870 | 1 Hr |
| 104 | 2/25/95 | 00000 | | | | 00000 | 30.69 | | SCPO#1 | 43,351,830 | 1 Hr | SCPO#3 | 43,351,870 | 1 Hr |
| 105 | 2/26/95 | 00000 | | | | 00000 | 31.65 | | SCPO#1 | 43,351,830 | 1 Hr | SCPO#3 | 43,351,870 | 1 Hr |
| 106 | 2/27/95 | 00000 | | | | 00000 | 32.64 | | SCPO#1 | 43,351,830 | 1 Hr | SCPO#3 | 43,351,870 | 1 Hr |
| 107 | 2/28/95 | 00000 | | | | 00000 | 30.66 | | SCPO#1 | 43,351,830 | 1 Hr | SCPO#3 | 43,351,870 | 1 Hr |
| 108 | 3/1/95 | 00000 | | | | 00000 | 31.18 | | SCPO#1 | 43,351,830 | 1 Hr | SCPO#3 | 43,351,870 | 1 Hr |
| 109 | 3/2/95 | 00000 | | | | 00000 | 29.44 | | SCPO#1 | 43,351,830 | 1 Hr | SCPO#3 | 43,351,870 | 1 Hr |
| 110 | 3/3/95 | 00000 | | | | 00000 | 29.54 | 40 | SCPO#3 | 43,351,870 | 1 Hr | SCPO#3 | 43,351,870 | 1 Hr |
| 111 | 3/4/95 | 00000 | | | | 00000 | 29.25 | | SCPO#3 | 43,351,870 | 1 Hr | SCPO#3 | 43,351,870 | 1 Hr |
| 112 | 3/5/95 | 00000 | | | | 00000 | 29.09 | | SCPO#3 | 43,351,870 | 1 Hr | SCPO#3 | 43,351,870 | 1 Hr |
| 113 | 3/6/95 | 00000 | | | | 00000 | 28.88 | | SCPO#3 | 43,351,870 | 1 Hr | SCPO#3 | 43,351,870 | 1 Hr |
| 114 | 3/7/95 | 00000 | | | | 00000 | 28.93 | | SCPO#3 | 43,351,870 | 1 Hr | SCPO#3 | 43,351,870 | 1 Hr |
| 115 | 3/8/95 | 00000 | | | | 00000 | 29.42 | | SCPO#3 | 43,351,870 | 1 Hr | SCPO#3 | 43,351,870 | 1 Hr |
| 116 | 3/9/95 | 00000 | | | | 00000 | 29.63 | | SCPO#3 | 43,351,870 | 1 Hr | SCPO#3 | 43,351,870 | 1 Hr |
| 117 | 3/10/95 | 00000 | | | | 00000 | 30.33 | 40 | SCPO#3 | 43,351,870 | 1 Hr | SCPO#3 | 43,351,870 | 1 Hr |
| 118 | 3/11/95 | 00000 | | | | 00000 | 29.13 | | SCPO#3 | 43,351,870 | 1 Hr | SCPO#3 | 43,351,870 | 1 Hr |
| 119 | 3/12/95 | 00000 | | | | 00000 | 29.88 | | SCPO#3 | 43,351,870 | 1 Hr | SCPO#3 | 43,351,870 | 1 Hr |
| 120 | 3/13/95 | 00000 | | | | 00000 | 30.63 | | SCPO#3 | 43,351,870 | 1 Hr | SCPO#3 | 43,351,870 | 1 Hr |
| 121 | 3/14/95 | 00000 | | | | 00000 | 30.78 | | SCPO#3 | 43,351,870 | 1 Hr | SCPO#3 | 43,351,870 | 1 Hr |
| 122 | 3/15/95 | 00000 | | | | 00000 | 30.77 | | SCPO#3 | 43,351,870 | 1 Hr | SCPO#3 | 43,351,870 | 1 Hr |
| 123 | 3/16/95 | 00000 | | | | 00000 | 30.39 | | SCPO#3 | 43,351,870 | 1 Hr | SCPO#3 | 43,351,870 | 1 Hr |
| 124 | 3/17/95 | 00000 | | | | 00000 | 31.50 | 41 | SCPO#3 | 43,351,870 | 1 Hr | SCPO#3 | 43,351,870 | 1 Hr |
| 125 | 3/18/95 | 00000 | | | | 00000 | 29.97 | | SCPO#3 | 43,351,870 | 1 Hr | SCPO#3 | 43,351,870 | 1 Hr |
| 126 | 3/19/95 | 00000 | | | | 00000 | 30.45 | | SCPO#3 | 43,351,870 | 1 Hr | SCPO#3 | 43,351,870 | 1 Hr |
| 127 | 3/20/95 | 00000 | | | | 00000 | 30.85 | | SCPO#3 | 43,351,870 | 1 Hr | SCPO#6 | 43,351,850 | 1 Hr |
| 128 | 3/21/95 | 00000 | | | | 00000 | 30.86 | | SCPO#3 | 43,351,870 | 1 Hr | SCPO#6 | 43,351,850 | 1 Hr |
| 129 | 3/22/95 | 00000 | | | | 00000 | 31.64 | | SCPO#3 | 43,351,870 | 1 Hr | SCPO#6 | 43,351,850 | 1 Hr |
| 130 | 3/23/95 | 00000 | | | | 00000 | 32.41 | | SCPO#3 | 43,351,870 | 1 Hr | SCPO#6 | 43,351,850 | 1 Hr |
| 131 | 3/24/95 | 00000 | | | | 00000 | 31.01 | | SCPO#3 | 43,351,870 | 1 Hr | SCPO#6 | 43,351,850 | 1 Hr |
| 132 | 3/25/95 | 00000 | | | | 00000 | 31.13 | 38 | SCPO#3 | 43,351,870 | 1 Hr | SCPO#3 | 43,351,870 | 1 Hr |
| 133 | 3/26/95 | 00000 | | | | 00000 | 30.64 | | SCPO#3 | 43,351,870 | 1 Hr | SCPO#3 | 43,351,870 | 1 Hr |
| 134 | 3/27/95 | 00000 | | | | 00000 | 30.14 | | SCPO#3 | 43,351,870 | 1 Hr | SCPO#3 | 43,351,870 | 1 Hr |
| 135 | 3/28/95 | 00000 | | | | 00000 | 30.90 | | SCPO#3 | 43,351,870 | 1 Hr | SCPO#3 | 43,351,870 | 1 Hr |
| 136 | 3/29/95 | 00000 | | | | 00000 | 30.47 | | SCPO#3 | 43,351,870 | 1 Hr | SCPO#3 | 43,351,870 | 1 Hr |
| 137 | 3/30/95 | 00000 | | | | 00000 | 30.37 | | SCPO#3 | 43,351,870 | 1 Hr | SCPO#3 | 43,351,870 | 1 Hr |
| 138 | 3/31/95 | 00000 | | | | 00000 | 30.57 | 44 | SCPO#3 | 43,351,870 | 1 Hr | SCPO#3 | 43,351,870 | 1 Hr |
| 139 | 4/1/95 | 00000 | | | | 00000 | 29.73 | | SCPO#3 | 43,351,870 | 1 Hr | SCPO#3 | 43,351,870 | 1 Hr |
| 140 | 4/2/95 | 00000 | | | | 00000 | 29.91 | | SCPO#3 | 43,351,870 | 1 Hr | SCPO#3 | 43,351,870 | 1 Hr |
| 141 | 4/3/95 | 00000 | | | | 00000 | 30.08 | | SCPO#3 | 43,351,870 | 1 Hr | SCPO#3 | 43,351,870 | 1 Hr |
| 142 | 4/4/95 | 00000 | | | | 00000 | 30.20 | | SCPO#3 | 43,351,870 | 1 Hr | SCPO#3 | 43,351,870 | 1 Hr |
| 143 | 4/5/95 | 00000 | | | | 00000 | 30.03 | | SCPO#3 | 43,351,870 | 1 Hr | SCPO#3 | 43,351,870 | 1 Hr |
| 144 | 4/6/95 | 00000 | | | | 00000 | 29.66 | | SCPO#3 | 43,351,870 | 1 Hr | SCPO#3 | 43,351,870 | 1 Hr |
| 145 | 4/7/95 | 00000 | | | | 00000 | 28.87 | 43 | SCPO#3 | 43,351,870 | 1 Hr | SCPO#3 | 43,351,870 | 1 Hr |
| 146 | 4/8/95 | 00000 | | | | 00000 | 29.68 | | SCPO#3 | 43,351,870 | 1 Hr | SCPO#3 | 43,351,870 | 1 Hr |
| 147 | 4/9/95 | 00000 | | | | 00000 | 30.25 | | SCPO#3 | 43,351,870 | 1 Hr | SCPO#3 | 43,351,870 | 1 Hr |
| 148 | 4/10/95 | 00000 | | | | 00000 | 30.95 | | SCPO#3 | 43,351,870 | 1 Hr | SCPO#3 | 43,351,870 | 1 Hr |
| 149 | 4/11/95 | 00000 | | | | 00000 | 29.98 | | SCPO#3 | 43,351,870 | 1 Hr | SCPO#3 | 43,351,870 | 1 Hr |

OUJ-475-.xls

| | | | | | | | | | | | |
|---|---|---|---|---|---|---|---|---|---|---|---|
| 150 | 4/12/95 | 00000 | .00000 | 30 17 | | SCPO#3 | 43,351,870 | 1 Hr | SCPO#3 | 43,351,870 | 1 Hr |
| 151 | 4/13/95 | 00000 | 00000 | 29 04 | | SCPO#3 | 43,351,870 | 1 Hr | SCPO#3 | 43,351,870 | 1 Hr |
| 152 | 4/14/95 | 00000 | 00000 | 30 28 | 40 | SCPO#3 | 43,351,870 | 1 Hr | SCPO#3 | 43,351,870 | 1 Hr |
| 153 | 4/15/95 | 00000 | 00000 | 30 04 | | SCPO#3 | 43,351,870 | 1 Hr | SCPO#3 | 43,351,870 | 1 Hr |
| 154 | 4/16/95 | 00000 | 00000 | 29 18 | | SCPO#3 | 43,351,870 | 1 Hr | SCPO#3 | 43,351,870 | 1 Hr |
| 155 | 4/17/95 | 00000 | 00000 | 29 18 | | SCPO#3 | 43,351,870 | 1 Hr | SCPO#3 | 43,351,870 | 1 Hr |
| 156 | 4/18/95 | 00000 | 00000 | 29 15 | | SCPO#3 | 43,351,870 | 1 Hr | SCPO#3 | 43,351,870 | 1 Hr |
| 157 | 4/19/95 | 00000 | 00000 | 28 86 | | SCPO#3 | 43,351,870 | 1 Hr | SCPO#3 | 43,351,870 | 1 Hr |
| 158 | 4/20/95 | 00000 | 00000 | 29 54 | | SCPO#3 | 43,351,870 | 1 Hr | SCPO#3 | 43,351,870 | 1 Hr |
| 159 | 4/21/95 | 00000 | 00000 | 29.56 | 40 | SCPO#3 | 43,351,870 | 1 Hr | SCPO#3 | 43,351,870 | 1 Hr |
| 160 | 4/22/95 | 00000 | 00000 | 29 36 | | SCPO#3 | 43,351,870 | 1 Hr | SCPO#3 | 43,351,870 | 1 Hr |
| 161 | 4/23/95 | 00000 | 00000 | 29 71 | | SCPO#3 | 43,351,870 | 1 Hr | SCPO#3 | 43,351,870 | 1 Hr |
| 162 | 4/24/95 | 00000 | 00000 | 31 07 | | SCPO#3 | 43,351,870 | 1 Hr | SCPO#3 | 43,351,870 | 1 Hr |
| 163 | 4/25/95 | 00000 | .00000 | 30 13 | | SCPO#3 | 43,351,870 | 1 Hr | SCPO#3 | 43,351,870 | 1 Hr |
| 164 | 4/26/95 | 00000 | .00000 | 30 25 | | SCPO#3 | 43,351,870 | 1 Hr | SCPO#3 | 43,351,870 | 1 Hr |
| 165 | 4/27/95 | 00000 | 00000 | 25 78 | | SCPO#3 | 43,351,870 | 1 Hr | SCPO#3 | 43,351,870 | 1 Hr |
| 166 | 4/28/95 | 00000 | 00000 | 29 64 | | SCPO#3 | 43,351,870 | 1 Hr | SCPO#3 | 43,351,870 | 1 Hr |
| 167 | 4/29/95 | 00000 | 00000 | 29 84 | 36 | SCPO#3 | 43,351,870 | 1 Hr | SCPO#3 | 43,351,870 | 1 Hr |
| 168 | 4/30/95 | 00000 | 00000 | 29 94 | | SCPO#3 | 43,351,870 | 1 Hr | SCPO#3 | 43,351,870 | 1 Hr |
| 169 | 5/1/95 | 00000 | 00000 | 30 04 | | SCPO#3 | 43,351,870 | 1 Hr | SCPO#3 | 43,351,870 | 1 Hr |
| 170 | 5/2/95 | 00000 | 00000 | 29 22 | | SCPO#3 | 43,351,870 | 1 Hr | SCPO#3 | 43,351,870 | 1 Hr |
| 171 | 5/3/95 | 00000 | 00000 | 30 07 | | SCPO#3 | 43,351,870 | 1 Hr | SCPO#3 | 43,351,870 | 1 Hr |
| 172 | 5/4/95 | 00000 | 00000 | 30 01 | | SCPO#3 | 43,351,870 | 1 Hr | SCPO#3 | 43,351,870 | 1 Hr |
| 173 | 5/5/95 | 00000 | 00000 | 30 27 | 38 | SCPO#3 | 43,351,870 | 1 Hr | SCPO#3 | 43,351,870 | 1 Hr |
| 174 | 5/6/95 | 00000 | 00000 | 30 00 | | SCPO#3 | 43,351,870 | 1 Hr | SCPO#3 | 43,351,870 | 1 Hr |
| 175 | 5/7/95 | 00000 | 00000 | 29 75 | | SCPO#3 | 43,351,870 | 1 Hr | SCPO#3 | 43,351,870 | 1 Hr |
| 176 | 5/8/95 | 00000 | 00000 | 29 52 | | SCPO#3 | 43,351,870 | 1 Hr | SCPO#3 | 43,351,870 | 1 Hr |
| 177 | 5/9/95 | 00000 | 00000 | 32 35 | | SCPO#3 | 43,351,870 | 1 Hr | SCPO#3 | 43,351,870 | 1 Hr |
| 178 | 5/10/95 | 00000 | 00000 | 30 17 | | SCPO#3 | 43,351,870 | 1 Hr | SCPO#3 | 43,351,870 | 1 Hr |
| 179 | 5/11/95 | 00000 | 00000 | 30 33 | 40 | SCPO#3 | 43,351,870 | 1 Hr | SCPO#3 | 43,351,870 | 1 Hr |
| 180 | 5/12/95 | 00000 | 00000 | 29 52 | | SCPO#3 | 43,351,870 | 1 Hr | SCPO#3 | 43,351,870 | 1 Hr |
| 181 | 5/13/95 | 00000 | 00000 | 29 71 | | SCPO#3 | 43,351,870 | 1 Hr | SCPO#3 | 43,351,870 | 1 Hr |
| 182 | 5/14/95 | 00000 | 00000 | 30 35 | | SCPO#3 | 43,351,870 | 1 Hr | SCPO#3 | 43,351,870 | 1 Hr |
| 183 | 5/15/95 | 00000 | 00000 | 30 67 | | SCPO#3 | 43,351,870 | 1 Hr | SCPO#3 | 43,351,870 | 1 Hr |
| 184 | 5/16/95 | 00000 | 00000 | 30 33 | | SCPO#3 | 43,351,870 | 1 Hr | SCPO#3 | 43,351,870 | 1 Hr |
| 185 | 5/17/95 | 00000 | 00000 | 30 12 | | SCPO#3 | 43,351,870 | 1 Hr | SCPO#3 | 43,351,870 | 1 Hr |
| 186 | 5/18/95 | 00000 | 00000 | 29 90 | | SCPO#3 | 43,351,870 | 1 Hr | SCPO#3 | 43,351,870 | 1 Hr |
| 187 | 5/19/95 | 00000 | 00000 | 30 74 | 38 | SCPO#3 | 43,351,870 | 1 Hr | SCPO#3 | 43,351,870 | 1 Hr |
| 188 | 5/20/95 | 00000 | 00000 | 30 50 | | SCPO#3 | 43,351,870 | 1 Hr | SCPO#3 | 43,351,870 | 1 Hr |
| 189 | 5/21/95 | 00000 | 00000 | 30 25 | | SCPO#3 | 43,351,870 | 1 Hr | SCPO#3 | 43,351,870 | 1 Hr |
| 190 | 5/22/95 | 00000 | 00000 | 30 02 | | SCPO#3 | 43,351,870 | 1 Hr | SCPO#3 | 43,351,870 | 1 Hr |
| 191 | 5/23/95 | 00000 | 00000 | 30 26 | | SCPO#3 | 43,351,870 | 1 Hr | SCPO#3 | 43,351,870 | 1 Hr |
| 192 | 5/24/95 | 00000 | 00000 | 29 92 | | SCPO#3 | 43,351,870 | 1 Hr | SCPO#3 | 43,351,870 | 1 Hr |
| 193 | 5/25/95 | 00000 | 00000 | 30 81 | | SCPO#3 | 43,351,870 | 1 Hr | SCPO#3 | 43,351,870 | 1 Hr |
| 194 | 5/26/95 | 00000 | 00000 | 28 99 | 35 | SCPO#3 | 43,351,870 | 1 Hr | SCPO#3 | 43,351,870 | 1 Hr |
| 195 | 5/27/95 | 00000 | 00000 | 29 71 | | SCPO#3 | 43,351,870 | 1 Hr | SCPO#3 | 43,351,870 | 1 Hr |
| 196 | 5/28/95 | 00000 | 00000 | 30 15 | | SCPO#3 | 43,351,870 | 1 Hr | SCPO#3 | 43,351,870 | 1 Hr |
| 197 | 5/29/95 | 00000 | 00000 | 30 60 | | SCPO#3 | 43,351,870 | 1 Hr | SCPO#3 | 43,351,870 | 1 Hr |
| 198 | 5/30/95 | 00000 | 00000 | 29 67 | | SCPO#3 | 43,351,870 | 1 Hr | SCPO#3 | 43,351,870 | 1 Hr |
| 199 | 5/31/95 | 00000 | 00000 | 29 70 | | SCPO#3 | 43,351,870 | 1 Hr | SCPO#3 | 43,351,870 | 1 Hr |
| 200 | 6/1/95 | 00000 | 00000 | 30 13 | | SCPO#3 | 43,351,870 | 1 Hr | SCPO#3 | 43,351,870 | 1 Hr |

OUJ-475-.xls Page 4 OUJ-475-.xls

09141691 .082898

OUJ-475-.xls

| | | | | | | | | | | | |
|---|---|---|---|---|---|---|---|---|---|---|---|
| 201 | 6/2/95 | 00000 | 00000 | 29.92 | 40 | SCPO#3 | 43,351,870 | 1 Hr | SCPO#3 | 43,351,870 | 1 Hr |
| 202 | 6/3/95 | 00000 | 00000 | 29.56 | | SCPO#3 | 43,351,870 | 1 Hr | SCPO#3 | 43,351,870 | 1 Hr |
| 203 | 6/4/95 | 00000 | 00000 | 29.70 | | SCPO#3 | 43,351,870 | 1 Hr | SCPO#3 | 43,351,870 | 1 Hr |
| 204 | 6/5/95 | 00000 | 00000 | 29.84 | | SCPO#3 | 43,351,870 | 1 Hr | SCPO#3 | 43,351,870 | 1 Hr |
| 205 | 6/6/95 | 00000 | 00000 | 29.86 | | SCPO#3 | 43,351,870 | 1 Hr | SCPO#3 | 43,351,870 | 1 Hr |
| 206 | 6/7/95 | 00000 | 00000 | 29.93 | | SCPO#3 | 43,351,870 | 1 Hr | SCPO#3 | 43,351,870 | 1 Hr |
| 207 | 6/8/95 | 00000 | 00000 | 29.66 | | SCPO#3 | 43,351,870 | 1 Hr | SCPO#3 | 43,351,870 | 1 Hr |
| 208 | 6/9/95 | 00000 | 00000 | 29.61 | 43 | SCPO#3 | 43,351,870 | 1 Hr | SCPO#3 | 43,351,870 | 1 Hr |
| 209 | 6/10/95 | 00000 | 00000 | 29.30 | | SCPO#3 | 43,351,870 | 1 Hr | SCPO#3 | 43,351,870 | 1 Hr |
| 210 | 6/11/95 | 00000 | 00000 | 29.90 | | SCPO#3 | 43,351,870 | 1 Hr | SCPO#3 | 43,351,870 | 1 Hr |
| 211 | 6/12/95 | 00000 | 00000 | 30.72 | | SCPO#3 | 43,351,870 | 1 Hr | SCPO#3 | 43,351,870 | 1 Hr |
| 212 | 6/13/95 | 00000 | 00000 | 30.82 | | SCPO#3 | 43,351,870 | 1 Hr | SCPO#3 | 43,351,870 | 1 Hr |
| 213 | 6/14/95 | 00000 | 00000 | 30.65 | | SCPO#3 | 43,351,870 | 1 Hr | SCPO#3 | 43,351,870 | 1 Hr |
| 214 | 6/15/95 | 00000 | 00000 | 31.14 | | SCPO#3 | 43,351,870 | 1 Hr | SCPO#3 | 43,351,870 | 1 Hr |
| 215 | 6/16/95 | 00000 | 00000 | 31.16 | | SCPO#3 | 43,351,870 | 1 Hr | SCPO#3 | 43,351,870 | 1 Hr |
| 216 | 6/17/95 | 00000 | 00000 | 30.23 | 41 | SCPO#3 | 43,351,870 | 1 Hr | SCPO#3 | 43,351,870 | 1 Hr |
| 217 | 6/18/95 | 00000 | 00000 | 30.88 | | SCPO#3 | 43,351,870 | 1 Hr | SCPO#3 | 43,351,870 | 1 Hr |
| 218 | 6/19/95 | 00000 | 00000 | 31.95 | | SCPO#3 | 43,351,870 | 1 Hr | SCPO#3 | 43,351,870 | 1 Hr |
| 219 | 6/20/95 | 00000 | 00000 | 31.23 | | SCPO#3 | 43,351,870 | 1 Hr | SCPO#3 | 43,351,870 | 1 Hr |
| 220 | 6/21/95 | 00000 | 00000 | 30.55 | | SCPO#3 | 43,351,870 | 1 Hr | SCPO#3 | 43,351,870 | 1 Hr |
| 221 | 6/22/95 | 00000 | 00000 | 29.94 | | SCPO#3 | 43,351,870 | 1 Hr | SCPO#3 | 43,351,870 | 1 Hr |
| 222 | 6/23/95 | 00000 | 00000 | 29.66 | 43 | SCPO#3 | 43,351,870 | 1 Hr | SCPO#3 | 43,351,870 | 1 Hr |
| 223 | 6/24/95 | 00000 | 00000 | 28.99 | | SCPO#3 | 43,351,870 | 1 Hr | SCPO#3 | 43,351,870 | 1 Hr |
| 224 | 6/25/95 | 00000 | 00000 | 29.41 | | SCPO#3 | 43,351,870 | 1 Hr | SCPO#3 | 43,351,870 | 1 Hr |
| 225 | 6/26/95 | 00000 | 00000 | 29.81 | | SCPO#3 | 43,351,870 | 1 Hr | SCPO#3 | 43,351,870 | 1 Hr |
| 226 | 6/27/95 | 00000 | 00000 | 29.01 | | SCPO#3 | 43,351,870 | 1 Hr | SCPO#3 | 43,351,870 | 1 Hr |
| 227 | 6/28/95 | 00000 | 00000 | 28.32 | | SCPO#3 | 43,351,870 | 1 Hr | SCPO#3 | 43,351,870 | 1 Hr |
| 228 | 6/29/95 | 00000 | 00000 | 29.36 | | SCPO#3 | 43,351,870 | 1 Hr | SCPO#3 | 43,351,870 | 1 Hr |
| 229 | 6/30/95 | 00000 | 00000 | 28.54 | | SCPO#3 | 43,351,870 | 1 Hr | SCPO#3 | 43,351,870 | 1 Hr |
| 230 | 7/1/95 | 00000 | 00000 | 28.01 | | SCPO#3 | 43,351,870 | 1 Hr | SCPO#3 | 43,351,870 | 1 Hr |
| 231 | 7/2/95 | 00000 | 00000 | 29.12 | | SCPO#3 | 43,351,870 | 1 Hr | SCPO#3 | 43,351,870 | 1 Hr |
| 232 | 7/3/95 | 00000 | 00000 | 30.22 | | SCPO#3 | 43,351,870 | 1 Hr | SCPO#3 | 43,351,870 | 1 Hr |
| 233 | 7/4/95 | 00000 | 00000 | 29.73 | | SCPO#3 | 43,351,870 | 1 Hr | SCPO#3 | 43,351,870 | 1 Hr |
| 234 | 7/5/95 | 00000 | 00000 | 30.67 | | SCPO#3 | 43,351,870 | 1 Hr | SCPO#3 | 43,351,870 | 1 Hr |
| 235 | 7/6/95 | 00000 | 00000 | 29.58 | | SCPO#3 | 43,351,870 | 1 Hr | SCPO#3 | 43,351,870 | 1 Hr |
| 236 | 7/7/95 | 00000 | 00000 | 29.96 | 27 | SCPO#3 | 43,351,870 | 1 Hr | SCPO#3 | 43,351,870 | 1 Hr |
| 237 | 7/8/95 | 00000 | 00000 | 30.24 | | SCPO#3 | 43,351,870 | 1 Hr | SCPO#3 | 43,351,870 | 1 Hr |
| 238 | 7/9/95 | 00000 | 00000 | 30.77 | | SCPO#3 | 43,351,870 | 1 Hr | SCPO#3 | 43,351,870 | 1 Hr |
| 239 | 7/10/95 | 00000 | 00000 | 31.29 | | SCPO#3 | 43,351,870 | 1 Hr | SCPO#3 | 43,351,870 | 1 Hr |
| 240 | 7/11/95 | 00000 | 00000 | 30.59 | | SCPO#3 | 43,351,870 | 1 Hr | SCPO#3 | 43,351,870 | 1 Hr |
| 241 | 7/12/95 | 00000 | 00000 | 29.39 | | SCPO#3 | 43,351,870 | 1 Hr | SCPO#3 | 43,351,870 | 1 Hr |
| 242 | 7/13/95 | 00000 | 00000 | 28.33 | | SCPO#3 | 43,351,870 | 1 Hr | SCPO#3 | 43,351,870 | 1 Hr |
| 243 | 7/14/95 | 00000 | 00000 | 28.74 | 37 | SCPO#3 | 43,351,870 | 1 Hr | SCPO#3 | 43,351,870 | 1 Hr |
| 244 | 7/15/95 | 00000 | 00000 | 25.29 | | SCPO#3 | 43,351,870 | 1 Hr | SCPO#3 | 43,351,870 | 1 Hr |
| 245 | 7/16/95 | 00000 | 00000 | 29.36 | | SCPO#3 | 43,351,870 | 1 Hr | SCPO#3 | 43,351,870 | 1 Hr |
| 246 | 7/17/95 | 00000 | 00000 | 29.43 | | SCPO#3 | 43,351,870 | 1 Hr | SCPO#3 | 43,351,870 | 1 Hr |
| 247 | 7/18/95 | 00000 | 00000 | 28.95 | | SCPO#3 | 43,351,870 | 1 Hr | SCPO#3 | 43,351,870 | 1 Hr |
| 248 | 7/19/95 | 00000 | 00000 | 28.28 | | SCPO#3 | 43,351,870 | 1 Hr | SCPO#3 | 43,351,870 | 1 Hr |
| 249 | 7/20/95 | 00000 | 00000 | 30.11 | | SCPO#3 | 43,351,870 | 1 Hr | SCPO#3 | 43,351,870 | 1 Hr |
| 250 | 7/21/95 | 00000 | 00000 | 29.15 | | SCPO#3 | 43,351,870 | 1 Hr | SCPO#3 | 43,351,870 | 1 Hr |
| 251 | 7/22/95 | 00000 | 00000 | 30.35 | | SCPO#3 | 43,351,870 | 1 Hr | SCPO#3 | 43,351,870 | 1 Hr |

09141591.082898

OUJ-475-.xls

| | | | | | | | | | | | | | |
|---|---|---|---|---|---|---|---|---|---|---|---|---|---|
| 252 | 7/23/95 | | 00000 | | 00000 | 31 18 | | SCPO#3 | 43,351,870 | 1 Hr | SCPO#3 | 43,351,870 | 1 Hr |
| 253 | 7/24/95 | | 00000 | | 00000 | 32 01 | 38 | SCPO#3 | 43,351,870 | 1 Hr | SCPO#3 | 43,351,870 | 1 Hr |
| 254 | 7/25/95 | | 00000 | | 00000 | 30 94 | | SCPO#3 | 43,351,870 | 1 Hr | SCPO#3 | 43,351,870 | 1 Hr |
| 255 | 7/26/95 | | 00000 | | 00000 | 29 86 | | SCPO#3 | 43,351,870 | 1 Hr | SCPO#3 | 43,351,870 | 1 Hr |
| 256 | 7/27/95 | | 00000 | | 00000 | 31 70 | | SCPO#3 | 43,351,870 | 1 Hr | SCPO#3 | 43,351,870 | 1 Hr |
| 257 | 7/28/95 | *Died 7/28/95* | #VALUE! | *Died 7/28/95* | #VALUE! | 28 85 | 30 | SCPO#3 | 43,351,870 | 1 Hr | SCPO#3 | 43,351,870 | 1 Hr |

OUJ-496 xls

DAY | DATE | CNTR ABDOMEN 1-3 (LA, NM, RA) | VAR 1-3 | LT ARM PT 1-2 (LA, NM, RA) | VAR 1-2 | RT LEG 1-2 (LA, NM, RA) | VAR 1-2 | RT HAM LEG 1-2 (LA, NM, RA) | VAR 1-2 | RT TOP LEG (LA, NM, RA) | VAR | TOP CTR LEG 1-2 (LA, NM, RA) | VAR | WEIGHT | HEMATO CRIT % | DEVICE | FREQ MHz | POWER | TIME | TREATMENT PARAMETERS FREQ MHz | POWER | TIME | DEVICE

Page 1

09141691.082898

Ouj-506-.xls

OUJ 506 Born 1/5/95 First tumor appeared on 10/23/95

| DAY | DATE | T-1 RT ABDOMEN Ln | Wd | Ht | Vol T-1 | T-2 LT SIDE Ln | Wd | Ht | Vol T-2 | T-3 BACK OF NECK Ln | Wd | Ht | Vol T-3 | T-4 LEFT ARM Ln | Wd | Ht | Vol T-4 | WEIGHT Gr | HEMATO-CRIT-% | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|---|---|---|---|---|---|---|---|
| 1 | 19-Oct | | | | 0.0000 | | | | 0.0000 | | | | 0.0000 | | | | 0.0000 | 29.25 | | | NO TREATMENT | | | NO TREATMENT | | | |
| 2 | 20-Oct | | | | 0.0000 | | | | 0.0000 | | | | 0.0000 | | | | 0.0000 | 30.06 | | | NO TREATMENT | | | NO TREATMENT | | | |
| 3 | 21-Oct | | | | 0.0000 | | | | 0.0000 | | | | 0.0000 | | | | 0.0000 | 29.59 | | | NO TREATMENT | | | NO TREATMENT | | | |
| 4 | 22-Oct | | | | 0.0000 | | | | 0.0000 | | | | 0.0000 | | | | 0.0000 | 29.79 | | | NO TREATMENT | | | NO TREATMENT | | | |
| 5 | 23-Oct | 0.030 | 0.030 | 0.030 | 0.0001 | | | | 0.0000 | | | | 0.0000 | | | | 0.0000 | 28.93 | 45 | | NO TREATMENT | | | NO TREATMENT | | | |
| 6 | 24-Oct | 0.030 | 0.030 | 0.030 | 0.0001 | | | | 0.0000 | | | | 0.0000 | | | | 0.0000 | 29.58 | | | NO TREATMENT | | | NO TREATMENT | | | |
| 7 | 25-Oct | 0.030 | 0.030 | 0.030 | 0.0001 | | | | 0.0000 | | | | 0.0000 | | | | 0.0000 | 30.51 | | | NO TREATMENT | | | NO TREATMENT | | | |
| 8 | 26-Oct | | | | 0.0000 | | | | 0.0000 | | | | 0.0000 | | | | 0.0000 | 29.74 | | | NO TREATMENT | | | NO TREATMENT | | | |
| 9 | 27-Oct | | | | 0.0000 | | | | 0.0000 | | | | 0.0000 | | | | 0.0000 | 29.65 | | | NO TREATMENT | | | NO TREATMENT | | | |
| 10 | 28-Oct | | | | 0.0000 | | | | 0.0000 | | | | 0.0000 | | | | 0.0000 | 29.89 | 39 | | NO TREATMENT | | | NO TREATMENT | | | |
| 11 | 29-Oct | | | | 0.0000 | | | | 0.0000 | | | | 0.0000 | | | | 0.0000 | 29.67 | | | NO TREATMENT | | | NO TREATMENT | | | |
| 12 | 30-Oct | 0.030 | 0.030 | 0.030 | 0.0001 | | | | 0.0000 | | | | 0.0000 | | | | 0.0000 | 29.37 | | | NO TREATMENT | | | NO TREATMENT | | | |
| 13 | 31-Oct | 0.030 | 0.030 | 0.030 | 0.0001 | | | | 0.0000 | | | | 0.0000 | | | | 0.0000 | 28.70 | | | NO TREATMENT | | | NO TREATMENT | | | |
| 14 | 1-Nov | 0.030 | 0.030 | 0.030 | 0.0001 | | | | 0.0000 | | | | 0.0000 | | | | 0.0000 | 29.32 | | | NO TREATMENT | | | NO TREATMENT | | | |
| 15 | 2-Nov | | | | 0.0000 | | | | 0.0000 | | | | 0.0000 | | | | 0.0000 | 29.33 | | | NO TREATMENT | | | NO TREATMENT | | | |
| 16 | 3-Nov | | | | 0.0000 | | | | 0.0000 | | | | 0.0000 | | | | 0.0000 | 29.48 | | | NO TREATMENT | | | NO TREATMENT | | | |
| 17 | 4-Nov | | | | 0.0000 | | | | 0.0000 | | | | 0.0000 | | | | 0.0000 | 29.05 | 45 | | NO TREATMENT | | | NO TREATMENT | | | |
| 18 | 5-Nov | | | | 0.0000 | | | | 0.0000 | | | | 0.0000 | | | | 0.0000 | 29.08 | | | NO TREATMENT | | | NO TREATMENT | | | |
| 19 | 6-Nov | | | | 0.0000 | | | | 0.0000 | | | | 0.0000 | | | | 0.0000 | 29.11 | | | NO TREATMENT | | | NO TREATMENT | | | |
| 20 | 7-Nov | | | | 0.0000 | 0.030 | 0.030 | 0.030 | 0.0001 | | | | 0.0000 | | | | 0.0000 | 29.56 | | | NO TREATMENT | | | NO TREATMENT | | | |
| 21 | 8-Nov | | | | 0.0000 | 0.030 | 0.030 | 0.030 | 0.0001 | | | | 0.0000 | | | | 0.0000 | 29.56 | | | NO TREATMENT | | | NO TREATMENT | | | |
| 22 | 9-Nov | | | | 0.0000 | 0.030 | 0.030 | 0.030 | 0.0001 | | | | 0.0000 | | | | 0.0000 | 28.68 | | | NO TREATMENT | | | NO TREATMENT | | | |
| 23 | 10-Nov | | | | 0.0000 | | | | 0.0000 | | | | 0.0000 | | | | 0.0000 | 29.30 | | | NO TREATMENT | | | NO TREATMENT | | | |
| 24 | 11-Nov | | | | 0.0000 | | | | 0.0000 | | | | 0.0000 | | | | 0.0000 | 28.71 | 45 | | NO TREATMENT | | | NO TREATMENT | | | |
| 25 | 12-Nov | | | | 0.0000 | | | | 0.0000 | | | | 0.0000 | | | | 0.0000 | 28.69 | | | NO TREATMENT | | | NO TREATMENT | | | |
| 26 | 13-Nov | | | | 0.0000 | | | | 0.0000 | | | | 0.0000 | | | | 0.0000 | 28.66 | | | NO TREATMENT | | | NO TREATMENT | | | |
| 27 | 14-Nov | | | | 0.0000 | | | | 0.0000 | | | | 0.0000 | | | | 0.0000 | 28.89 | | | NO TREATMENT | | | NO TREATMENT | | | |
| 28 | 15-Nov | | | | 0.0000 | | | | 0.0000 | | | | 0.0000 | | | | 0.0000 | 28.94 | | | NO TREATMENT | | | NO TREATMENT | | | |
| 29 | 16-Nov | | | | 0.0000 | | | | 0.0000 | | | | 0.0000 | | | | 0.0000 | 28.87 | | | NO TREATMENT | | | NO TREATMENT | | | |
| 30 | 17-Nov | | | | 0.0000 | | | | 0.0000 | | | | 0.0000 | | | | 0.0000 | 29.02 | | | NO TREATMENT | | | NO TREATMENT | | | |
| 31 | 18-Nov | | | | 0.0000 | | | | 0.0000 | | | | 0.0000 | | | | 0.0000 | 28.76 | 45 | | NO TREATMENT | | | NO TREATMENT | | | |
| 32 | 19-Nov | | | | 0.0000 | | | | 0.0000 | | | | 0.0000 | | | | 0.0000 | 28.90 | | | NO TREATMENT | | | NO TREATMENT | | | |
| 33 | 20-Nov | | | | 0.0000 | | | | 0.0000 | | | | 0.0000 | | | | 0.0000 | 29.03 | | | NO TREATMENT | | | NO TREATMENT | | | |
| 34 | 21-Nov | | | | 0.0000 | | | | 0.0000 | 0.030 | 0.030 | 0.030 | 0.0001 | | | | 0.0000 | 28.71 | | | NO TREATMENT | | | NO TREATMENT | | | |
| 35 | 22-Nov | | | | 0.0000 | | | | 0.0000 | 0.030 | 0.030 | 0.030 | 0.0001 | | | | 0.0000 | 28.97 | | | NO TREATMENT | | | NO TREATMENT | | | |
| 36 | 23-Nov | | | | 0.0000 | | | | 0.0000 | 0.030 | 0.030 | 0.030 | 0.0001 | | | | 0.0000 | 28.92 | | | NO TREATMENT | | | NO TREATMENT | | | |
| 37 | 24-Nov | | | | 0.0000 | | | | 0.0000 | 0.030 | 0.030 | 0.030 | 0.0001 | | | | 0.0000 | 28.86 | | | NO TREATMENT | | | NO TREATMENT | | | |
| 38 | 25-Nov | | | | 0.0000 | | | | 0.0000 | 0.030 | 0.030 | 0.030 | 0.0001 | | | | 0.0000 | 28.57 | 41 | | NO TREATMENT | | | NO TREATMENT | | | |
| 39 | 26-Nov | | | | 0.0000 | | | | 0.0000 | 0.030 | 0.030 | 0.030 | 0.0001 | | | | 0.0000 | 28.80 | | | NO TREATMENT | | | NO TREATMENT | | | |
| 40 | 27-Nov | | | | 0.0000 | | | | 0.0000 | 0.030 | 0.030 | 0.030 | 0.0001 | | | | 0.0000 | 29.05 | | | NO TREATMENT | | | NO TREATMENT | | | |
| 41 | 28-Nov | | | | 0.0000 | | | | 0.0000 | 0.030 | 0.030 | 0.030 | 0.0001 | | | | 0.0000 | 28.31 | | | NO TREATMENT | | | NO TREATMENT | | | |
| 42 | 29-Nov | | | | 0.0000 | | | | 0.0000 | | | | 0.0000 | | | | 0.0000 | 28.83 | | | NO TREATMENT | | | NO TREATMENT | | | |
| 43 | 30-Nov | | | | 0.0000 | | | | 0.0000 | | | | 0.0000 | | | | 0.0000 | 28.65 | | | NO TREATMENT | | | NO TREATMENT | | | |
| 44 | 1-Dec | | | | 0.0000 | | | | 0.0000 | | | | 0.0000 | | | | 0.0000 | 28.50 | | | NO TREATMENT | | | NO TREATMENT | | | |
| 45 | 2-Dec | | | | 0.0000 | | | | 0.0000 | | | | 0.0000 | | | | 0.0000 | 28.65 | | | NO TREATMENT | | | NO TREATMENT | | | |
| 46 | 3-Dec | | | | 0.0000 | | | | 0.0000 | | | | 0.0000 | | | | 0.0000 | 28.78 | | | NO TREATMENT | | | NO TREATMENT | | | |
| 47 | 4-Dec | | | | 0.0000 | | | | 0.0000 | | | | 0.0000 | | | | 0.0000 | 28.88 | 43 | | NO TREATMENT | | | NO TREATMENT | | | |
| 48 | 5-Dec | | | | 0.0000 | | | | 0.0000 | | | | 0.0000 | | | | 0.0000 | 28.51 | | | NO TREATMENT | | | NO TREATMENT | | | |
| 49 | 6-Dec | | | | 0.0000 | | | | 0.0000 | | | | 0.0000 | | | | 0.0000 | 28.47 | | | NO TREATMENT | | | NO TREATMENT | | | |
| 50 | 7-Dec | | | | 0.0000 | | | | 0.0000 | | | | 0.0000 | | | | 0.0000 | 29.07 | | | NO TREATMENT | | | NO TREATMENT | | | |
| 51 | 8-Dec | | | | 0.0000 | | | | 0.0000 | | | | 0.0000 | | | | 0.0000 | 28.95 | | | NO TREATMENT | | | NO TREATMENT | | | |
| 52 | 9-Dec | | | | 0.0000 | | | | 0.0000 | | | | 0.0000 | | | | 0.0000 | 28.80 | 42 | | NO TREATMENT | | | NO TREATMENT | | | |
| 53 | 10-Dec | | | | 0.0000 | | | | 0.0000 | | | | 0.0000 | | | | 0.0000 | 28.60 | | | NO TREATMENT | | | NO TREATMENT | | | |
| 54 | 11-Dec | | | | 0.0000 | | | | 0.0000 | 0.030 | 0.030 | 0.030 | 0.0001 | | | | 0.0000 | 28.25 | | | NO TREATMENT | | | NO TREATMENT | | | |
| 55 | 12-Dec | | | | 0.0000 | | | | 0.0000 | 0.030 | 0.030 | 0.030 | 0.0001 | | | | 0.0000 | 28.48 | | | NO TREATMENT | | | NO TREATMENT | | | |
| 56 | 13-Dec | | | | 0.0000 | | | | 0.0000 | 0.030 | 0.030 | 0.030 | 0.0001 | | | | 0.0000 | 29.25 | | | NO TREATMENT | | | NO TREATMENT | | | |
| 57 | 14-Dec | | | | 0.0000 | | | | 0.0000 | 0.030 | 0.030 | 0.030 | 0.0001 | | | | 0.0000 | 28.82 | | | NO TREATMENT | | | NO TREATMENT | | | |
| 58 | 15-Dec | | | | 0.0000 | | | | 0.0000 | 0.030 | 0.030 | 0.030 | 0.0001 | | | | 0.0000 | 29.34 | | | NO TREATMENT | | | NO TREATMENT | | | |
| 59 | 16-Dec | | | | 0.0000 | | | | 0.0000 | | | | 0.0000 | | | | 0.0000 | 29.15 | 44 | | NO TREATMENT | | | NO TREATMENT | | | |
| 60 | 17-Dec | | | | 0.0000 | | | | 0.0000 | | | | 0.0000 | | | | 0.0000 | 29.05 | | | NO TREATMENT | | | NO TREATMENT | | | |
| 61 | 18-Dec | | | | 0.0000 | | | | 0.0000 | | | | 0.0000 | | | | 0.0000 | 28.81 | | | NO TREATMENT | | | NO TREATMENT | | | |
| 62 | 19-Dec | | | | 0.0000 | | | | 0.0000 | | | | 0.0000 | | | | 0.0000 | 29.18 | | | NO TREATMENT | | | NO TREATMENT | | | |
| 63 | 20-Dec | | | | 0.0000 | | | | 0.0000 | | | | 0.0000 | | | | 0.0000 | 28.94 | | | NO TREATMENT | | | NO TREATMENT | | | |
| 64 | 21-Dec | | | | 0.0000 | | | | 0.0000 | | | | 0.0000 | | | | 0.0000 | 27.38 | | | NO TREATMENT | | | NO TREATMENT | | | |
| 65 | 22-Dec | | | | 0.0000 | | | | 0.0000 | | | | 0.0000 | | | | 0.0000 | 28.19 | | | NO TREATMENT | | | NO TREATMENT | | | |
| 66 | 23-Dec | | | | 0.0000 | | | | 0.0000 | | | | 0.0000 | | | | 0.0000 | 27.92 | 45 | | NO TREATMENT | | | NO TREATMENT | | | |
| 67 | 24-Dec | | | | 0.0000 | | | | 0.0000 | | | | 0.0000 | | | | 0.0000 | 28.30 | | | NO TREATMENT | | | NO TREATMENT | | | |
| 68 | 25-Dec | | | | 0.0000 | | | | 0.0000 | | | | 0.0000 | | | | 0.0000 | 28.65 | | | NO TREATMENT | | | NO TREATMENT | | | |
| 69 | 26-Dec | | | | 0.0000 | | | | 0.0000 | | | | 0.0000 | | | | 0.0000 | 29.05 | | | NO TREATMENT | | | NO TREATMENT | | | |
| 70 | 27-Dec | | | | 0.0000 | | | | 0.0000 | | | | 0.0000 | | | | 0.0000 | 28.93 | | | NO TREATMENT | | | NO TREATMENT | | | |

4/11/97 Page 1 Ouj-506-.xls 09141591.082898

| DAY | DATE | T-1 RT ABDOMEN Ln | Wd | Ht | Vol T-1 | T-2 LT SIDE Ln | Wd | Ht | Vol T-2 | T-3 BACK OF NECK Ln | Wd | Ht | Vol T-3 | T-4 LEFT ARM Ln | Wd | Ht | Vol T-4 | WEIGHT Gr | HEMATOCRIT % | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|---|---|---|---|---|---|---|---|
| 71 | 28-Dec | | | | 00000 | | | | 00000 | | | | 00000 | | | | 00000 | 28.70 | | | NO TREATMENT | | | NO TREATMENT | | | |
| 72 | 29-Dec | | | | 00000 | | | | 00000 | | | | 00000 | | | | 00000 | 28.87 | 43 | | NO TREATMENT | | | NO TREATMENT | | | |
| 73 | 30-Dec | | | | 00000 | | | | 00000 | | | | 00000 | | | | 00000 | 29.22 | | | NO TREATMENT | | | NO TREATMENT | | | |
| 74 | 31-Dec | | | | 00000 | | | | 00000 | | | | 00000 | 0.030 | 0.030 | 0.030 | 00001 | 29.33 | | | NO TREATMENT | | | NO TREATMENT | | | |
| 75 | 1-Jan | | | | 00000 | | | | 00000 | | | | 00000 | 0.050 | 0.050 | 0.050 | 00007 | 29.46 | | | NO TREATMENT | | | NO TREATMENT | | | |
| 76 | 2-Jan | | | | 00000 | | | | 00000 | | | | 00000 | 0.050 | 0.050 | 0.050 | 00007 | 29.53 | 43 | 8662A | 43351830.0 | 0.0 dBm | 1 Hr | 43351871.3 | 0.0 dBm | 1 Hr | Type "O" |
| 77 | 3-Jan | | | | 00000 | | | | 00000 | | | | 00000 | 0.050 | 0.050 | 0.050 | 00007 | 29.56 | | 8662A | 43351830.0 | 0.0 dBm | 1 Hr | 43351871.3 | 0.0 dBm | 1 Hr | Type "O" |
| 78 | 4-Jan | | | | 00000 | | | | 00000 | | | | 00000 | 0.050 | 0.050 | 0.050 | 00007 | 28.40 | | 8662A | 43351870.0 | 0.0 dBm | 1 Hr | 43351870.0 | 0.0 dBm | 1 Hr | Type "O" |
| 79 | 5-Jan | | | | 00000 | | | | 00000 | | | | 00000 | 0.050 | 0.050 | 0.050 | 00007 | 28.69 | | 8662A | 43351830.0 | 0.0 dBm | 1 Hr | 43351830.0 | 0.0 dBm | 1 Hr | Type "O" |
| 80 | 6-Jan | | | | 00000 | | | | 00000 | | | | 00000 | 0.050 | 0.050 | 0.050 | 00007 | 28.60 | 46 | 8662A | 43351830.0 | 0.0 dBm | 1 Hr | 43351850.0 | 0.0 dBm | 1 Hr | Type "R" |
| 81 | 7-Jan | | | | 00000 | | | | 00000 | | | | 00000 | 0.060 | 0.060 | 0.060 | 00011 | 28.40 | | | NO TREATMENT | | | NO TREATMENT | | | |
| 82 | 8-Jan | | | | 00000 | | | | 00000 | | | | 00000 | 0.070 | 0.070 | 0.070 | 00018 | 28.29 | | 8662A | 43351830.0 | 0.0 dBm | 1 Hr | 43351870.0 | 0.0 dBm | 1 Hr | Type "R" |
| 83 | 9-Jan | | | | 00000 | | | | 00000 | | | | 00000 | 0.070 | 0.070 | 0.070 | 00018 | 28.15 | | 8662A | 43351850.0 | 0.0 dBm | 1 Hr | 43351850.0 | 0.0 dBm | 1 Hr | Type "R" |
| 84 | 10-Jan | | | | 00000 | | | | 00000 | | | | 00000 | 0.070 | 0.070 | 0.070 | 00018 | 27.10 | | 8662A | 43351870.0 | 0.0 dBm | 1 Hr | 43351870.0 | 0.0 dBm | 1 Hr | Type "R" |
| 85 | 11-Jan | | | | 00000 | | | | 00000 | | | | 00000 | 0.070 | 0.070 | 0.070 | 00018 | 28.11 | | 8662A | 43351850.0 | 0.0 dBm | 1 Hr | 43351850.0 | 0.0 dBm | 1 Hr | Type "R" |
| 86 | 12-Jan | | | | 00000 | | | | 00000 | | | | 00000 | 0.070 | 0.070 | 0.070 | 00018 | 26.82 | | 8662A | 43351870.0 | 0.0 dBm | 1 Hr | 43351870.0 | 0.0 dBm | 1 Hr | Type "R" |
| 87 | 13-Jan | | | | 00000 | | | | 00000 | | | | 00000 | 0.070 | 0.070 | 0.070 | 00018 | 27.43 | 47 | 8662A | 43351870.0 | 0.0 dBm | 1 Hr | 43351870.0 | 0.0 dBm | 1 Hr | Type "R" |
| 88 | 14-Jan | | | | 00000 | | | | 00000 | | | | 00000 | 0.070 | 0.070 | 0.070 | 00018 | 27.44 | | | NO TREATMENT | | | NO TREATMENT | | | |
| 89 | 15-Jan | | | | 00000 | | | | 00000 | | | | 00000 | 0.070 | 0.070 | 0.070 | 00018 | 27.45 | | 8662A | 43351850.0 | 0.0 dBm | 1 Hr | 43351850.0 | 0.0 dBm | 1 Hr | Type "R" |
| 90 | 16-Jan | | | | 00000 | | | | 00000 | | | | 00000 | 0.050 | 0.050 | 0.050 | 00007 | 27.36 | | 8662A | 43351870.0 | 0.0 dBm | 1 Hr | 43351870.0 | 0.0 dBm | 1 Hr | Type "R" |
| 91 | 17-Jan | | | | 00000 | | | | 00000 | | | | 00000 | 0.050 | 0.050 | 0.050 | 00007 | 26.77 | | 8662A | 43351850.0 | 0.0 dBm | 1 Hr | 43351850.0 | 0.0 dBm | 1 Hr | Type "R" |
| 92 | 18-Jan | | | | 00000 | | | | 00000 | | | | 00000 | 0.050 | 0.050 | 0.050 | 00007 | 27.21 | | 8662A | 43351870.0 | 0.0 dBm | 1 Hr | 43351870.0 | 0.0 dBm | 1 Hr | Type "R" |
| 93 | 19-Jan | | | | 00000 | | | | 00000 | | | | 00000 | 0.050 | 0.050 | 0.050 | 00007 | 27.22 | | 8662A | 43351850.0 | 0.0 dBm | 1 Hr | 43351850.0 | 0.0 dBm | 1 Hr | Type "S" |
| 94 | 20-Jan | | | | 00000 | | | | 00000 | | | | 00000 | 0.050 | 0.050 | 0.050 | 00007 | 27.32 | 40 | 8662A | 43351870.0 | 0.0 dBm | 1 Hr | 43351870.0 | 0.0 dBm | 1 Hr | Type "S" |
| 95 | 21-Jan | | | | 00000 | | | | 00000 | | | | 00000 | 0.050 | 0.050 | 0.050 | 00007 | 27.70 | | | NO TREATMENT | | | NO TREATMENT | | | |
| 96 | 22-Jan | | | | 00000 | | | | 00000 | | | | 00000 | 0.050 | 0.050 | 0.050 | 00007 | 28.18 | | 8662A | 43351850.0 | 0.0 dBm | 1 Hr | 43351850.0 | 0.0 dBm | 1 Hr | Type "S" |
| 97 | 23-Jan | | | | 00000 | | | | 00000 | | | | 00000 | 0.050 | 0.050 | 0.050 | 00007 | 26.92 | | 8662A | 43351850.0 | 0.0 dBm | 1 Hr | 43351850.0 | 0.0 dBm | 1 Hr | Type "S" |
| 98 | 24-Jan | | | | 00000 | | | | 00000 | | | | 00000 | 0.050 | 0.050 | 0.050 | 00007 | 26.03 | | 8662A | 43351850.0 | 0.0 dBm | 1 Hr | 43351850.0 | 0.0 dBm | 1 Hr | Type "S" |
| 99 | 25-Jan | | | | 00000 | | | | 00000 | | | | 00000 | 0.030 | 0.030 | 0.030 | 00001 | 26.27 | | 8662A | 43351870.0 | 0.0 dBm | 1 Hr | 43351870.0 | 0.0 dBm | 1 Hr | Type "S" |
| 100 | 26-Jan | | | | 00000 | | | | 00000 | | | | 00000 | 0.030 | 0.030 | 0.030 | 00001 | 26.09 | | 8662A | 43351870.0 | 0.0 dBm | 1 Hr | 43351870.0 | 0.0 dBm | 1 Hr | Type "S" |
| 101 | 27-Jan | | | | 00000 | | | | 00000 | | | | 00000 | 0.030 | 0.030 | 0.030 | 00001 | 26.52 | 40 | 8662A | 43351850.0 | 0.0 dBm | 1 Hr | 43351850.0 | 0.0 dBm | 1 Hr | Type "S" |
| 102 | 28-Jan | | | | 00000 | | | | 00000 | | | | 00000 | 0.030 | 0.030 | 0.030 | 00001 | 26.53 | | | NO TREATMENT | | | NO TREATMENT | | | |
| 103 | 29-Jan | | | | 00000 | | | | 00000 | | | | 00000 | 0.030 | 0.030 | 0.030 | 00001 | 26.55 | | 8662A | 43351850.0 | 3.0 dBm | 1 Hr | 43351850.0 | 3.0 dBm | 1 Hr | Type "S" |
| 104 | 30-Jan | | | | 00000 | | | | 00000 | | | | 00000 | 0.030 | 0.030 | 0.030 | 00001 | 26.22 | | 8662A | 43351830.0 | 3.0 dBm | 1 Hr | 43351830.0 | 3.0 dBm | 1 Hr | Type "S" |
| 105 | 31-Jan | | | | 00000 | | | | 00000 | | | | 00000 | | | | 00000 | 26.03 | | 8662A | 43351850.0 | 3.0 dBm | 1 Hr | 43351850.0 | 3.0 dBm | 1 Hr | Type "S" |
| 106 | 1-Feb | | | | 00000 | | | | 00000 | | | | 00000 | | | | 00000 | 26.08 | | 8662A | 43351850.0 | 3.0 dBm | 1 Hr | 43351850.0 | 3.0 dBm | 1 Hr | Type "S" |
| 107 | 2-Feb | | | | 00000 | | | | 00000 | | | | 00000 | | | | 00000 | 26.62 | | 8662A | 43351830.0 | 3.0 dBm | 1 Hr | 43351830.0 | 3.0 dBm | 1 Hr | Type "S" |
| 108 | 3-Feb | | | | 00000 | | | | 00000 | | | | 00000 | | | | 00000 | 27.33 | 40 | 8662A | 43351830.0 | 3.0 dBm | 1 Hr | 43351830.0 | 3.0 dBm | 1 Hr | Type "S" |
| 109 | 4-Feb | | | | 00000 | | | | 00000 | | | | 00000 | | | | 00000 | 26.80 | | | NO TREATMENT | | | NO TREATMENT | | | |
| 110 | 5-Feb | | | | 00000 | | | | 00000 | | | | 00000 | | | | 00000 | 26.34 | | 8662A | 43351870.0 | 3.0 dBm | 1 Hr | 43351870.0 | 3.0 dBm | 1 Hr | Type "S" |
| 111 | 6-Feb | | | | 00000 | | | | 00000 | | | | 00000 | | | | 00000 | 26.74 | | 8662A | 43351870.0 | 3.0 dBm | 1 Hr | 43351870.0 | 3.0 dBm | 1 Hr | Type "S" |
| 112 | 7-Feb | | | | 00000 | | | | 00000 | | | | 00000 | | | | 00000 | 26.46 | | 8662A | 43351850.0 | 3.0 dBm | 1 Hr | 43351850.0 | 3.0 dBm | 1 Hr | Type "S" |
| 113 | 8-Feb | | | | 00000 | | | | 00000 | | | | 00000 | | | | 00000 | 26.42 | | 8662A | 43351850.0 | 3.0 dBm | 1 Hr | 43351850.0 | 3.0 dBm | 1 Hr | Type "S" |
| 114 | 9-Feb | | | | 00000 | | | | 00000 | | | | 00000 | | | | 00000 | 25.71 | | 8662A | 43351830.0 | 3.0 dBm | 1 Hr | 43351830.0 | 3.0 dBm | 1 Hr | Type "S" |
| 115 | 10-Feb | | | | 00000 | | | | 00000 | | | | 00000 | | | | 00000 | 26.21 | 46 | 8662A | 43351830.0 | 3.0 dBm | 1 Hr | 43351820.0 | 3.0 dBm | 1 Hr | Type "S" |
| 116 | 11-Feb | | | | 00000 | | | | 00000 | | | | 00000 | | | | 00000 | 26.40 | | | NO TREATMENT | | | NO TREATMENT | | | |
| 117 | 12-Feb | | | | 00000 | | | | 00000 | | | | 00000 | | | | 00000 | 26.64 | | 8662A | 43351870.0 | 3.0 dBm | 1 Hr | 43351870.0 | 3.0 dBm | 1 Hr | Type "S" |
| 118 | 13-Feb | | | | 00000 | | | | 00000 | | | | 00000 | | | | 00000 | 26.46 | | 8662A | 43351870.0 | 3.0 dBm | 1 Hr | 43351870.0 | 3.0 dBm | 1 Hr | Type "S" |
| 119 | 14-Feb | | | | 00000 | | | | 00000 | | | | 00000 | | | | 00000 | 26.58 | | 8662A | 43351850.0 | 3.0 dBm | 1 Hr | 43351850.0 | 3.0 dBm | 1 Hr | Type "S" |
| 120 | 15-Feb | | | | 00000 | | | | 00000 | | | | 00000 | | | | 00000 | 26.38 | | 8662A | 43351850.0 | 3.0 dBm | 1 Hr | 43351850.0 | 3.0 dBm | 1 Hr | Type "S" |
| 121 | 16-Feb | | | | 00000 | | | | 00000 | | | | 00000 | | | | 00000 | 25.75 | | 8662A | 43351830.0 | 3.0 dBm | 1 Hr | 43351830.0 | 3.0 dBm | 1 Hr | Type "S" |
| 122 | 17-Feb | | | | 00000 | | | | 00000 | | | | 00000 | | | | 00000 | 26.36 | 45 | 8662A | 43351830.0 | 3.0 dBm | 1 Hr | 43351830.0 | 3.0 dBm | 1 Hr | Type "S" |
| 123 | 18-Feb | | | | 00000 | | | | 00000 | | | | 00000 | | | | 00000 | 26.40 | | | NO TREATMENT | | | NO TREATMENT | | | |
| 124 | 19-Feb | | | | 00000 | | | | 00000 | | | | 00000 | | | | 00000 | 27.78 | | 8662A | 43351870.0 | 3.0 dBm | 1 Hr | 43351870.0 | 3.0 dBm | 1 Hr | Type "T" |
| 125 | 20-Feb | | | | 00000 | | | | 00000 | | | | 00000 | | | | 00000 | 27.03 | | 8662A | 43351870.0 | 3.0 dBm | 1 Hr | 43351870.0 | 3.0 dBm | 1 Hr | Type "T" |
| 126 | 21-Feb | | | | 00000 | | | | 00000 | | | | 00000 | | | | 00000 | 26.12 | | 8662A | 43351850.0 | 0.0 dBm | 1 Hr | 43351850.0 | 0.0 dBm | 1 Hr | Type "T" |
| 127 | 22-Feb | | | | 00000 | | | | 00000 | | | | 00000 | | | | 00000 | 25.05 | | 8662A | 43351850.0 | 0.0 dBm | 1 Hr | 43351850.0 | 0.0 dBm | 1 Hr | Type "T" |
| 128 | 23-Feb | | | | 00000 | | | | 00000 | | | | 00000 | | | | 00000 | 24.19 | | 8662A | 43351830.0 | 0.0 dBm | 1 Hr | 43351830.0 | 0.0 dBm | 1 Hr | Type "T" |
| 129 | 24-Feb | | | | 00000 | | | | 00000 | | | | 00000 | | | | 00000 | 25.24 | 45 | 8662A | 43351830.0 | 0.0 dBm | 1 Hr | 43351830.0 | 0.0 dBm | 1 Hr | Type "T" |
| 130 | 25-Feb | | | | 00000 | | | | 00000 | | | | 00000 | | | | 00000 | 26.80 | | | NO TREATMENT | | | NO TREATMENT | | | |
| 131 | 26-Feb | | | | 00000 | | | | 00000 | | | | 00000 | | | | 00000 | 26.87 | | 8662A | 43351870.0 | 0.0 dBm | 1 Hr | 43351870.0 | 0.0 dBm | 1 Hr | Type "T" |
| 132 | 27-Feb | | | | 00000 | | | | 00000 | | | | 00000 | | | | 00000 | 25.84 | | 8662A | 43351870.0 | 0.0 dBm | 1 Hr | 43351870.0 | 0.0 dBm | 1 Hr | Type "T" |
| 133 | 28-Feb | | | | 00000 | | | | 00000 | | | | 00000 | | | | 00000 | 25.46 | | 8662A | 43351850.0 | 0.0 dBm | 1 Hr | 43351850.0 | 0.0 dBm | 1 Hr | Type "T" |
| 134 | 29-Feb | | | | 00000 | | | | 00000 | | | | 00000 | | | | 00000 | 25.36 | | 8662A | 43351850.0 | 0.0 dBm | 1 Hr | 43351850.0 | 0.0 dBm | 1 Hr | Type "T" |
| 135 | 1-Mar | | | | 00000 | | | | 00000 | | | | 00000 | | | | 00000 | 24.51 | | 8662A | 43351830.0 | 0.0 dBm | 1 Hr | 43351830.0 | 0.0 dBm | 1 Hr | Type "T" |
| 136 | 2-Mar | | | | 00000 | | | | 00000 | | | | 00000 | | | | 00000 | 24.88 | 44 | 8662A | 43351830.0 | 0.0 dBm | 1 Hr | 43351830.0 | 0.0 dBm | 1 Hr | Type "T" |
| 137 | 3-Mar | | | | 00000 | | | | 00000 | | | | 00000 | | | | 00000 | 25.50 | | | NO TREATMENT | | | NO TREATMENT | | | |
| 138 | 4-Mar | | | | 00000 | | | | 00000 | | | | 00000 | | | | 00000 | 26.24 | | 8662A | 43351870.0 | 0.0 dBm | 1 Hr | 43351870.0 | 0.0 dBm | 1 Hr | Type "T" |
| 139 | 5-Mar | | | | 00000 | | | | 00000 | | | | 00000 | | | | 00000 | 26.18 | | 8662A | 43351870.0 | 0.0 dBm | 1 Hr | 43351870.0 | 0.0 dBm | 1 Hr | Type "U" |
| 140 | 6-Mar | | | | 00000 | | | | 00000 | | | | 00000 | | | | 00000 | 25.09 | | 8662A | 43351850.0 | 0.0 dBm | 1 Hr | 43351850.0 | 0.0 dBm | 1 Hr | Type "U" |
| 141 | 7-Mar | | | | 00000 | | | | 00000 | | | | 00000 | | | | 00000 | 24.87 | | 8662A | 43351850.0 | 0.0 dBm | 1 Hr | 43351850.0 | 0.0 dBm | 1 Hr | Type "U" |
| 142 | 8-Mar | | | | 00000 | | | | 00000 | | | | 00000 | | | | 00000 | 24.82 | | 8662A | 43351830.0 | 0.0 dBm | 1 Hr | 43351830.0 | 0.0 dBm | 1 Hr | Type "U" |

| DAY | DATE | T-1 RT ABDOMEN Ln | Wd | Ht | Vol T-1 | T-2 LT SIDE Ln | Wd | Ht | Vol T-2 | T-3 BACK OF NECK Ln | Wd | Ht | Vol T-1 | T-4 LEFT ARM Ln | Wd | Ht | Vol T-1 | WEIGHT Gr | HEMATOCRIT % | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|---|---|---|---|---|---|---|---|
| 143 | 9-Mar | | | | 00000 | | | | 00000 | | | | 00000 | | | | | | | | | | | | | | |
| 144 | 10-Mar | | | | 00000 | | | | 00000 | | | | 00000 | | | | 00000 | 26.10 | 36 | 8662A | 43351830.0 | 0.0 dBm | 1 Hr | 43351830.0 | 0.0 dBm | 1 Hr | Type "V" |
| 145 | 11-Mar | | | | 00000 | | | | 00000 | | | | 00000 | | | | 00000 | 24.70 | | | NO TREATMENT | | | NO TREATMENT | | | |
| 146 | 12-Mar | | | | 00000 | | | | 00000 | | | | 00000 | | | | 00000 | 23.76 | | 8662A | 43351870.0 | 0.0 dBm | 1 Hr | 43351870.0 | 0.0 dBm | 1 Hr | Type "U" |
| 147 | 13-Mar | | | | 00000 | | | | 00000 | | | | 00000 | | | | 00000 | 26.30 | | 8662A | 43351870.0 | 0.0 dBm | 1 Hr | 43351870.0 | 0.0 dBm | 1 Hr | Type "U" |
| 148 | 14-Mar | | | | 00000 | | | | 00000 | | | | 00000 | | | | 00000 | 25.78 | | 8662A | 43351850.0 | 0.0 dBm | 1 Hr | 43351850.0 | 0.0 dBm | 1 Hr | Type "U" |
| 149 | 15-Mar | | | | 00000 | | | | 00000 | | | | 00000 | | | | 00000 | 27.13 | | 8662A | 43351850.0 | 0.0 dBm | 1 Hr | 43351850.0 | 0.0 dBm | 1 Hr | Type "U" |
| 150 | 16-Mar | | | | 00000 | | | | 00000 | | | | 00000 | | | | 00000 | 27.43 | | 8662A | 43351830.0 | 0.0 dBm | 1 Hr | 43351830.0 | 0.0 dBm | 1 Hr | Type "U" |
| 151 | 17-Mar | | | | 00000 | | | | 00000 | | | | 00000 | | | | 00000 | 27.68 | 35 | 8662A | 43351830.0 | 0.0 dBm | 1 Hr | 43351830.0 | 0.0 dBm | 1 Hr | Type "U" |
| 152 | 18-Mar | | | | 00000 | | | | 00000 | | | | 00000 | | | | 00000 | 27.40 | | | NO TREATMENT | | | NO TREATMENT | | | |
| 153 | 19-Mar | | | | 00000 | | | | 00000 | | | | 00000 | | | | 00000 | 27.13 | | | NO TREATMENT | | | NO TREATMENT | | | |
| 154 | 20-Mar | | | | 00000 | | | | 00000 | | | | 00000 | | | | 00000 | 27.63 | | | NO TREATMENT | | | NO TREATMENT | | | |
| 155 | 21-Mar | | | | 00000 | | | | 00000 | | | | 00000 | | | | 00000 | 27.68 | | | NO TREATMENT | | | NO TREATMENT | | | |
| 156 | 22-Mar | | | | 00000 | | | | 00000 | | | | 00000 | | | | 00000 | 27.94 | | | NO TREATMENT | | | NO TREATMENT | | | |
| 157 | 23-Mar | | | | 00000 | | | | 00000 | | | | 00000 | | | | 00000 | 27.98 | | | NO TREATMENT | | | NO TREATMENT | | | |
| 158 | 24-Mar | | | | 00000 | | | | 00000 | | | | 00000 | | | | 00000 | 27.22 | 39 | | NO TREATMENT | | | NO TREATMENT | | | |
| 159 | 25-Mar | | | | 00000 | | | | 00000 | | | | 00000 | | | | 00000 | 27.30 | | | NO TREATMENT | | | NO TREATMENT | | | |
| 160 | 26-Mar | | | | 00000 | | | | 00000 | | | | 00000 | | | | 00000 | 27.35 | | | NO TREATMENT | | | NO TREATMENT | | | |
| 161 | 27-Mar | | | | 00000 | | | | 00000 | | | | 00000 | | | | 00000 | 27.81 | | | NO TREATMENT | | | NO TREATMENT | | | |
| 162 | 28-Mar | | | | 00000 | | | | 00000 | | | | 00000 | | | | 00000 | 27.50 | | | NO TREATMENT | | | NO TREATMENT | | | |
| 163 | 29-Mar | | | | 00000 | | | | 00000 | | | | 00000 | | | | 00000 | 27.36 | | | NO TREATMENT | | | NO TREATMENT | | | |
| 164 | 30-Mar | | | | 00000 | | | | 00000 | | | | 00000 | | | | 00000 | 27.90 | | | NO TREATMENT | | | NO TREATMENT | | | |
| 165 | 31-Mar | | | | 00000 | | | | 00000 | | | | 00000 | | | | 00000 | 28.55 | 39 | | NO TREATMENT | | | NO TREATMENT | | | |
| 166 | 1-Apr | | | | 00000 | | | | 00000 | | | | 00000 | | | | 00000 | 27.83 | | | NO TREATMENT | | | NO TREATMENT | | | |
| 167 | 2-Apr | | | | 00000 | | | | 00000 | | | | 00000 | | | | 00000 | 27.17 | | | NO TREATMENT | | | NO TREATMENT | | | |
| 168 | 3-Apr | | | | 00000 | | | | 00000 | | | | 00000 | | | | 00000 | 27.01 | | | NO TREATMENT | | | NO TREATMENT | | | |
| 169 | 4-Apr | | | | 00000 | | | | 00000 | | | | 00000 | | | | 00000 | 27.10 | | | NO TREATMENT | | | NO TREATMENT | | | |
| 170 | 5-Apr | | | | 00000 | | | | 00000 | | | | 00000 | | | | 00000 | 28.10 | | | NO TREATMENT | | | NO TREATMENT | | | |
| 171 | 6-Apr | | | | 00000 | | | | 00000 | | | | 00000 | | | | 00000 | 27.49 | | | NO TREATMENT | | | NO TREATMENT | | | |
| 172 | 7-Apr | | | | 00000 | | | | 00000 | | | | 00000 | | | | 00000 | 27.39 | 38 | | NO TREATMENT | | | NO TREATMENT | | | |
| 173 | 8-Apr | | | | 00000 | | | | 00000 | | | | 00000 | | | | 00000 | 27.30 | | | NO TREATMENT | | | NO TREATMENT | | | |
| 174 | 9-Apr | | | | 00000 | | | | 00000 | | | | 00000 | | | | 00000 | 27.21 | | | NO TREATMENT | | | NO TREATMENT | | | |
| 175 | 10-Apr | | | | 00000 | | | | 00000 | | | | 00000 | | | | 00000 | 27.46 | | | NO TREATMENT | | | NO TREATMENT | | | |
| 176 | 11-Apr | | | | 00000 | | | | 00000 | | | | 00000 | | | | 00000 | 27.30 | | | NO TREATMENT | | | NO TREATMENT | | | |
| 177 | 12-Apr | | | | 00000 | | | | 00000 | | | | 00000 | | | | 00000 | 27.18 | | | NO TREATMENT | | | NO TREATMENT | | | |
| 178 | 13-Apr | | | | 00000 | | | | 00000 | | | | 00000 | | | | 00000 | 26.63 | | | NO TREATMENT | | | NO TREATMENT | | | |
| 179 | 14-Apr | | | | 00000 | | | | 00000 | | | | 00000 | | | | 00000 | 26.84 | 44 | | NO TREATMENT | | | NO TREATMENT | | | |
| 180 | 15-Apr | | | | 00000 | | | | 00000 | | | | 00000 | | | | 00000 | 27.05 | | | NO TREATMENT | | | NO TREATMENT | | | |
| 181 | 16-Apr | | | | 00000 | | | | 00000 | | | | 00000 | | | | 00000 | 27.32 | | | NO TREATMENT | | | NO TREATMENT | | | |
| 182 | 17-Apr | | | | 00000 | | | | 00000 | | | | 00000 | | | | 00000 | 27.13 | | | NO TREATMENT | | | NO TREATMENT | | | |
| 183 | 18-Apr | | | | 00000 | | | | 00000 | | | | 00000 | | | | 00000 | 26.86 | | | NO TREATMENT | | | NO TREATMENT | | | |
| 184 | 19-Apr | | | | 00000 | | | | 00000 | | | | 00000 | | | | 00000 | 27.53 | | | NO TREATMENT | | | NO TREATMENT | | | |
| 185 | 20-Apr | | | | 00000 | | | | 00000 | | | | 00000 | | | | 00000 | 27.43 | | | NO TREATMENT | | | NO TREATMENT | | | |
| 186 | 21-Apr | | | | 00000 | | | | 00000 | | | | 00000 | | | | 00000 | 27.14 | 43 | | NO TREATMENT | | | NO TREATMENT | | | |
| 187 | 22-Apr | | | | 00000 | | | | 00000 | | | | 00000 | | | | 00000 | 27.45 | | | NO TREATMENT | | | NO TREATMENT | | | |
| 188 | 23-Apr | | | | 00000 | | | | 00000 | | | | 00000 | | | | 00000 | 27.61 | | | NO TREATMENT | | | NO TREATMENT | | | |
| 189 | 24-Apr | | | | 00000 | | | | 00000 | | | | 00000 | | | | 00000 | 25.02 | | | NO TREATMENT | | | NO TREATMENT | | | |
| 190 | 25-Apr | | | | 00000 | | | | 00000 | | | | 00000 | | | | 00000 | 27.62 | | | NO TREATMENT | | | NO TREATMENT | | | |
| 191 | 26-Apr | | | | 00000 | | | | 00000 | | | | 00000 | | | | 00000 | 27.45 | | | NO TREATMENT | | | NO TREATMENT | | | |
| 192 | 27-Apr | | | | 00000 | | | | 00000 | | | | 00000 | | | | 00000 | 25.84 | | | NO TREATMENT | | | NO TREATMENT | | | |
| 193 | 28-Apr | | | | 00000 | | | | 00000 | | | | 00000 | | | | 00000 | 27.04 | 41 | | NO TREATMENT | | | NO TREATMENT | | | |
| 194 | 29-Apr | | | | 00000 | | | | 00000 | | | | 00000 | | | | 00000 | 26.95 | | | NO TREATMENT | | | NO TREATMENT | | | |
| 195 | 30-Apr | | | | 00000 | | | | 00000 | | | | 00000 | | | | 00000 | 26.69 | | | NO TREATMENT | | | NO TREATMENT | | | |
| 196 | 1-May | | | | 00000 | | | | 00000 | | | | 00000 | | | | 00000 | 27.48 | | | NO TREATMENT | | | NO TREATMENT | | | |
| 197 | 2-May | | | | 00000 | 0.030 | 0.030 | 0.032 | 00001 | | | | 00000 | | | | 00000 | 26.42 | | | NO TREATMENT | | | NO TREATMENT | | | |
| 198 | 3-May | | | | 00000 | 0.050 | 0.050 | 0.050 | 00007 | | | | 00000 | | | | 00000 | 26.63 | | | NO TREATMENT | | | NO TREATMENT | | | |
| 199 | 4-May | | | | 00000 | 0.060 | 0.060 | 0.050 | 00009 | | | | 00000 | | | | 00000 | 27.16 | | | NO TREATMENT | | | NO TREATMENT | | | |
| 200 | 5-May | | | | 00000 | 0.070 | 0.070 | 0.070 | 00018 | | | | 00000 | | | | 00000 | 27.03 | 41 | 8662A | 43351870.0 | 0.0 dBm | 1 Hr | 43351870.0 | 0.0 dBm | 1 Hr | Type "S" |
| 201 | 6-May | | | | 00000 | 0.080 | 0.080 | 0.070 | 00023 | | | | 00000 | | | | 00000 | 26.95 | | | | | | | | | |
| 202 | 7-May | | | | 00000 | 0.100 | 0.110 | 0.080 | 00046 | | | | 00000 | | | | 00000 | 25.65 | | 8662A | 43351830.0 | 0.0 dBm | 1 Hr | 43351850.0 | 0.0 dBm | 1 Hr | Type "S" |
| 203 | 8-May | | | | 00000 | 0.110 | 0.110 | 0.080 | 00051 | | | | 00000 | | | | 00000 | 23.90 | | 8662A | 43351871.0 | 0.0 dBm | 1 Hr | 43351853.0 | 0.0 dBm | 1 Hr | Type "S" |
| 204 | 9-May | | | | 00000 | 0.110 | 0.120 | 0.070 | 00048 | | | | 00000 | | | | 00000 | 24.60 | | 8662A | 43351871.0 | 0.0 dBm | 1 Hr | 43351853.0 | 0.0 dBm | 1 Hr | Type "S" |
| 205 | 10-May | | | | 00000 | 0.120 | 0.110 | 0.070 | 00048 | | | | 00000 | | | | 00000 | 24.37 | | 8662A | 43351871.0 | 0.0 dBm | 1 Hr | 43351853.0 | 0.0 dBm | 1 Hr | Type "S" |
| 206 | 11-May | | | | 00000 | 0.110 | 0.110 | 0.070 | 00044 | | | | 00000 | | | | 00000 | 25.84 | | 8662A | 43351871.0 | 0.0 dBm | 1 Hr | 43351853.0 | 0.0 dBm | 1 Hr | Type "S" |
| 207 | 12-May | | | | 00000 | 0.110 | 0.115 | 0.065 | 00043 | T-5 P SHOLDER | | | #VALUE! | | | | 00000 | 22.29 | 43 | 8662A | 43351871.0 | 0.0 dBm | 1 Hr | 43351853.0 | 0.0 dBm | 1 Hr | Type "S" |
| 208 | 13-May | | | | 00000 | 0.110 | 0.120 | 0.060 | 00041 | Ln | Wd | Ht | #VALUE! | | | | 00000 | 15.70 | | | NO TREATMENT | | | NO TREATMENT | | | |
| 209 | 14-May | | | | 00000 | 0.120 | 0.120 | 0.050 | 00038 | | | | 00002 | | | | 00000 | 15.70 | | 8662A | 43351830.0 | 43351850.0 | | 43351870.0 | 0.0 dBm | 1 Hr | Type "S" |
| 210 | 15-May | | | | 00000 | 0.110 | 0.120 | 0.050 | 00035 | 0.090 | 0.090 | 0.050 | 00021 | | | | 00000 | 21.35 | | 8662A | 43351830.0 | 43351850.0 | | 43351850.0 | 0.0 dBm | 1 Hr | Type "S" |
| 211 | 16-May | | | | 00000 | 0.110 | 0.110 | 0.050 | 00032 | 0.100 | 0.100 | 0.040 | 00021 | | | | 00000 | 23.80 | | 8662A | 43351830.0 | 43351850.0 | | 43351850.0 | 0.0 dBm | 1 Hr | Type "S" |
| 212 | 17-May | | | | 00000 | 0.110 | 0.110 | 0.050 | 00032 | 0.110 | 0.120 | 0.050 | 00035 | | | | 00000 | 25.58 | | 8662A | 43346000.0 | 0.0 dBm | 3 Hr | 43351870.0 | 0.0 dBm | 1 Hr | Type "S" |
| 213 | 18-May | | | | 00000 | 0.120 | 0.120 | 0.050 | 00041 | 0.120 | 0.120 | 0.060 | 00045 | | | | 00000 | 27.55 | | 8662A | 43351871.0 | 0.0 dBm | 1 Hr | 43351853.0 | 0.0 dBm | 1 Hr | Type "S" |
| 214 | 19-May | | | | 00000 | 0.125 | 0.125 | 0.055 | 00049 | 0.120 | 0.125 | 0.065 | 00051 | | | | 00000 | 26.02 | 35 | 8662A | 43351830.0 | 43351850.0 | | 43351870.0 | 0.0 dBm | 1 Hr | Type "S" |
| | | | | | | | | | | | | | | | | | 00000 | 26.42 | | | NO TREATMENT | | | NO TREATMENT | | | |

09141691.082898

Ouj-506- xls

| DAY | DATE | T-1 RT ABDOMEN Ln | Wd | Ht | Vol T-1 | T-2 LT SIDE Ln | Wd | Ht | Vol T-2 | T-3 BACK OF NECK Ln | Wd | Ht | Vol T-1 |
|---|---|---|---|---|---|---|---|---|---|---|---|---|---|
| 215 | 20-May | | | | 00000 | 0 140 | 0 130 | 0 060 | 00057 | 0 120 | 0 130 | 0 070 | 00057 |
| 216 | 21-May | | | | 00000 | 0 150 | 0 130 | 0 060 | 00061 | 0 130 | 0 130 | 0 070 | 00062 |
| 217 | 22-May | | | | 00000 | 0 150 | 0 140 | 0 060 | 00066 | 0 150 | 0 140 | 0 070 | 00077 |
| 218 | 23-May | | | | 00000 | 0 150 | 0 160 | 0 060 | 00075 | 0 150 | 0 140 | 0 070 | 00077 |
| 219 | 24-May | | | | 00000 | 0 170 | 0 170 | 0 070 | 00106 | 0 140 | 0 140 | 0 070 | 00072 |
| 220 | 25-May | | | | 00000 | 0 170 | 0 180 | 0 070 | 00112 | 0 140 | 0 140 | 0 070 | 00072 |
| 221 | 26-May | | | | 00000 | 0 170 | 0 180 | 0 070 | 00112 | 0 140 | 0 140 | 0 070 | 00072 |
| 222 | 27-May | | | | 00000 | 0 180 | 0 190 | 0 100 | 00179 | 0 150 | 0 160 | 0 070 | 00088 |
| 223 | 28-May | | | | 00000 | 0 190 | 0 230 | 0 100 | 00195 | 0 150 | 0 170 | 0 070 | 00093 |
| 224 | 29-May | | | | 00000 | 0 190 | 0 230 | 0 100 | 00199 | 0 150 | 0 180 | 0 070 | 00099 |
| 225 | 30-May | | | | 00000 | 0 210 | 0 200 | 0 090 | 00198 | 0 150 | 0 170 | 0 070 | 00093 |
| 226 | 31-May | | | | 00000 | 0 210 | 0 210 | 0 100 | 00231 | 0 160 | 0 180 | 0 070 | 00106 |
| 227 | 1-Jun | | | | 00000 | 0 230 | 0 230 | 0 100 | 00277 | 0 160 | 0 170 | 0 090 | 00128 |
| 228 | 2-Jun | | | | 00000 | 0 230 | 0 230 | 0 100 | 00277 | 0 160 | 0 170 | 0 090 | 00128 |
| 229 | 3-Jun | | | | 00000 | 0 240 | 0 240 | 0 110 | 00332 | 0 170 | 0 170 | 0 100 | 00151 |
| 230 | 4-Jun | | | | 00000 | 0 250 | 0 250 | 0 110 | 00374 | 0 180 | 0 180 | 0 100 | 00170 |
| 231 | 5-Jun | | | | 00000 | 0 270 | 0 270 | 0 110 | 00425 | 0 170 | 0 180 | 0 100 | 00160 |
| 232 | 6-Jun | | | | 00000 | 0 280 | 0 290 | 0 120 | 00528 | 0 200 | 0 190 | 0 100 | 00199 |
| 233 | 7-Jun | | | | 00000 | 0 300 | 0 310 | 0 120 | 00584 | 0 200 | 0 200 | 0 100 | 00209 |
| 234 | 8-Jun | | | | 00000 | 0 320 | 0 330 | 0 130 | 00718 | 0 220 | 0 220 | 0 100 | 00253 |
| 235 | 9-Jun | | | | 00000 | 0 320 | 0 330 | 0 130 | 00718 | 0 220 | 0 220 | 0 100 | 00253 |
| 236 | 10-Jun | | | | 00000 | 0 330 | 0 350 | 0 130 | 00786 | 0 220 | 0 210 | 0 100 | 00242 |
| 237 | 11-Jun | | | | 00000 | 0 340 | 0 350 | 0 130 | 00810 | 0 220 | 0 220 | 0 100 | 00253 |
| 238 | 12-Jun | | | | 00000 | 0 340 | 0 350 | 0 130 | 00810 | 0 230 | 0 230 | 0 100 | 00277 |
| 239 | 13-Jun | | | | 00000 | 0 360 | 0 360 | 0 140 | 00950 | 0 240 | 0 240 | 0 100 | 00302 |
| 240 | 14-Jun | | | | 00000 | 0 360 | 0 360 | 0 140 | 00950 | 0 240 | 0 250 | 0 100 | 00314 |
| 241 | 15-Jun | | | | 00000 | 0 360 | 0 350 | 0 140 | 00923 | 0 240 | 0 250 | 0 110 | 00346 |
| 242 | 16-Jun | | | | 00000 | 0 360 | 0 350 | 0 150 | 00989 | 0 240 | 0 260 | 0 110 | 00359 |
| 243 | 17-Jun | | | | 00000 | 0 360 | 0 350 | 0 150 | 00989 | 0 240 | 0 260 | 0 110 | 00359 |
| 244 | 18-Jun | | | | 00000 | 0 380 | 0 350 | 0 150 | 01044 | 0 270 | 0 270 | 0 120 | 00458 |
| 245 | 19-Jun | | | | 00000 | 0 390 | 0 360 | 0 150 | 01102 | 0 280 | 0 270 | 0 120 | 00475 |
| 246 | 20-Jun | | | | 00000 | 0 390 | 0 360 | 0 150 | 01102 | 0 280 | 0 270 | 0 120 | 00475 |
| 247 | 21-Jun | | | | 00000 | 0 410 | 0 370 | 0 150 | 01191 | 0 300 | 0 310 | 0 130 | 00633 |
| 248 | 22-Jun | | | | 00000 | 0 400 | 0 360 | 0 160 | 01206 | 0 330 | 0 320 | 0 130 | 00719 |
| 249 | 23-Jun | | | | 00000 | 0 400 | 0 360 | 0 160 | 01206 | 0 330 | 0 320 | 0 130 | 00719 |
| 250 | 24-Jun | | | | 00000 | 0 430 | 0 370 | 0 160 | 01333 | 0 340 | 0 330 | 0 130 | 00764 |
| 251 | 25-Jun | | | | 00000 | 0 430 | 0 380 | 0 170 | 01454 | 0 360 | 0 350 | 0 140 | 00923 |
| 252 | 26-Jun | | | | 00000 | 0 430 | 0 390 | 0 170 | 01492 | 0 360 | 0 360 | 0 140 | 00950 |
| 253 | 27-Jun | | | | 00000 | 0 430 | 0 400 | 0 170 | 01531 | 0 360 | 0 370 | 0 140 | 00976 |
| 254 | 28-Jun | | | | 00000 | 0 430 | 0 390 | 0 180 | 01580 | 0 370 | 0 370 | 0 140 | 01003 |
| 255 | 29-Jun | | | | 00000 | 0 450 | 0 400 | 0 180 | 01696 | 0 390 | 0 370 | 0 140 | 01058 |
| 256 | 30-Jun | | | | 00000 | 0 450 | 0 400 | 0 180 | 01696 | 0 390 | 0 370 | 0 140 | 01058 |
| 257 | 1-Jul | | | | 00000 | 0 440 | 0 400 | 0 180 | 01658 | 0 400 | 0 380 | 0 140 | 01114 |
| 258 | 2-Jul | | | | 00000 | 0 440 | 0 420 | 0 180 | 01741 | 0 420 | 0 380 | 0 150 | 01253 |
| 259 | 3-Jul | | | | 00000 | 0 440 | 0 440 | 0 180 | 01824 | 0 440 | 0 400 | 0 160 | 01474 |
| 260 | 4-Jul | | | | 00000 | 0 450 | 0 440 | 0 180 | 01866 | 0 440 | 0 400 | 0 170 | 01566 |
| 261 | 5-Jul | | | | 00000 | 0 450 | 0 440 | 0 180 | 01866 | 0 430 | 0 390 | 0 170 | 01492 |
| 262 | 6-Jul | | | | 00000 | 0 440 | 0 440 | 0 180 | 01824 | 0 440 | 0 400 | 0 170 | 01566 |
| 263 | 7-Jul | | | | 00000 | 0 440 | 0 440 | 0 180 | 01824 | 0 440 | 0 400 | 0 170 | 01566 |
| 264 | 8-Jul | | | | 00000 | 0 430 | 0 440 | 0 180 | 01783 | 0 430 | 0 410 | 0 170 | 01569 |
| 265 | 9-Jul | | | | 00000 | 0 430 | 0 440 | 0 180 | 01783 | 0 430 | 0 400 | 0 170 | 01531 |
| 266 | 10-Jul | | | | 00000 | 0 420 | 0 440 | 0 180 | 01741 | 0 450 | 0 420 | 0 170 | 01682 |
| 267 | 11-Jul | | | | 00000 | 0 420 | 0 470 | 0 180 | 01860 | 0 450 | 0 410 | 0 170 | 01642 |
| 268 | 12-Jul | | Died 7/12/96 | | #VALUE! | | Died 7/12/96 | | #VALUE! | | Died 7/12/96 | | #VALUE! |
| 269 | 13-Jul | | | | | | | | | | | | |
| 270 | 14-Jul | | | | | | | | | | | | |

| DAY | T-4 LEFT ARM Ln | Wd | Ht | Vol T-1 | WEIGHT Gr | HEMATO-CRIT % | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|
| 215 | | | | 00000 | 27 66 | | 8662A | 433518500 | 0 0 dBm | 1 Hr | 433518700 | 0 0 dBm | 1 Hr | Type "S" |
| 216 | | | | 00000 | 27 50 | | 8662A | 433518500 | 0 0 dBm | 1 Hr | 433518700 | 0 0 dBm | 1 Hr | Type "S" |
| 217 | | | | 00000 | 28 72 | | 8662A | 433518710 | 0 0 dBm | 1 Hr | 433518700 | 0 0 dBm | 1 Hr | Type "S" |
| 218 | | | | 00000 | 27 70 | | 8662A | 433518710 | 0 0 dBm | 1 Hr | 433518530 | 0 0 dBm | 1 Hr | Type "S" |
| 219 | | | | 00000 | 27 32 | | 8662A | 433518710 | 0 0 dBm | 1 Hr | 433518530 | 0 0 dBm | 1 Hr | Type "S" |
| 220 | | | | 00000 | 27 71 | 43 | 8662A | 433518710 | 0 0 dBm | 1 Hr | 433460000 | 0 0 dBm | 1 Hr | Type "S" |
| 221 | | | | 00000 | 27 85 | | | NO TREATMENT | | | NO TREATMENT | | | |
| 222 | | | | 00000 | 28 00 | | 8662A | 433538000 | 0 0 dBm | 1 Hr | 433224850 | 0 0 dBm | 1 Hr | Type "S" |
| 223 | | | | 00000 | 28 68 | | 8662A | 433518700 | 0 0 dBm | 1 Hr | 433518700 | 0 0 dBm | 1 Hr | Type "S" |
| 224 | | | | 00000 | 28 23 | | SCPO3 | 433518700 | 0 0 dBm | 1 Hr | 433518700 | 0 0 dBm | 1 Hr | Type "E&I" |
| 225 | | | | 00000 | 27 66 | | SCPO3 | 433518700 | 0 0 dBm | 1 Hr | 433518700 | 0 0 dBm | 1 Hr | Type "E&I" |
| 226 | | | | 00000 | 28 43 | | SCPO3 | 433518700 | 0 0 dBm | 1 Hr | 433518700 | 0 0 dBm | 1 Hr | Type "E&I" |
| 227 | | | | 00000 | 28 21 | 42 | SCPO3 | 433518700 | 0 0 dBm | 1 Hr | 433518700 | 0 0 dBm | 1 Hr | Type "E&I" |
| 228 | | | | 00000 | 28 06 | | | NO TREATMENT | | | NO TREATMENT | | | |
| 229 | | | | 00000 | 27 93 | | 8662A | 433518710 | 0 0 dBm | 1 Hr | 433518530 | 0 0 dBm | 1 Hr | Type "S" |
| 230 | | | | 00000 | 27 84 | | 8662A | 433518710 | 0 0 dBm | 1 Hr | 433518530 | 0 0 dBm | 1 Hr | Type "S" |
| 231 | | | | 00000 | 27 72 | | 8662A | 433518700 | 0 0 dBm | 1 Hr | 433518530 | 0 0 dBm | 1 Hr | Type "S" |
| 232 | | | | 00000 | 27 55 | | 8662A | 433518300 | 0 0 dBm | 1 Hr | 433518300 | 0 0 dBm | 1 Hr | Type "S" |
| 233 | | | | 00000 | 27 31 | | 8662A | 433518700 | 0 0 dBm | 1 Hr | 433518700 | 0 0 dBm | 1 Hr | Type "S" |
| 234 | | | | 00000 | 27 01 | 40 | 8662A | 433518700 | 433460000 | | 433518530 | 0 0 dBm | 1, 5 5 | Type "S" |
| 235 | | | | 00000 | 27 12 | | | NO TREATMENT | | | NO TREATMENT | | | |
| 236 | | | | 00000 | 27 22 | | 8662A | 433518700 | 433460000 | | 433518530 | 0 0 dBm | 1. 5 5 | Type "S" |
| 237 | | | | 00000 | 27 30 | | 8662A | 433518710 | 0 0 dBm | 1 Hr | 433460000 | 0 0 dBm | 1 Hr | Type "S" |
| 238 | | | | 00000 | 28 87 | | 8662A | 433270000 | 433460000 | | 433530000 | 0 0 dBm | 5 1. 5 | Type "S" |
| 239 | | | | 00000 | 26 93 | | 8662A | 433220000 | 433460000 | | 433530000 | 0 0 dBm | 5.1 5 | Type "S" |
| 240 | | | | 00000 | 26 68 | | 8662A | 433220000 | 433460000 | | 433530000 | 0 0 dBm | 5.1 5 | Type "S" |
| 241 | | | | 00000 | 27 18 | 36 | 8662A | 433220000 | 433460000 | | 433530000 | 0 0 dBm | 5.1 5 | Type "S" |
| 242 | | | | 00000 | 27 22 | | | NO TREATMENT | | | NO TREATMENT | | | |
| 243 | | | | 00000 | 27 25 | | 8662A | 433220000 | 433460000 | | 433530000 | 0 0 dBm | 1. 5 5 | Type "S" |
| 244 | | | | 00000 | 28 70 | | 8662A | 433220000 | 433460000 | | 433530000 | 0 0 dBm | 1. 5. 5 | Type "S" |
| 245 | | | | 00000 | 27 56 | | 8662A | 433220000 | 433460000 | | 433530000 | 0 0 dBm | 5 1 5 | Type "S" |
| 246 | | | | 00000 | 27 74 | | 8662A | 433220000 | 433460000 | | 433530000 | 0 0 dBm | 5 1 5 | Type "S" |
| 247 | | | | 00000 | 27 89 | | 8662A | 433220000 | 433460000 | | 433530000 | 0 0 dBm | 5 1. 5 | Type "S" |
| 248 | | | | 00000 | 28 45 | | 8662A | 433220000 | 433460000 | | 433530000 | 0 0 dBm | 5.1. 5 | Type "S" |
| 249 | | | | 00000 | 28 75 | | | NO TREATMENT | | | NO TREATMENT | | | |
| 250 | | | | 00000 | 28 96 | 33 | 8662A | 433518700 | | | 433518700 | 0 0 dBm | 1, 1 | Type "S" |
| 251 | | | | 00000 | 28 33 | | 8662A | 433460000 | 438530000 | | 438710000 | 0 0 dBm | 1 5 5 | Type "S" |
| 252 | | | | 00000 | 28 58 | | 8662A | 433460000 | 438530000 | | 438710000 | 0 0 dBm | 1. 5. 5 | Type "S" |
| 253 | | | | 00000 | 29 60 | | 8662A | 433460000 | 438530000 | | 438710000 | 0 0 dBm | 1. 5 5 | Type "S" |
| 254 | | | | 00000 | 29 67 | | 8662A | 433460000 | 438530000 | | 438710000 | 0 0 dBm | 1. 5. 5 | Type "S" |
| 255 | | | | 00000 | 30 05 | 30 | 8662A | 433518700 | | | 433518700 | 0 0 dBm | 1, 1 | Type "S" |
| 256 | | | | 00000 | 31 08 | | | NO TREATMENT | | | NO TREATMENT | | | |
| 257 | | | | 00000 | 32 12 | | 8662A | 433518700 | | | 433518700 | 0 0 dBm | 1 1 | Type "S" |
| 258 | | | | 00000 | 32 87 | | 8662A | 433518700 | | | 433518700 | 0 0 dBm | 1 1 | Type "S" |
| 259 | | | | 00000 | 32 16 | | BOSCPO | 433518700 | | | 433518700 | 0 0 dBm | 1 1 | Type "W" |
| 260 | | | | 00000 | 32 06 | | BOSCPO | 433518700 | | | 433518700 | 0 0 dBm | 1 1 | Type "W" |
| 261 | | | | 00000 | 33 20 | | BOSCPO | 433518700 | | | 433518700 | 0 0 dBm | 1 1 | Type "W" |
| 262 | | | | 00000 | 32 85 | 23 | BOSCPO | 433518700 | | | 433518700 | 0 0 dBm | 1 1 | Type "W" |
| 263 | | | | 00000 | 31 72 | | | NO TREATMENT | | | NO TREATMENT | | | |
| 264 | | | | 00000 | 30 58 | | BOSCPO | 433518700 | | | 433518700 | 0 0 dBm | 1 1 | Type "W" |
| 265 | | | | 00000 | 31 26 | | BOSCPO | 433518700 | | | 433518700 | 0 0 dBm | 1 1 | Type "W" |
| 266 | | | | 00000 | 30 96 | | BOSCPO | 433518700 | | | 433518700 | 0 0 dBm | 1 1 | Type "W" |
| 267 | | | | 00000 | 32 2[illegible] | | BOSCPO | 433518700 | | | 433518700 | 0 0 dBm | 1 1 | Type "W" |
| 268 | | Died 7/12/96 | | #VALUE! | | | | | | | | | | |
| 269 | | | | | | | | | | | | | | |
| 270 | | | | | | | | | | | | | | |

4/11/97 Page 4 Ouj-506- xls

09141691 .082898

OUJ-516- xls

OUJ-516 Born 2/2/95 First tumor appeared on 07/31/95 BREAD 11/17/95

| DAY | DATE | Lower ABDOMEN T-1 Ln | Wd | Ht | Vol T-1 | LEG/ABDOMEN T-2 Ln | Wd | Ht | Vol T-2 |
|---|---|---|---|---|---|---|---|---|---|
| 1 | 31-Jul | 0 030 | 0 030 | 0 030 | 00001 | | | | 00000 |
| 2 | 1-Aug | 0 030 | 0 030 | 0 030 | 00001 | | | | 00000 |
| 3 | 2-Aug | 0 030 | 0 030 | 0 030 | 00001 | | | | 00000 |
| 4 | 3-Aug | 0 030 | 0 030 | 0 030 | 00001 | | | | 00000 |
| 5 | 4-Aug | 0 030 | 0 030 | 0 030 | 00001 | | | | 00000 |
| 6 | 5-Aug | 0 030 | 0 030 | 0 030 | 00001 | | | | 00000 |
| 7 | 6-Aug | 0 030 | 0 030 | 0 030 | 00001 | | | | 00000 |
| 8 | 7-Aug | 0 030 | 0 030 | 0 030 | 00001 | | | | 00000 |
| 9 | 8-Aug | 0 030 | 0 030 | 0 030 | 00001 | | | | 00000 |
| 10 | 9-Aug | 0 030 | 0 030 | 0 030 | 00001 | | | | 00000 |
| 11 | 10-Aug | 0 030 | 0 030 | 0 030 | 00001 | | | | 00000 |
| 12 | 11-Aug | 0 030 | 0 030 | 0 030 | 00001 | | | | 00000 |
| 13 | 12-Aug | | | | 00000 | | | | 00000 |
| 14 | 13-Aug | | | | 00000 | | | | 00000 |
| 15 | 14-Aug | | | | 00000 | | | | 00000 |
| 16 | 15-Aug | | | | 00000 | | | | 00000 |
| 17 | 16-Aug | | | | 00000 | | | | 00000 |
| 18 | 17-Aug | | | | 00000 | | | | 00000 |
| 19 | 18-Aug | | | | 00000 | | | | 00000 |
| 20 | 19-Aug | | | | 00000 | | | | 00000 |
| 21 | 20-Aug | | | | 00000 | | | | 00000 |
| 22 | 21-Aug | | | | 00000 | | | | 00000 |
| 23 | 22-Aug | | | | 00000 | | | | 00000 |
| 24 | 23-Aug | | | | 00000 | 0 050 | 0 050 | 0 050 | 00007 |
| 25 | 24-Aug | | | | 00000 | 0 050 | 0 050 | 0 050 | 00007 |
| 26 | 25-Aug | | | | 00000 | 0 050 | 0 050 | 0 050 | 00007 |
| 27 | 26-Aug | | | | 00000 | 0 050 | 0 050 | 0 050 | 00007 |
| 28 | 27-Aug | | | | 00000 | 0 050 | 0 050 | 0 050 | 00007 |
| 29 | 28-Aug | | | | 00000 | 0 050 | 0 050 | 0 050 | 00007 |
| 30 | 29-Aug | | | | 00000 | 0 050 | 0 050 | 0 050 | 00007 |
| 31 | 30-Aug | | | | 00000 | 0 050 | 0 050 | 0 050 | 00007 |
| 32 | 31-Aug | | | | 00000 | 0 050 | 0 050 | 0 050 | 00007 |
| 33 | 1-Sep | | | | 00000 | 0 060 | 0 060 | 0 060 | 00011 |
| 34 | 2-Sep | | | | 00000 | 0 060 | 0 060 | 0 060 | 00011 |
| 35 | 3-Sep | | | | 00000 | 0 060 | 0 060 | 0 060 | 00011 |
| 36 | 4-Sep | | | | 00000 | 0 070 | 0 070 | 0 070 | 00018 |
| 37 | 5-Sep | | | | 00000 | 0 070 | 0 070 | 0 070 | 00018 |
| 38 | 6-Sep | | | | 00000 | 0 050 | 0 050 | 0 050 | 00007 |
| 39 | 7-Sep | | | | 00000 | 0 050 | 0 050 | 0 050 | 00007 |
| 40 | 8-Sep | | | | 00000 | 0 050 | 0 050 | 0 050 | 00007 |
| 41 | 9-Sep | | | | 00000 | 0 050 | 0 050 | 0 050 | 00007 |
| 42 | 10-Sep | | | | 00000 | 0 050 | 0 050 | 0 050 | 00007 |
| 43 | 11-Sep | | | | 00000 | 0 050 | 0 050 | 0 050 | 00007 |
| 44 | 12-Sep | | | | 00000 | 0 030 | 0 030 | 0 030 | 00001 |
| 45 | 13-Sep | | | | 00000 | 0 030 | 0 030 | 0 030 | 00001 |
| 46 | 14-Sep | | | | 00000 | 0 030 | 0 030 | 0 030 | 00001 |
| 47 | 15-Sep | | | | 00000 | 0 030 | 0 030 | 0 030 | 00001 |
| 48 | 16-Sep | | | | 00000 | 0 030 | 0 030 | 0 030 | 00001 |
| 49 | 17-Sep | | | | 00000 | 0 030 | 0 030 | 0 030 | 00001 |
| 50 | 18-Sep | | | | 00000 | 0 030 | 0 030 | 0 030 | 00001 |
| 51 | 19-Sep | | | | 00000 | 0 030 | 0 030 | 0 030 | 00001 |
| 52 | 20-Sep | | | | 00000 | | | | 00000 |
| 53 | 21-Sep | | | | 00000 | | | | 00000 |
| 54 | 22-Sep | | | | 00000 | | | | 00000 |
| 55 | 23-Sep | | | | 00000 | | | | 00000 |
| 56 | 24-Sep | | | | 00000 | | | | 00000 |
| 57 | 25-Sep | | | | 00000 | 0 030 | 0 030 | 0 030 | 00001 |
| 58 | 26-Sep | | | | 00000 | 0 030 | 0 030 | 0 030 | 00001 |
| 59 | 27-Sep | | | | 00000 | 0 030 | 0 030 | 0 030 | 00001 |
| 60 | 28-Sep | | | | 00000 | 0 030 | 0 030 | 0 030 | 00001 |
| 61 | 29-Sep | | | | 00000 | 0 030 | 0 030 | 0 030 | 00001 |
| 62 | 30-Sep | | | | 00000 | 0 030 | 0 030 | 0 030 | 00001 |
| 63 | 1-Oct | | | | 00000 | 0 030 | 0 030 | 0 030 | 00001 |
| 64 | 2-Oct | | | | 00000 | 0 030 | 0 030 | 0 030 | 00001 |

| DAY | DATE | RT LEG T-3 Ln | Wd | Ht | Vol T-3 | RT NECK T-4 Ln | Wd | Ht | Vol T-4 | SHOLDER T-5 Ln | Wd | Ht | Vol T-5 | LT NECK T-4 Ln | Wd | Ht | Vol T-4 | RT SIDE AR Ln | Wd |
|---|---|---|---|---|---|---|---|---|---|---|---|---|---|---|---|---|---|---|---|
| 1 | 31-Jul | | | | 00000 | | | | 00000 | | | | 00000 | | | | 00000 | | |
| 2 | 1-Aug | | | | 00000 | | | | 00000 | | | | 00000 | | | | 00000 | | |
| 3 | 2-Aug | | | | 00000 | | | | 00000 | | | | 00000 | | | | 00000 | | |
| 4 | 3-Aug | | | | 00000 | | | | 00000 | | | | 00000 | | | | 00000 | | |
| 5 | 4-Aug | | | | 00000 | | | | 00000 | | | | 00000 | | | | 00000 | | |
| 6 | 5-Aug | | | | 00000 | | | | 00000 | | | | 00000 | | | | 00000 | | |
| 7 | 6-Aug | | | | 00000 | | | | 00000 | | | | 00000 | | | | 00000 | | |
| 8 | 7-Aug | | | | 00000 | | | | 00000 | | | | 00000 | | | | 00000 | | |
| 9 | 8-Aug | | | | 00000 | | | | 00000 | | | | 00000 | | | | 00000 | | |
| 10 | 9-Aug | | | | 00000 | | | | 00000 | | | | 00000 | | | | 00000 | | |
| 11 | 10-Aug | | | | 00000 | | | | 00000 | | | | 00000 | | | | 00000 | | |
| 12 | 11-Aug | | | | 00000 | | | | 00000 | | | | 00000 | | | | 00000 | | |
| 13 | 12-Aug | | | | 00000 | | | | 00000 | | | | 00000 | | | | 00000 | | |
| 14 | 13-Aug | | | | 00000 | | | | 00000 | | | | 00000 | | | | 00000 | | |
| 15 | 14-Aug | | | | 00000 | | | | 00000 | | | | 00000 | | | | 00000 | | |
| 16 | 15-Aug | | | | 00000 | | | | 00000 | | | | 00000 | | | | 00000 | | |
| 17 | 16-Aug | | | | 00000 | | | | 00000 | | | | 00000 | | | | 00000 | | |
| 18 | 17-Aug | | | | 00000 | | | | 00000 | | | | 00000 | | | | 00000 | | |
| 19 | 18-Aug | | | | 00000 | | | | 00000 | | | | 00000 | | | | 00000 | | |
| 20 | 19-Aug | | | | 00000 | | | | 00000 | | | | 00000 | | | | 00000 | | |
| 21 | 20-Aug | | | | 00000 | | | | 00000 | | | | 00000 | | | | 00000 | | |
| 22 | 21-Aug | | | | 00000 | | | | 00000 | | | | 00000 | | | | 00000 | | |
| 23 | 22-Aug | | | | 00000 | | | | 00000 | | | | 00000 | | | | 00000 | | |
| 24 | 23-Aug | | | | 00000 | | | | 00000 | | | | 00000 | | | | 00000 | | |
| 25 | 24-Aug | | | | 00000 | | | | 00000 | | | | 00000 | | | | 00000 | | |
| 26 | 25-Aug | | | | 00000 | | | | 00000 | | | | 00000 | | | | 00000 | | |
| 27 | 26-Aug | | | | 00000 | | | | 00000 | | | | 00000 | | | | 00000 | | |
| 28 | 27-Aug | | | | 00000 | | | | 00000 | | | | 00000 | | | | 00000 | | |
| 29 | 28-Aug | | | | 00000 | | | | 00000 | | | | 00000 | | | | 00000 | | |
| 30 | 29-Aug | | | | 00000 | | | | 00000 | | | | 00000 | | | | 00000 | | |
| 31 | 30-Aug | | | | 00000 | | | | 00000 | | | | 00000 | | | | 00000 | | |
| 32 | 31-Aug | | | | 00000 | | | | 00000 | | | | 00000 | | | | 00000 | | |
| 33 | 1-Sep | | | | 00000 | | | | 00000 | | | | 00000 | | | | 00000 | | |
| 34 | 2-Sep | | | | 00000 | | | | 00000 | | | | 00000 | | | | 00000 | | |
| 35 | 3-Sep | | | | 00000 | | | | 00000 | | | | 00000 | | | | 00000 | | |
| 36 | 4-Sep | | | | 00000 | | | | 00000 | | | | 00000 | | | | 00000 | | |
| 37 | 5-Sep | | | | 00000 | | | | 00000 | | | | 00000 | | | | 00000 | | |
| 38 | 6-Sep | | | | 00000 | | | | 00000 | | | | 00000 | | | | 00000 | | |
| 39 | 7-Sep | | | | 00000 | | | | 00000 | | | | 00000 | | | | 00000 | | |
| 40 | 8-Sep | | | | 00000 | | | | 00000 | | | | 00000 | | | | 00000 | | |
| 41 | 9-Sep | | | | 00000 | | | | 00000 | | | | 00000 | | | | 00000 | | |
| 42 | 10-Sep | | | | 00000 | | | | 00000 | | | | 00000 | | | | 00000 | | |
| 43 | 11-Sep | | | | 00000 | | | | 00000 | | | | 00000 | | | | 00000 | | |
| 44 | 12-Sep | | | | 00000 | | | | 00000 | | | | 00000 | | | | 00000 | | |
| 45 | 13-Sep | | | | 00000 | | | | 00000 | | | | 00000 | | | | 00000 | | |
| 46 | 14-Sep | | | | 00000 | | | | 00000 | | | | 00000 | | | | 00000 | | |
| 47 | 15-Sep | | | | 00000 | | | | 00000 | | | | 00000 | | | | 00000 | | |
| 48 | 16-Sep | | | | 00000 | | | | 00000 | | | | 00000 | | | | 00000 | | |
| 49 | 17-Sep | | | | 00000 | | | | 00000 | | | | 00000 | | | | 00000 | | |
| 50 | 18-Sep | | | | 00000 | | | | 00000 | | | | 00000 | | | | 00000 | | |
| 51 | 19-Sep | | | | 00000 | | | | 00000 | | | | 00000 | | | | 00000 | | |
| 52 | 20-Sep | | | | 00000 | | | | 00000 | | | | 00000 | | | | 00000 | | |
| 53 | 21-Sep | | | | 00000 | | | | 00000 | | | | 00000 | | | | 00000 | | |
| 54 | 22-Sep | | | | 00000 | | | | 00000 | | | | 00000 | | | | 00000 | | |
| 55 | 23-Sep | | | | 00000 | | | | 00000 | | | | 00000 | | | | 00000 | | |
| 56 | 24-Sep | | | | 00000 | | | | 00000 | | | | 00000 | | | | 00000 | | |
| 57 | 25-Sep | | | | 00000 | | | | 00000 | | | | 00000 | | | | 00000 | | |
| 58 | 26-Sep | | | | 00000 | | | | 00000 | | | | 00000 | | | | 00000 | | |
| 59 | 27-Sep | | | | 00000 | | | | 00000 | | | | 00000 | | | | 00000 | | |
| 60 | 28-Sep | | | | 00000 | | | | 00000 | | | | 00000 | | | | 00000 | | |
| 61 | 29-Sep | | | | 00000 | | | | 00000 | | | | 00000 | | | | 00000 | | |
| 62 | 30-Sep | | | | 00000 | | | | 00000 | | | | 00000 | | | | 00000 | | |
| 63 | 1-Oct | | | | 00000 | | | | 00000 | | | | 00000 | | | | 00000 | | |
| 64 | 2-Oct | | | | 00000 | | | | 00000 | | | | 00000 | | | | 00000 | | |

OUJ-516-.xls

| DAY | DATE | Lower ABDOMEN T-1 | | | Vol | LEG/ABDOMEN T-2 | | | Vol | RT LEG T-3 | | | Vol |
|---|---|---|---|---|---|---|---|---|---|---|---|---|---|
| | | Ln | Wd | Ht | T-1 | Ln | Wd | Ht | T-2 | Ln | Wd | Ht | T-3 |
| 65 | 3-Oct | | | | 00000 | 0.000 | 0.000 | 0.000 | 00000 | | | | 00000 |
| 66 | 4-Oct | | | | 00000 | | | | 00000 | | | | 00000 |
| 67 | 5-Oct | | | | 00000 | | | | 00000 | | | | 00000 |
| 68 | 6-Oct | | | | 00000 | | | | 00000 | | | | 00000 |
| 69 | 7-Oct | | | | 00000 | | | | 00000 | | | | 00000 |
| 70 | 8-Oct | | | | 00000 | | | | 00000 | | | | 00000 |
| 71 | 9-Oct | | | | 00000 | | | | 00000 | | | | 00000 |
| 72 | 10-Oct | | | | 00000 | | | | 00000 | | | | 00000 |
| 73 | 11-Oct | | | | 00000 | | | | 00000 | | | | 00000 |
| 74 | 12-Oct | | | | 00000 | | | | 00000 | | | | 00000 |
| 75 | 13-Oct | | | | 00000 | | | | 00000 | | | | 00000 |
| 76 | 14-Oct | | | | 00000 | | | | 00000 | | | | 00000 |
| 77 | 15-Oct | | | | 00000 | | | | 00000 | | | | 00000 |
| 78 | 16-Oct | | | | 00000 | | | | 00000 | | | | 00000 |
| 79 | 17-Oct | | | | 00000 | | | | 00000 | | | | 00000 |
| 80 | 18-Oct | | | | 00000 | | | | 00000 | | | | 00000 |
| 81 | 19-Oct | | | | 00000 | | | | 00000 | | | | 00000 |
| 82 | 20-Oct | | | | 00000 | | | | 00000 | | | | 00000 |
| 83 | 21-Oct | | | | 00000 | | | | 00000 | | | | 00000 |
| 84 | 22-Oct | | | | 00000 | | | | 00000 | | | | 00000 |
| 85 | 23-Oct | | | | 00000 | | | | 00000 | | | | 00000 |
| 86 | 24-Oct | | | | 00000 | | | | 00000 | | | | 00000 |
| 87 | 25-Oct | | | | 00000 | | | | 00000 | | | | 00000 |
| 88 | 26-Oct | | | | 00000 | | | | 00000 | | | | 00000 |
| 89 | 27-Oct | | | | 00000 | | | | 00000 | | | | 00000 |
| 90 | 28-Oct | | | | 00000 | | | | 00000 | 0.050 | 0.050 | 0.050 | 00007 |
| 91 | 29-Oct | | | | 00000 | | | | 00000 | 0.040 | 0.040 | 0.040 | 00003 |
| 92 | 30-Oct | | | | 00000 | | | | 00000 | 0.030 | 0.030 | 0.030 | 00001 |
| 93 | 31-Oct | | | | 00000 | | | | 00000 | | | | 00000 |
| 94 | 1-Nov | | | | 00000 | | | | 00000 | | | | 00000 |
| 95 | 2-Nov | | | | 00000 | | | | 00000 | | | | 00000 |
| 96 | 3-Nov | | | | 00000 | | | | 00000 | | | | 00000 |
| 97 | 4-Nov | | | | 00000 | | | | 00000 | | | | 00000 |
| 98 | 5-Nov | | | | 00000 | | | | 00000 | | | | 00000 |
| 99 | 6-Nov | | | | 00000 | | | | 00000 | | | | 00000 |
| 100 | 7-Nov | | | | 00000 | | | | 00000 | | | | 00000 |
| 101 | 8-Nov | | | | 00000 | | | | 00000 | | | | 00000 |
| 102 | 9-Nov | | | | 00000 | | | | 00000 | | | | 00000 |
| 103 | 10-Nov | | | | 00000 | | | | 00000 | | | | 00000 |
| 104 | 11-Nov | | | | 00000 | | | | 00000 | | | | 00000 |
| 105 | 12-Nov | | | | 00000 | | | | 00000 | | | | 00000 |
| 106 | 13-Nov | | | | 00000 | | | | 00000 | | | | 00000 |
| 107 | 14-Nov | | | | 00000 | | | | 00000 | | | | 00000 |
| 108 | 15-Nov | | | | 00000 | | | | 00000 | | | | 00000 |
| 109 | 16-Nov | | | | 00000 | | | | 00000 | | | | 00000 |
| 110 | 17-Nov | | | | 00000 | | | | 00000 | | | | 00000 |
| 111 | 18-Nov | | | | 00000 | | | | 00000 | | | | 00000 |
| 112 | 19-Nov | | | | 00000 | | | | 00000 | | | | 00000 |
| 113 | 20-Nov | | | | 00000 | | | | 00000 | | | | 00000 |
| 114 | 21-Nov | | | | 00000 | | | | 00000 | | | | 00000 |
| 115 | 22-Nov | | | | 00000 | | | | 00000 | | | | 00000 |
| 116 | 23-Nov | | | | 00000 | | | | 00000 | | | | 00000 |
| 117 | 24-Nov | | | | 00000 | | | | 00000 | | | | 00000 |
| 118 | 25-Nov | | | | 00000 | | | | 00000 | | | | 00000 |
| 119 | 26-Nov | | | | 00000 | | | | 00000 | | | | 00000 |
| 120 | 27-Nov | | | | 00000 | | | | 00000 | | | | 00000 |
| 121 | 28-Nov | | | | 00000 | | | | 00000 | | | | 00000 |
| 122 | 29-Nov | | | | 00000 | | | | 00000 | | | | 00000 |
| 123 | 30-Nov | | | | 00000 | | | | 00000 | | | | 00000 |
| 124 | 1-Dec | | | | 00000 | | | | 00000 | | | | 00000 |
| 125 | 2-Dec | | | | 00000 | | | | 00000 | | | | 00000 |
| 126 | 3-Dec | | | | 00000 | | | | 00000 | | | | 00000 |
| 127 | 4-Dec | | | | 00000 | | | | 00000 | | | | 00000 |
| 128 | 5-Dec | | | | 00000 | | | | 00000 | | | | 00000 |
| 129 | 6-Dec | | | | 00000 | | | | 00000 | | | | 00000 |
| 130 | 7-Dec | | | | 00000 | | | | 00000 | | | | 00000 |

| DAY | RT NECK T-4 | | | Vol | SHOLDER T-5 | | | Vol | LT NECK T-6 | | | Vol | RT SIDE AR | |
|---|---|---|---|---|---|---|---|---|---|---|---|---|---|---|
| | Ln | Wd | Ht | T-4 | Ln | Wd | Ht | T-5 | Ln | Wd | Ht | T-6 | Ln | Wd |
| 65 | | | | 00000 | | | | 00000 | | | | 00000 | | |
| 66 | | | | 00000 | | | | 00000 | | | | 00000 | | |
| 67 | | | | 00000 | | | | 00000 | | | | 00000 | | |
| 68 | | | | 00000 | | | | 00000 | | | | 00000 | | |
| 69 | | | | 00000 | | | | 00000 | | | | 00000 | | |
| 70 | | | | 00000 | | | | 00000 | | | | 00000 | | |
| 71 | | | | 00000 | | | | 00000 | | | | 00000 | | |
| 72 | | | | 00000 | | | | 00000 | | | | 00000 | | |
| 73 | | | | 00000 | | | | 00000 | | | | 00000 | | |
| 74 | | | | 00000 | | | | 00000 | | | | 00000 | | |
| 75 | | | | 00000 | | | | 00000 | | | | 00000 | | |
| 76 | | | | 00000 | | | | 00000 | | | | 00000 | | |
| 77 | | | | 00000 | | | | 00000 | | | | 00000 | | |
| 78 | | | | 00000 | | | | 00000 | | | | 00000 | | |
| 79 | | | | 00000 | | | | 00000 | | | | 00000 | | |
| 80 | | | | 00000 | | | | 00000 | | | | 00000 | | |
| 81 | | | | 00000 | | | | 00000 | | | | 00000 | | |
| 82 | | | | 00000 | | | | 00000 | | | | 00000 | | |
| 83 | | | | 00000 | | | | 00000 | | | | 00000 | | |
| 84 | | | | 00000 | | | | 00000 | | | | 00000 | | |
| 85 | | | | 00000 | | | | 00000 | | | | 00000 | | |
| 86 | | | | 00000 | | | | 00000 | | | | 00000 | | |
| 87 | | | | 00000 | | | | 00000 | | | | 00000 | | |
| 88 | | | | 00000 | | | | 00000 | | | | 00000 | | |
| 89 | | | | 00000 | | | | 00000 | | | | 00000 | | |
| 90 | | | | 00000 | | | | 00000 | | | | 00000 | | |
| 91 | | | | 00000 | | | | 00000 | | | | 00000 | | |
| 92 | | | | 00000 | | | | 00000 | | | | 00000 | | |
| 93 | | | | 00000 | | | | 00000 | | | | 00000 | | |
| 94 | | | | 00000 | | | | 00000 | | | | 00000 | | |
| 95 | | | | 00000 | | | | 00000 | | | | 00000 | | |
| 96 | | | | 00000 | | | | 00000 | | | | 00000 | | |
| 97 | 0.050 | 0.050 | 0.050 | 00007 | | | | 00000 | | | | 00000 | | |
| 98 | 0.050 | 0.050 | 0.050 | 00007 | | | | 00000 | | | | 00000 | | |
| 99 | 0.050 | 0.050 | 0.050 | 00007 | | | | 00000 | | | | 00000 | | |
| 100 | 0.070 | 0.070 | 0.070 | 00018 | | | | 00000 | | | | 00000 | | |
| 101 | 0.090 | 0.090 | 0.080 | 00030 | | | | 00000 | | | | 00000 | | |
| 102 | 0.100 | 0.100 | 0.070 | 00037 | | | | 00000 | | | | 00000 | | |
| 103 | 0.120 | 0.120 | 0.070 | 00053 | | | | 00000 | | | | 00000 | | |
| 104 | 0.120 | 0.120 | 0.070 | 00053 | | | | 00000 | | | | 00000 | | |
| 105 | 0.120 | 0.120 | 0.070 | 00053 | | | | 00000 | | | | 00000 | | |
| 106 | 0.120 | 0.120 | 0.070 | 00053 | | | | 00000 | | | | 00000 | | |
| 107 | 0.100 | 0.100 | 0.070 | 00037 | | | | 00000 | | | | 00000 | | |
| 108 | 0.100 | 0.100 | 0.070 | 00037 | | | | 00000 | | | | 00000 | | |
| 109 | 0.090 | 0.090 | 0.070 | 00030 | | | | 00000 | | | | 00000 | | |
| 110 | 0.090 | 0.090 | 0.070 | 00030 | | | | 00000 | | | | 00000 | | |
| 111 | 0.070 | 0.070 | 0.070 | 00018 | | | | 00000 | | | | 00000 | | |
| 112 | 0.060 | 0.060 | 0.050 | 00011 | | | | 00000 | | | | 00000 | | |
| 113 | 0.050 | 0.050 | 0.050 | 00007 | | | | 00000 | | | | 00000 | | |
| 114 | 0.050 | 0.050 | 0.050 | 00007 | | | | 00000 | | | | 00000 | | |
| 115 | 0.050 | 0.050 | 0.050 | 00007 | | | | 00000 | | | | 00000 | | |
| 116 | 0.050 | 0.050 | 0.050 | 00007 | | | | 00000 | | | | 00000 | | |
| 117 | 0.050 | 0.050 | 0.050 | 00007 | | | | 00000 | | | | 00000 | | |
| 118 | 0.030 | 0.030 | 0.030 | 00001 | | | | 00000 | | | | 00000 | | |
| 119 | 0.030 | 0.030 | 0.030 | 00001 | | | | 00000 | | | | 00000 | | |
| 120 | 0.030 | 0.030 | 0.030 | 00001 | | | | 00000 | | | | 00000 | | |
| 121 | | | | 00000 | | | | 00000 | | | | 00000 | | |
| 122 | | | | 00000 | | | | 00000 | | | | 00000 | | |
| 123 | | | | 00000 | | | | 00000 | | | | 00000 | | |
| 124 | | | | 00000 | | | | 00000 | | | | 00000 | | |
| 125 | | | | 00000 | | | | 00000 | | | | 00000 | | |
| 126 | | | | 00000 | | | | 00000 | | | | 00000 | | |
| 127 | | | | 00000 | | | | 00000 | | | | 00000 | | |
| 128 | | | | 00000 | | | | 00000 | | | | 00000 | | |
| 129 | | | | 00000 | | | | 00000 | | | | 00000 | | |
| 130 | | | | 00000 | | | | 00000 | | | | 00000 | | |

4/11/97 Page 2 OUJ-516-.xls 09141591.082898

OUJ-516-.xls

| DAY | DATE | Lower ABDOMEN T-1 | | | Vol | LEG/ABDOMEN T-2 | | | Vol | RT LEG T-3 | | | Vol | RT NECK T-4 | | | Vol | SHOLDER T-5 | | | Vol | LT NECK T-4 | | | Vol | RT SIDE AR | |
|---|---|---|---|---|---|---|---|---|---|---|---|---|---|---|---|---|---|---|---|---|---|---|---|---|---|---|---|
| | | Ln | Wd | Ht | T-1 | Ln | Wd | Ht | T-2 | Ln | Wd | Ht | T-3 | Ln | Wd | Ht | T-4 | Ln | Wd | Ht | T-5 | Ln | Wd | Ht | T-6 | Ln | Wd |
| 131 | 8-Dec | | | | 00000 | | | | 00000 | | | | 00000 | | | | 00000 | | | | 00000 | | | | 00000 | | |
| 132 | 9-Dec | | | | 00000 | | | | 00000 | | | | 00000 | | | | 00000 | | | | 00000 | | | | 00000 | | |
| 133 | 10-Dec | | | | 00000 | | | | 00000 | | | | 00000 | | | | 00000 | | | | 00000 | | | | 00000 | | |
| 134 | 11-Dec | | | | 00000 | | | | 00000 | | | | 00000 | | | | 00000 | | | | 00000 | | | | 00000 | | |
| 135 | 12-Dec | | | | 00000 | | | | 00000 | | | | 00000 | 0.050 | 0.050 | 0.050 | 00007 | | | | 00000 | | | | 00000 | | |
| 136 | 13-Dec | | | | 00000 | | | | 00000 | | | | 00000 | 0.050 | 0.050 | 0.050 | 00007 | | | | 00000 | | | | 00000 | | |
| 137 | 14-Dec | | | | 00000 | | | | 00000 | | | | 00000 | 0.030 | 0.030 | 0.030 | 00001 | | | | 00000 | | | | 00000 | | |
| 138 | 15-Dec | | | | 00000 | | | | 00000 | | | | 00000 | 0.050 | 0.050 | 0.050 | 00007 | | | | 00000 | | | | 00000 | | |
| 139 | 16-Dec | | | | 00000 | | | | 00000 | | | | 00000 | 0.100 | 0.100 | 0.070 | 00037 | | | | 00000 | | | | 00000 | | |
| 140 | 17-Dec | | | | 00000 | | | | 00000 | | | | 00000 | 0.100 | 0.100 | 0.070 | 00037 | | | | 00000 | | | | 00000 | | |
| 141 | 18-Dec | | | | 00000 | | | | 00000 | | | | 00000 | 0.100 | 0.100 | 0.080 | 00042 | | | | 00000 | | | | 00000 | | |
| 142 | 19-Dec | | | | 00000 | | | | 00000 | | | | 00000 | 0.070 | 0.070 | 0.060 | 00015 | | | | 00000 | | | | 00000 | | |
| 143 | 20-Dec | | | | 00000 | | | | 00000 | | | | 00000 | 0.240 | 0.230 | 0.130 | 00376 | | | | 00000 | | | | 00000 | | |
| 144 | 21-Dec | | | | 00000 | | | | 00000 | | | | 00000 | 0.240 | 0.250 | 0.130 | 00408 | | | | 00000 | | | | 00000 | | |
| 145 | 22-Dec | | | | 00000 | | | | 00000 | | | | 00000 | 0.240 | 0.250 | 0.130 | 00408 | | | | 00000 | | | | 00000 | | |
| 146 | 23-Dec | | | | 00000 | | | | 00000 | | | | 00000 | 0.240 | 0.250 | 0.130 | 00408 | | | | 00000 | | | | 00000 | | |
| 147 | 24-Dec | | | | 00000 | | | | 00000 | | | | 00000 | 0.240 | 0.250 | 0.130 | 00408 | | | | 00000 | | | | 00000 | | |
| 148 | 25-Dec | | | | 00000 | | | | 00000 | | | | 00000 | 0.240 | 0.250 | 0.130 | 00408 | | | | 00000 | | | | 00000 | | |
| 149 | 26-Dec | | | | 00000 | | | | 00000 | | | | 00000 | 0.240 | 0.250 | 0.130 | 00408 | | | | 00000 | | | | 00000 | | |
| 150 | 27-Dec | | | | 00000 | | | | 00000 | | | | 00000 | 0.260 | 0.250 | 0.130 | 00442 | | | | 00000 | | | | 00000 | | |
| 151 | 28-Dec | | | | 00000 | | | | 00000 | | | | 00000 | 0.270 | 0.250 | 0.130 | 00459 | | | | 00000 | | | | 00000 | | |
| 152 | 29-Dec | | | | 00000 | | | | 00000 | | | | 00000 | 0.280 | 0.250 | 0.130 | 00476 | | | | 00000 | | | | 00000 | | |
| 153 | 30-Dec | | | | 00000 | | | | 00000 | | | | 00000 | 0.280 | 0.250 | 0.130 | 00476 | | | | 00000 | | | | 00000 | | |
| 154 | 31-Dec | | | | 00000 | | | | 00000 | | | | 00000 | 0.290 | 0.260 | 0.130 | 00513 | | | | 00000 | | | | 00000 | | |
| 155 | 1-Jan | | | | 00000 | | | | 00000 | | | | 00000 | 0.300 | 0.270 | 0.130 | 00551 | | | | 00000 | | | | 00000 | | |
| 156 | 2-Jan | | | | 00000 | | | | 00000 | | | | 00000 | 0.320 | 0.290 | 0.130 | 00632 | | | | 00000 | | | | 00000 | | |
| 157 | 3-Jan | | | | 00000 | | | | 00000 | | | | 00000 | 0.320 | 0.290 | 0.130 | 00632 | | | | 00000 | | | | 00000 | | |
| 158 | 4-Jan | | | | 00000 | | | | 00000 | | | | 00000 | 0.320 | 0.300 | 0.130 | 00653 | | | | 00000 | | | | 00000 | | |
| 159 | 5-Jan | | | | 00000 | | | | 00000 | | | | 00000 | 0.110 | 0.200 | 0.090 | 00104 | 0.300 | 0.280 | 0.120 | 00528 | 0.050 | 0.050 | 0.050 | 00007 | | |
| 160 | 6-Jan | | | | 00000 | | | | 00000 | | | | 00000 | 0.180 | 0.200 | 0.100 | 00188 | 0.310 | 0.270 | 0.130 | 00570 | 0.070 | 0.070 | 0.070 | 00018 | | |
| 161 | 7-Jan | | | | 00000 | | | | 00000 | | | | 00000 | 0.180 | 0.200 | 0.100 | 00188 | 0.310 | 0.270 | 0.130 | 00570 | 0.070 | 0.070 | 0.070 | 00018 | | |
| 162 | 8-Jan | | | | 00000 | | | | 00000 | | | | 00000 | 0.170 | 0.200 | 0.100 | 00178 | 0.330 | 0.270 | 0.130 | 00606 | 0.090 | 0.090 | 0.070 | 00030 | | |
| 163 | 9-Jan | | | | 00000 | | | | 00000 | | | | 00000 | 0.170 | 0.200 | 0.100 | 00178 | 0.340 | 0.280 | 0.150 | 00748 | 0.100 | 0.100 | 0.070 | 00037 | | |
| 164 | 10-Jan | | | | 00000 | | | | 00000 | | | | 00000 | 0.170 | 0.200 | 0.100 | 00178 | 0.340 | 0.290 | 0.150 | 00774 | 0.100 | 0.100 | 0.070 | 00037 | | |
| 165 | 11-Jan | | | | 00000 | | | | 00000 | | | | 00000 | 0.180 | 0.210 | 0.100 | 00198 | 0.330 | 0.290 | 0.150 | 00751 | 0.090 | 0.100 | 0.080 | 00038 | | |
| 166 | 12-Jan | | | | 00000 | | | | 00000 | | | | 00000 | 0.170 | 0.210 | 0.100 | 00187 | 0.320 | 0.290 | 0.160 | 00777 | 0.090 | 0.100 | 0.070 | 00033 | 0.070 | 0.080 |
| 167 | 13-Jan | | | | 00000 | | | | 00000 | | | | 00000 | 0.160 | 0.210 | 0.100 | 00176 | 0.330 | 0.300 | 0.160 | 00754 | 0.100 | 0.100 | 0.070 | 00037 | 0.070 | 0.070 |
| 168 | 14-Jan | | | | 00000 | | | | 00000 | | | | 00000 | 0.160 | 0.210 | 0.100 | 00176 | 0.300 | 0.300 | 0.160 | 00754 | 0.100 | 0.100 | 0.070 | 00037 | 0.090 | 0.090 |
| 169 | 15-Jan | | | | 00000 | | | | 00000 | | | | 00000 | 0.160 | 0.210 | 0.100 | 00176 | 0.310 | 0.300 | 0.160 | 00779 | 0.100 | 0.100 | 0.070 | 00037 | 0.100 | 0.100 |
| 170 | 16-Jan | | | | 00000 | | | | 00000 | | | | 00000 | 0.170 | 0.210 | 0.100 | 00187 | 0.330 | 0.310 | 0.160 | 00857 | 0.110 | 0.100 | 0.070 | 00040 | 0.100 | 0.100 |
| 171 | 17-Jan | | | | 00000 | | | | 00000 | | | | 00000 | 0.170 | 0.210 | 0.100 | 00187 | 0.330 | 0.320 | 0.160 | 00885 | 0.110 | 0.110 | 0.070 | 00044 | 0.110 | 0.110 |
| 172 | 18-Jan | | | | 00000 | | | | 00000 | | | | 00000 | 0.180 | 0.200 | 0.100 | 00188 | 0.330 | 0.340 | 0.170 | 00999 | 0.120 | 0.110 | 0.070 | 00048 | 0.110 | 0.110 |
| 173 | 19-Jan | | | | 00000 | | | | 00000 | | | | 00000 | 0.180 | 0.200 | 0.100 | 00188 | 0.320 | 0.350 | 0.170 | 00997 | 0.120 | 0.100 | 0.070 | 00044 | 0.130 | 0.110 |
| 174 | 20-Jan | | | | 00000 | | | | 00000 | | | | 00000 | 0.180 | 0.200 | 0.100 | 00188 | 0.320 | 0.330 | 0.180 | 00995 | 0.130 | 0.100 | 0.070 | 00048 | 0.160 | 0.150 |
| 175 | 21-Jan | | | | 00000 | | | | 00000 | | | | 00000 | 0.180 | 0.200 | 0.100 | 00188 | 0.320 | 0.340 | 0.190 | 01082 | 0.120 | 0.100 | 0.070 | 00044 | 0.170 | 0.160 |
| 176 | 22-Jan | | | | 00000 | | | | 00000 | | | | 00000 | 0.180 | 0.200 | 0.100 | 00188 | 0.320 | 0.350 | 0.190 | 01114 | 0.120 | 0.100 | 0.070 | 00044 | 0.170 | 0.160 |
| 177 | 23-Jan | | | | 00000 | | | | 00000 | | | | 00000 | 0.160 | 0.180 | 0.090 | 00136 | 0.330 | 0.350 | 0.190 | 01149 | 0.120 | 0.100 | 0.070 | 00044 | 0.180 | 0.170 |
| 178 | 24-Jan | | | | 00000 | | | | 00000 | | | | 00000 | 0.160 | 0.180 | 0.090 | 00135 | 0.330 | 0.330 | 0.190 | 01083 | 0.130 | 0.100 | 0.070 | 00048 | 0.180 | 0.200 |
| 179 | 25-Jan | | | | 00000 | | | | 00000 | | | | 00000 | 0.160 | 0.170 | 0.090 | 00128 | 0.330 | 0.340 | 0.200 | 01175 | 0.130 | 0.100 | 0.070 | 00048 | 0.180 | 0.180 |
| 180 | 26-Jan | | | | 00000 | | | | 00000 | | | | 00000 | 0.160 | 0.160 | 0.090 | 00121 | 0.320 | 0.330 | 0.200 | 01106 | 0.120 | 0.100 | 0.070 | 00044 | 0.180 | 0.180 |
| 181 | 27-Jan | | | | 00000 | | | | 00000 | | | | 00000 | 0.150 | 0.150 | 0.090 | 00106 | 0.330 | 0.370 | 0.220 | 01406 | 0.120 | 0.100 | 0.070 | 00044 | 0.200 | 0.200 |
| 182 | 28-Jan | | | | 00000 | | | | 00000 | | | | 00000 | 0.150 | 0.150 | 0.090 | 00106 | 0.330 | 0.370 | 0.220 | 01406 | 0.120 | 0.100 | 0.070 | 00044 | 0.200 | 0.200 |
| 183 | 29-Jan | | | | 00000 | | | | 00000 | | | | 00000 | 0.150 | 0.160 | 0.090 | 00113 | 0.340 | 0.360 | 0.210 | 01346 | 0.120 | 0.100 | 0.070 | 00044 | 0.220 | 0.210 |
| 184 | 30-Jan | | | | 00000 | | | | 00000 | | | | 00000 | 0.140 | 0.150 | 0.090 | 00095 | 0.340 | 0.350 | 0.210 | 01346 | 0.130 | 0.100 | 0.070 | 00048 | 0.220 | 0.210 |
| 185 | 31-Jan | | | | 00000 | | | | 00000 | | | | 00000 | 0.140 | 0.140 | 0.090 | 00092 | 0.350 | 0.350 | 0.210 | 01385 | 0.120 | 0.100 | 0.070 | 00044 | 0.220 | 0.200 |
| 186 | 1-Feb | | | | 00000 | | | | 00000 | | | | 00000 | 0.130 | 0.130 | 0.090 | 00080 | 0.350 | 0.370 | 0.220 | 01491 | 0.120 | 0.100 | 0.070 | 00044 | 0.220 | 0.210 |
| 187 | 2-Feb | | | | 00000 | | | | 00000 | | | | 00000 | 0.120 | 0.130 | 0.080 | 00065 | 0.370 | 0.390 | 0.230 | 01737 | 0.120 | 0.100 | 0.070 | 00044 | 0.250 | 0.210 |
| 188 | 3-Feb | | | | 00000 | | | | 00000 | | | | 00000 | 0.110 | 0.130 | 0.080 | 00060 | 0.390 | 0.390 | 0.230 | 01831 | 0.120 | 0.100 | 0.070 | 00044 | 0.260 | 0.220 |
| 189 | 4-Feb | | | | 00000 | | | | 00000 | | | | 00000 | 0.110 | 0.130 | 0.080 | 00060 | 0.390 | 0.390 | 0.230 | 01831 | 0.110 | 0.090 | 0.070 | 00035 | 0.260 | 0.230 |
| 190 | 5-Feb | | | | 00000 | | | | 00000 | | | | 00000 | 0.110 | 0.130 | 0.080 | 00060 | 0.400 | 0.400 | 0.230 | 01926 | 0.100 | 0.090 | 0.070 | 00033 | 0.270 | 0.240 |
| 191 | 6-Feb | | | | 00000 | | | | 00000 | | | | 00000 | 0.110 | 0.120 | 0.050 | 00035 | 0.410 | 0.400 | 0.230 | 01975 | 0.100 | 0.090 | 0.070 | 00033 | 0.290 | 0.250 |
| 192 | 7-Feb | | | | 00000 | | | | 00000 | | | | 00000 | 0.090 | 0.100 | 0.070 | 00033 | 0.410 | 0.410 | 0.230 | 02024 | 0.100 | 0.090 | 0.070 | 00033 | 0.290 | 0.250 |
| 193 | 8-Feb | | | | 00000 | | | | 00000 | | | | 00000 | 0.090 | 0.090 | 0.070 | 00030 | 0.420 | 0.430 | 0.230 | 02175 | 0.090 | 0.090 | 0.070 | 00030 | 0.310 | 0.240 |
| 194 | 9-Feb | | | | 00000 | | | | 00000 | | | | 00000 | 0.090 | 0.080 | 0.070 | 00026 | 0.420 | 0.430 | 0.230 | 02175 | 0.090 | 0.090 | 0.070 | 00030 | 0.300 | 0.240 |
| 195 | 10-Feb | | | | 00000 | | | | 00000 | | | | 00000 | 0.070 | 0.070 | 0.070 | 00018 | 0.440 | 0.440 | 0.230 | 02331 | 0.070 | 0.070 | 0.070 | 00018 | 0.300 | 0.250 |
| 196 | 11-Feb | | | | 00000 | | | | 00000 | | | | 00000 | 0.070 | 0.070 | 0.070 | 00018 | 0.440 | 0.440 | 0.230 | 02331 | 0.070 | 0.070 | 0.070 | 00018 | 0.290 | 0.250 |

OUJ-516-.xls

| DAY | DATE | Lower ABDOMEN T-1 Ln | Wd | Ht | Vol T-1 | LEG/ABDOMEN T-2 Ln | Wd | Ht | Vol T-2 | RT LEG T-3 Ln | Wd | Ht | Vol T-3 |
|---|---|---|---|---|---|---|---|---|---|---|---|---|---|
| 197 | 12-Feb | | | | 00000 | | | | 00000 | | | | 00000 |
| 198 | 13-Feb | | | | 00000 | | | | 00000 | | | | 00000 |
| 199 | 14-Feb | | | | 00000 | | | | 00000 | | | | 00000 |
| 200 | 15-Feb | | | | 00000 | | | | 00000 | | | | 00000 |
| 201 | 16-Feb | | | | 00000 | | | | 00000 | | | | 00000 |
| 202 | 17-Feb | | | | 00000 | | | | 00000 | | | | 00000 |
| 203 | 18-Feb | | | | 00000 | | | | 00000 | | | | 00000 |
| 204 | 19-Feb | | | | 00000 | | | | 00000 | | | | 00000 |
| 205 | 20-Feb | | | | 00000 | | | | 00000 | | | | 00000 |
| 206 | 21-Feb | | | | 00000 | | | | 00000 | | | | 00000 |
| 207 | 22-Feb | | | | 00000 | | | | 00000 | | | | 00000 |
| 208 | 23-Feb | | | | 00000 | | | | 00000 | | | | 00000 |
| 209 | 24-Feb | | | | 00000 | | | | 00000 | | | | 00000 |
| 210 | 25-Feb | | | | 00000 | | | | 00000 | | | | 00000 |
| 211 | 26-Feb | | | | 00000 | | | | 00000 | | | | 00000 |
| 212 | 27-Feb | | | | 00000 | | | | 00000 | | | | 00000 |
| 213 | 28-Feb | | | | 00000 | | | | 00000 | | | | 00000 |
| 214 | 29-Feb | | | | 00000 | | | | 00000 | | | | 00000 |
| 215 | 1-Mar | | | | 00000 | | | | 00000 | | | | 00000 |
| 216 | 2-Mar | | | | 00000 | | | | 00000 | | | | 00000 |
| 217 | 3-Mar | | | | 00000 | | | | 00000 | | | | 00000 |
| 218 | 4-Mar | | | | 00000 | | | | 00000 | | | | 00000 |
| 219 | 5-Mar | | | | 00000 | | | | 00000 | | | | 00000 |
| 220 | 6-Mar | | | | 00000 | | | | 00000 | | | | 00000 |
| 221 | 7-Mar | | | | 00000 | | | | 00000 | | | | 00000 |
| 222 | 8-Mar | | | | 00000 | | | | 00000 | | | | 00000 |
| 223 | 9-Mar | | | | 00000 | | | | 00000 | | | | 00000 |
| 224 | 10-Mar | | | | 00000 | | | | 00000 | | | | 00000 |
| 225 | 11-Mar | | | | 00000 | | | | 00000 | | | | 00000 |
| 226 | 12-Mar | | | | 00000 | | | | 00000 | | | | 00000 |
| 227 | 13-Mar | | | | 00000 | | | | 00000 | | | | 00000 |
| 228 | 14-Mar | | | | 00000 | | | | 00000 | | | | 00000 |
| 229 | 15-Mar | | | | 00000 | | | | 00000 | | | | 00000 |
| 230 | 16-Mar | | | | 00000 | | | | 00000 | | | | 00000 |
| 231 | 17-Mar | | | | 00000 | | | | 00000 | | | | 00000 |
| 232 | 18-Mar | | | | 00000 | | | | 00000 | | | | 00000 |
| 233 | 19-Mar | | | | 00000 | | | | 00000 | | | | 00000 |
| 234 | 20-Mar | | | | 00000 | | | | 00000 | | | | 00000 |
| 235 | 21-Mar | | | | 00000 | | | | 00000 | | | | 00000 |
| 236 | 22-Mar | | | | 00000 | | | | 00000 | | | | 00000 |
| 237 | 23-Mar | | | | 00000 | | | | 00000 | | | | 00000 |
| 238 | 24-Mar | | | | 00000 | | | | 00000 | | | | 00000 |
| 239 | 25-Mar | | | | 00000 | | | | 00000 | | | | 00000 |
| 240 | 26-Mar | | Died 3 25 96 | | #VALUE! | | Died 3 26 96 | | #VALUE! | | Died 3 26 96 | | #VALUE! |

| DAY | RT NECK T-4 Ln | Wd | Ht | Vol T-4 | SHOLDER T-5 Ln | Wd | Ht | Vol T-5 | LT NECK T-6 Ln | Wd | Ht | Vol T-6 | RT SIDE AR Ln | Wd |
|---|---|---|---|---|---|---|---|---|---|---|---|---|---|---|
| 197 | 0.070 | 0.070 | 0.070 | 00018 | 0.430 | 0.430 | 0.230 | 02226 | 0.070 | 0.070 | 0.070 | 00018 | 0.290 | 0.250 |
| 198 | 0.070 | 0.070 | 0.070 | 00018 | 0.420 | 0.450 | 0.240 | 02375 | 0.070 | 0.070 | 0.070 | 00018 | 0.280 | 0.250 |
| 199 | 0.050 | 0.050 | 0.050 | 00007 | 0.440 | 0.450 | 0.260 | 02755 | 0.050 | 0.050 | 0.050 | 00007 | 0.290 | 0.270 |
| 200 | 0.050 | 0.050 | 0.050 | 00007 | 0.450 | 0.470 | 0.260 | 02879 | 0.050 | 0.050 | 0.050 | 00007 | 0.300 | 0.270 |
| 201 | 0.050 | 0.050 | 0.050 | 00007 | 0.470 | 0.470 | 0.260 | 03007 | 0.050 | 0.050 | 0.050 | 00007 | 0.310 | 0.280 |
| 202 | 0.050 | 0.050 | 0.050 | 00007 | 0.470 | 0.470 | 0.260 | 03007 | 0.050 | 0.050 | 0.050 | 00007 | 0.310 | 0.280 |
| 203 | 0.050 | 0.050 | 0.050 | 00007 | 0.470 | 0.470 | 0.260 | 03007 | 0.050 | 0.050 | 0.050 | 00007 | 0.300 | 0.290 |
| 204 | 0.050 | 0.050 | 0.050 | 00007 | 0.480 | 0.470 | 0.260 | 03071 | 0.050 | 0.050 | 0.050 | 00007 | 0.300 | 0.290 |
| 205 | 0.050 | 0.050 | 0.050 | 00007 | 0.500 | 0.470 | 0.250 | 03198 | 0.030 | 0.030 | 0.030 | 00001 | 0.300 | 0.290 |
| 206 | 0.030 | 0.030 | 0.030 | 00001 | 0.510 | 0.480 | 0.260 | 03332 | 0.030 | 0.030 | 0.030 | 00001 | 0.310 | 0.290 |
| 207 | 0.030 | 0.030 | 0.030 | 00001 | 0.500 | 0.480 | 0.260 | 03267 | 0.030 | 0.030 | 0.030 | 00001 | 0.300 | 0.280 |
| 208 | 0.030 | 0.030 | 0.030 | 00001 | 0.510 | 0.500 | 0.260 | 03471 | 0.030 | 0.030 | 0.030 | 00001 | 0.300 | 0.290 |
| 209 | | | | 00000 | 0.510 | 0.500 | 0.260 | 03471 | | | | 00000 | 0.310 | 0.290 |
| 210 | | | | 00000 | 0.510 | 0.500 | 0.260 | 03471 | | | | 00000 | 0.310 | 0.310 |
| 211 | | | | 00000 | 0.520 | 0.510 | 0.270 | 03748 | | | | 00000 | 0.320 | 0.330 |
| 212 | | | | 00000 | 0.510 | 0.490 | 0.280 | 03663 | | | | 00000 | 0.340 | 0.340 |
| 213 | | | | 00000 | 0.510 | 0.490 | 0.280 | 03663 | | | | 00000 | 0.350 | 0.340 |
| 214 | | | | 00000 | 0.540 | 0.500 | 0.280 | 03958 | | | | 00000 | 0.340 | 0.360 |
| 215 | | | | 00000 | 0.540 | 0.530 | 0.280 | 04195 | | | | 00000 | 0.340 | 0.340 |
| 216 | | | | 00000 | 0.550 | 0.530 | 0.300 | 04578 | | | | 00000 | 0.360 | 0.350 |
| 217 | | | | 00000 | 0.540 | 0.550 | 0.370 | 05753 | | | | 00000 | 0.360 | 0.375 |
| 218 | | | | 00000 | 0.540 | 0.570 | 0.430 | 06929 | | | | 00000 | 0.370 | 0.406 |
| 219 | | | | 00000 | 0.550 | 0.610 | 0.400 | 07025 | | | | 00000 | 0.400 | 0.400 |
| 220 | | | | 00000 | 0.590 | 0.610 | 0.410 | 07725 | | | | 00000 | 0.400 | 0.430 |
| 221 | | | | 00000 | 0.620 | 0.630 | 0.400 | 08179 | | | | 00000 | 0.410 | 0.430 |
| 222 | | | | 00000 | 0.590 | 0.610 | 0.390 | 07348 | | | | 00000 | 0.410 | 0.440 |
| 223 | | | | 00000 | 0.590 | 0.600 | 0.380 | 07042 | | | | 00000 | 0.420 | 0.440 |
| 224 | | | | 00000 | 0.600 | 0.600 | 0.370 | 06973 | | | | 00000 | 0.420 | 0.470 |
| 225 | | | | 00000 | 0.620 | 0.610 | 0.350 | 07128 | | | | 00000 | 0.430 | 0.490 |
| 226 | | | | 00000 | 0.620 | 0.620 | 0.370 | 07446 | | | | 00000 | 0.430 | 0.460 |
| 227 | | | | 00000 | 0.630 | 0.620 | 0.380 | 07770 | | | | 00000 | 0.430 | 0.450 |
| 228 | | | | 00000 | 0.600 | 0.610 | 0.370 | 07089 | | | | 00000 | 0.440 | 0.460 |
| 229 | | | | 00000 | 0.600 | 0.620 | 0.380 | 07400 | | | | 00000 | 0.450 | 0.460 |
| 230 | | | | 00000 | 0.620 | 0.640 | 0.380 | 07894 | | | | 00000 | 0.450 | 0.470 |
| 231 | | | | 00000 | 0.640 | 0.645 | 0.385 | 08320 | | | | 00000 | 0.435 | 0.465 |
| 232 | | | | 00000 | 0.660 | 0.650 | 0.390 | 08759 | | | | 00000 | 0.420 | 0.460 |
| 233 | | | | 00000 | 0.660 | 0.650 | 0.390 | 08759 | | | | 00000 | 0.430 | 0.460 |
| 234 | | | | 00000 | | | | 00000 | | | | 00000 | | |
| 235 | | | | 00000 | | | | 00000 | | | | 00000 | | |
| 236 | | | | 00000 | | | | 00000 | | | | 00000 | | |
| 237 | | | | 00000 | | | | 00000 | | | | 00000 | | |
| 238 | | | | 00000 | | | | 00000 | | | | 00000 | | |
| 239 | | | | 00000 | | | | 00000 | | | | 00000 | | |
| 240 | | Died 3 26 96 | | #VALUE! | | Died 3 26 96 | | #VALUE! | | Died 3 26 96 | | #VALUE! | | Died 3 26 |

OUJ-516-.xls

OUJ-516 Born 2/2/95 OUJ-516 Bor

| DAY | DATE | T-7 Ht | Vol T-7 | RT ARM PIT T-8 Ln | Wd | Ht | Vol T-8 | LT ARM T-9 Ln | Wd | Ht | Vol T-9 | WEIGHT Gr | HEMATO-CRIT-% | TREATMENT PARAMETERS DEVICE | FREQ MHz | POWER | TIME | FREQ MHz | POWER | TIME | DEVICE |
|---|---|---|---|---|---|---|---|---|---|---|---|---|---|---|---|---|---|---|---|---|---|
| 1 | 31-Jul | | 00000 | | | | 00000 | | | | 00000 | 36.76 | | 8662A | 43351830.0 | 0 DBm | 1 Hr | 43351870.0 | 0 DBm | 1 Hr | Type "N" |
| 2 | 1-Aug | | 00000 | | | | 00000 | | | | 00000 | 34.02 | | 8662A | 43351830.0 | 0 DBm | 1 Hr | 43351870.0 | 0 DBm | 1 Hr | Type "N" |
| 3 | 2-Aug | | 00000 | | | | 00000 | | | | 00000 | 33.25 | | 8662A | 43351830.0 | 0 DBm | 1 Hr | 43351870.0 | 0 DBm | 1 Hr | Type "N" |
| 4 | 3-Aug | | 00000 | | | | 00000 | | | | 00000 | 31.88 | | 8662A | 43351830.0 | 0 DBm | 1 Hr | 43351870.0 | 0 DBm | 1 Hr | Type "N" |
| 5 | 4-Aug | | 00000 | | | | 00000 | | | | 00000 | 32.95 | 47 | 8662A | 43351830.0 | 0 DBm | 1 Hr | 43351870.0 | 0 DBm | 1 Hr | Type "N" |
| 6 | 5-Aug | | 00000 | | | | 00000 | | | | 00000 | 31.11 | | 8662A | 43351830.0 | 0 DBm | 1 Hr | 43351870.0 | 0 DBm | 1 Hr | Type "N" |
| 7 | 6-Aug | | 00000 | | | | 00000 | | | | 00000 | 31.12 | | 8662A | 43351830.0 | 0 DBm | 1 Hr | 43351870.0 | 0 DBm | 1 Hr | Type "N" |
| 8 | 7-Aug | | 00000 | | | | 00000 | | | | 00000 | 32.70 | | 8662A | 43351830.0 | 0 DBm | 1 Hr | 43351870.0 | 0 DBm | 1 Hr | Type "N" |
| 9 | 8-Aug | | 00000 | | | | 00000 | | | | 00000 | 31.31 | | 8662A | 43351830.0 | 0 DBm | 1 Hr | 43351870.0 | 0 DBm | 1 Hr | Type "E &F" |
| 10 | 9-Aug | | 00000 | | | | 00000 | | | | 00000 | 31.45 | | 8662A | 43351830.0 | 0 DBm | 1 Hr | 43351870.0 | 0 DBm | 1 Hr | Type "E &F" |
| 11 | 10-Aug | | 00000 | | | | 00000 | | | | 00000 | 30.68 | 43 | 8662A | 43351830.0 | 0 DBm | 1 Hr | 43351870.0 | 0 DBm | 1 Hr | Type "E &F" |
| 12 | 11-Aug | | 00000 | | | | 00000 | | | | 00000 | 30.20 | | 8662A | 43351830.0 | 0 DBm | 1 Hr | 43351870.0 | 0 DBm | 1 Hr | Type "E &F" |
| 13 | 12-Aug | | 00000 | | | | 00000 | | | | 00000 | 30.62 | | 8662A | 43351830.0 | 0 DBm | 1 Hr | 43351870.0 | 0 DBm | 1 Hr | Type "E &F" |
| 14 | 13-Aug | | 00000 | | | | 00000 | | | | 00000 | 31.04 | | 8662A | 43351830.0 | 0 DBm | 1 Hr | 43351870.0 | 0 DBm | 1 Hr | Type "E &F" |
| 15 | 14-Aug | | 00000 | | | | 00000 | | | | 00000 | 31.44 | | 8662A | 43351830.0 | 0 DBm | 1 Hr | 43351870.0 | 0 DBm | 1 Hr | Type "E &F" |
| 16 | 15-Aug | | 00000 | | | | 00000 | | | | 00000 | 32.77 | | 8662A | 43351830.0 | 0 DBm | 1 Hr | 43351870.0 | 0 DBm | 1 Hr | Type "E &F" |
| 17 | 16-Aug | | 00000 | | | | 00000 | | | | 00000 | 31.77 | | 8662A | 43351830.0 | 0 DBm | 1 Hr | 43351870.0 | 0 DBm | 1 Hr | Type "E &F" |
| 18 | 17-Aug | | 00000 | | | | 00000 | | | | 00000 | 32.08 | | 8662A | 43351830.0 | 0 DBm | 1 Hr | 43351870.0 | 0 DBm | 1 Hr | Type "E &F" |
| 19 | 18-Aug | | 00000 | | | | 00000 | | | | 00000 | 32.00 | | 8662A | 43351830.0 | 0 DBm | 1 Hr | 43351870.0 | 0 DBm | 1 Hr | Type "E &F" |
| 20 | 19-Aug | | 00000 | | | | 00000 | | | | 00000 | 31.78 | 45 | 8662A | 43351830.0 | 0 DBm | 1 Hr | 43351870.0 | 0 DBm | 1 Hr | Type "E &F" |
| 21 | 20-Aug | | 00000 | | | | 00000 | | | | 00000 | 31.59 | | 8662A | 43351830.0 | 0 DBm | 1 Hr | 43351870.0 | 0 DBm | 1 Hr | Type "E &F" |
| 22 | 21-Aug | | 00000 | | | | 00000 | | | | 00000 | 31.44 | | 8662A | 43351830.0 | 0 DBm | 1 Hr | 43351870.0 | 0 DBm | 1 Hr | Type "E &F" |
| 23 | 22-Aug | | 00000 | | | | 00000 | | | | 00000 | 31.40 | | 8662A | 43351830.0 | 0 DBm | 1 Hr | 43351870.0 | 0 DBm | 1 Hr | Type "E &F" |
| 24 | 23-Aug | | 00000 | | | | 00000 | | | | 00000 | 32.17 | | 8662A | 43351830.0 | 0 DBm | 1 Hr | 43351870.0 | 0 DBm | 1 Hr | Type "E &F" |
| 25 | 24-Aug | | 00000 | | | | 00000 | | | | 00000 | 31.64 | | 8662A | 43351830.0 | 0 DBm | 1 Hr | 43351870.0 | 0 DBm | 1 Hr | Type "E &F" |
| 26 | 25-Aug | | 00000 | | | | 00000 | | | | 00000 | 31.31 | 43 | 8662A | 43351830.0 | 0 DBm | 1 Hr | 43351870.0 | 0 DBm | 1 Hr | Type "E &F" |
| 27 | 26-Aug | | 00000 | | | | 00000 | | | | 00000 | 31.36 | | 8662A | 43351830.0 | 0 DBm | 1 Hr | 43351870.0 | 0 DBm | 1 Hr | Type "E &F" |
| 28 | 27-Aug | | 00000 | | | | 00000 | | | | 00000 | 31.65 | | 8662A | 43351830.0 | 0 DBm | 1 Hr | 43351870.0 | 0 DBm | 1 Hr | Type "E &F" |
| 29 | 28-Aug | | 00000 | | | | 00000 | | | | 00000 | 32.03 | | 8662A | 43351830.0 | 0 DBm | 1 Hr | 43351870.0 | 0 DBm | 1 Hr | Type "E &F" |
| 30 | 29-Aug | | 00000 | | | | 00000 | | | | 00000 | 32.28 | | 8662A | 43351830.0 | 0 DBm | 1 Hr | 43351870.0 | 0 DBm | 1 Hr | Type "E &F" |
| 31 | 30-Aug | | 00000 | | | | 00000 | | | | 00000 | 34.15 | | 8662A | 43351830.0 | 0 DBm | 1 Hr | 43351870.0 | 0 DBm | 1 Hr | Type "E &F" |
| 32 | 31-Aug | | 00000 | | | | 00000 | | | | 00000 | 32.00 | | 8662A | 43351830.0 | 0 DBm | 1 Hr | 43351870.0 | 0 DBm | 1 Hr | Type "E &F" |
| 33 | 1-Sep | | 00000 | | | | 00000 | | | | 00000 | 31.22 | | 8662A | 43351830.0 | 0 DBm | 1/2 Hr | 43351870.0 | 0 DBm | 1/2 Hr | Type "E &F" |
| 34 | 2-Sep | | 00000 | | | | 00000 | | | | 00000 | 31.87 | | 8662A | 43351830.0 | 0 DBm | 1/2 Hr | 43351870.0 | 0 DBm | 1/2 Hr | Type "E &F" |
| 35 | 3-Sep | | 00000 | | | | 00000 | | | | 00000 | 31.41 | | 8662A | 43351830.0 | 0 DBm | 1/2 Hr | 43351870.0 | 0 DBm | 1/2 Hr | Type "E &F" |
| 36 | 4-Sep | | 00000 | | | | 00000 | | | | 00000 | 31.05 | | 8662A | 43351830.0 | 0 DBm | 1/2 Hr | 43351870.0 | 0 DBm | 1/2 Hr | Type "E &F" |
| 37 | 5-Sep | | 00000 | | | | 00000 | | | | 00000 | 31.29 | 45 | 8662A | 43351830.0 | 0 DBm | 1/2 Hr | 43351870.0 | 0 DBm | 1/2 Hr | Type "E &F" |
| 38 | 6-Sep | | 00000 | | | | 00000 | | | | 00000 | 30.68 | | 8662A | 43351830.0 | 0 DBm | 1/2 Hr | 43351870.0 | 0 DBm | 1/2 Hr | Type "E &F" |
| 39 | 7-Sep | | 00000 | | | | 00000 | | | | 00000 | 30.85 | | 8662A | 43351830.0 | 0 DBm | 1/2 Hr | 43351870.0 | 0 DBm | 1/2 Hr | Type "E &F" |
| 40 | 8-Sep | | 00000 | | | | 00000 | | | | 00000 | 29.86 | | 8662A | 43351830.0 | 0 DBm | 1/2 Hr | 43351870.0 | 0 DBm | 1/2 Hr | Type "E &F" |
| 41 | 9-Sep | | 00000 | | | | 00000 | | | | 00000 | 31.08 | | 8662A | 43351830.0 | 0 DBm | 1/2 Hr | 43351870.0 | 0 DBm | 1/2 Hr | Type "E &F" |
| 42 | 10-Sep | | 00000 | | | | 00000 | | | | 00000 | 31.45 | | 8662A | 43351830.0 | 0 DBm | 1/2 Hr | 43351870.0 | 0 DBm | 1/2 Hr | Type "E &F" |
| 43 | 11-Sep | | 00000 | | | | 00000 | | | | 00000 | 31.96 | 45 | 8662A | 43351830.0 | 0 DBm | 1/2 Hr | 43351870.0 | 0 DBm | 1/2 Hr | Type "E &F" |
| 44 | 12-Sep | | 00000 | | | | 00000 | | | | 00000 | 31.38 | | 8662A | 43351830.0 | 0 DBm | 1/2 Hr | 43351870.0 | 0 DBm | 1/2 Hr | Type "E &F" |
| 45 | 13-Sep | | 00000 | | | | 00000 | | | | 00000 | 32.54 | | 8662A | 43351830.0 | 0 DBm | 1/2 Hr | 43351870.0 | 0 DBm | 1/2 Hr | Type "E &F" |
| 46 | 14-Sep | | 00000 | | | | 00000 | | | | 00000 | 30.61 | | 8662A | 43351830.0 | 0 DBm | 1 Hr | 43351870.0 | 0 DBm | 1 Hr | Type "E &F" |
| 47 | 15-Sep | | 00000 | | | | 00000 | | | | 00000 | 29.84 | | 8662A | 43351830.0 | 0 DBm | 1 Hr | 43351870.0 | 0 DBm | 1 Hr | Type "E &F" |
| 48 | 16-Sep | | 00000 | | | | 00000 | | | | 00000 | 30.36 | | 8662A | 43351830.0 | 0 DBm | 1 Hr | 43351870.0 | 0 DBm | 1 Hr | Type "E &F" |
| 49 | 17-Sep | | 00000 | | | | 00000 | | | | 00000 | 31.00 | | 8662A | 43351830.0 | 0 DBm | 1 Hr | 43351870.0 | 0 DBm | 1 Hr | Type "E &F" |
| 50 | 18-Sep | | 00000 | | | | 00000 | | | | 00000 | 31.60 | 37 | 8662A | 43351830.0 | 0 DBm | 1 Hr | 43351870.0 | 0 DBm | 1 Hr | Type "E &F" |
| 51 | 19-Sep | | 00000 | | | | 00000 | | | | 00000 | 30.85 | | 8662A | 43351830.0 | 0 DBm | 1 Hr | 43351870.0 | 0 DBm | 1 Hr | Type "E &F" |
| 52 | 20-Sep | | 00000 | | | | 00000 | | | | 00000 | 28.69 | | 8662A | 43351830.0 | 0 DBm | 1 Hr | 43351870.0 | 0 DBm | 1 Hr | Type "E &F" |
| 53 | 21-Sep | | 00000 | | | | 00000 | | | | 00000 | 28.20 | | 8662A | 43351830.0 | 0 DBm | 1 Hr | 43351870.0 | 0 DBm | 1 Hr | Type "E &F" |
| 54 | 22-Sep | | 00000 | | | | 00000 | | | | 00000 | 28.49 | | 8662A | 43351830.0 | 0 DBm | 1 Hr | 43351870.0 | 0 DBm | 1 Hr | Type "E &F" |
| 55 | 23-Sep | | 00000 | | | | 00000 | | | | 00000 | 25.08 | | 8662A | 43351830.0 | 0 DBm | 1 Hr | 43351870.0 | 0 DBm | 1 Hr | Type "E &F" |
| 56 | 24-Sep | | 00000 | | | | 00000 | | | | 00000 | 29.44 | | 8662A | 43351830.0 | 0 DBm | 1 Hr | 43351870.0 | 0 DBm | 1 Hr | Type "E &F" |
| 57 | 25-Sep | | 00000 | | | | 00000 | | | | 00000 | 29.81 | | 8662A | 43351830.0 | 0 DBm | 1 Hr | 43351870.0 | 0 DBm | 1 Hr | Type "E &F" |
| 58 | 26-Sep | | 00000 | | | | 00000 | | | | 00000 | 30.03 | 43 | 8662A | 43351830.0 | 0 DBm | 1 Hr | 43351870.0 | 0 DBm | 1 Hr | Type "E &F" |
| 59 | 27-Sep | | 00000 | | | | 00000 | | | | 00000 | 29.66 | | 8662A | 43351830.0 | 0 DBm | 1 Hr | 43351870.0 | 0 DBm | 1 Hr | Type "E &F" |
| 60 | 28-Sep | | 00000 | | | | 00000 | | | | 00000 | 28.56 | | 8662A | 43351830.0 | 0 DBm | 1 Hr | 43351870.0 | 0 DBm | 1 Hr | Type "E &F" |
| 61 | 29-Sep | | 00000 | | | | 00000 | | | | 00000 | 28.61 | | 8662A | 43351830.0 | 0 DBm | 1 Hr | 43351870.0 | 0 DBm | 1 Hr | Type "E &F" |
| 62 | 30-Sep | | 00000 | | | | 00000 | | | | 00000 | 29.41 | | 8662A | 43351830.0 | 0 DBm | 1 Hr | 43351870.0 | 0 DBm | 1 Hr | Type "E &F" |
| 63 | 1-Oct | | 00000 | | | | 00000 | | | | 00000 | 29.11 | | 8662A | 43351830.0 | 0 DBm | 1 Hr | 43351870.0 | 0 DBm | 1 Hr | Type "E &F" |
| 64 | 2-Oct | | 00000 | | | | 00000 | | | | 00000 | 28.81 | 45 | 8662A | 43351830.0 | 0 DBm | 1 Hr | 43351870.0 | 0 DBm | 1 Hr | Type "E &F" |

4/11/97 Page 5 OUJ-516-.xls

OUJ-516-.xls

| DAY | DATE | T-7 Ht | Vol T-7 | RT ARM PIT T-8 Ln | RT ARM PIT T-8 Wd | RT ARM PIT T-8 Ht | Vol T-8 | LT ARM T-9 Ln | LT ARM T-9 Wd | LT ARM T-9 Ht | Vol T-9 | WEIGHT Gr | HEMATO-CRIT % | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|---|---|
| 65 | 3-Oct | | 00000 | | | | 00000 | | | | 00000 | 27 84 | | 8662A | 43351830 0 | 0 DBm | 1 Hr | 43351870 0 | 0 DBm | 1 Hr | Type "E &F" |
| 66 | 4-Oct | | 00000 | | | | 00000 | | | | 00000 | 27 76 | | 8662A | 43351830 0 | 0 DBm | 1 Hr | 43351870 0 | 0 DBm | 1 Hr | Type "E &F" |
| 67 | 5-Oct | | 00000 | | | | 00000 | | | | 00000 | 27 55 | | 8662A | 43351830 0 | 0 DBm | 1 Hr | 43351870 0 | 0 DBm | 1 Hr | Type "E &F" |
| 68 | 6-Oct | | 00000 | | | | 00000 | | | | 00000 | 27 64 | | 8662A | | | | 43351871 3 | 0 DBm | 1 Hr | Type "E &F" |
| 69 | 7-Oct | | 00000 | | | | 00000 | | | | 00000 | 28 42 | | 8662A | | | | 43351871 3 | 0 DBm | 1 Hr | Type "E &F" |
| 70 | 8-Oct | | 00000 | | | | 00000 | | | | 00000 | 28 57 | | 8662A | | | | 43351871 3 | 0 DBm | 1 Hr | Type "E &F" |
| 71 | 9-Oct | | 00000 | | | | 00000 | | | | 00000 | 28 75 | | 8662A | | | | 43351871 3 | 0 DBm | 1 Hr | Type "E &F" |
| 72 | 10-Oct | | 00000 | | | | 00000 | | | | 00000 | 28 86 | 46 | | NO TREATMENT | | | NO TREATMENT | | | |
| 73 | 11-Oct | | 00000 | | | | 00000 | | | | 00000 | 28 35 | | | NO TREATMENT | | | NO TREATMENT | | | |
| 74 | 12-Oct | | 00000 | | | | 00000 | | | | 00000 | 28 56 | | | NO TREATMENT | | | NO TREATMENT | | | |
| 75 | 13-Oct | | 00000 | | | | 00000 | | | | 00000 | 29 14 | | | NO TREATMENT | | | NO TREATMENT | | | |
| 76 | 14-Oct | | 00000 | | | | 00000 | | | | 00000 | 29 50 | | | NO TREATMENT | | | NO TREATMENT | | | |
| 77 | 15-Oct | | 00000 | | | | 00000 | | | | 00000 | 29 65 | | | NO TREATMENT | | | NO TREATMENT | | | |
| 78 | 16-Oct | | 00000 | | | | 00000 | | | | 00000 | 29 80 | 45 | | NO TREATMENT | | | NO TREATMENT | | | |
| 79 | 17-Oct | | 00000 | | | | 00000 | | | | 00000 | 29 41 | | | NO TREATMENT | | | NO TREATMENT | | | |
| 80 | 18-Oct | | 00000 | | | | 00000 | | | | 00000 | 29 62 | | | NO TREATMENT | | | NO TREATMENT | | | |
| 81 | 19-Oct | | 00000 | | | | 00000 | | | | 00000 | 28 31 | | | NO TREATMENT | | | NO TREATMENT | | | |
| 82 | 20-Oct | | 00000 | | | | 00000 | | | | 00000 | 28 52 | | | NO TREATMENT | | | NO TREATMENT | | | |
| 83 | 21-Oct | | 00000 | | | | 00000 | | | | 00000 | 27 52 | | | NO TREATMENT | | | NO TREATMENT | | | |
| 84 | 22-Oct | | 00000 | | | | 00000 | | | | 00000 | 28 05 | | | NO TREATMENT | | | NO TREATMENT | | | |
| 85 | 23-Oct | | 00000 | | | | 00000 | | | | 00000 | 28 56 | 42 | | NO TREATMENT | | | NO TREATMENT | | | |
| 86 | 24-Oct | | 00000 | | | | 00000 | | | | 00000 | 28 05 | | | NO TREATMENT | | | NO TREATMENT | | | |
| 87 | 25-Oct | | 00000 | | | | 00000 | | | | 00000 | 28 00 | | | NO TREATMENT | | | NO TREATMENT | | | |
| 88 | 26-Oct | | 00000 | | | | 00000 | | | | 00000 | 27 38 | | | NO TREATMENT | | | NO TREATMENT | | | |
| 89 | 27-Oct | | 00000 | | | | 00000 | | | | 00000 | 27 78 | | | NO TREATMENT | | | NO TREATMENT | | | |
| 90 | 28-Oct | | 00000 | | | | 00000 | | | | 00000 | 28 38 | 43 | | NO TREATMENT | | | NO TREATMENT | | | |
| 91 | 29-Oct | | 00000 | | | | 00000 | | | | 00000 | 28 72 | | | NO TREATMENT | | | NO TREATMENT | | | |
| 92 | 30-Oct | | 00000 | | | | 00000 | | | | 00000 | 29 04 | | | NO TREATMENT | | | NO TREATMENT | | | |
| 93 | 31-Oct | | 00000 | | | | 00000 | | | | 00000 | 28 47 | | | NO TREATMENT | | | NO TREATMENT | | | |
| 94 | 1-Nov | | 00000 | | | | 00000 | | | | 00000 | 28 52 | | | NO TREATMENT | | | NO TREATMENT | | | |
| 95 | 2-Nov | | 00000 | | | | 00000 | | | | 00000 | 27 17 | | 8662A | 43322492 0 | 0 DBm | 1 Hr | 43353850 0 | 0 DBm | 1 Hr | Type "P" |
| 96 | 3-Nov | | 00000 | | | | 00000 | | | | 00000 | 28 39 | | 8662A | 43322492 0 | 0 DBm | 1 Hr | 43353850 0 | 0 DBm | 1 Hr | Type "P" |
| 97 | 4-Nov | | 00000 | | | | 00000 | | | | 00000 | 28 11 | 40 | 8662A | 43322492 0 | 0 DBm | 1 Hr | 43353850 0 | 0 DBm | 1 Hr | Type "P" |
| 98 | 5-Nov | | 00000 | | | | 00000 | | | | 00000 | 28 45 | | 8662A | 43322492 0 | 0 DBm | 1 Hr | 43353850 0 | 0 DBm | 1 Hr | Type "P" |
| 99 | 6-Nov | | 00000 | | | | 00000 | | | | 00000 | 28 84 | | 8662A | 43322492 0 | 0 DBm | 1 Hr | 43353850 0 | 0 DBm | 1 Hr | Type "P" |
| 100 | 7-Nov | | 00000 | | | | 00000 | | | | 00000 | 28 30 | | 8662A | 43322492 0 | 0 DBm | 1 Hr | 43353850 0 | 0 DBm | 1 Hr | Type "P" |
| 101 | 8-Nov | | 00000 | | | | 00000 | | | | 00000 | 28 32 | | 8662A | 43322492 0 | 0 DBm | 1 Hr | 43353850 0 | 0 DBm | 1 Hr | Type "P" |
| 102 | 9-Nov | | 00000 | | | | 00000 | | | | 00000 | 28 00 | | 8662A | 43346000 0 | 0 DBm | 1 Hr | 43322480 0 | 0 DBm | 1 Hr | Type "P" |
| 103 | 10-Nov | | 00000 | | | | 00000 | | | | 00000 | 27 65 | | 8662A | 43346000 0 | 0 DBm | 1 Hr | 43322480 0 | 0 DBm | 1 Hr | Type "P" |
| 104 | 11-Nov | | 00000 | | | | 00000 | | | | 00000 | 27 58 | 38 | 8662A | 43346000 0 | 0 DBm | 1 Hr | 43322480 0 | 0 DBm | 1 Hr | Type "P" |
| 105 | 12-Nov | | 00000 | | | | 00000 | | | | 00000 | 27 85 | | 8662A | 43346000 0 | 0 DBm | 1 Hr | 43322480 0 | 0 DBm | 1 Hr | Type "P" |
| 106 | 13-Nov | | 00000 | | | | 00000 | | | | 00000 | 28 35 | | 8662A | 43346000 0 | 0 DBm | 1 Hr | 43322480 0 | 0 DBm | 1 Hr | Type "P" |
| 107 | 14-Nov | | 00000 | | | | 00000 | | | | 00000 | 28 51 | | 8662A | 43346000 0 | 0 DBm | 1 Hr | 43322480 0 | 0 DBm | 1 Hr | Type "P" |
| 108 | 15-Nov | | 00000 | | | | 00000 | | | | 00000 | 28 42 | | 8662A | 43346000 0 | 0 DBm | 1 Hr | 43322480 0 | 0 DBm | 1 Hr | Type "P" |
| 109 | 16-Nov | | 00000 | | | | 00000 | | | | 00000 | 28 09 | | 8662A | 43346000 0 | 0 DBm | 1 Hr | 43322480 0 | 0 DBm | 1 Hr | Type "P" |
| 110 | 17-Nov | | 00000 | | | | 00000 | | | | 00000 | 28 06 | | 8662A | 43346000 0 | 0 DBm | 1 Hr | 43322480 0 | 0 DBm | 1 Hr | Type "P" |
| 111 | 18-Nov | | 00000 | | | | 00000 | | | | 00000 | 28 00 | 43 | 8662A | 43353850 0 | 0 DBm | 1 Hr | 43322485 0 | 0 DBm | 1 Hr | Type "P" |
| 112 | 19-Nov | | 00000 | | | | 00000 | | | | 00000 | 28 48 | | 8662A | 43353850 0 | 0 DBm | 1 Hr | 43322485 0 | 0 DBm | 1 Hr | Type "P" |
| 113 | 20-Nov | | 00000 | | | | 00000 | | | | 00000 | 28 95 | | 8662A | 43353850 0 | 0 DBm | 1 Hr | 43322485 0 | 0 DBm | 1 Hr | Type "P" |
| 114 | 21-Nov | | 00000 | | | | 00000 | | | | 00000 | 29 06 | | 8662A | 43353850 0 | 0 DBm | 1 Hr | 43322485 0 | 0 DBm | 1 Hr | Type "P" |
| 115 | 22-Nov | | 00000 | | | | 00000 | | | | 00000 | 28 58 | | 8662A | 43353850 0 | 0 DBm | 1 Hr | 43322485 0 | 0 DBm | 1 Hr | Type "P" |
| 116 | 23-Nov | | 00000 | | | | 00000 | | | | 00000 | 28 22 | | 8662A | 43353850 0 | 0 DBm | 1 Hr | 43322485 0 | 0 DBm | 1 Hr | Type "P" |
| 117 | 24-Nov | | 00000 | | | | 00000 | | | | 00000 | 27 92 | | 8662A | 43353850 0 | 0 DBm | 1 Hr | 43322485 0 | 0 DBm | 1 Hr | Type "P" |
| 118 | 25-Nov | | 00000 | | | | 00000 | | | | 00000 | 28 39 | 44 | 8662A | 43353850 0 | 0 DBm | 1 Hr | 43322485 0 | 0 DBm | 1 Hr | Type "P" |
| 119 | 26-Nov | | 00000 | | | | 00000 | | | | 00000 | 28 65 | | 8662A | 43353850 0 | 0 DBm | 1 Hr | 43322485 0 | 0 DBm | 1 Hr | Type "P" |
| 120 | 27-Nov | | 00000 | | | | 00000 | | | | 00000 | 28 90 | | 8662A | 43353850 0 | 0 DBm | 1 Hr | 43322485 0 | 0 DBm | 1 Hr | Type "P" |
| 121 | 28-Nov | | 00000 | | | | 00000 | | | | 00000 | 28 29 | | 8662A | 43351853 0 | 0 DBm | 1 Hr | 43351871 0 | 0 DBm | 1 Hr | Type "P" |
| 122 | 29-Nov | | 00000 | | | | 00000 | | | | 00000 | 28 40 | | 8662A | 43351853 0 | 0 DBm | 1 Hr | 43351871 0 | 0 DBm | 1 Hr | Type "P" |
| 123 | 30-Nov | | 00000 | | | | 00000 | | | | 00000 | 28 09 | | 8662A | 43351853 0 | 0 DBm | 1 Hr | 43351871 0 | 0 DBm | 1 Hr | Type "P" |
| 124 | 1-Dec | | 00000 | | | | 00000 | | | | 00000 | 28 28 | | | NO TREATMENT | | | NO TREATMENT | | | |
| 125 | 2-Dec | | 00000 | | | | 00000 | | | | 00000 | 28 60 | | | NO TREATMENT | | | NO TREATMENT | | | |
| 126 | 3-Dec | | 00000 | | | | 00000 | | | | 00000 | 28 95 | | | NO TREATMENT | | | NO TREATMENT | | | |
| 127 | 4-Dec | | 00000 | | | | 00000 | | | | 00000 | 29 25 | 43 | | NO TREATMENT | | | NO TREATMENT | | | |
| 128 | 5-Dec | | 00000 | | | | 00000 | | | | 00000 | 28 78 | | | NO TREATMENT | | | NO TREATMENT | | | |
| 129 | 6-Dec | | 00000 | | | | 00000 | | | | 00000 | 29 13 | | | NO TREATMENT | | | NO TREATMENT | | | |
| 130 | 7-Dec | | 00000 | | | | 00000 | | | | 00000 | 28 72 | | | NO TREATMENT | | | NO TREATMENT | | | |

| DAY | DATE | T-7 Ht | Vol T-7 | RT ARM PIT T-8 Ln | RT ARM PIT T-8 Wd | RT ARM PIT T-8 Ht | Vol T-8 | LT ARM T-9 Ln | LT ARM T-9 Wd | LT ARM T-9 Ht | Vol T-9 | WEIGHT Gr | HEMATO-CRIT-% | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|---|---|
| 131 | 8-Dec | | 00000 | | | | 00000 | | | | 00000 | 28 61 | | | NO TREATMENT | | | NO TREATMENT | | | |
| 132 | 9-Dec | | 00000 | | | | 00000 | | | | 00000 | 28 46 | 39 | | NO TREATMENT | | | NO TREATMENT | | | |
| 133 | 10-Dec | | 00000 | | | | 00000 | | | | 00000 | 28 80 | | | NO TREATMENT | | | NO TREATMENT | | | |
| 134 | 11-Dec | | 00000 | | | | 00000 | | | | 00000 | 28 18 | | | NO TREATMENT | | | NO TREATMENT | | | |
| 135 | 12-Dec | | 00000 | | | | 00000 | | | | 00000 | 28 18 | | | NO TREATMENT | | | NO TREATMENT | | | |
| 136 | 13-Dec | | 00000 | | | | 00000 | | | | 00000 | 28 08 | | | NO TREATMENT | | | NO TREATMENT | | | |
| 137 | 14-Dec | | 00000 | | | | 00000 | | | | 00000 | 27 73 | | | NO TREATMENT | | | NO TREATMENT | | | |
| 138 | 15-Dec | | 00000 | | | | 00000 | | | | 00000 | 28 21 | | 8662A | 43351830 0 | 0 DBm | 1 Hr | 43351870 0 | 0 DBm | 1 Hr | Type "P" |
| 139 | 16-Dec | | 00000 | | | | 00000 | | | | 00000 | 28 00 | 35 | 8662A | 43351830 0 | 0 DBm | 1 Hr | 43351870 0 | 0 DBm | 1 Hr | Type "P" |
| 140 | 17-Dec | | 00000 | | | | 00000 | | | | 00000 | 27 97 | | 8662A | 43351830 0 | 0 DBm | 1 Hr | 43351870 0 | 0 DBm | 1 Hr | Type "P" |
| 141 | 18-Dec | | 00000 | | | | 00000 | | | | 00000 | 27 94 | | 8662A | 43351853 0 | 0 DBm | 1 Hr | 43351871 0 | 0 DBm | 1 Hr | Type "P" |
| 142 | 19-Dec | | 00000 | | | | 00000 | | | | 00000 | 27 78 | | 8662A | 43322485 0 | 0 DBm | 1 Hr | 43351871 0 | 0 DBm | 1 Hr | Type "P" |
| 143 | 20-Dec | | 00000 | | | | 00000 | | | | 00000 | 27 58 | | 8662A | 43322460 0 | 0 DBm | 1 Hr | 43353000 0 | 0 DBm | 1 Hr | Type "P" |
| 144 | 21-Dec | | 00000 | | | | 00000 | | | | 00000 | 28 75 | | 8662A | 43346000 0 | 0 DBm | 1 Hr | 43322480 0 | 0 DBm | 1 Hr | Type "P" |
| 145 | 22-Dec | | 00000 | | | | 00000 | | | | 00000 | 27 33 | | 8662A | 43346000 0 | 0 DBm | 1 Hr | 43322480 0 | 0 DBm | 1 Hr | Type "P" |
| 146 | 23-Dec | | 00000 | | | | 00000 | | | | 00000 | 26 77 | 37 | 8662A | 43346000 0 | 0 DBm | 1 Hr | 43322480 0 | 0 DBm | 1 Hr | Type "P" |
| 147 | 24-Dec | | 00000 | | | | 00000 | | | | 00000 | 27 00 | | 8662A | 43346000 0 | 0 DBm | 1 Hr | 43322480 0 | 0 DBm | 1 Hr | Type "P" |
| 148 | 25-Dec | | 00000 | | | | 00000 | | | | 00000 | 27 40 | | 8662A | 43346000 0 | 0 DBm | 1 Hr | 43322480 0 | 0 DBm | 1 Hr | Type "P" |
| 149 | 26-Dec | | 00000 | | | | 00000 | | | | 00000 | 28 73 | | 8662A | 43346000 0 | 0 DBm | 1 Hr | 43322480 0 | 0 DBm | 1 Hr | Type "P" |
| 150 | 27-Dec | | 00000 | | | | 00000 | | | | 00000 | 28 47 | | 8662A | 43346000 0 | 0 DBm | 1 Hr | 43322480 0 | 0 DBm | 1 Hr | Type "O" |
| 151 | 28-Dec | | 00000 | | | | 00000 | | | | 00000 | 28 22 | | 8662A | 43353800 0 | 0 DBm | 1 Hr | 43353800 0 | 0 DBm | 1 Hr | Type "O" |
| 152 | 29-Dec | | 00000 | | | | 00000 | | | | 00000 | 28 73 | | 8662A | 43322485 0 | 0 DBm | 1 Hr | 43322485 0 | 0 DBm | 1 Hr | Type "O" |
| 153 | 30-Dec | | 00000 | | | | 00000 | | | | 00000 | 28 26 | 44 | 8662A | 43351871 3 | 0 DBm | 1 Hr | 43351830 0 | 0 DBm | 1 Hr | Type "O" |
| 154 | 31-Dec | | 00000 | | | | 00000 | | | | 00000 | 28 70 | | 8662A | 43351871 3 | 0 DBm | 1 Hr | 43351830 0 | 0 DBm | 1 Hr | Type "Q" |
| 155 | 1-Jan | | 00000 | | | | 00000 | | | | 00000 | 29 12 | | 8662A | 43353800 0 | 0 DBm | 1 Hr | 43322485 0 | 0 DBm | 1 Hr | Type "O" |
| 156 | 2-Jan | | 00000 | | | | 00000 | | | | 00000 | 28 35 | | 8662A | 43353800 0 | 0 DBm | 1 Hr | 43353800 0 | 0 DBm | 1 Hr | Type "O" |
| 157 | 3-Jan | | 00000 | | | | 00000 | | | | 00000 | 28 32 | | 8662A | 43353850 0 | 0 DBm | 1 Hr | 43353850 0 | 0 DBm | 1 Hr | Type "O" |
| 158 | 4-Jan | | 00000 | | | | 00000 | | | | 00000 | 28 27 | | 8662A | 43346000 0 | 0 DBm | 1 Hr | 43346000 0 | 0 DBm | 1 Hr | Type "O" |
| 159 | 5-Jan | | 00000 | | | | 00000 | | | | 00000 | 28 85 | | 8662A | 43351830 0 | 0 DBm | 1 Hr | 43351870 0 | 0 DBm | 1 Hr | Type "O" |
| 160 | 6-Jan | | 00000 | | | | 00000 | | | | 00000 | 27 86 | 42 | 8662A | 43351830 0 | 0 DBm | 1 Hr | 43351870 0 | 0 DBm | 1 Hr | Type "R" |
| 161 | 7-Jan | | 00000 | | | | 00000 | | | | 00000 | 27 65 | | 8662A | 43351830 0 | 0 DBm | 1 Hr | 43351870 0 | 0 DBm | 1 Hr | Type "R" |
| 162 | 8-Jan | | 00000 | | | | 00000 | | | | 00000 | 27 45 | | 8662A | 43351830 0 | 0 DBm | 1 Hr | 43351870 0 | 0 DBm | 1 Hr | Type "R" |
| 163 | 9-Jan | | 00000 | | | | 00000 | | | | 00000 | 27 74 | | 8662A | 43351870 0 | 0 DBm | 1 Hr | 43351870 0 | 0 DBm | 1 Hr | Type "R" |
| 164 | 10-Jan | | 00000 | | | | 00000 | | | | 00000 | 27 55 | | 8662A | 43351850 0 | 0 DBm | 1 Hr | 43351850 0 | 0 DBm | 1 Hr | Type "R" |
| 165 | 11-Jan | | 00000 | | | | 00000 | | | | 00000 | 28 14 | | 8662A | 43351870 0 | 0 DBm | 1 Hr | 43351870 0 | 0 DBm | 1 Hr | Type "R" |
| 166 | 12-Jan | 0 050 | 00015 | | | | 00000 | | | | 00000 | 26 45 | | 8662A | 43351850 0 | 0 DBm | 1 Hr | 43351850 0 | 0 DBm | 1 Hr | Type "R" |
| 167 | 13-Jan | 0 070 | 00018 | | | | 00000 | | | | 00000 | 28 18 | 36 | 8662A | 43351870 0 | 0 DBm | 1 Hr | 43351870 0 | 0 DBm | 1 Hr | Type "R" |
| 168 | 14-Jan | 0 070 | 00030 | | | | 00000 | | | | 00000 | 28 40 | | 8662A | 43351870 0 | 0 DBm | 1 Hr | 43351870 0 | 0 DBm | 1 Hr | Type "R" |
| 169 | 15-Jan | 0 070 | 00037 | 0 090 | 0 090 | 0 070 | 00030 | | | | 00000 | 28 51 | | 8662A | 43351870 0 | 0 DBm | 1 Hr | 43351870 0 | 0 DBm | 1 Hr | Type "R" |
| 170 | 16-Jan | 0 070 | 00037 | 0 110 | 0 110 | 0 070 | 00044 | | | | 00000 | 27 91 | | 8662A | 43351850 0 | 0 DBm | 1 Hr | 43351850 0 | 0 DBm | 1 Hr | Type "R" |
| 171 | 17-Jan | 0 070 | 00044 | 0 110 | 0 100 | 0 070 | 00040 | | | | 00000 | 26 49 | | 8662A | 43351850 0 | 0 DBm | 1 Hr | 43351850 0 | 0 DBm | 1 Hr | Type "R" |
| 172 | 18-Jan | 0 070 | 00044 | 0 100 | 0 100 | 0 070 | 00037 | | | | 00000 | 27 92 | | 8662A | 43351870 0 | 0 DBm | 1 Hr | 43351870 0 | 0 DBm | 1 Hr | Type "R" |
| 173 | 19-Jan | 0 070 | 00052 | 0 120 | 0 110 | 0 070 | 00048 | | | | 00000 | 28 81 | | 8662A | 43351850 0 | 0 DBm | 1 Hr | 43351850 0 | 0 DBm | 1 Hr | Type "R" |
| 174 | 20-Jan | 0 070 | 00088 | 0 140 | 0 150 | 0 070 | 00077 | | | | 00000 | 28 12 | 40 | 8662A | 43351870 0 | 0 DBm | 1 Hr | 43351850 0 | 0 DBm | 1 Hr | Type "S" |
| 175 | 21-Jan | 0 070 | 00100 | 0 150 | 0 170 | 0 080 | 00107 | | | | 00000 | 28 50 | | 8662A | 43351870 0 | 0 DBm | 1 Hr | 43351850 0 | 0 DBm | 1 Hr | Type "S" |
| 176 | 22-Jan | 0 070 | 00100 | 0 160 | 0 180 | 0 090 | 00135 | | | | 00000 | 28 81 | | 8662A | 43322485 0 | 0 DBm | 1 Hr | 43351850 0 | 0 DBm | 1 Hr | Type "S" |
| 177 | 23-Jan | 0 070 | 00112 | 0 180 | 0 200 | 0 100 | 00186 | | | | 00000 | 28 98 | | 8662A | 43351850 0 | 0 DBm | 1 Hr | 43351850 0 | 0 DBm | 1 Hr | Type "S" |
| 178 | 24-Jan | 0 090 | 00170 | 0 190 | 0 220 | 0 120 | 00263 | | | | 00000 | 27 75 | | 8662A | 43351870 0 | 0 DBm | 1 Hr | 43351870 0 | 0 DBm | 1 Hr | Type "S" |
| 179 | 25-Jan | 0 090 | 00153 | 0 200 | 0 190 | 0 100 | 00199 | | | | 00000 | 27 29 | | 8662A | 43351870 0 | 0 DBm | 1 Hr | 43351870 0 | 0 DBm | 1 Hr | Type "S" |
| 180 | 26-Jan | 0 090 | 00153 | 0 210 | 0 200 | 0 100 | 00220 | | | | 00000 | 26 88 | | 8662A | 43351870 0 | 0 DBm | 1 Hr | 43351870 0 | 0 DBm | 1 Hr | Type "S" |
| 181 | 27-Jan | 0 100 | 00209 | 0 210 | 0 250 | 0 100 | 00275 | | | | 00000 | 28 52 | 38 | 8662A | 43351850 0 | 3 DBm | 1 Hr | 43351850 0 | 3 DBm | 1 Hr | Type "S" |
| 182 | 28-Jan | 0 100 | 00209 | 0 210 | 0 250 | 0 100 | 00275 | | | | 00000 | 28 55 | | 8662A | 43351850 0 | 3 DBm | 1 Hr | 43351850 0 | 3 DBm | 1 Hr | Type "S" |
| 183 | 29-Jan | 0 090 | 00218 | 0 220 | 0 250 | 0 100 | 00288 | | | | 00000 | 28 63 | | 8662A | 43351830 0 | 3 DBm | 1 Hr | 43351830 0 | 3 DBm | 1 Hr | Type "S" |
| 184 | 30-Jan | 0 090 | 00218 | 0 230 | 0 250 | 0 110 | 00331 | | | | 00000 | 28 77 | | 8662A | 43351830 0 | 3 DBm | 1 Hr | 43351830 0 | 3 DBm | 1 Hr | Type "S" |
| 185 | 31-Jan | 0 090 | 00207 | 0 230 | 0 280 | 0 110 | 00371 | | | | 00000 | 28 25 | | 8662A | 43351830 0 | 3 DBm | 1 Hr | 43351830 0 | 3 DBm | 1 Hr | Type "S" |
| 186 | 1-Feb | 0 090 | 00218 | 0 240 | 0 300 | 0 110 | 00415 | 0 100 | 0 100 | 0 080 | 00042 | 28 84 | | 8662A | 43351850 0 | 3 DBm | 1 Hr | 43351850 0 | 3 DBm | 1 Hr | Type "S" |
| 187 | 2-Feb | 0 090 | 00247 | 0 260 | 0 310 | 0 110 | 00464 | 0 110 | 0 110 | 0 090 | 00057 | 28 75 | | 8662A | 43351870 0 | 3 DBm | 1 Hr | 43351870 0 | 3 DBm | 1 Hr | Type "S" |
| 188 | 3-Feb | 0 090 | 00269 | 0 270 | 0 320 | 0 120 | 00543 | 0 120 | 0 110 | 0 100 | 00069 | 28 78 | 38 | 8662A | 43351850 0 | 3 DBm | 1 Hr | 43351850 0 | 3 DBm | 1 Hr | Type "S" |
| 189 | 4-Feb | 0 090 | 00282 | 0 270 | 0 320 | 0 120 | 00543 | 0 130 | 0 110 | 0 110 | 00062 | 29 02 | | 8662A | 43351870 0 | 3 DBm | 1 Hr | 43351870 0 | 3 DBm | 1 Hr | Type "S" |
| 190 | 5-Feb | 0 090 | 00305 | 0 280 | 0 380 | 0 120 | 00568 | 0 140 | 0 120 | 0 110 | 00097 | 29 21 | | 8662A | 43351870 0 | 3 DBm | 1 Hr | 43351870 0 | 3 DBm | 1 Hr | Type "S" |
| 191 | 6-Feb | 0 090 | 00342 | 0 300 | 0 350 | 0 120 | 00716 | 0 150 | 0 140 | 0 110 | 00121 | 29 52 | | 8662A | 43351870 0 | 3 DBm | 1 Hr | 43351870 0 | 3 DBm | 1 Hr | Type "S" |
| 192 | 7-Feb | 0 100 | 00380 | 0 320 | 0 350 | 0 120 | 00724 | 0 160 | 0 140 | 0 110 | 00129 | 29 34 | | 8662A | 43351870 0 | 3 DBm | 1 Hr | 43351870 0 | 3 DBm | 1 Hr | Type "S" |
| 193 | 8-Feb | 0 100 | 00389 | 0 350 | 0 310 | 0 130 | 00738 | 0 160 | 0 150 | 0 110 | 00155 | 33 07 | | 8662A | 43351830 0 | 3 DBm | 1 Hr | 43351830 0 | 3 DBm | 1 Hr | Type "S" |
| 194 | 9-Feb | 0 100 | 00377 | 0 310 | 0 370 | 0 130 | 00781 | 0 180 | 0 160 | 0 120 | 00181 | 28 92 | | 8662A | 43351830 0 | 3 DBm | 1 Hr | 43351830 0 | 3 DBm | 1 Hr | Type "S" |
| 195 | 10-Feb | 0 110 | 00432 | 0 350 | 0 420 | 0 150 | 01154 | 0 190 | 0 200 | 0 120 | 00239 | 30 83 | 35 | 8662A | 43351850 0 | 3 DBm | 1 Hr | 43351850 0 | 3 DBm | 1 Hr | Type "S" |
| 196 | 11-Feb | 0 110 | 00417 | 0 340 | 0 420 | 0 150 | 01121 | 0 190 | 0 200 | 0 120 | 00239 | 31 00 | | 8662A | 43351850 0 | 3 DBm | 1 Hr | 43351850 0 | 3 DBm | 1 Hr | Type "S" |

OUJ-516-.xls

| DAY | DATE | T-7 Ht | Vol T-7 | RT ARM PIT T-4 Ln | Wd | Ht | Vol T-4 | LT ARM T-9 Ln | Wd | Ht | Vol T-9 | WEIGHT Gr | HEMATO-CRIT % | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|---|---|---|---|---|---|
| 197 | 12-Feb | 0.110 | 00417 | 0.340 | 0.420 | 0.150 | 01121 | 0.190 | 0.200 | 0.120 | 00235 | 31.53 | | 8662A | 43351850.0 | 3 DBm | 1 Hr | 43351850.0 | 3 DBm | 1 Hr | Type "S" |
| 198 | 13-Feb | 0.120 | 00440 | 0.350 | 0.400 | 0.150 | 01099 | 0.190 | 0.220 | 0.120 | 00263 | 31.75 | | 8662A | 43351850.0 | 3 DBm | 1 Hr | 43351850.0 | 3 DBm | 1 Hr | Type "S" |
| 199 | 14-Feb | 0.140 | 00574 | 0.350 | 0.390 | 0.150 | 01102 | 0.210 | 0.220 | 0.130 | 00314 | 31.61 | | 8662A | 43351830.0 | 3 DBm | 1 Hr | 43351830.0 | 3 DBm | 1 Hr | Type "S" |
| 200 | 15-Feb | 0.140 | 00594 | 0.380 | 0.390 | 0.150 | 01164 | 0.220 | 0.230 | 0.140 | 00371 | 31.04 | | 8662A | 43353800.0 | 3 DBm | 1 Hr | 43322480.0 | 3 DBm | 1 Hr | Type "S" |
| 201 | 16-Feb | 0.150 | 00682 | 0.380 | 0.390 | 0.150 | 01164 | 0.230 | 0.230 | 0.150 | 00415 | 30.72 | | 8662A | | | | 43351870.0 | 0 DBm | 3 Hr | Type "S" |
| 202 | 17-Feb | 0.150 | 00682 | 0.350 | 0.460 | 0.150 | 01264 | 0.280 | 0.260 | 0.150 | 00572 | 31.56 | 32 | 8662A | | | | 43351870.0 | 0 DBm | 3 Hr | Type "S" |
| 203 | 18-Feb | 0.150 | 00683 | 0.350 | 0.460 | 0.150 | 01264 | 0.280 | 0.270 | 0.150 | 00594 | 32.50 | | 8662A | | | | 43351870.0 | 0 DBm | 3 Hr | Type "T" |
| 204 | 19-Feb | 0.150 | 00683 | 0.360 | 0.460 | 0.150 | 01300 | 0.280 | 0.280 | 0.150 | 00616 | 33.45 | | 8662A | | | | 43351870.0 | 0 DBm | 3 Hr | Type "T" |
| 205 | 20-Feb | 0.150 | 00683 | 0.370 | 0.450 | 0.150 | 01337 | 0.300 | 0.310 | 0.150 | 00730 | 33.16 | | 8662A | 43351871.0 | 0 DBm | 2 Hr | 43351853.0 | 0 DBm | 1 Hr | Type "T" |
| 206 | 21-Feb | 0.150 | 00706 | 0.380 | 0.450 | 0.150 | 01343 | 0.320 | 0.320 | 0.170 | 00911 | 32.82 | | 8662A | 43351871.0 | 0 DBm | 2 Hr | 43351853.0 | 0 DBm | 1 Hr | Type "T" |
| 207 | 22-Feb | 0.160 | 00704 | 0.380 | 0.460 | 0.150 | 01373 | 0.310 | 0.310 | 0.160 | 00805 | 32.48 | | 8662A | 43351871.0 | 0 DBm | 1 Hr | 43351853.0 | 0 DBm | 2 Hr | Type "T" |
| 208 | 23-Feb | 0.160 | 00729 | 0.390 | 0.470 | 0.150 | 01439 | 0.310 | 0.310 | 0.160 | 00805 | 30.98 | | 8662A | 43351850.0 | 0 DBm | 3 Hr | | | | Type "T" |
| 209 | 24-Feb | 0.160 | 00753 | 0.390 | 0.500 | 0.150 | 01531 | 0.350 | 0.350 | 0.160 | 01026 | 32.43 | 28 | 8662A | 43351850.0 | 0 DBm | 3 Hr | | | | Type "T" |
| 210 | 25-Feb | 0.160 | 00805 | 0.390 | 0.500 | 0.150 | 01531 | 0.370 | 0.410 | 0.170 | 01350 | 42.48 | | 8662A | 43351850.0 | 0 DBm | 3 Hr | | | | Type "T" |
| 211 | 26-Feb | 0.160 | 00885 | 0.400 | 0.500 | 0.150 | 01571 | 0.390 | 0.460 | 0.180 | 01690 | 32.53 | | 8662A | 43351853.0 | 0 DBm | 1 Hr | 43351871.0 | 0 DBm | 2 Hr | Type "T" |
| 212 | 27-Feb | 0.170 | 01079 | 0.430 | 0.480 | 0.170 | 01837 | 0.410 | 0.480 | 0.200 | 02060 | 33.26 | | 8662A | 43351853.0 | 0 DBm | 1 Hr | 43351871.0 | 0 DBm | 2 Hr | Type "T" |
| 213 | 28-Feb | 0.170 | 01059 | 0.420 | 0.490 | 0.160 | 01724 | 0.340 | 0.470 | 0.200 | 01673 | 34.05 | | 8662A | | | | 43351871.0 | 0 DBm | 2 Hr | Type "T" |
| 214 | 29-Feb | 0.170 | 01089 | 0.430 | 0.500 | 0.180 | 02026 | 0.370 | 0.490 | 0.200 | 01898 | 35.73 | | | NO TREATMENT | | | NO TREATMENT | | | Type "T" |
| 215 | 1-Mar | 0.170 | 01029 | 0.450 | 0.500 | 0.190 | 02238 | 0.410 | 0.510 | 0.230 | 02518 | 35.67 | | | NO TREATMENT | | | NO TREATMENT | | | Type "T" |
| 216 | 2-Mar | 0.170 | 01121 | 0.460 | 0.500 | 0.190 | 02288 | 0.430 | 0.510 | 0.230 | 02640 | 36.03 | 24 | | NO TREATMENT | | | NO TREATMENT | | | Type "T" |
| 217 | 3-Mar | 0.185 | 01307 | 0.490 | 0.500 | 0.200 | 02565 | 0.475 | 0.540 | 0.235 | 03156 | 37.08 | | | NO TREATMENT | | | NO TREATMENT | | | Type "T" |
| 218 | 4-Mar | 0.200 | 01550 | 0.510 | 0.500 | 0.210 | 02803 | 0.540 | 0.570 | 0.240 | 03867 | 38.15 | | | NO TREATMENT | | | NO TREATMENT | | | Type "T" |
| 219 | 5-Mar | 0.220 | 01843 | 0.530 | 0.510 | 0.220 | 03113 | 0.550 | 0.590 | 0.240 | 04151 | 37.94 | | | NO TREATMENT | | | NO TREATMENT | | | Type "U" |
| 220 | 6-Mar | 0.240 | 02161 | 0.530 | 0.530 | 0.230 | 03382 | 0.580 | 0.610 | 0.250 | 04816 | 34.01 | | | NO TREATMENT | | | NO TREATMENT | | | Type "U" |
| 221 | 7-Mar | 0.250 | 02307 | 0.560 | 0.590 | 0.230 | 03978 | 0.600 | 0.630 | 0.270 | 05343 | 34.97 | | | NO TREATMENT | | | NO TREATMENT | | | Type "U" |
| 222 | 8-Mar | 0.260 | 02455 | 0.580 | 0.540 | 0.230 | 03771 | 0.630 | 0.660 | 0.280 | 06095 | 33.75 | | | NO TREATMENT | | | NO TREATMENT | | | Type "U" |
| 223 | 9-Mar | 0.270 | 02612 | 0.590 | 0.550 | 0.240 | 04077 | 0.640 | 0.680 | 0.280 | 06379 | 33.51 | 17 | | NO TREATMENT | | | NO TREATMENT | | | Type "V" |
| 224 | 10-Mar | 0.275 | 02842 | 0.600 | 0.555 | 0.225 | 04097 | 0.630 | 0.690 | 0.280 | 06372 | 33.80 | | | NO TREATMENT | | | NO TREATMENT | | | Type "V" |
| 225 | 11-Mar | 0.280 | 03089 | 0.610 | 0.560 | 0.230 | 04113 | 0.620 | 0.700 | 0.280 | 06362 | 34.23 | | | NO TREATMENT | | | NO TREATMENT | | | Type "V" |
| 226 | 12-Mar | 0.290 | 03003 | 0.620 | 0.560 | 0.230 | 04180 | 0.630 | 0.730 | 0.300 | 07223 | 34.44 | | | NO TREATMENT | | | NO TREATMENT | | | Type "U" |
| 227 | 13-Mar | 0.290 | 02938 | 0.630 | 0.560 | 0.240 | 04433 | 0.650 | 0.740 | 0.290 | 07302 | 34.09 | | | NO TREATMENT | | | NO TREATMENT | | | Type "U" |
| 228 | 14-Mar | 0.300 | 03179 | 0.640 | 0.560 | 0.250 | 04691 | 0.650 | 0.740 | 0.300 | 07554 | 33.25 | | | NO TREATMENT | | | NO TREATMENT | | | Type "U" |
| 229 | 15-Mar | 0.310 | 03359 | 0.670 | 0.560 | 0.250 | 04910 | 0.670 | 0.760 | 0.310 | 08264 | 33.27 | | | NO TREATMENT | | | NO TREATMENT | | | Type "U" |
| 230 | 16-Mar | 0.320 | 03543 | 0.680 | 0.570 | 0.250 | 05073 | 0.680 | 0.750 | 0.320 | 08544 | 32.96 | 12 | | NO TREATMENT | | | NO TREATMENT | | | Type "U" |
| 231 | 17-Mar | 0.325 | 03441 | 0.690 | 0.575 | 0.250 | 05192 | 0.680 | 0.750 | 0.320 | 08544 | 32.00 | | | NO TREATMENT | | | NO TREATMENT | | | Type "U" |
| 232 | 18-Mar | 0.330 | 03338 | 0.700 | 0.580 | 0.250 | 05314 | 0.680 | 0.760 | 0.330 | 08928 | 31.20 | | | NO TREATMENT | | | NO TREATMENT | | | Type "U" |
| 233 | 19-Mar | 0.350 | 03524 | 0.720 | 0.590 | 0.250 | 05560 | 0.732 | 0.780 | 0.340 | 10135 | 30.84 | | | NO TREATMENT | | | NO TREATMENT | | | Type "U" |
| 234 | 20-Mar | | 00000 | | | | 00000 | 0.750 | 0.800 | 0.370 | 11622 | 31.80 | | | NO TREATMENT | | | NO TREATMENT | | | Type "U" |
| 235 | 21-Mar | | 00000 | | | | 00000 | 0.770 | 0.830 | 0.420 | 13323 | 32.80 | | | NO TREATMENT | | | NO TREATMENT | | | Type "U" |
| 236 | 22-Mar | | 00000 | | | | 00000 | 0.790 | 0.860 | 0.440 | 15649 | 33.21 | | | NO TREATMENT | | | NO TREATMENT | | | Type "U" |
| 237 | 23-Mar | | 00000 | | | | 00000 | 0.780 | 0.870 | 0.490 | 17407 | 33.90 | | | NO TREATMENT | | | NO TREATMENT | | | Type "U" |
| 238 | 24-Mar | | 00000 | | | | 00000 | 0.785 | 0.870 | 0.495 | 17697 | 34.15 | | | NO TREATMENT | | | NO TREATMENT | | | Type "U" |
| 239 | 25-Mar | | 00000 | | | | 00000 | 0.793 | 0.870 | 0.500 | 17990 | 34.41 | | | NO TREATMENT | | | NO TREATMENT | | | Type "U" |
| 240 | 26-Mar | 6 | #VALUE | | Died 3/26/96 | | #VALUE | | Died 3/26/96 | | #VALUE! | | | | NO TREATMENT | | | NO TREATMENT | | | Type "U" |

09141691.082898

OUJ-526-.xls

*OUJ-526 Born 2/2/95 First tumor appeared on 10/28/95*

| DAY | DATE | T-1 Right Side Ln | Wd | Ht | Vol T-1 | T-2 Back of Neck Ln | Wd | Ht | Vol T-2 | T-3 R Outer Leg Ln | Wd | Ht | Vol T-3 | T-5 Lt Outer Leg T-4 Back Side Ln | Wd | Ht | Vol T-4,5 | T-6 L Arm Pit Ln | Wd | Ht |
|---|---|---|---|---|---|---|---|---|---|---|---|---|---|---|---|---|---|---|---|---|
| 1 | 28-Oct | 0 030 | 0 030 | 0 030 | 00001 | | | | 00000 | | | | 00000 | | | | 00000 | | | |
| 2 | 29-Oct | 0 030 | 0 030 | 0 030 | 00001 | | | | 00000 | | | | 00000 | | | | 00000 | | | |
| 3 | 30-Oct | 0 030 | 0 030 | 0 030 | 00001 | | | | 00000 | | | | 00000 | | | | 00000 | | | |
| 4 | 31-Oct | 0 030 | 0 030 | 0 030 | 00001 | | | | 00000 | | | | 00000 | | | | 00000 | | | |
| 5 | 1-Nov | 0 030 | 0 030 | 0 030 | 00001 | | | | 00000 | | | | 00000 | | | | 00000 | | | |
| 6 | 2-Nov | 0 030 | 0 030 | 0 030 | 00001 | | | | 00000 | | | | 00000 | | | | 00000 | | | |
| 7 | 3-Nov | | | | 00000 | | | | 00000 | | | | 00000 | | | | 00000 | | | |
| 8 | 4-Nov | | | | 00000 | | | | 00000 | | | | 00000 | | | | 00000 | | | |
| 9 | 5-Nov | | | | 00000 | | | | 00000 | | | | 00000 | | | | 00000 | | | |
| 10 | 6-Nov | | | | 00000 | | | | 00000 | | | | 00000 | | | | 00000 | | | |
| 11 | 7-Nov | | | | 00000 | | | | 00000 | | | | 00000 | | | | 00000 | | | |
| 12 | 8-Nov | | | | 00000 | | | | 00000 | | | | 00000 | | | | 00000 | | | |
| 13 | 9-Nov | | | | 00000 | | | | 00000 | | | | 00000 | | | | 00000 | | | |
| 14 | 10-Nov | | | | 00000 | | | | 00000 | | | | 00000 | | | | 00000 | | | |
| 15 | 11-Nov | | | | 00000 | | | | 00000 | | | | 00000 | | | | 00000 | | | |
| 16 | 12-Nov | | | | 00000 | | | | 00000 | | | | 00000 | | | | 00000 | | | |
| 17 | 13-Nov | | | | 00000 | | | | 00000 | | | | 00000 | | | | 00000 | | | |
| 18 | 14-Nov | | | | 00000 | | | | 00000 | | | | 00000 | | | | 00000 | | | |
| 19 | 15-Nov | | | | 00000 | 0 050 | 0 050 | 0 050 | 00007 | | | | 00000 | | | | 00000 | | | |
| 20 | 16-Nov | | | | 00000 | 0 050 | 0 050 | 0 050 | 00007 | | | | 00000 | | | | 00000 | | | |
| 21 | 17-Nov | | | | 00000 | 0 070 | 0 070 | 0 050 | 00013 | | | | 00000 | | | | 00000 | | | |
| 22 | 18-Nov | | | | 00000 | 0 090 | 0 090 | 0 050 | 00021 | | | | 00000 | | | | 00000 | | | |
| 23 | 19-Nov | | | | 00000 | 0 100 | 0 100 | 0 070 | 00037 | | | | 00000 | | | | 00000 | | | |
| 24 | 20-Nov | | | | 00000 | 0 110 | 0 100 | 0 080 | 00046 | | | | 00000 | | | | 00000 | | | |
| 25 | 21-Nov | | | | 00000 | 0 110 | 0 110 | 0 080 | 00051 | | | | 00000 | | | | 00000 | | | |
| 26 | 22-Nov | | | | 00000 | 0 110 | 0 110 | 0 080 | 00051 | | | | 00000 | | | | 00000 | | | |
| 27 | 23-Nov | | | | 00000 | 0 110 | 0 110 | 0 080 | 00051 | | | | 00000 | | | | 00000 | | | |
| 28 | 24-Nov | | | | 00000 | 0 110 | 0 110 | 0 080 | 00051 | | | | 00000 | | | | 00000 | | | |
| 29 | 25-Nov | | | | 00000 | 0 110 | 0 110 | 0 090 | 00057 | | | | 00000 | | | | 00000 | | | |
| 30 | 26-Nov | | | | 00000 | 0 110 | 0 110 | 0 090 | 00057 | | | | 00000 | | | | 00000 | | | |
| 31 | 27-Nov | | | | 00000 | 0 110 | 0 110 | 0 100 | 00063 | | | | 00000 | | | | 00000 | | | |
| 32 | 28-Nov | | | | 00000 | 0 110 | 0 110 | 0 100 | 00063 | | | | 00000 | | | | 00000 | | | |
| 33 | 29-Nov | | | | 00000 | 0 110 | 0 120 | 0 110 | 00076 | | | | 00000 | | | | 00000 | | | |
| 34 | 30-Nov | | | | 00000 | 0 110 | 0 120 | 0 110 | 00076 | | | | 00000 | | | | 00000 | | | |
| 35 | 1-Dec | | | | 00000 | 0 110 | 0 120 | 0 110 | 00076 | | | | 00000 | | | | 00000 | | | |
| 36 | 2-Dec | | | | 00000 | 0 110 | 0 120 | 0 110 | 00076 | | | | 00000 | | | | 00000 | | | |
| 37 | 3-Dec | | | | 00000 | 0 110 | 0 120 | 0 110 | 00076 | | | | 00000 | | | | 00000 | | | |
| 38 | 4-Dec | | | | 00000 | 0 110 | 0 120 | 0 110 | 00076 | | | | 00000 | | | | 00000 | | | |
| 39 | 5-Dec | | | | 00000 | 0 120 | 0 120 | 0 110 | 00083 | | | | 00000 | | | | 00000 | | | |
| 40 | 6-Dec | | | | 00000 | 0 120 | 0 120 | 0 110 | 00083 | | | | 00000 | | | | 00000 | | | |
| 41 | 7-Dec | | | | 00000 | 0 110 | 0 120 | 0 110 | 00076 | | | | 00000 | | | | 00000 | | | |
| 42 | 8-Dec | | | | 00000 | 0 110 | 0 110 | 0 100 | 00063 | | | | 00000 | | | | 00000 | | | |
| 43 | 9-Dec | | | | 00000 | 0 100 | 0 100 | 0 100 | 00052 | | | | 00000 | | | | 00000 | | | |
| 44 | 10-Dec | | | | 00000 | 0 100 | 0 100 | 0 100 | 00052 | | | | 00000 | | | | 00000 | | | |
| 45 | 11-Dec | | | | 00000 | 0 090 | 0 100 | 0 090 | 00042 | | | | 00000 | | | | 00000 | | | |
| 46 | 12-Dec | | | | 00000 | 0 090 | 0 100 | 0 090 | 00042 | | | | 00000 | | | | 00000 | | | |

09141691.080298

OUJ-526-.xls

| DAY | DATE | T-1 Right Side Ln | Wd | Ht | Vol T-1 | T- 2 Back of Neck Ln | Wd | Ht | Vol T-2 | T- 3 R Outer Leg Ln | Wd | Ht | Vol T-3 | T- 4 Back Side Ln | Wd | Ht | Vol T-4,5 | T- 6 L Arm Pit Ln | Wd | Ht |
|---|---|---|---|---|---|---|---|---|---|---|---|---|---|---|---|---|---|---|---|---|
| 47 | 13-Dec | | | | 00000 | 0 100 | 0 100 | 0 090 | 00047 | | | | 00000 | | | | 00000 | | | |
| 48 | 14-Dec | | | | 00000 | 0 100 | 0 100 | 0 090 | 00047 | | | | 00000 | | | | 00000 | | | |
| 49 | 15-Dec | | | | 00000 | 0 100 | 0 100 | 0 080 | 00042 | | | | 00000 | | | | 00000 | | | |
| 50 | 16-Dec | | | | 00000 | 0 100 | 0 100 | 0 070 | 00037 | | | | 00000 | | | | 00000 | | | |
| 51 | 17-Dec | | | | 00000 | 0 100 | 0 100 | 0 070 | 00037 | | | | 00000 | | | | 00000 | | | |
| 52 | 18-Dec | | | | 00000 | 0 090 | 0 090 | 0 070 | 00030 | | | | 00000 | 0 030 | 0 030 | 0 030 | 00001 | | | |
| 53 | 19-Dec | | | | 00000 | 0 090 | 0 080 | 0 070 | 00026 | 0 030 | 0 030 | 0 030 | 00001 | 0 050 | 0 050 | 0 050 | 00007 | | | |
| 54 | 20-Dec | | | | 00000 | 0 070 | 0 070 | 0 070 | 00018 | 0 050 | 0 050 | 0 050 | 00007 | 0 070 | 0 070 | 0 070 | 00018 | | | |
| 55 | 21-Dec | | | | 00000 | 0 050 | 0 050 | 0 050 | 00008 | 0 050 | 0 050 | 0 050 | 00007 | 0 090 | 0 090 | 0 100 | 00042 | | | |
| 56 | 22-Dec | | | | 00000 | 0 030 | 0 030 | 0 030 | 00001 | 0 050 | 0 050 | 0 050 | 00007 | 0 110 | 0 110 | 0 085 | 00054 | | | |
| 57 | 23-Dec | | | | 00000 | 0 030 | 0 030 | 0 030 | 00001 | | | | 00000 | 0 130 | 0 130 | 0 070 | 00062 | | | |
| 58 | 24-Dec | | | | 00000 | | | | 00000 | | | | 00000 | 0 130 | 0 130 | 0 070 | 00052 | | | |
| 59 | 25-Dec | | | | 00000 | | | | 00000 | | | | 00000 | 0 130 | 0 130 | 0 070 | 00062 | | | |
| 60 | 26-Dec | | | | 00000 | | | | 00000 | | | | 00000 | 0 140 | 0 150 | 0 070 | 00077 | | | |
| 61 | 27-Dec | | | | 00000 | | | | 00000 | | | | 00000 | 0 140 | 0 140 | 0 070 | 00072 | | | |
| 62 | 28-Dec | | | | 00000 | | | | 00000 | | | | 00000 | 0 150 | 0 160 | 0 070 | 00088 | | | |
| 63 | 29-Dec | | | | 00000 | | | | 00000 | | | | 00000 | 0 150 | 0 160 | 0 070 | 00088 | | | |
| 64 | 30-Dec | | | | 00000 | | | | 00000 | | | | 00000 | 0 170 | 0 180 | 0 100 | 00160 | | | |
| 65 | 31-Dec | | | | 00000 | | | | 00000 | | | | 00000 | 0 170 | 0 180 | 0 100 | 00160 | | | |
| 66 | 1-Jan | | | | 00000 | | | | 00000 | | | | 00000 | 0 180 | 0 180 | 0 090 | 00153 | | | |
| 67 | 2-Jan | | | | 00000 | | | | 00000 | | | | 00000 | 0 220 | 0 190 | 0 090 | 00197 | | | |
| 68 | 3-Jan | | | | 00000 | | | | 00000 | | | | 00000 | 0 210 | 0 220 | 0 090 | 00218 | | | |
| 69 | 4-Jan | | | | 00000 | | | | 00000 | | | | 00000 | 0 230 | 0 220 | 0 110 | 00291 | | | |
| 70 | 5-Jan | | | | 00000 | | | | 00000 | | | | 00000 | 0 260 | 0 250 | 0 120 | 00408 | | | |
| 71 | 6-Jan | | | | 00000 | | | | 00000 | | | | 00000 | 0 280 | 0 270 | 0 150 | 00594 | | | |
| 72 | 7-Jan | | | | 00000 | | | | 00000 | | | | 00000 | 0 280 | 0 270 | 0 150 | 00594 | | | |
| 73 | 8-Jan | | | | 00000 | | | | 00000 | | | | 00000 | 0 300 | 0 270 | 0 150 | 00636 | | | |
| 74 | 9-Jan | | | | 00000 | | | | 00000 | | | | 00000 | 0 300 | 0 270 | 0 150 | 00636 | | | |
| 75 | 10-Jan | | | | 00000 | | | | 00000 | | | | 00000 | 0 320 | 0 270 | 0 150 | 00678 | | | |
| 76 | 11-Jan | | | | 00000 | | | | 00000 | | | | 00000 | 0 310 | 0 270 | 0 150 | 00657 | | | |
| 77 | 12-Jan | | | | 00000 | | | | 00000 | | | | 00000 | 0 290 | 0 270 | 0 150 | 00615 | | | |
| 78 | 13-Jan | | | | 00000 | | | | 00000 | | | | 00000 | 0 340 | 0 260 | 0 150 | 00694 | | | |
| 79 | 14-Jan | | | | 00000 | | | | 00000 | | | | 00000 | 0 340 | 0 260 | 0 150 | 00694 | | | |
| 80 | 15-Jan | | | | 00000 | | | | 00000 | | | | 00000 | 0 330 | 0 260 | 0 150 | 00674 | | | |
| 81 | 16-Jan | | | | 00000 | | | | 00000 | | | | 00000 | 0 320 | 0 250 | 0 180 | 00754 | | | |
| 82 | 17-Jan | | | | 00000 | | | | 00000 | | | | 00000 | 0 330 | 0 250 | 0 170 | 00764 | | | |
| 83 | 18-Jan | | | | 00000 | | | | 00000 | | | | 00000 | 0 320 | 0 250 | 0 170 | 00712 | | | |
| 84 | 19-Jan | | | | 00000 | | | | 00000 | | | | 00000 | 0 330 | 0 260 | 0 170 | 00764 | | | |
| 85 | 20-Jan | | | | 00000 | | | | 00000 | | | | 00000 | 0 340 | 0 290 | 0 200 | 01032 | | | |
| 86 | 21-Jan | | | | 00000 | | | | 00000 | | | | 00000 | 0 340 | 0 290 | 0 200 | 01032 | | | |
| 87 | 22-Jan | | | | 00000 | | | | 00000 | | | | 00000 | 0 350 | 0 290 | 0 190 | 01010 | | | |
| 88 | 23-Jan | | | | 00000 | | | | 00000 | | | | 00000 | 0 350 | 0 270 | 0 180 | 00890 | | | |
| 89 | 24-Jan | | | | 00000 | | | | 00000 | | | | 00000 | 0 370 | 0 280 | 0 190 | 01030 | | | |
| 90 | 25-Jan | | | | 00000 | | | | 00000 | | | | 00000 | 0 380 | 0 280 | 0 200 | 01114 | | | |
| 91 | 26-Jan | | | | 00000 | | | | 00000 | | | | 00000 | 0 390 | 0 290 | 0 200 | 01184 | | | |
| 92 | 27-Jan | | | | 00000 | | | | 00000 | | | | 00000 | 0 390 | 0 290 | 0 200 | 01184 | | | |
| 93 | 28-Jan | | | | 00000 | | | | 00000 | | | | 00000 | 0 390 | 0 290 | 0 200 | 01184 | | | |
| 94 | 29-Jan | | | | 00000 | | | | 00000 | | | | 00000 | 0 380 | 0 290 | 0 190 | 01095 | | | |

4/11/97 Page 2 OUJ-526-.xls

OUJ-526-.xls

| DAY | DATE | T-1 Right Side | | | Vol | T-2 Back of Neck | | | Vol | T-3 R Outer Leg | | | Vol | T-4 Back Side | | | Vol | T-6 L Arm Pit | | |
|---|---|---|---|---|---|---|---|---|---|---|---|---|---|---|---|---|---|---|---|---|
| | | Ln | Wd | Ht | T-1 | Ln | Wd | Ht | T-2 | Ln | Wd | Ht | T-3 | Ln | Wd | Ht | T-4,5 | Ln | Wd | Ht |
| 95 | 30-Jan | | | | 00000 | | | | 00000 | | | | 00000 | 0.390 | 0.290 | 0.190 | 01125 | | | |
| 96 | 31-Jan | | | | 00000 | | | | 00000 | | | | 00000 | 0.390 | 0.280 | 0.190 | 01066 | | | |
| 97 | 1-Feb | | | | 00000 | | | | 00000 | | | | 00000 | 0.380 | 0.290 | 0.190 | 01096 | | | |
| 98 | 2-Feb | | | | 00000 | | | | 00000 | | | | 00000 | 0.400 | 0.290 | 0.190 | 01154 | | | |
| 99 | 3-Feb | | | | 00000 | | | | 00000 | | | | 00000 | 0.420 | 0.280 | 0.190 | 01170 | | | |
| 100 | 4-Feb | | | | 00000 | | | | 00000 | | | | 00000 | 0.420 | 0.280 | 0.190 | 01170 | | | |
| 101 | 5-Feb | | | | 00000 | | | | 00000 | | | | 00000 | 0.420 | 0.280 | 0.200 | 01231 | | | |
| 102 | 6-Feb | | | | 00000 | | | | 00000 | | | | 00000 | 0.410 | 0.300 | 0.200 | 01288 | | | |
| 103 | 7-Feb | | | | 00000 | | | | 00000 | | | | 00000 | 0.430 | 0.300 | 0.200 | 01351 | | | |
| 104 | 8-Feb | | | | 00000 | | | | 00000 | | | | 00000 | 0.450 | 0.290 | 0.190 | 01298 | | | |
| 105 | 9-Feb | | | | 00000 | | | | 00000 | | | | 00000 | 0.450 | 0.300 | 0.200 | 01413 | | | |
| 106 | 10-Feb | | | | 00000 | | | | 00000 | | | | 00000 | 0.480 | 0.320 | 0.200 | 01608 | | | |
| 107 | 11-Feb | | | | 00000 | | | | 00000 | | | | 00000 | 0.490 | 0.330 | 0.200 | 01693 | | | |
| 108 | 12-Feb | | | | 00000 | | | | 00000 | | | | 00000 | 0.490 | 0.330 | 0.200 | 01693 | | | |
| 109 | 13-Feb | | | | 00000 | | | | 00000 | | | | 00000 | 0.480 | 0.330 | 0.200 | 01658 | | | |
| 110 | 14-Feb | | | | 00000 | | | | 00000 | | | | 00000 | 0.490 | 0.330 | 0.200 | 01693 | | | |
| 111 | 15-Feb | | | | 00000 | | | | 00000 | | | | 00000 | 0.510 | 0.340 | 0.210 | 01906 | | | |
| 112 | 16-Feb | | | | 00000 | | | | 00000 | | | | 00000 | 0.500 | 0.340 | 0.210 | 01869 | | | |
| 113 | 17-Feb | | | | 00000 | | | | 00000 | | | | 00000 | 0.500 | 0.340 | 0.210 | 01869 | | | |
| 114 | 18-Feb | | | | 00000 | | | | 00000 | | | | 00000 | 0.500 | 0.340 | 0.210 | 01869 | | | |
| 115 | 19-Feb | | | | 00000 | | | | 00000 | | | | 00000 | 0.490 | 0.350 | 0.210 | 01885 | | | |
| 116 | 20-Feb | | | | 00000 | | | | 00000 | | | | 00000 | 0.500 | 0.360 | 0.220 | 02073 | | | |
| 117 | 21-Feb | | | | 00000 | | | | 00000 | | | | 00000 | 0.500 | 0.350 | 0.210 | 01924 | | | |
| 118 | 22-Feb | | | | 00000 | | | | 00000 | | | | 00000 | 0.500 | 0.360 | 0.210 | 01979 | | | |
| 119 | 23-Feb | | | | 00000 | | | | 00000 | | | | 00000 | 0.510 | 0.350 | 0.220 | 02056 | | | |
| 120 | 24-Feb | | | | 00000 | | | | 00000 | | | | 00000 | 0.540 | 0.360 | 0.240 | 02442 | | | |
| 121 | 25-Feb | | | | 00000 | | | | 00000 | | | | 00000 | 0.550 | 0.360 | 0.240 | 02488 | | | |
| 122 | 26-Feb | | | | 00000 | | | | 00000 | | | | 00000 | 0.550 | 0.360 | 0.240 | 02488 | | | |
| 123 | 27-Feb | | | | 00000 | | | | 00000 | | | | 00000 | 0.560 | 0.370 | 0.260 | 02820 | | | |
| 124 | 28-Feb | | | | 00000 | | | | 00000 | | | | 00000 | 0.560 | 0.380 | 0.260 | 02896 | | | |
| 125 | 29-Feb | | | | 00000 | | | | 00000 | | | | 00000 | 0.560 | 0.370 | 0.260 | 02820 | | | |
| 126 | 1-Mar | | | | 00000 | | | | 00000 | | | | 00000 | 0.540 | 0.380 | 0.260 | 02793 | | | |
| 127 | 2-Mar | | | | 00000 | | | | 00000 | | | | 00000 | 0.550 | 0.370 | 0.260 | 02770 | | | |
| 128 | 3-Mar | | | | 00000 | | | | 00000 | | | | 00000 | 0.560 | 0.350 | 0.250 | 02638 | | | |
| 129 | 4-Mar | | | | 00000 | | | | 00000 | | | | 00000 | 0.570 | 0.350 | 0.230 | 02402 | | | |
| 130 | 5-Mar | | | | 00000 | | | | 00000 | | | | 00000 | 0.580 | 0.350 | 0.230 | 02444 | | | |
| 131 | 6-Mar | | | | 00000 | | | | 00000 | | | | 00000 | 0.580 | 0.350 | 0.230 | 02444 | | | |
| 132 | 7-Mar | | | | 00000 | | | | 00000 | | | | 00000 | 0.590 | 0.350 | 0.260 | 02891 | | | |
| 133 | 8-Mar | | | | 00000 | | | | 00000 | | | | 00000 | 0.600 | 0.350 | 0.210 | 02309 | | | |
| 134 | 9-Mar | | | | 00000 | | | | 00000 | | | | 00000 | 0.600 | 0.360 | 0.220 | 02488 | | | |
| 135 | 10-Mar | | | | 00000 | | | | 00000 | | | | 00000 | 0.610 | 0.360 | 0.240 | 02759 | | | |
| 136 | 11-Mar | | | | 00000 | | | | 00000 | | | | 00000 | 0.620 | 0.370 | 0.250 | 03002 | | | |
| 137 | 12-Mar | | | | 00000 | | | | 00000 | | | | 00000 | 0.620 | 0.360 | 0.250 | 02921 | | | |
| 138 | 13-Mar | | | | 00000 | | | | 00000 | | | | 00000 | 0.620 | 0.360 | 0.250 | 02921 | | | |
| 139 | 14-Mar | | | | 00000 | | | | 00000 | | | | 00000 | 0.620 | 0.350 | 0.240 | 02726 | | | |
| 140 | 15-Mar | | | | 00000 | | | | 00000 | | | | 00000 | 0.620 | 0.350 | 0.240 | 02726 | | | |
| 141 | 16-Mar | | | | 00000 | | | | 00000 | | | | 00000 | 0.630 | 0.350 | 0.250 | 02886 | | | |
| 142 | 17-Mar | | | | 00000 | | | | 00000 | | | | 00000 | 0.640 | 0.350 | 0.250 | 02932 | | | |

09141691.082898

OUJ-526-.xls

| DAY | DATE | T-1 Right Side Ln | Wd | Ht | Vol T-1 | T-2 Back of Neck Ln | Wd | Ht | Vol T-2 | T-3 R Outer Leg Ln | Wd | Ht | Vol T-3 | T-4 Back Side Ln | Wd | Ht | Vol T-4,5 | T-6 L Arm Pit Ln | Wd | Ht |
|---|---|---|---|---|---|---|---|---|---|---|---|---|---|---|---|---|---|---|---|---|
| 143 | 18-Mar | | | | 00000 | | | | 00000 | | | | 00000 | 0 650 | 0 360 | 0 260 | 03185 | 0 110 | 0.150 | 0 070 |
| 144 | 19-Mar | | | | 00000 | | | | 00000 | | | | 00000 | 0 650 | 0 350 | 0 250 | 02977 | 0 130 | 0 160 | 0 070 |
| 145 | 20-Mar | | | | 00000 | | | | 00000 | | | | 00000 | 0 660 | 0 340 | 0 250 | 02937 | 0 150 | 0 160 | 0 070 |
| 146 | 21-Mar | | | | 00000 | | | | 00000 | | | | 00000 | 0 680 | 0 350 | 0 260 | 03239 | 0 160 | 0 170 | 0 070 |
| 147 | 22-Mar | | | | 00000 | | | | 00000 | | | | 00000 | 0 670 | 0 360 - | 0 260 | 03283 | 0 180 | 0 170 | 0 070 |
| 148 | 23-Mar | | | | 00000 | | | | 00000 | | | | 00000 | 0 680 | 0 350 | 0 260 | 03239 | 0 190 | 0 190 | 0.080 |
| 149 | 24-Mar | | | | 00000 | | | | 00000 | | | | 00000 | 0 680 | 0 350 | 0 250 | 03115 | 0.190 | 0 190 | 0 080 |
| 150 | 25-Mar | | | | 00000 | | | | 00000 | | | | 00000 | 0 680 | 0 350 | 0 250 | 03115 | 0 190 | 0 200 | 0 080 |
| 151 | 26-Mar | | | | 00000 | | | | 00000 | | | | 00000 | 0 670 | 0 350 | 0 250 | 03069 | 0 210 | 0.210 | 0.080 |
| 152 | 27-Mar | | | | 00000 | | | | 00000 | | | | 00000 | 0 680 | 0 360 | 0 240 | 03076 | 0.210 | 0.220 | 0 080 |
| 153 | 28-Mar | | | | 00000 | | | | 00000 | | | | 00000 | 0 690 | 0 350 | 0 240 | 03034 | 0.210 | 0 230 | 0 090 |
| 154 | 29-Mar | | | | 00000 | | | | 00000 | | | | 00000 | 0 700 | 0 350 | 0.240 | 03078 | 0.210 | 0 220 | 0 090 |
| 155 | 30-Mar | | | | 00000 | | | | 00000 | | | | 00000 | 0 700 | 0 350 | 0 240 | 03078 | 0.210 | 0.220 | 0.090 |
| 156 | 31-Mar | | | | 00000 | | | | 00000 | | | | 00000 | 0 710 | 0 350 | 0 240 | 03122 | 0.210 | 0.220 | 0 090 |
| 157 | 1-Apr | | | | 00000 | | | | 00000 | | | | 00000 | 0 720 | 0 350 | 0 250 | .03298 | 0 210 | 0 220 | 0 100 |
| 158 | 2-Apr | | | | 00000 | | | | 00000 | | | | 00000 | 0 730 | 0 350 | 0 250 | .03344 | 0.230 | 0.220 | 0 100 |
| 159 | 3-Apr | | | | 00000 | | | | 00000 | | | | 00000 | 0 740 | 0 360 | 0 260 | 03626 | 0.240 | 0 220 | 0 100 |
| 160 | 4-Apr | | | | 00000 | | | | 00000 | | | | 00000 | 0 740 | 0 370 | 0 280 | 04013 | 0 240 | 0 230 | 0 100 |
| 161 | 5-Apr | | | | 00000 | | | | 00000 | | | | 00000 | 0 740 | 0 370 | 0 290 | .04157 | 0 240 | 0.240 | 0 110 |
| 162 | 6-Apr | | | | 00000 | | | | 00000 | | | | 00000 | 0 750 | 0 390 | 0 280 | 04287 | 0 240 | 0 230 | 0 120 |
| 163 | 7-Apr | | | | 00000 | | | | 00000 | | | | 00000 | 0 770 | 0 400 | 0 300 | 04837 | 0.240 | 0.230 | 0 120 |
| 164 | 8-Apr | | | | 00000 | | | | 00000 | | | | 00000 | 0 790 | 0 420 | 0 310 | 05385 | 0.270 | 0 250 | 0 120 |
| 165 | 9-Apr | | | | 00000 | | | | 00000 | | | | 00000 | 0 820 | 0 430 | 0 320 | .05907 | 0 280 | 0 260 | 0 130 |
| 166 | 10-Apr | | | | 00000 | | | | 00000 | | | | 00000 | 0 840 | 0 440 | 0 340 | 06579 | 0 270 | 0.280 | 0 130 |
| 167 | 11-Apr | | | | 00000 | | | | 00000 | | | | 00000 | 0 850 | 0 440 | 0 330 | 06461 | 0.280 | 0.280 | 0 130 |
| 168 | 12-Apr | | *Died 4/12/96* | | #VALUE! | | *Died 4/12/96* | | #VALUE! | | *Died 4/12/96* | | #VALUE! | | *Died 4/12/96* | | #VALUE! | | *Died 4/12/96* | |

OUJ-526-.xls

*OUJ-526 Born 2/2/95*

| DAY | DATE | Vol T-6 | WEIGHT Gr | HEMATO-CRIT-% | DEVICE | FREQ MHz | TIME | TREATMENT PARAMETERS FREQ MHz | TIME | FREQ MHz | TIME | POWER | DEVICE |
|---|---|---|---|---|---|---|---|---|---|---|---|---|---|
| 1 | 28-Oct | 00000 | 27 63 | 45 | | | | NO TREATMENT | | NO TREATMENT | | | |
| 2 | 29-Oct | 00000 | 27 75 | | | | | NO TREATMENT | | NO TREATMENT | | | |
| 3 | 30-Oct | 00000 | 27 92 | | | | | NO TREATMENT | | NO TREATMENT | | | |
| 4 | 31-Oct | 00000 | 27 47 | | | | | NO TREATMENT | | NO TREATMENT | | | |
| 5 | 1-Nov | 00000 | 27 58 | | | | | NO TREATMENT | | NO TREATMENT | | | |
| 6 | 2-Nov | 00000 | 27 44 | | | | | NO TREATMENT | | NO TREATMENT | | | |
| 7 | 3-Nov | 00000 | 27 57 | | | | | NO TREATMENT | | NO TREATMENT | | | |
| 8 | 4-Nov | 00000 | 28 07 | 45 | | | | NO TREATMENT | | NO TREATMENT | | | |
| 9 | 5-Nov | 00000 | 28 50 | | | | | NO TREATMENT | | NO TREATMENT | | | |
| 10 | 6-Nov | 00000 | 28 92 | | | | | NO TREATMENT | | NO TREATMENT | | | |
| 11 | 7-Nov | 00000 | 28 71 | | | | | NO TREATMENT | | NO TREATMENT | | | |
| 12 | 8-Nov | 00000 | 28 76 | | | | | NO TREATMENT | | NO TREATMENT | | | |
| 13 | 9-Nov | 00000 | 28 63 | | | | | NO TREATMENT | | NO TREATMENT | | | |
| 14 | 10-Nov | 00000 | 27 82 | | | | | NO TREATMENT | | NO TREATMENT | | | |
| 15 | 11-Nov | 00000 | 28 16 | 46 | | | | NO TREATMENT | | NO TREATMENT | | | |
| 16 | 12-Nov | 00000 | 27 90 | | | | | NO TREATMENT | | NO TREATMENT | | | |
| 17 | 13-Nov | 00000 | 27 73 | | | | | NO TREATMENT | | NO TREATMENT | | | |
| 18 | 14-Nov | 00000 | 27 88 | | | | | NO TREATMENT | | NO TREATMENT | | | |
| 19 | 15-Nov | 00000 | 27 51 | | | | | NO TREATMENT | | NO TREATMENT | | | |
| 20 | 16-Nov | 00000 | 27 56 | | | | | NO TREATMENT | | NO TREATMENT | | | |
| 21 | 17-Nov | 00000 | 27 71 | | | | | NO TREATMENT | | NO TREATMENT | | | |
| 22 | 18-Nov | 00000 | 27 56 | 43 | | | | NO TREATMENT | | NO TREATMENT | | | |
| 23 | 19-Nov | 00000 | 27 90 | | | | | NO TREATMENT | | NO TREATMENT | | | |
| 24 | 20-Nov | 00000 | 28 25 | | | | | NO TREATMENT | | NO TREATMENT | | | |
| 25 | 21-Nov | 00000 | 28 37 | | | | | NO TREATMENT | | NO TREATMENT | | | |
| 26 | 22-Nov | 00000 | 27 35 | | | | | NO TREATMENT | | NO TREATMENT | | | |
| 27 | 23-Nov | 00000 | 27 30 | | | | | NO TREATMENT | | NO TREATMENT | | | |
| 28 | 24-Nov | 00000 | 27 24 | | 8662A | 43322485 0 | 1 Hr | | | 43351871 0 | 1 Hr | 0 0 dBm | Type "P" |
| 29 | 25-Nov | 00000 | 27 09 | 38 | 8662A | 43322485 0 | 1 Hr | | | 43351871 0 | 1 Hr | 0 0 dBm | Type "P" |
| 30 | 26-Nov | 00000 | 27 58 | | | | | | | | | | |
| 31 | 27-Nov | 00000 | 28 08 | | 8662A | | | 43351853 0 | 1 Hr | 43351871 0 | 1 Hr | 0 0 dBm | Type "P" |
| 32 | 28-Nov | 00000 | 28 43 | | 8662A | | | 43351853 0 | 1 Hr | 43351871 0 | 1 Hr | 3 0 dBm | Type "P" |
| 33 | 29-Nov | 00000 | 28 80 | | 8662A | 43346000 0 | 2 Hr | | | | | 3 0 dBm | Type "P" |
| 34 | 30-Nov | 00000 | 27 80 | | 8662A | | | 43353850 0 | 2 Hr | | | 0 0 dBm | Type "P" |
| 35 | 1-Dec | 00000 | 27 94 | | 8662A | 43345000 0 | 1 Hr | 43353850 0 | 1Hr | | | 0 0 dBm | Type "P" |
| 36 | 2-Dec | 00000 | 28 20 | | 8662A | 43345000 0 | 1 Hr | 43353850 0 | 1Hr | | | 0 0 dBm | Type "P" |
| 37 | 3-Dec | 00000 | 28 40 | | | | | | | | | | |
| 38 | 4-Dec | 00000 | 28 60 | 45 | 8662A | 43351530 0 | 2 Hr | | | | | 0 0 dBm | Type "P" |
| 39 | 5-Dec | 00000 | 28 36 | | 8662A | 43351830 0 | 2 Hr | | | | | 0 0 dBm | Type "P" |
| 40 | 6-Dec | 00000 | 28 05 | | 8662A | 43351830 0 | 2 Hr | | | | | 0 0 dBm | Type "P" |
| 41 | 7-Dec | 00000 | 27 81 | | 8662A | 43351830 0 | 2 Hr | | | | | 0 0 dBm | Type "P" |
| 42 | 8-Dec | 00000 | 28 17 | | 8662A | 43351830 0 | 2 Hr | | | | | 0 0 dBm | Type "P" |
| 43 | 9-Dec | 00000 | 28 90 | 43 | 8662A | 43351830 0 | 2 Hr | | | | | 0 0 dBm | Type "P" |
| 44 | 10-Dec | 00000 | 28 40 | | | | | | | | | | |
| 45 | 11-Dec | 00000 | 27 86 | | 8662A | 43351830 0 | 2 Hr | | | | | 0 0 dBm | Type "P" |
| 46 | 12-Dec | 00000 | 27 91 | | 8662A | 43351830 0 | 2 Hr | | | | | 0 0 dBm | Type "P" |

4/11/97 Page 5 OUJ-526-.xls

OUJ-526-.xls

| DAY | DATE | Vol T-6 | WEIGHT Gr | HEMATO-CRIT-% | DEVICE | FREQ MHz | TIME | TREATMENT PARAMETERS FREQ MHz | TIME | FREQ MHz | TIME | POWER | DEVICE |
|---|---|---|---|---|---|---|---|---|---|---|---|---|---|
| 47 | 13-Dec | 00000 | 28 19 | | 8662A | 43351830 0 | 2 Hr | | | | | 0 0 dBm | Type "P" |
| 48 | 14-Dec | 00000 | 27 21 | | 8662A | 43351830 0 | 2 Hr | | | | | 0 0 dBm | Type "P" |
| 49 | 15-Dec | 00000 | 28 02 | | 8662A | 43351830 0 | 1 Hr | | | 43351870 0 | 1 Hr | 0 0 dBm | Type "P" |
| 50 | 16-Dec | 00000 | 28 03 | 42 | 8662A | 43351830 0 | 1 Hr | | | 43351870 0 | 1 Hr | 0 0 dBm | Type "P" |
| 51 | 17-Dec | 00000 | 28 40 | | | | | | | | | | |
| 52 | 18-Dec | 00000 | 29 01 | | 8662A | 43351830 0 | 1 Hr | | | 43351870 0 | 1 Hr | 0 0 dBm | Type "P" |
| 53 | 19-Dec | 00000 | 28 30 | | 8662A | 43351830 0 | 1 Hr | | | 43351870 0 | 1 Hr | 0 0 dBm | Type "P" |
| 54 | 20-Dec | 00000 | 27 77 | | 8662A | | | 43351853 0 | 1 Hr | 43351871 0 | 1 Hr | 0 0 dBm | Type "P" |
| 55 | 21-Dec | 00000 | 28 43 | | 8662A | | | 43351853 0 | 1 Hr | 43351871 0 | 1 Hr | 0 0 dBm | Type "P" |
| 56 | 22-Dec | 00000 | 27 45 | | 8662A | | | 43353800 0 | 1 Hr | 43351853 0 | 1 Hr | 0 0 dBm | Type "P" |
| 57 | 23-Dec | 00000 | 27 59 | 42 | 8662A | 43346000 0 | 1 Hr | 43353800 0 | 1 Hr | | | 0 0 dBm | Type "P" |
| 58 | 24-Dec | 00000 | 27 80 | | | | | | | | | | |
| 59 | 25-Dec | 00000 | 28 00 | | | | | | | | | | |
| 60 | 26-Dec | 00000 | 28 25 | | 8662A | 43346000 0 | 1 Hr | 43353800 0 | 1 Hr | | | 0 0 dBm | Type "P" |
| 61 | 27-Dec | 00000 | 27 99 | | 8662A | | | 43353800 0 | 2 Hr | | | 0 0 dBm | Type "Q" |
| 62 | 28-Dec | 00000 | 28 11 | | 8662A | 43322485 0 | 2 Hr | | | | | 0 0 dBm | Type "Q" |
| 63 | 29-Dec | 00000 | 27 88 | | 8662A | 43346000 0 | 2 Hr | | | | | 0.0 dBm | Type "Q" |
| 64 | 30-Dec | 00000 | 27 51 | 35 | 8662A | 43351830 0 | 1 Hr | | | 43351871 3 | 1 Hr | 0 0 dBm | Type "Q" |
| 65 | 31-Dec | 00000 | 27 95 | | | | | | | | | | |
| 66 | 1-Jan | 00000 | 28 40 | | 8662A | 43351830 0 | 1 Hr | | | 43351871 3 | 1 Hr | 0 0 dBm | Type "Q" |
| 67 | 2-Jan | 00000 | 27 65 | | 8662A | 43322485 0 | 1 Hr | 43353850 0 | 1 Hr | | | 0 0 dBm | Type "Q" |
| 68 | 3-Jan | 00000 | 27 71 | | 8662A | 43351830 0 | 1 Hr | 43351871 3 | 1 Hr | | | 0 0 dBm | Type "Q" |
| 69 | 4-Jan | 00000 | 27 54 | | 8662A | 43346000 0 | 1 Hr | 43353850 0 | 1 Hr | | | 0.0 dBm | Type "Q" |
| 70 | 5-Jan | 00000 | 28 00 | | 8662A | 43346000 0 | 1 Hr | 43353850 0 | 1 Hr | | | 0 0 dBm | Type "R" |
| 71 | 6-Jan | 00000 | 26 74 | 41 | 8662A | 43346000 0 | 1 Hr | 43353850 0 | 1 Hr | | | 0 0 dBm | Type "R" |
| 72 | 7-Jan | 00000 | 25 80 | | | | | | | | | | |
| 73 | 8-Jan | 00000 | 25 88 | | 8662A | | | 43351850 0 | 1 Hr | 43351870 0 | 1 Hr | 0 0 dBm | Type "R" |
| 74 | 9-Jan | 00000 | 26 23 | | 8662A | | | 43351850 0 | 2 Hr | | | 0 0 dBm | Type "R" |
| 75 | 10-Jan | 00000 | 25 64 | | 8662A | | | 43351850 0 | 2 Hr | | | 0 0 dBm | Type "R" |
| 76 | 11-Jan | 00000 | 26 99 | | 8662A | | | | | 43351870 0 | 2 Hr | 0 0 dBm | Type "R" |
| 77 | 12-Jan | 00000 | 26 54 | | 8662A | | | | | 43351870.0 | 2 Hr | 0 0 dBm | Type "R" |
| 78 | 13-Jan | 00000 | 27 81 | 41 | 8662A | | | 43351850 0 | 2 Hr | | | 0 0 dBm | Type "R" |
| 79 | 14-Jan | 00000 | 27 60 | | | | | | | | | | |
| 80 | 15-Jan | 00000 | 27 33 | | 8662A | | | | | 43351870 0 | 2 Hr | 0 0 dBm | Type "R" |
| 81 | 16-Jan | 00000 | 27 32 | | 8662A | | | 43351850 0 | 2 Hr | | | 0 0 dBm | Type "R" |
| 82 | 17-Jan | 00000 | 26 47 | | 8662A | | | 43351850 0 | 2 Hr | | | 0 0 dBm | Type "R" |
| 83 | 18-Jan | 00000 | 27 88 | | 8662A | | | | | 43351870 0 | 2 Hr | 0 0 dBm | Type "R" |
| 84 | 19-Jan | 00000 | 27 39 | | 8662A | | | 43351850 0 | 2 Hr | | | 0 0 dBm | Type "R" |
| 85 | 20-Jan | 00000 | 27 22 | 39 | 8662A | | | | | 43351870 0 | 2 Hr | 0 0 dBm | Type "S" |
| 86 | 21-Jan | 00000 | 27 60 | | | | | | | | | | |
| 87 | 22-Jan | 00000 | 29 09 | | 8662A | | | 43351850 0 | 2 Hr | | | 0 0 dBm | Type "S" |
| 88 | 23-Jan | 00000 | 25 89 | | 8662A | 43351830 0 | 2 Hr | | | | | 0 0 dBm | Type "S" |
| 89 | 24-Jan | 00000 | 25 95 | | 8662A | | | | | 43351870 0 | 2 Hr | 0 0 dBm | Type "S" |
| 90 | 25-Jan | 00000 | 27 15 | | 8662A | | | 43351850 0 | 2 Hr | | | 0 0 dBm | Type "S" |
| 91 | 26-Jan | 00000 | 25 75 | | 8662A | 43351830 0 | 2 Hr | | | | | 0 0 dBm | Type "S" |
| 92 | 27-Jan | 00000 | 26 98 | 40 | 8662A | 43351830 0 | 2 Hr | | | | | 0 0 dBm | Type "S" |
| 93 | 28-Jan | 00000 | 27 15 | | | | | | | | | | |
| 94 | 29-Jan | 00000 | 27 43 | | 8662A | 43351830 0 | 2 Hr | | | | | 3 0 dBm | Type "S" |

4/11/97 Page 6 OUJ-526-.xls

86828O " T69TWT60

OUJ-526-.xls

| DAY | DATE | Vol T-6 | WEIGHT Gr | HEMATO-CRIT-% | DEVICE | FREQ MHz | TIME | TREATMENT PARAMETERS FREQ MHz | TIME | FREQ MHz | TIME | POWER | DEVICE |
|---|---|---|---|---|---|---|---|---|---|---|---|---|---|
| 47 | 13-Dec | 00000 | 28 19 | | 8662A | 43351830 0 | 2 Hr | | | | | 0 0 dBm | Type "P" |
| 48 | 14-Dec | 00000 | 27 21 | | 8662A | 43351830 0 | 2 Hr | | | | | 0 0 dBm | Type "P" |
| 49 | 15-Dec | 00000 | 28 02 | | 8662A | 43351830 0 | 1 Hr | | | 43351870 0 | 1 Hr | 0 0 dBm | Type "P" |
| 50 | 16-Dec | 00000 | 28 03 | 42 | 8662A | 43351830 0 | 1 Hr | | | 43351870 0 | 1 Hr | 0 0 dBm | Type "P" |
| 51 | 17-Dec | 00000 | 28 40 | | | | | | | | | | |
| 52 | 18-Dec | 00000 | 29 01 | | 8662A | 43351830 0 | 1 Hr | | | 43351870 0 | 1 Hr | 0 0 dBm | Type "P" |
| 53 | 19-Dec | 00000 | 28 30 | | 8662A | 43351830 0 | 1 Hr | | | 43351870 0 | 1 Hr | 0 0 dBm | Type "P" |
| 54 | 20-Dec | 00000 | 27 77 | | 8662A | | | 43351853 0 | 1 Hr | 43351871 0 | 1 Hr | 0 0 dBm | Type "P" |
| 55 | 21-Dec | 00000 | 28 43 | | 8662A | | | 43351853 0 | 1 Hr | 43351871.0 | 1 Hr | 0 0 dBm | Type "P" |
| 56 | 22-Dec | 00000 | 27 45 | | 8662A | | | 43353800 0 | 1 Hr | 43351853 0 | 1 Hr | 0 0 dBm | Type "P" |
| 57 | 23-Dec | 00000 | 27 59 | 42 | 8662A | 43346000 0 | 1 Hr | 43353800 0 | 1 Hr | | | 0.0 dBm | Type "P" |
| 58 | 24-Dec | 00000 | 27 80 | | | | | | | | | | |
| 59 | 25-Dec | 00000 | 28 00 | | | | | | | | | | |
| 60 | 26-Dec | 00000 | 28 25 | | 8662A | 43346000 0 | 1 Hr | 43353800 0 | 1 Hr | | | 0 0 dBm | Type "P" |
| 61 | 27-Dec | 00000 | 27 99 | | 8662A | | | 43353800 0 | 2 Hr | | | 0 0 dBm | Type "Q" |
| 62 | 28-Dec | 00000 | 28 11 | | 8662A | 43322485 0 | 2 Hr | | | | | 0 0 dBm | Type "Q" |
| 63 | 29-Dec | 00000 | 27 88 | | 8662A | 43346000 0 | 2 Hr | | | | | 0 0 dBm | Type "Q" |
| 64 | 30-Dec | 00000 | 27 51 | 35 | 8662A | 43351830 0 | 1 Hr | | | 43351871 3 | 1 Hr | 0 0 dBm | Type "Q" |
| 65 | 31-Dec | 00000 | 27 95 | | | | | | | | | | |
| 66 | 1-Jan | 00000 | 28 40 | | 8662A | 43351830 0 | 1 Hr | | | 43351871 3 | 1 Hr | 0 0 dBm | Type "Q" |
| 67 | 2-Jan | 00000 | 27 65 | | 8662A | 43322485 0 | 1 Hr | 43353850 0 | 1 Hr | | | 0 0 dBm | Type "Q" |
| 68 | 3-Jan | 00000 | 27 71 | | 8662A | 43351830 0 | 1 Hr | 43351871 3 | 1 Hr | | | 0 0 dBm | Type "Q" |
| 69 | 4-Jan | 00000 | 27 54 | | 8662A | 43346000 0 | 1 Hr | 43353850 0 | 1 Hr | | | 0 0 dBm | Type "Q" |
| 70 | 5-Jan | 00000 | 28 00 | | 8662A | 43346000 0 | 1 Hr | 43353850 0 | 1 Hr | | | 0 0 dBm | Type "R" |
| 71 | 6-Jan | 00000 | 25 74 | 41 | 8662A | 43346000 0 | 1 Hr | 43353850 0 | 1 Hr | | | 0 0 dBm | Type "R" |
| 72 | 7-Jan | 00000 | 26 80 | | | | | | | | | | |
| 73 | 8-Jan | 00000 | 26 88 | | 8662A | | | 43351850 0 | 1 Hr | 43351870 0 | 1 Hr | 0 0 dBm | Type "R" |
| 74 | 9-Jan | 00000 | 26 23 | | 8662A | | | 43351850 0 | 2 Hr | | | 0 0 dBm | Type "R" |
| 75 | 10-Jan | 00000 | 25 84 | | 8662A | | | 43351850 0 | 2 Hr | | | 0 0 dBm | Type "R" |
| 76 | 11-Jan | 00000 | 26 99 | | 8662A | | | | | 43351870 0 | 2 Hr | 0 0 dBm | Type "R" |
| 77 | 12-Jan | 00000 | 26 54 | | 8662A | | | | | 43351870 0 | 2 Hr | 0 0 dBm | Type "R" |
| 78 | 13-Jan | 00000 | 27 81 | 41 | 8662A | | | 43351850 0 | 2 Hr | | | 0 0 dBm | Type "R" |
| 79 | 14-Jan | 00000 | 27 60 | | | | | | | | | | |
| 80 | 15-Jan | 00000 | 27 33 | | 8662A | | | | | 43351870 0 | 2 Hr | 0 0 dBm | Type "R" |
| 81 | 16-Jan | 00000 | 27 22 | | 8662A | | | 43351850 0 | 2 Hr | | | 0 0 dBm | Type "R" |
| 82 | 17-Jan | 00000 | 25 47 | | 8662A | | | 43351850 0 | 2 Hr | | | 0 0 dBm | Type "R" |
| 83 | 18-Jan | 00000 | 27 88 | | 8662A | | | | | 43351870 0 | 2 Hr | 0 0 dBm | Type "R" |
| 84 | 19-Jan | 00000 | 27 39 | | 8662A | | | 43351850 0 | 2 Hr | | | 0 0 dBm | Type "R" |
| 85 | 20-Jan | 00000 | 27 22 | 39 | 8662A | | | | | 43351870 0 | 2 Hr | 0 0 dBm | Type "S" |
| 86 | 21-Jan | 00000 | 27 50 | | | | | | | | | | |
| 87 | 22-Jan | 00000 | 28 29 | | 8662A | | | 43351850 0 | 2 Hr | | | 0 0 dBm | Type "S" |
| 88 | 23-Jan | 00000 | 25 99 | | 8662A | 43351830 0 | 2 Hr | | | | | 0 0 dBm | Type "S" |
| 89 | 24-Jan | 00000 | 26 96 | | 8662A | | | | | 43351870 0 | 2 Hr | 0 0 dBm | Type "S" |
| 90 | 25-Jan | 00000 | 27 15 | | 8662A | | | 43351850 0 | 2 Hr | | | 0 0 dBm | Type "S" |
| 91 | 26-Jan | 00000 | 25 75 | | 8662A | 43351830 0 | 2 Hr | | | | | 0.0 dBm | Type "S" |
| 92 | 27-Jan | 00000 | 26 98 | 40 | 8662A | 43351830 0 | 2 Hr | | | | | 0 0 dBm | Type "S" |
| 93 | 28-Jan | 00000 | 27 15 | | | | | | | | | | |
| 94 | 29-Jan | 00000 | 27 43 | | 8662A | 43351830 0 | 2 Hr | | | | | 3 0 dBm | Type "S" |

4/11/97 Page 6 OUJ-526-.xls

OUJ-526-.xls

| DAY | DATE | Vol T-6 | WEIGHT Gr | HEMATO-CRIT-% | DEVICE | FREQ MHz | TIME | TREATMENT PARAMETERS FREQ MHz | TIME | FREQ MHz | TIME | POWER | DEVICE |
|---|---|---|---|---|---|---|---|---|---|---|---|---|---|
| 95 | 30-Jan | 00000 | 26 57 | | 8662A | | | | | 43351870 0 | 2 Hr | 3 0 dBm | Type "S" |
| 96 | 31-Jan | .00000 | 26 29 | | 8662A | | | 43351850 0 | 2 Hr | | | 3 0 dBm | Type "S" |
| 97 | 1-Feb | 00000 | 26 73 | | 8662A | 43351830 0 | 2 Hr | | | | | 3 0 dBm | Type "S" |
| 98 | 2-Feb | 00000 | 27 19 | | 8662A | | | 43351850 0 | 2 Hr | | | 3 0 dBm | Type "S" |
| 99 | 3-Feb | 00000 | 27 19 | 40 | 8662A | 43351830 0 | 2 Hr | | | | | 3 0 dBm | Type "S" |
| 100 | 4-Feb | 00000 | 27 20 | | | | | | | | | | |
| 101 | 5-Feb | 00000 | 27 21 | | 8662A | | | | | 43351870 0 | 2 Hr | 3 0 dBm | Type "S" |
| 102 | 6-Feb | .00000 | 27 57 | | 8662A | 43351830 0 | 2 Hr | | | | | 3 0 dBm | Type "S" |
| 103 | 7-Feb | 00000 | 27 94 | | 8662A | 43351830 0 | 2 Hr | | | | | 3.0 dBm | Type "S" |
| 104 | 8-Feb | 00000 | 28 48 | | 8662A | | | | | 43351870 0 | 2 Hr | 3 0 dBm | Type "S" |
| 105 | 9-Feb | 00000 | 27 05 | | 8662A | | | | | 43351870.0 | 2 Hr | 3 0 dBm | Type "S" |
| 106 | 10-Feb | 00000 | 27 66 | 41 | 8662A | | | 43351850 0 | 2 Hr | | | 3 0 dBm | Type "S" |
| 107 | 11-Feb | 00000 | 27 68 | | | | | | | | | | |
| 108 | 12-Feb | 00000 | 27 71 | | 8662A | | | 43351850 0 | 1 Hr | 43351853 0 | 1 Hr | 3 0 dBm | Type "S" |
| 109 | 13-Feb | 00000 | 27 95 | | 8662A | 43346000.0 | 1 Hr | 43351850 0 | 1 Hr | | | 3 0 dBm | Type "S" |
| 110 | 14-Feb | 00000 | 26 32 | | 8662A | | | 43351871 0 | 2 Hr | | | 3 0 dBm | Type "S" |
| 111 | 15-Feb | 00000 | 28 29 | | 8662A | | | 43351850 0 | 1 Hr | 43351853 0 | 1 Hr | 3 0 dBm | Type "S" |
| 112 | 16-Feb | 00000 | 27 74 | | 8662A | | | 43351850 0 | 1 Hr | 43351853 0 | 1 Hr | 3 0 dBm | Type "S" |
| 113 | 17-Feb | 00000 | 27 53 | 39 | 8662A | | | 43351850 0 | 2 Hr | 43351853 0 | 1 Hr | 3 0 dBm | Type "S" |
| 114 | 18-Feb | 00000 | 26 25 | | | | | | | | | | |
| 115 | 19-Feb | 00000 | 29 00 | | 8662A | | | 43351850 0 | 1 Hr | 43351853 0 | 1 Hr | 3 0 dBm | Type "T" |
| 116 | 20-Feb | 00000 | 29 07 | | 8662A | | | 43351853 0 | 2 Hr | 43351871 0 | 1 Hr | 3 0 dBm | Type "T" |
| 117 | 21-Feb | 00000 | 27 08 | | 8662A | | | 43351853 0 | 2 Hr | 43351871.0 | 1 Hr | 0 0 dBm | Type "T" |
| 118 | 22-Feb | 00000 | 27 95 | | 8662A | | | 43351853 0 | 1 Hr | 43351871 0 | 2 Hr | 0 0 dBm | Type "T" |
| 119 | 23-Feb | 00000 | 26 75 | | 8662A | | | | | 43351870 0 | 3 Hr | 0 0 dBm | Type "T" |
| 120 | 24-Feb | 00000 | 27 08 | 40 | 8662A | | | | | 43351870 0 | 3 Hr | 0 0 dBm | Type "T" |
| 121 | 25-Feb | 00000 | 27 80 | | | | | | | | | | |
| 122 | 26-Feb | 00000 | 26 50 | | 8662A | | | 43351850 0 | 3 Hr | | | 0 0 dBm | Type "T" |
| 123 | 27-Feb | .00000 | 27 61 | | 8662A | | | 43351853 0 | 1 Hr | 43351871 0 | 2 Hr | 0 0 dBm | Type "T" |
| 124 | 28-Feb | 00000 | 27 67 | | 8662A | 43322485 0 | 1 Hr | 43346000 0 | 2 Hr | | | 0 0 dBm | Type "T" |
| 125 | 29-Feb | 00000 | 27 65 | | 8662A | 43322485 0 | 1 Hr | 43346000 0 | 2 Hr | | | 0 0 dBm | Type "T" |
| 126 | 1-Mar | 00000 | 27 09 | | 8662A | 43322485 0 | 1 Hr | 43346000 0 | 2 Hr | | | 0 0 dBm | Type "T" |
| 127 | 2-Mar | 00000 | 26 95 | 36 | 8662A | 43322485 0 | 1 Hr | | | 43353800 0 | 2 Hr | 0 0 dBm | Type "T" |
| 128 | 3-Mar | 00000 | 26 75 | | | | | | | | | | |
| 129 | 4-Mar | 00000 | 26 58 | | 8662A | 43322485 0 | 1 Hr | | | 43353800 0 | 2 Hr | 0 0 dBm | Type "T" |
| 130 | 5-Mar | 00000 | 27 92 | | 8662A | 43322485 0 | 1 Hr | 43346000 0 | 1 Hr | 43353850 0 | 1 Hr | 0 0 dBm | Type "U" |
| 131 | 6-Mar | 00000 | 27 44 | | 8662A | 43322485 0 | 1 Hr | 43346000 0 | 1 Hr | 43353850 0 | 1 Hr | 0 0 dBm | Type "U" |
| 132 | 7-Mar | 00000 | 27 54 | | 8662A | | | 43351853 0 | 2 Hr | 43351871 0 | 1 Hr | 0 0 dBm | Type "U" |
| 133 | 8-Mar | 00000 | 27 45 | | 8662A | | | 43351853 0 | 2 Hr | 43351871 0 | 1 Hr | 0 0 dBm | Type "U" |
| 134 | 9-Mar | 00000 | 26 75 | 37 | 8662A | 43322485 0 | 1 Hr | 43346000 0 | 2 Hr | | | 0 0 dBm | Type "V" |
| 135 | 10-Mar | 00000 | 27 65 | | | | | | | | | | |
| 136 | 11-Mar | 00000 | 27 55 | | 8662A | 43322480 0 | 1 Hr | 43322485 0 | 1 Hr | 43353800 0 | 1 Hr | 0 0 dBm | Type "V" |
| 137 | 12-Mar | 00000 | 27 62 | | 8662A | | | 43346000 0 | 3 Hr | | | 0 0 dBm | Type "U" |
| 138 | 13-Mar | 00000 | 28 27 | | 8662A | | | 43346000 0 | 3 Hr | | | 0 0 dBm | Type "U" |
| 139 | 14-Mar | 00000 | 28 33 | | 8662A | | | 43346000 0 | 3 Hr | | | 0 0 dBm | Type "U" |
| 140 | 15-Mar | 00000 | 28 59 | | 8662A | 43351830 0 | 1 Hr | | | 43351853 0 | 2 Hr | 0 0 dBm | Type "U" |
| 141 | 16-Mar | 00000 | 28 35 | 37 | 8662A | | | 43346000 0 | 3 Hr | | | 0 0 dBm | Type "U" |
| 142 | 17-Mar | 00000 | 28 36 | | | | | | | | | 0 0 dBm | Type "U" |

4/11/97 Page 7 OUJ-526-.xls

OUJ-526-.xls

| DAY | DATE | Vol T-6 | WEIGHT Gr | HEMATO-CRIT-% | DEVICE | FREQ MHz | TIME | FREQ MHz | TIME | FREQ MHz | TIME | POWER | DEVICE |
|---|---|---|---|---|---|---|---|---|---|---|---|---|---|
| | | | | | | TREATMENT PARAMETERS | | | | | | | |
| 143 | 18-Mar | 00060 | 28 38 | | 8662A | 43322480 0 | 1 Hr | | | 43353800 0 | 2 Hr | 0 0 dBm | Type "U" |
| 144 | 19-Mar | 00076 | 27 79 | | 8662A | 43322480 0 | 1 Hr | 43346000 0 | 1 Hr | 43353800 0 | 1 Hr | 0 0 dBm | Type "U" |
| 145 | 20-Mar | 00088 | 27 98 | | 8662A | | | 43351853 0 | 2 Hr | | | 0 0 dBm | Type "U" |
| 146 | 21-Mar | 00100 | 28 37 | | 8662A | | | 43351853 0 | 3 Hr | | | 0 0 dBm | Type "U" |
| 147 | 22-Mar | 00112 | 28 41 | | 8662A | | | 43346000 0 | 3 Hr | | | 0 0 dBm | Type "U" |
| 148 | 23-Mar | 00151 | 28 60 | 31 | 8662A | | | 43322485 0 | 2 Hr | 43353800 0 | 1 Hr | 0 0 dBm | Type "U" |
| 149 | 24-Mar | .00151 | 28 90 | | | | | | | | | | |
| 150 | 25-Mar | 00159 | 29 12 | | 8662A | | | 43322485 0 | 2 Hr | 43353800 0 | 1 Hr | 0.0 dBm | Type "U" |
| 151 | 26-Mar | 00185 | 28 75 | | 8662A | | | 43351870 0 | 1 Hr | 43351871 0 | 2 Hr | 0 0 dBm | Type "U" |
| 152 | 27-Mar | 00193 | 28 58 | | 8662A | | | 43346000 0 | 1 Hr | 43351871 0 | 2 Hr | 0 0 dBm | Type "U" |
| 153 | 28-Mar | 00228 | 28 87 | | 8662A | | | 43346000 0 | 1 Hr | 43351871 0 | 2 Hr | 0 0 dBm | Type "U" |
| 154 | 29-Mar | 00218 | 28 79 | | 8662A | | | 43346000 0 | 3 Hr | | | 0 0 dBm | Type "U" |
| 155 | 30-Mar | 00218 | 29 30 | 36 | 8662A | | | 43346000 0 | 3 Hr | | | 0 0 dBm | Type "U" |
| 156 | 31-Mar | 00218 | 29 60 | | | | | | | | | | |
| 157 | 1-Apr | .00242 | 29 85 | | 8662A | | | 43322485 0 | 2 Hr | 43353800 0 | 1 Hr | 0 0 dBm | Type "U" |
| 158 | 2-Apr | 00265 | 30 13 | | 8662A | | | | | 43351871.0 | 3 Hr | 0.0 dBm | Type "U" |
| 159 | 3-Apr | 00276 | 30 03 | | 8662A | | | 43351853 0 | 3 Hr | | | 0.0 dBm | Type "U" |
| 160 | 4-Apr | .00289 | 29 17 | | 8662A | 43322492.0 | 1 Hr | 43346090 0 | 1 Hr | | | 0 0 dBm | Type "U" |
| 161 | 5-Apr | 00332 | 29 08 | | 8662A | 43322492 0 | 1 Hr | 43346090 0 | 1 Hr | | | 0 0 dBm | Type "U" |
| 162 | 6-Apr | 00347 | 29 59 | 34 | 8662A | 43322552 0 | 2 Hr | | | | | 0.0 dBm | Type "U" |
| 163 | 7-Apr | 00347 | 30 00 | | | | | | | | | | |
| 164 | 8-Apr | 00424 | 30 45 | | 8662A | 43322492 0 | 1 Hr | 43346090 0 | 1 Hr | 43351853 0 | 1 Hr | 0 0 dBm | Type "U" |
| 165 | 9-Apr | 00495 | 30 68 | | 8662A | 43322492 0 | 1 Hr | 43346000 0 | 1 Hr | 43351871 0 | 1 Hr | 0 0 dBm | Type "U" |
| 166 | 10-Apr | .00514 | 31 59 | | 8662A | 43322492 0 | 1 Hr | 43346090 0 | 2 Hr | | | 0 0 dBm | Type "U" |
| 167 | 11-Apr | 00534 | 31 87 | | 8662A | | | | | | | 0 0 dBm | Type "U" |
| 168 | 12-Apr | #VALUE' | | | 8662A | | | | | | | 0.0 dBm | Type "U" |

09144691.082898

OUJ-650 Born 4/4/95 First tumor appeared on 12/13/95

| DAY | DATE | T-1 L Bottom Ln | Wd | Ht | Vol T-1 | T-2 R Abdomen Ln | Wd | Ht | Vol T-2 | T-3 L Abdomen Ln | Wd | Ht | Vol T-3 | WEIGHT Gr | HEMATO-CRIT-% | DEVICE | FREQ MHz | TIME | TREATMENT PARAMETERS FREQ MHz | TIME | FREQ MHz | TIME | POWER | DEVICE |
|---|---|---|---|---|---|---|---|---|---|---|---|---|---|---|---|---|---|---|---|---|---|---|---|---|
| 1 | 13-Dec | | | | 00000 | | | | 00000 | | | | 00000 | 33 42 | | 8662A | 43322480 0 | 1/3 Hr | 43353800 0 | 1/3 Hr | | | 0 0 dBm | Type "P" |
| 2 | 14-Dec | 0 070 | 0 070 | 0 070 | 00018 | | | | 00000 | | | | 00000 | 31 43 | | 8662A | 43322485 0 | 1/2 Hr | 43346000 0 | 1/2 Hr | | | 0 0 dBm | Type "P" |
| 3 | 15-Dec | 0 080 | 0 090 | 0 080 | 00030 | | | | 00000 | | | | 00000 | 31 40 | | 8662A | 43353850 0 | 1/2 Hr | 43346000 0 | 1/2 Hr | | | 0 0 dBm | Type "P" |
| 4 | 16-Dec | 0 100 | 0 100 | 0 070 | 00037 | | | | 00000 | | | | 00000 | 29 88 | 48 | 8662A | 43322485 0 | 1/2 Hr | 43346000 0 | 1/2 Hr | 43353800 0 | 1/2 Hr | 0 0 dBm | Type "P" |
| 5 | 17-Dec | 0 100 | 0 100 | 0 070 | 00037 | | | | 00000 | | | | 00000 | 30 10 | | | | | | | | | | |
| 6 | 18-Dec | 0 090 | 0 100 | 0 080 | 00038 | | | | 00000 | | | | 00000 | 30 33 | | 8662A | | | 43322485 0 | 1 Hr | 43353800 0 | 1 Hr | 0 0 dBm | Type "P" |
| 7 | 19-Dec | 0 100 | 0 090 | 0 090 | 00042 | | | | 00000 | | | | 00000 | 29 79 | | 8662A | 43000000 0 | 1 Hr | 43346000 0 | 1 Hr | | | 0 0 dBm | Type "P" |
| 8 | 20-Dec | 0 150 | 0 110 | 0 120 | 00104 | | | | 00000 | | | | 00000 | 29 39 | | 8662A | | | 43346000 0 | 1 Hr | 43353800 0 | 1 Hr | 0 0 dBm | Type "P" |
| 9 | 21-Dec | 0 160 | 0 140 | 0 110 | 00129 | | | | 00000 | | | | 00000 | 29 83 | | 8662A | | | 43346000 0 | 1 Hr | 43353800 0 | 1 Hr | 0 0 dBm | Type "P" |
| 10 | 22-Dec | 0 160 | 0 140 | 0 110 | 00129 | | | | 00000 | | | | 00000 | 28 80 | | 8662A | | | 43346000 0 | 1 Hr | 43353800 0 | 1 Hr | 0 0 dBm | Type "P" |
| 11 | 23-Dec | 0 170 | 0 160 | 0 110 | 00157 | | | | 00000 | | | | 00000 | 29 67 | 46 | 8662A | | | 43346000 0 | 1 Hr | 43353800 0 | 1 Hr | 0 0 dBm | Type "P" |
| 12 | 24-Dec | 1 900 | 0 180 | 0 110 | 01969 | | | | 00000 | | | | 00000 | 30 30 | | | | | | | | | | |
| 13 | 25-Dec | 0 200 | 0 180 | 0 110 | 00719 | | | | 00000 | | | | 00000 | 30 80 | | | | | | | | | | |
| 14 | 26-Dec | 0 210 | 0 200 | 0 110 | 00742 | | | | 00000 | | | | 00000 | 31 51 | | 8662A | | | 43322480 0 | 2 Hr | | | 0 0 dBm | Type "P" |
| 15 | 27-Dec | 0 200 | 0 190 | 0 110 | 00718 | | | | 00000 | | | | 00000 | 30 56 | | 8662A | | | 43322485 0 | 2 Hr | | | 0 0 dBm | Type "Q" |
| 16 | 28-Dec | 0 180 | 0 170 | 0 110 | 00176 | | | | 00000 | | | | 00000 | 30 89 | | 8662A | | | 43322485 0 | 2 Hr | | | 0 0 dBm | Type "Q" |
| 17 | 29-Dec | 0 190 | 0 170 | 0 110 | 00186 | | | | 00000 | | | | 00000 | 30 32 | | 8662A | | | 43353800 0 | 2 Hr | | | 0 0 dBm | Type "Q" |
| 18 | 30-Dec | 0 190 | 0 170 | 0 110 | 00186 | | | | 00000 | | | | 00000 | 29 80 | 42 | | | | | | | | | |
| 19 | 31-Dec | 0 190 | 0 170 | 0 110 | 00186 | | | | 00000 | | | | 00000 | 30 10 | | 8662A | 43351830 0 | 1 Hr | | | 43351871 3 | 1 Hr | 0 0 dBm | Type "Q" |
| 20 | 1-Jan | 0 190 | 0 170 | 0 110 | 00186 | | | | 00000 | | | | 00000 | 30 43 | | 8662A | 43351830 0 | 1 Hr | | | 43351871 3 | 1 Hr | 0 0 dBm | Type "Q" |
| 21 | 2-Jan | 0 180 | 0 170 | 0 110 | 00176 | | | | 00000 | | | | 00000 | 29 03 | | 8662A | 43351830 0 | 1 Hr | | | 43351871 3 | 1 Hr | 0 0 dBm | Type "Q" |
| 22 | 3-Jan | 0 170 | 0 170 | 0 110 | 00166 | | | | 00000 | | | | 00000 | 28 29 | | 8662A | 43351830 0 | 1 Hr | | | 43351871 3 | 1 Hr | 0 0 dBm | Type "Q" |
| 23 | 4-Jan | 0 150 | 0 140 | 0 110 | 00121 | | | | 00000 | | | | 00000 | 29 31 | | 8662A | 43351830 0 | 1 Hr | | | 43351871 3 | 1 Hr | 0 0 dBm | Type "Q" |
| 24 | 5-Jan | 0 150 | 0 140 | 0 110 | 00121 | | | | 00000 | | | | 00000 | 29 53 | | 8662A | 43351830 0 | 1 Hr | | | 43351871 3 | 1 Hr | 0 0 dBm | Type "Q" |
| 25 | 6-Jan | 0 140 | 0 140 | 0 110 | 00113 | | | | 00000 | | | | 00000 | 29 62 | 47 | 8662A | 43351830 0 | 1 Hr | | | 43351871 3 | 1 Hr | 0 0 dBm | Type "R" |
| 26 | 7-Jan | 0 140 | 0 140 | 0 110 | 00113 | | | | 00000 | | | | 00000 | 29 40 | | | | | | | | | | |
| 27 | 8-Jan | 0 140 | 0 140 | 0 110 | 00113 | | | | 00000 | | | | 00000 | 29 14 | | 8662A | | | 43351850 0 | 1 Hr | 43351870 0 | 1 Hr | 0 0 dBm | Type "R" |
| 28 | 9-Jan | 0 140 | 0 140 | 0 110 | 00113 | | | | 00000 | | | | 00000 | 28 30 | | 8662A | | | 43351850 0 | 1 Hr | 43351870 0 | 1 Hr | 0 0 dBm | Type "R" |
| 29 | 10-Jan | 0 120 | 0 120 | 0 100 | 00075 | | | | 00000 | | | | 00000 | 28 26 | | 8662A | | | 43351850 0 | 1 Hr | 43351870 0 | 1 Hr | 0 0 dBm | Type "R" |
| 30 | 11-Jan | 0 120 | 0 130 | 0 110 | 00090 | | | | 00000 | | | | 00000 | 28 82 | | 8662A | | | | | 43351870 0 | 2 Hr | 0 0 dBm | Type "R" |
| 31 | 12-Jan | 0 110 | 0 110 | 0 100 | 00063 | | | | 00000 | | | | 00000 | 28 21 | | 8662A | | | 43351850 0 | 2 Hr | | | 0 0 dBm | Type "R" |
| 32 | 13-Jan | 0 100 | 0 100 | 0 070 | 00037 | | | | 00000 | | | | 00000 | 29 00 | 45 | 8662A | | | | | 43351870 0 | 2 Hr | 0 0 dBm | Type "R" |
| 33 | 14-Jan | 0 100 | 0 090 | 0 070 | 00033 | | | | 00000 | | | | 00000 | 29 35 | | | | | | | | | | |
| 34 | 15-Jan | 0 100 | 0 090 | 0 070 | 00033 | | | | 00000 | | | | 00000 | 29 70 | | 8662A | | | 43351850 0 | 2 Hr | | | 0 0 dBm | Type "R" |
| 35 | 16-Jan | 0 090 | 0 080 | 0 070 | 00030 | | | | 00000 | | | | 00000 | 28 38 | | 8662A | | | | | 43351870 0 | 2 Hr | 0 0 dBm | Type "R" |
| 36 | 17-Jan | 0 090 | 0 090 | 0 070 | 00030 | | | | 00000 | | | | 00000 | 27 60 | | 8662A | | | 43351850 0 | 2 Hr | | | 0 0 dBm | Type "R" |
| 37 | 18-Jan | 0 090 | 0 090 | 0 070 | 00030 | | | | 00000 | | | | 00000 | 30 18 | | 8662A | | | 43351850 0 | 2 Hr | | | 0 0 dBm | Type "R" |
| 38 | 19-Jan | 0 070 | 0 070 | 0 050 | 00013 | | | | 00000 | | | | 00000 | 30 11 | | 8662A | | | | | 43351870 0 | 2 Hr | 0 0 dBm | Type "R" |
| 39 | 20-Jan | 0 070 | 0 070 | 0 070 | 00018 | | | | 00000 | | | | 00000 | 28 71 | 45 | 8662A | | | | | 43351870 0 | 2 Hr | 0 0 dBm | Type "S" |
| 40 | 21-Jan | 0 070 | 0 070 | 0 070 | 00018 | | | | 00000 | | | | 00000 | 28 10 | | | | | | | | | | |
| 41 | 22-Jan | 0 070 | 0 070 | 0 070 | 00018 | | | | 00000 | | | | 00000 | 27 57 | | 8662A | | | 43351850 0 | 2 Hr | | | 0 0 dBm | Type "S" |
| 42 | 23-Jan | 0 070 | 0 070 | 0 070 | 00018 | | | | 00000 | | | | 00000 | 28 38 | | 8662A | | | 43351850 0 | 2 Hr | | | 0 0 dBm | Type "S" |
| 43 | 24-Jan | 0 070 | 0 070 | 0 070 | 00018 | | | | 00000 | | | | 00000 | 28 15 | | 8662A | | | | | 43351870 0 | 2 Hr | 0 0 dBm | Type "S" |
| 44 | 25-Jan | 0 070 | 0 070 | 0 070 | 00018 | | | | 00000 | | | | 00000 | 27 65 | | 8662A | | | | | 43351870 0 | 2 Hr | 0 0 dBm | Type "S" |
| 45 | 26-Jan | 0 050 | 0 050 | 0 050 | 00007 | | | | 00000 | | | | 00000 | 26 35 | | 8662A | | | 43351850 0 | 2 Hr | | | 0 0 dBm | Type "S" |
| 46 | 27-Jan | 0 050 | 0 050 | 0 030 | 00004 | | | | 00000 | | | | 00000 | 27 06 | 46 | 8662A | | | 43351850 0 | 2 Hr | | | 0 0 dBm | Type "S" |
| 47 | 28-Jan | 0 050 | 0 050 | 0 030 | 00004 | | | | 00000 | | | | 00000 | 27 35 | | | | | | | | | | |
| 48 | 29-Jan | 0 050 | 0 050 | 0 030 | 00004 | | | | 00000 | | | | 00000 | 27 57 | | 8662A | 43351830 0 | 2 Hr | | | | | 0 0 dBm | Type "S" |
| 49 | 30-Jan | 0 050 | 0 050 | 0 030 | 00004 | | | | 00000 | | | | 00000 | 27 78 | | 8662A | 43351830 0 | 2 Hr | | | | | 0 0 dBm | Type "S" |
| 50 | 31-Jan | 0 030 | 0 030 | 0 030 | 00001 | | | | 00000 | | | | 00000 | 28 73 | | 8662A | | | 43351850 0 | 2 Hr | | | 0 0 dBm | Type "S" |
| 51 | 1-Feb | 0 030 | 0 030 | 0 030 | 00001 | | | | 00000 | | | | 00000 | 28 81 | | 8662A | | | 43351850 0 | 2 Hr | | | 0 0 dBm | Type "S" |
| 52 | 2-Feb | 0 030 | 0 030 | 0 030 | 00001 | | | | 00000 | | | | 00000 | 27 43 | | 8662A | 43351830 0 | 2 Hr | | | | | 0 0 dBm | Type "S" |
| 53 | 3-Feb | 0 030 | 0 030 | 0 030 | 00001 | | | | 00000 | | | | 00000 | 27 67 | 45 | 8662A | 43351830 0 | 2 Hr | | | | | 0 0 dBm | Type "S" |
| 54 | 4-Feb | 0 030 | 0 030 | 0 030 | 00001 | | | | 00000 | | | | 00000 | 27 45 | | | | | | | | | | |
| 55 | 5-Feb | 0 030 | 0 030 | 0 030 | 00001 | 0 050 | 0 050 | 0 030 | 00004 | | | | 00000 | 27 25 | | 8662A | | | | | 43351870 0 | 2 Hr | 0 0 dBm | Type "S" |
| 56 | 6-Feb | 0 030 | 0 030 | 0 030 | 00001 | 0 030 | 0 030 | 0 030 | 00001 | | | | 00000 | 27 40 | | 8662A | | | | | 43351870 0 | 2 Hr | 0 0 dBm | Type "S" |
| 57 | 7-Feb | 0 030 | 0 030 | 0 030 | 00001 | 0 030 | 0 030 | 0 030 | 00001 | | | | 00000 | 27 40 | | 8662A | | | | | 43351870 0 | 2 Hr | 0 0 dBm | Type "S" |
| 58 | 8-Feb | 0 030 | 0 030 | 0 030 | 00001 | 0 030 | 0 030 | 0 030 | 00001 | | | | 00000 | 28 77 | | 8662A | | | 43351850 0 | 2 Hr | | | 0 0 dBm | Type "S" |
| 59 | 9-Feb | 0 030 | 0 030 | 0 030 | 00001 | 0 030 | 0 030 | 0 030 | 00001 | | | | 00000 | 29 86 | | 8662A | 43351830 0 | 2 Hr | | | | | 0 0 dBm | Type "S" |
| 60 | 10-Feb | | | | 00000 | | | | 00000 | | | | 00000 | 29 62 | 42 | 8662A | 43351830 0 | 2 Hr | | | | | 0 0 dBm | Type "S" |
| 61 | 11-Feb | | | | 00000 | | | | 00000 | | | | 00000 | 29 05 | | | | | | | | | | |
| 62 | 12-Feb | | | | 00000 | | | | 00000 | | | | 00000 | 28 58 | | 8662A | | | 43351850 0 | 2 Hr | | | 0 0 dBm | Type "S" |
| 63 | 13-Feb | | | | 00000 | | | | 00000 | | | | 00000 | 28 77 | | 8662A | | | 43351850 0 | 2 Hr | | | 0 0 dBm | Type "S" |
| 64 | 14-Feb | | | | 00000 | 0 030 | 0 030 | 0 030 | 00001 | | | | 00000 | 27 73 | | 8662A | | | | | 43351870 0 | 2 Hr | 0 0 dBm | Type "S" |
| 65 | 15-Feb | | | | 00000 | 0 050 | 0 050 | 0 030 | 00004 | | | | 00000 | 28 56 | | 8662A | | | | | 43351870 0 | 2 Hr | 0 0 dBm | Type "S" |
| 66 | 16-Feb | | | | 00000 | 0 050 | 0 050 | 0 030 | 00004 | | | | 00000 | 29 38 | | 8662A | 43351830 0 | 2 Hr | | | | | 0 0 dBm | Type "S" |

09141691.022898

| DAY | DATE | T-1 L Bottom Ln | Wd | Ht | Vol T-1 | T-2 R Abdomen Ln | Wd | Ht | Vol T-2 | T-3 L Abdomen Ln | Wd | Ht | Vol T-3 | WEIGHT Gr |
|---|---|---|---|---|---|---|---|---|---|---|---|---|---|---|
| 67 | 17-Feb | | | | 00000 | 0 050 | 0 050 | 0 050 | 00007 | | | | 00000 | 27 95 |
| 68 | 18-Feb | | | | 00000 | 0 050 | 0 050 | 0 050 | 00007 | | | | 00000 | 28 50 |
| 69 | 19-Feb | | | | 00000 | 0 050 | 0 050 | 0 050 | 00007 | | | | 00000 | 29 21 |
| 70 | 20-Feb | | | | 00000 | 0 050 | 0 050 | 0 050 | 00007 | | | | 00000 | 27 69 |
| 71 | 21-Feb | | | | 00000 | 0 050 | 0 050 | 0 050 | 00007 | | | | 00000 | 27 12 |
| 72 | 22-Feb | | | | 00000 | 0 030 | 0 030 | 0 030 | 00001 | | | | 00000 | 27 01 |
| 73 | 23-Feb | | | | 00000 | 0 030 | 0 030 | 0 030 | 00001 | | | | 00000 | 25 93 |
| 74 | 24-Feb | | | | 00000 | 0 030 | 0 030 | 0 030 | 00001 | | | | 00000 | 26 48 |
| 75 | 25-Feb | | | | 00000 | 0 030 | 0 030 | 0 030 | 00001 | | | | 00000 | 26 70 |
| 76 | 26-Feb | | | | 00000 | 0 030 | 0 030 | 0 030 | 00001 | | | | 00000 | 26 95 |
| 77 | 27-Feb | | | | 00000 | | | | 00000 | | | | 00000 | 28 86 |
| 78 | 28-Feb | | | | 00000 | | | | 00000 | | | | 00000 | 26 37 |
| 79 | 29-Feb | | | | 00000 | | | | 00000 | | | | 00000 | 26 32 |
| 80 | 1-Mar | | | | 00000 | | | | 00000 | | | | 00000 | 25 44 |
| 81 | 2-Mar | | | | 00000 | | | | 00000 | | | | 00000 | 26 04 |
| 82 | 3-Mar | | | | 00000 | | | | 00000 | | | | 00000 | 26 60 |
| 83 | 4-Mar | | | | 00000 | | | | 00000 | | | | 00000 | 27 21 |
| 84 | 5-Mar | | | | 00000 | | | | 00000 | 0 050 | 0 050 | 0 050 | 00007 | 27 40 |
| 85 | 6-Mar | | | | 00000 | | | | 00000 | 0 050 | 0 050 | 0 050 | 00007 | 26 10 |
| 86 | 7-Mar | | | | 00000 | | | | 00000 | 0 050 | 0 050 | 0 050 | 00007 | 26 40 |
| 87 | 8-Mar | | | | 00000 | | | | 00000 | 0 050 | 0 050 | 0 050 | 00007 | 25 87 |
| 88 | 9-Mar | | | | 00000 | | | | 00000 | 0 050 | 0 050 | 0 050 | 00007 | 27 00 |
| 89 | 10-Mar | | | | 00000 | | | | 00000 | 0 050 | 0 050 | 0 050 | 00007 | 26 60 |
| 90 | 11-Mar | | | | 00000 | | | | 00000 | 0 050 | 0 050 | 0 050 | 00007 | 26 13 |
| 91 | 12-Mar | | | | 00000 | | | | 00000 | 0 050 | 0 050 | 0 050 | 00007 | 26 36 |
| 92 | 13-Mar | | | | 00000 | | | | 00000 | 0 030 | 0 030 | 0 030 | 00001 | 26 71 |
| 93 | 14-Mar | | | | 00000 | | | | 00000 | 0 030 | 0 030 | 0 030 | 00001 | 27 27 |
| 94 | 15-Mar | | | | 00000 | | | | 00000 | 0 050 | 0 050 | 0 050 | 00007 | 27 55 |
| 95 | 16-Mar | | | | 00000 | | | | 00000 | 0 050 | 0 050 | 0 050 | 00007 | 27 19 |
| 96 | 17-Mar | | | | 00000 | | | | 00000 | 0 050 | 0 050 | 0 050 | 00007 | 27 10 |
| 97 | 18-Mar | | | | 00000 | | | | 00000 | 0 050 | 0 050 | 0 050 | 00007 | 27 00 |
| 98 | 19-Mar | | | | 00000 | | | | 00000 | 0 050 | 0 050 | 0 050 | 00007 | 26 02 |
| 99 | 20-Mar | | | | 00000 | | | | 00000 | 0 050 | 0 050 | 0 050 | 00007 | 26 27 |
| 100 | 21-Mar | | | | 00000 | | | | 00000 | 0 050 | 0 050 | 0 050 | 00007 | 26 42 |
| 101 | 22-Mar | | | | 00000 | | | | 00000 | 0 050 | 0 050 | 0 050 | 00007 | 25 78 |
| 102 | 23-Mar | | | | 00000 | | | | 00000 | | | | 00000 | 26 89 |
| 103 | 24-Mar | | | | 00000 | | | | 00000 | | | | 00000 | 26 40 |
| 104 | 25-Mar | | | | 00000 | | | | 00000 | | | | 00000 | 25 94 |
| 105 | 26-Mar | | | | 00000 | | | | 00000 | | | | 00000 | 26 66 |
| 106 | 27-Mar | | | | 00000 | | | | 00000 | | | | 00000 | 26 57 |
| 107 | 28-Mar | | | | 00000 | | | | 00000 | | | | 00000 | 26 52 |
| 108 | 29-Mar | | | | 00000 | | | | 00000 | | | | 00000 | 25 41 |
| 109 | 30-Mar | | | | 00000 | | | | 00000 | | | | 00000 | 26 20 |
| 110 | 31-Mar | | | | 00000 | | | | 00000 | | | | 00000 | 25 95 |
| 111 | 1-Apr | | | | 00000 | | | | 00000 | | | | 00000 | 25 74 |

| DAY | HEMATO-CRIT-% | TREATMENT PARAMETERS DEVICE | FREQ MHz | TIME | FREQ MHz | TIME | FREQ MHz | TIME | POWER | DEVICE |
|---|---|---|---|---|---|---|---|---|---|---|
| 67 | 43 | 8662A | | | | | 43351870 0 | 2 Hr | 0 0 dBm | Type "S" |
| 68 | | | | | | | | | | |
| 69 | | 8662A | | | | | 43351870 0 | 3 Hr | 0 0 dBm | Type "T" |
| 70 | | 8662A | 43351830 0 | 2 Hr | 43351850 0 | 1 Hr | | | 3 0 dBm | Type "T" |
| 71 | | 8662A | | | 43351853 0 | 2 Hr | 43351871 0 | 1 Hr | 0 0 dBm | Type "T" |
| 72 | | 8662A | | | 43351853 0 | 2 Hr | 43351871 0 | 1 Hr | 0 0 dBm | Type "T" |
| 73 | | 8662A | | | 43351853 0 | 1 Hr | 43351871 0 | 2 Hr | 0 0 dBm | Type "T" |
| 74 | 40 | 8662A | | | | | 43351870 0 | 3 Hr | 0 0 dBm | Type "T" |
| 75 | | | | | | | | | | |
| 76 | | 8662A | | | 43351853 0 | 2 Hr | 43351871 0 | 1 Hr | 0 0 dBm | Type "T" |
| 77 | | 8662A | | | 43351853 0 | 2 Hr | 43351871 0 | 1 Hr | 0 0 dBm | Type "T" |
| 78 | | 8662A | | | 43351853 0 | 2 Hr | 43351871 0 | 1 Hr | 0 0 dBm | Type "T" |
| 79 | | 8662A | | | 43351853 0 | 2 Hr | 43351871 0 | 1 Hr | 0 0 dBm | Type "T" |
| 80 | | 8662A | | | 43351850 0 | 1 Hr | 43351870 0 | 2 Hr | 0 0 dBm | Type "T" |
| 81 | 43 | 8662A | 43351830 0 | 1 Hr | 43351850 0 | 1 Hr | 43351870 0 | 1 Hr | 0 0 dBm | Type "T" |
| 82 | | | | | | | | | | |
| 83 | | 8662A | 43351830 0 | 1 Hr | 43351850 0 | 1 Hr | 43351870 0 | 1 Hr | 0 0 dBm | Type "T" |
| 84 | | 8662A | | | 43351853 0 | 2 Hr | 43351871 0 | 1 Hr | 0 0 dBm | Type "U" |
| 85 | | 8662A | | | 43351853 0 | 2 Hr | 43351871 0 | 1 Hr | 0 0 dBm | Type "U" |
| 86 | | 8662A | | | 43351853 0 | 1 Hr | 43351871 0 | 2 Hr | 0 0 dBm | Type "U" |
| 87 | | 8662A | 43351830 0 | 1 Hr | 43351850 0 | 1 Hr | 43351870 0 | 1 Hr | 0 0 dBm | Type "U" |
| 88 | 41 | 8662A | 43351830 0 | 1 Hr | 43351850 0 | 1 Hr | 43351870 0 | 1 Hr | 0 0 dBm | Type "V" |
| 89 | | | | | | | | | | |
| 90 | | 8662A | 43322485 0 | 1 Hr | 43346000 0 | 1 Hr | 43353800 0 | 1 Hr | 0 0 dBm | Type "U" |
| 91 | | 8662A | | | 43351853 0 | 2 Hr | 43351871 0 | 1 Hr | 0 0 dBm | Type "U" |
| 92 | | 8662A | | | 43351853 0 | 2 Hr | 43351871 0 | 1 Hr | 0 0 dBm | Type "U" |
| 93 | | 8662A | | | 43351853 0 | 2 Hr | 43351871 0 | 1 Hr | 0 0 dBm | Type "U" |
| 94 | | 8662A | 43351830 0 | 1 Hr | 43351853 0 | 2 Hr | | | 0 0 dBm | Type "U" |
| 95 | 39 | 8662A | | | 43351853 0 | 2 Hr | 43351871 0 | 1 Hr | 0 0 dBm | Type "U" |
| 96 | | | | | | | | | | |
| 97 | | 8662A | | | 43351853 0 | 2 Hr | 43351871 0 | 1 Hr | 0 0 dBm | Type "U" |
| 98 | | 8662A | | | 43351853 0 | 2 Hr | 43351871 0 | 1 Hr | 0 0 dBm | Type "U" |
| 99 | | 8662A | | | 43351853 0 | 1 Hr | 43351871 0 | 2 Hr | 0 0 dBm | Type "U" |
| 100 | | 8662A | | | 43351853 0 | 2 Hr | 43351871 0 | 1 Hr | 0 0 dBm | Type "U" |
| 101 | | 8662A | | | 43351853 0 | 1 Hr | 43351871 0 | 2 Hr | 0 0 dBm | Type "U" |
| 102 | 44 | 8662A | | | 43351853 0 | 1 Hr | 43351871 0 | 2 Hr | 0 0 dBm | Type "U" |
| 103 | | | | | | | | | | |
| 104 | | 8662A | | | 43351853 0 | 1 Hr | 43351871 0 | 2 Hr | 0 0 dBm | Type "U" |
| 105 | | 8662A | | | 43351853 0 | 1 Hr | 43351871 0 | 2 Hr | 0 0 dBm | Type "U" |
| 106 | | 8662A | | | 43351853 0 | 1 Hr | 43351871 0 | 2 Hr | 0 0 dBm | Type "U" |
| 107 | | 8662A | | | 43351853 0 | 1 Hr | 43351871 0 | 2 Hr | 0 0 dBm | Type "U" |
| 108 | | | | | | | | | | |
| 109 | 38 | | | | | | | | | |
| 110 | | | | | | | | | | |
| 111 | | | | | | | | | | |

*APPENDICES B1 - B10*

CONTROL MOUSE DATA

Index (Pages numbered on back)

| *Appendix* | *Subject* | *Pages* |
|---|---|---|
| B1 | A 486 | 95-97 |
| B2 | A 488 | 98-100 |
| B3 | A 490 | 101-102 |
| B4 | A 492 | 103-105 |
| B5 | A 500 | 106 |
| B6 | A 538 | 107-108 |
| B7 | A 540 | 109-110 |
| B8 | A 542 | 111-112 |
| B9 | A 592 | 113 |
| B10 | A 594 | 114 |

09161591 .082898

A-486-DA.xls

| DAY | DATE | X | Y | Z | EVOL | X | Y | Z | EVOL | WEIGHT | HEMA- |
|---|---|---|---|---|---|---|---|---|---|---|---|
| | DOB 11/27/94 | A-486 LT ARM T-1 | | | | A-486 LT IN'R LEG T-2 | | | | GRAMS | TOCRIT |
| 1 | 9-Aug | 0.050 | 0.050 | 0.050 | .00007 | | | | 00000 | 28.78 | |
| 2 | 10-Aug | 0.050 | 0.050 | 0.050 | 00007 | | | | .00000 | 28.31 | |
| 3 | 11-Aug | 0.060 | 0.060 | 0.060 | 00011 | | | | 00000 | 29.18 | |
| 4 | 12-Aug | 0.060 | 0.060 | 0.060 | 00011 | | | | .00000 | 29.08 | |
| 5 | 13-Aug | 0.070 | 0.070 | 0.070 | 00018 | | | | 00000 | 28.99 | |
| 6 | 14-Aug | 0.080 | 0.080 | 0.070 | 00023 | | | | 00000 | 28.89 | |
| 7 | 15-Aug | 0.080 | 0.080 | 0.070 | 00023 | | | | 00000 | 28.88 | |
| 8 | 16-Aug | 0.080 | 0.080 | 0.070 | .00023 | | | | 00000 | 28.86 | |
| 9 | 17-Aug | 0.080 | 0.080 | 0.070 | 00023 | | | | 00000 | 28.85 | |
| 10 | 18-Aug | 0.080 | 0.080 | 0.060 | 00020 | | | | 00000 | 28.83 | |
| 11 | 19-Aug | 0.080 | 0.080 | 0.060 | .00020 | | | | 00000 | 28.82 | |
| 12 | 20-Aug | 0.080 | 0.080 | 0.060 | 00020 | | | | .00000 | 28.80 | |
| 13 | 21-Aug | 0.080 | 0.080 | 0.050 | .00017 | | | | 00000 | 28.79 | |
| 14 | 22-Aug | 0.080 | 0.080 | 0.050 | .00017 | | | | 00000 | 28.59 | |
| 15 | 23-Aug | 0.080 | 0.080 | 0.050 | .00017 | | | | 00000 | 28.66 | |
| 16 | 24-Aug | 0.080 | 0.080 | 0.050 | 00017 | | | | 00000 | 28.75 | |
| 17 | 25-Aug | 0.080 | 0.080 | 0.050 | .00017 | | | | 00000 | 28.76 | |
| 18 | 26-Aug | 0.090 | 0.090 | 0.050 | 00021 | | | | 00000 | 31.66 | |
| 19 | 27-Aug | 0.100 | 0.100 | 0.050 | 00026 | | | | 00000 | 30.83 | |
| 20 | 28-Aug | 0.100 | 0.100 | 0.050 | .00026 | | | | 00000 | 29.99 | |
| 21 | 29-Aug | 0.110 | 0.110 | 0.050 | 00032 | | | | 00000 | 29.16 | |
| 22 | 30-Aug | 0.110 | 0.110 | 0.050 | 00032 | | | | .00000 | 28.32 | |
| 23 | 31-Aug | 0.124 | 0.125 | 0.065 | .00053 | | | | 00000 | 28.36 | |
| 24 | 1-Sep | 0.139 | 0.141 | 0.080 | 00082 | | | | 00000 | 28.41 | |
| 25 | 2-Sep | 0.153 | 0.157 | 0.095 | 00119 | | | | 00000 | 28.45 | |
| 26 | 3-Sep | 0.167 | 0.173 | 0.110 | 00166 | | | | 00000 | 28.50 | |
| 27 | 4-Sep | 0.181 | 0.189 | 0.125 | 00224 | | | | 00000 | 28.54 | |
| 28 | 5-Sep | 0.196 | 0.204 | 0.140 | 00293 | | | | 00000 | 28.59 | |
| 29 | 6-Sep | 0.210 | 0.220 | 0.155 | 00375 | | | | 00000 | 28.63 | |
| 30 | 7-Sep | 0.224 | 0.236 | 0.170 | 00470 | | | | 00000 | 28.68 | |
| 31 | 8-Sep | 0.239 | 0.251 | 0.185 | 00581 | | | | 00000 | 28.72 | |
| 32 | 9-Sep | 0.253 | 0.267 | 0.200 | 00707 | | | | 00000 | 28.76 | |
| 33 | 10-Sep | 0.267 | 0.283 | 0.215 | 00850 | | | | 00000 | 28.81 | |
| 34 | 11-Sep | 0.281 | 0.299 | 0.230 | 01012 | | | | 00000 | 28.85 | |
| 35 | 12-Sep | 0.295 | 0.314 | 0.245 | 01192 | | | | 00000 | 28.90 | |
| 36 | 13-Sep | 0.310 | 0.330 | 0.260 | 01392 | | | | 00000 | 28.94 | |
| 37 | 14-Sep | 0.300 | 0.360 | 0.270 | 01527 | | | | 00000 | 28.66 | |
| 38 | 15-Sep | 0.200 | 0.200 | 0.100 | 00209 | | | | 00000 | 28.78 | |
| 39 | 16-Sep | 0.280 | 0.400 | 0.160 | 00938 | | | | 00000 | 28.98 | |
| 40 | 17-Sep | 0.220 | 0.250 | 0.230 | 00562 | | | | 00000 | 29.86 | |
| 41 | 18-Sep | 0.390 | 0.500 | 0.290 | 02950 | | | | 00000 | 29.83 | |
| 42 | 19-Sep | 0.400 | 0.510 | 0.290 | 03097 | | | | 00000 | 30.41 | |
| 43 | 20-Sep | 0.430 | 0.450 | 0.340 | 03444 | | | | 00000 | 30.78 | |
| 44 | 21-Sep | 0.460 | 0.450 | 0.350 | 03793 | | | | 00000 | 29.51 | |
| 45 | 22-Sep | 0.460 | 0.470 | 0.400 | 04527 | | | | 00000 | 30.27 | |
| 46 | 23-Sep | 0.460 | 0.480 | 0.430 | 04970 | | | | 00000 | 30.12 | |
| 47 | 24-Sep | 0.460 | 0.480 | 0.430 | 04970 | | | | 00000 | 29.59 | |
| 48 | 25-Sep | 0.470 | 0.480 | 0.430 | 05078 | | | | 00000 | 29.21 | |

Prepared by Bob DeVries 4/11/97

A-486-DA.xls

| | | | | | | | | | | | |
|---|---|---|---|---|---|---|---|---|---|---|---|
| 49 | 26-Sep | 0 470 | 0 500 | 0 470 | 05782 | | | | 00000 | 30 47 | |
| 50 | 27-Sep | 0 490 | 0 540 | 0 480 | 06649 | | | | 00000 | 30 21 | |
| 51 | 28-Sep | 0 490 | 0 570 | 0 530 | 07749 | | | | 00000 | 29.77 | |
| 52 | 29-Sep | 0 500 | 0 570 | 0 500 | 07460 | | | | 00000 | 30 29 | |
| 53 | 30 Sep | 0 510 | 0 570 | 0 500 | 07609 | | | | 00000 | 30 23 | |
| 54 | 1-Oct | 0 530 | 0 580 | 0 500 | 08046 | | | | 00000 | 30 15 | |
| 55 | 2-Oct | 0 540 | 0 580 | 0 500 | 08198 | | | | 00000 | 30 09 | 41 |
| 56 | 3-Oct | 0 560 | 0 570 | 0 480 | 08021 | | | | 00000 | 29 98 | |
| 57 | 4-Oct | 0 560 | 0 580 | 0 520 | 08842 | | | | 00000 | 31.33 | |
| 58 | 5-Oct | 0 580 | 0 630 | 0 520 | 09947 | 0 030 | 0 030 | 0 030 | 00001 | 30.97 | |
| 59 | 6-Oct | 0 590 | 0 640 | 0 550 | 10872 | 0 030 | 0 030 | 0 030 | 00001 | 31 42 | |
| 60 | 7-Oct | 0 600 | 0 640 | 0 560 | 11257 | 0 030 | 0 030 | 0 030 | 00001 | 31 15 | |
| 61 | 8-Oct | 0 600 | 0 640 | 0 560 | 11257 | 0 030 | 0 030 | 0 030 | 00001 | 30 95 | |
| 62 | 9-Oct | 0 610 | 0 640 | 0 570 | 11649 | 0 030 | 0 030 | 0 030 | 00001 | 30 71 | |
| 63 | 10-Oct | 0 680 | 0 660 | 0 570 | 13392 | 0 030 | 0 030 | 0 030 | 00001 | 32 67 | 30 |
| 64 | 11-Oct | 0 700 | 0 690 | 0 610 | 15424 | 0 030 | 0 030 | 0 030 | 00001 | 31 88 | |
| 65 | 12-Oct | 0 730 | 0 720 | 0 640 | 17610 | 0 010 | 0 010 | 0 010 | 00000 | 31 52 | |
| 66 | 13-Oct | 0 680 | 0 760 | 0 670 | 18127 | 0 010 | 0 010 | 0 010 | 00000 | 32.26 | |
| 67 | 14-Oct | 0 700 | 0 780 | 0 670 | 19151 | | | | 00000 | 32 28 | |
| 68 | 15-Oct | 0 720 | 0 800 | 0 670 | 20203 | | | | 00000 | 32 30 | |
| 69 | 16-Oct | 0 730 | 0 820 | 0 670 | 20996 | | | | 00000 | 32 31 | |
| 70 | 17-Oct | 0 780 | 0 820 | 0 660 | 22099 | | | | 00000 | 33 40 | |
| 71 | 18-Oct | 0 800 | 0 780 | 0 530 | 17313 | | | | 00000 | 28 67 | |
| 72 | 19-Oct | 0 740 | 0 740 | 0 540 | 15480 | | | | 00000 | 28 94 | |
| 73 | 20-Oct | 0 750 | 0 760 | 0 530 | 15815 | | | | 00000 | 29 96 | |
| 74 | 21-Oct | 0 770 | 0 760 | 0 540 | 16543 | | | | 00000 | 30 40 | |
| 75 | 22-Oct | 0 790 | 0 770 | 0 550 | 17514 | | | | 00000 | 30 90 | |
| 76 | 23-Oct | 0 800 | 0 790 | 0 560 | 18528 | | | | 00000 | 31 45 | |
| 77 | 24-Oct | 0 800 | 0 810 | 0 560 | 18997 | | | | 00000 | 31 85 | |
| 78 | 25-Oct | 0 810 | 0 820 | 0 560 | 19472 | | | | 00000 | 32 22 | |
| 79 | 26-Oct | 0 800 | 0 810 | 0 600 | 20354 | | | | 00000 | 30 64 | |
| 80 | 27-Oct | 0 820 | 0 840 | 0 630 | 22717 | | | | 00000 | 30 44 | 20 |
| 81 | 28-Oct | 0 860 | 0 840 | 0 630 | 23825 | | | | 00000 | 31 15 | |
| 82 | 29 Oct | 0 900 | 0 850 | 0 630 | 25230 | | | | 00000 | 31 81 | |
| 83 | 30-Oct | 0 950 | 0 850 | 0 630 | 26912 | | | | 00000 | 32 23 | 25 |
| 84 | 31-Oct | 0 940 | 0 880 | 0 650 | 28148 | | | | 00000 | 32 04 | |
| 85 | 1-Nov | 0 940 | 0 870 | 0 650 | 29112 | | | | 00000 | 33 04 | |
| 86 | 2-Nov | 0 960 | 0 930 | 0 700 | 32717 | | | | 00000 | 34 55 | |
| 87 | 3-Nov | 0 950 | 0 950 | 0 680 | 32465 | | | | 00000 | 34 58 | |
| 88 | 4-Nov | 0 950 | 0 980 | 0 680 | 33491 | | | | 00000 | 35 50 | |
| 89 | 5-Nov | 0 970 | 1 000 | 0 680 | 34530 | | | | 00000 | 36 50 | |
| 90 | 6-Nov | 0 980 | 1 020 | 0 680 | 35584 | | | | 00000 | 37 17 | |
| 91 | 7-Nov | 0 980 | 1 090 | 0 720 | 40263 | | | | 00000 | 35 89 | |
| 92 | 8 Nov | 0 980 | 1 050 | 0 780 | 42417 | | | | 00000 | 37 18 | 32 |
| 93 | 9 Nov | 0 980 | 1 070 | 0 800 | 43915 | | | | 00000 | 34 57 | |
| 94 | 10-Nov | 1 030 | 1 070 | 0 660 | 38079 | | | | 00000 | 34 95 | |
| 95 | 11-Nov | 1 040 | 1 090 | 0 670 | 39760 | | | | 00000 | 34 36 | |
| 96 | 12-Nov | 1 050 | 1 110 | 0 670 | 40879 | | | | 00000 | 33 78 | |
| 97 | 13-Nov | 1 060 | 1 130 | 0 680 | 42539 | | | | 00000 | 33 19 | 25 |
| 98 | 14-Nov | | *Died 11/14/95* | | #VALUE! | | *Died 11/14/95* | | #VALUE! | | |

Prepared by Bob DeVries 4/11/97

Page 2

09141591.082898

A-486-DA.xls

| | T-1 AVERAGE GROWTH | | | | T-2 AVERAGE GROWTH | | | |
|---|---|---|---|---|---|---|---|---|
| 99 | | | | | | | | |
| 100 | 0 486 | 0 505 | 0 380 | 0 112 | 0 026 | 0 026 | 0 026 | 0 000 |

Prepared by Bob DeVries 4/11/97

A-488-DA.xls

| DAY | DATE | X | Y | Z | EVOL | X | Y | Z | EVOL | X | Y | Z | EVOL | X | Y | Z | EVOL | WEIGHT | HEMA- |
|---|---|---|---|---|---|---|---|---|---|---|---|---|---|---|---|---|---|---|---|
| | DOB 11/28/94 | A-488 LT SIDE T-1 | | | | A-488 LT NECK T-2 | | | | A-488 LT BOTTOM T-3 | | | | A-488 LT ARM T-4 | | | | GRAMS | TOCRIT |
| 1 | 7/20/95 | 0.050 | 0.050 | 0.050 | 00007 | | | | 00000 | | | | 00000 | | | | 00000 | 36.58 | |
| 2 | 7/21/95 | 0.050 | 0.050 | 0.050 | 00007 | 0.050 | 0.050 | 0.050 | 00007 | | | | 00000 | | | | 00000 | 35.98 | |
| 3 | 7/22/95 | 0.060 | 0.060 | 0.060 | 00011 | 0.060 | 0.060 | 0.060 | 00011 | | | | 00000 | | | | 00000 | 35.85 | |
| 4 | 7/23/95 | 0.070 | 0.070 | 0.070 | 00018 | 0.070 | 0.070 | 0.070 | 00018 | | | | 00000 | | | | 00000 | 35.73 | 45 |
| 5 | 7/24/95 | 0.070 | 0.070 | 0.070 | 00018 | 0.070 | 0.070 | 0.070 | 00018 | | | | 00000 | | | | 00000 | 35.56 | |
| 6 | 7/25/95 | 0.070 | 0.070 | 0.070 | 00018 | 0.080 | 0.080 | 0.080 | 00027 | | | | 00000 | | | | 00000 | 35.39 | |
| 7 | 7/26/95 | 0.070 | 0.070 | 0.070 | 00018 | 0.080 | 0.080 | 0.080 | 00027 | | | | 00000 | | | | 00000 | 35.22 | |
| 8 | 7/27/95 | 0.070 | 0.070 | 0.070 | 00018 | 0.100 | 0.100 | 0.100 | 00052 | 0.070 | 0.070 | 0.070 | 00018 | | | | 00000 | 35.05 | |
| 9 | 7/28/95 | 0.070 | 0.070 | 0.050 | 00013 | 0.100 | 0.100 | 0.070 | 00037 | 0.070 | 0.070 | 0.070 | 00018 | | | | 00000 | 35.38 | |
| 10 | 7/29/95 | 0.070 | 0.070 | 0.050 | 00013 | 0.100 | 0.100 | 0.070 | 00037 | 0.070 | 0.070 | 0.070 | 00018 | | | | 00000 | 35.18 | |
| 11 | 7/30/95 | 0.070 | 0.070 | 0.050 | 00013 | 0.100 | 0.100 | 0.070 | 00037 | 0.070 | 0.070 | 0.070 | 00018 | | | | 00000 | 34.98 | |
| 12 | 7/31/95 | 0.070 | 0.070 | 0.050 | 00013 | 0.100 | 0.100 | 0.070 | 00037 | 0.070 | 0.070 | 0.070 | 00018 | | | | 00000 | 34.78 | |
| 13 | 8/1/95 | 0.070 | 0.070 | 0.050 | 00013 | 0.100 | 0.100 | 0.070 | 00037 | 0.070 | 0.070 | 0.070 | 00018 | | | | 00000 | 34.58 | |
| 14 | 8/2/95 | 0.070 | 0.070 | 0.050 | 00013 | 0.100 | 0.100 | 0.070 | 00037 | 0.070 | 0.070 | 0.070 | 00018 | | | | 00000 | 34.38 | |
| 15 | 8/3/95 | 0.070 | 0.070 | 0.050 | 00013 | 0.100 | 0.100 | 0.070 | 00037 | 0.070 | 0.070 | 0.070 | 00018 | | | | 00000 | 35.18 | |
| 16 | 8/4/95 | 0.070 | 0.070 | 0.050 | 00013 | 0.100 | 0.100 | 0.050 | 00026 | 0.070 | 0.070 | 0.070 | 00018 | | | | 00000 | 35.31 | 45 |
| 17 | 8/5/95 | 0.070 | 0.070 | 0.050 | 00013 | 0.100 | 0.100 | 0.050 | 00026 | 0.070 | 0.070 | 0.070 | 00018 | | | | 00000 | 33.90 | |
| 18 | 8/6/95 | 0.070 | 0.070 | 0.050 | 00013 | 0.100 | 0.100 | 0.050 | 00026 | 0.070 | 0.070 | 0.070 | 00018 | | | | 00000 | 34.70 | |
| 19 | 8/7/95 | 0.070 | 0.070 | 0.050 | 00013 | 0.130 | 0.130 | 0.070 | 00062 | 0.120 | 0.120 | 0.070 | 00053 | | | | 00000 | 35.35 | |
| 20 | 8/8/95 | 0.070 | 0.070 | 0.050 | 00013 | 0.130 | 0.130 | 0.070 | 00062 | 0.100 | 0.100 | 0.070 | 00037 | | | | 00000 | 35.27 | |
| 21 | 8/9/95 | 0.070 | 0.070 | 0.050 | 00013 | 0.130 | 0.130 | 0.070 | 00062 | 0.100 | 0.100 | 0.070 | 00037 | | | | 00000 | 34.54 | |
| 22 | 8/10/95 | 0.070 | 0.070 | 0.050 | 00013 | 0.130 | 0.130 | 0.070 | 00062 | 0.100 | 0.100 | 0.070 | 00037 | | | | 00000 | 35.11 | |
| 23 | 8/11/95 | 0.080 | 0.080 | 0.050 | 00017 | 0.120 | 0.120 | 0.050 | 00038 | 0.100 | 0.100 | 0.080 | 00042 | | | | 00000 | 35.40 | |
| 24 | 8/12/95 | 0.080 | 0.080 | 0.050 | 00017 | 0.110 | 0.110 | 0.050 | 00032 | 0.100 | 0.100 | 0.080 | 00042 | | | | 00000 | 35.30 | |
| 25 | 8/13/95 | 0.080 | 0.080 | 0.050 | 00017 | 0.100 | 0.100 | 0.040 | 00021 | 0.100 | 0.100 | 0.080 | 00042 | | | | 00000 | 35.20 | |
| 26 | 8/14/95 | 0.080 | 0.080 | 0.050 | 00017 | 0.090 | 0.090 | 0.040 | 00017 | 0.100 | 0.100 | 0.080 | 00042 | | | | 00000 | 35.10 | |
| 27 | 8/15/95 | 0.070 | 0.070 | 0.050 | 00013 | 0.080 | 0.080 | 0.030 | 00010 | 0.100 | 0.100 | 0.070 | 00037 | | | | 00000 | 35.00 | |
| 28 | 8/16/95 | 0.070 | 0.070 | 0.050 | 00013 | 0.070 | 0.070 | 0.030 | 00008 | 0.100 | 0.100 | 0.070 | 00037 | | | | 00000 | 34.90 | |
| 29 | 8/17/95 | 0.070 | 0.070 | 0.050 | 00013 | 0.050 | 0.060 | 0.020 | 00004 | 0.090 | 0.090 | 0.070 | 00030 | | | | 00000 | 34.80 | |
| 30 | 8/18/95 | 0.050 | 0.050 | 0.050 | 00009 | 0.050 | 0.050 | 0.020 | 00003 | 0.090 | 0.090 | 0.050 | 00025 | | | | 00000 | 34.70 | |
| 31 | 8/19/95 | 0.060 | 0.050 | 0.050 | 00009 | 0.040 | 0.040 | 0.010 | 00001 | 0.090 | 0.090 | 0.060 | 00025 | | | | 00000 | 34.60 | |
| 32 | 8/20/95 | 0.060 | 0.050 | 0.050 | 00009 | 0.020 | 0.020 | 0.010 | 00000 | 0.090 | 0.090 | 0.060 | 00025 | | | | 00000 | 34.50 | |
| 33 | 8/21/95 | 0.050 | 0.050 | 0.050 | 00007 | | | | 00000 | 0.090 | 0.090 | 0.050 | 00021 | | | | 00000 | 34.44 | |
| 34 | 8/22/95 | 0.050 | 0.050 | 0.050 | 00007 | | | | 00000 | 0.090 | 0.090 | 0.050 | 00021 | | | | 00000 | 35.30 | |
| 35 | 8/23/95 | 0.060 | 0.050 | 0.050 | 00011 | | | | 00000 | 0.100 | 0.100 | 0.050 | 00026 | | | | 00000 | 35.11 | |
| 36 | 8/24/95 | 0.050 | 0.050 | 0.050 | 00011 | | | | 00000 | 0.100 | 0.100 | 0.050 | 00026 | | | | 00000 | 35.29 | |
| 37 | 8/25/95 | 0.060 | 0.050 | 0.050 | 00011 | | | | 00000 | 0.100 | 0.100 | 0.050 | 00026 | | | | 00000 | 35.41 | |
| 38 | 8/26/95 | 0.050 | 0.050 | 0.050 | 00011 | | | | 00000 | 0.100 | 0.100 | 0.050 | 00026 | | | | 00000 | 35.48 | |
| 39 | 8/27/95 | 0.060 | 0.050 | 0.060 | 00011 | | | | 00000 | 0.100 | 0.100 | 0.050 | 00026 | | | | 00000 | 33.92 | |
| 40 | 8/28/95 | 0.050 | 0.050 | 0.060 | 00011 | | | | 00000 | 0.100 | 0.100 | 0.050 | 00026 | | | | 00000 | 32.36 | |
| 41 | 8/29/95 | 0.050 | 0.050 | 0.050 | 00011 | | | | 00000 | 0.100 | 0.100 | 0.050 | 00026 | | | | 00000 | 30.80 | |
| 42 | 8/30/95 | 0.050 | 0.050 | 0.050 | 00007 | | | | 00000 | 0.100 | 0.100 | 0.050 | 00026 | | | | 00000 | 29.24 | |
| 43 | 8/31/95 | 0.080 | 0.050 | 0.070 | 00023 | | | | 00000 | 0.100 | 0.100 | 0.050 | 00026 | | | | 00000 | 29.56 | |
| 44 | 9/1/95 | 0.110 | 0.110 | 0.090 | 00057 | | | | 00000 | 0.100 | 0.100 | 0.050 | 00026 | | | | 00000 | 29.87 | |
| 45 | 9/2/95 | 0.140 | 0.140 | 0.110 | 00113 | | | | 00000 | 0.100 | 0.100 | 0.050 | 00026 | | | | 00000 | 30.19 | |
| 46 | 9/3/95 | 0.170 | 0.170 | 0.130 | 00197 | | | | 00000 | 0.100 | 0.100 | 0.050 | 00026 | | | | 00000 | 30.51 | |
| 47 | 9/4/95 | 0.200 | 0.200 | 0.150 | 00314 | | | | 00000 | 0.100 | 0.100 | 0.050 | 00026 | | | | 00000 | 30.82 | |
| 48 | 9/5/95 | 0.230 | 0.230 | 0.170 | 00471 | | | | 00000 | 0.100 | 0.100 | 0.050 | 00026 | | | | 00000 | 31.14 | |
| 49 | 9/6/95 | 0.290 | 0.290 | 0.190 | 00537 | | | | 00000 | 0.100 | 0.100 | 0.050 | 00026 | | | | 00000 | 31.45 | |

Prepared by Bob DeVries 4/11/97

Page 1

A-488-DA.xls

| | | | | | | | | | | | | | | |
|---|---|---|---|---|---|---|---|---|---|---|---|---|---|---|
| 50 | 9/7/95 | 0.320 | 0.320 | 0.210 | 01126 | 00000 | 0.100 | 0.100 | 0.050 | .00026 | .00000 | 31.77 | |
| 51 | 9/8/95 | 0.350 | 0.350 | 0.230 | 01475 | 00000 | 0.100 | 0.100 | 0.050 | 00026 | .00000 | 32.09 | |
| 52 | 9/9/95 | 0.380 | 0.380 | 0.250 | 01890 | 00000 | 0.100 | 0.100 | 0.050 | 00026 | .00000 | 32.48 | |
| 53 | 9/10/95 | 0.410 | 0.390 | 0.260 | 02176 | 00000 | 0.100 | 0.100 | 0.050 | 00026 | .00000 | 32.72 | |
| 54 | 9/11/95 | 0.440 | 0.400 | 0.270 | 02488 | 00000 | 0.100 | 0.100 | 0.050 | 00026 | 00000 | 33.04 | |
| 55 | 9/12/95 | 0.460 | 0.410 | 0.280 | 02764 | 00000 | 0.100 | 0.100 | 0.050 | 00026 | .00000 | 33.35 | |
| 56 | 9/13/95 | 0.470 | 0.410 | 0.280 | 02825 | 00000 | 0.100 | 0.100 | 0.070 | 00037 | .00000 | 33.67 | |
| 57 | 9/14/95 | 0.500 | 0.470 | 0.270 | 03322 | 00000 | 0.100 | 0.100 | 0.070 | 00037 | 00000 | 34.14 | |
| 58 | 9/15/95 | 0.510 | 0.460 | 0.330 | 04053 | 00000 | 0.100 | 0.100 | 0.070 | 00037 | .00000 | 33.44 | |
| 59 | 9/16/95 | 0.510 | 0.420 | 0.400 | 04485 | 00000 | 0.100 | 0.100 | 0.100 | 00052 | .00000 | 33.44 | |
| 60 | 9/17/95 | 0.510 | 0.460 | 0.350 | 04298 | 00000 | 0.100 | 0.100 | 0.100 | 00052 | .00000 | 34.25 | |
| 61 | 9/18/95 | 0.540 | 0.480 | 0.260 | 04885 | .00000 | 0.100 | 0.100 | 0.100 | 00052 | .00000 | 33.88 | |
| 62 | 9/19/95 | 0.520 | 0.420 | 0.360 | 04116 | 00000 | 0.100 | 0.100 | 0.100 | 00052 | 00000 | 34.26 | |
| 63 | 9/20/95 | 0.520 | 0.430 | 0.360 | 04214 | 00000 | 0.100 | 0.100 | 0.100 | 00052 | 00000 | 34.20 | |
| 64 | 9/21/95 | 0.520 | 0.450 | 0.430 | 05267 | 00000 | 0.100 | 0.100 | 0.100 | 00052 | .00000 | 32.84 | |
| 65 | 9/22/95 | 0.580 | 0.450 | 0.450 | 06285 | 00000 | 0.100 | 0.100 | 0.100 | 00052 | .00000 | 33.55 | |
| 66 | 9/23/95 | 0.580 | 0.470 | 0.450 | 06422 | 00000 | 0.100 | 0.100 | 0.100 | 00052 | 00000 | 34.15 | |
| 67 | 9/24/95 | 0.585 | 0.500 | 0.465 | 07120 | 00000 | 0.100 | 0.100 | 0.100 | 00052 | .00000 | 33.03 | |
| 68 | 9/25/95 | 0.590 | 0.520 | 0.480 | 07709 | .00000 | 0.100 | 0.100 | 0.100 | 00052 | 00000 | 31.90 | |
| 69 | 9/26/95 | 0.590 | 0.520 | 0.480 | 07709 | 00000 | 0.100 | 0.100 | 0.100 | 00052 | 00000 | 31.81 | |
| 70 | 9/27/95 | 0.590 | 0.520 | 0.480 | 07709 | 00000 | 0.100 | 0.100 | 0.100 | 00052 | 00000 | 31.85 | |
| 71 | 9/28/95 | 0.650 | 0.550 | 0.490 | 09170 | 00000 | 0.120 | 0.100 | 0.100 | 00063 | 00000 | 31.12 | |
| 72 | 9/29/95 | 0.660 | 0.550 | 0.450 | 08707 | 00000 | 0.100 | 0.100 | 0.100 | 00052 | 00000 | 31.58 | |
| 73 | 9/30/95 | 0.660 | 0.570 | 0.450 | 09059 | 00000 | 0.100 | 0.100 | 0.100 | 00052 | 00000 | 31.06 | |
| 74 | 10/1/95 | 0.670 | 0.570 | 0.470 | 09396 | 00000 | 0.100 | 0.100 | 0.100 | 00052 | 00000 | 30.55 | |
| 75 | 10/2/95 | 0.670 | 0.590 | 0.480 | 09765 | 00000 | 0.090 | 0.090 | 0.080 | 00034 | .00000 | 30.03 | 40 |
| 76 | 10/3/95 | 0.590 | 0.600 | 0.400 | 07413 | 00000 | 0.090 | 0.090 | 0.080 | 00034 | 00000 | 30.51 | |
| 77 | 10/4/95 | 0.630 | 0.570 | 0.450 | 09211 | 00000 | 0.090 | 0.090 | 0.080 | 00034 | .00000 | 31.19 | |
| 78 | 10/5/95 | 0.690 | 0.580 | 0.490 | 10266 | 00000 | 0.090 | 0.090 | 0.080 | 00034 | .00000 | 30.82 | |
| 79 | 10/6/95 | 0.670 | 0.570 | 0.530 | 10595 | .00000 | 0.090 | 0.090 | 0.070 | 00030 | 00000 | 30.83 | |
| 80 | 10/7/95 | 0.690 | 0.590 | 0.510 | 10685 | 00000 | 0.090 | 0.090 | 0.070 | 00030 | .00000 | 31.25 | |
| 81 | 10/8/95 | 0.700 | 0.580 | 0.500 | 10627 | 00000 | 0.090 | 0.090 | 0.070 | 00030 | 00000 | 31.67 | |
| 82 | 10/9/95 | 0.710 | 0.590 | 0.480 | 10526 | 00000 | 0.090 | 0.090 | 0.070 | 00030 | 00000 | 32.09 | |
| 83 | 10/10/95 | 0.710 | 0.630 | 0.510 | 11942 | 00000 | 0.080 | 0.080 | 0.050 | 00017 | 00000 | 31.59 | 40 |
| 84 | 10/11/95 | 0.730 | 0.690 | 0.560 | 14766 | 00000 | 0.080 | 0.080 | 0.050 | 00017 | 00000 | 32.70 | |
| 85 | 10/12/95 | 0.780 | 0.670 | 0.600 | 15415 | 00000 | 0.050 | 0.060 | 0.050 | 00009 | 00000 | 32.08 | |
| 86 | 10/13/95 | 0.810 | 0.710 | 0.600 | 16064 | 00000 | 0.060 | 0.060 | 0.050 | 00009 | 00000 | 32.84 | |
| 87 | 10/14/95 | 0.830 | 0.710 | 0.590 | 18201 | 00000 | 0.060 | 0.060 | 0.050 | 00009 | .00000 | 33.15 | |
| 88 | 10/15/95 | 0.840 | 0.710 | 0.580 | 18108 | 00000 | 0.050 | 0.060 | 0.050 | 00009 | 00000 | 33.46 | |
| 89 | 10/16/95 | 0.850 | 0.710 | 0.570 | 18008 | 00000 | 0.060 | 0.060 | 0.050 | 00009 | 00000 | 33.77 | |
| 90 | 10/17/95 | 0.850 | 0.720 | 0.550 | 17621 | 00000 | 0.100 | 0.100 | 0.050 | 00026 | 00000 | 32.41 | |
| 91 | 10/18/95 | 0.880 | 0.750 | 0.570 | 19694 | 00000 | 0.140 | 0.110 | 0.080 | 00064 | 00000 | 32.50 | |
| 92 | 10/19/95 | 0.880 | 0.760 | 0.570 | 19957 | 00000 | 0.140 | 0.120 | 0.090 | 00079 | 00000 | 31.93 | |
| 93 | 10/20/95 | 0.860 | 0.750 | 0.550 | 19584 | 00000 | 0.170 | 0.130 | 0.090 | 00104 | 00000 | 32.32 | |
| 94 | 10/21/95 | 0.850 | 0.740 | 0.590 | 19426 | 00000 | 0.170 | 0.130 | 0.090 | 00104 | 00000 | 32.50 | |
| 95 | 10/22/95 | 0.840 | 0.720 | 0.600 | 18997 | 00000 | 0.160 | 0.120 | 0.090 | 00090 | 00000 | 32.70 | |
| 96 | 10/23/95 | 0.820 | 0.700 | 0.610 | 18330 | 00000 | 0.160 | 0.120 | 0.090 | 00090 | 00000 | 32.95 | |
| 97 | 10/24/95 | 0.820 | 0.705 | 0.615 | 18612 | 00000 | 0.150 | 0.120 | 0.090 | 00085 | 00000 | 33.15 | |
| 98 | 10/25/95 | 0.820 | 0.710 | 0.620 | 18896 | 00000 | 0.140 | 0.120 | 0.090 | 00079 | 00000 | 33.26 | |
| 99 | 10/26/95 | 0.830 | 0.720 | 0.620 | 19396 | 00000 | 0.160 | 0.130 | 0.100 | 00109 | 00000 | 33.63 | |
| 100 | 10/27/95 | 0.850 | 0.740 | 0.610 | 20086 | 00000 | 0.190 | 0.140 | 0.100 | 00139 | 00000 | 35.44 | 40 |

Prepared by Bob DeVries 4/11/97

09141691.082898

09141691.082898

A-488-DA.xls

| | | | | | | | | | | | | | | | | | | |
|---|---|---|---|---|---|---|---|---|---|---|---|---|---|---|---|---|---|---|
| 101 | 10/28/95 | 0 890 | 0 750 | 0 640 | 22354 | | | | 00000 | 0 190 | 0 150 | 0 110 | 00164 | | | | 00000 | 35 84 |
| 102 | 10/29/95 | 0 930 | 0 750 | 0 680 | 24830 | | | | 00000 | 0 190 | 0 150 | 0 120 | 00179 | | | | .00000 | 36 23 |
| 103 | 10/30/95 | 0 970 | 0 760 | 0 710 | 27401 | | | | 00000 | 0 190 | 0 160 | 0 130 | .00207 | | | | .00000 | 36 63 | 37 |
| 104 | 10/31/95 | 0 970 | 0 750 | 0 780 | 29705 | | | | 00000 | 0 230 | 0 190 | 0 140 | 00320 | | | | .00000 | 34.66 |
| 105 | 11/1/95 | 0 970 | 0 780 | 0 820 | 32479 | | | | 00000 | 0 230 | 0 250 | 0 140 | 00421 | | | | 00000 | 35.78 |
| 106 | 11/2/95 | 0 970 | 0 830 | 0 850 | 35825 | | | | 00000 | 0 230 | 0 250 | 0 160 | 00482 | | | | 00000 | 34 56 |
| 107 | 11/3/95 | 0 970 | 0 860 | 0 790 | 34500 | | | | 00000 | 0 240 | 0.250 | 0 170 | 00534 | | | | .00000 | 34 43 |
| 108 | 11/4/95 | 0 970 | 0 880 | 0 770 | 34408 | | | | 00000 | 0 240 | 0 250 | 0 170 | .00534 | | | | .00000 | 34.14 |
| 109 | 11/5/95 | 0 960 | 0 910 | 0 760 | 34757 | | | | 00000 | 0 240 | 0 250 | 0 170 | 00534 | | | | 00000 | 33 85 |
| 110 | 11/6/95 | 0 960 | 0 930 | 0 740 | 34586 | | | | 00000 | 0 240 | 0 250 | 0 170 | 00534 | | | | 00000 | 33.56 |
| 111 | 11/7/95 | 0 950 | 0 940 | 0 760 | 35903 | | | | 00000 | 0 240 | 0 250 | 0 170 | 00534 | 0 380 | 0 310 | 0.200 | 01233 | 35.30 |
| 112 | 11/8/95 | 1 020 | 0 900 | 0 790 | 37955 | | | | 00000 | 0 260 | 0 250 | 0 200 | 00681 | 0 400 | 0 320 | 0.200 | 01340 | 34 68 | 30 |
| 113 | 11/9/95 | 1 050 | 0 940 | 0 800 | 41336 | | | | 00000 | 0 260 | 0 280 | 0 200 | 00762 | 0 400 | 0.330 | 0.210 | .01451 | 33.71 |
| 114 | 11/10/95 | 1 080 | 0 950 | 0 770 | 41793 | | | | 00000 | 0.250 | 0 280 | 0 200 | 00733 | 0 400 | 0.310 | 0.230 | .01493 | 33 49 |
| 115 | 11/11/95 | 1 080 | 0 960 | 0 770 | 41793 | | | | 00000 | 0.250 | 0 280 | 0 200 | 00733 | 0 400 | 0 310 | 0.230 | 01493 | 33.39 |
| 116 | 11/12/95 | 1 080 | 0 960 | 0 770 | 41793 | | | | .00000 | 0.250 | 0 280 | 0 200 | 00733 | 0 400 | 0 310 | 0.230 | 01493 | 33.29 |
| 117 | 11/13/95 | DIED 11/13/95 | | | #VALUE! | DIED 11/13/95 | | | #VALUE! | DIED 11/13/95 | | | #VALUE! | DIED 11/13/95 | | | #VALUE! | 33.19 |
| | | T-1 AVERAGE GROWTH | | | | T-2 AVERAGE GROWTH | | | | T-3 AVERAGE GROWTH | | | | | | | | |
| | | 0 458 | 0 404 | 0 337 | 0 094 | 0 089 | 0 089 | 0 056 | 0 000 | 0 119 | 0 116 | 0 085 | 0 001 | | | | | |

Prepared by Bob DeVries 4/11/97

Page 3

09147193.082898

A-490-DA.xls

| DAY | DATE | X | Y | Z | EVOL | X | Y | Z | EVOL | X | Y | Z | EVOL | X | Y | Z | EVOL | WEIGHT GRAMS | |
|---|---|---|---|---|---|---|---|---|---|---|---|---|---|---|---|---|---|---|---|
| | DOB 12/19/94 | A-490 RT SIDE T-1 | | | | A-490 LT SIDE T-2 | | | | A-490 LT SIDE T-3 | | | | A-490 RT THIGH T-4 | | | | | |
| 1 | 10/11/95 | 0 150 | 0 150 | 0 120 | 00141 | 0 150 | 0 150 | 0 150 | 00177 | 0 100 | 0 100 | 0 100 | 00052 | | | | .00000 | 29.11 | 44 |
| 2 | 10/12/95 | 0 150 | 0 100 | 0 120 | 00094 | 0 150 | 0 150 | 0 150 | 00177 | 0 100 | 0 100 | 0 100 | .00052 | | | | .00000 | 28.19 | |
| 3 | 10/13/95 | 0 150 | 0 100 | 0 120 | 00094 | 0 150 | 0 150 | 0 150 | 00177 | 0 100 | 0 100 | 0 100 | 00052 | | | | .00000 | 29 77 | |
| 4 | 10/14/95 | 0 150 | 0 110 | 0 120 | 00104 | 0 170 | 0 170 | 0 150 | 00227 | 0 100 | 0 100 | 0 100 | 00052 | | | | .00000 | 29.90 | |
| 5 | 10/15/95 | 0 160 | 0 110 | 0 120 | 00111 | 0 190 | 0 180 | 0 150 | 00259 | 0 100 | 0 100 | 0 100 | 00052 | | | | .00000 | 30.20 | |
| 6 | 10/16/95 | 0 160 | 0 120 | 0 120 | .00121 | 0 200 | 0 200 | 0 150 | 00314 | 0 100 | 0 100 | 0 100 | 00052 | | | | .00000 | 30 49 | |
| 7 | 10/17/95 | 0 180 | 0 160 | 0 120 | 00181 | 0 200 | 0 250 | 0 200 | 00524 | 0 150 | 0 150 | 0 150 | 00177 | | | | .00000 | 30.24 | |
| 8 | 10/18/95 | 0.230 | 0 200 | 0 130 | 00313 | 0 240 | 0 270 | 0 210 | 00712 | 0 180 | 0 180 | 0 160 | 00271 | | | | 00000 | 30 69 | |
| 9 | 10/19/95 | 0 260 | 0 240 | 0 150 | 00490 | 0 270 | 0 270 | 0 210 | 00801 | 0 220 | 0 220 | 0 160 | 00405 | | | | .00000 | 30 01 | |
| 10 | 10/20/95 | 0 300 | 0 250 | 0 150 | 00589 | 0 300 | 0 310 | 0 230 | .01120 | 0 230 | 0 220 | 0 160 | 00424 | | | | .00000 | 30 47 | |
| 11 | 10/21/95 | 0 310 | 0 260 | 0 150 | 00633 | 0 320 | 0 330 | 0 230 | 01271 | 0 230 | 0 230 | 0 150 | 00443 | | | | .00000 | 30.90 | |
| 12 | 10/22/95 | 0 320 | 0.260 | 0 150 | 00653 | 0 330 | 0 350 | 0 230 | 01391 | 0 240 | 0 240 | 0 160 | 00482 | | | | .00000 | 31.30 | |
| 13 | 10/23/95 | 0 330 | 0.270 | 0 160 | .00746 | 0 340 | 0 370 | 0 230 | 01515 | 0.240 | 0 250 | 0 160 | 00503 | | | | .00000 | 31.52 | |
| 14 | 10/24/95 | 0 350 | 0 285 | 0 160 | 00836 | 0 350 | 0 385 | 0 230 | 01622 | 0 260 | 0 250 | 0 160 | 00544 | | | | .00000 | 30 50 | |
| 15 | 10/25/95 | 0 360 | 0 300 | 0 160 | 00905 | 0 360 | 0 400 | 0 230 | 01734 | 0 270 | 0 250 | 0 160 | .00565 | | | | .00000 | 29.74 | |
| 16 | 10/26/95 | 0 410 | 0 340 | 0 220 | 01605 | 0 400 | 0 410 | 0 250 | 02146 | 0 270 | 0 250 | 0 200 | .00707 | | | | 00000 | 29.14 | |
| 17 | 10/27/95 | 0 460 | 0 360 | 0 240 | 02081 | 0 440 | 0 410 | 0 250 | 02361 | 0 270 | 0 270 | 0 220 | 00840 | | | | 00000 | 29 83 | 40 |
| 18 | 10/28/95 | 0 490 | 0 400 | 0 260 | 02668 | 0 465 | 0 430 | 0 270 | 02826 | 0 280 | 0.290 | 0 220 | 00935 | | | | .00000 | 30 30 | |
| 19 | 10/29/95 | 0 520 | 0 460 | 0 280 | 03506 | 0 490 | 0 450 | 0 280 | .03232 | 0 290 | 0 310 | 0 220 | 01035 | | | | .00000 | 30 90 | |
| 20 | 10/30/95 | 0 540 | 0 540 | 0 300 | 04580 | 0 510 | 0 460 | 0 300 | 03684 | 0 300 | 0 330 | 0 210 | 01088 | | | | 00000 | 31.14 | 34 |
| 21 | 10/31/95 | 0 530 | 0 390 | 0 350 | 03895 | 0 500 | 0 480 | 0 300 | 03769 | 0 280 | 0 320 | 0 200 | 00938 | | | | 00000 | 30.33 | |
| 22 | 11/1/95 | 0 510 | 0 450 | 0 400 | 04805 | 0 480 | 0 480 | 0 370 | .04463 | 0 280 | 0 400 | 0 200 | 01173 | | | | 00000 | 32 44 | |
| 23 | 11/2/95 | 0 560 | 0 470 | 0 410 | 05649 | 0 520 | 0 470 | 0 340 | 04350 | 0 320 | 0 420 | 0 220 | 01548 | | | | 00000 | 31.61 | |
| 24 | 11/3/95 | 0 520 | 0 500 | 0 440 | 05989 | 0.540 | 0 460 | 0 380 | 04941 | 0 330 | 0 380 | 0 240 | 01576 | | | | .00000 | 32.21 | |
| 25 | 11/4/95 | 0 560 | 0 510 | 0 430 | 05429 | 0 560 | 0 470 | 0 390 | 05374 | 0 350 | 0 400 | 0 300 | 02199 | | | | .00000 | 32 70 | |
| 26 | 11/5/95 | 0 620 | 0 510 | 0 420 | 05952 | 0 580 | 0 480 | 0 400 | 05830 | 0 370 | 0 420 | 0 340 | 02766 | | | | .00000 | 33 20 | |
| 27 | 11/6/95 | 0 680 | 0 520 | 0 410 | 07589 | 0 600 | 0 490 | 0 410 | 06310 | 0.380 | 0 430 | 0 360 | 03079 | | | | .00000 | 33.59 | |
| 28 | 11/7/95 | 0 680 | 0 530 | 0 400 | 07547 | 0 650 | 0 520 | 0 410 | 07366 | 0 380 | 0 460 | 0 330 | 03020 | | | | 00000 | 33.16 | |
| 29 | 11/8/95 | 0 680 | 0 580 | 0 440 | 09085 | 0 540 | 0 670 | 0 440 | 08334 | 0 430 | 0 500 | 0 360 | 04277 | 0 190 | 0 240 | 0 180 | .00430 | 34 41 | 30 |
| 30 | 11/9/95 | 0 700 | 0 610 | 0 440 | 09836 | 0 550 | 0 670 | 0 380 | 07331 | 0 460 | 0 510 | 0 400 | 04913 | 0 200 | 0 270 | 0 200 | 00565 | 35 11 | |
| 31 | 11/10/95 | 0 730 | 0 630 | 0 430 | 10353 | 1 070 | 0 640 | 0 410 | 14698 | | | | 00000 | 0 220 | 0 260 | 0 200 | 00599 | 34 92 | |
| 32 | 11/11/95 | 0 730 | 0 640 | 0 430 | 10517 | 1 040 | 0 660 | 0 490 | 17607 | | | | 00000 | 0 250 | 0 250 | 0 220 | .00720 | 35 80 | |
| 33 | 11/12/95 | 0 740 | 0 640 | 0 430 | 10651 | 0 990 | 0 680 | 0 550 | 19383 | | | | 00000 | 0 290 | 0 240 | 0 240 | 00874 | 36 80 | |
| 34 | 11/13/95 | 0 740 | 0 650 | 0 430 | 10828 | 0 950 | 0 690 | 0 620 | 21276 | | | | 00000 | 0 330 | 0 220 | 0 260 | 00988 | 37 66 | |
| 35 | 11/14/95 | 0 740 | 0 680 | 0 450 | 11854 | 1 000 | 0 720 | 0 570 | 21484 | | | | 00000 | 0 300 | 0 220 | 0.240 | 00829 | 39 12 | |
| 36 | 11/15/95 | 0 760 | 0 700 | 0 470 | 13090 | 1 000 | 0 740 | 0 630 | 24406 | | | | 00000 | 0 300 | 0 200 | 0 240 | 00754 | 38 97 | 32 |
| 37 | 11/16/95 | 0 780 | 0 690 | 0 470 | 13242 | 1 000 | 0 760 | 0 630 | 25065 | | | | 00000 | 0 310 | 0 240 | 0 230 | 00896 | 39 02 | |
| 38 | 11/17/95 | 0 800 | 0 720 | 0 470 | 14172 | 1 060 | 0 790 | 0 630 | 27618 | | | | 00000 | 0 350 | 0 280 | 0 230 | 01180 | 40 48 | |
| 39 | 11/18/95 | 0 830 | 0 720 | 0 460 | 14391 | 1 070 | 0 810 | 0 640 | 29038 | | | | 00000 | 0 380 | 0 300 | 0 240 | 01422 | 41 50 | |
| 40 | 11/19/95 | 0 860 | 0 720 | 0 450 | 14911 | 1 080 | 0 830 | 0 650 | 30502 | | | | 00000 | 0 410 | 0 310 | 0 240 | 01597 | 42 50 | |
| 41 | 11/20/95 | 0 890 | 0 720 | 0 450 | 15096 | 1 090 | 0 850 | 0 660 | 32012 | | | | 00000 | 0 450 | 0 320 | 0 250 | 01885 | 43 50 | 27 |
| 42 | 11/21/95 | 0 850 | 0 700 | 0 450 | 15127 | 1 090 | 0 900 | 0 690 | 35435 | | | | 00000 | 0 450 | 0 300 | 0 250 | 01767 | 43 88 | |
| 43 | 11/22/95 | 0 850 | 0 730 | 0 480 | 15775 | 1 080 | 0 950 | 0 690 | 37451 | | | | 00000 | 0 470 | 0 320 | 0 270 | 02126 | 44 12 | |
| 44 | 11/23/95 | 0 850 | 0 780 | 0 510 | 17701 | 1 080 | 0 950 | 0 690 | 37061 | | | | 00000 | 0 485 | 0 330 | 0 270 | 02262 | 45 50 | |
| 45 | 11/24/95 | 0 850 | 0 850 | 0 550 | 20803 | 1 080 | 0 950 | 0 690 | 37061 | | | | 00000 | 0 500 | 0 350 | 0 270 | 02474 | 46 96 | |
| 46 | 11/25/95 | 0 850 | 0 850 | 0 550 | .20803 | 1 080 | 0 980 | 0 710 | 39339 | | | | 00000 | 0 510 | 0 350 | 0 280 | .02616 | 46.66 | |
| 47 | 11/26/95 | 0 850 | 0 850 | 0 550 | 20803 | 1 080 | 1 050 | 0 730 | 43336 | | | | 00000 | 0 510 | 0 350 | 0.290 | 02710 | 46 36 | |
| 48 | 11/27/95 | 0 850 | 0 850 | 0 550 | .20803 | 1 090 | 1 090 | 0 750 | 46648 | | | | 00000 | 0 520 | 0 350 | 0 310 | .02954 | 46 06 | |

Prepared by Bob DeVries 4/11/97

09141691 .080298

A-490-DA.xls

| | | | | | | | | | | | | | | | | | | |
|---|---|---|---|---|---|---|---|---|---|---|---|---|---|---|---|---|---|---|
| 49 | 11/28/95 | 0.850 | 0.850 | 0.550 | 20803 | 1.090 | 1.100 | 0.750 | 47076 | | | | 00000 | 0.520 | 0.350 | 0.310 | 02954 | 39.35 |
| 50 | 11/29/95 | | *Died 11/29/95* | | #VALUE! | | *Died 11/29/95* | | #VALUE! | | *Died 11/29/95* | | #VALUE! | | *Died 11/29/95* | | #VALUE! | 39.88 |
| | | | *T-1 AVERAGE GROWTH* | | | | *T-2 AVERAGE GROWTH* | | | | *T-3 AVERAGE GROWTH* | | | | | | | |
| | | 0.560 | 0.491 | 0.340 | 0.078 | 0.644 | 0.560 | 0.413 | 0.137 | 0.254 | 0.276 | 0.202 | 0.011 | | | | | |

Prepared by Bob DeVries 4/11/97

Page 2

A-492-DA.xls

| DAY | DATE | X | Y | Z | EVOL | X | Y | Z | EVOL | X | Y | Z | EVOL | X | Y | Z | EVOL | WEIGHT GRAMS | H'CRIT |
|---|---|---|---|---|---|---|---|---|---|---|---|---|---|---|---|---|---|---|---|
| | | A-492 RT ABDOMEN T-1 | | | | A-492 LT ABDOMEN T-2 | | | | A-492 RT ARM T-3 | | | | A-492 LT ARM T-4 | | | | | |
| 1 | 15-Sep | 0 030 | 0 030 | 0 030 | 00001 | | | | 00000 | | | | 00000 | | | | .00000 | 29 62 | |
| 2 | 16-Sep | 0 030 | 0 030 | 0 030 | 00001 | | | | 00000 | | | | 00000 | | | | .00000 | 29.29 | |
| 3 | 17-Sep | 0 050 | 0 050 | 0 050 | 00007 | | | | 00000 | | | | 00000 | | | | .00000 | 30 45 | |
| 4 | 18-Sep | 0 100 | 0 100 | 0 100 | 00052 | | | | 00000 | | | | 00000 | | | | .00000 | 30 47 | |
| 5 | 19-Sep | 0 050 | 0 050 | 0 050 | 00007 | | | | 00000 | | | | 00000 | | | | 00000 | 30.09 | |
| 6 | 20-Sep | 0 050 | 0 050 | 0 050 | 00007 | | | | 00000 | | | | 00000 | | | | .00000 | 29.86 | |
| 7 | 21-Sep | 0 050 | 0 050 | 0 050 | 00007 | | | | 00000 | | | | 00000 | | | | 00000 | 28.88 | |
| 8 | 22-Sep | 0.050 | 0 050 | 0 050 | 00007 | | | | .00000 | | | | 00000 | | | | .00000 | 29.35 | |
| 9 | 23-Sep | 0 050 | 0 050 | 0 050 | 00007 | | | | .00000 | | | | 00000 | | | | .00000 | 29.62 | |
| 10 | 24-Sep | 0 030 | 0 030 | 0 030 | 00001 | | | | .00000 | | | | 00000 | | | | .00000 | 29 11 | |
| 11 | 25-Sep | 0 030 | 0 030 | 0 030 | 00001 | | | | 00000 | | | | 00000 | | | | .00000 | 28 61 | |
| 12 | 26-Sep | 0 030 | 0 030 | 0 030 | 00001 | | | | 00000 | | | | 00000 | | | | .00000 | 29.58 | |
| 13 | 27-Sep | 0 030 | 0 030 | 0 030 | 00001 | | | | .00000 | | | | 00000 | | | | .00000 | 27.84 | |
| 14 | 28-Sep | 0 030 | 0 030 | 0 030 | 00001 | | | | 00000 | | | | 00000 | | | | .00000 | 28.53 | |
| 15 | 29-Sep | 0 030 | 0 030 | 0 030 | .00001 | | | | 00000 | | | | 00000 | | | | .00000 | 28.91 | |
| 16 | 30-Sep | 0 030 | 0 030 | 0 030 | 00001 | | | | 00000 | | | | 00000 | | | | .00000 | 28.85 | |
| 17 | 1-Oct | | | | .00000 | | | | 00000 | | | | 00000 | | | | .00000 | 28 60 | |
| 18 | 2-Oct | | | | 00000 | 0 050 | 0 050 | 0 050 | 00007 | | | | .00000 | | | | .00000 | 28 42 | 45 |
| 19 | 3-Oct | | | | .00000 | 0 050 | 0 050 | 0 050 | .00007 | | | | 00000 | | | | 00000 | 28.54 | |
| 20 | 4-Oct | | | | 00000 | 0 050 | 0 050 | 0 050 | 00007 | | | | 00000 | | | | .00000 | 29.13 | |
| 21 | 5-Oct | | | | 00000 | 0 030 | 0 030 | 0 030 | 00001 | | | | 00000 | | | | 00000 | 28.81 | |
| 22 | 6-Oct | | | | 00000 | 0 030 | 0 030 | 0 030 | 00001 | | | | 00000 | | | | .00000 | 29.33 | |
| 23 | 7-Oct | | | | 00000 | 0 040 | 0 040 | 0 040 | 00003 | | | | 00000 | | | | .00000 | 29.38 | |
| 24 | 8-Oct | | | | 00000 | 0 040 | 0 040 | 0 040 | 00003 | | | | 00000 | | | | 00000 | 29 42 | |
| 25 | 9-Oct | | | | 00000 | 0 050 | 0 050 | 0 050 | 00007 | | | | 00000 | | | | 00000 | 29 45 | |
| 26 | 10-Oct | | | | 00000 | 0 050 | 0 050 | 0 050 | 00007 | | | | 00000 | | | | .00000 | 28.60 | 42 |
| 27 | 11-Oct | | | | 00000 | 0 050 | 0 050 | 0 050 | 00007 | 0 100 | 0 100 | 0 100 | 00052 | | | | 00000 | 29 43 | |
| 28 | 12-Oct | | | | 00000 | 0.050 | 0 050 | 0 050 | 00007 | 0 100 | 0 100 | 0 110 | 00058 | 0 090 | 0 090 | 0 070 | 00030 | 28 68 | |
| 29 | 13-Oct | | | | 00000 | 0 050 | 0 050 | 0 050 | 00007 | 0 100 | 0 100 | 0 100 | 00052 | 0 090 | 0 090 | 0 060 | 00025 | 29 43 | |
| 30 | 14-Oct | | | | 00000 | 0 040 | 0 040 | 0 040 | 00003 | 0 100 | 0 100 | 0 100 | 00052 | 0 090 | 0 090 | 0 070 | 00030 | 29.70 | |
| 31 | 15-Oct | | | | 00000 | 0 040 | 0 040 | 0 040 | 00003 | 0 100 | 0 100 | 0 100 | 00052 | 0 090 | 0 090 | 0 080 | 00034 | 29 90 | |
| 32 | 16-Oct | | | | 00000 | 0 030 | 0 030 | 0 030 | 00001 | 0 100 | 0 100 | 0 100 | 00052 | 0 100 | 0 100 | 0 090 | 00047 | 30 12 | |
| 33 | 17-Oct | | | | 00000 | 0 030 | 0 030 | 0 030 | 00001 | 0 150 | 0 150 | 0 150 | 00177 | 0 120 | 0 120 | 0 110 | 00083 | 29 26 | |
| 34 | 18-Oct | | | | 00000 | 0 030 | 0 030 | 0 030 | 00001 | 0 200 | 0 180 | 0 150 | 00263 | 0 180 | 0 160 | 0 160 | 00271 | 29 50 | |
| 35 | 19-Oct | | | | 00000 | 0 030 | 0 030 | 0 030 | 00001 | 0 240 | 0 200 | 0 150 | 00377 | 0 210 | 0 200 | 0 160 | .00352 | 28 78 | |
| 36 | 20-Oct | | | | 00000 | 0 030 | 0 030 | 0 030 | 00001 | 0 270 | 0 240 | 0 200 | 00578 | 0 240 | 0 210 | 0 170 | .00449 | 29 22 | |
| 37 | 21-Oct | | | | 00000 | 0 030 | 0 030 | 0 030 | 00001 | 0 270 | 0 240 | 0 200 | 00578 | 0 260 | 0 240 | 0 170 | 00555 | 29.23 | |
| 38 | 22-Oct | | | | 00000 | 0 030 | 0 030 | 0 030 | 00001 | 0 270 | 0 240 | 0 200 | 00678 | 0 280 | 0 270 | 0 170 | 00673 | 29 25 | |
| 39 | 23-Oct | | | | 00000 | 0 030 | 0 030 | 0 030 | 00001 | 0 270 | 0 240 | 0 200 | 00678 | 0 290 | 0.290 | 0 170 | 00748 | 29.27 | |
| 40 | 24-Oct | | | | 00000 | | | | 00000 | 0 280 | 0 270 | 0 200 | 00792 | 0 290 | 0 290 | 0 170 | 00748 | 29 26 | |
| 41 | 25-Oct | | | | 00000 | | | | 00000 | 0 300 | 0 300 | 0 200 | 00942 | 0 290 | 0 300 | 0 180 | 00820 | 29.26 | |
| 42 | 26-Oct | | | | 00000 | | | | 00000 | 0 350 | 0 300 | 0 220 | 01209 | 0 290 | 0 290 | 0 190 | 00837 | 28 63 | |
| 43 | 27-Oct | | | | 00000 | | | | 00000 | 0 340 | 0 300 | 0 240 | 01282 | 0 290 | 0 280 | 0 200 | 00850 | 29 84 | 43 |
| 44 | 28-Oct | | | | 00000 | | | | 00000 | 0 350 | 0 300 | 0 250 | 01374 | 0 310 | 0 310 | 0 230 | 01157 | 29.92 | |
| 45 | 29-Oct | | | | 00000 | | | | 00000 | 0 350 | 0 300 | 0 250 | 01374 | 0 330 | 0 340 | 0 250 | 01468 | 29 99 | |
| 46 | 30-Oct | | | | 00000 | | | | 00000 | 0 360 | 0 300 | 0 260 | 01470 | 0 340 | 0.370 | 0.280 | .01844 | 30 05 | 43 |
| 47 | 31-Oct | | | | 00000 | | | | 00000 | 0 340 | 0 220 | 0 270 | 01538 | 0 320 | 0 380 | 0.270 | 01719 | 28 61 | |
| 48 | 1-Nov | | | | 00000 | | | | 00000 | 0 350 | 0 280 | 0 260 | 01334 | 0 330 | 0 400 | 0.270 | 01866 | 29 49 | |

Prepared by Bob DeVries 4/11/97

A-492-DA.xls

| | | | | | | | | | | | | | |
|---|---|---|---|---|---|---|---|---|---|---|---|---|---|
| 49 | 2-Nov | 00000 | 00000 | 0.360 | 0.300 | 0.280 | 01583 | 0.350 | 0.400 | 0.270 | .01979 | 28.96 | |
| 50 | 3-Nov | 00000 | 00000 | 0.400 | 0.360 | 0.310 | .02237 | 0.370 | 0.440 | 0.260 | .02216 | 28.88 | |
| 51 | 4-Nov | 00000 | 00000 | 0.420 | 0.340 | 0.290 | .02168 | 0.355 | 0.450 | 0.270 | .02258 | 29.00 | |
| 52 | 5-Nov | 00000 | 00000 | 0.440 | 0.320 | 0.270 | 01990 | 0.340 | 0.450 | 0.290 | 02323 | 29.10 | |
| 53 | 6-Nov | 00000 | 00000 | 0.450 | 0.300 | 0.250 | 01767 | 0.330 | 0.460 | 0.300 | .02384 | 29.24 | |
| 54 | 7-Nov | 00000 | 00000 | 0.410 | 0.360 | 0.290 | 02241 | 0.380 | 0.480 | 0.320 | .03056 | 29.55 | |
| 55 | 8-Nov | 00000 | 00000 | 0.460 | 0.350 | 0.300 | .02529 | 0.420 | 0.530 | 0.360 | .04195 | 31.49 | 40 |
| 56 | 9-Nov | 00000 | 00000 | 0.440 | 0.340 | 0.290 | 02271 | 0.410 | 0.490 | 0.360 | .03786 | 30.03 | |
| 57 | 10-Nov | 00000 | 00000 | 0.470 | 0.350 | 0.320 | 02756 | 0.430 | 0.500 | 0.380 | 04277 | 29.88 | |
| 58 | 11-Nov | 00000 | 00000 | 0.430 | 0.340 | 0.320 | 02449 | 0.450 | 0.490 | 0.380 | .04386 | 29.76 | |
| 59 | 12-Nov | 00000 | 00000 | 0.390 | 0.320 | 0.320 | .02091 | 0.460 | 0.490 | 0.390 | .04602 | 29.66 | |
| 60 | 13-Nov | 00000 | 00000 | 0.350 | 0.310 | 0.320 | 01818 | 0.470 | 0.480 | 0.390 | .04606 | 29.46 | |
| 61 | 14-Nov | 00000 | 00000 | 0.390 | 0.310 | 0.300 | .01899 | 0.480 | 0.500 | 0.360 | .04523 | 31.17 | |
| 62 | 15-Nov | .00000 | 00000 | 0.380 | 0.340 | 0.300 | 02029 | 0.460 | 0.540 | 0.380 | .04941 | 30.31 | 46 |
| 63 | 16-Nov | 00000 | 00000 | 0.380 | 0.340 | 0.290 | .01961 | 0.470 | 0.510 | 0.370 | .04643 | 32.11 | |
| 64 | 17-Nov | .00000 | .00000 | 0.400 | 0.350 | 0.300 | 02199 | 0.460 | 0.530 | 0.370 | .04722 | 31.42 | |
| 65 | 18-Nov | 00000 | 00000 | 0.400 | 0.380 | 0.320 | .02546 | 0.480 | 0.530 | 0.350 | .04661 | 31.60 | |
| 66 | 19-Nov | 00000 | 00000 | 0.410 | 0.410 | 0.340 | 02992 | 0.490 | 0.530 | 0.330 | 04486 | 31.80 | |
| 67 | 20-Nov | .00000 | 00000 | 0.410 | 0.440 | 0.360 | 03400 | 0.500 | 0.530 | 0.310 | 04301 | 32.05 | 41 |
| 68 | 21-Nov | .00000 | 00000 | 0.430 | 0.430 | 0.330 | 03194 | 0.500 | 0.430 | 0.320 | .03602 | 31.57 | |
| 69 | 22-Nov | 00000 | 00000 | 0.420 | 0.440 | 0.330 | 03193 | 0.520 | 0.540 | 0.420 | .06174 | 32.02 | |
| 70 | 23-Nov | 00000 | .00000 | 0.440 | 0.470 | 0.370 | 04006 | 0.520 | 0.520 | 0.410 | .05804 | 32.20 | |
| 71 | 24-Nov | 00000 | 00000 | 0.450 | 0.500 | 0.400 | 04712 | 0.520 | 0.500 | 0.400 | .05444 | 32.46 | |
| 72 | 25-Nov | 00000 | 00000 | 0.470 | 0.500 | 0.390 | 04798 | 0.530 | 0.510 | 0.390 | .05519 | 32.55 | |
| 73 | 26-Nov | 00000 | 00000 | 0.500 | 0.500 | 0.380 | .04973 | 0.540 | 0.520 | 0.390 | 05733 | 32.65 | |
| 74 | 27-Nov | 00000 | 00000 | 0.520 | 0.500 | 0.370 | 05036 | 0.550 | 0.530 | 0.380 | 05799 | 32.78 | |
| 75 | 28-Nov | 00000 | 00000 | 0.550 | 0.500 | 0.370 | 05327 | 0.600 | 0.540 | 0.380 | .06445 | 32.41 | |
| 76 | 29-Nov | 00000 | 00000 | 0.570 | 0.490 | 0.370 | 05410 | 0.640 | 0.610 | 0.380 | .07766 | 33.63 | 35 |
| 77 | 30-Nov | 00000 | 00000 | 0.570 | 0.480 | 0.370 | 05299 | 0.640 | 0.610 | 0.380 | 07766 | 32.70 | |
| 78 | 1-Dec | 00000 | 00000 | 0.560 | 0.460 | 0.390 | 05259 | 0.500 | 0.660 | 0.370 | 06392 | 33.26 | |
| 79 | 2-Dec | 00000 | 00000 | 0.540 | 0.450 | 0.390 | 04961 | 0.520 | 0.650 | 0.390 | .05901 | 33.66 | |
| 80 | 3-Dec | 00000 | 00000 | 0.520 | 0.450 | 0.390 | 04777 | 0.530 | 0.640 | 0.410 | 07280 | 34.10 | |
| 81 | 4-Dec | 00000 | 00000 | 0.500 | 0.450 | 0.390 | 04594 | 0.540 | 0.630 | 0.430 | 07658 | 34.51 | |
| 82 | 5-Dec | 00000 | 00000 | 0.660 | 0.470 | 0.390 | 06233 | 0.570 | 0.650 | 0.430 | 08340 | 34.29 | |
| 83 | 6-Dec | 00000 | 00000 | 0.680 | 0.510 | 0.410 | 07444 | 0.600 | 0.650 | 0.430 | 08779 | 34.76 | 38 |
| 84 | 7-Dec | 00000 | 00000 | 0.590 | 0.510 | 0.430 | 06773 | 0.630 | 0.690 | 0.430 | 09785 | 34.62 | |
| 85 | 8-Dec | 00000 | .00000 | 0.730 | 0.540 | 0.400 | 06255 | 0.650 | 0.720 | 0.430 | 10697 | 34.67 | |
| 86 | 9-Dec | 00000 | 00000 | 0.740 | 0.540 | 0.400 | 08358 | 0.690 | 0.730 | 0.430 | .11339 | 35.47 | |
| 87 | 10-Dec | 00000 | 00000 | 0.740 | 0.540 | 0.400 | 08358 | 0.720 | 0.740 | 0.430 | 11994 | 36.00 | |
| 88 | 11-Dec | 00000 | 00000 | 0.750 | 0.540 | 0.400 | 06481 | 0.750 | 0.750 | 0.440 | 12957 | 36.55 | |
| 89 | 12-Dec | 00000 | 00000 | 0.770 | 0.550 | 0.410 | 09090 | 0.750 | 0.770 | 0.440 | 13302 | 36.65 | |
| 90 | 13-Dec | 00000 | 00000 | 0.790 | 0.550 | 0.420 | 09727 | 0.750 | 0.790 | 0.440 | 13648 | 36.73 | 17 |
| 91 | 14-Dec | 00000 | 00000 | 0.800 | 0.600 | 0.420 | 10554 | 0.790 | 0.830 | 0.440 | .15103 | 37.34 | |
| 92 | 15-Dec | 00000 | 00000 | 0.810 | 0.630 | 0.400 | 10595 | 0.800 | 0.810 | 0.480 | 16283 | 37.92 | |
| 93 | 16-Dec | 00000 | 00000 | 0.800 | 0.650 | 0.390 | 10617 | 0.800 | 0.790 | 0.490 | 16212 | 35.50 | |
| 94 | 17-Dec | 00000 | 00000 | 0.800 | 0.670 | 0.370 | 10362 | 0.800 | 0.760 | 0.510 | 16233 | 34.00 | |
| 95 | 18-Dec | 00000 | 00000 | 0.790 | 0.690 | 0.350 | 09958 | 0.800 | 0.730 | 0.520 | .15898 | 32.59 | |
| 96 | 19-Dec | 00000 | 00000 | 0.810 | 0.650 | 0.350 | 09547 | 0.780 | 0.720 | 0.510 | 14994 | 31.90 | |
| 97 | 20-Dec | 00000 | 00000 | 0.830 | 0.610 | 0.350 | 09277 | 0.760 | 0.720 | 0.490 | 14037 | 31.30 | 9 |
| 98 | 21-Dec | 00000 | 00000 | 0.780 | 0.610 | 0.370 | 09216 | 0.780 | 0.730 | 0.500 | .14904 | 32.45 | |

Prepared by Bob DeVries 4/11/97

A-492-DA.xls

| | | | | | | | | | | | | | | | | | | |
|---|---|---|---|---|---|---|---|---|---|---|---|---|---|---|---|---|---|---|
| 99 | 22-Dec | | | | 00000 | | | | 00000 | 0 590 | 0 510 | 0 370 | 05828 | 0 720 | 0 720 | 0 490 | 13298 | 32.70 |
| 100 | 23-Dec | | | | 00000 | | | | .00000 | 0 590 | 0 520 | 0 370 | 05943 | 0 720 | 0 710 | 0 490 | .13113 | 33 50 |
| 101 | 24-Dec | | | | 00000 | | | | 00000 | 0 590 | 0 530 | 0 370 | 06057 | 0 720 | 0 710 | 0 480 | 12845 | 34.30 |
| 102 | 25-Dec | | | | 00000 | | | | 00000 | 0 590 | 0 540 | 0 360 | 06004 | 0 730 | 0 700 | 0 480 | .12840 | 35 10 |
| 103 | 26-Dec | | | | 00000 | | | | 00000 | 0 590 | 0 550 | 0 360 | 06116 | 0 730 | 0 690 | 0 470 | .12393 | 35 90 |
| 104 | 27-Dec | | | | 00000 | | | | 00000 | 0 580 | 0 550 | 0 360 | 06012 | 0 730 | 0 690 | 0 470 | .12393 | 36 84 |
| 105 | 28-Dec | *Died 12/29/95* | | | #VALUE! | *Died 12/29/95* | | | #VALUE! | *Died 12/29/95* | | | #VALUE! | *Died 12/29/95* | | | #VALUE! | |
| | | *T-1 AVERAGE GROWTH* | | | | *T-2 AVERAGE GROWTH* | | | | *T-3 AVERAGE GROWTH* | | | | *T-4 AVERAGE GROWTH* | | | | |
| | | 0 042 | 0 042 | 0 042 | 0 000 | 0 039 | 0 039 | 0 039 | 0.000 | 0 468 | 0.398 | 0 305 | 0 040 | 0 485 | 0 506 | 0.339 | .06190 | |

Prepared by Bob DeVries 4/11/97

A-500-DA.xls

| DAY | DATE | X | Y | Z | EVOL | X | Y | Z | EVOL | X | Y | Z | EVOL | WEIGHT GRAMS | H CRIT |
|---|---|---|---|---|---|---|---|---|---|---|---|---|---|---|---|
| | | A-500 RT SIDE T-1 | | | | A-500 LT LEG T-2 | | | | A-500 RT BOT T-3 | | | | | |
| 1 | 15-Sep | 0 300 | 0 230 | 0 390 | 0141 | 0 100 | 0 100 | 0 100 | .0005 | 0 100 | 0 100 | 0 100 | 0005 | 34 15 | |
| 2 | 16-Sep | 0 310 | 0 240 | 0 390 | 0152 | 0 310 | 0 340 | 0 300 | 0166 | 0 150 | 0 150 | 0 150 | 0018 | 33 60 | |
| 3 | 17-Sep | 0 280 | 0 310 | 0 330 | 0150 | 0 330 | 0 250 | 0 300 | 0130 | 0 150 | 0 150 | 0 100 | .0012 | 33 44 | |
| 4 | 18-Sep | 0 330 | 0 310 | 0 250 | 0134 | 0 390 | 0.310 | 0 200 | 0127 | 0 200 | 0 370 | 0 190 | 0074 | 33 46 | |
| 5 | 19-Sep | 0 330 | 0 270 | 0 330 | 0154 | 0 390 | 0 320 | 0 210 | 0137 | 0 260 | 0 280 | 0 210 | .0080 | 34 07 | |
| 6 | 20-Sep | 0 320 | 0 300 | 0 310 | 0156 | 0 410 | 0.340 | 0 250 | 0182 | 0 250 | 0 260 | 0.200 | 0068 | 34 54 | |
| 7 | 21-Sep | 0 360 | 0 350 | 0 370 | 0244 | 0 340 | 0 340 | 0.300 | .0182 | 0 310 | 0 310 | 0 260 | 0131 | 33 02 | |
| 8 | 22-Sep | 0 360 | 0 340 | 0 350 | 0224 | 0 350 | 0.370 | 0 270 | 0183 | 0 300 | 0 320 | 0.300 | 0151 | 33.94 | |
| 9 | 23-Sep | 0 400 | 0 390 | 0 400 | 0327 | 0 400 | 0 390 | 0 290 | 0237 | 0 330 | 0.350 | 0 320 | 0193 | 34 27 | |
| 10 | 24-Sep | 0 445 | 0 410 | 0 405 | 0387 | 0 405 | 0 400 | 0 320 | 0271 | 0 340 | 0.375 | 0.360 | 0240 | 34 57 | |
| 11 | 25-Sep | 0 490 | 0 430 | 0 410 | .0452 | 0 410 | 0.410 | 0 360 | 0317 | 0 350 | 0 400 | 0 400 | .0293 | 34 74 | |
| 12 | 26-Sep | 0 480 | 0 450 | 0 380 | 0430 | 0 470 | 0 480 | 0 360 | .0425 | 0 500 | 0 470 | 0 400 | .0492 | 35.72 | |
| 13 | 27-Sep | 0 480 | 0.450 | 0 380 | 0430 | 0 420 | 0 490 | 0 360 | 0388 | 0.530 | 0 520 | 0 410 | .0592 | 35.91 | |
| 14 | 28-Sep | 0 490 | 0 450 | 0 430 | 0496 | 0 420 | 0 500 | 0 360 | .0396 | 0 600 | 0 580 | 0 400 | 0729 | 34 90 | |
| 15 | 29-Sep | 0 530 | 0 450 | 0 410 | 0512 | 0 430 | 0 530 | 0.290 | .0346 | 0 660 | 0 590 | 0 450 | 0917 | 34 38 | |
| 16 | 30-Sep | 0 540 | 0 470 | 0 430 | 0571 | 0 425 | 0 540 | 0 280 | 0336 | 0 670 | 0 620 | 0 470 | 1022 | 34 88 | |
| 17 | 1-Oct | 0 540 | 0 490 | 0 440 | 0509 | 0 420 | 0 545 | 0 270 | 0324 | 0 680 | 0 640 | 0 485 | 1105 | 35 28 | |
| 18 | 2-Oct | 0 550 | 0 500 | 0 450 | 0548 | 0 410 | 0 550 | 0.250 | 0295 | 0 690 | 0 650 | 0 500 | 1174 | 35 71 | 16 |
| 19 | 3-Oct | 0 560 | 0 490 | 0 430 | 0618 | 0 390 | 0 560 | 0.240 | 0274 | 0 700 | 0 710 | 0 500 | 1301 | 34.24 | |
| 20 | 4-Oct | 0 580 | 0 520 | 0 410 | 0647 | 0 390 | 0 550 | 0 250 | 0281 | 0 720 | 0 730 | 0 550 | 1513 | 35 68 | |
| 21 | 5-Oct | 0 530 | 0 450 | 0 390 | 0487 | 0 390 | 0 530 | 0 280 | 0303 | 0 800 | 0 840 | 0 540 | 1900 | 32 73 | |
| 22 | 6-Oct | 0 460 | 0 350 | 0 400 | .0337 | 0 400 | 0 510 | 0 270 | .0288 | 0 830 | 0 830 | 0 570 | 2056 | 32 97 | |
| 23 | 7-Oct | 0 440 | 0 370 | 0 370 | 0315 | 0 390 | 0 505 | 0 260 | 0268 | 0 820 | 0 820 | 0 570 | 2005 | 33 30 | |
| 24 | 8-Oct | 0 410 | 0 385 | 0 345 | 0285 | 0 380 | 0 500 | 0 240 | 0239 | 0 810 | 0 810 | 0 570 | 1958 | 33.60 | |
| 25 | 9-Oct | 0 390 | 0 400 | 0 320 | 0261 | 0 370 | 0 490 | 0 210 | 0199 | 0 800 | 0 800 | 0 570 | 1910 | 33 80 | |
| 26 | 10-Oct | 0 350 | 0 350 | 0 280 | 0180 | 0 370 | 0 480 | 0 200 | 0186 | 0 830 | 0 850 | 0 540 | 1994 | 31 90 | 14 |
| 27 | 11-Oct | DIED 10/11/95 | | | #VALUE! | DIED 10/11/95 | | | #VALUE! | DIED 10/11/95 | | | #VALUE! | | |

Prepared by Bob DeVries 4/11/97

Page 1

A-538-DA.xls

| DAY | DATE | X | Y | Z | EVOL | X | Y | Z | EVOL | X | Y | Z | EVOL | WEIGHT GRAMS | |
|---|---|---|---|---|---|---|---|---|---|---|---|---|---|---|---|
| | | A-538 LT SIDE T-1 | | | | A-538 LT CHEEK T-2 | | | | A-538 RT ARMPIT T-3 | | | | | |
| 1 | 19-Oct | 0.200 | 0.300 | 0.160 | 00503 | | | | 00000 | | | | .00000 | 29.67 | |
| 2 | 20-Oct | 0.200 | 0.340 | 0.190 | 00676 | | | | .00000 | | | | .00000 | 30.24 | |
| 3 | 21-Oct | 0.220 | 0.340 | 0.190 | 00744 | | | | 00000 | | | | .00000 | 30.10 | |
| 4 | 22-Oct | 0.240 | 0.330 | 0.190 | 00788 | | | | .00000 | | | | 00000 | 30.00 | |
| 5 | 23-Oct | 0.260 | 0.330 | 0.190 | 00853 | | | | 00000 | | | | 00000 | 29.93 | |
| 6 | 24-Oct | 0.250 | 0.350 | 0.200 | 00916 | | | | 00000 | | | | .00000 | 30.12 | |
| 7 | 25-Oct | 0.250 | 0.380 | 0.220 | 01094 | | | | 00000 | | | | 00000 | 30.20 | |
| 8 | 26-Oct | 0.260 | 0.300 | 0.240 | 00980 | | | | 00000 | | | | .00000 | 29.30 | |
| 9 | 27-Oct | 0.260 | 0.340 | 0.240 | 01111 | | | | .00000 | | | | 00000 | 29.69 | 46 |
| 10 | 28-Oct | 0.280 | 0.340 | 0.240 | 01195 | | | | .00000 | | | | 00000 | 29.80 | |
| 11 | 29-Oct | 0.290 | 0.340 | 0.240 | 01239 | | | | .00000 | | | | 00000 | 29.87 | |
| 12 | 30-Oct | 0.300 | 0.340 | 0.240 | 01282 | | | | 00000 | | | | 00000 | 29.93 | 41 |
| 13 | 31-Oct | 0.300 | 0.320 | 0.240 | 01206 | | | | .00000 | | | | 00000 | 29.51 | |
| 14 | 1-Nov | 0.310 | 0.300 | 0.230 | .01120 | | | | 00000 | | | | .00000 | 30.26 | |
| 15 | 2-Nov | 0.350 | 0.290 | 0.250 | .01328 | | | | 00000 | | | | 00000 | 30.34 | |
| 16 | 3-Nov | 0.340 | 0.210 | 0.250 | .00934 | | | | 00000 | | | | .00000 | 30.39 | |
| 17 | 4-Nov | 0.350 | 0.240 | 0.240 | 01086 | | | | .00000 | | | | .00000 | 30.20 | |
| 18 | 5-Nov | 0.390 | 0.270 | 0.240 | 01289 | | | | .00000 | | | | .00000 | 30.10 | |
| 19 | 6-Nov | 0.390 | 0.300 | 0.220 | 01347 | | | | .00000 | | | | .00000 | 30.02 | |
| 20 | 7-Nov | 0.390 | 0.330 | 0.260 | 01752 | | | | 00000 | | | | 00000 | 29.94 | |
| 21 | 8-Nov | 0.400 | 0.340 | 0.290 | 02055 | | | | 00000 | | | | 00000 | 30.67 | 45 |
| 22 | 9-Nov | 0.400 | 0.300 | 0.280 | 01759 | | | | 00000 | | | | 00000 | 28.55 | |
| 23 | 10-Nov | 0.410 | 0.340 | 0.280 | 02043 | | | | 00000 | | | | 00000 | 28.86 | |
| 24 | 11-Nov | 0.430 | 0.360 | 0.300 | 02431 | | | | 00000 | | | | 00000 | 29.20 | |
| 25 | 12-Nov | 0.470 | 0.370 | 0.320 | 02913 | | | | 00000 | | | | .00000 | 29.60 | |
| 26 | 13-Nov | 0.500 | 0.380 | 0.330 | 03262 | | | | 00000 | | | | 00000 | 29.88 | |
| 27 | 14-Nov | 0.520 | 0.400 | 0.320 | 03484 | | | | 00000 | | | | 00000 | 29.16 | |
| 28 | 15-Nov | 0.540 | 0.420 | 0.320 | 03799 | | | | 00000 | | | | .00000 | 29.41 | 42 |
| 29 | 16-Nov | 0.570 | 0.410 | 0.320 | 03915 | | | | 00000 | | | | 00000 | 29.33 | |
| 30 | 17-Nov | 0.600 | 0.410 | 0.320 | 04121 | | | | 00000 | | | | 00000 | 30.45 | |
| 31 | 18-Nov | 0.620 | 0.420 | 0.330 | 04499 | | | | 00000 | | | | 00000 | 30.41 | |
| 32 | 19-Nov | 0.640 | 0.440 | 0.330 | 04865 | | | | 00000 | | | | 00000 | 30.38 | |
| 33 | 20-Nov | 0.660 | 0.450 | 0.340 | 05286 | | | | 00000 | | | | 00000 | 30.33 | 46 |
| 34 | 21-Nov | 0.650 | 0.490 | 0.340 | 05669 | | | | 00000 | | | | 00000 | 30.07 | |
| 35 | 22-Nov | 0.670 | 0.490 | 0.350 | 06015 | 0.220 | 0.240 | 0.200 | 00553 | | | | 00000 | 29.97 | |
| 36 | 23-Nov | 0.685 | 0.510 | 0.360 | 05584 | 0.220 | 0.240 | 0.200 | 00553 | | | | .00000 | 30.50 | |
| 37 | 24-Nov | 0.700 | 0.530 | 0.360 | 05992 | 0.220 | 0.240 | 0.200 | 00553 | | | | 00000 | 31.23 | |
| 38 | 25-Nov | 0.700 | 0.520 | 0.370 | 07050 | 0.240 | 0.240 | 0.200 | 00503 | | | | 00000 | 31.30 | |
| 39 | 26-Nov | 0.700 | 0.510 | 0.380 | 07102 | 0.270 | 0.240 | 0.200 | 00678 | | | | 00000 | 31.40 | |
| 40 | 27-Nov | 0.700 | 0.500 | 0.390 | 07146 | 0.290 | 0.250 | 0.200 | 00759 | | | | 00000 | 31.56 | |
| 41 | 28-Nov | 0.700 | 0.500 | 0.390 | 07146 | 0.300 | 0.270 | 0.220 | 00933 | | | | 00000 | 31.65 | |
| 42 | 29-Nov | [illegible] | 0.550 | 0.390 | 07860 | 0.340 | 0.300 | 0.220 | 01175 | | | | 00000 | 32.41 | 41 |
| 43 | 30-Nov | 0.780 | 0.530 | 0.390 | 08440 | 0.350 | 0.320 | 0.220 | 01327 | | | | 00000 | 32.39 | |
| 44 | 1-Dec | 0.760 | 0.520 | 0.400 | 09275 | 0.350 | 0.440 | 0.260 | 02096 | | | | 00000 | 32.12 | |
| 45 | 2-Dec | 0.780 | 0.540 | 0.400 | 08820 | 0.350 | 0.450 | 0.260 | 02144 | | | | 00000 | 32.80 | |
| 46 | 3-Dec | 0.800 | 0.560 | 0.400 | 09381 | 0.360 | 0.460 | 0.260 | 02254 | | | | 00000 | 33.20 | |
| 47 | 4-Dec | 0.820 | 0.570 | 0.400 | 09787 | 0.370 | 0.470 | 0.260 | 02367 | | | | .00000 | 33.54 | |
| 48 | 5-Dec | 0.860 | 0.560 | 0.450 | 11345 | 0.400 | 0.470 | 0.260 | 02559 | | | | 00000 | 33.48 | |

Prepared by Bob DeVries 4/11/97

A-538-DA.xls

| | | | | | | | | | | | | | | | |
|---|---|---|---|---|---|---|---|---|---|---|---|---|---|---|---|
| 49 | 6-Dec | 0.850 | 0.560 | 0.450 | 11345 | 0.420 | 0.490 | 0.300 | 03232 | 0.200 | 0.200 | 0.200 | 00419 | 34.32 | 30 |
| 50 | 7-Dec | 0.870 | 0.580 | 0.450 | 11887 | 0.450 | 0.500 | 0.300 | 03534 | 0.210 | 0.200 | 0.180 | 00396 | 34.86 | |
| 51 | 8-Dec | 0.870 | 0.590 | 0.450 | .12092 | 0.440 | 0.500 | 0.330 | 03801 | 0.210 | 0.200 | 0.180 | 00396 | 34.83 | |
| 52 | 9-Dec | 0.890 | 0.600 | 0.470 | 13139 | 0.500 | 0.540 | 0.330 | 04664 | 0.210 | 0.210 | 0.190 | 00439 | 35.50 | |
| 53 | 10-Dec | 0.900 | 0.600 | 0.480 | 13569 | 0.550 | 0.570 | 0.330 | 05416 | 0.220 | 0.220 | 0.200 | 00507 | 36.20 | |
| 54 | 11-Dec | 0.910 | 0.610 | 0.490 | 14239 | 0.590 | 0.590 | 0.330 | .06014 | 0.230 | 0.230 | 0.200 | 00554 | 36.97 | |
| 55 | 12-Dec | 0.930 | 0.620 | 0.470 | 14187 | 0.590 | 0.590 | 0.330 | .06014 | 0.240 | 0.240 | 0.200 | .00603 | 37.20 | |
| 56 | 13-Dec | 0.950 | 0.630 | 0.460 | .14412 | 0.590 | 0.590 | 0.330 | 06014 | 0.250 | 0.250 | 0.210 | .00687 | 37.43 | 29 |
| 57 | 14-Dec | 0.940 | 0.630 | 0.460 | 14261 | 0.660 | 0.640 | 0.330 | 07297 | 0.290 | 0.280 | 0.210 | .00893 | 37.65 | |
| 58 | 15-Dec | 0.930 | 0.620 | 0.460 | 13885 | 0.660 | 0.640 | 0.340 | 07518 | 0.290 | 0.270 | 0.210 | 00861 | 38.15 | |
| 59 | 16-Dec | 0.910 | 0.610 | 0.450 | 13077 | 0.700 | 0.680 | 0.350 | 08722 | 0.290 | 0.270 | 0.210 | 00861 | 37.60 | |
| 60 | 17-Dec | 0.880 | 0.610 | 0.440 | 12365 | 0.750 | 0.710 | 0.350 | 09757 | 0.290 | 0.270 | 0.210 | 00861 | 36.90 | |
| 61 | 18-Dec | 0.850 | 0.600 | 0.430 | 11480 | 0.800 | 0.740 | 0.360 | .11157 | 0.290 | 0.270 | 0.210 | .00861 | 36.24 | |
| 62 | 19-Dec | 0.870 | 0.590 | 0.430 | 11555 | 0.780 | 0.740 | 0.360 | .10878 | 0.310 | 0.300 | 0.220 | 01071 | 37.20 | |
| 63 | 20-Dec | 0.890 | 0.590 | 0.430 | 11820 | 0.750 | 0.740 | 0.360 | 10460 | 0.330 | 0.330 | 0.220 | 01254 | 38.26 | 21 |
| 64 | 21-Dec | 0.930 | 0.620 | 0.470 | 14187 | 0.760 | 0.780 | 0.360 | .11172 | 0.330 | 0.330 | 0.230 | 01311 | 38.65 | |
| 65 | 22-Dec | 0.980 | 0.790 | 0.570 | 23102 | 0.780 | 0.780 | 0.390 | 12421 | 0.330 | 0.330 | 0.230 | .01311 | 39.82 | |
| 66 | 23-Dec | 1.000 | 0.820 | 0.570 | 24468 | 0.800 | 0.800 | 0.390 | 13067 | 0.350 | 0.330 | 0.240 | 01451 | 40.80 | |
| 67 | 24-Dec | 1.050 | 0.840 | 0.560 | 25857 | 0.810 | 0.810 | 0.390 | 13395 | 0.380 | 0.340 | 0.250 | 01691 | 41.90 | |
| 68 | 25-Dec | 1.100 | 0.850 | 0.560 | 27733 | 0.820 | 0.820 | 0.440 | .15488 | 0.410 | 0.340 | 0.260 | .01897 | 42.80 | |
| 69 | 26-Dec | 1.130 | 0.890 | 0.550 | 28957 | 0.830 | 0.830 | 0.440 | .15868 | 0.440 | 0.350 | 0.260 | .02096 | 43.80 | |
| 70 | 27-Dec | 1.160 | 0.920 | 0.540 | 30169 | 0.830 | 0.850 | 0.440 | 16250 | 0.460 | 0.350 | 0.270 | 02276 | 44.75 | 27 |
| 71 | 28-Dec | 1.220 | 1.000 | 0.550 | 35127 | 0.850 | 0.870 | 0.450 | 17421 | 0.460 | 0.380 | 0.285 | 02608 | 44.00 | |
| 72 | 29-Dec | 1.280 | 1.040 | 0.560 | 39025 | 0.870 | 0.890 | 0.460 | 18646 | 0.460 | 0.400 | 0.300 | .02890 | 43.38 | |
| 73 | 30-Dec | 1.290 | 1.060 | 0.570 | 40803 | 0.880 | 0.900 | 0.480 | 19901 | 0.470 | 0.400 | 0.310 | 03051 | 43.70 | |
| 74 | 31-Dec | 1.290 | 1.070 | 0.580 | 41910 | 0.880 | 0.920 | 0.490 | 20767 | 0.470 | 0.400 | 0.310 | 03051 | 44.00 | |
| 75 | 1-Jan | 1.300 | 1.090 | 0.590 | 43766 | 0.890 | 0.940 | 0.500 | 21898 | 0.480 | 0.400 | 0.320 | 03216 | 44.31 | |
| 76 | 2-Jan | 1.300 | 1.100 | 0.610 | 45665 | 0.890 | 0.960 | 0.500 | 22364 | 0.480 | 0.400 | 0.320 | 03216 | 45.18 | |
| 77 | 3-Jan | 1.300 | 1.100 | 0.610 | 45665 | 0.900 | 0.950 | 0.510 | 23068 | 0.480 | 0.400 | 0.320 | 03216 | 43.22 | 24 |
| 78 | 4-Jan | 1.300 | 1.100 | 0.610 | 45665 | 0.920 | 0.970 | 0.540 | 25227 | 0.460 | 0.400 | 0.320 | 03082 | 44.61 | |
| 79 | 5-Jan | 1.300 | 1.110 | 0.610 | 46080 | 0.920 | 0.970 | 0.560 | 26162 | 0.480 | 0.400 | 0.300 | 03015 | 44.33 | |
| 80 | 6-Jan | 1.280 | 1.150 | 0.620 | 47777 | 0.930 | 0.980 | 0.570 | 27196 | 0.480 | 0.400 | 0.300 | 03015 | 44.70 | |
| 81 | 7-Jan | 1.250 | 1.200 | 0.640 | 50658 | 0.940 | 0.990 | 0.580 | 28256 | 0.490 | 0.400 | 0.300 | 03078 | 45.00 | |
| 82 | 8-Jan | 1.240 | 1.250 | 0.660 | 53554 | 0.950 | 0.990 | 0.580 | 28556 | 0.300 | 0.400 | 0.300 | 01885 | 45.50 | |
| 83 | 9-Jan | 1.210 | 1.280 | 0.670 | .54323 | 0.960 | 1.000 | 0.590 | 29651 | 0.300 | 0.400 | 0.300 | 01885 | 45.80 | |
| 84 | 10-Jan | 1.190 | 1.300 | 0.680 | 55070 | 0.970 | 1.000 | 0.590 | 29950 | 0.310 | 0.400 | 0.300 | 01947 | 46.20 | 23 |
| 85 | 11-Jan | 1.180 | 1.310 | 0.690 | 55837 | 0.970 | 1.010 | 0.600 | 30772 | 0.310 | 0.400 | 0.300 | 01947 | 46.58 | |
| 86 | 12-Jan | 1.200 | 1.300 | 0.690 | 56350 | 0.970 | 1.010 | 0.630 | 32311 | 0.330 | 0.400 | 0.300 | 02073 | 47.33 | |
| 87 | 13-Jan | | | | 00000 | | | | 00000 | | | | 00000 | | |
| 88 | 14-Jan | | | | 00000 | | | | 00000 | | | | 00000 | | |
| 89 | 15-Jan | | *Died 1/15/96* | | #VALUE! | | *Died 1/15/96* | | #VALUE! | | *Died 1/15/96* | | #VALUE! | | |
| | | | *T-1 AVERAGE GROWTH* | | | | *T-2 AVERAGE GROWTH* | | | | *T-3 AVERAGE GROWTH* | | | | |
| | | 0.740 | 0.593 | 0.399 | 0.142 | 0.538 | 0.658 | 0.369 | 0.112 | 0.357 | 0.328 | 0.254 | 0.018 | | |

Prepared by Bob DeVries 4/11/97

A-540-DA.xls

| DAY | DATE | X | Y | Z | EVOL | X | Y | Z | EVOL | WEIGHT | HE |
|---|---|---|---|---|---|---|---|---|---|---|---|
| | DOB 3/25/95 | A-540 NECK T-1 | | | | | A-540 T-2 | | | GRAMS | CT |
| 1 | 15-Nov | 0 280 | 0 260 | 0 210 | 00800 | | | | .00000 | 29 97 | 40 |
| 2 | 16-Nov | 0 290 | 0 280 | 0 230 | 00978 | | | | 00000 | 30 89 | |
| 3 | 17-Nov | 0 290 | 0 290 | 0 230 | 01013 | | | | 00000 | 30 11 | |
| 4 | 18-Nov | 0 290 | 0 290 | 0 230 | 01013 | | | | 00000 | 30 11 | |
| 5 | 19-Nov | 0 300 | 0 290 | 0 240 | .01093 | | | | .00000 | 30 10 | |
| 6 | 20-Nov | 0 300 | 0 290 | 0 240 | .01093 | | | | .00000 | 30.10 | 41 |
| 7 | 21-Nov | 0 320 | 0 290 | 0 240 | 01166 | | | | 00000 | 29 92 | |
| 8 | 22-Nov | 0 360 | 0 340 | 0 220 | .01410 | | | | .00000 | 30 17 | |
| 9 | 23-Nov | 0 380 | 0 360 | 0 220 | .01576 | | | | .00000 | 30 50 | |
| 10 | 24-Nov | 0 400 | 0 370 | 0 220 | 01705 | | | | 00000 | 30 94 | |
| 11 | 25-Nov | 0 420 | 0 390 | 0 240 | 02058 | | | | 00000 | 31.30 | |
| 12 | 26-Nov | 0 440 | 0 410 | 0 260 | .02455 | | | | 00000 | 31 50 | |
| 13 | 27-Nov | 0 450 | 0 430 | 0.280 | .02836 | | | | .00000 | 31 64 | |
| 14 | 28-Nov | 0 450 | 0 430 | 0.260 | .02634 | | | | 00000 | 29 92 | |
| 15 | 29-Nov | 0 470 | 0 440 | 0 260 | 02815 | | | | .00000 | 30.29 | 29 |
| 16 | 30-Nov | 0 530 | 0 450 | 0 260 | 03246 | | | | 00000 | 29 83 | |
| 17 | 1-Dec | 0 490 | 0 440 | 0 300 | .03385 | | | | 00000 | 29 61 | |
| 18 | 2-Dec | 0 510 | 0 450 | 0 320 | .03845 | | | | .00000 | 29 90 | |
| 19 | 3-Dec | 0 530 | 0 460 | 0 330 | 04212 | | | | 00000 | 30 38 | |
| 20 | 4-Dec | 0 550 | 0 470 | 0 340 | 04601 | | | | 00000 | 30 78 | |
| 21 | 5-Dec | 0 550 | 0 460 | 0 340 | 04503 | | | | 00000 | 29 63 | |
| 22 | 6-Dec | 0 550 | 0 500 | 0 340 | 04895 | | | | 00000 | 30 60 | 28 |
| 23 | 7-Dec | 0 570 | 0 530 | 0 370 | 05852 | | | | 00000 | 30 06 | |
| 24 | 8-Dec | 0 580 | 0 550 | 0 400 | 06680 | | | | 00000 | 29 97 | |
| 25 | 9-Dec | 0 600 | 0 570 | 0 400 | 07161 | | | | 00000 | 29 94 | |
| 26 | 10-Dec | 0 600 | 0 590 | 0 400 | 07413 | | | | 00000 | 29 93 | |
| 27 | 11-Dec | 0 610 | 0 610 | 0 400 | .07792 | | | | 00000 | 29 91 | |
| 28 | 12-Dec | 0 650 | 0 620 | 0 410 | 08550 | | | | 00000 | 30 50 | |
| 29 | 13-Dec | 0 680 | 0 630 | 0 410 | 09195 | | | | .00000 | 31 26 | 26 |
| 30 | 14-Dec | 0 700 | 0 650 | 0 430 | 10242 | | | | 00000 | 30 47 | |
| 31 | 15-Dec | 0 720 | 0 680 | 0 450 | 11534 | | | | 00000 | 35 56 | |
| 32 | 16-Dec | 0 740 | 0 680 | 0 440 | 11591 | | | | 00000 | 35 20 | |
| 33 | 17-Dec | 0 760 | 0 690 | 0 440 | 12079 | | | | 00000 | 34 00 | |
| 34 | 18-Dec | 0 800 | 0 690 | 0 430 | 12426 | | | | 00000 | 33 38 | |
| 35 | 19-Dec | 0 820 | 0 710 | 0 440 | 13410 | | | | 00000 | 33 00 | |
| 36 | 20-Dec | 0 840 | 0 720 | 0 450 | 14248 | | | | 00000 | 32 65 | 19 |
| 37 | 21-Dec | 0 750 | 0 890 | 0 450 | 15725 | | | | 00000 | 34 22 | |
| 38 | 22-Dec | 0 810 | 0 790 | 0 650 | 21774 | | | | 00000 | 35 08 | |
| 39 | 23-Dec | 0 850 | 0 820 | 0 670 | 24447 | | | | 00000 | 35 60 | |
| 40 | 24-Dec | 0 890 | 0 850 | 0 690 | 27326 | | | | 00000 | 35 20 | |
| 41 | 25-Dec | 0 930 | 0 850 | 0 710 | 30419 | | | | 00000 | 35 80 | |
| 42 | 26-Dec | 1 000 | 0 910 | 0 730 | 34776 | | | | 00000 | 37 90 | |
| 43 | 27-Dec | 1 060 | 0 950 | 0 740 | 39010 | | | | 00000 | 38 77 | 26 |
| 44 | 28-Dec | 1 070 | 0 980 | 0 720 | 39524 | | | | 00000 | 38 00 | |
| 45 | 29-Dec | 1 090 | 0 910 | 0 700 | 36348 | | | | 00000 | 37 47 | |
| 46 | 30-Dec | 1 090 | 0 910 | 0 700 | 36348 | | | | 00000 | 36 00 | |
| 47 | 31-Dec | 1 100 | 0 910 | 0.700 | 36662 | | | | 00000 | 34 50 | |
| 48 | 1-Jan | 1 100 | 0 910 | 0 700 | 36662 | | | | 00000 | 33 08 | |

Prepared by Bob DeVries 4/11/97

Page 1

A-540-DA.xls

| | | | | | | | |
|---|---|---|---|---|---|---|---|
| 49 | 2-Jan | *Died 01/02/96* | | | #VALUE! | | 00000 |
| 50 | | *T-1 AVERAGE GROWTH* | | | | | |
| | | 0.637 | 0.584 | 0.413 | 0.119 | | |

Prepared by Bob DeVries 4/11/97

A-542-DA.xls

| DAY | DATE | X | Y | Z | EVOL | X | Y | Z | EVOL | WEIGHT | HE |
|---|---|---|---|---|---|---|---|---|---|---|---|
| | DOB 03/25/95 | A-542 NECK T-1 | | | | A-542 LT ARM T-2 | | | | GRAMS | CT |
| 1 | 27-Nov | 0.350 | 0.400 | 0.360 | .02638 | | | | 00000 | 28.99 | |
| 2 | 28-Nov | 0.370 | 0.410 | 0.370 | 02938 | | | | 00000 | 29.65 | |
| 3 | 29-Nov | 0.400 | 0.450 | 0.400 | 03769 | | | | 00000 | 29.47 | 40 |
| 4 | 30-Nov | 0.440 | 0.480 | 0.430 | 04754 | | | | 00000 | 29.26 | |
| 5 | 1-Dec | 0.470 | 0.500 | 0.400 | 04921 | | | | 00000 | 29.68 | |
| 6 | 2-Dec | 0.480 | 0.520 | 0.410 | 05357 | | | | 00000 | 29.90 | |
| 7 | 3-Dec | 0.490 | 0.540 | 0.430 | 05956 | | | | 00000 | 30.20 | |
| 8 | 4-Dec | 0.500 | 0.550 | 0.440 | 06334 | | | | 00000 | 30.36 | |
| 9 | 5-Dec | 0.510 | 0.550 | 0.440 | 06461 | | | | 00000 | 30.19 | |
| 10 | 6-Dec | 0.510 | 0.550 | 0.450 | .06608 | | | | .00000 | 30.73 | 40 |
| 11 | 7-Dec | 0.550 | 0.580 | 0.470 | 07849 | | | | 00000 | 31.18 | |
| 12 | 8-Dec | 0.550 | 0.620 | 0.480 | .08569 | | | | .00000 | 31.69 | |
| 13 | 9-Dec | 0.570 | 0.690 | 0.490 | .10089 | | | | .00000 | 32.20 | |
| 14 | 10-Dec | 0.590 | 0.760 | 0.510 | .11972 | | | | 00000 | 32.90 | |
| 15 | 11-Dec | 0.610 | 0.830 | 0.520 | 13782 | | | | 00000 | 33.33 | |
| 16 | 12-Dec | 0.650 | 0.845 | 0.530 | .15239 | | | | 00000 | 33.90 | |
| 17 | 13-Dec | 0.690 | 0.850 | 0.520 | 16154 | 0.300 | 0.240 | 0.150 | 00565 | 34.59 | 34 |
| 18 | 14-Dec | 0.710 | 0.920 | 0.540 | .18465 | 0.300 | 0.240 | 0.150 | 00565 | 35.65 | |
| 19 | 15-Dec | 0.720 | 0.890 | 0.550 | .18450 | 0.280 | 0.270 | 0.150 | 00594 | 35.39 | |
| 20 | 16-Dec | 0.800 | 0.940 | 0.580 | .22833 | 0.280 | 0.270 | 0.210 | 00831 | 36.00 | |
| 21 | 17-Dec | 0.890 | 0.980 | 0.600 | 27396 | 0.270 | 0.270 | 0.260 | 00992 | 36.80 | |
| 22 | 18-Dec | 0.950 | 1.010 | 0.620 | .31470 | 0.270 | 0.270 | 0.300 | 01145 | 37.56 | |
| 23 | 19-Dec | 0.920 | 1.050 | 0.650 | 32871 | 0.250 | 0.260 | 0.250 | 00851 | 38.75 | |
| 24 | 20-Dec | 0.890 | 1.090 | 0.690 | 35041 | 0.190 | 0.250 | 0.200 | 00497 | 40.02 | 33 |
| 25 | 21-Dec | 0.910 | 1.120 | 0.690 | .35815 | 0.240 | 0.250 | 0.200 | 00653 | 40.04 | |
| 26 | 22-Dec | 0.960 | 1.010 | 0.610 | 30953 | 0.230 | 0.380 | 0.200 | 00915 | 39.57 | |
| 27 | 23-Dec | 0.950 | 1.010 | 0.600 | 30455 | 0.230 | 0.380 | 0.200 | 00915 | 38.80 | |
| 28 | 24-Dec | 0.960 | 1.010 | 0.600 | 30455 | 0.220 | 0.380 | 0.200 | 00875 | 38.20 | |
| 29 | 25-Dec | 0.950 | 1.010 | 0.590 | 29636 | 0.220 | 0.380 | 0.200 | 00875 | 37.60 | |
| 30 | 26-Dec | 0.950 | 1.010 | 0.590 | .29636 | 0.210 | 0.380 | 0.200 | 00836 | 37.00 | |
| 31 | 27-Dec | 0.940 | 1.010 | 0.590 | 29224 | 0.200 | 0.380 | 0.190 | 00756 | 35.36 | 32 |
| 32 | 28-Dec | 0.950 | 1.015 | 0.530 | .26754 | 0.225 | 0.380 | 0.210 | 00940 | 37.40 | |
| 33 | 29-Dec | 0.950 | 1.020 | 0.450 | .23058 | 0.250 | 0.390 | 0.220 | 01123 | 38.52 | |
| 34 | 30-Dec | 0.970 | 1.040 | 0.470 | 24621 | 0.270 | 0.400 | 0.220 | 01244 | 39.10 | |
| 35 | 31-Dec | 0.980 | 1.070 | 0.480 | 26349 | 0.290 | 0.410 | 0.230 | 01432 | 39.70 | |
| 36 | 1-Jan | 0.980 | 1.090 | 0.490 | 27401 | 0.320 | 0.410 | 0.230 | 01580 | 40.20 | |
| 37 | 2-Jan | 0.980 | 1.110 | 0.520 | 29612 | 0.320 | 0.430 | 0.240 | 01729 | 41.92 | |
| 38 | 3-Jan | 0.960 | 1.140 | 0.510 | 29219 | 0.340 | 0.470 | 0.240 | 02008 | 43.00 | 30 |
| 39 | 4-Jan | 0.930 | 1.260 | 0.520 | 31899 | 0.350 | 0.470 | 0.250 | 02303 | 45.30 | |
| 40 | 5-Jan | 0.950 | 1.110 | 0.520 | 29008 | 0.400 | 0.470 | 0.270 | 02657 | 37.13 | |
| 41 | 6-Jan | 0.950 | 1.110 | 0.540 | 30123 | 0.440 | 0.490 | 0.310 | 03499 | 37.40 | |
| 42 | 7-Jan | 0.960 | 1.110 | 0.560 | 31239 | 0.480 | 0.510 | 0.350 | 04485 | 37.80 | |
| 43 | 8-Jan | 0.960 | 1.100 | 0.580 | 32063 | 0.530 | 0.530 | 0.390 | 05735 | 38.10 | |
| 44 | 9-Jan | 0.960 | 1.100 | 0.600 | 33169 | 0.570 | 0.540 | 0.410 | 05606 | 38.40 | |
| 45 | 10-Jan | 0.960 | 1.100 | 0.620 | 34275 | 0.610 | 0.550 | 0.430 | 07552 | 38.60 | 30 |
| 46 | 11-Jan | 0.950 | 1.100 | 0.620 | 34275 | 0.660 | 0.550 | 0.440 | 08361 | 38.80 | |
| 47 | 12-Jan | 0.950 | 1.000 | 0.630 | 31331 | 0.650 | 0.570 | 0.430 | 08340 | 38.84 | |
| 48 | 13-Jan | 0.990 | 1.000 | 0.630 | 32651 | 0.710 | 0.590 | 0.440 | 09649 | 39.80 | |

Prepared by Bob DeVries 4/11/97

Page 1

A-542-DA.xls

| | | | | | | | | | | | |
|---|---|---|---|---|---|---|---|---|---|---|---|
| 49 | 14-Jan | 1.020 | 1.010 | 0.620 | .33437 | 0.780 | 0.600 | 0.450 | 11025 | 40.70 | |
| 50 | 15-Jan | 1.050 | 1.010 | 0.620 | .34421 | 0.840 | 0.610 | 0.450 | 12071 | 41.65 | |
| 51 | 16-Jan | 1.040 | 0.970 | 0.620 | .32743 | 0.830 | 0.640 | 0.460 | 12792 | 42.40 | |
| 52 | 17-Jan | 1.040 | 0.990 | 0.580 | .31262 | 0.870 | 0.640 | 0.470 | .13700 | 40.85 | 30 |
| 53 | 18-Jan | | *Died 1/18/96* | | #VALUE! | | *Died 1/18/96* | | #VALUE! | | |
| 54 | 19-Jan | | *T-1 AVERAGE GROWTH* | | | | *T-2 AVERAGE GROWTH* | | | | |
| 55 | 20-Jan | 0.803 | 0.897 | 0.536 | 0.226 | 0.401 | 0.424 | 0.284 | 0.034 | | |

A-592-DA xls

| DAY | DATE | X | Y | Z | EVOL | X | Y | Z | EVOL | X | Y | Z | EVOL | WEIGHT GRAMS | HE CT |
|---|---|---|---|---|---|---|---|---|---|---|---|---|---|---|---|
| | DOB 6/27/95 | | A-592 LT LEG T-1 | | | | A-592 LT ARMPIT T-2 | | | | A-592 RT ARM T-3 | | | | |
| 1 | 16-Jan | 0 480 | 0 380 | 0 170 | 0162 | | | | 0000 | | | | 0000 | 32 86 | |
| 2 | 17-Jan | 0 530 | 0 380 | 0 200 | 0211 | 0 210 | 0 200 | 0 110 | 0024 | | | | 0000 | 31 03 | 41 |
| 3 | 18-Jan | 0 550 | 0 430 | 0 220 | 0272 | 0 200 | 0 200 | 0 100 | .0021 | | | | .0000 | 31 64 | |
| 4 | 19-Jan | 0 560 | 0 440 | 0 220 | 0284 | 0.200 | 0 200 | 0 100 | 0021 | | | | 0000 | 30.94 | |
| 5 | 20-Jan | 0 620 | 0 480 | 0.250 | 0389 | 0 200 | 0 190 | 0 100 | .0020 | | | | .0000 | 30 60 | |
| 6 | 21-Jan | 0 680 | 0 530 | 0.280 | 0528 | 0 200 | 0 190 | 0 100 | 0020 | | | | 0000 | 31.20 | |
| 7 | 22-Jan | 0 740 | 0.570 | 0 300 | 0662 | 0 200 | 0 180 | 0 100 | 0019 | | | | .0000 | 31 98 | |
| 8 | 23-Jan | 0 800 | 0 610 | 0 300 | 0766 | 0 190 | 0 170 | 0 100 | 0017 | | | | 0000 | 32 51 | |
| 9 | 24-Jan | 0 810 | 0 670 | 0 300 | 0852 | 0.200 | 0 180 | 0 110 | 0021 | | | | .0000 | 34 80 | 35 |
| 10 | 25-Jan | 0 830 | 0 680 | 0 310 | 0916 | 0.200 | 0 210 | 0 110 | 0024 | | | | 0000 | 36 02 | |
| 11 | 26-Jan | 0 920 | 0 750 | 0 340 | 1228 | 0.200 | 0 210 | 0 110 | 0024 | | | | .0000 | 35.83 | |
| 12 | 27-Jan | 0 950 | 0 750 | 0 350 | 1305 | 0.200 | 0.210 | 0 110 | 0024 | | | | 0000 | 36.80 | |
| 13 | 28-Jan | 0 990 | 0 750 | 0 350 | 1360 | 0 190 | 0 200 | 0 110 | .0022 | | | | .0000 | 37 80 | |
| 14 | 29-Jan | 1 030 | 0 750 | 0 460 | 1860 | 0 190 | 0 200 | 0 110 | 0022 | 0 260 | 0 270 | 0 080 | 0029 | 38.59 | |
| 15 | 30-Jan | 1 110 | 0 810 | 0 490 | 2306 | 0.210 | 0 200 | 0 110 | 0024 | 0 260 | 0 280 | 0 090 | 0034 | 42.38 | |
| 16 | 31-Jan | 1 150 | 0 850 | 0 500 | 2559 | 0 240 | 0 200 | 0 110 | 0028 | 0 260 | 0 290 | 0 120 | 0047 | 42 30 | 25 |
| 17 | 1-Feb | 1 170 | 0 840 | 0 540 | 2778 | 0 230 | 0 200 | 0 110 | 0026 | 0 280 | 0 300 | 0 120 | 0053 | 42 44 | |
| 18 | 2-Feb | 1 220 | 1 000 | 0 590 | 3768 | 0 250 | 0 260 | 0 110 | 0037 | 0 270 | 0 290 | 0 120 | .0049 | 44.98 | |
| 19 | 3-Feb | 1 340 | 1 070 | 0 610 | 4579 | 0 250 | 0 260 | 0 110 | 0037 | 0 290 | 0 290 | 0 120 | 0053 | 45 97 | |
| 20 | 4-Feb | 1 360 | 1 100 | 0 650 | 5091 | 0 230 | 0 250 | 0 110 | 0033 | 0 310 | 0 300 | 0 140 | .0068 | 46 80 | |
| 21 | 5-Feb | 1 480 | 1 140 | 0 690 | 6094 | 0 220 | 0 240 | 0 120 | 0033 | 0 330 | 0 300 | 0 150 | 0078 | 48 63 | |
| 22 | 6-Feb | 1 430 | 1 150 | 0 710 | 6112 | 0 220 | 0 240 | 0 120 | 0033 | 0 340 | 0 310 | 0 150 | .0083 | 50 98 | |
| 23 | 7-Feb | 1 500 | 1 200 | 0 760 | 7161 | 0.220 | 0 240 | 0 120 | 0033 | 0 360 | 0 340 | 0 160 | 0103 | 51.25 | 20 |
| 24 | 8-Feb | 1 520 | 1 240 | 0 760 | 7499 | 0 200 | 0 210 | 0 120 | 0026 | 0 360 | 0 340 | 0 160 | 0103 | 53 65 | |
| 25 | 9-Feb | 1 600 | 1 250 | 0 760 | 7957 | 0 210 | 0 210 | 0 130 | 0030 | 0 360 | 0 340 | 0 160 | 0103 | 54 20 | |
| 26 | 10-Feb | 1 640 | 1 270 | 0 760 | 8287 | 0 220 | 0 210 | 0 130 | 0031 | 0 360 | 0 350 | 0 160 | 0106 | 54 80 | |
| 27 | 11-Feb | 1 680 | 1 290 | 0 760 | 8622 | 0 230 | 0 220 | 0 130 | 0034 | 0 360 | 0 360 | 0.170 | .0115 | 56 40 | |
| 28 | 12-Feb | 1 750 | 1 300 | 0 760 | 9051 | 0 240 | 0 220 | 0 140 | 0039 | 0 360 | 0 370 | 0 170 | 0119 | 56.06 | |
| 29 | 13-Feb | 1 700 | 1 340 | 0 760 | 9053 | 0 220 | 0 220 | 0 120 | 0030 | 0 350 | 0 360 | 0 170 | 0115 | 50.11 | |
| 30 | 14-Feb | 1 680 | 1 250 | 0 690 | 8192 | 0 220 | 0 260 | 0 140 | 0042 | 0 380 | 0 350 | 0 210 | 0150 | 50 57 | |
| 31 | 15 Feb | | Died 2/15/96 | | #VALUE! | | Died 2/15/96 | | #VALUE! | | Died 2/15/96 | | #VALUE! | | |

Prepared by Bob DeVries 4/11/97

Page 1

A-594-DA.xls

| DAY | DATE | X | Y | Z | EVOL | X | Y | Z | EVOL | WEIGHT GRAMS | HECT |
|---|---|---|---|---|---|---|---|---|---|---|---|
| | DOB 6/27/95 | A-594 RT SIDE T-1 | | | | A-594 T-2 | | | | | |
| 1 | 12-Jan | 0.160 | 0.200 | 0.090 | .00151 | | | | .00000 | 41.92 | |
| 2 | 13-Jan | 0.200 | 0.210 | 0.090 | .00198 | | | | .00000 | 41.40 | |
| 3 | 14-Jan | 0.240 | 0.220 | 0.100 | .00276 | | | | .00000 | 40.80 | |
| 4 | 15-Jan | 0.270 | 0.230 | 0.100 | .00325 | | | | .00000 | 40.20 | |
| 5 | 16-Jan | 0.270 | 0.220 | 0.090 | .00280 | | | | .00000 | 39.95 | |
| 6 | 17-Jan | 0.280 | 0.230 | 0.100 | .00337 | | | | .00000 | 39.73 | 41 |
| 7 | 18-Jan | 0.260 | 0.240 | 0.110 | .00359 | | | | .00000 | 39.49 | |
| 8 | 19-Jan | 0.280 | 0.280 | 0.140 | .00575 | | | | .00000 | 39.60 | |
| 9 | 20-Jan | 0.300 | 0.280 | 0.150 | .00660 | | | | .00000 | 39.10 | |
| 10 | 21-Jan | 0.340 | 0.290 | 0.150 | .00774 | | | | .00000 | 38.50 | |
| 11 | 22-Jan | 0.360 | 0.290 | 0.160 | .00874 | | | | .00000 | 38.06 | |
| 12 | 23-Jan | 0.390 | 0.300 | 0.230 | .01409 | | | | .00000 | 39.57 | |
| 13 | 24-Jan | 0.450 | 0.340 | 0.240 | .01922 | | | | .00000 | 39.28 | 43 |
| 14 | 25-Jan | 0.460 | 0.360 | 0.260 | .02254 | | | | .00000 | 39.32 | |
| 15 | 26-Jan | 0.500 | 0.390 | 0.290 | .02960 | | | | .00000 | 39.09 | |
| 16 | 27-Jan | 0.520 | 0.420 | 0.290 | .03316 | | | | .00000 | 38.80 | |
| 17 | 28-Jan | 0.530 | 0.440 | 0.290 | .03540 | | | | .00000 | 38.30 | |
| 18 | 29-Jan | 0.550 | 0.470 | 0.290 | .03924 | | | | .00000 | 37.97 | |
| 19 | 30-Jan | 0.560 | 0.490 | 0.290 | .04166 | | | | .00000 | 38.79 | |
| 20 | 31-Jan | 0.590 | 0.530 | 0.340 | .05566 | | | | .00000 | 38.82 | 38 |
| 21 | 1-Feb | 0.640 | 0.570 | 0.340 | .06493 | | | | .00000 | 39.08 | |
| 22 | 2-Feb | 0.670 | 0.610 | 0.360 | .07702 | | | | .00000 | 39.85 | |
| 23 | 3-Feb | 0.700 | 0.640 | 0.370 | .08678 | | | | .00000 | 39.65 | |
| 24 | 4-Feb | 0.740 | 0.670 | 0.360 | .09344 | | | | .00000 | 39.90 | |
| 25 | 5-Feb | 0.790 | 0.700 | 0.360 | .10422 | | | | .00000 | 40.20 | |
| 26 | 6-Feb | 0.860 | 0.790 | 0.300 | .10670 | | | | .00000 | 39.53 | |
| 27 | 7-Feb | 0.920 | 0.940 | 0.340 | .15393 | | | | .00000 | 38.66 | 32 |
| 28 | 8-Feb | 1.020 | 1.010 | 0.290 | .15640 | | | | .00000 | 37.37 | |
| 29 | 9-Feb | 1.030 | 1.030 | 0.290 | .16106 | | | | .00000 | 36.40 | |
| 30 | 10-Feb | 1.050 | 1.050 | 0.280 | .16160 | | | | .00000 | 35.00 | |
| 31 | 11-Feb | 1.060 | 1.070 | 0.280 | .16625 | | | | .00000 | 33.50 | |
| 32 | 12-Feb | 1.070 | 1.080 | 0.280 | .16939 | | | | .00000 | 31.95 | |
| 33 | 13-Feb | 1.110 | 1.060 | 0.310 | .19094 | | | | .00000 | 30.87 | |
| 34 | 14-Feb | 1.110 | 1.100 | 0.270 | .17258 | | | | .00000 | 33.88 | 20 |
| 35 | 15-Feb | 1.170 | 1.090 | 0.270 | .18026 | | | | .00000 | 34.31 | |
| 36 | 16-Feb | Died 2/16/96 | | | #VALUE! | | | | .00000 | | |

Prepared by Bob DeVries 4/11/97

Page 1

WO 98/29156                                              PCT/US97/23845

*APPENDIX C*

TREATED MOUSE DATA (EXTERNAL MODULATOR EMBODIMENT)

Index (Pages numbered on back)

| Appendix | Subject | Pages |
|---|---|---|
| C1 | OUJ-738 | 116 |

Surbeck, et al., Therapeutic Apparatus and Method

OUJ-738-DATA 4-18-97
OUJ-738 Born ---- First tumor appeared on 3/5/97

Device Code: SW & HP=Short Wire and Homer's Pulser
Device Code: SW & NP=Short Wire and New Pulser

| DAY | DATE | T-1 Lt Underarm Ln | Wd | Ht | Vol T-1 | WEIGHT Gr | HEMATO-CRIT-% | DEVICE | TREATMENT PARAMETERS FREQ MHz | POWER | TIME | FREQ MHz | POWER | TIME | DEVICE |
|---|---|---|---|---|---|---|---|---|---|---|---|---|---|---|---|
| 1 | 5-Mar | 0.110 | 0.110 | 0.110 | .00070 | 37.95 | | 8662A | 43351855.0 | | | 43353800.0 | 0.0 dBm | 1, 1 | SW & HP |
| 2 | 6-Mar | 0.110 | 0.110 | 0.110 | .00070 | 36.83 | | 8662A | 43351855.0 | | | 43353800.0 | 0.0 dBm | 1, 1 | SW & HP |
| 3 | 7-Mar | 0.100 | 0.110 | 0.100 | .00058 | 36.00 | | 8662A | 43351855.0 | | | 43353800.0 | 0.0 dBm | 1, 1 | SW & HP |
| 4 | 8-Mar | 0.110 | 0.100 | 0.100 | .00058 | 36.02 | 46 | 8662A | 43351855.0 | | | 43353800.0 | 0.0 dBm | 1, 1 | SW & HP |
| 5 | 9-Mar | 0.110 | 0.100 | 0.100 | .00058 | 36.25 | | | NO TREATMENT | | | NO TREATMENT | | | |
| 6 | 10-Mar | 0.100 | 0.100 | 0.100 | .00052 | 36.56 | | 8662A | 43351855.0 | | | 43353800.0 | 0.0 dBm | 1, 1 | SW & NP |
| 7 | 11-Mar | 0.110 | 0.100 | 0.090 | .00052 | 35.32 | | 8662A | 43351855.0 | | | 43353800.0 | 0.0 dBm | 1, 1 | SW & NP |
| 8 | 12-Mar | 0.110 | 0.110 | 0.080 | .00051 | 34.88 | | 8662A | 43346000.0 | | | 43353800.0 | 0.0 dBm | 1, 1 | SW & NP |
| 9 | 13-Mar | 0.120 | 0.120 | 0.070 | .00053 | 35.11 | | 8662A | 43351855.0 | | | 43346000.0 | 0.0 dBm | 1, 1 | SW & NP |
| 10 | 14-Mar | 0.130 | 0.120 | 0.070 | .00057 | 34.91 | | 8662A | 43351855.0 | | | 43353800.0 | 0.0 dBm | 1, 1 | SW & NP |
| 11 | 15-Mar | 0.140 | 0.130 | 0.060 | .00057 | 34.84 | 44 | 8662A | 43351855.0 | | | 43353800.0 | 0.0 dBm | 1, 1 | SW & HP |
| 12 | 16-Mar | 0.145 | 0.130 | 0.065 | .00064 | 35.20 | | | NO TREATMENT | | | NO TREATMENT | | | |
| 13 | 17-Mar | 0.150 | 0.130 | 0.070 | .00071 | 35.58 | | 8662A | 43351855.0 | | | 43353800.0 | 0.0 dBm | 1, 1 | SW & HP |
| 14 | 18-Mar | 0.150 | 0.130 | 0.070 | .00071 | 35.25 | | 8662A | 43351855.0 | | | 43353800.0 | 0.0 dBm | 1, 1 | SW & HP |
| 15 | 19-Mar | 0.150 | 0.120 | 0.070 | .00066 | 33.66 | | 8662A | 43351855.0 | | | 43353800.0 | 0.0 dBm | 1, 1 | SW & HP |
| 16 | 20-Mar | 0.160 | 0.120 | 0.070 | .00070 | 33.81 | | 8662A | 43351855.0 | | | 43353800.0 | 0.0 dBm | 1, 1 | SW & HP |
| 17 | 21-Mar | 0.160 | 0.120 | 0.070 | .00070 | 32.67 | | 8662A | 43351855.0 | | | 43353800.0 | 0.0 dBm | 1, 1 | SW & HP |
| 18 | 22-Mar | 0.160 | 0.130 | 0.070 | .00076 | 32.83 | 43 | 8662A | 43351855.0 | | | 43353800.0 | 0.0 dBm | 1, 1 | SW & HP |
| 19 | 23-Mar | 0.160 | 0.130 | 0.070 | .00076 | 33.23 | | | NO TREATMENT | | | NO TREATMENT | | | |
| 20 | 24-Mar | 0.170 | 0.130 | 0.080 | .00093 | 33.63 | | 8662A | 43351855.0 | | | 43353800.0 | "-40 dBm | 1, 1 | SW & HP |
| 21 | 25-Mar | 0.180 | 0.130 | 0.080 | .00098 | 33.01 | | 8662A | 43351855.0 | | | 43353800.0 | "-50 dBm | 1, 1 | SW & HP |
| 22 | 26-Mar | 0.190 | 0.130 | 0.070 | .00091 | 32.69 | | 8662A | 43351855.0 | | | 43353800.0 | 0.0 dBm | 1, 1 | SW & HP |
| 23 | 27-Mar | 0.190 | 0.130 | 0.080 | .00103 | 31.25 | | 8662A | 43351855.0 | | | 43353800.0 | 0.0 dBm | 1, 1 | SW & HP |
| 24 | 28-Mar | 0.190 | 0.130 | 0.080 | .00103 | 31.63 | | 8662A | 43351855.0 | | | 43353800.0 | 0.0 dBm | 1, 1 | SW & HP |
| 25 | 29-Mar | 0.190 | 0.130 | 0.080 | .00103 | 31.11 | 44 | 8662A | 43351855.0 | | | 43353800.0 | 0.0 dBm | 1, 1 | SW & HP |
| 26 | 30-Mar | 0.190 | 0.130 | 0.080 | .00103 | 31.36 | | | NO TREATMENT | | | NO TREATMENT | | | |
| 27 | 31-Mar | 0.200 | 0.130 | 0.070 | .00095 | 31.64 | | 8662A | 43351855.0 | | | 43353800.0 | 0.0 dBm | 1, 1 | SW & HP |
| 28 | 1-Apr | 0.210 | 0.130 | 0.070 | .00100 | 31.83 | | 8662A | 43351855.0 | | | 43353800.0 | 0.0 dBm | 1, 1 | SW & HP |
| 29 | 2-Apr | 0.210 | 0.130 | 0.070 | .00100 | 31.11 | | 8662A | 43351855.0 | | | 43353800.0 | 0.0 dBm | 1, 1 | SW & HP |
| 30 | 3-Apr | 0.210 | 0.140 | 0.070 | .00108 | 31.80 | | 8662A | 43351855.0 | | | 43353800.0 | 0.0 dBm | 1, 1 | SW & HP |
| 31 | 4-Apr | 0.220 | 0.140 | 0.080 | .00129 | 30.98 | | 8662A | 43351855.0 | | | 43353800.0 | 0.0 dBm | 1, 1 | SW & HP |
| 32 | 5-Apr | | | | .00000 | | | | NO TREATMENT | | | NO TREATMENT | | | |
| 33 | 6-Apr | | | | .00000 | | | | | | | | | | |

09141691.082898

We claim:

1. Therapeutic apparatus comprising means for generating a first square wave of approximately 60 Hz, at a duty cycle of approximately 50%;

means for generating a second square wave of approximately 1.167 Hz, at a duty cycle of approximately 50%;

means for ANDing said first square wave and said second square wave;

a series LC filtering means comprising an inductor and a variable capacitor;

a quartz crystal with a resonant frequency in the radio frequency range, serially driven by said signal through said LC filtering means;

a wire loop, one end of which is connected to the output of said generating means, and the other end of which is grounded with respect to said generating means.

2. The apparatus of claim 1, wherein said wire loop is made from approximately five turns spaced approximately 3.175 mm. apart of a wire approximately 60 cm. long.

3. The apparatus of claim 2, wherein said apparatus is enclosed in a housing, and said loop is mounted on the exterior surface of said housing.

4. The apparatus of claim 3, wherein the power supply for the apparatus comprises a battery housed within the apparatus so as to render the apparatus self-contained.

5. The apparatus of claim 3, wherein the power supply for the apparatus comprises an external, power line driven transformer.

* * * * *